(12) United States Patent  
Sun et al.

(10) Patent No.: US 11,004,536 B2  
(45) Date of Patent: May 11, 2021

(54) CELL-FREE BIOMOLECULAR BREADBOARDS AND RELATED METHODS AND ARRANGEMENTS

(71) Applicant: CALIFORNIA INSTITUTE OF TECHNOLOGY, Pasadena, CA (US)

(72) Inventors: Zachary Z. Sun, Pittsburgh, PA (US); Richard M. Murray, Pasadena, CA (US); Vipul Singhal, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 375 days.

(21) Appl. No.: 15/046,374

(22) Filed: Feb. 17, 2016

(65) Prior Publication Data

US 2017/0024512 A1    Jan. 26, 2017

Related U.S. Application Data

(60) Provisional application No. 62/117,319, filed on Feb. 17, 2015, provisional application No. 62/143,878, filed on Apr. 7, 2015.

(51) Int. Cl.
| | |
|---|---|
| *G01N 33/48* | (2006.01) |
| *G01N 33/50* | (2006.01) |
| *G16B 5/00* | (2019.01) |
| *G16B 35/00* | (2019.01) |
| *G16C 20/60* | (2019.01) |
| *C12N 15/10* | (2006.01) |
| *C12Q 1/6897* | (2018.01) |
| *C12N 15/52* | (2006.01) |

(52) U.S. Cl.
CPC ........... *G16B 5/00* (2019.02); *C12N 15/1075* (2013.01); *C12N 15/1086* (2013.01); *C12N 15/1089* (2013.01); *C12N 15/1093* (2013.01); *C12N 15/52* (2013.01); *C12Q 1/6897* (2013.01); *G16B 35/00* (2019.02); *G16C 20/60* (2019.02)

(58) Field of Classification Search
None
See application file for complete search history.

(56) References Cited

U.S. PATENT DOCUMENTS

| | | | |
|---|---|---|---|
| 2009/0123971 A1* | 5/2009 | Paulsel | C12N 9/93 435/69.4 |
| 2013/0130347 A1* | 5/2013 | Delisa | C12N 15/115 435/188 |
| 2016/0002611 A1 | 1/2016 | Mershin et al. | |

OTHER PUBLICATIONS

Schreiber et al. Interaction of barnase with its polypeptide inhibitor barstar studied by protein engineering. Biochemistry, vol. 32, pp. 5145-5150. (Year: 1993).*

Sheinerman et al. On the role of electrostatic interactions in the design of protein-protein interfaces. Journal of Molecular Biology, vol. 318, pp. 161-177. (Year: 2002).*

(Continued)

*Primary Examiner* — Russell S Negin

(74) *Attorney, Agent, or Firm* — Greenberg Traurig, LLP; Fang Xie

(57) ABSTRACT

Provided herein are methods and arrangements and related cell-free biomolecular breadboards configured to design, build, implement, debug, and/or test a genetic circuit to be operated in a target environment, by testing in a cell-free system under conditions of the target environment, molecular components of the genetic circuit and/or combinations thereof to select the molecular components and/or combinations thereof of a genetic circuit operative in the target environment.

28 Claims, 136 Drawing Sheets

Specification includes a Sequence Listing.

(56) References Cited

OTHER PUBLICATIONS

Blanch et al. Biochemical Engineering. New York: Marcel Dekker, Inc., pp. 60-67. (Year: 1996).*
Noireaux et al. Principles of cell-free genetic circuit assembly. PNAS, vol. 100, pp. 12672-12677. (Year: 2003).*
Saito, et al., "Synthetic translational regulation by an L7Ae-kink-turn RNP switch", Nature Chemical Biology, vol. 6, pp. 71-78, Jan. 2010.
Shin, et al., "An E coli Cell-Free Expression Toolbox: Application to Synthetic Gene Circuits and Artificial Cells", Americal Chemical Society, vol. 1, pp. 29-41, (2011).
Takahashi, et al., "Rapidly Characterizing the Fast Dynamics of RNA Genetic Circuitry with Cell-Free Transcription—Translation (TX-TL) Systems", American Chemical Society, ACS Synth. Biol., vol. 4, pp. 503-515, (2015).
Sun, et al., "Protocols for Implementing an *Escherichia coli* Based TX-TL Cell-Free Expression System for Synthetic Biology", Journal of Visualized Experiments, vol. 79, e50762, pp. 1-14, Sep. 2013.
Siegal-Gaskins, et al., "Gene Circuit Performance Characterization and Resource Usage in a Cell-Free Breadboard", American Chemical Society, Special Issue: Cell-Free Synthetic Biology, Dec. 8, 2013.
Sun, et al., "Linear DNA for Rapid Prototyping of Synthetic Biological Circuits in an *Escherichia coli* Based TX-TL Cell-Free System", American Chemical Society, Special Issue: Cell-Free Synthetic Biology, Sep. 5, 2013.
Siegal-Gaskins, et al., "Biomolecular resource utilization in elementary cell-free gene circuits", pp. 1531-1536, American Control Conference (ACC) Washington, DC, USA, Jun. 17-19, 2013.

\* cited by examiner

Coherent FFL
Coherent type 1 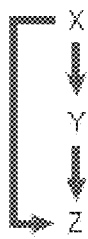
Coherent type 2 
Coherent type 3 
Coherent type 4 
Incoherent FFL
Incoherent type 1 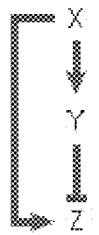
Incoherent type 2 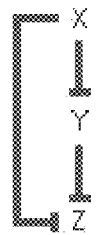
Incoherent type 3 
Incoherent type 4 
FIG. 4

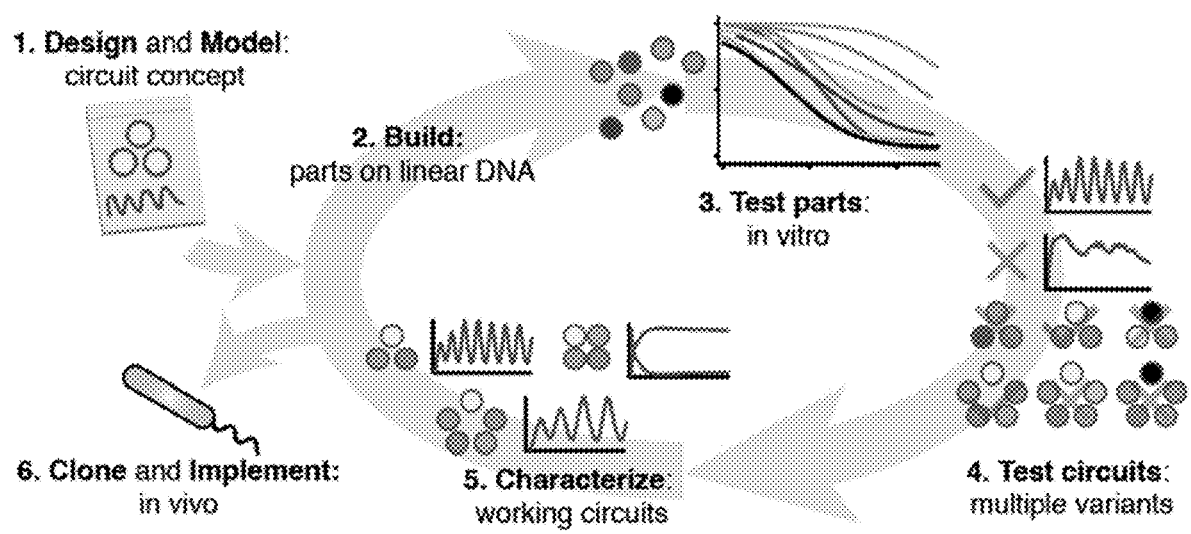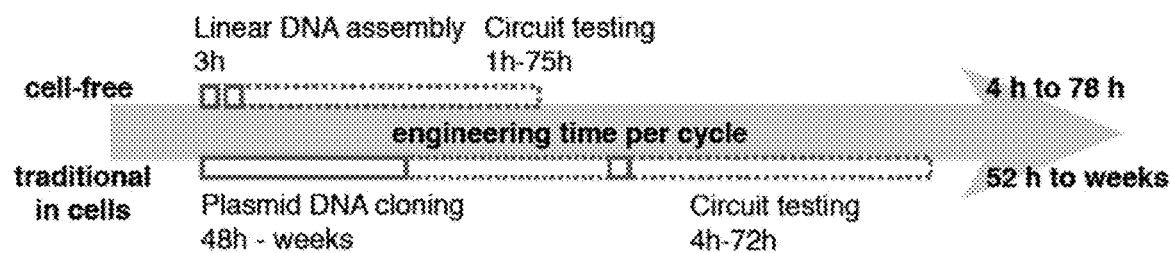
FIG. 6

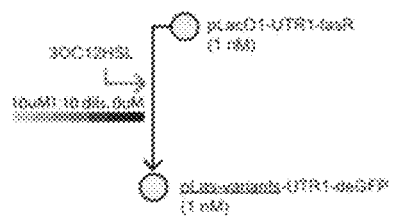
FIG. 9A
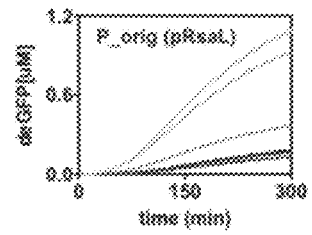
FIG. 9B
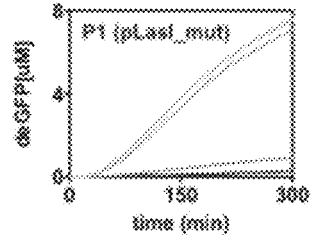
FIG. 9C
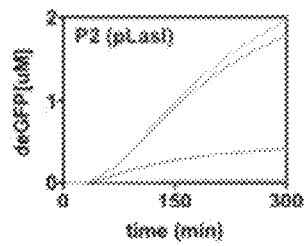
FIG. 9D
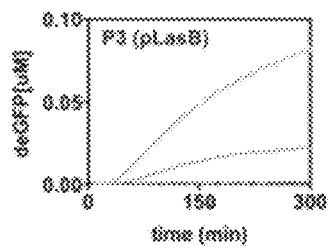
FIG. 9E
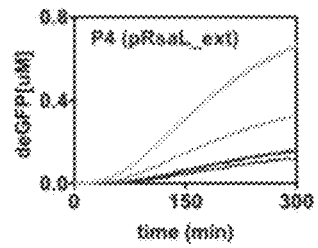
FIG. 9F
|  | P_orig (pRsaL) | P1 (pLasI_mut) | P2 (pLasI) | P3 (pLasB) | P4 (pRsaL_ext) |
|---|---|---|---|---|---|
| Vmax | 1.134 +/- 0.068 | 7.604 +/- 0.214 | 1.957 +/- 0.165 | 0.082 +/- 0.004 | 0.706 +/- 0.055 |
| h | 0.734 +/- 0.163 | 1.990 +/- 0.353 | 1.517 +/- 0.561 | na | 0.598 +/- 0.163 |
| Khalf | 0.020 +/- 0.007 | 0.027 +/- 0.005 | 0.231 +/- 0.090 | na | 0.008 +/- 0.004 |
| Kprime | 0.056 +/- 0.044 | 0.001 +/- 0.001 | 0.108 +/- 0.139 | na | 0.053 +/- 0.053 |
FIG. 9G

FIG. 11B - Continued
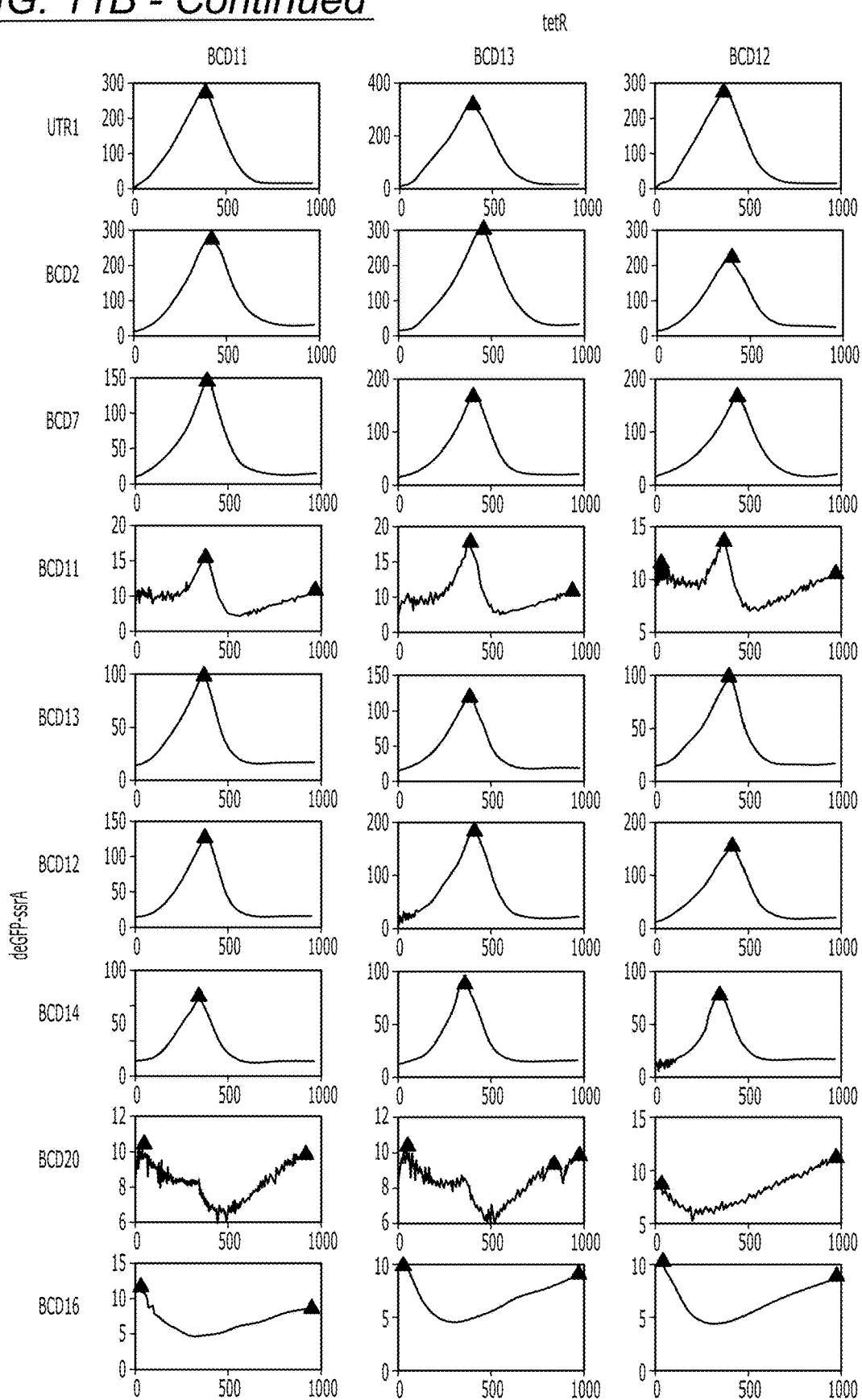

FIG. 11B - Continued
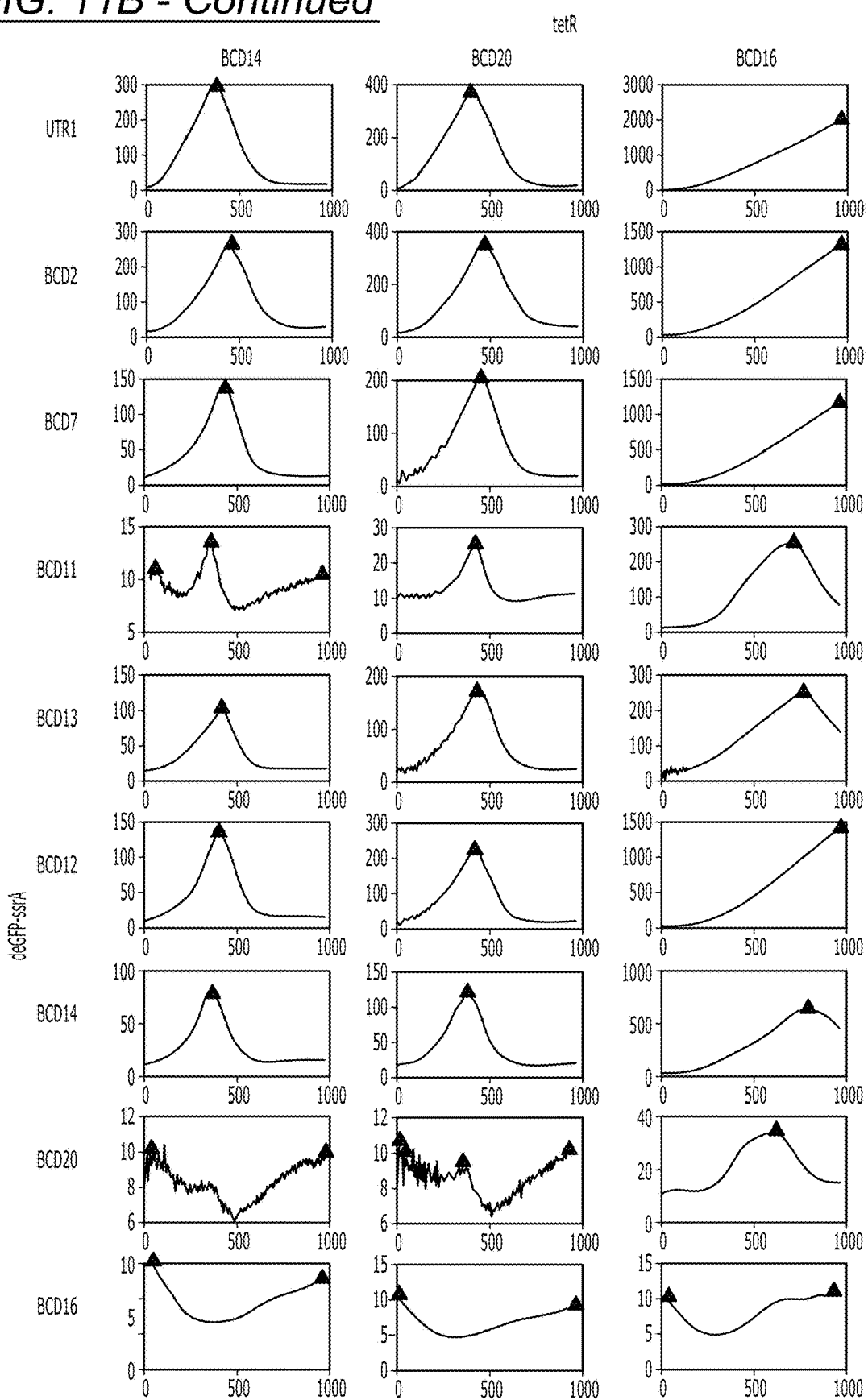

FIG. 11B - Continued
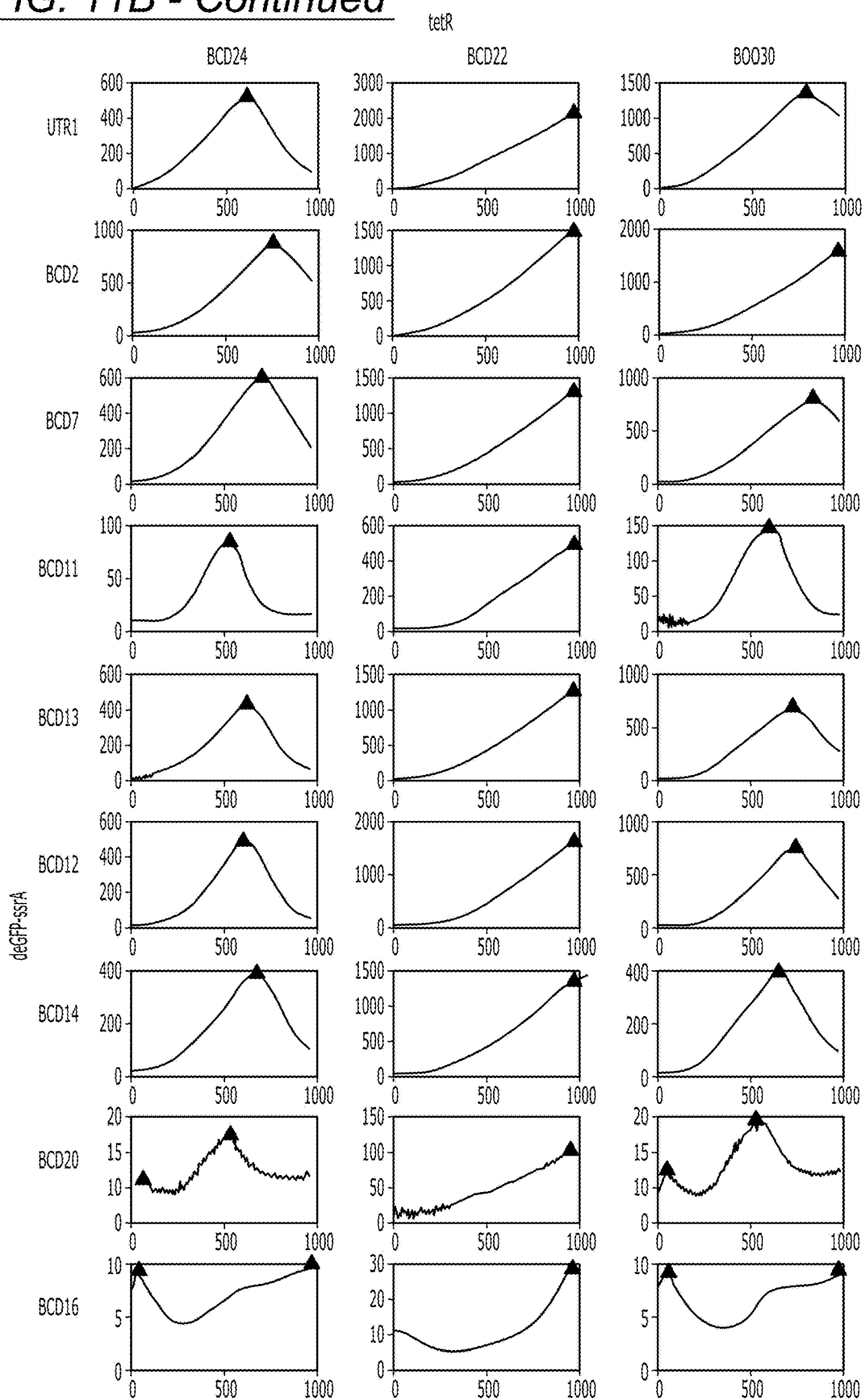

FIG. 11B - Continued
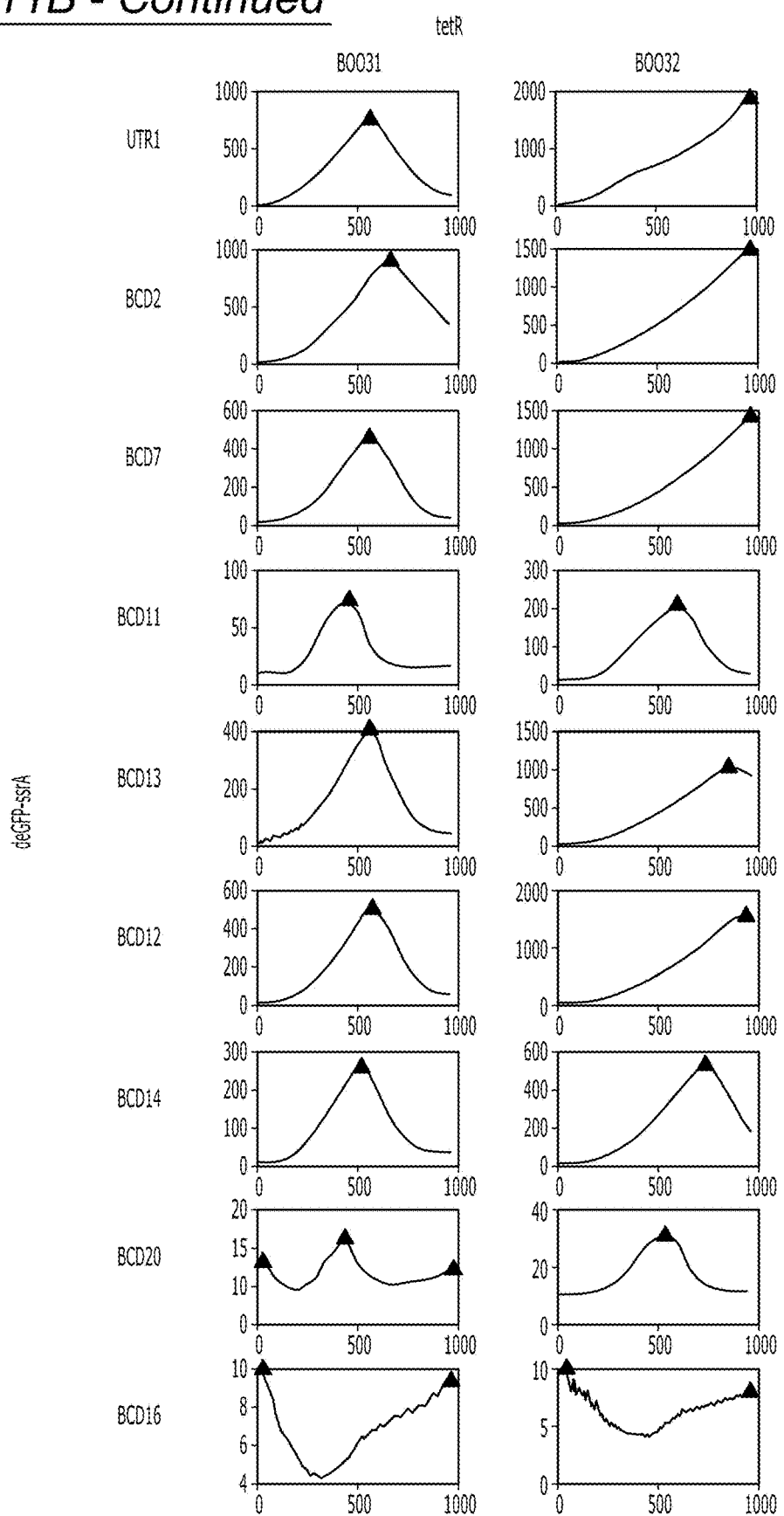

FIG. 11B - Continued
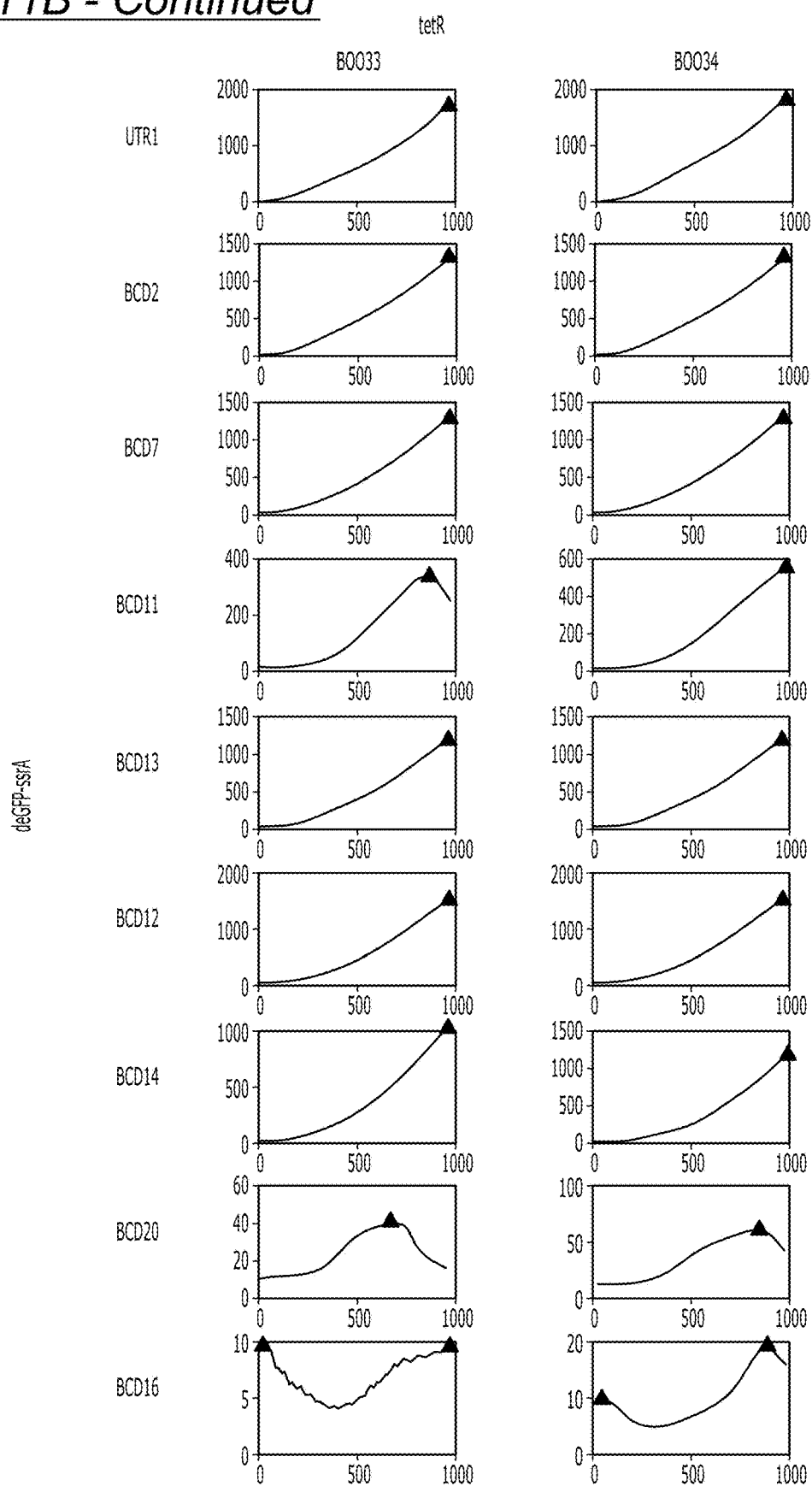

FIG. 11B - Continued
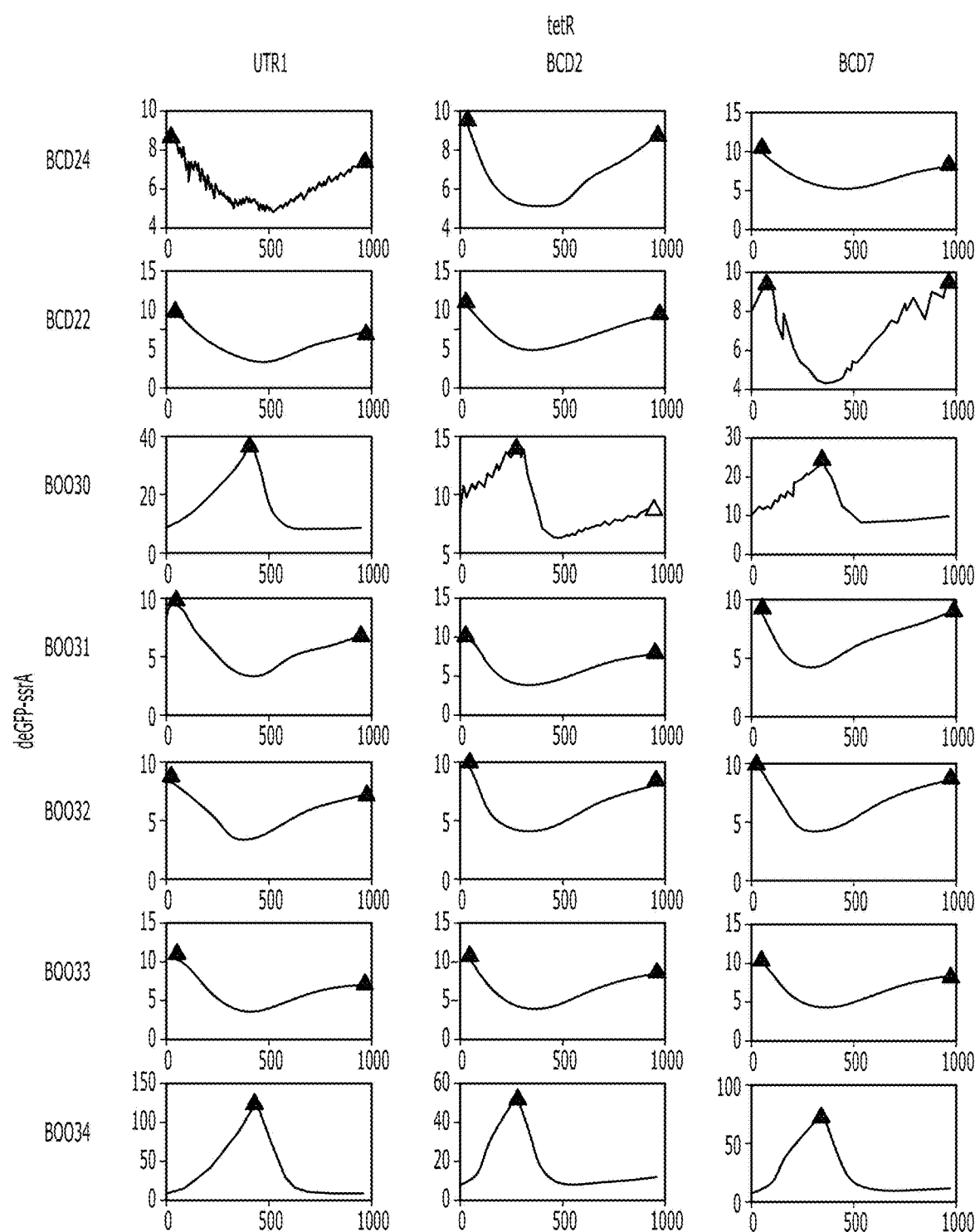

FIG. 11B - Continued
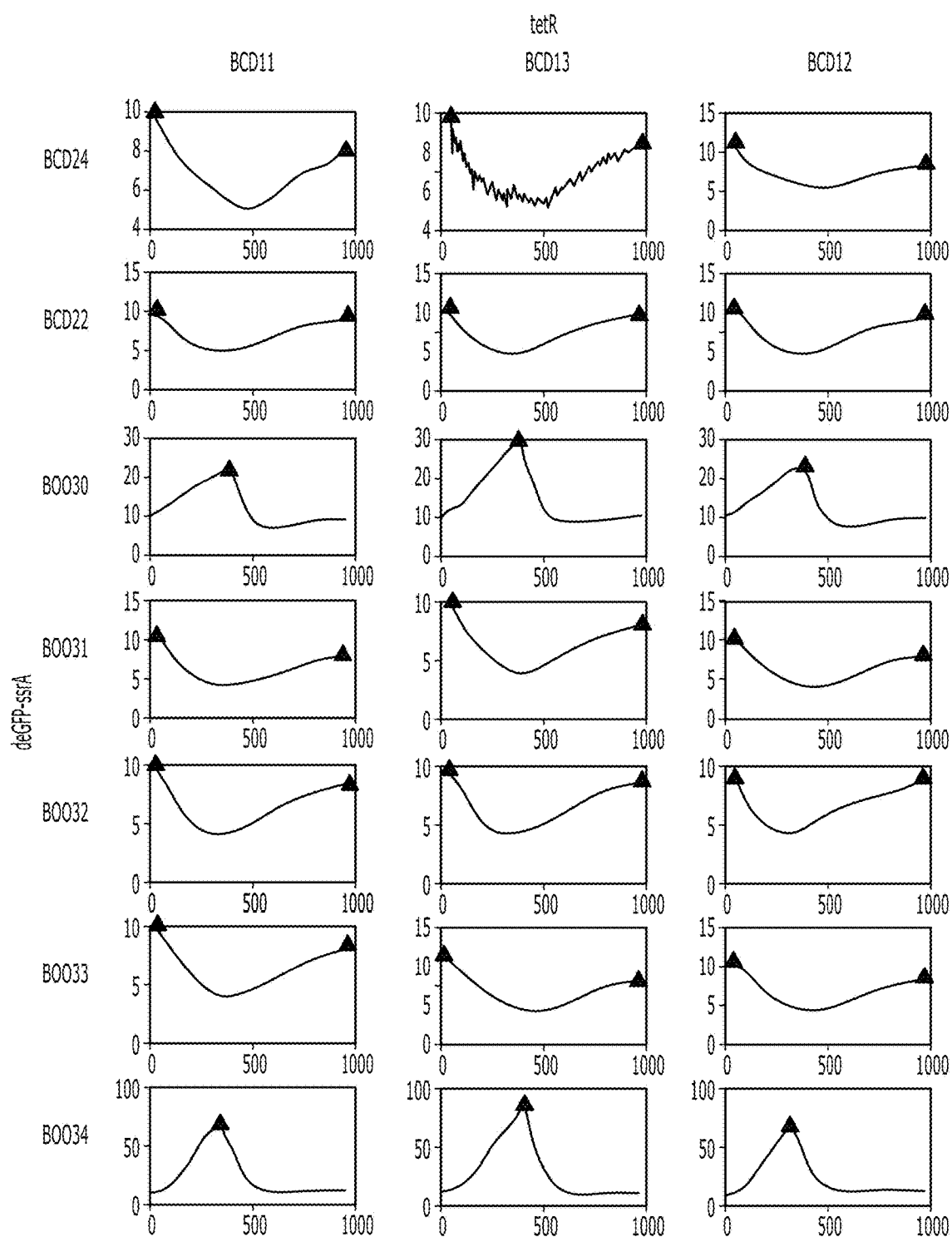

FIG. 11B - Continued
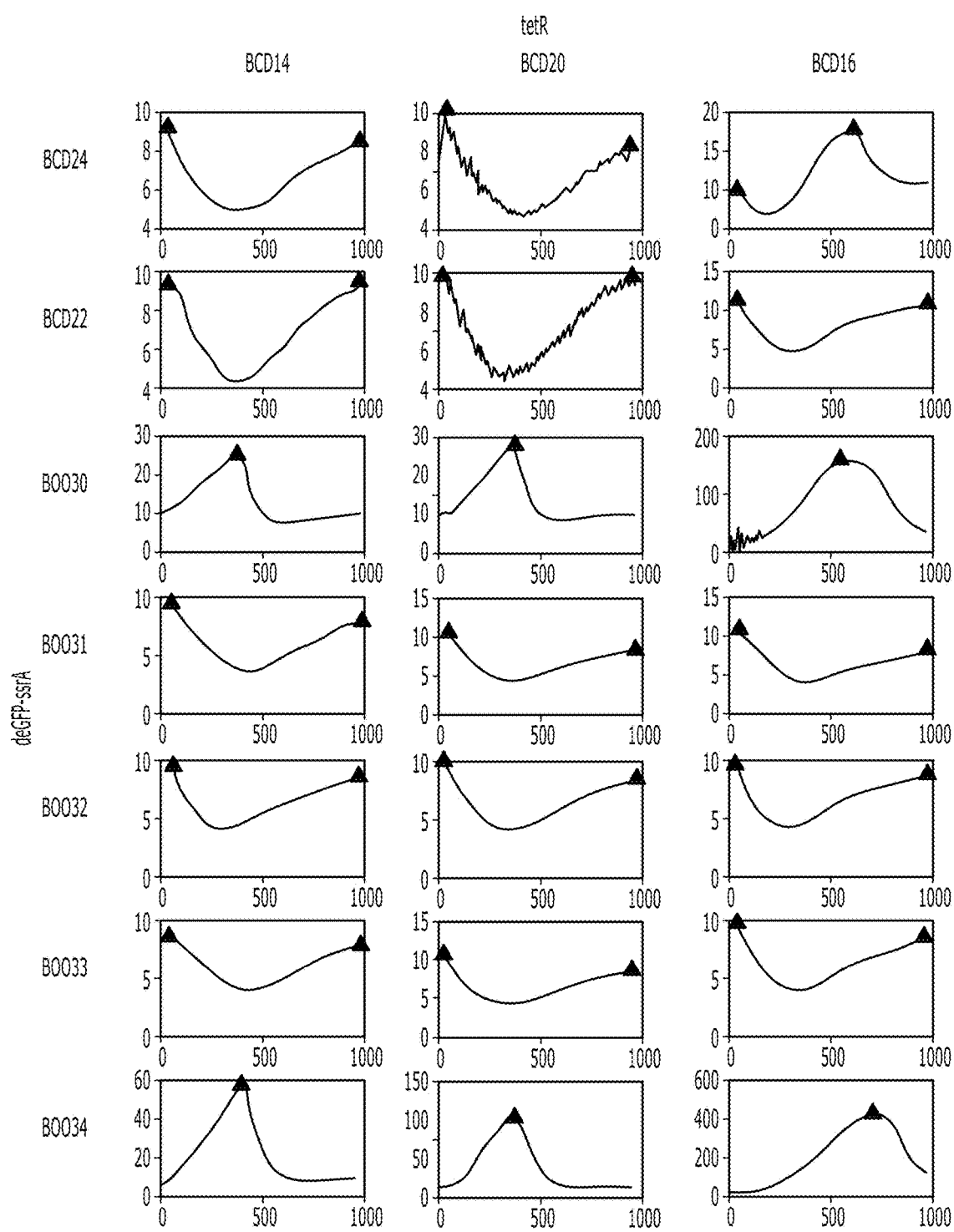

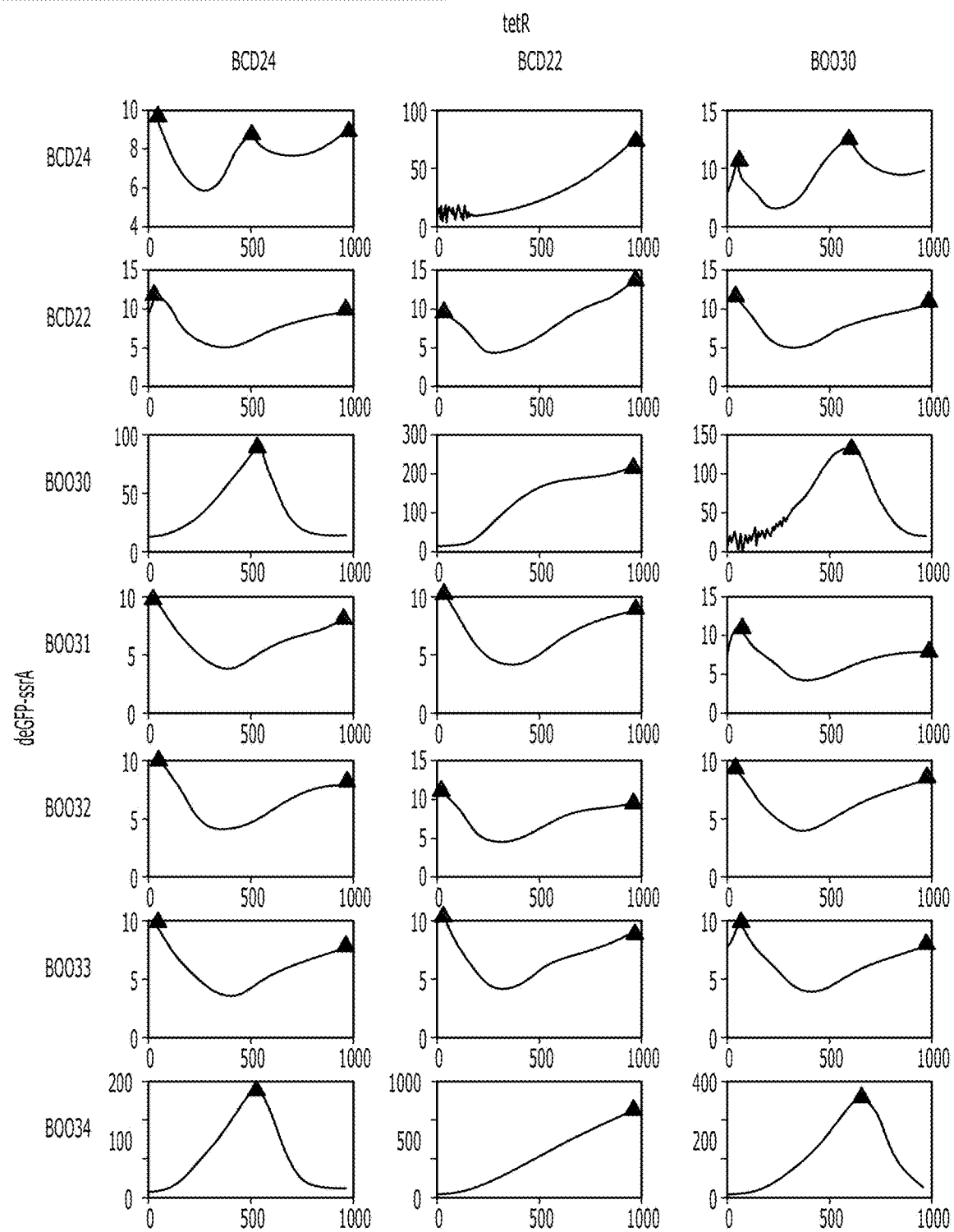
FIG. 11B - Continued

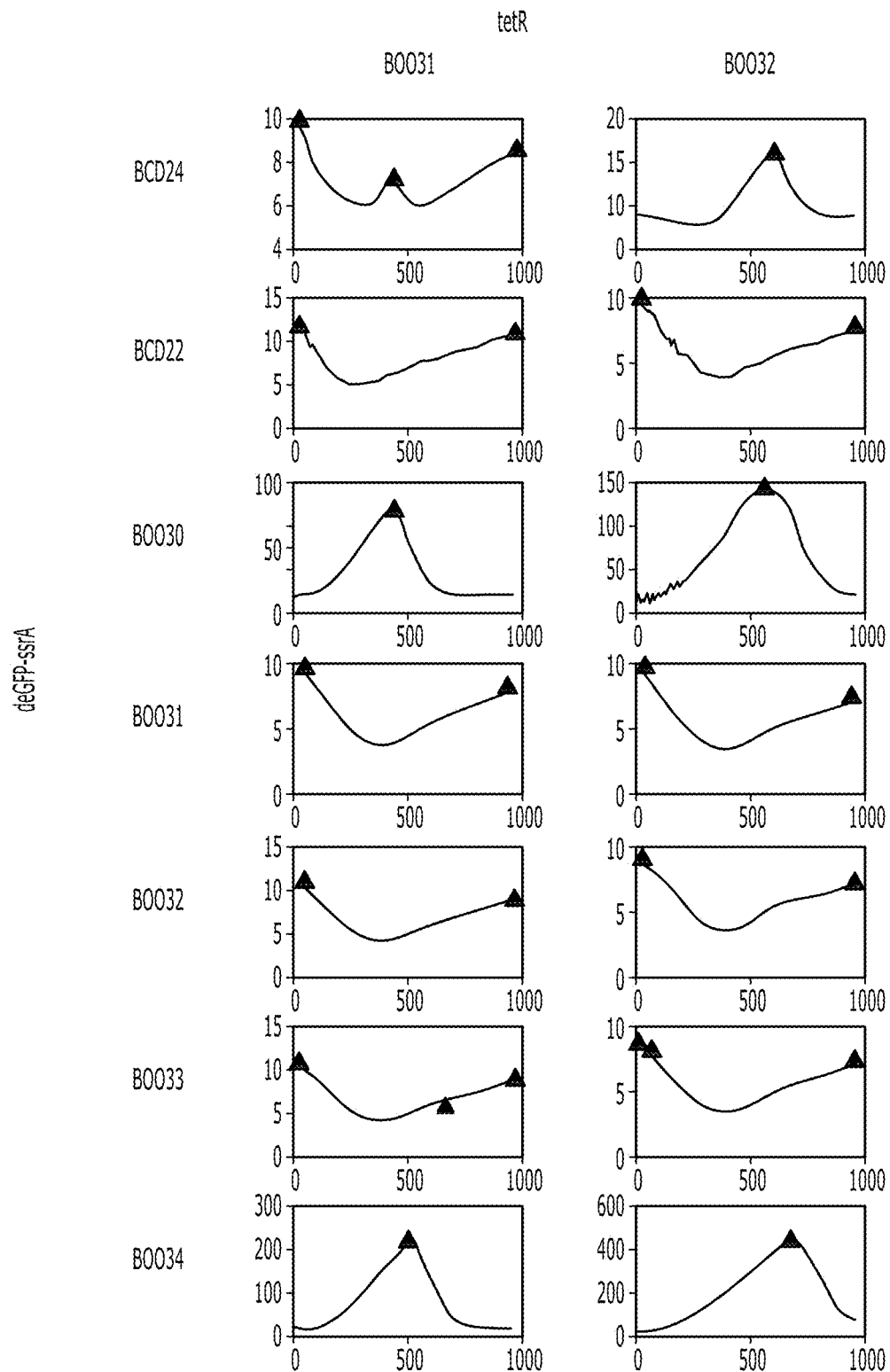
FIG. 11B - Continued

FIG. 11B - Continued
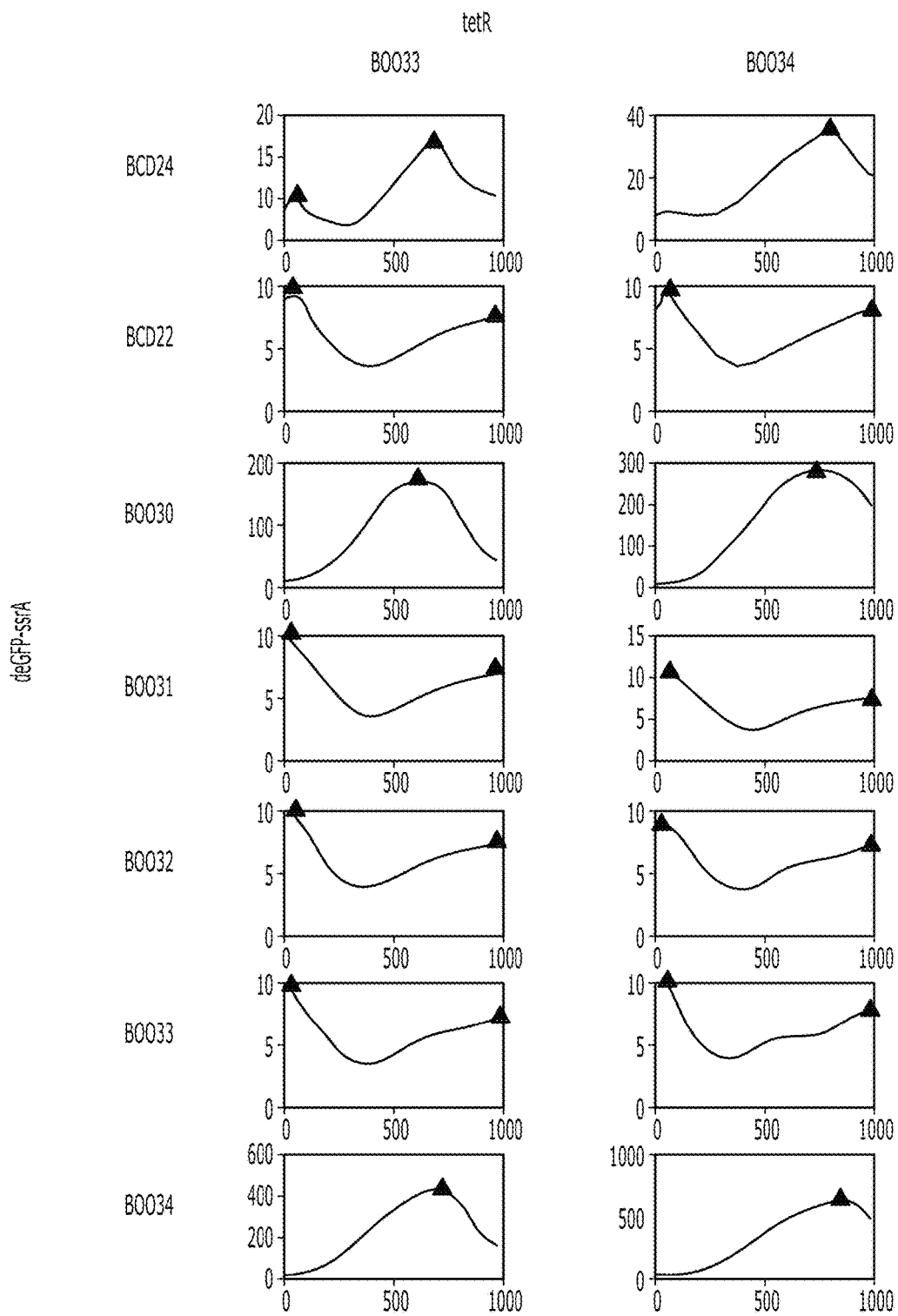

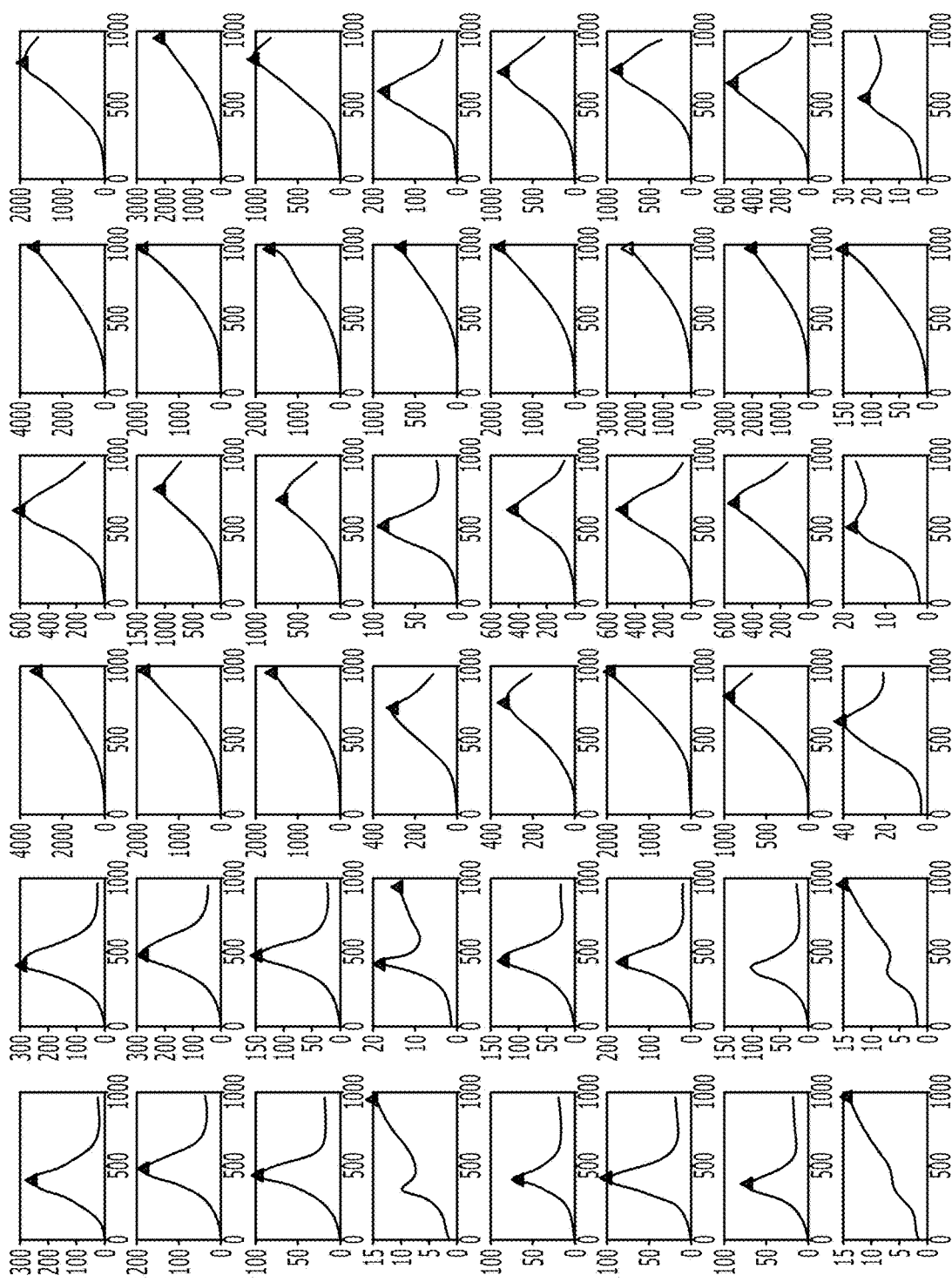
FIG. 11C -Cont'd

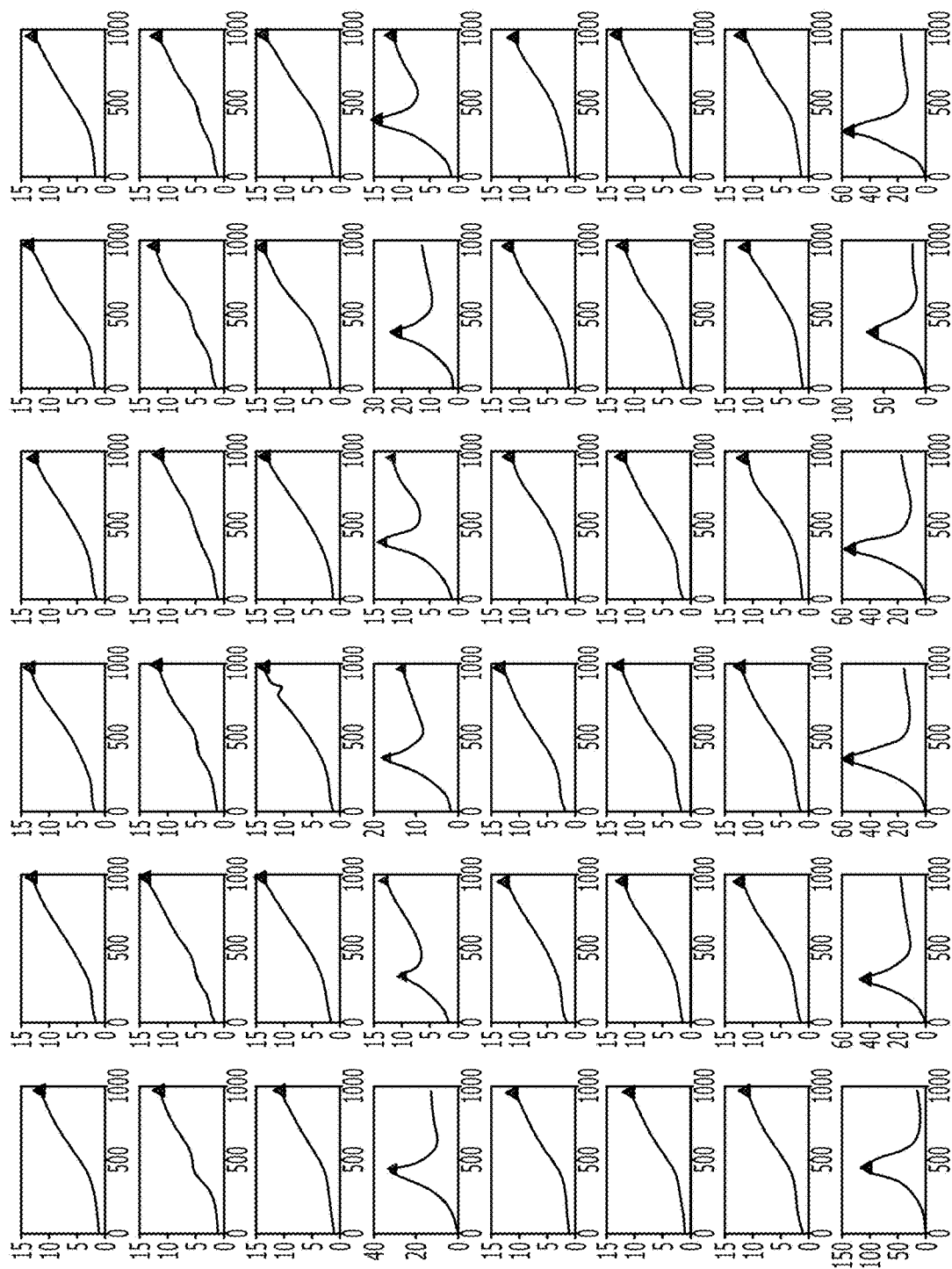
FIG. 11C - Cont'd

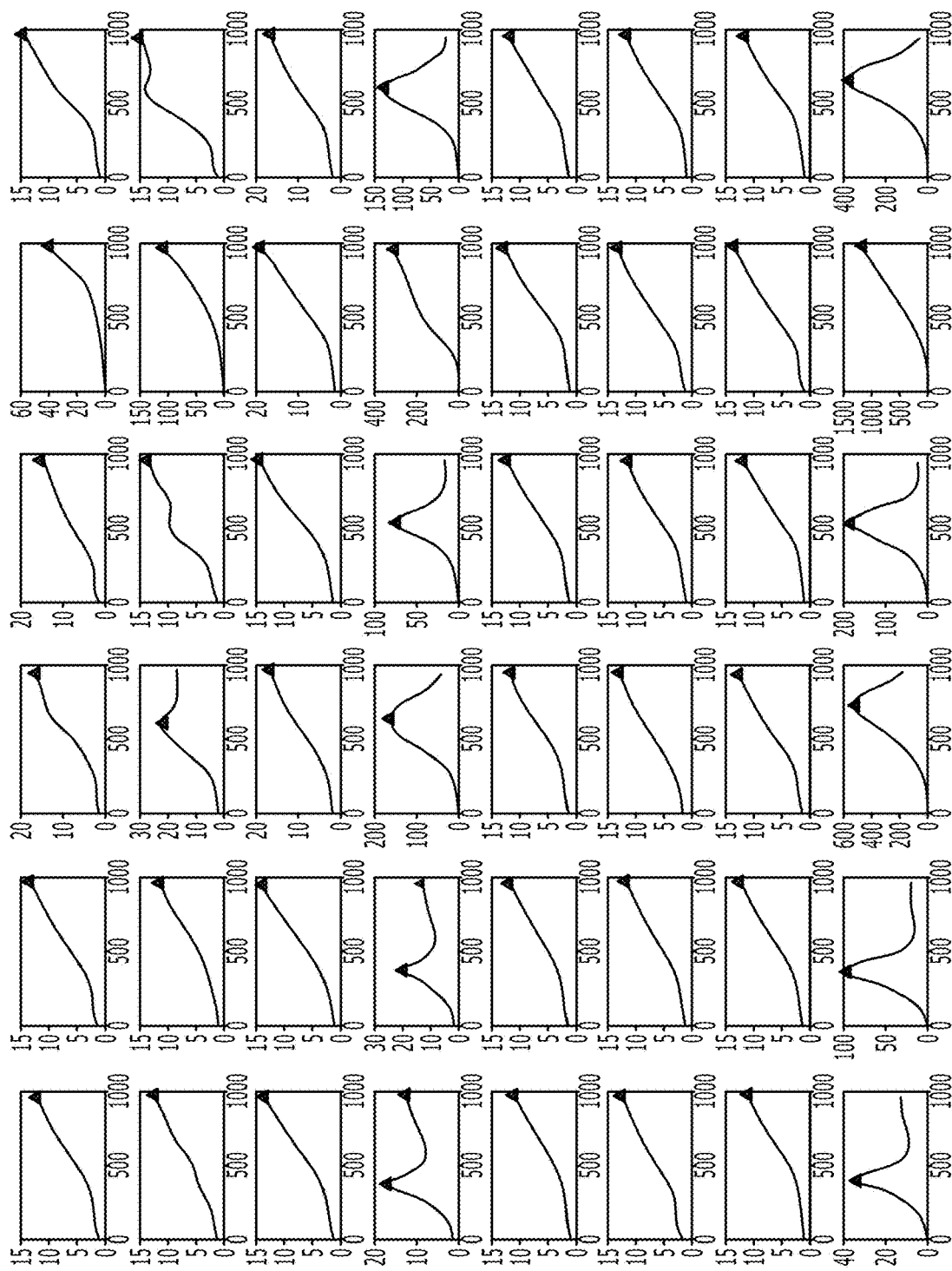
FIG. 11C -Cont'd

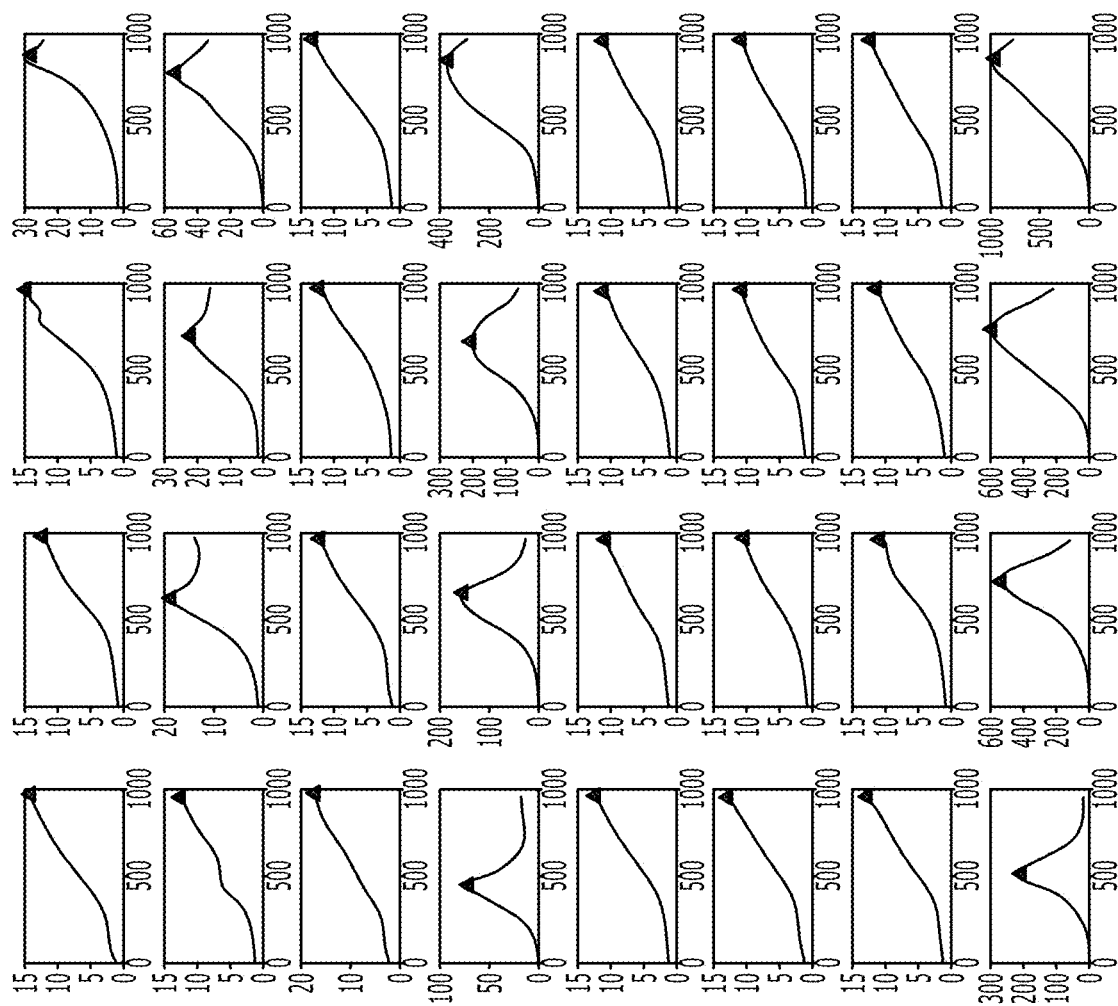
FIG. 11C -Cont'd

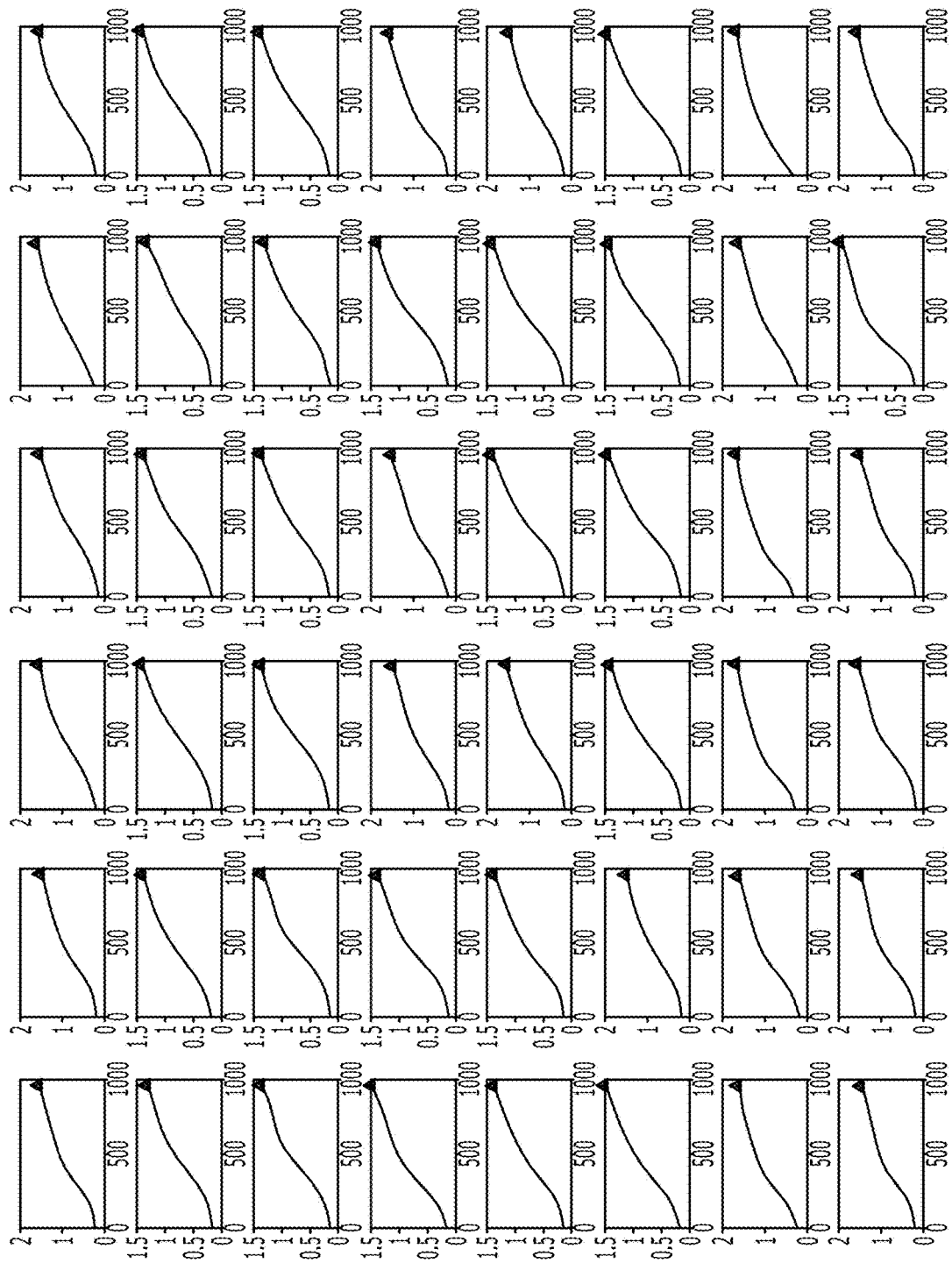
FIG. 11D -Cont'd

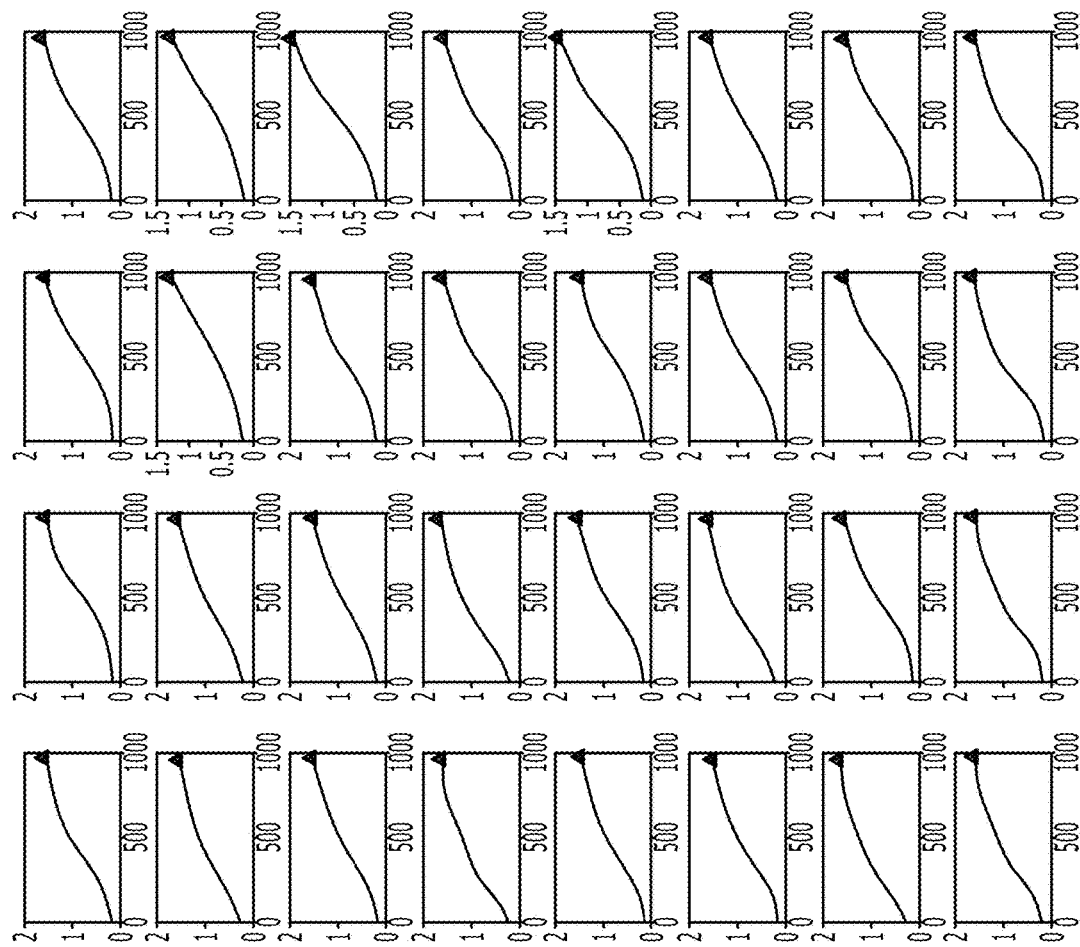
FIG. 11D - Cont'd

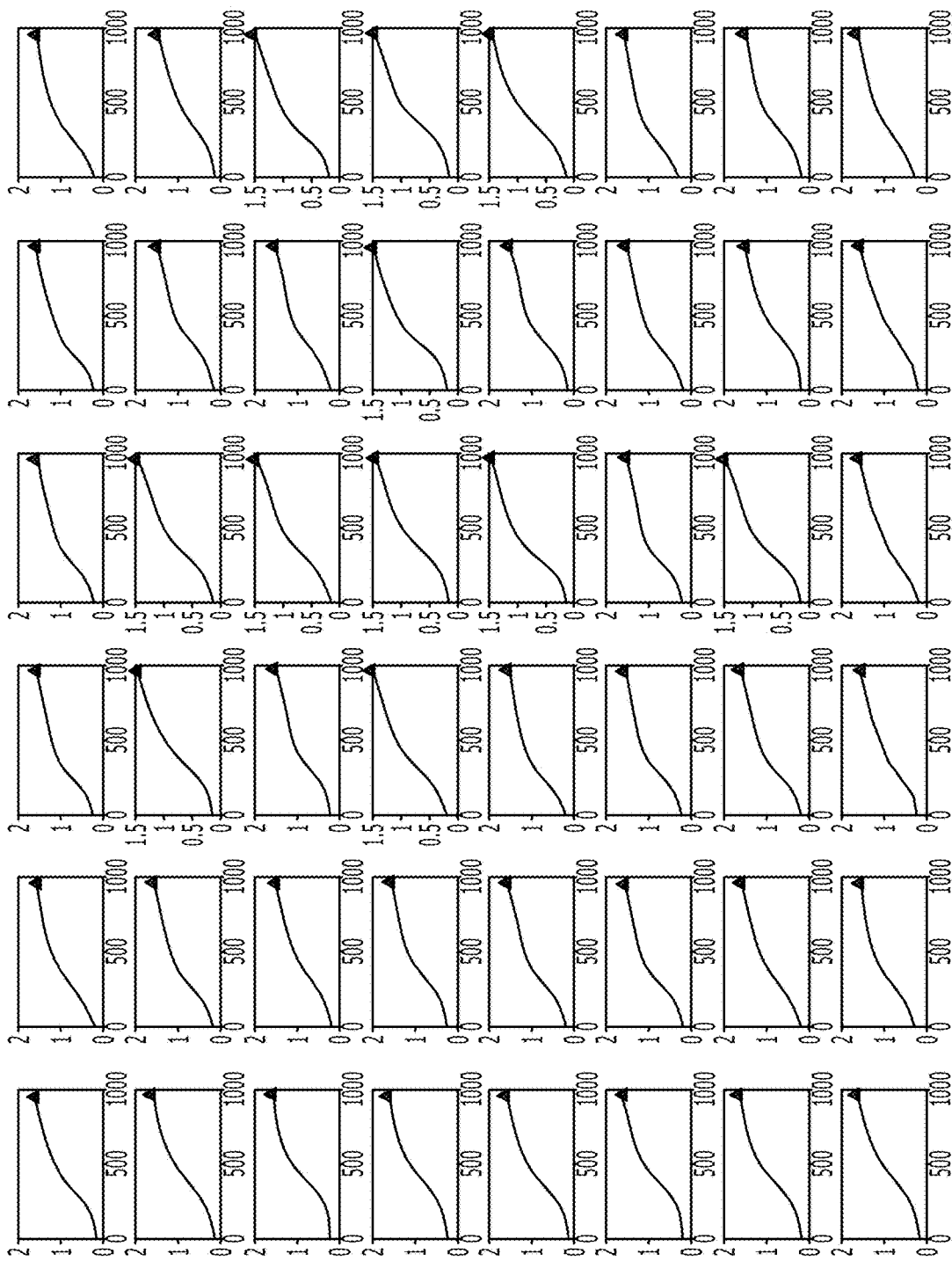
FIG. 11D - Cont'd

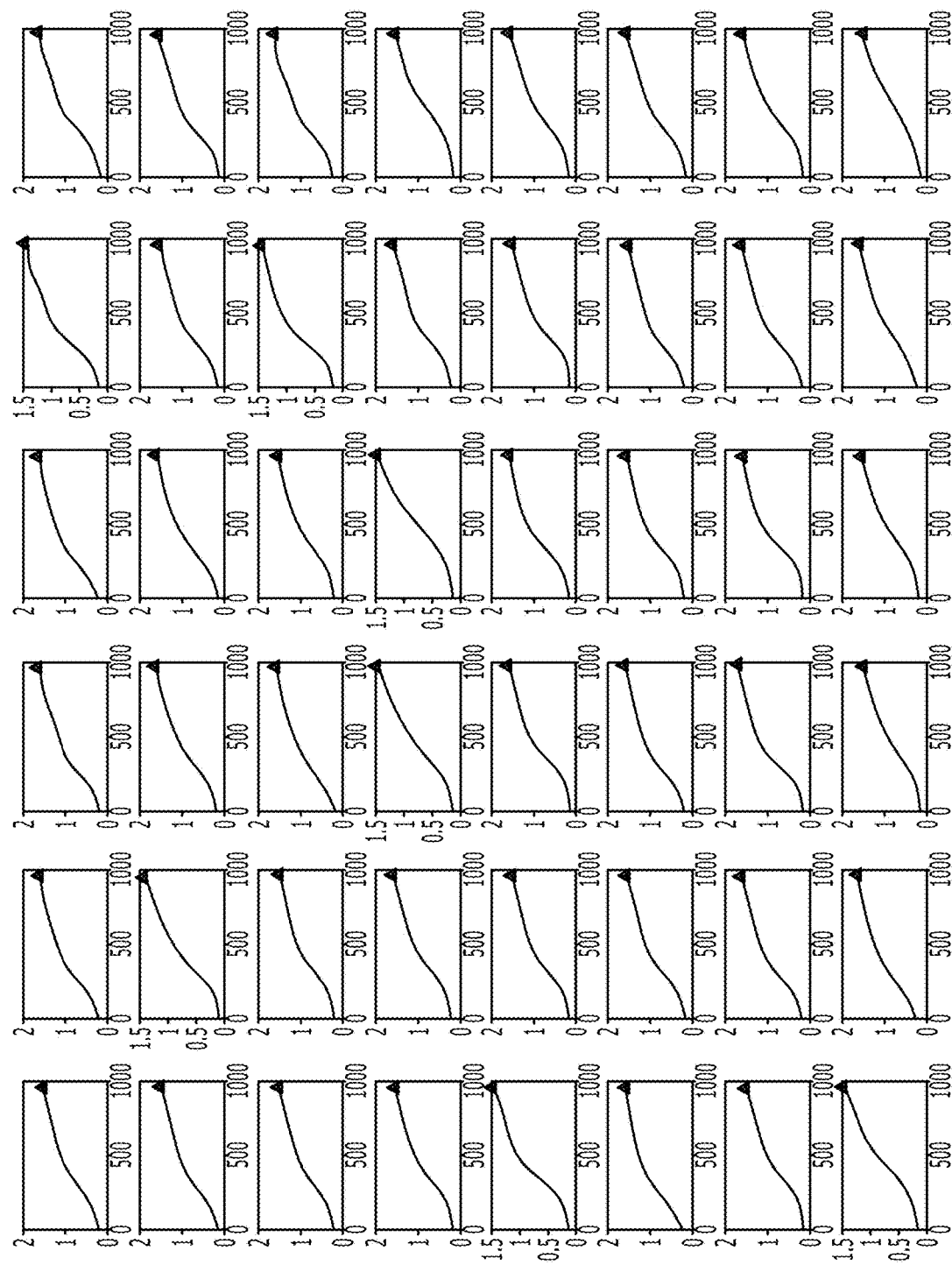
FIG. 11D -Cont'd

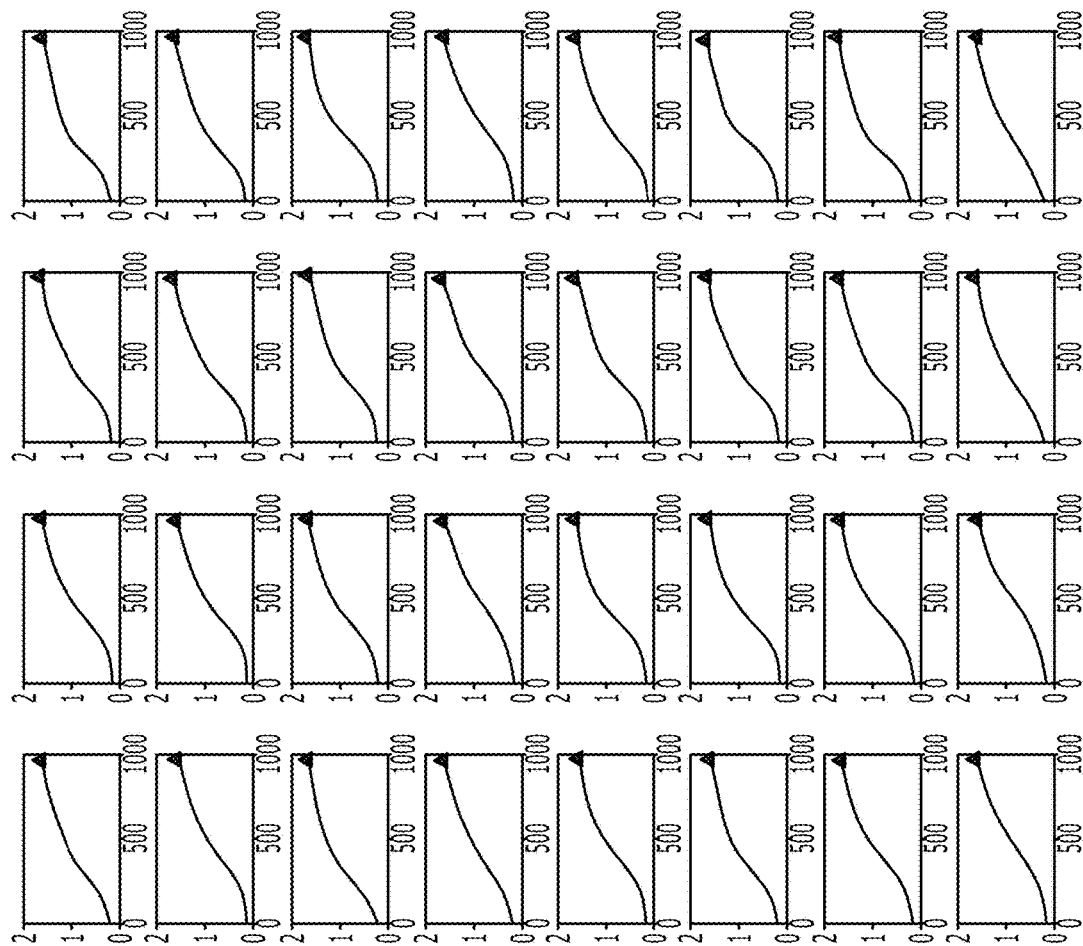
FIG. 11D - Cont'd

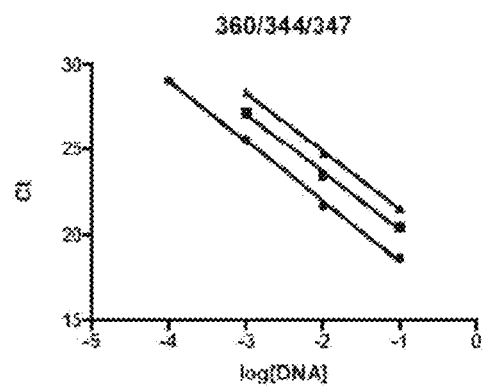
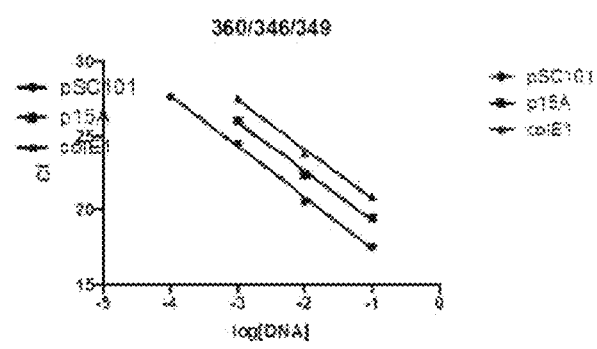
FIG. 13A
FIG. 13B
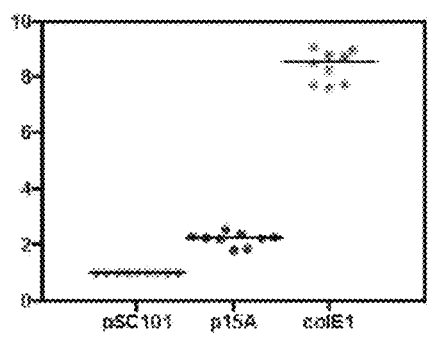
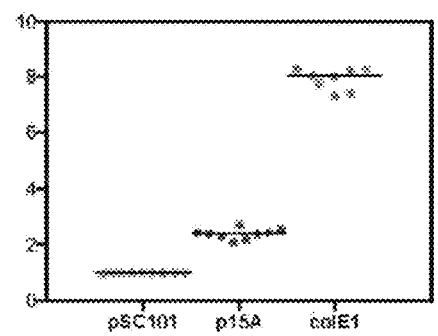
FIG. 13C
FIG. 13D

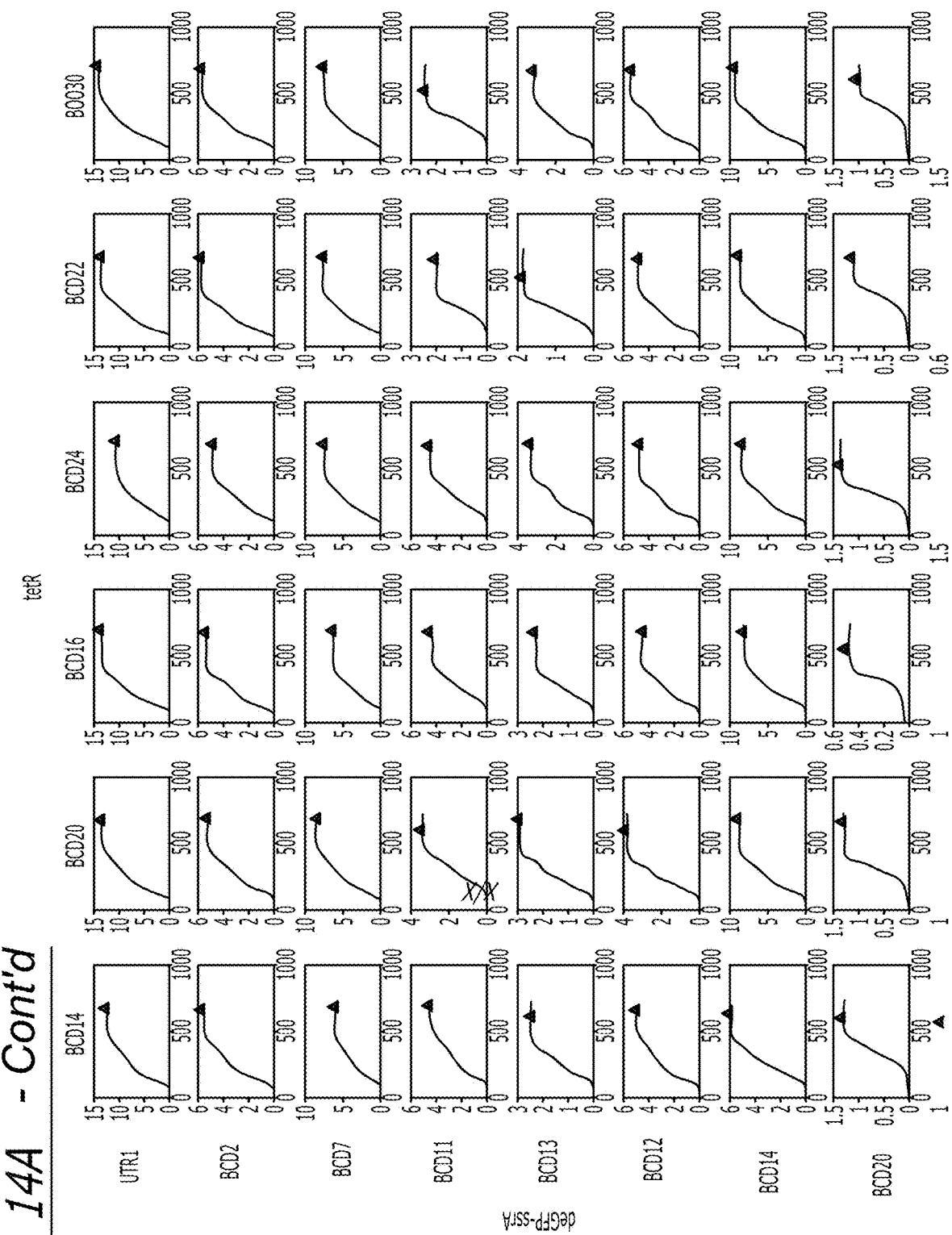
FIG. 14A - Cont'd

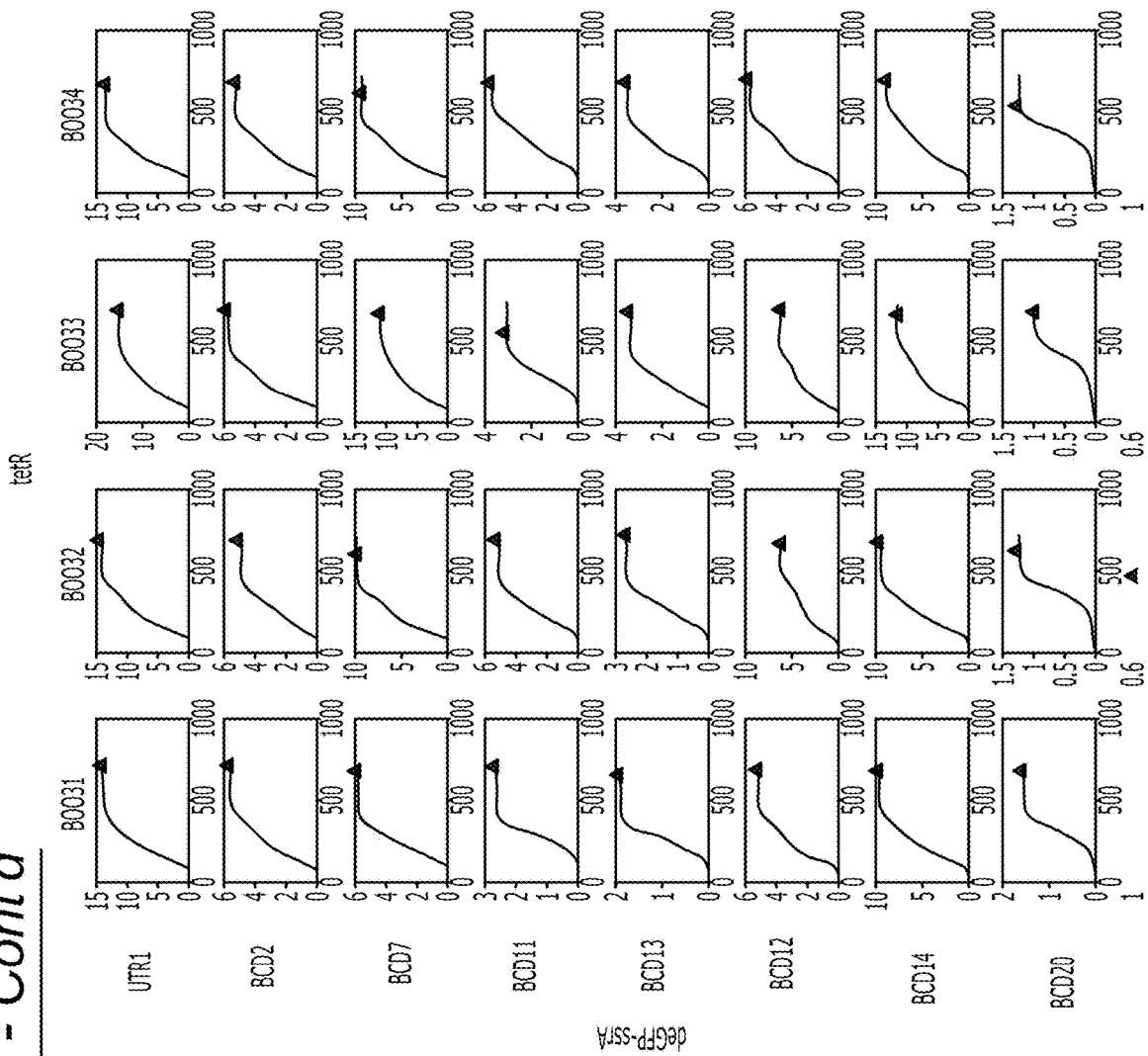
FIG. 14A - Cont'd

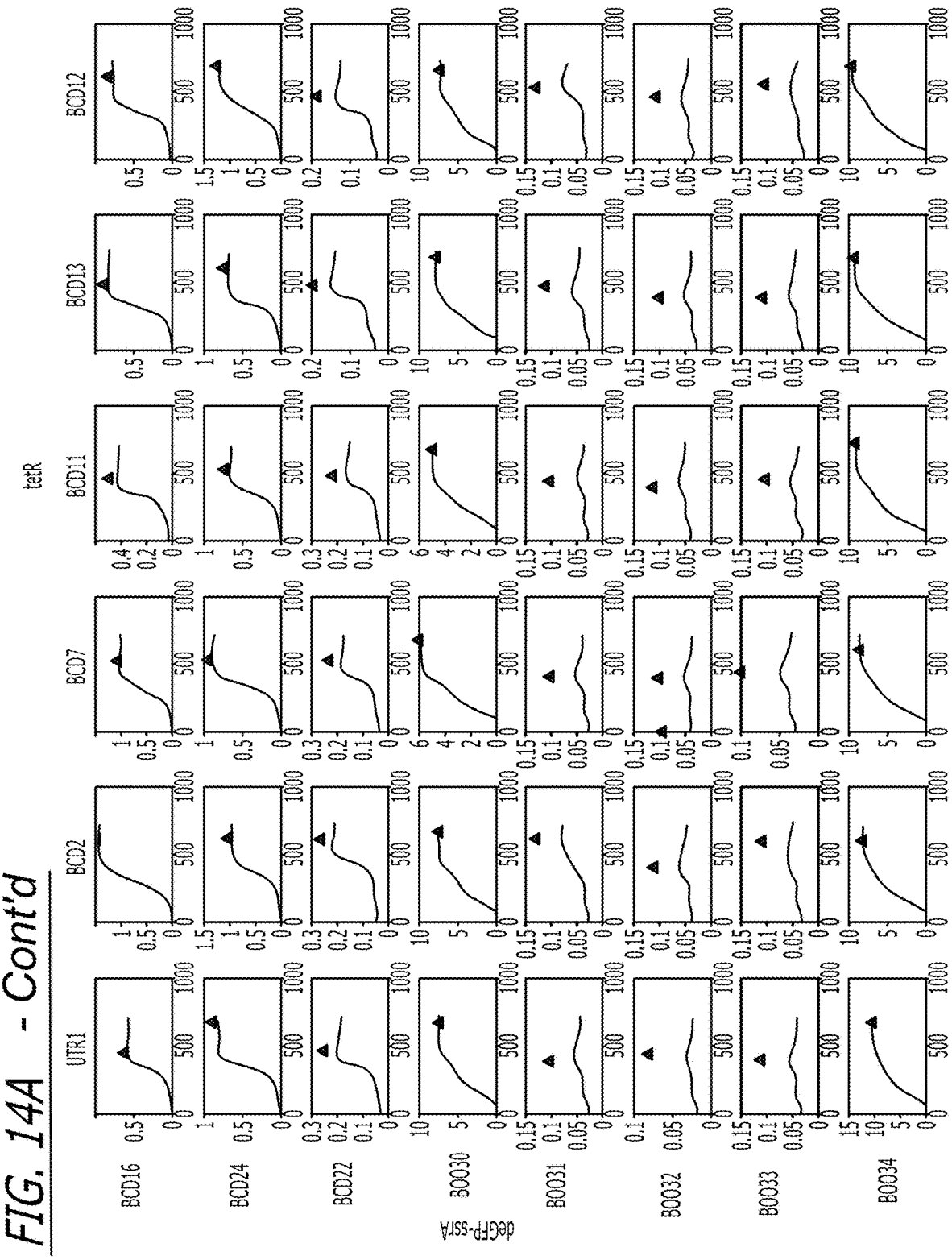
FIG. 14A - Cont'd

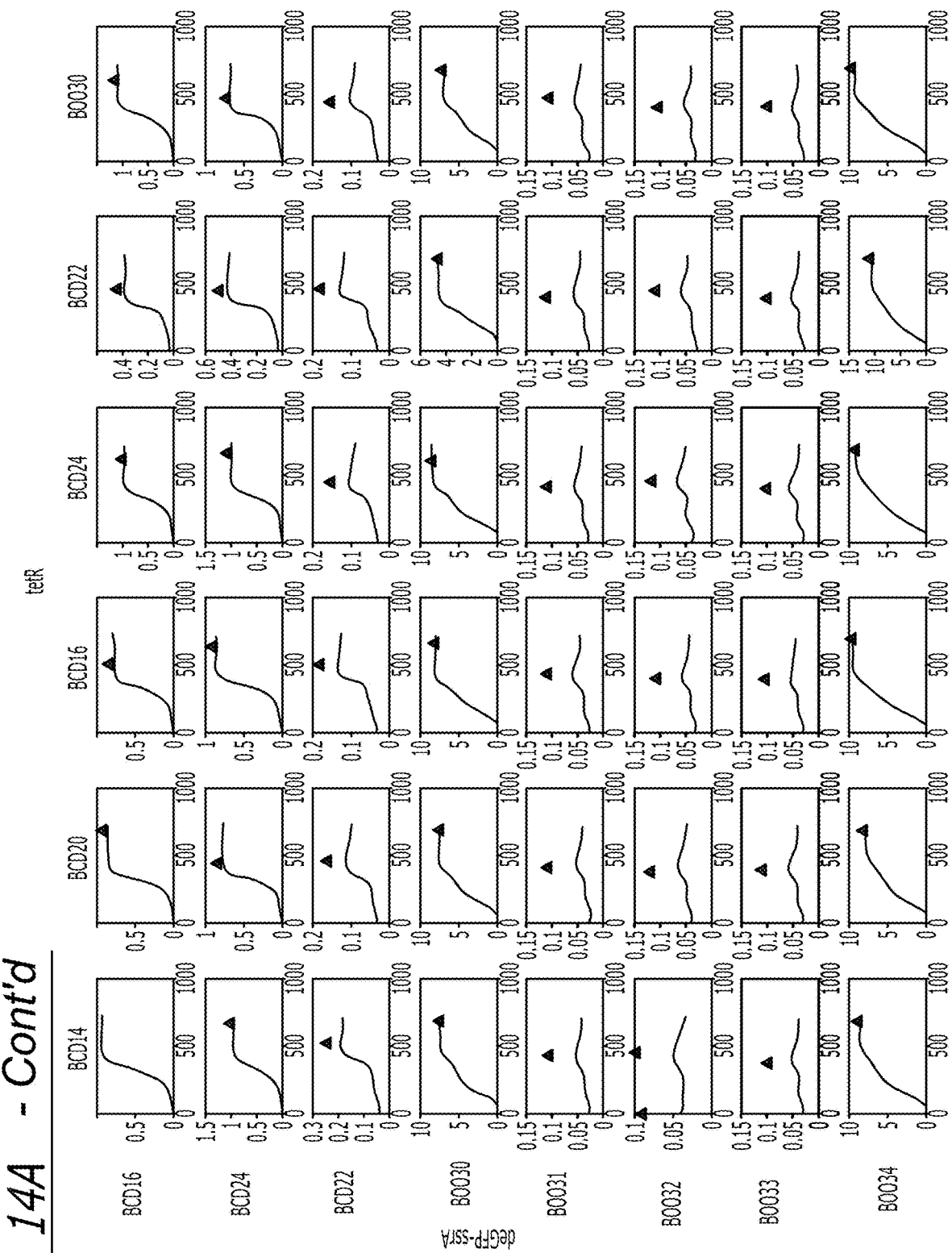
FIG. 14A - Cont'd

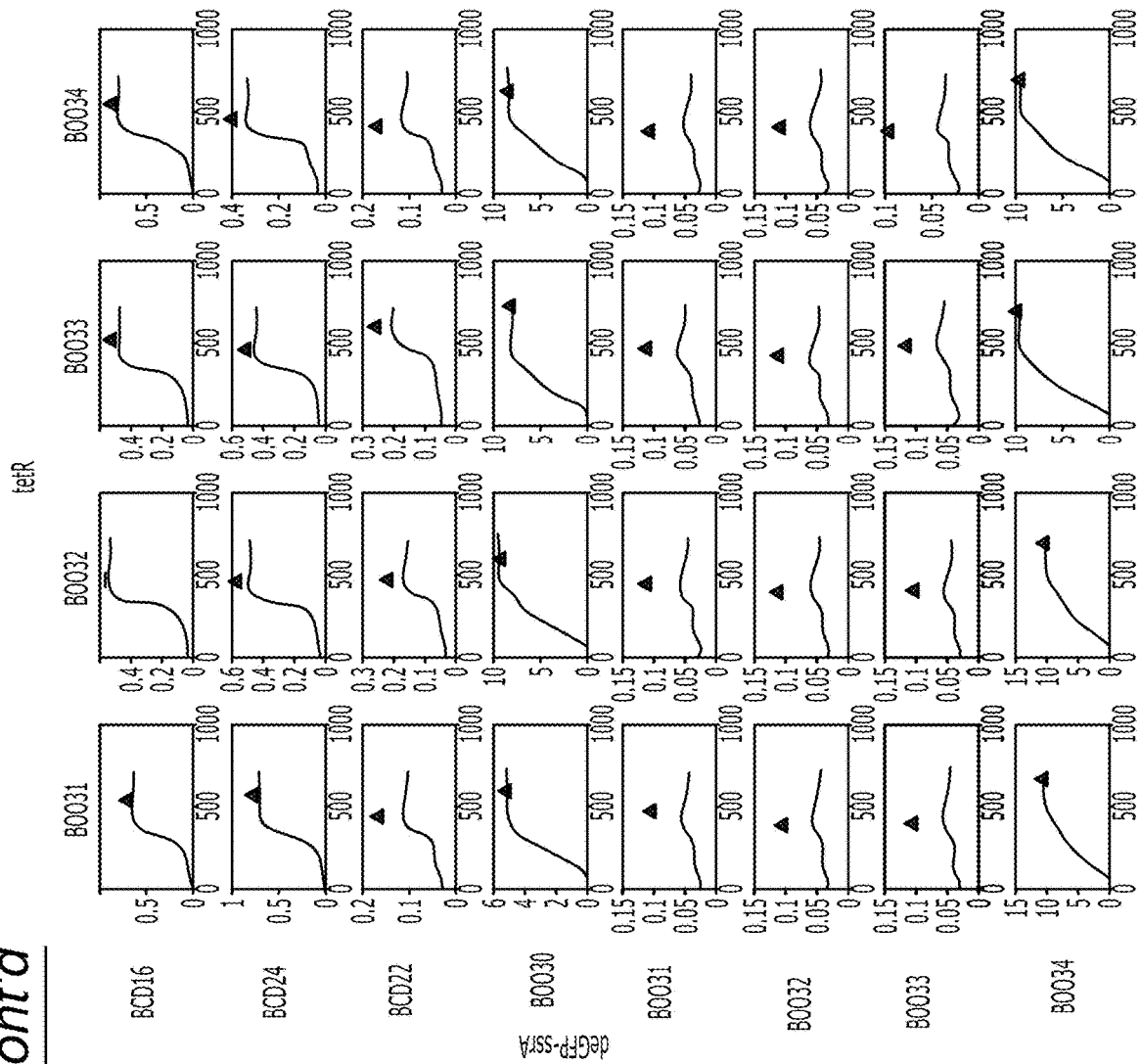
FIG. 14A - Cont'd

FIG. 16 – Cont'd
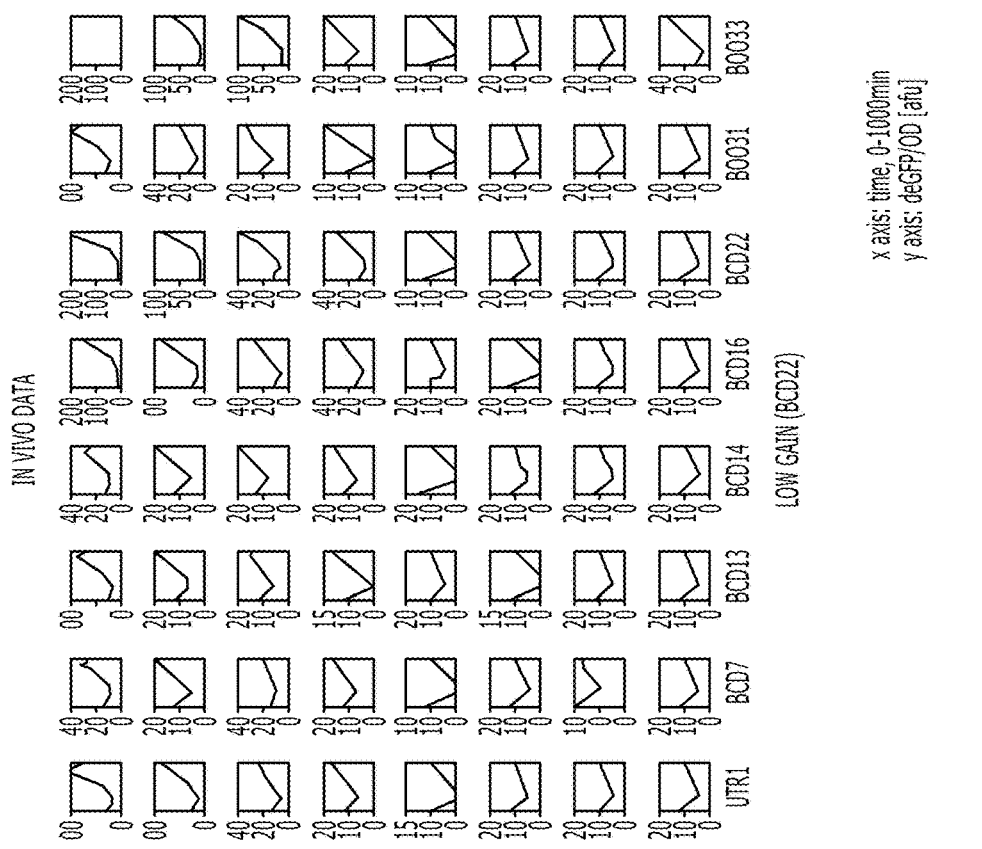
2) Sensitivity to gain (lasR)
Bottom: TX-TL prediction,
and in silico prediction.
Right: In vivo data fro 64 different
levels of lasR for 64 different
circuit variants.
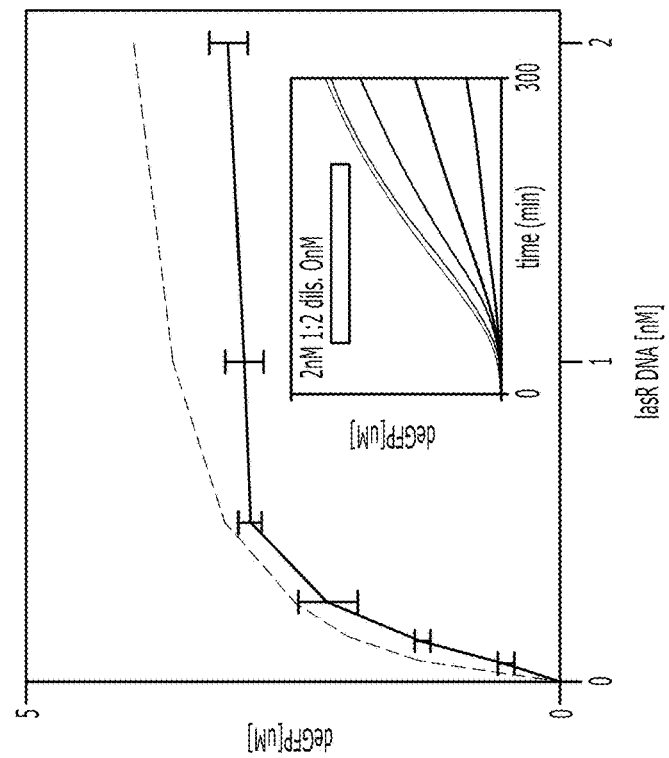

>360: Plac_BCD22_lasR_T500

ATGCATGTTTGTCTTCTTGATCGGGCACGTAAGAGGTTCCAACTTTCACCATAATGAAATAAGATCACTACCGGGCGTATTTTTTGAGTTATCGAGATT
TTCAGGAGCTAAGGAAGCTAAAATGCGCTCACGCAACTGGTCCAGAACCTTGACCGAACGCAGCGGTGGTAACGGCGCAGTGGCGGTTTTCATGGCT
TGTTATGACTGTTTTTTTGGGGTACAGTCTATGCCTCGGGCATCCAAGCAGCAAGCGCGTTACGCCGTGGGTCGATGTTTGATGTTATGGAGCAGCAA
CGATGTTACGCAGCAGGGCAGTCGCCCTAAAACAAAGTTAAACATCATGAGGGAAGCGGTGATCGCCGAAGTATCGACTCAACTATCAGAGGTAGTT
GGCGTCATCGAGCGCCATCTCGAACCGACGTTGCTGGCCGTACATTTGTACGGCTCCGCAGTGGATGGCGGCCTGAAGCCACACAGTGATATTGATTT
GCTGGTTACGGTGACCGTAAGGCTTGATGAAACAACGCGGCGAGCTTTGATCAACGACCTTTTGGAAACTTCGGCTTCCCCTGGAGAGAGCGAGATT
CTCCGCGCTGTAGAAGTCACCATTGTTGTGCACGACGACATCATTCCGTGGCGTTATCCAGCTAAGCGCGAACTGCAATTTGGAGAATGGCAGCGCA
ATGACATTCTTGCAGGTATCTTCGAGCCAGCCACGATCGACATTGATCTGGCTATCTTGCTGACAAAAGCAAGAGAACATAGCGTTGCCTTGGTAGGT
CCAGCGGCGGAGGAACTCTTTGATCCGGTTCCTGAACAGGATCTATTTGAGGCGCTAAATGAAACCTTAACGCTATGGAACTCGCCGCCCGACTGGG
CTGGCGATGAGCGAAATGTAGTGCTTACGTTGTCCCGCATTTGGTACAGCGCAGTAACCGGCAAAATCGCGCCGAAGGATGTCGCTGCCGACTGGGC
AATGGAGCGCCTGCCGGCCCAGTATCAGCCCGTCATACTTGAAGCTAGACAGGCTTATCTTGGACAAGAAGAAGATCGCTTGGCCTCGCGCGCAGAT
CAGTTGGAAGAATTTGTCCACTACGTGAAAGGCGAGATCACCAAGGTAGTCGGCAAATAATTTGATATCGAGCTCGCTTGGACTCCTGTTGATAGATC
CAGTAATGACCTCAGAACTCCATCTGGATTTGTTCAGAACGCTCGGTTGCCGCCGGGCGTTTTTATTGGTGAGAATCCAAGCCTCGGTGAGAATCCA
AGCCTCGATCAACGTCTCATTTTCGCCAAAAGTTGGCCCAGGGCTTCCCGGTATCAACAGGGACACCAGGATTTATTTATTCTGCGAAGTGATCTTCC
GTCACAGGTATTTATTCGGCGCAAAGTGCGTCGGGTGATGCTGCCAACTTACTGATTTAGTGTATGATGGTGTTTTTGAGGTGCTCCAGTGGCTTCTGT
TTCTATCAGCTGTCCCTCCTGTTCAGCTACTGACGGGGTGGTGCGTAACGGCAAAAGCACCGCCGGACATCAGCGGTAGCGGAGTGTATACTGGCTTA
CTATGTTGGCACTGATGAGGGTGTCAGTGAAGTGCTTCATGTGGCAGGAGAAAAAAGGCTGCACCGGTGCGTCAGCAGAATATGTGATACAGGATAT
ATTCCGCTTCCTCGCTCACTGACTCGCTACGCTCGGTCGTTCGACTGCGGCGAGCGGAAATGGCTTACGAACGGGGCGGAGATTTCCTGGAAGATGCC
AGGAAGATACTTAACAGGGAAGTGAGAGGGCCGCGGCAAAGCCGTTTTTCCATAGGCTCCGCCCCCCTGACAAGCATCACGAAATCTGACGCTCAAA
TCAGTGGTGGCGAAACCCGACAGGACTATAAAGATACCAGGCGTTTCCCCCTGGCGGCTCCCTCGTGCGCTCTCCTGTTCCTGCCTTTCGGTTTACCG
GTGTCATTCCGCTGTTATGGCCGCGTTTGTCTCATTCCACGCCTGACACTCAGTTCCGGGTAGGCAGTTCGCTCCAAGCTGGACTGTATGCACGAACCC
CCCGTTCAGTCCGACCGCTGCGCCTTATCCGGTAACTATCGTCTTGAGTCCAACCCGGAAAGACATGCAAAAGCACCACTGGCAGCAGCCACTGGTA
ATTGATTTAGAGGAGTTAGTCTTGAAGTCATGCGCCGGTTAAGGCTAAACTGAAAGGACAAGTTTTGGTGACTGCGCTCCTCCAAGCCAGTTACCTCG
GTTCAAAGAGTTGGTAGCTCAGAGAACCTTCGAAAAACCGCCCTGCAAGGCGGTTTTTTCGTTTCAGAGCAAGAGATTACGCGCAGACCAAAACGA
TCTCAAGAAGATCATCTTATTAATCAGATAAAATATTTCTAGATTTCAGTGCAATTTATCTCTTCAAATGTAGCACCTGAAGTCAGCCCCATACGATAT
AAGTTGTAATTCTCATGTTTGACAGCTTATCATCGATAAGCTTCCGATGGCGCGCCGAGAGGCTTTACACTTTATGCTTCCGGCTGAAGACAAGGCAC
GACTCTCAAGGACAGAAAAGCCCGCCTTTCGGCGGGCTTTGAGTTCATTATTAGAGAGTAATAAGACCCAAATTAACGGCCATAATGGCCGCTACGC
GGCGGGAGGTCACACCGAACTTCCGCCGAATATTTCCCATATGGAAGTTCACATTGGCTTCCGAGCAGTTGCAGATAACCGATATCTCCCAACTGGTC
TTGCCGATGGCGCACCACTGCAACACTTCCTTCTCCCGGCTGGTCAGAACCACCGGTTTGCTGACCGGATGTTCGAAGGCCAGTCCGGCACCGCTTTG
CAGTGCGTAGTCCTTGAGCATCCACAGGGTCGGCAGGACCGACTCTATGAAACGGTTGGCCTCGGCCCGGTTTTCCGCTTCCACGCTGAGGCTCAGCG
CGCCGAGTTCGCCGCGAGCACCATGCAGCGGCATGGTCAGCCCATACACCAGGCCGGCGGCCGAGGCTTCCTCGAAGAACTCGTGCTGCTTTCGCGT
CTGGTAGATGGACGGTTCCCAGAAAATCGGCAGTACGCTCTGGGTACAGTGACTGACCGTCGGGTCGACCCGCGCGTAGCCAGCCCGGTCGTAATGC
TCGCGCCAGGCGGCCGGGTAGTTGCCGACGATGAAGGCGTTCTCGTAGTCCTGGCTGTCCTTAGGCAACAGGCCGAACAGGATCTTCGAGAATCCAA
GGTCGCTCGCCATCTTCTGGAGGATGGCGCTCCACTCCAATTTTCCACTTGAGCGTTCCAGCTCAAGAAAACCGTCAACCAAGGCCATTAGAAACTTT
CCTCAGCATGATTAAGATGTTTCAGTACGAAAATTGCTTTCATTGTTGATCTCCTTTTTAAGTGAACTTGGGCCCGCTTGCTGTGCTCAGTATCTTGTTA
TCCGCTCACAATGTCAATGTTATCCGCTCACATTTATGAACAGCA

FIG. 17A

428> PRsaL-tetO1_BCD2_deGFP-ssrA_B1002 (utilizing promoter "POrig_tetO1")

```
GCATTGCTGTTCAACTAGCAAATGAGATAGATTTCGGTGAACCCGGACCCTTGCTAGGCTCGATCCCTATCAGTGATAGAGAAGCGGGCCCAAGTTC
ACTTAAAAAGGAGATCAACAATGAAAGCAATTTTCGTACTGAAACATCTTAATCATGCTAAGGAGGTTTTCTAATGGAGCTTTTCACTGGCGTTGTTC
CCATCCTGGTCGAGCTGGACGGCGACGTAAACGGCCACAAGTTCAGCGTGTCCGGCGAGGGCGAGGGCGATGCCACCTACGGCAAGCTGACCCTGA
AGTTCATCTGCACCACCGGCAAGCTGCCCGTGCCCTGGCCCACCCTCGTGACCACCCTGACCTACGGCGTGCAGTGCTTCAGCCGCTACCCCGACCAC
ATGAAGCAGCACGACTTCTTCAAGTCCGCCATGCCCGAAGGCTACGTCCAGGAGCGCACCATCTTCTTCAAGGACGACGGCAACTACAAGACCCGCG
CCGAGGTGAAGTTCGAGGGCGACACCCTGGTGAACCGCATCGAGCTGAAGGGCATCGACTTCAAGGAGGACGGCAACATCCTGGGGCACAAGCTGG
AGTACAACTACAACAGCCACAACGTCTATATCATGGCCGACAAGCAGAAGAACGGCATCAAGGTGAACTTCAAGATCCGCCACAACATCGAGGACG
GCAGCGTGCAGCTCGCCGACCACTACCAGCAGAACACCCCCATCGGCGACGGCCCCGTGCTGCTGCCCGACAACCACTACCTGAGCACCCAGTCCGC
CCTGAGCAAAGACCCCAACGAGAAGCGCGATCACATGGTCCTGCTGGAGTTCGTGACCGCCGCCGGGATCGCAGCAAACGACGAAAACTACGCTTTA
GCTGCTTAATGAACTCGCAAAAAACCCCGCTTCGGCGGGGTTTTTTCGCCCTTGAGAGTCGGGCATTGTCTTCGCTCCTTCCGGTGGGCGCGGGGCAT
GACTATCGTCGCCGCACTTATGACTGTGTTCTTTATCATGCAACTCGTAGGACAGGTGCCGGCAGCGCTCTTCCGCTTCCTCGCTCACTGACTCGCTGC
GCTCGGTCGTTCGGCTGCGGCGAGCGGTATCAGCTCACTCAAAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTTTCCATAGGCTCCGCCCCCCTGACGAGCATCACAAAAATCG
ACGCTCAAGTCAGAGGTGGCGAAACCCGACAGGACTATAAAGATACCAGGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCTTATCCGGTAACTATCGTCTTGAGTCCAACCCGGTAAGACACGACTTA
TCGCCACTGGCAGCAGCCACTGGTAACAGGATTAGCAGAGCGAGGTATGTAGGCGGTGCTACAGAGTTCTTGAAGTGGTGGCCTAACTACGGCTACA
CTAGAAGAACAGTATTTGGTATCTGCGCTCTGCTGAAGCCAGTTACCTTCGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTAGATCCTTTTAAATTAAAAATGAAGTTTTAAATCAATCT
AAAGTATATATGAGTAAACTTGGTCTGACAGTTACCAATGCTTAATCAGTGAGGCACCTATCTCAGCGATCTGTCTATTTCGTTCATCCATAGTTGCCT
GACTCCCCGTCGTGTAGATAACTACGATACGGGAGGGCTTACCATCTGGCCCCAGTGCTGCAATGATACCGCGTGACCCACGCTCACCGGCTCCAGAT
TTATCAGCAATAAACCAGCCAGCCGGAAGGGCCGAGCGCAGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAGGCATCGTGGTGTCACGCTCGTCGTTTGGTATGGCTTCATTCA
GCTCCGGTTCCCAACGATCAAGGCGAGTTGCATGATCCCCCATGTTGTGCAAAAAAGCGGTTAGCTCCTTCGGTCCTCCGATCGTTGTCAGAAGTAAG
TTGGCCGCAGTGTTATCACTCATGGTTATGGCAGCACTGCATAATTCTCTTACTGTCATGCCATCCGTAAGATGCTTTTCTGTGACTGGTGAGTACTCA
ACCAAGTCATTCTGAGAATAGTGTATGCGGCGACCGAGTTGCTCTTGCCCGGCGTCAACACGGGATAAACCGCGCCACATAGCAGAACTTTAAAAG
TGCTCATCATTGGAAAACGTTCTTCGGGGCGAAAACTCTCAAGGATCTTACCGCTGTTGAGATCCAGTTCGATGTAACCCACTCGTGCACCCAACTGA
TCTTCAGCATCTTTTACTTTCACCAGCGTTTCTGGGTGAGCAAAAACAGGAAGGCAAAATGCCGCAAAAAAGGGAATAAGGGCGACACGGAAATGTT
GAATACTCATACTCTTCCTTTTTCAATATTATTGAAGCATTTATCAGGGTTATTGTCTCATGAGCGGATACATATTTGAATGTATTTAGAAAAATAAAC
AAATAGGGGTTCCGCGCACATTTCCCCGAAAAGTGCCACCTGACGTCTAAGAAACCATTATTATCATGACATTAACCTATAAAAATAGGCGTATCAC
GAGGCCCTTTCGTGTTCAAGAATTCTGGCGAATCCTCTGACCAGCCAGAAAACGACCTTTCTGTGGTGAAACCGGATGCTGCAATTCAGAGCGCCAGC
AAGTGGGGGACAGCAGATGACCTGACCGCCGCAGAGTGGATGTTTGACATGGTGATGACTATCGCACCATCAGCCAGAAAACCGAATTTGCTGGGT
    GGGCTAACGATATCCGCCTGATGCGTGAACGTGACGGACGTAACGAAGACAACCAC
```

FIG. 17B

347>PLasI_1SNP_-10-tetO1_BCD2_deGFP-ssrA_B1002 (utilizing promoter pLasI_mut_tetO1, P1_tetO1)

```
GCATTGCTGTTCTTCGAGCCTAGCAAGGGTCCGGGTTCACCGAAATCTATCTCATTTGCTAGTTATAAAATTATGAAATTTGCGTAAATTCCCTATCAG
TGATAGAGATTCAGAAGCGGGCCCAAGTTCACTTAAAAAGGAGATCAACAATGAAAGCAATTTTCGTACTGAAACATCTTAATCATGCTAAGGAGGT
TTTCTAATGGAGCTTTTCACTGGCGTTGTTCCCATCCTGGTCGAGCTGGACGGCGACGTAAACGGCCACAAGTTCAGCGTGTCCGGCGAGGGCGAGGG
CGATGCCACCTACGGCAAGCTGACCCTGAAGTTCATCTGCACCACCGGCAAGCTGCCCGTGCCCTGGCCCACCCTCGTGACCACCCTGACCTACGGCG
TGCAGTGCTTCAGCCGCTACCCCGACCACATGAAGCAGCACGACTTCTTCAAGTCCGCCATGCCCGAAGGCTACGTCCAGGAGCGCACCATCTTCTTC
AAGGACGACGGCAACTACAAGACCCGCGCCGAGGTGAAGTTCGAGGGCGACACCCTGGTGAACCGCATCGAGCTGAAGGGCATCGACTTCAAGGAG
GACGGCAACATCCTGGGGCACAAGCTGGAGTACAACTACAACAGCCACAACGTCTATATCATGGCCGACAAGCAGAAGAACGGCATCAAGGTGAAC
TTCAAGATCCGCCACAACATCGAGGACGGCAGCGTGCAGCTCGCCGACCACTACCAGCAGAACACCCCCATCGGCGACGGCCCCGTGCTGCTGCCCG
ACAACCACTACCTGAGCACCCAGTCCGCCCTGAGCAAAGACCCCAACGAGAAGCGCGATCACATGGTCCTGCTGGAGTTCGTGACCGCCGCCGGGAT
CGCAGCAAACGACGAAAACTACGCTTTAGCTGCTTAATGAACTCGCAAAAAACCCCGCTTCGGCGGGGTTTTTCGCCCTTGAGAGTCGGGCATTGTC
TTCGCTCCTTCCGGTGGGCGCGGGGCATGACTATCGTCGCCGCACTTATGACTGTGTTCTTTATCATGCAACTCGTAGGACAGGTGCCGGCAGCGCTC
TTCCGCTTCCTCGCTCACTGACTCGCTGCGCTCGGTCGTTCGGCTGCGGCGAGCGGTATCAGCTCACTCAAAGGCGGTAATACGGTTATCCACAGAAT
CAGGGGATAACGCAGGAAAGAACATGTGAGCAAAAGGCCAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTCCCTTCGGGAAGCGTGGCGCTTTCTCATAGCTCACGCTGTAG
GTATCTCAGTTCGGTGTAGGTCGTTCGCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGGTATGTAGGCGGTGCTACAGAGTTC
TTGAAGTGGTGGCCTAACTACGGCTACACTAGAAGAACAGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTTACCAATGCTTAATCAGTGAGGCACCTATCTCAGCGA
TCTGTCTATTTCGTTCATCCATAGTTGCCTGACTCCCCGTCGTGTAGATAACTACGATACGGGAGGGCTTACCATCTGGCCCCAGTGCTGCAATGATAC
CGCCGTGACCCACGCTCACCGGCTCCAGATTTATCAGCAATAAACCAGCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGTTAATAGTTTGCGCAACGTTGTTGCCATTGCTACAGGCATCGTGGTGT
CACGCTCGTCGTTTGGTATGGCTTCATTCAGCTCCGGTTCCCAACGATCAAGGCGAGTTGCATGATCCCCCATGTTGTGCAAAAAAGCGGTTAGCTCC
TTCGGTCCTCCGATCGTTGTCAGAAGTAAGTTGGCCGCAGTGTTATCACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTGTATGCGGCGACCGAGTTGCTCTTGCCCGGCGTCAACACGGGATAA
TACCGCGCCACATAGCAGAACTTTAAAAGTGCTCATCATTGGAAAACGTTCTTCGGGGCGAAAACTCTCAAGGATCTTACCGCTGTTGAGATCCAGTT
CGATGTAACCCACTCGTGCACCCAACTGATCTTCAGCATCTTTTACTTTCACCAGCGTTTCTGGGTGAGCAAAAACAGGAAGGCAAAATGCCGCAAAA
AAGGGAATAAGGGCGACACGGAAATGTTGAATACTCATACTCTTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCCCGAAAAGTGCCACCTGACGTCTAAGAAACCATTATTATCATGA
CATTAACCTATAAAAATAGGCGTATCACGAGGCCCTTTCGTGTTCAAGAATTCTGGCGAATCCTCTGACCAGCCAGAAAACGACCTTTCTGTGGTGAA
ACCGGATGCTGCAATTCAGAGCGCCAGCAAGTGGGGGACAGCAGATGACCTGACCGCCGCAGAGTGGATGTTTGACATGGTGATGACTATCGCACCA
TCAGCCAGAAAACCGAATTTTGCTGGGTGGGCTAACGATATCCGCCTGATGCGTGAACGTGACGGACGTAACGAAGACAACCAC
```

FIG. 17C

429> PLasI-tetO1_BCD2_deGFP-ssrA_B1002 (utilizing promoter P2_tetO1)

GCATTGCTGTTCTTCGAGCCTAGCAAGGGTCCGGGTTCACCGAAATCTATCTCATTTGCTAGTTATAAAATTATGAAATTTGCATAAATTCCCTATCAG
TGATAGAGATTCAGAAGCGGGCCCAAGTTCACTTAAAAAGGAGATCAACAATGAAAGCAATTTTCGTACTGAAACATCTTAATCATGCTAAGGAGGT
TTTCTAATGGAGCTTTTCACTGGCGTTGTTCCCATCCTGGTCGAGCTGGACGGCGACGTAAACGGCCACAAGTTCAGCGTGTCCGGCGAGGGCGAGGG
CGATGCCACCTACGGCAAGCTGACCCTGAAGTTCATCTGCACCACCGGCAAGCTGCCCGTGCCCTGGCCCACCCTCGTGACCACCCTGACCTACGGCG
TGCAGTGCTTCAGCCGCTACCCCGACCACATGAAGCAGCACGACTTCTTCAAGTCCGCCATGCCCGAAGGCTACGTCCAGGAGCGCACCATCTTCTTC
AAGGACGACGGCAACTACAAGACCCGCGCCGAGGTGAAGTTCGAGGGCGACACCCTGGTGAACCGCATCGAGCTGAAGGGCATCGACTTCAAGGAG
GACGGCAACATCCTGGGGCACAAGCTGGAGTACAACTACAACAGCCACAACGTCTATATCATGGCCGACAAGCAGAAGAACGGCATCAAGGTGAAC
TTCAAGATCCGCCACAACATCGAGGACGGCAGCGTGCAGCTCGCCGACCACTACCAGCAGAACACCCCCATCGGCGACGGCCCCGTGCTGCTGCCCG
ACAACCACTACCTGAGCACCCAGTCCGCCCTGAGCAAAGACCCCAACGAGAAGCGCGATCACATGGTCCTGCTGGAGTTCGTGACCGCCGCCGGGAT
CGCAGCAAACGACGAAAACTACGCTTTAGCTGCTTAATGAACTCGCAAAAAACCCCGCTTCGGCGGGGTTTTTTCGCCCTTGAGAGTCGGGCATTGTC
TTCGCTCCTTCCGGTGGGCGCGGGGCATGACTATCGTCGCCGCACTTATGACTGTGTTCTTTATCATGCAACTCGTAGGACAGGTGCCGGCAGCGCTC
TTCCGCTTCCTCGCTCACTGACTCGCTGCGCTCGGTCGTTCGGCTGCGGCGAGCGGTATCAGCTCACTCAAAGGCGGTAATACGGTTATCCACAGAAT
CAGGGGATAACGCAGGAAAGAACATGTGAGCAAAAGGCCAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTCCCTTCGGGAAGCGTGGCGCTTTCTCATAGCTCACGCTGTAG
GTATCTCAGTTCGGTGTAGGTCGTTCGCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGGTATGTAGGCGGTGCTACAGAGTTC
TTGAAGTGGTGGCCTAACTACGGCTACACTAGAAGAACAGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTTACCAATGCTTAATCAGTGAGGCACCTATCTCAGCGA
TCTGTCTATTTCGTTCATCCATAGTTGCCTGACTCCCCGTCGTGTAGATAACTACGATACGGGAGGGCTTACCATCTGGCCCCAGTGCTGCAATGATAC
CGCGTGACCCACGCTCACCGGCTCCAGATTTATCAGCAATAAACCAGCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGTTAATAGTTTGCGCAACGTTGTTGCCATTGCTACAGGCATCGTGGTGT
CACGCTCGTCGTTTGGTATGGCTTCATTCAGCTCCGGTTCCCAACGATCAAGGCGAGTTGCATGATCCCCCATGTTGTGCAAAAAAGCGGTTAGCTCC
TTCGGTCCTCCGATCGTTGTCAGAAGTAAGTTGGCCGCAGTGTTATCACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTGTATGCGGCGACCGAGTTGCTCTTGCCCGGCGTCAACACGGGATAA
TACCGCGCCACATAGCAGAACTTTAAAAGTGCTCATCATTGGAAAACGTTCTTCGGGGCGAAAACTCTCAAGGATCTTACCGCTGTTGAGATCCAGTT
CGATGTAACCCACTCGTGCACCCAACTGATCTTCAGCATCTTTTACTTTCACCAGCGTTTCTGGGTGAGCAAAAACAGGAAGGCAAATGCCGCAAAA
AAGGGAATAAGGGCGACACGGAAATGTTGAATACTCATACTCTTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCCCGAAAAGTGCCACCTGACGTCTAAGAAACCATTATTATCATGA
CATTAACCTATAAAAATAGGCGTATCACGAGGCCCTTTCGTGTTCAAGAATTCTGGCGAATCCTCTGACCAGCCAGAAAACGACCTTTCTGTGGTGAA
ACCGGATGCTGCAATTCAGAGCGCCAGCAAGTGGGGACAGCAGATGACCTGACCGCCGCAGAGTGGATGTTTGACATGGTGATGACTATCGCACCA
TCAGCCAGAAAACCGAATTTTGCTGGGTGGGCTAACGATATCCGCCTGATGCGTGAACGTGACGGACGTAACGAAGACAACCAC

FIG. 17D

430> PLasB-tetO1_BCD2_deGFP-ssrA_B1002 (utilizing promoter P3_tetO1)

GCATTGCTGTTCTGCAGCAGCGGATCGTCGGCGAGCGTCACCTGAAGCTGGTGCTGAAAAGCGAATGCGGCTCGCTGCAACTGGATGGCATTGCCTT
CAACATCGACCGCGAGCAGTGGCCCAACCCTACCGTGCGCTGGGCCGAGCTGGCCTACAAGCTCGACGTCAACGAATTCCGCGGCCAGGAAAGCGTG
CAACTGATGATCGTCCACATGGCCCCTCGCTGAGCGCGTCCCGGAGCTGGGGGCAACCTAGCTGCCACCTGCTTTTCTGCTAGCTATTCCAGCGAAAA
CATACAGATTTCCGGCGAAATCAAGGCTACCTGCCAGTTCTGGCAGGTTTGGCCGCGGGTTCTTTTTGGTCCCTATCAGTGATAGAGATACACGAAAG
CACCGTCAAGCGGGCCCAAGTTCACTTAAAAAGGAGATCAACAATGAAAGCAATTTTCGTACTGAAACATCTTAATCATGCTAAGGAGGTTTTCTAA
TGGAGCTTTTCACTGGCGTTGTTCCCATCCTGGTCGAGCTGGACGGCGACGTAAACGGCCACAAGTTCAGCGTGTCCGGCGAGGGCGAGGGCGATGC
CACCTACGGCAAGCTGACCCTGAAGTTCATCTGCACCACCGGCAAGCTGCCCGTGCCCTGGCCCACCCTCGTGACCACCCTGACCTACGGCGTGCAGT
GCTTCAGCCGCTACCCCGACCACATGAAGCAGCACGACTTCTTCAAGTCCGCCATGCCCGAAGGCTACGTCCAGGAGCGCACCATCTTCTTCAAGGAC
GACGGCAACTACAAGACCCGCGCCGAGGTGAAGTTCGAGGGCGACACCCTGGTGAACCGCATCGAGCTGAAGGGCATCGACTTCAAGGAGGACGGC
AACATCCTGGGGCACAAGCTGGAGTACAACTACAACAGCCACAACGTCTATATCATGGCCGACAAGCAGAAGAACGGCATCAAGGTGAACTTCAAG
ATCCGCCACAACATCGAGGACGGCAGCGTGCAGCTCGCCGACCACTACCAGCAGAACACCCCCATCGGCGACGGCCCCGTGCTGCTGCCCGACAACC
ACTACCTGAGCACCCAGTCCGCCCTGAGCAAAGACCCCAACGAGAAGCGCGATCACATGGTCCTGCTGGAGTTCGTGACCGCCGCGGGATCGCAGC
AAACGACGAAAACTACGCTTTAGCTGCTTAATGAACTCGCAAAAAACCCCGCTTCGGCGGGGTTTTTTCGCCCTTGAGAGTCGGGCATTGTCTTCGCT
CCTTCCGGTGGGCGCGGGGCATGACTATCGTCGCCGCACTTATGACTGTGTTCTTTATCATGCAACTCGTAGGACAGGTGCCGGCAGCGCTCTTCCGC
TTCCTCGCTCACTGACTCGCTGCGCTCGGTCGTTCGGCTGCGGCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACTATAAAGATACCAGGCGTTTCCCCCTGGAAGCTCCCTCGT
GCGCTCTCCTGTTCCGACCCTGCCGCTTACCGGATACCTGTCCGCCTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGATTAGCAGAGCGAGGTATGTAGGCGGTGCTACAGAGTTCTTGAA
GTGGTGGCCTAACTACGGCTACACTAGAAGAACAGTATTTGGTATCTGCGCTCTGCTGAAGCCAGTTACCTTCGGAAAAAGAGTTGGTAGCTCTTGAT
CCGGCAAACAAACCACCGCTGGTAGCGGTGGTTTTTTTGTTTGCAAGCAGCAGATTACGCGCAGAAAAAAAGGATCTCAAGAAGATCCTTTGATCTTT
TCTACGGGGTCTGACGCTCAGTGGAACGAAAACTCACGTTAAGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTACCAATGCTTAATCAGTGAGGCACCTATCTCAGCGATCTGTC
TATTTCGTTCATCCATAGTTGCCTGACTCCCCGTCGTGTAGATAACTACGATACGGGAGGGCTTACCATCTGGCCCCAGTGCTGCAATGATACCGCGT
GACCCACGCTCACCGGCTCCAGATTTATCAGCAATAAACCAGCCAGCCGGAAGGGCCGAGCGCAGAAGTGGTCCTGCAACTTTATCCGCCTCCATCC
AGTCTATTAATTGTTGCCGGGAAGCTAGAGTAAGTAGTTCGCCAGTTAATAGTTTGCGCAACGTTGTTGCCATTGCTACAGGCATCGTGGTGTCACGC
TCGTCGTTTGGTATGGCTTCATTCAGCTCCGGTTCCCAACGATCAAGGCGAGTTGCATGATCCCCCATGTTGTGCAAAAAAGCGGTTAGCTCCTTCGGT
CCTCCGATCGTTGTCAGAAGTAAGTTGGCCGCAGTGTTATCACTCATGGTTATGGCAGCACTGCATAATTCTCTTACTGTCATGCCATCCGTAAGATGC
TTTTCTGTGACTGGTGAGTACTCAACCAAGTCATTCTGAGAATAGTGTATGCGGCGACCGAGTTGCTCTTGCCCGGCGTCAACACGGGATAATACCGC
GCCACATAGCAGAACTTTAAAAGTGCTCATCATTGGAAAACGTTCTTCGGGGCGAAAACTCTCAAGGATCTTACCGCTGTTGAGATCCAGTTCGATGT
AACCCACTCGTGCACCCAACTGATCTTCAGCATCTTTTACTTTCACCAGCGTTTCTGGGTGAGCAAAAACAGGAAGGCAAAATGCCGCAAAAAAGGG
AATAAGGGCGACACGGAAATGTTGAATACTCATACTCTTCCTTTTTCAATATTATTGAAGCATTTATCAGGGTTATTGTCTCATGAGCGGATACATATT
TGAATGTATTTAGAAAAATAAACAAATAGGGGTTCCGCGCACATTTCCCCGAAAAGTGCCACCTGACGTCTAAGAAACCATTATTATCATGACATTA
ACCTATAAAAATAGGCGTATCACGAGGCCCTTTCGTGTTCAAGAATTCTGGCGAATCCTCTGACCAGCCAGAAAACGACCTTTCTGTGGTGAAACCGG
ATGCTGCAATTCAGAGCGCCAGCAAGTGGGGGACAGCAGATGACCTGACCGCCGCAGAGTGGATGTTGACATGGTGATGACTATCGCACCATCAGC
CAGAAAACCGAATTTTGCTGGGTGGGCTAACGATATCCGCCTGATGCGTGAACGTGACGGACGTAACGAAGACAACCAC

FIG. 17E

431> PRasL long (las)-tetO1_BCD2_deGFP-ssrA_B1002 (utilizing promoter pRsaL_ext_tetO1, aka P4_tetO1)

```
GCATTGCTGTTCAACTAGCAAATGAGATAGATTTCGGTGAACCCGGACCCTTGCTAGGCTCTCCCTATCAGTGATAGAGAGAAGAAACGTCAAGCGG
GCCCAAGTTCACTTAAAAAGGAGATCAACAATGAAAGCAATTTTCGTACTGAAACATCTTAATCATGCTAAGGAGGTTTTCTAATGGAGCTTTTCACT
GGCGTTGTTCCCATCCTGGTCGAGCTGGACGGCGACGTAAACGGCCACAAGTTCAGCGTGTCCGGCGAGGGCGAGGGCGATGCCACCTACGGCAAGC
TGACCCTGAAGTTCATCTGCACCACCGGCAAGCTGCCCGTGCCCTGGCCCACCCTCGTGACCACCCTGACCTACGGCGTGCAGTGCTTCAGCCGCTAC
CCCGACCACATGAAGCAGCACGACTTCTTCAAGTCCGCCATGCCCGAAGGCTACGTCCAGGAGCGCACCATCTTCTTCAAGGACGACGGCAACTACA
AGACCCGCGCCGAGGTGAAGTTCGAGGGCGACACCCTGGTGAACCGCATCGAGCTGAAGGGCATCGACTTCAAGGAGGACGGCAACATCCTGGGGC
ACAAGCTGGAGTACAACTACAACAGCCACAACGTCTATATCATGGCCGACAAGCAGAAGAACGGCATCAAGGTGAACTTCAAGATCCGCCACAACA
TCGAGGACGGCAGCGTGCAGCTCGCCGACCACTACCAGCAGAACACCCCCATCGGCGACGGCCCCGTGCTGCTGCCCGACAACCACTACCTGAGCAC
CCAGTCCGCCCTGAGCAAAGACCCCAACGAGAAGCGCGATCACATGGTCCTGCTGGAGTTCGTGACCGCCGCCGGGATCGCAGCAAACGACGAAAA
CTACGCTTTAGCTGCTTAATGAACTCGCAAAAAACCCCGCTTCGGCGGGGTTTTTTCGCCCTTGAGAGTCGGGCATTGTCTTCGCTCCTTCCGGTGGGC
GCGGGGCATGACTATCGTCGCCGCACTTATGACTGTGTTCTTTATCATGCAACTCGTAGGACAGGTGCCGGCAGCGCTCTTCCGCTTCCTCGCTCACTG
ACTCGCTGCGCTCGGTCGTTCGGCTGCGGCGAGCGGTATCAGCTCACTCAAAGGCGGTAATACGGTTATCCACAGAATCAGGGGATAACGCAGGAAA
GAACATGTGAGCAAAAGGCCAGCAAAAGGCCAGGAACCGTAAAAAGGCCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTGGCGCTTTCTCATAGCTCACGCTGTAGGTATCTCAGTTCGGTGTAGG
TCGTTCGCTCCAAGCTGGGCTGTGTGCACGAACCCCCCGTTCAGCCCGACCGCTGCGCCTTATCCGGTAACTATCGTCTTGAGTCCAACCCGGTAAGA
CACGACTTATCGCCACTGGCAGCAGCCACTGGTAACAGGATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAAAAAGGATCTCAAGAAGATCCTTTGATCTTTTCTACGGGGTCTG
ACGCTCAGTGGAACGAAAACTCACGTTAAGGGATTTTGGTCATGAGATTATCAAAAAGGATCTTCACCTAGATCCTTTTAAATTAAAAATGAAGTTTT
AAATCAATCTAAAGTATATATGAGTAAACTTGGTCTGACAGTTACCAATGCTTAATCAGTGAGGCACCTATCTCAGCGATCTGTCTATTTCGTTCATCC
ATAGTTGCCTGACTCCCCGTCGTGTAGATAACTACGATACGGGAGGGCTTACCATCTGGCCCCAGTGCTGCAATGATACCGCGTGACCCACGCTCACC
GGCTCCAGATTTATCAGCAATAAACCAGCCAGCCGGAAGGGCCGAGCGCAGAAGTGGTCCTGCAACTTTATCCGCCTCCATCCAGTCTATTAATTGTT
GCCGGGAAGCTAGAGTAAGTAGTTCGCCAGTTAATAGTTTGCGCAACGTTGTTGCCATTGCTACAGGCATCGTGGTGTCACGCTCGTCGTTTGGTATG
GCTTCATTCAGCTCCGGTTCCCAACGATCAAGGCGAGTTGCATGATCCCCCATGTTGTGCAAAAAAGCGGTTAGCTCCTTCGGTCCTCCGATCGTTGTC
AGAAGTAAGTTGGCCGCAGTGTTATCACTCATGGTTATGGCAGCACTGCATAATTCTCTTACTGTCATGCCATCCGTAAGATGCTTTTCTGTGACTGGT
GAGTACTCAACCAAGTCATTCTGAGAATAGTGTATGCGGCGACCGAGTTGCTCTTGCCCGGCGTCAACACGGGATAATACCGCGCCACATAGCAGAA
CTTTAAAAGTGCTCATCATTGGAAAACGTTCTTCGGGGCGAAAACTCTCAAGGATCTTACCGCTGTTGAGATCCAGTTCGATGTAACCCACTCGTGCA
CCCAACTGATCTTCAGCATCTTTTACTTTCACCAGCGTTTCTGGGTGAGCAAAAACAGGAAGGCAAAATGCCGCAAAAAAGGGAATAAGGGCGACAC
GGAAATGTTGAATACTCATACTCTTCCTTTTTCAATATTATTGAAGCATTTATCAGGGTTATTGTCTCATGAGCGGATACATATTTGAATGTATTTAGA
AAAATAAACAAATAGGGGTTCCGCGCACATTTCCCCGAAAAGTGCCACCTGACGTCTAAGAAACCATTATTATCATGACATTAACCTATAAAAATAG
GCGTATCACGAGGCCCTTTCGTGTTCAAGAATTCTGGCGAATCCTCTGACCAGCCAGAAAACGACCTTTCTGTGGTGAAACCGGATGCTGCAATTCAG
AGCGCCAGCAAGTGGGGGACAGCAGATGACCTGACCGCCGCAGAGTGGATGTTTGACATGGTGATGACTATCGCACCATCAGCCAGAAAACCGAAT
TTTGCTGGGTGGGCTAACGATATCCGCCTGATGCGTGAACGTGACGGACGTAACGAAGACAACCAC
```

FIG. 17F

165> PRsaL_UTR1_deGFP_T500 (utilizing promoter POrig)

GCATTGCTGTTCCGCTGGGCATGCAACTAGCAAATGAGATAGATTTCGGTGAACCCGGACCCTTGCTAGGCTCGAAAGCAATAATTTTGTTTAACTTT
AAGAAGGAGATATACCATGGAGCTTTTCACTGGCGTTGTTCCCATCCTGGTCGAGCTGGACGGCGACGTAAACGGCCACAAGTTCAGCGTGTCCGGC
GAGGGCGAGGGCGATGCCACCTACGGCAAGCTGACCCTGAAGTTCATCTGCACCACCGGCAAGCTGCCCGTGCCCTGGCCCACCCTCGTGACCACCC
TGACCTACGGCGTGCAGTGCTTCAGCCGCTACCCCGACCACATGAAGCAGCACGACTTCTTCAAGTCCGCCATGCCCGAAGGCTACGTCCAGGAGCG
CACCATCTTCTTCAAGGACGACGGCAACTACAAGACCCGCGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGCCACAACGTCTATATCATGGCCGACAAGCAGAAGAACGGC
ATCAAGGTGAACTTCAAGATCCGCCACAACATCGAGGACGGCAGCGTGCAGCTCGCCGACCACTACCAGCAGAACACCCCCATCGGCGACGGCCCC
GTGCTGCTGCCCGACAACCACTACCTGAGCACCCAGTCCGCCCTGAGCAAAGACCCCAACGAGAAGCGCGATCACATGGTCCTGCTGGAGTTCGTGA
CCGCCGCCGGGATCTAATGAAGCATCTGGTGAATAACTCGAGCAAAGCCCGCCGAAAGGCGGGCTTTTCTGTGTCGACCGATGCCCTTGAGAGTCGG
GCATTGTCTTCGCTCCTTCCGGTGGGCGCGGGGCATGACTATCGTCGCCGCACTTATGACTGTGTTCTTTATCATGCAACTCGTAGGACAGGTGCCGGC
AGCGCTCTTCCGCTTCCTCGCTCACTGACTCGCTGCGCTCGGTCGTTCGGCTGCGGCGAGCGGTATCAGCTCACTCAAAGGCGGTAATACGGTTATCC
ACAGAATCAGGGGATAACGCAGGAAAGAACATGTGAGCAAAAGGCCAGCAAAAGGCCAGGAACCGTAAAAAGGCCGCGTTGCTGGCGTTTTTCCAT
AGGCTCCGCCCCCCTGACGAGCATCACAAAAATCGACGCTCAAGTCAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTCAC
GCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAAC
TATCGTCTTGAGTCCAACCCGGTAAGACACGACTTATCGCCACTGGCAGCAGCCACTGGTAACAGGATTAGCAGAGCGAGGTATGTAGGCGGTGCTA
CAGAGTTCTTGAAGTGGTGGCCTAACTACGGCTACACTAGAAGAACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAACTTGGTCTGACAGTTACCAATGCTTAATCAGTGAGGCACCTAT
CTCAGCGATCTGTCTATTTCGTTCATCCATAGTTGCCTGACTCCCCGTCGTGTAGATAACTACGATACGGGAGGGCTTACCATCTGGCCCCAGTGCTGC
AATGATACCGCGTGACCCACGCTCACCGGCTCCAGATTTATCAGCAATAAACCAGCCAGCCGGAAGGGCCGAGCGCAGAAGTGGTCCTGCAACTTTA
TCCGCCTCCATCCAGTCTATTAATTGTTGCCGGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTGCATGATCCCCATGTTGTGCAAAAAAGCGGT
TAGCTCCTTCGGTCCTCCGATCGTTGTCAGAAGTAAGTTGGCCGCAGTGTTATCACTCATGGTTATGGCAGCACTGCATAATTCTCTTACTGTCATGCC
ATCCGTAAGATGCTTTTCTGTGACTGGTGAGTACTCAACCAAGTCATTCTGAGAATAGTGTATGCGGCGACCGAGTTGCTCTTGCCCGGCGTCAACAC
GGGATAATACCGCGCCACATAGCAGAACTTTAAAAGTGCTCATCATTGGAAAACGTTCTTCGGGGCGAAAACTCTCAAGGATCTTACCGCTGTTGAG
ATCCAGTTCGATGTAACCCACTCGTGCACCCAACTGATCTTCAGCATCTTTTACTTTCACCAGCGTTTCTGGGTGAGCAAAAACAGGAAGGCAAAATG
CCGCAAAAAAGGGAATAAGGGCGACACGGAAATGTTGAATACTCATACTCTTCCTTTTTCAATATTATTGAAGCATTTATCAGGGTTATTGTCTCATG
AGCGGATACATATTTGAATGTATTTAGAAAAATAAACAAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTTCGTGTTCAAGAATTCTGGCGAATCCTCTGACCAGCCAGAAAACGACCTTTC
TGTGGTGAAACCGGATGCTGCAATTCAGAGCGCCAGCAAGTGGGGGACAGCAGATGACCTGACCGCCGCAGAGTGGATGTTGACATGGTGATGACT
ATCGCACCATCAGCCAGAAAACCGAATTTTGCTGGGTGGGCTAACGATATCCGCCTGATGCGTGAACGTGACGGACGTAACGAAGACAACCAC

FIG. 18A

196> PLasI_1SNP_-10_UTR1_deGFP_T500 (utilizing promoter pLasI_mut aka P1)

```
GCATTGCTGTTCCGCTGGGCATGCTTCGAGCCTAGCAAGGGTCCGGGTTCACCGAAATCTATCTCATTTGCTAGTTATAAAATTATGAAATTTGCGTA
AATTCTTCAGAAGCAATAATTTTGTTTAACTTTAAGAAGGAGATATACCATGGAGCTTTTCACTGGCGTTGTTCCCATCCTGGTCGAGCTGGACGGCG
ACGTAAACGGCCACAAGTTCAGCGTGTCCGGCGAGGGCGAGGGCGATGCCACCTACGGCAAGCTGACCCTGAAGTTCATCTGCACCACCGGCAAGCT
GCCCGTGCCCTGGCCCACCCTCGTGACCACCCTGACCTACGGCGTGCAGTGCTTCAGCCGCTACCCCGACCACATGAAGCAGCACGACTTCTTCAAGT
CCGCCATGCCCGAAGGCTACGTCCAGGAGCGCACCATCTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTGGGGCACAAGCTGGAGTACAACTACAACAGCCACAACG
TCTATATCATGGCCGACAAGCAGAAGAACGGCATCAAGGTGAACTTCAAGATCCGCCACAACATCGAGGACGGCAGCGTGCAGCTCGCCGACCACT
ACCAGCAGAACACCCCCATCGGCGACGGCCCCGTGCTGCTGCCCGACAACCACTACCTGAGCACCCAGTCCGCCCTGAGCAAAGACCCCAACGAGAA
GCGCGATCACATGGTCCTGCTGGAGTTCGTGACCGCCGCCGGGATCTAATGAAGCATCTGGTGAATAACTCGAGCAAAGCCCGCCGAAAGGCGGGCT
TTTCTGTGTCGACCGATGCCCTTGAGAGTCGGGCATTGTCTTCGCTCCTTCCGGTGGGCGCGGGGCATGACTATCGTCGCCGCACTTATGACTGTGTTC
TTTATCATGCAACTCGTAGGACAGGTGCCGGCAGCGCTCTTCCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCTGACGAGCATCACAAAAATCGACGCTCAAGTCAGAGGTGGCGAAACCCGA
CAGGACTATAAAGATACCAGGCGTTTCCCCCTGGAAGCTCCCTCGTGCGCTCTCCTGTTCCGACCCTGCCGCTTACCGGATACCTGTCCGCCTTTCTCC
CTTCGGGAAGCGTGGCGCTTTCTCATAGCTCACGCTGTAGGTATCTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACTACGGCTACACTAGAAGAACAGTATTTGGTATCTGCGCT
CTGCTGAAGCCAGTTACCTTCGGAAAAAGAGTTGGTAGCTCTTGATCCGGCAAACAAACCACCGCTGGTAGCGGTGGTTTTTTTGTTTGCAAGCAGCA
GATTACGCGCAGAAAAAAAGGATCTCAAGAAGATCCTTTGATCTTTTCTACGGGGTCTGACGCTCAGTGGAACGAAAACTCACGTTAAGGGATTTTG
GTCATGAGATTATCAAAAAGGATCTTCACCTAGATCCTTTTAAATTAAAAATGAAGTTTTAAATCAATCTAAAGTATATATGAGTAAACTTGGTCTGA
CAGTTACCAATGCTTAATCAGTGAGGCACCTATCTCAGCGATCTGTCTATTTCGTTCATCCATAGTTGCCTGACTCCCCGTCGTGTAGATAACTACGAT
ACGGGAGGGCTTACCATCTGGCCCCAGTGCTGCAATGATACCGCGTGACCCACGCTCACCGGCTCCAGATTTATCAGCAATAAACCAGCCAGCGGA
AGGGCCGAGCGCAGAAGTGGTCCTGCAACTTTATCCGCCTCCATCCAGTCTATTAATTGTTGCCGGGAAGCTAGAGTAAGTAGTTCGCCAGTTAATAG
TTTGCGCAACGTTGTTGCCATTGCTACAGGCATCGTGGTGTCACGCTCGTCGTTTGGTATGGCTTCATTCAGCTCCGGTTCCCAACGATCAAGGCGAGT
TGCATGATCCCCCATGTTGTGCAAAAAAGCGGTTAGCTCCTTCGGTCCTCCGATCGTTGTCAGAAGTAAGTTGGCCGCAGTGTTATCACTCATGGTTAT
GGCAGCACTGCATAATTCTCTTACTGTCATGCCATCCGTAAGATGCTTTTCTGTGACTGGTGAGTACTCAACCAAGTCATTCTGAGAATAGTGTATGCG
GCGACCGAGTTGCTCTTGCCCGGCGTCAACACGGGATAATACCGCGCCACATAGCAGAACTTTAAAAGTGCTCATCATTGGAAAACGTTCTTCGGGG
CGAAAACTCTCAAGGATCTTACCGCTGTTGAGATCCAGTTCGATGTAACCCACTCGTGCACCCAACTGATCTTCAGCATCTTTTACTTTCACCAGCGTT
TCTGGGTGAGCAAAAACAGGAAGGCAAAATGCCGCAAAAAAGGGAATAAGGGCGACACGGAAATGTTGAATACTCATACTCTTCCTTTTTCAATATT
ATTGAAGCATTTATCAGGGTTATTGTCTCATGAGCGGATACATATTTGAATGTATTTAGAAAAATAAACAAATAGGGGTTCCGCGCACATTTCCCCGA
AAAGTGCCACCTGACGTCTAAGAAACCATTATTATCATGACATTAACCTATAAAAATAGGCGTATCACGAGGCCCTTTCGTGTTCAAGAATTCTGGCG
AATCCTCTGACCAGCCAGAAAACGACCTTTCTGTGGTGAAACCGGATGCTGCAATTCAGAGCGCCAGCAAGTGGGGGACAGCAGATGACCTGACCGC
CGCAGAGTGGATGTTTGACATGGTGATGACTATCGCACCATCAGCCAGAAAACCGAATTTTGCTGGGTGGGCTAACGATATCCGCCTGATGCGTGAA
CGTGACGGACGTAACGAAGACAACCAC
```

FIG. 18B

197> PLasI-_UTR1_deGFP_T500 (utilizing promoter P2)

GCATTGCTGTTCCGCTGGGCATGCTTCGAGCCTAGCAAGGGTCCGGGTTCACCGAAATCTATCTCATTTGCTAGTTATAAAATTATGAAATTTGCATA
AATTCTTCAGAAGCAATAATTTTGTTTAACTTTAAGAAGGAGATATACCATGGAGCTTTTCACTGGCGTTGTTCCCATCCTGGTCGAGCTGGACGGCG
ACGTAAACGGCCACAAGTTCAGCGTGTCCGGCGAGGGCGAGGGCGATGCCACCTACGGCAAGCTGACCCTGAAGTTCATCTGCACCACCGGCAAGCT
GCCCGTGCCCTGGCCCACCCTCGTGACCACCCTGACCTACGGCGTGCAGTGCTTCAGCCGCTACCCCGACCACATGAAGCAGCACGACTTCTTCAAGT
CCGCCATGCCCGAAGGCTACGTCCAGGAGCGCACCATCTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTGGGGCACAAGCTGGAGTACAACTACAACAGCCACAACG
TCTATATCATGGCCGACAAGCAGAAGAACGGCATCAAGGTGAACTTCAAGATCCGCCACAACATCGAGGACGGCAGCGTGCAGCTCGCCGACCACT
ACCAGCAGAACACCCCCATCGGCGACGGCCCCGTGCTGCTGCCCGACAACCACTACCTGAGCACCCAGTCCGCCCTGAGCAAAGACCCCAACGAGAA
GCGCGATCACATGGTCCTGCTGGAGTTCGTGACCGCCGCCGGGATCTAATGAAGCATCTGGTGAATAACTCGAGCAAAGCCCGCCGAAAGGCGGGCT
TTTCTGTGTCGACCGATGCCCTTGAGAGTCGGGCATTGTCTTCGCTCCTTCCGGTGGGCGCGGGGCATGACTATCGTCGCCGCACTTATGACTGTGTTC
TTTATCATGCAACTCGTAGGACAGGTGCCGGCAGCGCTCTTCCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCTGACGAGCATCACAAAAATCGACGCTCAAGTCAGAGGTGGCGAAACCCGA
CAGGACTATAAAGATACCAGGCGTTTCCCCCTGGAAGCTCCCTCGTGCGCTCTCCTGTTCCGACCCTGCCGCTTACCGGATACCTGTCCGCCTTTCTCC
CTTCGGGAAGCGTGGCGCTTTCTCATAGCTCACGCTGTAGGTATCTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACTACGGCTACACTAGAAGAACAGTATTTGGTATCTGCGCT
CTGCTGAAGCCAGTTACCTTCGGAAAAAGAGTTGGTAGCTCTTGATCCGGCAAACAAACCACCGCTGGTAGCGGTGGTTTTTTTGTTTGCAAGCAGCA
GATTACGCGCAGAAAAAAAGGATCTCAAGAAGATCCTTTGATCTTTTCTACGGGGTCTGACGCTCAGTGGAACGAAAACTCACGTTAAGGGATTTTG
GTCATGAGATTATCAAAAAGGATCTTCACCTAGATCCTTTTAAATTAAAAATGAAGTTTTAAATCAATCTAAAGTATATATGAGTAAACTTGGTCTGA
CAGTTACCAATGCTTAATCAGTGAGGCACCTATCTCAGCGATCTGTCTATTTCGTTCATCCATAGTTGCCTGACTCCCCGTCGTGTAGATAACTACGAT
ACGGGAGGGCTTACCATCTGGCCCCAGTGCTGCAATGATACCGCGTGACCCACGCTCACCGGCTCCAGATTTATCAGCAATAAACCAGCCAGCGGA
AGGGCCGAGCGCAGAAGTGGTCCTGCAACTTTATCCGCCTCCATCCAGTCTATTAATTGTTGCCGGGAAGCTAGAGTAAGTAGTTCGCCAGTTAATAG
TTTGCGCAACGTTGTTGCCATTGCTACAGGCATCGTGGTGTCACGCTCGTCGTTTGGTATGGCTTCATTCAGCTCCGGTTCCCAACGATCAAGGCGAGT
TGCATGATCCCCCATGTTGTGCAAAAAAGCGGTTAGCTCCTTCGGTCCTCCGATCGTTGTCAGAAGTAAGTTGGCCGCAGTGTTATCACTCATGGTTAT
GGCAGCACTGCATAATTCTCTTACTGTCATGCCATCCGTAAGATGCTTTTCTGTGACTGGTGAGTACTCAACCAAGTCATTCTGAGAATAGTGTATGCG
GCGACCGAGTTGCTCTTGCCCGGCGTCAACACGGGATAATACCGCGCCACATAGCAGAACTTTAAAAGTGCTCATCATTGGAAAACGTTCTTCGGGG
CGAAAACTCTCAAGGATCTTACCGCTGTTGAGATCCAGTTCGATGTAACCCACTCGTGCACCCAACTGATCTTCAGCATCTTTTACTTTCACCAGCGTT
TCTGGGTGAGCAAAAACAGGAAGGCAAAATGCCGCAAAAAAGGGAATAAGGGCGACACGGAAATGTTGAATACTCATACTCTTCCTTTTTCAATATT
ATTGAAGCATTTATCAGGGTTATTGTCTCATGAGCGGATACATATTTGAATGTATTTAGAAAAATAAACAAATAGGGGTTCCGCGCACATTTCCCCGA
AAAGTGCCACCTGACGTCTAAGAAACCATTATTATCATGACATTAACCTATAAAAATAGGCGTATCACGAGGCCCTTTCGTGTTCAAGAATTCTGGCG
AATCCTCTGACCAGCCAGAAAACGACCTTTCTGTGGTGAAACCGGATGCTGCAATTCAGAGCGCCAGCAAGTGGGGGACAGCAGATGACCTGACCGC
CGCAGAGTGGATGTTTGACATGGTGATGACTATCGCACCATCAGCCAGAAAACCGAATTTTGCTGGGTGGGCTAACGATATCCGCCTGATGCGTGAA
CGTGACGGACGTAACGAAGACAACCAC

FIG. 18C

198> PLasB-_UTR1_deGFP_T500 (utilizing promoter P3)

```
GCATTGCTGTTCCGCTGGGCATGCTGCAGCAGCGGATCGTCGGCGAGCGTCACCTGAAGCTGGTGCTGAAAAGCGAATGCGGCTCGCTGCAACTGGA
TGGCATTGCCTTCAACATCGACCGCGAGCAGTGGCCCAACCCTACCGTGCGCTGGGCCGAGCTGGCCTACAAGCTCGACGTCAACGAATTCCGCGGC
CAGGGAAAGCGTGCAACTGATGATCGTCCACATGGCCCCTCGCTGAGCGCGTCCCGGAGCTGGGGGCAACCTAGCTGCCACCTGCTTTTCTGCTAGCTA
TTCCAGCGAAAACATACAGATTTCCGGCGAAATCAAGGCTACCTGCCAGTTCTGGCAGGTTTGGCCGCGGGTTCTTTTTGGTACACGAAAGCACCGTC
AAGCAATAATTTTGTTTAACTTTAAGAAGGAGATATACCATGGAGCTTTTCACTGGCGTTGTTCCCATCCTGGTCGAGCTGGACGGCGACGTAAACGG
CCACAAGTTCAGCGTGTCCGGCGAGGGCGAGGGCGATGCCACCTACGGCAAGCTGACCCTGAAGTTCATCTGCACCACCGGCAAGCTGCCCGTGCCC
TGGCCCACCCTCGTGACCACCCTGACCTACGGCGTGCAGTGCTTCAGCCGCTACCCCGACCACATGAAGCAGCACGACTTCTTCAAGTCCGCCATGCC
CGAAGGCTACGTCCAGGAGCGCACCATCTTCTTCAAGGACGACGGCAACTACAAGACCCGCGCCGAGGTGAAGTTCGAGGGCGACACCCTGGTGAA
CCGCATCGAGCTGAAGGGCATCGACTTCAAGGAGGACGGCAACATCCTGGGGCACAAGCTGGAGTACAACTACAACAGCCACAACGTCTATATCAT
GGCCGACAAGCAGAAGAACGGCATCAAGGTGAACTTCAAGATCCGCCACAACATCGAGGACGGCAGCGTGCAGCTCGCCGACCACTACCAGCAGAA
CACCCCCATCGGCGACGGCCCCGTGCTGCTGCCCGACAACCACTACCTGAGCACCCAGTCCGCCCTGAGCAAAGACCCCAACGAGAAGCGCGATCAC
ATGGTCCTGCTGGAGTTCGTGACCGCCGCCGGGATCTAATGAAGCATCTGGTGAATAACTCGAGCAAAGCCCGCCGAAAGGCGGGCTTTTCTGTGTC
GACCGATGCCCTTGAGAGTCGGGCATTGTCTTCGCTCCTTCCGGTGGGCGCGGGGCATGACTATCGTCGCCGCACTTATGACTGTGTTCTTTATCATGC
AACTCGTAGGACAGGTGCCGGCAGCGCTCTTCCGCTTCCTCGCTCACTGACTCGCTGCGCTCGGTCGTTCGGCTGCGGCGAGCGGTATCAGCTCACTC
AAAGGCGGTAATACGGTTATCCACAGAATCAGGGGATAACGCAGGAAAGAACATGTGAGCAAAAGGCCAGCAAAAGGCCAGGAACCGTAAAAAGG
CCGCGTTGCTGGCGTTTTTCCATAGGCTCCGCCCCCTGACGAGCATCACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGACACGACTTATCGCCACTGGCAGCAGCCACTGGTAACAGGATTAGCAG
AGCGAGGTATGTAGGCGGTGCTACAGAGTTCTTGAAGTGGTGGCCTAACTACGGCTACACTAGAAGAACAGTATTTGGTATCTGCGCTCTGCTGAAG
CCAGTTACCTTCGGAAAAAGAGTTGGTAGCTCTTGATCCGGCAAACAAACCACCGCTGGTAGCGGTGGTTTTTTGTTTGCAAGCAGCAGATTACGCG
CAGAAAAAAAGGATCTCAAGAAGATCCTTTGATCTTTTCTACGGGGTCTGACGCTCAGTGGAACGAAAACTCACGTTAAGGGATTTTGGTCATGAGA
TTATCAAAAAGGATCTTCACCTAGATCCTTTTAAATTAAAAATGAAGTTTTAAATCAATCTAAAGTATATATGAGTAAACTTGGTCTGACAGTTACCA
ATGCTTAATCAGTGAGGCACCTATCTCAGCGATCTGTCTATTTCGTTCATCCATAGTTGCCTGACTCCCCGTCGTGTAGATAACTACGATACGGGAGG
GCTTACCATCTGGCCCCAGTGCTGCAATGATACCGCGTGACCCACGCTCACCGGCTCCAGATTTATCAGCAATAAACCAGCCAGCCGGAAGGGCCGA
GCGCAGAAGTGGTCCTGCAACTTTATCCGCCTCCATCCAGTCTATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCTTCATTCAGCTCCGGTTCCCAACGATCAAGGCGAGTTGCATGAT
CCCCCATGTTGTGCAAAAAAGCGGTTAGCTCCTTCGGTCCTCCGATCGTTGTCAGAAGTAAGTTGGCCGCAGTGTTATCACTCATGGTTATGGCAGCA
CTGCATAATTCTCTTACTGTCATGCCATCCGTAAGATGCTTTTCTGTGACTGGTGAGTACTCAACCAAGTCATTCTGAGAATAGTGTATGCGGCGACCG
AGTTGCTCTTGCCCGGCGTCAACACGGGATAATACCGCGCCACATAGCAGAACTTTAAAAGTGCTCATCATTGGAAAACGTTCTTCGGGGCGAAAAC
TCTCAAGGATCTTACCGCTGTTGAGATCCAGTTCGATGTAACCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAATAAACAAATAGGGGTTCCGCGCACATTTCCCCGAAAAGTGC
CACCTGACGTCTAAGAAACCATTATTATCATGACATTAACCTATAAAAATAGGCGTATCACGAGGCCCTTTCGTGTTCAAGAATTCTGGCGAATCCTC
TGACCAGCCAGAAAACGACCTTTCTGTGGTGAAACCGGATGCTGCAATTCAGAGCGCCAGCAAGTGGGGGACAGCAGATGACCTGACCGCCGCAGA
GTGGATGTTTGACATGGTGATGACTATCGCACCATCAGCCAGAAAACCGAATTTTGCTGGGTGGGCTAACGATATCCGCCTGATGCGTGAACGTGAC
GGACGTAACGAAGACAACCAC
```

FIG. 18D

199> PRasL long (las)-_UTR1_deGFP_T500 (utilizing promoter P4)

GCATTGCTGTTCCGCTGGGCATGCAACTAGCAAATGAGATAGATTTCGGTGAACCCGGACCCTTGCTAGGCTCGAAGAAACGTCAAGCAATAATTTT
GTTTAACTTTAAGAAGGAGATATACCATGGAGCTTTTCACTGGCGTTGTTCCCATCCTGGTCGAGCTGGACGGCGACGTAAACGGCCACAAGTTCAGC
GTGTCCGGCGAGGGCGAGGGCGATGCCACCTACGGCAAGCTGACCCTGAAGTTCATCTGCACCACCGGCAAGCTGCCCGTGCCCTGGCCCACCCTCG
TGACCACCCTGACCTACGGCGTGCAGTGCTTCAGCCGCTACCCCGACCACATGAAGCAGCACGACTTCTTCAAGTCCGCCATGCCCGAAGGCTACGTC
CAGGAGCGCACCATCTTCTTCAAGGACGACGGCAACTACAAGACCCGCGCCGAGGTGAAGTTCGAGGGCGACACCCTGGTGAACCGCATCGAGCTG
AAGGGCATCGACTTCAAGGAGGACGGCAACATCCTGGGGCACAAGCTGGAGTACAACTACAACAGCCACAACGTCTATATCATGGCCGACAAGCAG
AAGAACGGCATCAAGGTGAACTTCAAGATCCGCCACAACATCGAGGACGGCAGCGTGCAGCTCGCCGACCACTACCAGCAGAACACCCCCATCGGC
GACGGCCCCGTGCTGCTGCCCGACAACCACTACCTGAGCACCCAGTCCGCCCTGAGCAAAGACCCCAACGAGAAGCGCGATCACATGGTCCTGCTGG
AGTTCGTGACCGCCGCCGGGATCTAATGAAGCATCTGGTGAATAACTCGAGCAAAGCCCGCCGAAAGGCGGGCTTTTCTGTGTCGACCGATGCCCTT
GAGAGTCGGGCATTGTCTTCGCTCCTTCCGGTGGGCGCGGGGCATGACTATCGTCGCCGCACTTATGACTGTGTTCTTTATCATGCAACTCGTAGGAC
AGGTGCCGGCAGCGCTCTTCCGCTTCCTCGCTCACTGACTCGCTGCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGCTCAAGTCAGAGGTGGCGAAACCCGACAGGACTATAAAGATACCAGGC
GTTTCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCCAAGCTGGGCTGTGTGCACGAACCCCCCGTTCAGCCCGACCGCTGCGCCTT
ATCCGGTAACTATCGTCTTGAGTCCAACCCGGTAAGACACGACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGAACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAACGAAAACTCACGTTAAGGGATTTTGGTCATGAGATTATCAAAAAGGAT
CTTCACCTAGATCCTTTTAAATTAAAAATGAAGTTTTAAATCAATCTAAAGTATATATGAGTAAACTTGGTCTGACAGTTACCAATGCTTAATCAGTG
AGGCACCTATCTCAGCGATCTGTCTATTTCGTTCATCCATAGTTGCCTGACTCCCCGTCGTGTAGATAACTACGATACGGGAGGGCTTACCATCTGGCC
CCAGTGCTGCAATGATACCGCGTGACCCACGCTCACCGGCTCCAGATTTATCAGCAATAAACCAGCCAGCCGGAAGGGCCGAGCGCAGAAGTGGTCC
TGCAACTTTATCCGCCTCCATCCAGTCTATTAATTGTTGCCGGGAAGCTAGAGTAAGTAGTTCGCCAGTTAATAGTTTGCGCAACGTTGTTGCCATTGC
TACAGGCATCGTGGTGTCACGCTCGTCGTTTGGTATGGCTTCATTCAGCTCCGGTTCCCAACGATCAAGGCGAGTTGCATGATCCCCCATGTTGTGCA
AAAAAGCGGTTAGCTCCTTCGGTCCTCCGATCGTTGTCAGAAGTAAGTTGGCCGCAGTGTTATCACTCATGGTTATGGCAGCACTGCATAATTCTCTT
ACTGTCATGCCATCCGTAAGATGCTTTTCTGTGACTGGTGAGTACTCAACCAAGTCATTCTGAGAATAGTGTATGCGGCGACCGAGTTGCTCTTGCCC
GGCGTCAACACGGGATAATACCGCGCCACATAGCAGAACTTTAAAAGTGCTCATCATTGGAAAACGTTCTTCGGGGCGAAAACTCTCAAGGATCTTA
CCGCTGTTGAGATCCAGTTCGATGTAACCCACTCGTGCACCCAACTGATCTTCAGCATCTTTTACTTTCACCAGCGTTTCTGGGTGAGCAAAAACAGG
AAGGCAAAATGCCGCAAAAAAGGGAATAAGGGCGACACGGAAATGTTGAATACTCATACTCTTCCTTTTTCAATATTATTGAAGCATTTATCAGGGT
TATTGTCTCATGAGCGGATACATATTTGAATGTATTTAGAAAAATAAACAAATAGGGGTTCCGCGCACATTTCCCCGAAAAGTGCCACCTGACGTCTA
AGAAACCATTATTATCATGACATTAACCTATAAAAATAGGCGTATCACGAGGCCCTTTCGTGTTCAAGAATTCTGGCGAATCCTCTGACCAGCCAGAA
AACGACCTTTCTGTGGTGAAACCGGATGCTGCAATTCAGAGCGCCAGCAAGTGGGGACAGCAGATGACCTGACCGCCGCAGAGTGGATGTTTGACA
TGGTGATGACTATCGCACCATCAGCCAGAAAACCGAATTTTGCTGGGTGGGCTAACGATATCCGCCTGATGCGTGAACGTGACGGACGTAACGAAGA
CAACCAC

FIG. 18E

163> pLacO1-UTR1-lasR

ATGCTATGTTGTCTTCGCTCCTTCCGGTGGGCGCGGGGCATGACTATCGTCGCCGCACTTATGACTGTGTTCTTTATCATGCAACTCGTAGGACAGGTG
CCGGCAGCGCTCTTCCGCTTCCTCGCTCACTGACTCGCTGCGCTCGGTCGTTCGGCTGCGGCGAGCGGTATCAGCTCACTCAAAGGCGGTAATACGGT
TATCCACAGAATCAGGGGATAACGCAGGAAAGAACATGTGAGCAAAAGGCCAGCAAAAGGCCAGGAACCGTAAAAAGGCCGCGTTGCTGGCGTTTT
TCCATAGGCTCCGCCCCCCTGACGAGCATCACAAAAATCGACGCTCAAGTCAGAGGTGGCGAAACCCGACAGGACTATAAAGATACCAGGCGTTTCC
CCCTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCG
GTAACTATCGTCTTGAGTCCAACCCGGTAAGACACGACTTATCGCCACTGGCAGCAGCCACTGGTAACAGGATTAGCAGAGCGAGGTATGTAGGCGG
TGCTACAGAGTTCTTGAAGTGGTGGCCTAACTACGGCTACACTAGAAGAACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTTGCAAGCAGCAGATTACGCGCAGAAAAAAGGATCTCA
AGAAGATCCTTTGATCTTTTCTACGGGGTCTGACGCTCAGTGGAACGAAAACTCACGTTAAGGGATTTTGGTCATGAGATTATCAAAAAGGATCTTCA
CCTAGATCCTTTTAAATTAAAAATGAAGTTTTAAATCAATCTAAAGTATATATGAGTAAACTTGGTCTGACAGTTACCAATGCTTAATCAGTGAGGCA
CCTATCTCAGCGATCTGTCTATTTCGTTCATCCATAGTTGCCTGACTCCCCGTCGTGTAGATAACTACGATACGGGAGGGCTTACCATCTGGCCCCAGT
GCTGCAATGATACCGCGTGACCCACGCTCACCGGCTCCAGATTTATCAGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTAAGTAGTTCGCCAGTTAATAGTTTGCGCAACGTTGTTGCCATTGCTACAG
GCATCGTGGTGTCACGCTCGTCGTTTGGTATGGCTTCATTCAGCTCCGGTTCCCAACGATCAAGGCGAGTTGCATGATCCCCCATGTTGTGCAAAAA
GCGGTTAGCTCCTTCGGTCCTCCGATCGTTGTCAGAAGTAAGTTGGCCGCAGTGTTATCACTCATGGTTATGGCAGCACTGCATAATTCTCTTACTGTC
ATGCCATCCGTAAGATGCTTTTCTGTGACTGGTGAGTACTCAACCAAGTCATTCTGAGAATAGTGTATGCGGCGACCGAGTTGCTCTTGCCCGGCGTC
AACACGGATAATACCGCGCCACATAGCAGAACTTTAAAAGTGCTCATCATTGGAAAACGTTCTTCGGGGCGAAAACTCTCAAGGATCTTACCGCTG
TTGAGATCCAGTTCGATGTAACCCACTCGTGCACCCAACTGATCTTCAGCATCTTTTACTTTCACCAGCGTTTCTGGGTGAGCAAAAACAGGAAGGCA
AAATGCCGCAAAAAAGGGAATAAGGGCGACACGGAAATGTTGAATACTCATACTCTTCCTTTTTCAATATTATTGAAGCATTTATCAGGGTTATTGTC
TCATGAGCGGATACATATTTGAATGTATTTAGAAAAATAAACAAATAGGGGTTCCGCGCACATTTCCCCGAAAAGTGCCACCTGACGTCTAAGAAAC
CATTATTATCATGACATTAACCTATAAAAATAGGCGTATCACGAGGCCCTTTCGTGTTCAAGAATTCTGGCGAATCCTCTGACCAGCCAGAAAACGAC
CTTTCTGTGGTGAAACCGGATGCTGCAATTCAGAGCGCCAGCAAGTGGGGGACAGCAGATGACCTGACCGCCGCAGAGTGGATGTTGACATGGTGA
TGACTATCGCACCATCAGCCAGAAAACCGAATTTTGCTGGGTGGGCTAACGATATCCGCCTGATGCGTGAACGTGACGGACGTAACGAAGACAAGGC
ACGACTCTCAAGGGCATCGGTCGACACAGAAAAGCCCGCCTTTCGGCGGGCTTTGCTCGAGTTATTCACCAGATGCTTCATTATTAGAGAGTAATAAG
ACCCAAATTAACGGCCATAATGGCCGCTACGCGGCGGGAGGTCACACCGAACTTCCGCCGAATATTTCCCATATGGAAGTTCACATTGGCTTCCGAG
CAGTTGCAGATAACCGATATCTCCCAACTGGTCTTGCCGATGCGCACCACTGCAACACTTCCTTCTCCCGGCTGGTCAGAACCACCGGTTTGCTGAC
CGGATGTTCGAAGGCCAGTCCGGCACCGCTTTGCAGTGCGTAGTCCTTGAGCATCCACAGGGTCGGCAGGACCGACTCTATGAAACGGTTGGCCTCG
GCCCGGTTTTCCGCTTCCACGCTGAGGCTCAGCGCGCCGAGTTCGCCGCGAGCACCATGCAGCGGCATGGTCAGCCCATACACCAGGCCGGCGGCCG
AGGCTTCCTCGAAGAACTCGTGCTGCTTTCGCGTCTGGTAGATGGACGGTTCCCAGAAAATCGGCAGTACGCTCTGGGTACAGTGACTGACCGTCGGG
TCGACCCGCGCGTAGCCAGCCCGGTCGTAATGCTCGCGCCAGGCGGCCGGGTAGTTGCCGACGATGAAGGCGTTCTCGTAGTCCTGGCTGTCCTTAGG
CAACAGGCCGAACAGGATCTTCGAGAATCCAAGGTCGCTCGCCATCTTCTGGAGGATGGCGCTCCACTCCAATTTTCCACTTGAGCGTTCCAGCTCAA
GAAAACCGTCAACCAAGGCCATGGTATATCTCCTTCTTAAAGTTAAACAAAATTATTGCTTGCTGTGCTCAGTATCTTGTTATCCGCTCACAATGTCAA
TGTTATCCGCTCACATTTATGCATGCCCAGCGGAACAGCA

FIG. 18F

PLasI_1SNP_-10_tetO1 (P1_tetO1)-(blank)-deGFP-ssrA-B1002 "BACKBONE"

```
AATGGAGCTTTTCACTGGCGTTGTTCCCATCCTGGTCGAGCTGGACGGCGACGTAAACGGCCACAAGTTCAGCGTGTCCGGCGAGGGCGAGGGCGAT
GCCACCTACGGCAAGCTGACCCTGAAGTTCATCTGCACCACCGGCAAGCTGCCCGTGCCCTGGCCCACCCTCGTGACCACCCTGACCTACGGCGTGCA
GTGCTTCAGCCGCTACCCCGACCACATGAAGCAGCACGACTTCTTCAAGTCCGCCATGCCCGAAGGCTACGTCCAGGAGCGCACCATCTTCTTCAAGG
ACGACGGCAACTACAAGACCCGCGCCGAGGTGAAGTTCGAGGGCGACACCCTGGTGAACCGCATCGAGCTGAAGGGCATCGACTTCAAGGAGGACG
GCAACATCCTGGGGCACAAGCTGGAGTACAACTACAACAGCCACAACGTCTATATCATGGCCGACAAGCAGAAGAACGGCATCAAGGTGAACTTCA
AGATCCGCCACAACATCGAGGACGGCAGCGTGCAGCTCGCCGACCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGATCACATGGTCCTGCTGGAGTTCGTGACCGCCGCCGGGATCGCA
GCAAACGACGAAAACTACGCTTTAGCTGCTTAATGAACTCGCAAAAAACCCCGCTTCGGCGGGGTTTTTTCGCCCTTGAGAGTCGGGCATTGTCTTCG
CTCCTTCCGGTGGGCGCGGGGCATGACTATCGTCGCCGCACTTATGACTGTGTTCTTTATCATGCAACTCGTAGGACAGGTGCCGGCAGCGCTCTTCC
GCTTCCTCGCTCACTGACTCGCTGCGCTCGGTCGTTCGGCTGCGGCGAGCGGTATCAGCTCACTCAAAGGCGGTAATACGGTTATCCACAGAATCAGG
GGATAACGCAGGAAAGAACATGTGAGCAAAAGGCCAGCAAAAGGCCAGGAACCGTAAAAAGGCCGCGTTGCTGGCGTTTTTCCATAGGCTCCGCCC
CCCTGACGAGCATCACAAAAATCGACGCTCAAGTCAGAGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGGGAAGCGTGGCGCTTTCTCATAGCTCACGCTGTAGGTAT
CTCAGTTCGGTGTAGGTCGTTCGCTCCAAGCTGGGCTGTGTGCACGAACCCCCCGTTCAGCCCGACCGCTGCGCCTTATCCGGTAACTATCGTCTTGA
GTCCAACCCGGTAAGACACGACTTATCGCCACTGGCAGCAGCCACTGGTAACAGGATTAGCAGAGCGAGGTATGTAGGCGGTGCTACAGAGTTCTTG
AAGTGGTGGCCTAACTACGGCTACACTAGAAGAACAGTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTTGGTCATGAGATTATCAAAAAGGATCTTCACCTAGATCCTTTTAAA
TTAAAAATGAAGTTTTAAATCAATCTAAAGTATATATGAGTAAACTTGGTCTGACAGTTACCAATGCTTAATCAGTGAGGCACCTATCTCAGCGATCT
GTCTATTTCGTTCATCCATAGTTGCCTGACTCCCCGTCGTGTAGATAACTACGATACGGGAGGGCTTACCATCTGGCCCCAGTGCTGCAATGATACCG
CGTGACCCACGCTCACCGGCTCCAGATTTATCAGCAATAAACCAGCCAGCCGGAAGGGCCGAGCGCAGAAGTGGTCCTGCAACTTTATCCGCCTCCA
TCCAGTCTATTAATTGTTGCCGGGAAGCTAGAGTAAGTAGTTCGCCAGTTAATAGTTTGCGCAACGTTGTTGCCATTGCTACAGGCATCGTGGTGTCA
CGCTCGTCGTTTGGTATGGCTTCATTCAGCTCCGGTTCCCAACGATCAAGGCGAGTTGCATGATCCCCCATGTTGTGCAAAAAAGCGGTTAGCTCCTT
GGTCCTCCGATCGTTGTCAGAAGTAAGTTGGCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGCTCTTGCCCGGCGTCAACACGGGATAATAC
CGCGCCACATAGCAGAACTTTAAAAGTGCTCATCATTGGAAAACGTTCTTCGGGGCGAAAACTCTCAAGGATCTTACCGCTGTTGAGATCCAGTTCGA
TGTAACCCACTCGTGCACCCAACTGATCTTCAGCATCTTTTACTTTCACCAGCGTTTCTGGGTGAGCAAAAACAGGAAGGCAAAATGCCGCAAAAAA
GGGAATAAGGGCGACACGGAAATGTTGAATACTCATACTCTTCCTTTTTCAATATTATTGAAGCATTTATCAGGGTTATTGTCTCATGAGCGGATACA
TATTTGAATGTATTTAGAAAAATAAACAAATAGGGGTTCCGCGCACATTTCCCCGAAAAGTGCCACCTGACGTCTAAGAAACCATTATTATCATGACA
TTAACCTATAAAAATAGGCGTATCACGAGGCCCTTTCGTGTTCAAGAATTCTGGCGAATCCTCTGACCAGCCAGAAAACGACCTTTCTGTGGTGAAAC
CGGATGCTGCAATTCAGAGCGCCAGCAAGTGGGGGACAGCAGATGACCTGACCGCCGCAGAGTGGATGTTTGACATGGTGATGACTATCGCACCATC
AGCCAGAAACCGAATTTTGCTGGGTGGGCTAACGATATCCGCCTGATGCGTGAACGTGACGGACGTAACGAAGACAACCACGCATTGCTGTTCTTC
GAGCCTAGCAAGGGTCCGGGTTCACCGAAATCTATCTCATTTGCTAGTTATAAAATTATGAAATTTGCGTAAATTCCCTATCAGTGATAGAGATTCAG
                                    AAGC[ INSERT RBS SEQUENCE HERE ]
```

FIG. 19A

| | |
|---|---|
| 273, UTR1 > AATAATTTTGTTTAACTTTAAGAAGGAGATATAC | |
| 387, BCD7 > GGGCCCAAGTTCACTTAAAAAGGAGATCAACAATGAAAGCAATTTTCGTACTGAAACATCTTAATCATGCTGGGGAGGGTTTCT | |
| 389, BCD13 > GGGCCCAAGTTCACTTAAAAAGGAGATCAACAATGAAAGCAATTTTCGTACTGAAACATCTTAATCATGCAATGGAGGCTTTCT | |
| 391, BCD14 > GGGCCCAAGTTCACTTAAAAAGGAGATCAACAATGAAAGCAATTTTCGTACTGAAACATCTTAATCATGCGGTGGAGGGTTTCT | |
| 392, BCD16 > GGGCCCAAGTTCACTTAAAAAGGAGATCAACAATGAAAGCAATTTTCGTACTGAAACATCTTAATCATGCTTAGGAGTCTTTCT | |
| 349, BCD22 > GGGCCCAAGTTCACTTAAAAAGGAGATCAACAATGAAAGCAATTTTCGTACTGAAACATCTTAATCATGCCTAGGAAGTTTTCT | |
| 395, B0031 > TACTAGAGTCACACAGGAAACCTACTC | |
| 397, B0033 > TACTAGAGTCACACAGGACTACTC | |
| 347, BCD2 > GGGCCCAAGTTCACTTAAAAAGGAGATCAACAATGAAAGCAATTTTCGTACTGAAACATCTTAATCATGCTAAGGAGGTTTTCT | |
| 388, BCD11 > GGGCCCAAGTTCACTTAAAAAGGAGATCAACAATGAAAGCAATTTTCGTACTGAAACATCTTAATCATGCGGGGGAGTGTTTCT | |
| 390, BCD12 > GGGCCCAAGTTCACTTAAAAAGGAGATCAACAATGAAAGCAATTTTCGTACTGAAACATCTTAATCATGCTGCGGAGGGTTTCT | |
| 348, BCD20 > GGGCCCAAGTTCACTTAAAAAGGAGATCAACAATGAAAGCAATTTTCGTACTGAAACATCTTAATCATGCTGAGGAAAGTTTCT | |
| 393, BCD24 > GGGCCCAAGTTCACTTAAAAAGGAGATCAACAATGAAAGCAATTTTCGTACTGAAACATCTTAATCATGCGATGGACGGTTTCT | |
| 394, B0030 > TACTAGAGATTAAAGAGGAGAAATACTC | |
| 396, B0032 > TACTAGAGTCACACAGGAAAGTACTC | |
| 398, B0034 > TACTAGAGAAAGAGGAGAAATACTC | |

FIG. 19B

PLasI_1SNP_-10(P1)-(blank)-tetR-T500 "BACKBONE"

>AATGTCTAGATTAGATAAAAGTAAAGTGATTAACAGCGCATTAGAGCTGCTTAATGAGGTCGGAATCGAAGGTTTAACAACCCGTAAACTCGCCCA
GAAGCTAGGTGTAGAGCAGCCTACATTGTATTGGCATGTAAAAAATAAGCGGGCTTTGCTCGACGCCTTAGCCATTGAGATGTTAGATAGGCACCAT
ACTCACTTTTGCCCTTTAGAAGGGGAAAGCTGGCAAGATTTTTTACGTAATAACGCTAAAAGTTTTAGATGTGCTTTACTAAGTCATCGCGATGGAGC
AAAAGTACATTTAGGTACACGGCCTACAGAAAAACAGTATGAAACTCTCGAAAATCAATTAGCCTTTTTATGCCAACAAGGTTTTTCACTAGAGAAT
GCATTATATGCACTCAGCGCTGTGGGGCATTTTACTTTAGGTTGCGTATTGGAAGATCAAGAGCATCAAGTCGCTAAAGAAGAAAGGGAAACACCTA
CTACTGATAGTATGCCGCCATTATTACGACAAGCTATCGAATTATTTGATCACCAAGGTGCAGAGCCAGCCTTCTTATTCGGCCTTGAATTGATCATAT
GCGGATTAGAAAAACAACTTAAATGTGAAAGTGGGTCTTAATGAACTCAAAGCCCGCCGAAAGGCGGGCTTTTCTGTCCTTGAGAGTCGTATGTTGT
CTTCTAAGGATCCAAACTCGAGTAAGGATCTCCAGGCATCAAATAAAACGAAAGGCTCAGTCGAAAGACTGGGCCTTTCGTTTTATCTGTTGTTTGTC
GGTGAACGCTCTCTACTAGAGTCACACTGGCTCACCTTCGGGTGGGCCTTTCTGCGTTTATACCTAGGGTACGGGTTTGCTGCCCGCAAACGGGCTG
TTCTGGTGTTGCTAGTTTGTTATCAGAATCGCAGATCCGGCTTCAGCCGGTTTGCCGGCTGAAAGCGCTATTTCTTCCAGAATTGCCATGATTTTTCC
CCACGGGAGGCGTCACTGGCTCCCGTGTTGTCGGCAGCTTTGATTCGATAAGCAGCATCGCCTGTTTCAGGCTGTCTATGTGTGACTGTTGAGCTGTA
ACAAGTTGTCTCAGGTGTTCAATTTCATGTTCTAGTTGCTTTGTTTTACTGGTTTCACCTGTTCTATTAGGTGTTACATGCTGTTCATCTGTTACATTGTC
GATCTGTTCATGGTGAACAGCTTTGAATGCACCAAAAACTCGTAAAAGCTCTGATGTATCTATCTTTTTTACACCGTTTTCATCTGTGCATATGGACAG
TTTTTCCCTTTGATATGTAACGGTGAACAGTTGTTCTACTTTTGTTTGTTAGTCTTGATGCTTCACTGATAGATACAAGAGCCATAAGAACCTCAGATCC
TTCCGTATTTAGCCAGTATGTTCTCTAGTGTGGTTCGTTGTTTTTGCGTGAGCCATGAGAACGAACCATTGAGATCATACTTACTTTGCATGTCACTCA
AAAATTTTGCCTCAAAACTGGTGAGCTGAATTTTTGCAGTTAAAGCATCGTGTAGTGTTTTTCTTAGTCCGTTATGTAGGTAGGAATCTGATGTAATGG
TTGTTGGTATTTTGTCACCATTCATTTTTATCTGGTTGTTCTCAAGTTCGGTTACGAGATCCATTTGTCTATCTAGTTCAACTTGGAAAATCAACGTATC
AGTCGGGCGGCCTCGCTTATCAACCACCAATTTCATATTGCTGTAAGTGTTTAAATCTTTACTTATTGGTTTCAAAACCCATTGGTTAAGCCTTTTAAA
CTCATGGTAGTTATTTTCAAGCATTAACATGAACTTAAATTCATCAAGGCTAATCTCTATATTTGCCTTGTGAGTTTCTTTTGTGTTAGTTCTTTTAAT
AACCACTCATAAATCCTCATAGAGTATTTGTTTTCAAAAGACTTAACATGTTCCAGATTATATTTTATGAATTTTTTTAACTGGAAAAGATAAGGCAAT
ATCTCTTCACTAAAAACTAATTCTAATTTTTCGCTTGAGAACTTGGCATAGTTTGTCCACTGGAAAATCTCAAAGCCTTTAACCAAAGGATTCCTGATT
TCCACAGTTCTCGTCATCAGCTCTCTGGTTGCTTTAGCTAATACACCATAAGCATTTTCCCTACTGATGTTCATCATCTGAGCGTATTGGTTATAAGTG
AACGATACCGTCCGTTCTTTCCTTGTAGGGTTTTCAATCGTGGGGTTGAGTAGTGCCACACAGCATAAAATTAGCTTGGTTTCATGCTCCGTTAAGTCA
TAGCGACTAATCGCTAGTTCATTTGCTTTGAAAACAACTAATTCAGACATACATCTCAATTGGTCTAGGTGATTTTAATCACTATACCAATTGAGATGG
GCTAGTCAATGATAATTACTAGTCCTTTTCCCGGGTGATCTGGGTATCTGTAAATTCTGCTAGACCTTTGCTGGAAAACTTGTAAATTCTGCTAGACCC
TCTGTAAATTCCGCTAGACCTTTGTGTGTTTTTTTGTTTATATTCAAGTGGTTATAATTTATAGAATAAAGAAAGAATAAAAAAAGATAAAAAGAAT
AGATCCCAGCCCTGTGTATAACTCACTACTTTAGTCAGTTCCGCAGTATTACAAAAGGATGTCGCAAACGCTGTTTGCTCCTCTACAAAACAGACCTT
AAAACCCTAAAGGCTTAAGTAGCACCCTCGCAAGCTCGGGCAAATCGCTGAATATTCCTTTTGTCTCCGACCATCAGGCACCTGAGTCGCTGTCTTTT
TCGTGACATTCAGTTCGCTGCGCTCACGGCTCTGGCAGTGAATGGGGGTAAATGGCACTACAGGCGCCTTTATGGATTCATGCAAGGAAACTACCCA
TAATACAAGAAAAGCCCGTCACGGGCTTCTCAGGGCGTTTTATGGCGGGTCTGCTATGTGGTGCTATCTGACTTTTTGCTGTTCAGCAGTTCCTGCCCT
CTGATTTTCCAGTCTGACCACTTCGGATTATCCCGTGACAGGTCATTCAGACTGGCTAATGCACCCAGTAAGGCAGCGGTATCATCAACAGGCTTACC
CGTCTTACTGTCCCTAGTGCTTGGATTCTCACCAATAAAAACGCCCGGCGGCAACCGAGCGTTCTGAACAAATCCAGATGGAGTTCTGAGGTCATTA
CTGGATCTATCAACAGGAGTCCAAGCGAGCTCTCGAACCCCAGAGTCCCGCTCAGAAGAACTCGTCAAGAAGGCGATAGAAGGCGATGCGCTGCGA
ATCGGGAGCGGCGATACCGTAAAGCACGAGGAAGCGGTCAGCCCATTCGCCGCCAAGCTCTTCAGCAATATCACGGGTAGCCAACGCTATGTCCTGA
TAGCGGTCCGCCACACCCAGCCGGCCACAGTCGATGAATCCAGAAAAGCGGCCATTTTCCACCATGATATTCGGCAAGCAGGCATCGCCATGGGTCA
CGACGAGATCCTCGCCGTCGGGCATGCGCGCCTTGAGCCTGGCGAACAGTTCGGCTGGCGCGAGCCCCTGATGCTCTTCGTCCAGATCATCCTGATCG
ACAAGACCGGCTTCCATCCGAGTACGTGCTCGCTCGATGCGATGTTTCGCTTGGTGGTCGAATGGGCAGGTAGCCGGATCAAGCGTATGCAGCCGCC
GCATTGCATCAGCCATGATGGATACTTTCTCGGCAGGAGCAAGGTGAGATGACAGGAGATCCTGCCCCGGCACTTCGCCCAATAGCAGCCAGTCCCT
TCCCGCTTCAGTGACAACGTCGAGCACAGCTGCGCAAGGAACGCCCGTCGTGGCCAGCCACGATAGCCGCGCTGCCTCGTCCTGCAGTTCATTCAGG
GCACCGGACAGGTCGGTCTTGACAAAAAGAACCGGGCGCCCCTGCGCTGACAGCCGGAACACGGCGGCATCAGAGCAGCCGATTGTCTGTTGTGCCC
AGTCATAGCCGAATAGCCTCTCCACCCAAGCGGCCGGAGAACCTGCGTGCAATCCATCTTGTTCAATCATGCGAAACGATCCTCATCCTGTCTCTTGA
TCAGATCATGATCCCCTGCGCCATCAGATCCTTGGCGGCAAGAAAGCCATCCAGTTTACTTTGCAGGGCTTCCCAACCTTACCAGAGGGCGCCCCAGC
TGGCAATTCCGACGTCGGTGCCTAATGAGTGAGCTAACTTACATTAATTGCGTTGCGCTCACTGCCCGCTTTCCAGTCGGGAAACCTGAAGACAAATG
TGCATTGCTGTTCTTCGAGCCTAGCAAGGGTCCGGGTTCACCGAAATCTATCTCATTTGCTAGTTATAAAATTATGAAATTTGCGTAAATTCTTCAGAA
GC [ INSERT RBS SEQUENCE HERE ]

FIG. 19C

373: Plac_BCD2_lasR_T500

>ATGCATGTTTGTCTTCTTGATCGGGCACGTAAGAGGTTCCAACTTTCACCATAATGAAATAAGATCACTACCGGGCGTATTTTTTGAGTTATCGAGA
TTTTCAGGAGCTAAGGAAGCTAAAATGCGCTCACGCAACTGGTCCAGAACCTTGACCGAACGCAGCGGTGGTAACGGCGCAGTGGCGGTTTTCATGG
CTTGTTATGACTGTTTTTTTGGGGTACAGTCTATGCCTCGGGCATCCAAGCAGCAAGCGCGTTACGCCGTGGGTCGATGTTTGATGTTATGGAGCAGC
AACGATGTTACGCAGCAGGGCAGTCGCCCTAAAACAAAGTTAAACATCATGAGGGAAGCGGTGATCGCCGAAGTATCGACTCAACTATCAGAGGTA
GTTGGCGTCATCGAGCGCCATCTCGAACCGACGTTGCTGGCCGTACATTTGTACGGCTCCGCAGTGGATGGCGGCCTGAAGCCACACAGTGATATTGA
TTTGCTGGTTACGGTGACCGTAAGGCTTGATGAAACAACGCGGCGAGCTTTGATCAACGACCTTTTGGAAACTTCGGCTTCCCCTGGAGAGAGCGAG
ATTCTCCGCGCTGTAGAAGTCACCATTGTTGTGCACGACGACATCATTCCGTGGCGTTATCCAGCTAAGCGCGAACTGCAATTGGAGAATGGCAGCG
CAATGACATTCTTGCAGGTATCTTCGAGCCAGCCACGATCGACATTGATCTGGCTATCTTGCTGACAAAAGCAAGAGAACATAGCGTTGCCTTGGTAG
GTCCAGCGGCGGAGGAACTCTTTGATCCGGTTCCTGAACAGGATCTATTTGAGGCGCTAAATGAAACCTTAACGCTATGGAACTCGCCGCCCGACTG
GGCTGGCGATGAGCGAAATGTAGTGCTTACGTTGTCCCGCATTTGGTACAGCGCAGTAACCGGCAAAATCGCGCCGAAGGATGTCGCTGCCGACTGG
GCAATGGAGCGCCTGCCGGCCCAGTATCAGCCCGTCATACTTGAAGCTAGACAGGCTTATCTTGGACAAGAAGAAGATCGCTTGGCCTCGCGCGCAG
ATCAGTTGGAAGAATTTGTCCACTACGTGAAAGGCGAGATCACCAAGGTAGTCGGCAAATAATTTGATATCGAGCTCGCTTGGACTCCTGTTGATAG
ATCCAGTAATGACCTCAGAACTCCATCTGGATTTGTTCAGAACGCTCGGTTGCCGCCGGGCGTTTTTATTGGTGAGAATCCAAGCCTCGGTGAGAAT
CCAAGCCTCGATCAACGTCTCATTTTCGCCAAAAGTTGGCCCAGGGCTTCCCGGTATCAACAGGGACACCAGGATTTATTTATTCTGCGAAGTGATCT
TCCGTCACAGGTATTTATTCGGCGCAAAGTGCGTCGGGTGATGCTGCCAACTTACTGATTTAGTGTATGATGGTGTTTTTGAGGTGCTCCAGTGGCTTC
TGTTTCTATCAGCTGTCCCTCCTGTTCAGCTACTGACGGGGTGGTGCGTAACGGCAAAAGCACCGCCGGACATCAGCGGTAGCGGAGTGTATACTGGC
TTACTATGTTGGCACTGATGAGGGTGTCAGTGAAGTGCTTCATGTGGCAGGAGAAAAAAGGCTGCACCGGTGCGTCAGCAGAATATGTGATACAGGA
TATATTCCGCTTCCTCGCTCACTGACTCGCTACGCTCGGTCGTTCGACTGCGGCGAGCGGAAATGGCTTACGAACGGGCGGAGATTTCCTGGAAGAT
GCCAGGAAGATACTTAACAGGGAAGTGAGAGGGCCGCGGCAAAGCCGTTTTTCCATAGGCTCCGCCCCCCTGACAAGCATCACGAAATCTGACGCTC
AAATCAGTGGTGGCGAAACCCGACAGGACTATAAAGATACCAGGCGTTTCCCCCTGGCGGCTCCCTCGTGCGCTCTCCTGTTCCTGCCTTTCGGTTTA
CCGGTGTCATTCCGCTGTTATGGCCGCGTTTGTCTCATTCCACGCCTGACACTCAGTTCCGGGTAGGCAGTTCGCTCCAAGCTGGACTGTATGCACGAA
CCCCCCGTTCAGTCCGACCGCTGCGCCTTATCCGGTAACTATCGTCTTGAGTCCAACCCGGAAAGACATGCAAAAGCACCACTGGCAGCAGCCACTG
GTAATTGATTTAGAGGAGTTAGTCTTGAAGTCATGCGCCGGTTAAGGCTAAACTGAAAGGACAAGTTTTGGTGACTGCGCTCCTCCAAGCCAGTTACC
TCGGTTCAAAGAGTTGGTAGCTCAGAGAACCTTCGAAAAACCGCCCTGCAAGGCGGTTTTTTCGTTTTCAGAGCAAGAGATTACGCGCAGACCAAA
CGATCTCAAGAAGATCATCTTATTAATCAGATAAAATATTTCTAGATTTCAGTGCAATTTATCTCTTCAAATGTAGCACCTGAAGTCAGCCCCATACG
ATATAAGTTGTAATTCTCATGTTTGACAGCTTATCATCGATAAGCTTCCGATGGCGCGCCGAGAGGCTTTACACTTTATGCTTCCGGCTGAAGACAAG
GCACGACTCTCAAGGACAGAAAAGCCCGCCTTTCGGCGGGCTTTGAGTTCATTATTAGAGAGTAATAAGACCCAAATTAACGGCCATAATGGCCGCT
ACGCGGCGGGAGGTCACACCGAACTTCCGCCGAATATTTCCCATATGGAAGTTCACATTGGCTTCCGAGCAGTTGCAGATAACCGATATCTCCCAACT
GGTCTTGCCGATGGCGCACCACTGCAACACTTCCTTCTCCCGGCTGGTCAGAACCACCGGTTTGCTGACCGGATGTTCGAAGGCCAGTCCGGCCACCGC
TTTGCAGTGCGTAGTCCTTGAGCATCCACAGGGTCGGCAGGACCGACTCTATGAAACGGTTGGCCTCGGCCCGGTTTCCGCTTCCACGCTGAGGCTC
AGCGCGCCGAGTTCGCCGCGAGCACCATGCAGCGGCATGGTCAGCCCATACACCAGGCCGGCGGCCGAGGCTTCCTCGAAGAACTCGTGCTGCTTTC
GCGTCTGGTAGATGGACGGTTCCCAGAAAATCGGCAGTACGCTCTGGGTACAGTGACTGACCGTCGGGTCGACCCGCGCGTAGCCAGCCCGGTCGTA
ATGCTCGCGCCAGGCGGCCGGGTAGTTGCCGACGATGAAGGCGTTCTCGTAGTCCTGGCTGTCCTTAGGCAACAGGCCGAACAGGATCTTCGAGAAT
CCAAGGTCGCTCGCCATCTTCTGGAGGATGGCGCTCCACTCCAATTTCCACTTGAGCGTTCCAGCTCAAGAAAACCGTCAACCAAGGCCATTAGAAA
ACCTCCTTAGCATGATTAAGATGTTTCAGTACGAAAATTGCTTTCATTGTTGATCTCCTTTTTAAGTGAACTTGGGCCCGCTTGCTGTGCTCAGTATCTT
GTTATCCGCTCACAATGTCAATGTTATCCGCTCACATTTATGAACAGCA

FIG. 20A

374: Plac_BCD2_lasR_T500

>ATGCATGTTTGTCTTCTTGATCGGGCACGTAAGAGGTTCCAACTTTCACCATAATGAAATAAGATCACTACCGGGCGTATTTTTTGAGTTATCGAGA
TTTTCAGGAGCTAAGGAAGCTAAAATGCGCTCACGCAACTGGTCCAGAACCTTGACCGAACGCAGCGGTGGTAACGGCGCAGTGGCGGTTTTCATGG
CTTGTTATGACTGTTTTTTTGGGGTACAGTCTATGCCTCGGGCATCCAAGCAGCAAGCGCGTTACGCCGTGGGTCGATGTTTGATGTTATGGAGCAGC
AACGATGTTACGCAGCAGGGCAGTCGCCCTAAAACAAAGTTAAACATCATGAGGGAAGCGGTGATCGCCGAAGTATCGACTCAACTATCAGAGGTA
GTTGGCGTCATCGAGCGCCATCTCGAACCGACGTTGCTGGCCGTACATTTGTACGGCTCCGCAGTGGATGGCGGCCTGAAGCCACACAGTGATATTGA
TTTGCTGGTTACGGTGACCGTAAGGCTTGATGAAACAACGCGGCGAGCTTTGATCAACGACCTTTTGGAAACTTCGGCTTCCCCTGGAGAGAGCGAG
ATTCTCCGCGCTGTAGAAGTCACCATTGTTGTGCACGACGACATCATTCCGTGGCGTTATCCAGCTAAGCGCGAACTGCAATTGGAGAATGGCAGCG
CAATGACATTCTTGCAGGTATCTTCGAGCCAGCCACGATCGACATTGATCTGGCTATCTTGCTGACAAAAGCAAGAGAACATAGCGTTGCCTTGGTAG
GTCCAGCGGCGGAGGAACTCTTTGATCCGGTTCCTGAACAGGATCTATTTGAGGCGCTAAATGAAACCTTAACGCTATGGAACTCGCCGCCCGACTG
GGCTGGCGATGAGCGAAATGTAGTGCTTACGTTGTCCCGCATTTGGTACAGCGCAGTAACCGGCAAAATCGCGCCGAAGGATGTCGCTGCCGACTGG
GCAATGGAGCGCCTGCCGGCCCAGTATCAGCCCGTCATACTTGAAGCTAGACAGGCTTATCTTGGACAAGAAGAAGATCGCTTGGCCTCGCGCGCAG
ATCAGTTGGAAGAATTTGTCCACTACGTGAAAGGCGAGATCACCAAGGTAGTCGGCAAATAATTTGATATCGAGCTCGCTTGGACTCCTGTTGATAG
ATCCAGTAATGACCTCAGAACTCCATCTGGATTTGTTCAGAACGCTCGGTTGCCGCCGGGCGTTTTTATTGGTGAGAATCCAAGCCTCGGTGAGAAT
CCAAGCCTCGATCAACGTCTCATTTTCGCCAAAAGTTGGCCCAGGGCTTCCCGGTATCAACAGGGACACCAGGATTTATTTATTCTGCGAAGTGATCT
TCCGTCACAGGTATTTATTCGGCGCAAAGTGCGTCGGGTGATGCTGCCAACTTACTGATTTAGTGTATGATGGTGTTTTTGAGGTGCTCCAGTGGCTTC
TGTTTCTATCAGCTGTCCCTCCTGTTCAGCTACTGACGGGGTGGTGCGTAACGGCAAAAGCACCGCCGGACATCAGCGGTAGCGGAGTGTATACTGGC
TTACTATGTTGGCACTGATGAGGGTGTCAGTGAAGTGCTTCATGTGGCAGGAGAAAAAAGGCTGCACCGGTGCGTCAGCAGAATATGTGATACAGGA
TATATTCCGCTTCCTCGCTCACTGACTCGCTACGCTCGGTCGTTCGACTGCGGCGAGCGGAAATGGCTTACGAACGGGGCGGAGATTTCCTGGAAGAT
GCCAGGAAGATACTTAACAGGGAAGTGAGAGGGCCGCGGCAAAGCCGTTTTTCCATAGGCTCCGCCCCCCTGACAAGCATCACGAAATCTGACGCTC
AAATCAGTGGTGGCGAAACCCGACAGGACTATAAAGATACCAGGCGTTTCCCCCTGGCGGCTCCCTCGTGCGCTCTCCTGTTCCTGCCTTTCGGTTTA
CCGGTGTCATTCCGCTGTTATGGCCGCGTTTGTCTCATTCCACGCCTGACACTCAGTTCCGGGTAGGCAGTTCGCTCCAAGCTGGACTGTATGCACGAA
CCCCCCGTTCAGTCCGACCGCTGCGCCTTATCCGGTAACTATCGTCTTGAGTCCAACCCGGAAAGACATGCAAAAGCACCACTGGCAGCAGCCACTG
GTAATTGATTTAGAGGAGTTAGTCTTGAAGTCATGCGCCGGTTAAGGCTAAACTGAAAGGACAAGTTTTGGTGACTGCGCTCCTCCAAGCCAGTTACC
TCGGTTCAAAGAGTTGGTAGCTCAGAGAACCTTCGAAAAACCGCCCTGCAAGGCGGTTTTTTCGTTTTCAGAGCAAGAGATTACGCGCAGACCAAA
CGATCTCAAGAAGATCATCTTATTAATCAGATAAAATATTTCTAGATTTCAGTGCAATTTATCTCTTCAAATGTAGCACCTGAAGTCAGCCCCATACG
ATATAAGTTGTAATTCTCATGTTTGACAGCTTATCATCGATAAGCTTCCGATGGCGCGCCGAGAGGCTTTACACTTTATGCTTCCGGCTGAAGACAAG
GCACGACTCTCAAGGACAGAAAAGCCCGCCTTTCGGCGGGCTTTGAGTTCATTATTAGAGAGTAATAAGACCCAAATTAACGGCCATAATGGCCGCT
ACGCGGCGGGAGGTCACACCGAACTTCCGCCGAATATTTCCCATATGGAAGTTCACATTGGCTTCCGAGCAGTTGCAGATAACCGATATCTCCCAACT
GGTCTTGCCGATGGCGCACCACTGCAACACTTCCTTCTCCCGGCTGGTCAGAACCACCGGTTTGCTGACCGGATGTTCGAAGGCCAGTCCGGCCACCGC
TTTGCAGTGCGTAGTCCTTGAGCATCCACAGGGTCGGCAGGACCGACTCTATGAAACGGTTGGCCTCGGCCCGGTTTCCGCTTCCACGCTGAGGCTC
AGCGCGCCGAGTTCGCCGCGAGCACCATGCAGCGGCATGGTCAGCCCATACACCAGGCCGGCGGCCGAGGCTTCCTCGAAGAACTCGTGCTGCTTTC
GCGTCTGGTAGATGGACGGTTCCCAGAAAATCGGCAGTACGCTCTGGGTACAGTGACTGACCGTCGGGTCGACCCGCGCGTAGCCAGCCCGGTCGTA
ATGCTCGCGCAGGCGGCCGGGTAGTTGCCGACGATGAAGGCGTTCTCGTAGTCCTGGCTGTCCTTAGGCAACAGGCCGAACAGGATCTTCGAGAAT
CCAAGGTCGCTCGCCATCTTCTGGAGGATGGCGCTCCACTCCAATTTCCACTTGAGCGTTCCAGCTCAAGAAAACCGTCAACCAAGGCCATTAGAAA
ACTTCCTAGGCATGATTAAGATGTTTCAGTACGAAAATTGCTTTCATTGTTGATCTCCTTTTTAAGTGAACTTGGGCCCGCTTGCTGTGCTCAGTATCTT
GTTATCCGCTCACAATGTCAATGTTATCCGCTCACATTTATGAACAGCA

FIG. 20B

A) Linear DNAs used in this study.

| Name | Description | Notes |
|---|---|---|
| pJ23119-tetO-BCD2-phlF-ssrA(LAA) | # 3n2, 5n1, 4n | |
| pLacI-BCD2-tetR-ssrA(LAA) | & 5n1, 4n | |
| pLambdaCI-BCD2-lacI-ssrA(LAA) | % 5n1 | |
| pPhlF-BCD2-srpR-ssrA(LAA) | # 3n2, 5n1, 4n | |
| pSrpR-BCD2-lambdaCI-ssrA(LAA) | # 5n1 | |
| pSrpR-BCD2-tetR-ssrA(LAA) | # 3n2 | |
| pPhlF-BCD2-srpR | # 3n2/no-ssrA | |
| pSrpR-BCD2-tetR | # 3n2/no-ssrA | |
| pTetR-BCD2-phlF | # 3n2/no-ssrA | |
| pSrpR-BCD2-lacI-ssrA(LAA) | # 4n | |
| pBetI-BCD7-QacR-ssrA(LAA) | # 5n2 | |
| pPhlF-BCD7-srpR-ssrA(LAA) | # 5n2 | |
| pQacR-BCD7-tetR-ssrA(LAA) | # 5n2 | |
| PSrpR-BCD7-BetI-ssrA(LAA) | # 5n2 | |
| pTetR-BCD7-phlF-ssrA(LAA) | # 5n2 | |
| pJ23151-BCD7-betI | $ transfer fxns | |
| pJ23151-BCD7-lacI | $ transfer fxns | |
| pJ23151-BCD7-lambdaCI | $ transfer fxns | |
| pJ23151-BCD7-phlF | $ transfer fxns | |
| pJ23151-BCD7-qacR | $ transfer fxns | |
| pJ23151-BCD7-srpR | $ transfer fxns | |
| pJ23151-BCD7-tetR | $ transfer fxns | |
| pLacI-BCD2-sfGFP-ssrA(LAA) | & test reporter | |
| pLambdaCI-BCD2-sfGFP-ssrA(LAA) | % test reporter | |
| pPhlF-BCD2-sfGFP-ssrA(LAA) | # test reporter | |
| pSrpR-BCD2-sfGFP-ssrA(LAA) | # test reporter | |
| pTetR-BCD2-sfGFP-ssrA(LAA) | # test reporter | |

\# Promoter from Stanton et al. (2014)
$ Promoter from Anderson promoter panel
% Promoter from Elowitz and Leibler (2000)
& Promoter from Lutz and Bujard (1997)

FIG. 21A

B) Plasmids used in this study.

| Name | Description | Resistance | Copy number | Notes |
|---|---|---|---|---|
| pZS1 | % Original repressilator plasmid | ampR | pSC101 | |
| pZS1 w/ OR2* mutation | % | ampR | pSC101 | minimize passages |
| pZE21-GFP(AAV) | % Original repressilator reporter (pTetO1) | kanR | colE1 | |
| pZE21-sfGFP(ASV) | % pZE21-GFPAAV with sfGFP replacement | kanR | colE1 | |
| pET21a(+)-Histag-Cerulean | Expression vector for Cerulean purification | ampR | colE1 | c. Transcriptic Inc. |
| pET21a(+)-Histag-Citrine | Expression vector for Citrine purification | ampR | colE1 | c. Transcriptic Inc. |
| pET21a(+)-Histag-mCherry | Expression vector for mCherry purification | ampR | colE1 | c. Transcriptic Inc. |
| pTetR(r)-BCD7-Citrine | % transfer fxns | kanR | pSC101* | |
| pTetR-BCD7-Citrine | # transfer fxns | kanR | pSC101* | c. Transcriptic Inc. |
| pSrpR-BCD7-Citrine | # transfer fxns | kanR | pSC101* | c. Transcriptic Inc. |
| pQacR-BCD7-Citrine | # transfer fxns, in vivo reporter | kanR | pSC101* | c. Transcriptic Inc. |
| pPhlF-BCD7-Citrine | # transfer fxns, in vivo reporter | kanR | pSC101* | c. Transcriptic Inc. |
| pLacI-BCD7-Citrine | & transfer fxns | kanR | pSC101* | c. Transcriptic Inc. |
| pLacI(r)-BCD7-Citrine | % transfer fxns | kanR | pSC101* | |
| pCI(OR2*)-BCD7-Citrine | * transfer fxns | kanR | pSC101* | |
| pCI-BCD7-Citrine | % transfer fxns | kanR | pSC101* | |
| pBetI-BCD7-Citrine | # transfer fxns | kanR | pSC101* | c. Transcriptic Inc. |
| 3n1 | oscillator plasmid | kanR | pSC101* | minimize passages |
| 3n2 | oscillator plasmid | kanR | pSC101* | minimize passages |
| 5n1 | oscillator plasmid | kanR | pSC101* | minimize passages |
| 5n2 | oscillator plasmid | kanR | pSC101* | minimize passages |
| pBetI-BCD7-phlF-ssrA(LAA) | # for building 3n1 | ampR | pSC101* | |
| pBetI-BCD7-qacR-ssrA(LAA) | # for building 3n2 | ampR | pSC101* | |
| pLacO1-BCD7-tetR-ssrA(LAA) | & for building 3n1 | ampR | colE1 | amplify in lacI repressor strain |
| pLambdaCI-BCD7-lacI-ssrA(LAA) | % for building 5n1 | ampR | colE1 | amplify in lambdaCI repressor strain |
| pPhlF-BCD7-srpR-ssrA(LAA) | # for building 3n1, 3n2, 5n1, 5n2 | ampR | pSC101* | |
| pQacR-BCD7-tetR-ssrA(LAA) | # for building 3n2 | ampR | pSC101* | |
| pSrpR-BCD7-betI-ssrA(LAA) | # for building 3n1, 3n2 | ampR | pSC101* | |
| pSrpR-BCD7-lambdaCI-ssrA(LAA) | # for building 5n1 | ampR | pSC101* | |
| pSrpR-BCD7-tetR-ssrA(LAA) | # for building 3n2 | ampR | pSC101* | |
| pTetR-BCD7-phlF-ssrA(LAA) | # for building 3n2, 5n1, 5n2 | ampR | colE1 | amplify in tetR repressor strain |

FIG. 21B

| | | | | |
|---|---|---|---|---|
| pPhlF-BCD20-sfGFP-ssrA(LAA) | # 1 color strong reporter used in study | ampR | colE1 | |
| pPhlF-BCD22-sfGFP-ssrA(LAA) | # 1 color weak reporter used in study | ampR | colE1 | |
| pPhlF-BCD20-Citrine-ssrA(LAA) | # for building 3-color reporter plasmid | ampR | colE1 | |
| pSrpR-BCD20-Cerulean-ssrA(LAA) | # for building 3-color reporter plasmid | ampR | colE1 | |
| pTetR-BCD20-mCherry-ssrA(LAA) | # for building 3-color reporter plasmid | ampR | colE1 | |
| 3-color BCD20 reporter: pPhlF/pSrpR/pJ23119-tetO | 3 color reporter plasmid | cmR | colE1 | minimize passages |
| pTetR(r)-Citrine(ASV) | % in vitro reporter | kanR | colE1 | |
| pTetR(r)-Cerulean(ASV) | % in vitro reporter | kanR | colE1 | |
| pLacI(r)-mCherry(ASV) | % in vitro reporter | kanR | colE1 | |
| pLacI(r)-Cerulean(ASV) | % in vitro reporter | kanR | colE1 | |
| pCI-Citrine-(ASV) | % in vitro reporter | kanR | colE1 | |
| pLacI(r)/TetR(ASV) | % for initial conditions experiment | kanR | colE1 | |
| pTetR(r)-CI(ASV) | % for initial conditions experiment | kanR | colE1 | |

\# Promoter from Stanton et al. (2014)
$ Promoter from Anderson promoter panel
% Promoter from Elowitz and Leibler (2000)
& Promoter from Lutz and Bujard (1997)
\* Promoter from Rosenfeld et al. (2005)

FIG. 21C

C) Strains used in this study.

| Name | E. coli type | Resistance | Notes |
|---|---|---|---|
| Rosetta2 | JS006 | cmR | |
| pZS1 + pZE21-GFP(AAV) | JS006 | kanR ampR | |
| pET21a(+)-Histag-Citrine | BL21-DE3 | ampR | |
| pET21a(+)-Histag-Cerulean | BL21-DE3 | ampR | |
| pET21a(+)-Histag-mCherry | BL21-DE3 | ampR | |
| 3n1 + pPhlF-BCD20-sfGFP-ssrA(LAA) | JS006 | kanR ampR | minimize passages |
| 3n1 + pPhlF-BCD22-sfGFP-ssrA(LAA) | JS006 | kanR ampR | minimize passages |
| 3n2 + pPhlF-BCD20-sfGFP-ssrA(LAA) | JS006 | kanR ampR | minimize passages |
| 3n2 + pPhlF-BCD22-sfGFP-ssrA(LAA) | JS006 | kanR ampR | minimize passages |
| 5n1 + pPhlF-BCD20-sfGFP-ssrA(LAA) | JS006 | kanR ampR | cells unhealthy, minimize passages |
| 5n1 + pPhlF-BCD22-sfGFP-ssrA(LAA) | JS006 | kanR ampR | minimize passages |
| 5n2 + pPhlF-BCD20-sfGFP-ssrA(LAA) | JS006 | kanR ampR | minimize passages |
| 5n2 + pPhlF-BCD22-sfGFP-ssrA(LAA) | JS006 | kanR ampR | minimize passages |
| 3n2 + 3-color BCD20 reporter, pPhlF/pSrpR/pJ23119-tetO | JS006 | kanR cmR | minimize passages |
| pZS1 + pZE21-eGFP(ASV) | JS006 | kanR ampR | |
| pZS1 w/ OR2* mutation + pZS21-eGFP(ASV) | JS006 | kanR ampR | |

FIG. 21D

D) DNA concentrations used in experiments.

| Experiment | DNA and concentration | Type of DNA |
|---|---|---|
| Repressilator orig./O₂²*, 3color | Repressilator pZS1 or pZS1 w/ O₂²* mutation, 0.5 nM (if not otherwise indicated) | Plasmid |
| | pTetR(r)-Cerulean(ASV), 5 nM | Plasmid |
| | pLacI(r)-mCherry(ASV), 5 nM | Plasmid |
| | pCI-Citrine(ASV), 5 nM | Plasmid |
| Repressilator, initial conditions | Reaction in nano-reactor: | |
| | Repressilator pZS1, 5 nM | Plasmid |
| | pLacI(r)-Cerulean(ASV), 5 nM | Plasmid |
| | pTetR(r)-Citrine-(ASV), 5 nM | Plasmid |
| | Pre-synthesis reaction (CI): | |
| | pTetR(r)-Citrine(ASV), 5 nM | Plasmid |
| | pTetR(r)-CI(ASV), 5 nM | Plasmid |
| | Pre-synthesis reaction (TetR): | |
| | pLacI(r)-Cerulean(ASV), 5 nM | Plasmid |
| | pLacI(r)TetR(ASV), 5 nM | Plasmid |
| Response curve measurements | Promoter plasmid: pXXX-BCD7-Citrine, 1 nM | Plasmid |
| | Repressor template: pJ23151-BCD7-XXX, 0-2.5 nM | Linear |
| | Repressor reporter: pJ23151-BCD7-Cerulean, 0-2.5 nM | Linear |
| 3n1 | 3n1 oscillator plasmid, 5 nM | Plasmid |
| | pPhlF-BCD7-Citrine, 2.5 nM | Plasmid |
| 3n2 | pJ23119-tetO-BCD2-phlF-ssrA(LAA), 1.5 nM | Linear |
| | pPhlF-BCD2-srpR-ssrA(LAA), 12 nM | Linear |
| | pSrpR-BCD2-tetR-ssrA(LAA), 34 nM | Linear |
| | pTetR(r)-Cerulean(ASV), 5 nM | Plasmid |
| 3n2/no-ssrA | pJ23119-tetO-BCD2-phlF, 1.5 nM | Linear |
| | pPhlF-BCD2-srpR, 12 nM | Linear |
| | pSrpR-BCD2-tetR, 34 nM | Linear |
| | pTetR(r)-Cerulean(ASV), 5 nM | Plasmid |
| 4n | pJ23119-tetO-BCD2-phlF-ssrA(LAA), 0.75 nM | Linear |
| | pLacI-BCD2-tetR-ssrA(LAA), 6 nM | Linear |

FIG. 21E

|  | pPhlF-BCD2-srpR-ssrA(LAA), 6 nM | Linear |
|---|---|---|
|  | pSrpR-BCD2-lacI-ssrA(LAA), 12 nM | Linear |
|  | pTetR(r)-Cerulean(ASV), 2.5 nM | Plasmid |
|  | pLacI(r)-mCherry(ASV), 2.5 nM | Plasmid |
|  | pPhlF-BCD7-Citrine, 2.5 nM | Plasmid |
|  |  |  |
| Sn1 | pJ23119-tetO-BCD2-phlF-ssrA(LAA), 1.1 nM | Linear |
|  | pLacI-BCD2-tetR-ssrA(LAA), 16.8 nM | Linear |
|  | pLambdaCI-BCD2-lacI-ssrA(LAA), 1.4 nM | Linear |
|  | pPhlF-BCD2-srpR-ssrA(LAA), 5.6 nM | Linear |
|  | pSrpR-BCD2-lambdaCI-ssrA(LAA), 11.2 nM | Linear |
|  | pCI-Citrine(ASV), 3 nM | Plasmid |
|  | pTetR(r)-Cerulean(ASV), 2.5 nM | Plasmid |
|  |  |  |
| Sn1, plasmid DNA | Sn1 oscillator plasmid, 5 nM | Plasmid |
|  | pTetR(r)-Cerulean(ASV), 5 nM | Plasmid |
|  | pLacI(r)-mCherry(ASV), 5 nM | Plasmid |
|  | pCI-Citrine(ASV), 5 nM | Plasmid |
|  |  |  |
| Sn2 | pBetI-BCD7-QacR-ssrA(LAA), 1 nM | Linear |
|  | pPhlF-BCD7-srpR-ssrA(LAA), 12 nM | Linear |
|  | pQacR-BCD7-tetR-ssrA(LAA), 4 nM | Linear |
|  | pSrpR-BCD7-BetI-ssrA(LAA), 24 nM | Linear |
|  | pTetR-BCD7-phlF-ssrA(LAA), 4 nM | Linear |
|  | pTetR(r)-Cerulean(ASV), 2.5 nM | Plasmid |
|  | pQacR-BCD7-Citrine, 2.5 nM | Plasmid |

FIG. 21F

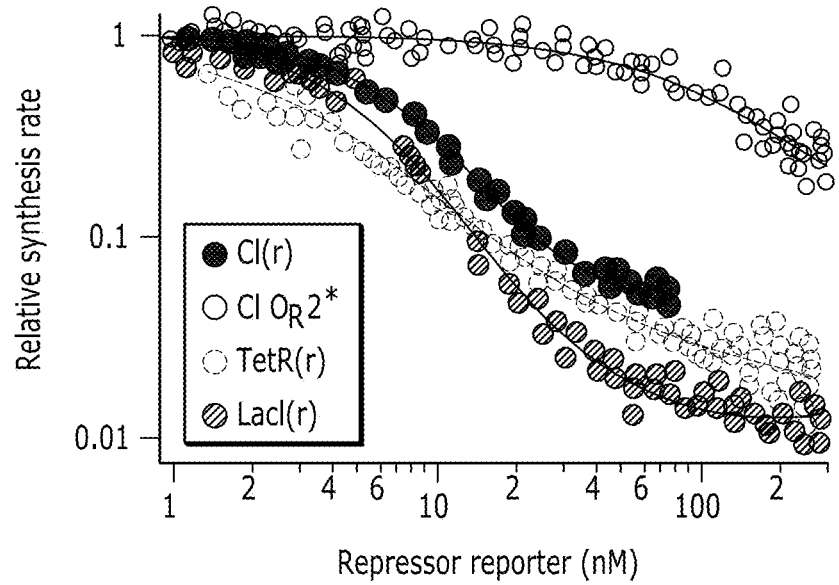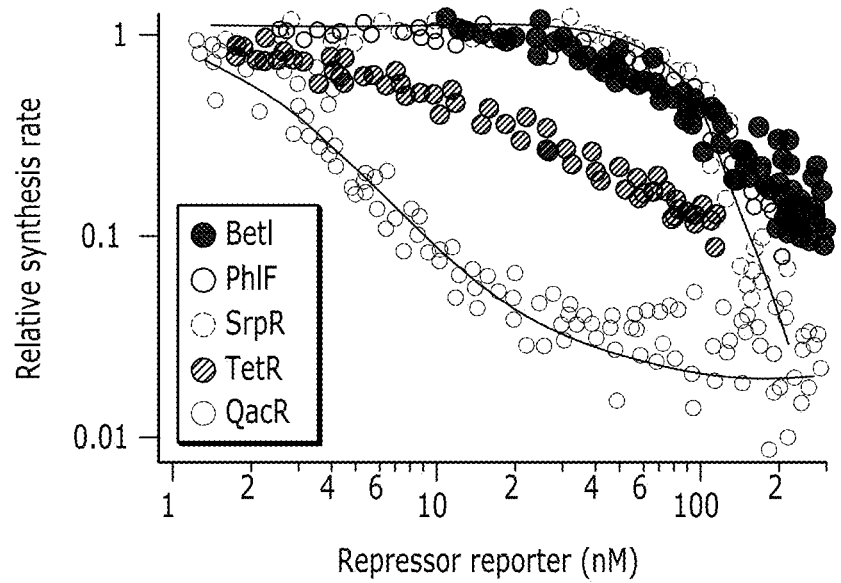
FIG. 23A

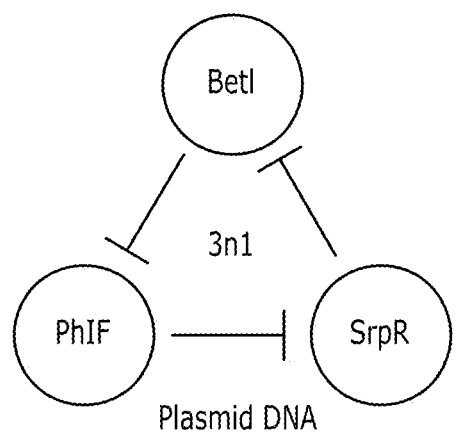
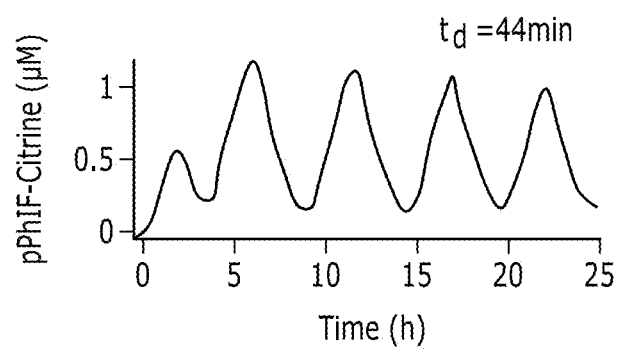
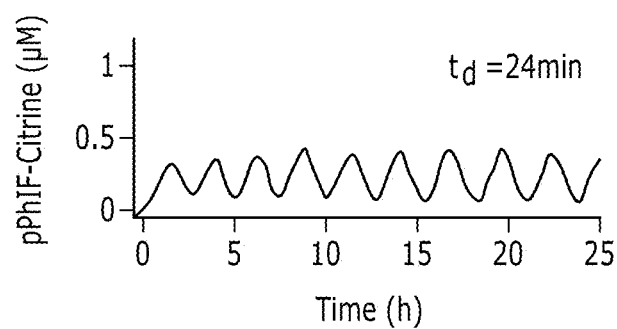
FIG. 23B

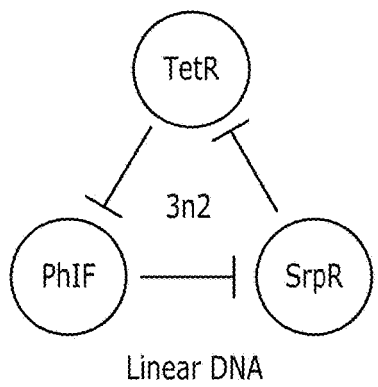
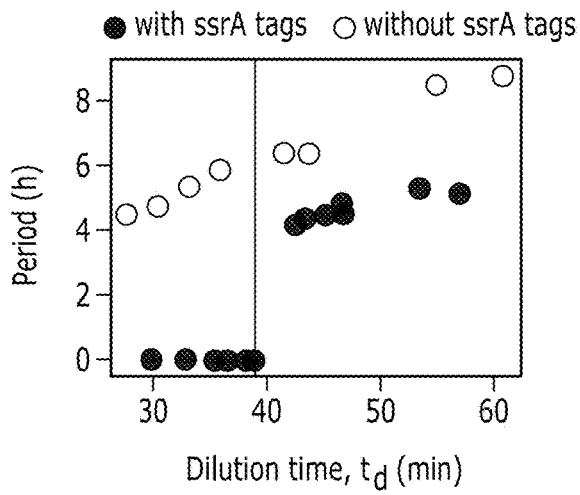
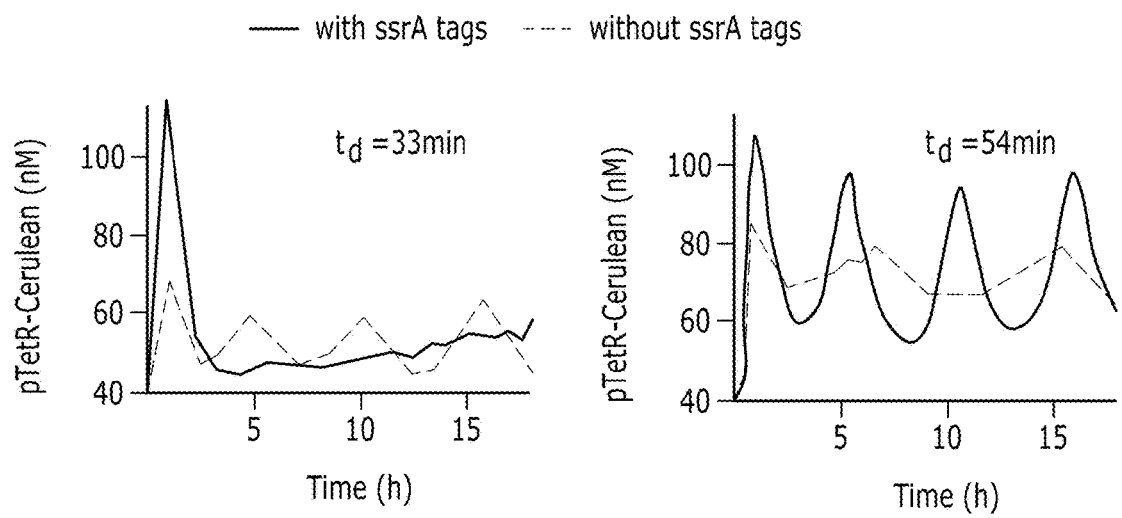
FIG. 23C

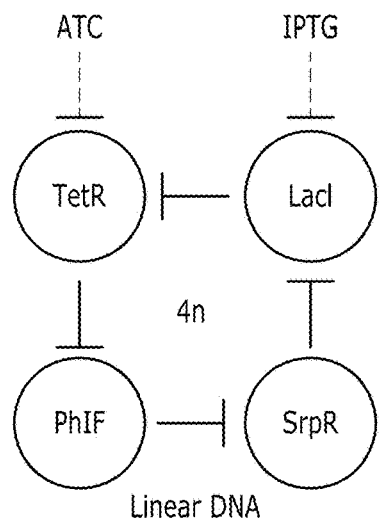
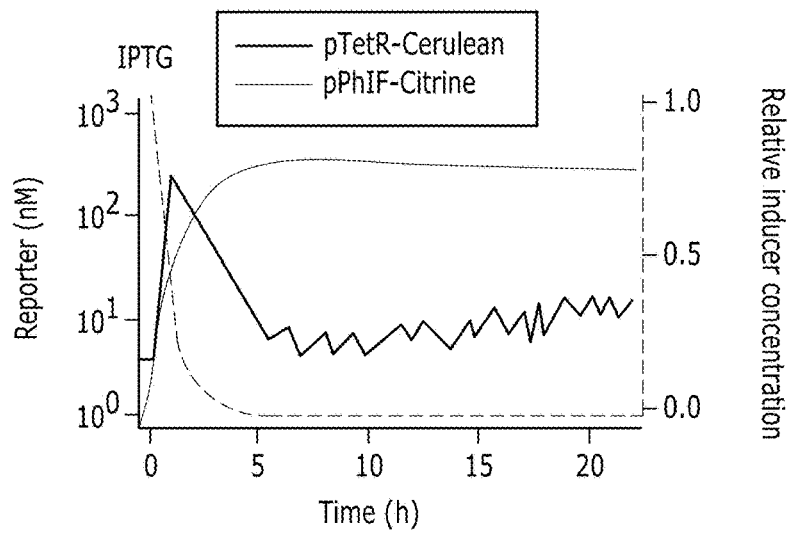
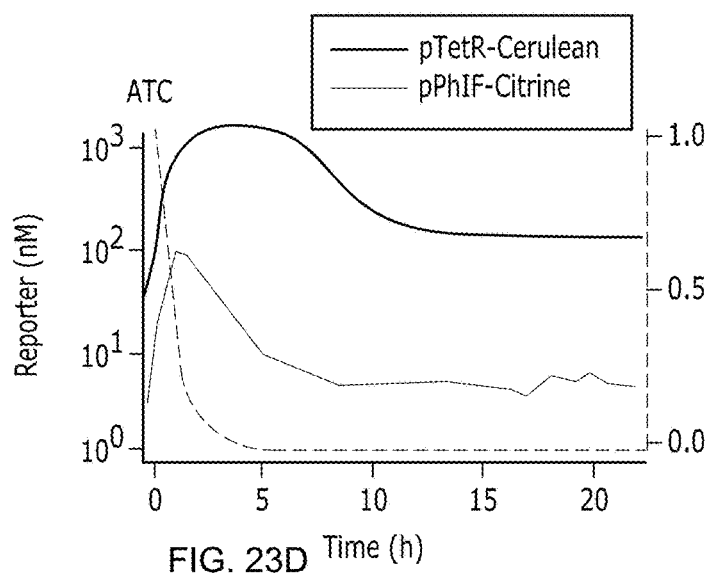
FIG. 23D

>pRsaL (aka POrig)
AGAACGGTCTCAGCATTGCTGTTCAACTAGCAAATGAGATAGATTTCGGTGAACCCGGACCCTTGCTAGGCTCGAA
AGCTGAGACCTTAC >pLasI_1SNP_-10 (aka pLasI_mut, P1)

AGAACGGTCTCAGCATTGCTGTTCCGCTGGGCATGCTTCGAGCCTAGCAAGGGTCCGGGTTCACCGAAATCTATCT
CATTTGCTAGTTATAAAATTATGAAATTTGCGTAAATTCTTCAGAAGCTGAGACCTTACG

>pLasI (aka P2)
AGAACGGTCTCAGCATTGCTGTTCCGCTGGGCATGCTTCGAGCCTAGCAAGGGTCCGGGTTCACCGAAATCTATCT
CATTTGCTAGTTATAAAATTATGAAATTTGCATAAATTCTTCAGAAGCTGAGACCTTACG >pLasB (aka P3)
AGAACGGTCTCAGCATTGCTGTTCCGCTGGGCATGCTGCAGCAGCGGATCGTCGGCGAGCGTCACCTGAAGCTGGT
GCTGAAAAGCGAATGCGGCTCGCTGCAACTGGATGGCATTGCCTTCAACATCGACCGCGAGCAGTGGCCCAACCC
TACCGTGCGCTGGGCCGAGCTGGCCTACAAGCTCGACGTCAACGAATTCCGCGGCCAGGAAAGCGTGCAACTGAT
GATCGTCCACATGGCCCCTCGCTGAGCGCGTCCCGGAGCTGGGGGCAACCTAGCTGCCACCTGCTTTTCTGCTAGC
TATTCCAGCGAAAACATACAGATTTCCGGCGAAATCAAGGCTACCTGCCAGTTCTGGCAGGTTTGGCCGCGGGTTC
TTTTTGGTACACGAAAGCACCGTCAAGCTGAGACCTTACG >pRasL_long(las) (aka pRsaL_ext, P4)

AGAACGGTCTCAGCATTGCTGTTCCGCTGGGCATGCAACTAGCAAATGAGATAGATTTCGGTGAACCCGGACCCTT
GCTAGGCTCGAAGAAACGTCAAGCTGAGACCTTACG

FIG. 37

212 P1_tetO(variant1)-UTR1-deGFP-T500

GCATTGCTGTTCCGCTGGGCATGCTTCGAGCCTAGCAAGGGTCCGGGTTCACCGAAATCTATCTCATTTGCTAGTTATAAAATTATGAAATTTGCGTA
AATTCCCTATCAGTGATAGAGATTCAGAAGCAATAATTTTGTTTAACTTTAAGAAGGAGATATACCATGGAGCTTTTCACTGGCGTTGTTCCCATCCTG
GTCGAGCTGGACGGCGACGTAAACGGCCACAAGTTCAGCGTGTCCGGCGAGGGCGAGGGCGATGCCACCTACGGCAAGCTGACCCTGAAGTTCATCT
GCACCACCGGCAAGCTGCCCGTGCCCTGGCCCACCCTCGTGACCACCCTGACCTACGGCGTGCAGTGCTTCAGCCGCTACCCCGACCACATGAAGCA
GCACGACTTCTTCAAGTCCGCCATGCCCGAAGGCTACGTCCAGGAGCGCACCATCTTCTTCAAGGACGACGGCAACTACAAGACCCGCGCCGAGGTG
AAGTTCGAGGGCGACACCCTGGTGAACCGCATCGAGCTGAAGGGCATCGACTTCAAGGAGGACGGCAACATCCTGGGGCACAAGCTGGAGTACAAC
TACAACAGCCACAACGTCTATATCATGGCCGACAAGCAGAAGAACGGCATCAAGGTGAACTTCAAGATCCGCCACAACATCGAGGACGGCAGCGTG
CAGCTCGCCGACCACTACCAGCAGAACACCCCCATCGGCGACGGCCCCGTGCTGCTGCCCGACAACCACTACCTGAGCACCCAGTCCGCCCTGAGCA
AAGACCCCAACGAGAAGCGCGATCACATGGTCCTGCTGGAGTTCGTGACCGCCGCCGGGATCTAATGAAGCATCTGGTGAATAACTCGAGCAAAGCC
CGCCGAAAGGCGGGCTTTTCTGTGTCGACCGATGCCCTTGAGAGTCGGGCATTGTCTTCGCTCCTTCCGGTGGGCGCGGGGCATGACTATCGTCGCCG
CACTTATGACTGTGTTCTTTATCATGCAACTCGTAGGACAGGTGCCGGCAGCGCTCTTCCGCTTCCTCGCTCACTGACTCGCTGCGCTCGGTCGTTCGG
CTGCGGCGAGCGGTATCAGCTCACTCAAAGGCGGTAATACGGTTATCCACAGAATCAGGGGATAACGCAGGAAAGAACATGTGAGCAAAAGGCCAG
CAAAAGGCCAGGAACCGTAAAAAGGCCGCGTTGCTGGCGTTTTTCCATAGGCTCCGCCCCCTGACGAGCATCACAAAAATCGACGCTCAAGTCAGA
GGTGGCGAAACCCGACAGGACTATAAAGATACCAGGCGTTTCCCCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACGCTGTAGGTATCTCAGTTCGGTGTAGGTCGTTCGCTCCAAGCTGGGCTGT
GTGCACGAACCCCCCGTTCAGCCCGACCGCTGCGCCTTATCCGGTAACTATCGTCTTGAGTCCAACCCGGTAAGACACGACTTATCGCCACTGGCAGC
AGCCACTGGTAACAGGATTAGCAGAGCGAGGTATGTAGGCGGTGCTACAGAGTTCTTGAAGTGGTGGCCTAACTACGGCTACACTAGAAGAACAGTA
TTTGGTATCTGCGCTCTGCTGAAGCCAGTTACCTTCGGAAAAAGAGTTGGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATCCTTTGATCTTTTCTACGGGGTCTGACGCTCAGTGGAACGAAAACTCA
CGTTAAGGGATTTTGGTCATGAGATTATCAAAAAGGATCTTCACCTAGATCCTTTTAAATTAAAAATGAAGTTTTAAATCAATCTAAAGTATATATGA
GTAAACTTGGTCTGACAGTTACCAATGCTTAATCAGTGAGGCACCTATCTCAGCGATCTGTCTATTTCGTTCATCCATAGTTGCCTGACTCCCCGTCGT
GTAGATAACTACGATACGGGAGGGCTTACCATCTGGCCCCAGTGCTGCAATGATACCGCGTGACCCACGCTCACCGGCTCCAGATTTATCAGCAATA
AACCAGCCAGCCGGAAGGGCCGAGCGCAGAAGTGGTCCTGCAACTTTATCCGCCTCCATCCAGTCTATTAATTGTTGCCGGGAAGCTAGAGTAAGTA
GTTCGCCAGTTAATAGTTTGCGCAACGTTGTTGCCATTGCTACAGGCATCGTGGTGTCACGCTCGTCGTTTGGTATGGCTTCATTCAGCTCCGGTTCCC
AACGATCAAGGCGAGTTGCATGATCCCCCATGTTGTGCAAAAAAGCGGTTAGCTCCTTCGGTCCTCCGATCGTTGTCAGAAGTAAGTTGGCCGCAGTG
TTATCACTCATGGTTATGGCAGCACTGCATAATTCTCTTACTGTCATGCCATCCGTAAGATGCTTTTCTGTGACTGGTGAGTACTCAACCAAGTCATTC
TGAGAATAGTGTATGCGGCGACCGAGTTGCTCTTGCCCGGCGTCAACACGGGATAATACCGCGCCACATAGCAGAACTTTAAAAGTGCTCATCATTG
GAAAACGTTCTTCGGGGCGAAAACTCTCAAGGATCTTACCGCTGTTGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAAGGGAATAAGGGCGACACGGAAATGTTGAATACTCATA
CTCTTCCTTTTTCAATATTATTGAAGCATTTATCAGGGTTATTGTCTCATGAGCGGATACATATTTGAATGTATTTAGAAAAATAAACAAATAGGGGTT
CCGCGCACATTTCCCCGAAAAGTGCCACCTGACGTCTAAGAAACCATTATTATCATGACATTAACCTATAAAAATAGGCGTATCACGAGGCCCTTTCG
TGTTCAAGAATTCTGGCGAATCCTCTGACCAGCCAGAAAACGACCTTTCTGTGGTGAAACCGGATGCTGCAATTCAGAGCGCCAGCAAGTGGGGGAC
AGCAGATGACCTGACCGCCGCAGAGTGGATGTTTGACATGGTGATGACTATCGCACCATCAGCCAGAAAACCGAATTTTGCTGGGTGGGCTAACGAT
ATCCGCCTGATGCGTGAACGTGACGGACGTAACGAAGACAACCAC

FIG. 40A

213 P1_tetO(variant2)-UTR1-deGFP-T500

```
GCATTGCTGTTCCGCTGGGCATGCTTCGAGCCTAGCAAGGGTCCGGGTTCACCGAAATCTATCTCATTTGCTAGTTATAAAATTATGAAATTTGCGTA
AATTCTTCAGTCCCTATCAGTGATAGAGAAAGCAATAATTTTGTTTAACTTTAAGAAGGAGATATACCATGGAGCTTTTCACTGGCGTTGTTCCCATCC
TGGTCGAGCTGGACGGCGACGTAAACGGCCACAAGTTCAGCGTGTCCGGCGAGGGCGAGGGCGATGCCACCTACGGCAAGCTGACCCTGAAGTTCA
TCTGCACCACCGGCAAGCTGCCCGTGCCCTGGCCCACCCTCGTGACCACCCTGACCTACGGCGTGCAGTGCTTCAGCCGCTACCCCGACCACATGAAG
CAGCACGACTTCTTCAAGTCCGCCATGCCCGAAGGCTACGTCCAGGAGCGCACCATCTTCTTCAAGGACGACGGCAACTACAAGACCCGCGCCGAGG
TGAAGTTCGAGGGCGACACCCTGGTGAACCGCATCGAGCTGAAGGGCATCGACTTCAAGGAGGACGGCAACATCCTGGGGCACAAGCTGGAGTACA
ACTACAACAGCCACAACGTCTATATCATGGCCGACAAGCAGAAGAACGGCATCAAGGTGAACTTCAAGATCCGCCACAACATCGAGGACGGCAGCG
TGCAGCTCGCCGACCACTACCAGCAGAACACCCCCATCGGCGACGGCCCCGTGCTGCTGCCCGACAACCACTACCTGAGCACCCAGTCCGCCCTGAG
CAAAGACCCCAACGAGAAGCGCGATCACATGGTCCTGCTGGAGTTCGTGACCGCCGCCGGGATCTAATGAAGCATCTGGTGAATAACTCGAGCAAAG
CCCGCCGAAAGGCGGGCTTTTCTGTGTCGACCGATGCCCTTGAGAGTCGGGCATTGTCTTCGCTCCTTCCGGTGGGCGCGGGGCATGACTATCGTCGC
CGCACTTATGACTGTGTTCTTTATCATGCAACTCGTAGGACAGGTGCCGGCAGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCTCACGCTGTAGGTATCTCAGTTCGGTGTAGGTCGTTCGCTCCAAGCTGGGCT
GTGTGCACGAACCCCCCGTTCAGCCCGACCGCTGCGCCTTATCCGGTAACTATCGTCTTGAGTCCAACCCGGTAAGACACGACTTATCGCCACTGGCA
GCAGCCACTGGTAACAGGATTAGCAGAGCGAGGTATGTAGGCGGTGCTACAGAGTTCTTGAAGTGGTGGCCTAACTACGGCTACACTAGAAGAACA
GTATTTGGTATCTGCGCTCTGCTGAAGCCAGTTACCTTCGGAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGATCTTTTCTACGGGGTCTGACGCTCAGTGGAACGAAAACT
CACGTTAAGGGATTTTGGTCATGAGATTATCAAAAAGGATCTTCACCTAGATCCTTTTAAATTAAAAATGAAGTTTTAAATCAATCTAAAGTATATAT
GAGTAAACTTGGTCTGACAGTTACCAATGCTTAATCAGTGAGGCACCTATCTCAGCGATCTGTCTATTTCGTTCATCCATAGTTGCCTGACTCCCCGTC
GTGTAGATAACTACGATACGGGAGGGCTTACCATCTGGCCCCAGTGCTGCAATGATACCGCGTGACCCACGCTCACCGGCTCCAGATTTATCAGCAAT
AAACCAGCCAGCCGGAAGGGCCGAGCGCAGAAGTGGTCCTGCAACTTTATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCATCGTGGTGTCACGCTCGTCGTTTGGTATGGCTTCATTCAGCTCCGGTTCC
CAACGATCAAGGCGAGTTGCATGATCCCCCATGTTGTGCAAAAAAGCGGTTAGCTCCTTCGGTCCTCCGATCGTTGTCAGAAGTAAGTTGGCCGCAGT
GTTATCACTCATGGTTATGGCAGCACTGCATAATTCTCTTACTGTCATGCCATCCGTAAGATGCTTTTCTGTGACTGGTGAGTACTCAACCAAGTCATT
CTGAGAATAGTGTATGCGGCGACCGAGTTGCTCTTGCCCGGCGTCAACACGGGATAATACCGCGCCACATAGCAGAACTTTAAAAGTGCTCATCATT
GGAAAACGTTCTTCGGGGCGAAAACTCTCAAGGATCTTACCGCTGTTGAGATCCAGTTCGATGTAACCCACTCGTGCACCCAACTGATCTTCAGCATC
TTTTACTTTCACCAGCGTTTCTGGGTGAGCAAAAACAGGAAGGCAAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCGGATACATATTTGAATGTATTTAGAAAAATAAACAAATAGGGGT
TCCGCGCACATTTCCCCGAAAAGTGCCACCTGACGTCTAAGAAACCATTATTATCATGACATTAACCTATAAAAATAGGCGTATCACGAGGCCCTTTC
GTGTTCAAGAATTCTGGCGAATCCTCTGACCAGCCAGAAAACGACCTTTCTGTGGTGAAACCGGATGCTGCAATTCAGAGCGCCAGCAAGTGGGGGA
CAGCAGATGACCTGACCGCCGCAGAGTGGATGTTTGACATGGTGATGACTATCGCACCATCAGCCAGAAAACCGAATTTTGCTGGGTGGGCTAACGA
TATCCGCCTGATGCGTGAACGTGACGGACGTAACGAAGACAACCAC
```

FIG. 40B 220 pLas(P1)_UTR1_tetR_B1002

>GCATTGCTGTTCCGCTGGGCATGCTTCGAGCCTAGCAAGGGTCCGGGTTCACCGAAATCTATCTCATTTGCTAGTTATAAAATTATGAAATTTGCGTA
AATTCTTCAGAAGCAATAATTTTGTTTAACTTTAAGAAGGAGATATACCATGTCTAGATTAGATAAAAGTAAAGTGATTAACAGCGCATTAGAGCTGC
TTAATGAGGTCGGAATCGAAGGTTTAACAACCCGTAAACTCGCCCAGAAGCTAGGTGTAGAGCAGCCTACATTGTATTGGCATGTAAAAAATAAGCG
GGCTTTGCTCGACGCCTTAGCCATTGAGATGTTAGATAGGCACCATACTCACTTTTGCCCTTTAGAAGGGGAAAGCTGGCAAGATTTTTTACGTAATA
ACGCTAAAAGTTTTAGATGTGCTTTACTAAGTCATCGCGATGGAGCAAAAGTACATTTAGGTACACGGCCTACAGAAAAACAGTATGAAACTCTCGA
AAATCAATTAGCCTTTTTATGCCAACAAGGTTTTTCACTAGAGAATGCATTATATGCACTCAGCGCTGTGGGGCATTTTACTTTAGGTTGCGTATTGGA
AGATCAAGAGCATCAAGTCGCTAAAGAAGAAAGGGAAACACCTACTACTGATAGTATGCCGCCATTATTACGACAAGCTATCGAATTATTTGATCAC
CAAGGTGCAGAGCCAGCCTTCTTATTCGGCCTTGAATTGATCATATGCGGATTAGAAAAACAACTTAAATGTGAAAGTGGGTCTTAATGAACTCGCA
AAAAACCCCGCTTCGGCGGGGTTTTTTCGCGTCGACCGATGCCCTTGAGAGTCGGGCATTGTCTTCGCTCCTTCCGGTGGGCGCGGGGCATGACTATC
GTCGCCGCACTTATGACTGTGTTCTTTATCATGCAACTCGTAGGACAGGTGCCGGCAGCGCTCTTCCGCTTCCTCGCTCACTGACTCGCTGCGCTCGGT
CGTTCGGCTGCGGCGAGCGGTATCAGCTCACTCAAAGGCGGTAATACGGTTATCCACAGAATCAGGGGATAACGCAGGAAAGAACATGTGAGCAAA
AGGCCAGCAAAAGGCCAGGAACCGTAAAAAGGCCGCGTTGCTGGCGTTTTTCCATAGGCTCCGCCCCCTGACGAGCATCACAAAAATCGACGCTCA
AGTCAGAGGTGGCGAAACCCGACAGGACTATAAAGATACCAGGCGTTTCCCCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCATAGCTCACGCTGTAGGTATCTCAGTTCGGTGTAGGTCGTTCGCTCCAAGCT
GGGCTGTGTGCACGAACCCCCCGTTCAGCCCGACCGCTGCGCCTTATCCGGTAACTATCGTCTTGAGTCCAACCCGGTAAGACACGACTTATCGCCAC
TGGCAGCAGCCACTGGTAACAGGATTAGCAGAGCGAGGTATGTAGGCGGTGCTACAGAGTTCTTGAAGTGGTGGCCTAACTACGGCTACACTAGAAG
AACAGTATTTGGTATCTGCGCTCTGCTGAAGCCAGTTACCTTCGGAAAAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAGAAGATCCTTTGATCTTTTCTACGGGGTCTGACGCTCAGTGGAACGAA
AACTCACGTTAAGGGATTTTGGTCATGAGATTATCAAAAAGGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTCAGCGATCTGTCTATTTCGTTCATCCATAGTTGCCTGACTCCC
CGTCGTGTAGATAACTACGATACGGGAGGGCTTACCATCTGGCCCCAGTGCTGCAATGATACCGCGTGACCCACGCTCACCGGCTCCAGATTTATCAG
CAATAAACCAGCCAGCCGGAAGGGCCGAGCGCAGAAGTGGTCCTGCAACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAGGCATCGTGGTGTCACGCTCGTCGTTTGGTATGGCTTCATTCAGCTCCGG
TTCCCAACGATCAAGGCGAGTTGCATGATCCCCCATGTTGTGCAAAAAAGCGGTTAGCTCCTTCGGTCCTCCGATCGTTGTCAGAAGTAAGTTGGCCG
CAGTGTTATCACTCATGGTTATGGCAGCACTGCATAATTCTCTTACTGTCATGCCATCCGTAAGATGCTTTTCTGTGACTGGTGAGTACTCAACCAAGT
CATTCTGAGAATAGTGTATGCGGCGACCGAGTTGCTCTTGCCCGGCGTCAACACGGGATAATACCGCGCCACATAGCAGAACTTTAAAAGTGCTCAT
CATTGGAAAACGTTCTTCGGGGCGAAAACTCTCAAGGATCTTACCGCTGTTGAGATCCAGTTCGATGTAACCCACTCGTGCACCCAACTGATCTTCAG
CATCTTTTACTTTCACCAGCGTTTCTGGGTGAGCAAAAACAGGAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGCGGATACATATTTGAATGTATTTAGAAAAATAAACAAATAGG
GGTTCCGCGCACATTTCCCCGAAAAGTGCCACCTGACGTCTAAGAAACCATTATTATCATGACATTAACCTATAAAAATAGGCGTATCACGAGGCCCT
TTCGTGTTCAAGAATTCTGGCGAATCCTCTGACCAGCCAGAAAACGACCTTTCTGTGGTGAAACCGGATGCTGCAATTCAGAGCGCCAGCAAGTGGG
GGACAGCAGATGACCTGACCGCCGCAGAGTGGATGTTTGACATGGTGATGACTATCGCACCATCAGCCAGAAAACCGAATTTTGCTGGGTGGGCTAA
CGATATCCGCCTGATGCGTGAACGTGACGGACGTAACGAAGACAACCAC

FIG. 42

```
% set up extract and buffer tubes (Simbiology 'Model' objects) with parameters from a
    configuration file identified to a particular extract batch.
tube1 = txtl_extract('E1');
tube2 = txtl_buffer('E1');
tube3 = txtl_newtube('negative_autoreg');
% add DNA specifying a negative autoregulation circuit
txtl_add_dna(tube3, 'ptet(50)', 'rbs(20)','tetR(1200)', 1, 'plasmid');
txtl_add_dna(tube3, 'ptet(50)', 'rbs(20)','deGFP(1000)', 1, 'plasmid');
% combine tubes, add inducer, 'run' the experiment and visualize results
Mobj = txtl_combine({tube1, tube2, tube3}); % Simbiology Model object
txtl_addspecies(Mobj, 'aTc', 500);
[simData] = txtl_runsim(Mobj, 14*60*60); % 14 hours
txtl_plot(simData, Mobj);
```

FIG. 47

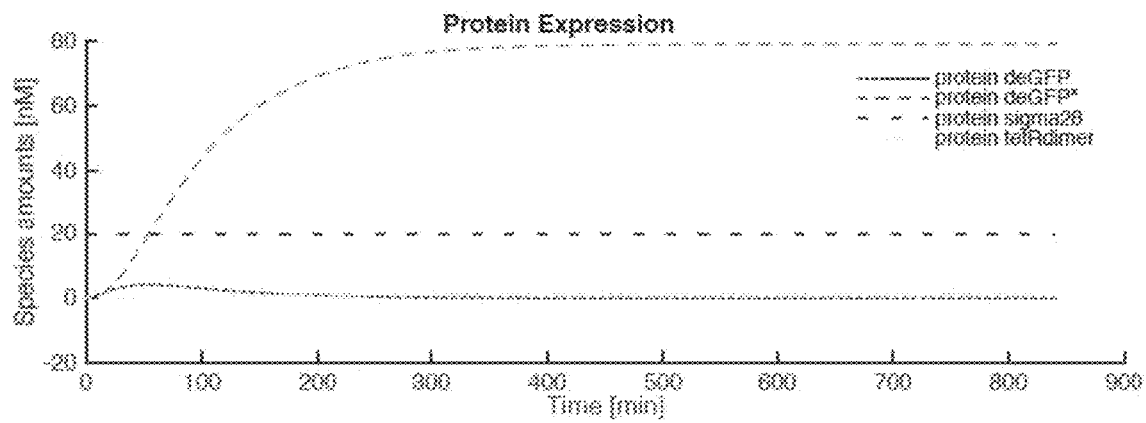
FIG. 48A
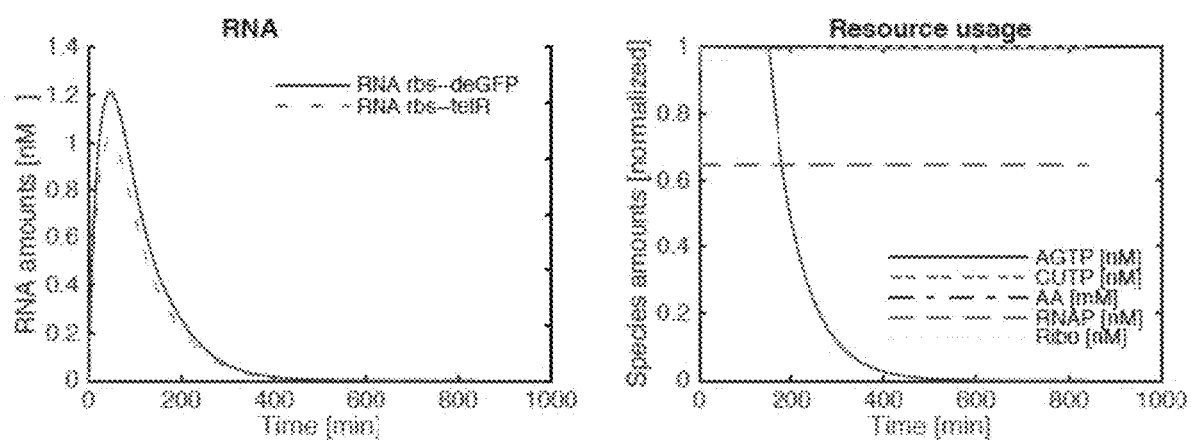
FIG. 48B
FIG. 48C

| Exp # | Schematic | Property being tested |
|---|---|---|
| 1 | 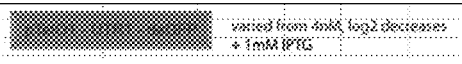 | pTet promoter consititutive production strength |
| 2 |  | pLac consititutive production strength |
| 3 | 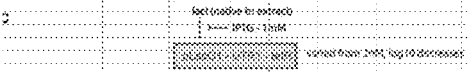 | tetR repression strength |
| 4 |  | aTc induction strength |
| 5 | 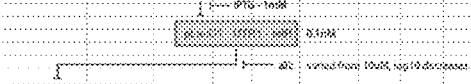 | 3OC12HSL induction strength |
FIG. 50

```
tube1 = txtl_extract('E38_2');
tube2 = txtl_buffer('E38_2');
tube3 = txtl_newtube('IFFL_vary30C12');
dna_lasR = txtl_add_dna(tube3, 'plac(50)', 'rbs(20)', 'lasR(1000)', 1, 'plasmid');
dna_tetR = txtl_add_dna(tube3, 'plas(50)', 'rbs(20)', 'tetR(1000)', 0.1, 'plasmid');
dna_deGFP = txtl_add_dna(tube3, 'plas_ptet(50)', 'rbs(20)', 'deGFP(1000)', 1, 'plasmid');
Mobj = txtl_combine([tube1, tube2, tube3]);
txtl_addspecies(Mobj, 'OC12HSL', 1000);
txtl_addspecies(Mobj, 'aTc', 10000);
configsetObj = getconfigset(Mobj);
set(configsetObj.SolverOptions, 'AbsoluteToleranceScaling', 1);
set(configsetObj.SolverOptions, 'AbsoluteTolerance', 1.0e-8);
set(configsetObj.SolverOptions, 'AbsoluteToleranceStepSize', 8*60*60*1.0e-8*0.1);
set(configsetObj.SolverOptions, 'RelativeTolerance', 1.0e-6);
[simData] = txtl_runsim(Mobj,8*60*60);
```

FIG. 55

| Linear DNA | Promoter | 5' UTR | CDS | Terminator |
|---|---|---|---|---|
| VioA | J23151 | BCD5 | vioA | T14 |
| VioB | J23151 | BCD5 | vioB | T14 |
| VioC | J23151 | BCD5 | vioC | T14 |
| VioD | J23151 | BCD5 | vioD | T14 |
| VioE | J23151 | BCD5 | vioE | T14 |

FIG. 58

CELL-FREE BIOMOLECULAR BREADBOARDS AND RELATED METHODS AND ARRANGEMENTS

CROSS REFERENCE TO RELATED APPLICATIONS

The present application claims priority to U.S. Provisional Application No. 62/117,319, entitled "In Vitro Biomolecular Breadboard Rapid and Predictive Prototyping of In Vivo Synthetic Dynamic Circuits" filed on Feb. 17, 2015, and to U.S. Provisional Application No. 62/143,878, entitled "In Vitro Method for Rapidly Exploring Generic Pathways that Produce Biological Products" filed on Apr. 7, 2015, the disclosure of each of which is incorporated by reference in its entirety.

STATEMENT OF GOVERNMENT GRANT

This invention was made with government support under Grant No. HR0011-12-C-0065 awarded by DARPA. The government has certain rights in the invention.

FIELD

The present disclosure relates to a cell-free biomolecular breadboard and related methods and arrangements. In particular, the present disclosure relates to a cell-free biomolecular breadboard configured for designing, building, implementing, debugging and/or testing synthetic dynamic circuits in a target environment and related methods and arrangements.

BACKGROUND

Synthetic biology has emerged as a useful approach to decoding fundamental laws underlying biological control. Recent efforts have produced many systems and approaches and generated substantial insights on how to engineer biological functions and efficiently optimize synthetic pathways.

Despite efforts and progresses, current approaches to perform such engineering are often laborious, costly and difficult. Challenges still remain in developing engineering-driven approaches and systems to accelerate the design-build-test cycles required for reprogramming existing biological systems, constructing new biological systems and testing genetic circuits for transformative future applications in diverse areas including biology, engineering, green chemistry, agriculture and medicine.

SUMMARY

Provided herein are methods and arrangements that in several embodiments can be used to design, build, implement, debug, and/or test a wide variety of genetic circuits, to be operated in a target environment, and a cell-free biomolecular breadboard configured accordingly.

A genetic circuit in the sense of the disclosure is a collection of molecular components connected one to another by biochemical reactions according to a circuit design to form a fully connected network of interacting components. In the genetic circuit at least one molecular component is a reportable element detectable when the genetic circuit operates according to the circuit design.

According to a first aspect, a method is described to build in a cell-free system a genetic circuit operative in a target environment. The method comprises: providing sets of polynucleotides, polypeptides and/or metabolites, each set capable of reacting in a cell-free mixture comprising constituent chemicals of the cell-free system providing the molecular components of the genetic circuit.

The method further comprises testing combinations of the each set of polynucleotides, polypeptides and/or metabolites in a cell-free mixture under conditions of the target environment, the cell-free mixture comprising constituent chemicals of the cell-free system, the testing providing selected combinations of the each sets of polynucleotides, polypeptides and/or metabolites capable of reacting in the cell-free mixture to provide molecular components of the genetic circuit under conditions of the target environment.

The method also comprises contacting the selected combinations of the each set of polynucleotides, polypeptides and/or metabolites with a cell-free mixture comprising constituent chemicals of the cell-free system, and retesting under conditions of the target environment the selected combinations providing a further selected combination of the each set of polynucleotides, polypeptides and/or metabolites capable of providing in the cell-free mixture the reportable molecular component of the genetic circuit operative in the target environment.

According to a second aspect, a method is described to build in a cell-free system a genetic circuit operative in a target environment. The method comprises: providing sets of polynucleotides, polypeptides and/or metabolites, each set capable of reacting in a cell-free mixture comprising constituent chemicals of the cell-free system, providing the molecular components of the genetic circuit.

The method further comprises testing each set of polynucleotides, polypeptides and/or metabolites in separate cell-free mixtures under conditions of the target environment, each cell-free mixture comprising constituent chemicals of the cell-free system, the testing providing, for the each set, selected polynucleotides, polypeptides and/or metabolites capable of reacting in the cell-free mixture, providing one molecular component of the genetic circuit under the conditions of the target environment.

The method also comprises contacting combinations of the each set of selected polynucleotides, polypeptides and/or metabolites with a cell-free mixture under the conditions of the target environment, the cell-free mixture comprising constituent chemicals of the cell-free system, the contacting providing a selected combination of the each set of polynucleotides, polypeptides and/or metabolites capable of providing in the cell-free mixture the reportable molecular component of the genetic circuit operative in the target environment under conditions of the target environment.

According to a third aspect a method is described to build in a cell-free system a genetic circuit operative in a target environment. The method comprises: providing sets of polynucleotides, polypeptides and/or metabolites, each set capable of reacting in a cell-free mixture comprising constituent chemicals of the cell-free system to provide the molecular components of the genetic circuit.

The method also comprises testing each set of polynucleotides, polypeptides and/or metabolites in separate cell-free mixtures, each cell-free mixture comprising constituent chemicals of the cell-free system, the testing of each set performed under conditions of the target environment to provide for each set, selected polynucleotides, polypeptides and/or metabolites capable of reacting in the cell-free mixture to provide a molecular component of the genetic circuit under the conditions of the target environment.

The method further comprises testing combinations of the each set of selected polynucleotides, polypeptides and/or metabolites under conditions of the target environment in separate cell-free mixtures, each comprising constituent chemicals of the cell-free system, the testing resulting in selecting combinations of the each sets of selected polynucleotides, polypeptides and/or metabolites capable of reacting in the cell-free mixture to provide the molecular components of the genetic circuit under conditions of the target environment.

The method also comprises contacting the selected combinations of the each set of selected polynucleotides, polypeptides and/or metabolites with a cell-free mixture comprising constituent chemicals of the cell-free system, and retesting the selected combinations to provide a further selected combination of the each set of selected polynucleotides, polypeptides and/or metabolites capable of providing in the cell-free mixture under the conditions of the target system the reportable molecular component of the genetic circuit operative in the target environment.

According to a fourth aspect a method is described to build in a cell-free system a genetic circuit operative in a target environment. The method comprises: providing a genetic circuit herein described and testing each molecular component, selecting for each tested molecular component a set of polynucleotides, polypeptides and/or metabolites capable of reacting in a cell-free mixture comprising constituent chemicals of the cell-free system to provide the molecular component under conditions of the target environment.

The method further comprises testing molecular components of the genetic circuit and/or combinations thereof, selecting sets of polynucleotides, polypeptides and/or metabolites or combinations thereof, each set capable of reacting in the cell-free system providing the molecular components under conditions of the target environment.

The method also comprises building the genetic circuit by further selecting the selected sets of polynucleotides, polypeptides and/or metabolites or combinations thereof, the further selected sets capable of reacting in the cell-free mixture to provide the reportable molecular component of the genetic circuit.

According to a fifth aspect, a method is described to debug in a cell-free system a genetic circuit operative in a target environment. The method comprises providing a genetic circuit and testing one or more molecular components of the genetic circuit in the cell-free system under conditions of the target environment to select molecular components provided by sets of polynucleotides, polypeptides and/or metabolites, each set capable of reacting in a cell-free mixture comprising constituent chemicals of the cell-free system to provide one molecular component of the genetic circuit. The method further comprises providing a variation of the genetic circuit by replacing one or more molecular components of the genetic circuit with a molecular component selected by the testing of one or more molecular components thus resulting in a variated genetic circuit; and optionally iterating the testing of the one or more molecular components on the variated genetic circuit and the providing a variation of the circuit, to debug in the cell-free system the genetic circuit operative in the target environment.

According to a sixth aspect, an arrangement is described to build and/or debug in a cell-free system, a genetic circuit operative in a target environment, the arrangement comprising sets of polynucleotides, polypeptides and/or metabolites, each set capable of reacting in a cell-free mixture comprising constituent chemicals of the cell-free system providing the molecular components of the genetic circuit, the sets capable of providing when comprised in a single cell-free mixture the reporting molecular component of the genetic circuit according to methods for building and/or debugging a genetic circuit of the present disclosure.

According to a seventh aspect, a method is described of testing in a cell-free system a variation of a genetic circuit operative in a target environment. The method comprises: providing the genetic circuit and testing a variation of the genetic circuit in the cell-free system under conditions of the target environment by detecting modifications in molecular components provided in the cell-free system following testing of the molecular components, testing of combinations of molecular components and/or testing of the genetic circuit, each testing performed with and without the variation in the cell-free system. In the method, the molecular components of the genetic circuit are provided in the cell-free system by sets of polynucleotides, polypeptides and/or metabolites, each set capable of reacting in a cell-free mixture comprising constituent chemicals of the cell-free system to provide one molecular component of the genetic circuit.

According to an eighth aspect, an arrangement is described to test variation in a cell-free system of a genetic circuit operative in a target environment, the arrangement comprising a combination of sets of selected polynucleotides, polypeptides and/or metabolites, each combination of the each set capable of providing when comprised in a single cell-free mixtures the reportable molecular component the genetic circuit built and/or debugged according to methods, of the present disclosure; and at least one reagent capable of performing a variation of the genetic circuit and in particular a variation in at least one of the molecular components of the genetic circuit.

According to a ninth aspect, a method is described of testing in a cell-free system a genetic circuit operative in a target environment. The method comprises providing a genetic circuit and testing the genetic circuit or a portion thereof in the cell-free system under conditions of the target environment to select one or more molecular components provided by sets of polynucleotides, polypeptides and/or metabolites, each set capable of reacting in a cell-free mixture comprising constituent chemicals of the cell-free system to provide one molecular component of the genetic circuit. The method further comprises providing a variation of the genetic circuit by replacing one or more molecular components of the genetic circuit with the one or more molecular components selected by the testing and/or by adding to the genetic circuit the one or more molecular components selected by the testing. The method also comprises iterating the testing of one or more molecular components and the providing a variation of the genetic circuit to provide in the cell-free system a variated genetic circuit operative in the target environment.

According to a tenth aspect, an arrangement is described to test variation in a cell-free system, of a genetic circuit operative in a target environment, the arrangement comprising a combination of sets of polynucleotides, polypeptides and/or metabolites, each set capable of reacting in a cell-free mixture comprising constituent chemicals of the cell-free system providing the molecular components of the genetic circuit, the combination capable of providing when comprised in a single cell-free mixture the reportable molecular component of the genetic circuit built according to methods for building and/or debugging a genetic circuit of the present disclosure. The system further comprises at least one set polynucleotides, polypeptides and/or metabolites providing additional molecular components for simultaneous, combined or sequential use in method to test a variation of the genetic circuit according to the present disclosure.

According to an eleventh aspect, a cell-free biomolecular breadboard is described comprising a combination of protocols, devices, reaction mixtures, in silico systems, in vitro systems and/or in vivo systems, for testing in a cell-free system one or more genetic circuits or portions of circuits operative in a target environment according to methods herein described.

The cell-free biomolecular breadboard herein described and related methods and arrangements allow in several embodiments rapid and/or cost effective building of a genetically encoded circuit operative in a target environment through efficient addition, modification or elimination of molecular components and/or molecules functional to the related expression rendering the genetic circuit inoperative in the target environment.

The cell-free biomolecular breadboard herein described and related methods and arrangements allow in several embodiments rapid and efficient debugging of a genetic circuit operative in a target environment, based on identification of molecular components that are inoperative the genetic circuit when operated in the target environment.

The cell-free biomolecular breadboard herein described and related methods and arrangements allow in several embodiments rapid, efficient and/or cost effective testing in a cell-free system of variations of a genetic circuit, operative in a target environment, related molecular components and/or combinations thereof.

The cell-free biomolecular breadboard herein described and related methods and arrangements allow in several embodiments efficient and effective tools to rapidly and precisely characterize native and engineered genetic circuits in an in vivo or in vitro biological environment.

The cell-free biomolecular breadboard herein described and related methods and arrangements allow in several embodiments ready designing, building, implementation, characterization and/or engineering in a cell-free system of genetic circuits subsequently transferred to cellular hosts or other target environment, for additional testing implementation, characterization and/or engineering in the cellular host or other target environment.

The cell-free biomolecular breadboard herein described and related methods and arrangements can be used in connection with various applications wherein designing, building, testing and/or debugging of a genetic circuit is desired. For example, the cell-free biomolecular breadboard herein described and related methods and arrangements can be used in biological systems engineering and component characterization to perform extensive, quantitative and rapid network characterizations in vitro. Additional exemplary applications include uses of the cell-free biomolecular breadboard herein described and related methods and arrangements in several fields including basic biology research, applied biology, bio-engineering, bio-energy, medical research, medical diagnostics, therapeutics, biofuels, agriculture, environmental monitoring and remediation, molecular detection, bio-defense and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 4 shows eight types of feedforward loops (FFLs). Transcription regulatory factor X regulates transcription regulatory factor Y, and both jointly regulate Z. Regular arrows indicate that the interactions between two nodes is activating. Flat-head arrows indicate that the interactions between two nodes is repressing.

FIG. 6 shows a schematic illustrating the basic "workflow" of an exemplary prototyping and debugging of a biomolecular circuit. The overall workflow is referred to as the "design, build, test" (DBT) cycle, which involves methods of implementing the DBT cycle using a combination of models, cell-free expression systems and in vivo circuits.

FIG. 9A shows an exemplary open-loop version of an exemplary feed-forward loop, comprising two nodes: pLacO1-UTR1-lasR and pLas-variants-UTR1-deGFP. Each lasR promoter variant is tested in TX-TL by varying 3OC12HSL. Shown in each plot is the mean of 3 independent experiments. FIGS. 9B-F show on each panel deGFP amount as a function of time for each pLas variant (five promoters: P_orig, P1, P2, P3 and P4). In FIG. 9B, a previous reporter from the literature, pRsaL (P0, or P_orig), is tested. In FIG. 9C, pLasI with a mutation in the −10 region (P1) is tested. In FIG. 9D, pLasI wildtype (P2) is tested. In FIG. 9E, pLasB wildtype (P3) is tested. In FIG. 9F, pRsaL with a extended region (P4) is tested. FIG. 9G shows the best fit values for relevant promoter characteristics. Data is derived from endpoint values in TX-TL per promoter at time=300 min for varying 3OC12HSL, where each experiment is conducted three times with newly prepared DNA sources.

FIGS. 13A-D show quantitative PCR to quantify relative plasmid copy number in vivo from two strains.

FIG. 17A shows the sequence listing for plasmid 360 (PlacO1_BCD22_lasR_T500) (SEQ ID NO: 1). FIG. 17B shows the sequence listing for plasmid 428 (PRsaL-tetO1_BCD2_deGFP-ssrA_B1002) (SEQ ID NO: 2) utilizing promoter "POrig_tetO1". FIG. 17C shows the sequence listing for plasmid 347 (PLasI_1SNP_-10-tetO1_BCD2_deGFP-ssrA_B1002) (SEQ ID NO: 3) utilizing promoter "P1_tetO1". FIG. 17D shows the sequence listing for plasmid 429 (PLasI-tetO1_BCD2_deGFP-ssrA_B1002) (SEQ ID NO: 4) utilizing promoter "P2_tetO1". FIG. 17E shows the sequence listing for plasmid 430 (PLasB-tetO1_BCD2_deGFP-ssrA_B1002) (SEQ ID NO: 5) utilizing promoter "P3_tetO1". FIG. 17F shows the sequence listing for plasmid 431 (PRasL long (las)-tetO1_BCD2_deGFP-ssrA_B1002) (SEQ ID NO: 6) utilizing promoter "P4_tetO1".

FIG. 18A shows the sequence listing for plasmid 165 (PRsaL_UTR1_deGFP_T500) (SEQ ID NO: 7) utilizing promoter "Porig". FIG. 18B shows the sequence listing for plasmid 196 (PLasI_1SNP_-10_UTR1_deGFP_T500) (SEQ ID NO: 8) utilizing promoter "P1". FIG. 18C shows the sequence listing for plasmid 197 (PLasI-_UTR1_deGFP_T500) (SEQ ID NO: 9) utilizing promoter "P2". FIG. 18D shows the sequence listing for plasmid 198 (PLasB_UTR1_deGFP_T500) (SEQ ID NO: 10) utilizing promoter "P3". FIG. 18E shows the sequence listing for plasmid 199 (PRasL long (las)-_UTR1_deGFP_T500) (SEQ ID NO: 11) utilizing promoter "P4". FIG. 18F shows the sequence listing for plasmid 163 (pLacO1-UTR1-lasR) (SEQ ID NO: 12).

FIG. 19A shows the sequence listing of the shared backbone sequence of the plasmids carrying the deGFP-ssrA coding gene (PLasI_1SNP_-10_tetO1 (P1_tetO1)-(blank)-deGFP-ssrA-B1002) (SEQ ID NO: 13). FIG. 19B lists 16 variant RBS sequences (SEQ ID NO: 14-29) to be inserted to the plasmid backbone sequence shown in FIG. 19A and FIG. 19C. FIG. 19C shows the sequence listing of the shared backbone sequence of the plasmids carrying tetR (PLasI_1SNP_-10(P1)-(blank)-tetR-T500) (SEQ ID NO: 30).

FIGS. 20A and 20B show the sequence listing for plasmid 373: Plac_BCD2_lasR_T500 (SEQ ID NO: 31), and plasmid 374: Plac_BCD22_lasR_T500 (SEQ ID NO: 32).

FIG. 21A summaries in a table the linear DNA constructs used in Examples 33-40. FIGS. 21B and 21C summaries in a table the plasmids used in Examples 33-40. FIG. 21D lists in a table the strains used in Examples 33-40. FIGS. 21E and 21F list in a table DNA concentrations used in Examples 33-40.

FIG. 22A shows an embodiment of cell-free systems to characterize the original repressilator and a modified version with a point mutation in the CI promoter ($O_R2^*$) located in one of the binding sites of the CI repressor. FIG. 22B shows expression from the three promoters of the repressilator and the $O_R2^*$ version at different dilution times. FIG. 22C shows oscillation periods of the repressilator as a function of dilution time. In the $O_R2^*$ version sustained oscillations were supported in a narrower range of dilution times as compared to the original repressilator network. FIG. 22D shows phase portrait of repressilator oscillations starting from different initial TetR and CI repressor concentrations.

FIGS. 23A-F demonstrate cell-free prototyping and characterization of negative feedback circuits. FIG. 23A shows transfer functions of the repressilator repressor-promoter pairs (top) and TetR homologs (bottom). The TetR repressor was tested against two different promoters: the promoter used in the repressilator (top panel) and the J23119-TetR promoter [2](bottom panel). Lines are Hill function fits. FIG. 23B shows oscillations of a novel 3-node ring oscillator (3n1) constructed on plasmid DNA. FIG. 23C shows two versions of a second 3-node ring oscillator (3n2) on linear DNA were used to study the effect of ClpXP degradation on oscillator function. One version was ssrA-tagged on all repressor genes while the other version did not carry degradation tags on the repressors. The same reporter with a medium-strength degradation tag was used in both versions. FIG. 23D shows a 4-node cyclic negative feedback network on linear DNA has two stable steady states that depend on the initial conditions. IPTG switched the network into the state where pPhlF was on and pTetR off. An initial pulse of aTc resulted in the opposite stable steady state. FIG. 23E shows oscillations of two novel 5-node ring oscillators (5n1, 5n2) constructed on linear DNA. FIG. 23F shows 5-node ring oscillators oscillate with longer periods than 3-node ring oscillators, as predicted by simulations and shown by experimental data.

FIG. 27A shows time series traces of 3-node ring oscillators running in E. coli (mother machine). Single trap traces of 3n1 and 3n2 observed for 36 h in vivo using a strong pPhlF sfGFP-ssrA reporter and a representative image from an "on" and "off" state of oscillation. Scale bar: 5 µm. FIG. 27B shows time series traces of 5-node ring oscillators running in E. coli (mother machine). Single trap traces of 5n1 and 5n2 observed for 72 h in vivo using a weak pPhlF sfGFP-ssrA reporter. FIG. 27C shows 3n1 displays population-wide oscillation pulses in vivo (CellASIC). Time series micrographs of 3n1 under a strong pPhlF sfGFP-ssrA reporter every 160 min; inset shows individual cells of the initial microcolony. Scale bar: 10 µm and 5 µm (inset). FIG. 27D shows relationship between period and division time in vivo. Left, 3n1 in vivo under a strong pPhlF sfGFP-ssrA reporter. The in vitro data is shown for comparison. Each point in the in vivo data corresponds to the period and division time from a CellASIC experiment run under different media type and flow rates. Right, 5n2 in vivo under a weak pPhlF sfGFP-ssrA reporter. In vivo periods determined at 29° C. and 21° C. growth temperature in mother machine experiments. Boxes represent the inner quartile range with the median. FIG. 27E shows influence of reporter concentration on oscillation periods by competing for ClpXP degradation. Left, with constant amounts of ClpXP the reporter concentration affects repressor degradation and thus oscillation period. Histograms of the periods observed with a weak and a strong pPhlF sfGFP-ssrA reporter for both 3n1 and 5n2 run in the mother machine. Dashed lines indicate the medians.

FIG. 29A shows traditional testing of circuits, where parts are cloned onto a single plasmid or sets of complementary plasmids, tested in vivo, and cycled back to construction. FIG. 29B shows rapid prototyping procedure, where circuits are cycled between construction on linear DNA and testing in TX-TL. When a final circuit prototype is completed, only 1 cycle occurs of plasmid DNA construction and circuit implementation in vivo.

FIG. 30A shows comparison of deGFP time-series fluorescence for plasmid DNA, linear DNA without gamS protection, and linear DNA with gamS protection. Plasmid DNA used is pBEST-OR2-OR1-Pr-UTR1-deGFP-T500, linear DNA is an 810 bp PCR product with no steric protection ends, and each is supplied at 16 nM. FIG. 30B shows endpoint deGFP expression after 8 hours of 2 nM of linear DNA plotted against signal for different working concentrations of gamS, without prior incubation of the protein with crude extract. FIG. 30C shows endpoint deGFP expression from plasmid and linear DNA with or without gamS protein, at increasing DNA concentrations. Correlation of 0.98 on plasmid DNA is for 0 nM-4 nM values only; correlation of 0.99 on linear DNA is for 0 nM-16 nM. FIG. 30D shows protection of 2 nM of linear DNA using different amounts of non-coding DNA at template ends.

FIG. 31A shows an overview of the rapid assembly and prototyping procedure, where DNA parts are assembled using Golden Gate assembly ("GGA") to create a plasmid, which is then directly used as a PCR template to create linear DNA at high concentrations suitable for TX-TL. In parallel, the assembly product can also be propagated in vivo to yield more copies of clonal plasmid. FIG. 31B shows results from agarose gel of a gene assembled from 5 standard pieces of 66 bp, 103 bp, 110 bp, 707 bp, and 2376 bp. Shown are 50 ng each of starting fragments (except 66 bp), fragments post-assembly before and after exonuclease digestion ("exo"), and rapid assembly PCR product ("RAP") compared to post-cloned PCR product ("pos"). Arrow indicates expected size of 892 bp. FIG. 31C shows functional testing of 4 nM of rapid assembly or post-cloned products, with or without 0.5 mM IPTG inducer. Experiment conducted in the presence of 2 nM P1-tetO1-lacI linear DNA. Linear DNA is protected with 31 bp of steric protection and with gamS. Error bars represent one standard deviation from three independent experiments.

FIG. 33A shows a five-piece standard adopted with specific ligation ends for a promoter, 5' UTR, coding sequence, terminator, and vector based on the previously used pBEST backbone. FIG. 33B shows a diagram of sequences for ligation at each site.

In FIG. 36A, the pulse is beginning to be generated, and the top node is expressing a protein to activate the middle node and bottom node (where the bottom node is the reporter). In FIG. 36B, the bottom node is fully expressing and is reflected in signal over time. At the same time, the middle node is starting to express as well, but the product of the middle note (in this case tetR) is bound to free aTc. In FIG. 36C, there is decreasing free aTc, and the product of the middle note is starting to act on the bottom node to repress the bottom node promoter. In FIG. 36D, the bottom node is fully repressed and there is a decrease in signal from degradation of the reporter (if the reporter is -ssrA tagged) and/or dilution of the cell or cell-free system.

FIG. 37 shows the sequence listing for promoters Porig and P1-P4 (SEQ ID NO: 33-37).

FIGS. 40A and 40B show the sequence listing for plasmid 212 and 213 (SEQ ID NO: 41-42).

FIG. 42 shows the sequence listing for plasmid 220 (SEQ ID NO: 43).

In FIG. 43A, For the I-FFL, each of five parameters is individually modified, while other parameters are kept constant at 1 uM 3OC12HSL, 10 uM aTc, 1 nM pLac-lasR, 0.1 nM pLas-tetR, and 1 nM pLas-tetO-deGFP. All reactions contain 1 mM IPTG to remove residual lacI, and are run in triplicate using new DNA sources. In FIG. 43B, pLas-tetO-deGFP plasmid is varied and output deGFP is measured at t=300 minutes. Experiment data is in black and blue. Inlet shows time-series data. In FIG. 43C, 3OC12 is varied and output deGFP is measured at t=300 minutes. In FIG. 43D, pLac-lasR plasmid is varied and output deGFP is measured at t=300 minutes. In FIG. 43E, aTc is varied and time to repression is shown. Time to repression is determined as the time where production rate reaches half-maximum. In FIG. 43F, pLas-tetR plasmid is varied. No aTc was added to this experiment to probe the direct effect of tetR.

FIG. 47 provides in one embodiment a set of commands used to build a circuit from the tetR-pTet-aTc part and the GFP reporter part in the in silico toolbox.

FIGS. 48A-C show the output of the txtl_plot command in the in silico modeling toolbox. FIG. 48A provides the trajectories for the protein concentrations as a function of time in the simulation. FIG. 48B plots the concentration of the RNA (Y axis) in the simulation as a function of time. FIG. 48C plots the amounts of the AGTP (sum of the concentrations of the ATP and GTP), CUTP (sum of the concentrations of the CTP and UTP), amino acids, Ribosomes and RNAP normalized to their ininital (maximum) values.

FIG. 50 provides the characterization experiments carried out to provide in vitro data to fit in silico models. Experiment 1 is the constitutive expression of GFP under the control of the pTet promoter, with the amount of pTet-GFP varying over (4 nM, 2 nM, 1 nM, 0.5 nM, 0.25 nM, 0.125 nM, 0 nM). Experiment 2 is the constitutive expression of GFP under the control of the pLac promoter, with the pLac-GFP DNA varying over (2 nM, 1 nM, 0.5 nM, 0.25 nM, 0.125 nM, 0.0625 nM, 0 nM). Experiment 3 is the repression of the expression of the pTet-GFP gene (at 1 nM) by varying the amounts of tetR produced by varying the amounts of pLac-tetR gene over (2 nM, 0.2 nM, 0.02 nM, 0.002 nM, 0.0002 nM, 0.00002 nM, 0 nM). Experiment 4 is the induction (depression) of the repressed pTet-GFP gene by adding varying amounts of aTc to the system (10 uM, 1 uM, 0.1 uM, 0.01 uM, 0.001 uM, 0.0001 uM, 0.00001 uM). Here, the pLac-tetR DNA is at 0.1 nM, and the pTet-GFP DNA is at 1 nM. Experiment 5 is the induction of activated pLas-GFP expression. the pLac-lasR and pLas-GFP DNAs are at 1 nM, and the inducer 3OC12HSL is varied over (10 uM, 1 uM, 0.1 uM, 0.01 uM, 0.001 uM, 0.0001 uM, 0.00001 uM).

FIGS. 51A-D provide the in silico toolbox code for generating the biochemical reactions and species for each experiment shown in FIG. 50. These figures also provide the list of the parameters estimated from the data from each experiment. The parameter estimation procedure is detailed in FIGS. 52 and 53. FIG. 51A corresponds to experiment 1, where the pTet constitutive expression strength is observed by measuring the GFP expression under the pTet promoter. Parameters associated with the binding of (sigma 70 factor bound) RNA Polymerase to the DNA containing the pTet promoter (TXTL_PTET_RNAPbound_F and TXTL_PTET_RNAPbound_R) was estimated. Some core parameters fix for the rest of the characterization steps are also determined. FIG. 51B shows the code, reactions, species associated with experiment 2, which is the constitutive expression of GFP under the control of pLac. The parameters to be estimated are the forward and reverse reaction rates for the sigma 70 bound RNA Polymerase to bind to the pLac DNA, with the core parameters determined in the characterization due to experiment 1 held fixed. FIG. 51C shows the model created for the pTet-tetR-aTc repression-induction system. The parameters estimated were the tetR dimerization forward and backward rates, and the pTet sequestration (by tetR dimers) binding and unbinding rates to characterize the tetR repression strength (experiment 3) and the aTc-tetR dimer binding unbinding rates (experiment 4). This figure also shows the parameter values fixed for this simulation that were derived from the previous two experiments/characterizations (FIGS. 51A and 51B). FIG. 51D shows the model generated for the pLas-lasR-3OC12HSL activation system, which was used in conjunction with data from experiment 5. Here, the parameters for the (sigma 70 bound) RNA Polymerase binding to the unactivated (TXTL_PLAS_RNAPbound_F/R) and activated (TXTL_PLAS_TFRNAPbound_F/R) promoter site, the transcription factor binding to the promoter site (TXTL_PLAS_TF-BIND_F/R) and the inducer binding to the activator protein (TXTL_INDUCER_LUXR_AHL_F/R) were determined by fitting the model behavior to the data from experiment 5.

FIG. 54A: varying pTet-GFP DNA, as per Experiment 1. FIG. 54B: varying the pLac-GFP DNA, as per Experiment 2. FIG. 54C: Varying the tetR DNA, as per experiment 3. FIG. 54D: Varying the aTc, as per experiment 4. FIG. 54E: Varying the 3OC12HSL, as per experiment 5.

FIG. 55 provides the toolbox code used to generate the full IFFL in silico, after the parts have been characterized and the estimated parameter values have been used to update the part configuration files.

FIG. 58, originally from work exemplified in [5] demonstrates the components that can make up linear DNA pieces to express vioA, vioB, vioC, vioD and vioE. J23151 is a constitutive promoter, BCD5 is a RBS, and T14 is a terminator from [6].

DETAILED DESCRIPTION

Provided herein are methods and arrangements that in several embodiments can be used to design, build, implement, debug, and/or test a wide variety of genetic circuits, operative in a target environment, and a cell-free biomolecular breadboard configured accordingly.

The term "biomolecular breadboard" used herein refers to a system configured to allow testing of one or more features of a genetic circuit in a controlled setting. A "cell-free biomolecular breadboard" is a biomolecular breadboard configured to allow testing of the one or more features of a genetic circuit in a cell-free system.

Cell-free biomolecular breadboards in the sense of the disclosure typically comprise combinations of protocols, devices, reaction mixtures, in silico systems, in vitro systems and/or in vivo systems that can be used to design, build, debug and characterize through testing genetic circuits.

Figure 1:
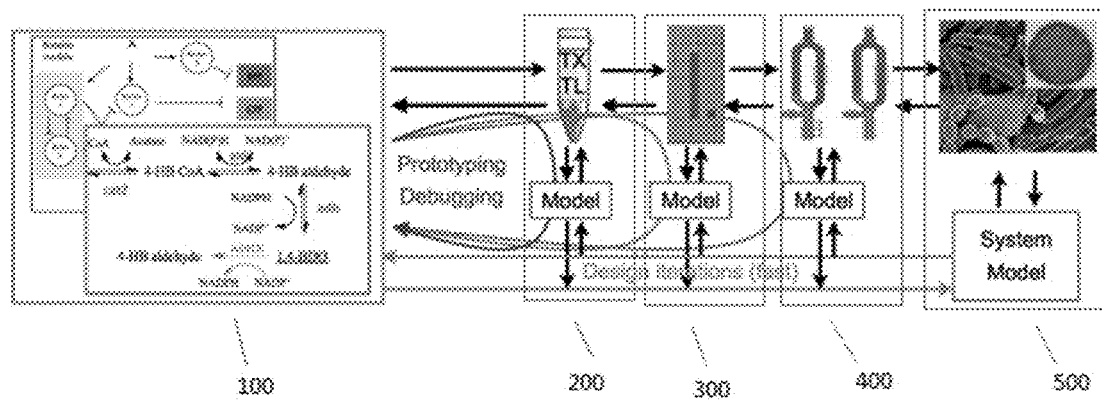
FIG. 1 provides a schematic overview of an exemplary basic breadboarding process. 100 illustrates the types of circuits designed and implemented, including a biomolecular "event detector" and a pathway for producing 1,4 butanediol. 200 shows the main component of the breadboard is the TX-TL extract system. A detailed modelling toolbox is also available for simulation and analysis of circuits and pathways. 300 and 400 illustrate the use of a commercially-available droplet-based microfluidic system and a continuous flow reactor (development jointly with EPFL). 500 illustrates that the circuits can be transformed into E. coli.

Reference is made to the illustration FIG. 1 provides a schematic overview of the basic elements of the cell-free breadboarding process, through a sequence of steps taking place in in vitro test environments using a combination of devices and environments which allows rapid iterations between experiments, modeling, optimization and design of a genetic circuit. In particular, 100 illustrates a genetic circuit that can be implemented and transformed into a cell or other biomolecular chassis, in which the elements of the topmost circuit are molecular components of a metabolic pathway for producing a reporting 1,4 butanediol and the elements of the partially hidden circuit are a set of genetic components that perform a logical operation on two chemical inputs (partially hidden). 200 shows a TX-TL extract system that can be used to implement the genetic circuit and/or perform reactions of the related 1,4 butanediol producing pathway, alone or together with a detailed modelling toolbox for simulation and analysis of circuits and pathways. 300 and 400 illustrate a commercially-available droplet-based microfluidic system and a continuous flow reactor (development jointly with EPFL) that can be used in addition to the TX-TL extract of 200. The genetic circuits can be transformed into E. coli in 500.

In cell-free biomolecular breadboards in accordance with the present disclosure the breadboard components are configured to allow testing in a cell-free system of a genetic circuit operative in a target environment.

The term "genetic circuit," "biological circuit," or "circuit," as used herein indicates a collection of molecular components (herein also indicated as nodes) connected one to another by biochemical reactions according to a circuit design. In particular, in a genetic circuit the molecular components are connected one to another by the biochemical reactions so that the collection of molecular components is capable to provide a specific output in response to one or more inputs.

The term "molecular component" or "node" as used herein in connection with the genetic circuit indicates a chemical compound comprised in a cellular environment.

Exemplary molecular components thus comprise polynucleotides, such as ribonucleic acids or deoxyribonucleic acids, polypeptides, polysaccharides, lipids, amino acids, peptides, sugars and/or other small or large molecules and/or polymers that can be found in a cellular environment.

In genetic circuits in the sense of the present disclosure, the molecular components forming parts of the genetic circuit can be genetic molecular components or cellular molecular components.

The term "genetic molecular component" as used herein indicates a molecular unit formed by a gene, an RNA transcribed from the gene or a portion thereof and optionally a protein translated from the transcribed RNA. In genetic circuits herein described, the biochemical reactions connecting the genetic molecular component to another molecular component of the circuit can involve any one of the gene, the transcribed RNA and/or the polypeptide forming the molecular component.

A gene comprised in a genetic molecular component is a polynucleotide that can be transcribed to provide an RNA and typically comprises coding regions as well as one or more regulatory sequence regions which is a segment of a nucleic acid molecule which is capable of increasing or decreasing transcription or translation of the gene within an organism either in vitro or in vivo. In particular coding regions of a gene herein described can comprise one or more protein coding regions which when transcribed and translated produce a polypeptide, or if an RNA is the final product (for example if the polynucleotide codes for a activating RNA that translationally activates a YUNR motif [7]) only a functional RNA sequence that is not meant to be translated. Regulatory regions of a gene herein described comprise promoters, transcription factor binding sites, operators, activator binding sites, repressor binding sites, enhancers, protein-protein binding domains, RNA binding domains, DNA binding domains, silencers, insulators and additional regulatory regions that can alter gene expression in response to developmental and/or external stimuli as will be recognized by a person skilled in the art.

An RNA of a genetic molecular component comprises any RNA that can be transcribed from a gene, such as a messenger ribonucleic acid (mRNA), short interfering ribonucleic acid, and ribonucleic acid capable of acting as regulating factors in the cell. mRNA comprised in a genetic molecular component comprise regions coding for the protein as well as regulatory regions e.g. ribosome binding site domains ("RBS"), which is a segment of the upstream (5') part of an mRNA molecule to which the ribosomal machinery of a cell binds to position the message correctly for the initiation of translation. RBSs control the accuracy and efficiency with which the translation of mRNA begins. mRNA can have additional control elements encoded, such as riboregulator sequences or other sequences that form hairpins, thereby blocking the access of the ribosome to the Shine-Delgarno sequence and requiring an external source, such as an activating RNA, to obtain access to the Shine-Delgarno sequence. Other RNAs that serve regulatory roles that can comprise the genetic molecular component include riboswitches, aptamers (e.g. malachite green, Spinach), aptazymes, guide CRISPR RNAs, and other RNAs reviewed in [8] or known to those skilled in the art.

A protein comprised in a molecular component can be proteins with activating, inhibiting, binding, converting, or reporting functions. Proteins that have activating or inhibiting functions typically act on operator sites encoded on DNA, but can also act on other molecular components. Proteins that have binding functions typically act on other proteins, but can also act on other molecular components. Proteins that have converting functions typically act on small molecules, and convert small molecules from one small molecule to another by conducting a chemical or enzymatic reaction. Proteins with converting functions can also act on other molecular components. Proteins with reporting functions have the ability to be easily detectable by commonly used detection methods (absorbance, fluorescence, for example), or otherwise cause a reaction on another molecular component that causes easy detection by a secondary assay (eg. adjusts the level of a metabolite that can then be assayed for). The activating, inhibiting binding, converting, or reporting functions of a protein typically form the interactions between genetic components of a circuit. Exemplary proteins that can be comprised in a genetic molecular component comprise monomeric proteins and multimeric proteins, proteins with tertiarty or quaternary structure, proteins with linkers, proteins with non-natural amino acids, proteins with different binding domains, and other proteins known to those skilled in the art. Specific exemplary proteins include TetR, LacI, LambdaCI, PhlF, SrpR, QacI, BetR, LmrA, AmeR, LitR, met, AraC, LasR, LuxR, IpgC, MxiE, Gal4, GCN4, GR, SP1, CREB, and others known to a skilled person in the art.

Figure 56A:
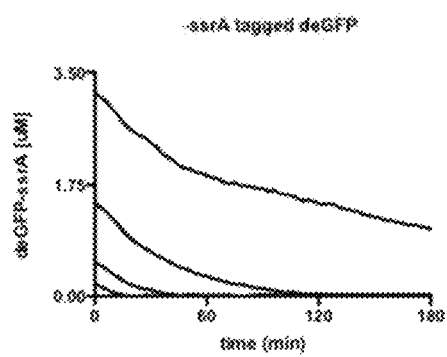
FIGS. 56A-B plot deGFP degradation over time for fluorescently tagged -ssrA deGFP (FIG. 56A) and non-ssrA tagged deGFP (FIG. 56B).
Figure 56B:
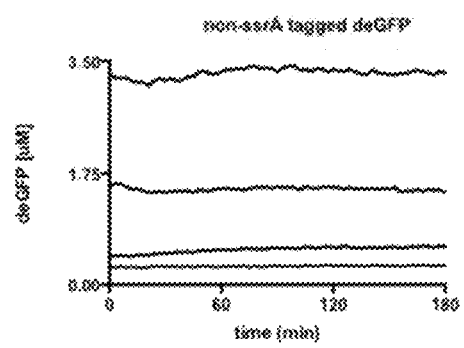

The term "cellular molecular component" indicates a molecular component not encoded by a gene, or indicates a molecular component transcribed and/or translated by a gene but comprised in the circuit without the corresponding gene. Exemplary cellular components comprise polynucleotides, polypeptides, polysaccharides, small molecules and additional chemical compounds that are present in a cellular environment and are identifiable by a skilled person. Polysaccharides, small molecules, and additional chemical compounds can include, for example, NAD, FAD, ATP, GTP, CTP, TTP, AMP, GMP, ADP, GDP, Vitamin B1, B12, citric acid, glucose, pyruvate, 3-phosphoglyceric acid, phosphoenolpyruvate, amino acids, PEG-8000, FiColl 400, spermidine, DTT, b-mercaptoethanol maltose, maltodextrin, fructose, HEPES, Tris-Cl, acetic acid, aTc, IPTG, 3OC12HSL, 3OC6HSL, vanillin, malachite green, Spinach, succinate, tryptophan, and others known to those skilled in the art. Polynucleotides can include RNA regulatory factors (small activating RNA, small interfering RNA), or "junk" decoy DNA that either saturates DNA-binding enzymes (such as exonuclease) or contains operator sites to sequester activator or repressor enzymes present in the system (for example, as demonstrated in [9]). Polypeptides can include those present in the genetic circuit but not produced by genetic components in the circuit (such as lacI or tetR in FIG. 22D), or those added to affect the molecular components of the circuit, such as gamS in FIGS. 30A-D and Example 43 or deGFP-ssrA in FIGS. 56A-B.

In some embodiments of genetic circuits herein described, one or more molecular components is a recombinant molecular component that can be provided by genetic recombination (such as molecular cloning) and/or chemical synthesis to bring together molecules or related portions from multiple sources, thus creating molecular components that would not otherwise be found in a single source.

In embodiments of the cell-free molecular breadboard herein described, a genetic circuit comprises at least one genetic molecular component or at least two genetic molecular components, and possibly one or more cellular molecular components, connected one to another in accordance to a circuit design by activating, inhibiting, binding or converting reactions to form a fully connected network of interacting components.

The term "activating" as used herein in connection with a molecular component of a genetic circuit refers to a reaction involving the molecular component which results in an increased presence of the molecular component in the cellular environment. For example, activation of a genetic molecular component indicates one or more reactions involving the gene, RNA and/or protein of the genetic molecular component resulting in an increased presence of the gene, RNA and/or protein of the genetic molecular component (e.g. by increased expression of the gene of the molecular component, and/or an increased translation of the RNA). Activation of a cellular molecular component indicates one or more reactions resulting in an increased production of the cellular molecular components (e.g. a polysaccharide or a metabolite) in the cellular environment. Activators can also include those formed by combinations of proteins that must bind into a complex to activate, such as mxiE and ipcG as demonstrated in [10].

Activation of a molecular component of a genetic circuit by another molecular component of the circuit can be performed by direct or indirect reaction of the molecular components. Examples of a direct activation of a genetic molecular component comprise in a circuit the production of an alternate sigma factor (molecular component of the circuit) that drives the expression of a gene controlled by the alternate sigma factor promoter (other molecular component of the circuit), or the production of a small ribonucleic acid (molecular component of the circuit) that increases expression of a riboregulator-controlled RNA (molecular component of the circuit). Specific examples of this include the activity of sigma28 or sigma54 as demonstrated in [11]. Examples of indirect activation of a genetic molecular component comprise the production of a activating protein (eg. lasR) (molecular component of the circuit), as shown in Example 12, which when in tandem with a small molecule (eg. 3OC12HSL) (possibly an additional molecular component of the circuit) causes the increase of expression of a gene, or the production of a protein that regulates an intermediate protein that increases the expression of a target gene (molecular component of the circuit), such as in Examples 37 and 38 where two cascades of repression in effect cause activation.

The term "inhibiting" as used herein in connection with a molecular component of a genetic circuit refers to a reaction involving the molecular component of the genetic circuit and resulting in a decreased presence of the molecular component in the cellular environment. For example, inhibition of a genetic molecular component indicates one or more reactions involving the gene, RNA and/or protein of the genetic molecular component resulting in a decreased presence of the gene, RNA and/or protein (e.g. by decreased expression of the gene of the molecular component, and/or a decreased translation of the RNA). Inhibition of a cellular molecular component indicates one or more reactions resulting in a decreased production or increased conversion, sequestration or degradation of the cellular molecular components (e.g. a polysaccharide or a metabolite) in the cellular environment. Examples of inhibition of a cellular molecular component comprise the conversion of a metabolite via an enzyme, such as tryptophan by VioA as shown in Example 52 in which the genetic component VioA converts tryptophan to IPA, thus decreasing the presence of tryptophan.

Inhibition can be performed in the genetic circuit by direct reaction of a molecular component of the genetic circuit with another molecular component of the circuit or indirectly by reaction of products of a reaction of the molecular components of the genetic circuit with the another molecular component of the circuit. An example of direct inhibition of a genetic molecular component of a genetic circuit comprises the reaction of a repressing protein (eg. tetR) that reduces the expression of a gene controlled by a gene controlled by a tetR promoter, as demonstrated in Example 16. Other examples include the repression of CI, CI OR2*, TetR, LacI, BetI, PhlF, SrpR, QacR in FIG. 23A or Example 38. Examples of indirect inhibition of a genetic molecular component, comprise the reaction of an alternate sigma factor (eg. sigma28), which reduces the production of a primary sigma factor (eg. sigma70) controlled gene through resource competition or sequesteration.

The term "binding" as used herein in connection with molecular components of a genetic circuit refers to the connecting or uniting two or more molecular components of the circuit by a bond, link, force or tie in order to keep two or more molecular components together, which encompasses either direct or indirect binding where, for example, a first molecular component is directly bound to a second molecular component, or one or more intermediate molecules are disposed between the first molecular component and the second molecular component another molecular component of the circuit. Exemplary bonds comprise covalent bond, ionic bond, van der waals interactions and other bonds identifiable by a skilled person. In some embodiments, the binding can be direct, such as the production of a polypeptide scaffold that directly binds to a scaffold-binding element of a protein. In other embodiments, the binding may be indirect, such as the co-localization of multiple protein elements on one scaffold. In some instances binding of a molecular component with another molecular component can result in sequestering the molecular component, thus providing a type of inhibition of said molecular component. or ma In some instances binding of a molecular component with another molecular component can change the activity or function of the molecular component, as in the case of allosteric interactions between proteins, thus providing a type of activation or inhibition of the bound component.

The term "converting" as used herein in connection with a molecular component of the circuit refers to the direct or indirect conversion of the molecular component into another molecular component. An example of this is the conversion of chemical X by protein A to chemical Y that is then further converted by protein B to chemical Z. This is exemplified by the conversion of tryptophan (a molecular component) with vioA (a genetic component) to IPA (a molecular component), that with vioB can be converted to a third molecular component, as shown in Example 52 and FIG. 57.

In embodiments of a genetic circuit the molecular components are connected one with another according to a circuit design in which a molecular component is an input and another molecular component is an output. In particular, a genetic circuit typically has one or more input or start molecular component which activates, inhibits, binds and/or convert another molecular component, one or more output or end molecular component which are activated, inhibited, bound and/or converted by another molecular component, and intermediary molecular components each inhibiting, binding and/or converting another molecular component and being activated, inhibited, bound and/or converted by another molecular component.

In embodiments herein described, the molecular components are typically connected together according to the circuit design in defined patterns of interactions between components called motif. A motif typically has inputs and outputs and performs an information processing function that is one level higher than recombinant genetic components.

Exemplary motifs that can be used to connect collections molecular components in a genetic circuit according to a circuit design comprise a feed-forward loop (wherein the output is a pulse) [12] as shown in Examples 6-8 and Examples 10-11, an oscillator (wherein the output is an oscillatory output) as shown in Examples 33-40 [3], a repression cascade (wherein the output is repression of the expression of a molecular component of the circuit) [13], a switch (wherein the output is expression of either one molecular component of the circuit in response to one input or another molecular component of the circuit in response to another input) as shown in Example 47 and FIGS. 3A-B and FIG. 34A-C [14], or a cascade (wherein the circuit transmits the input signal to an output signal) [11], and other circuit designs which will be identifiable by a skilled person upon reading of the present disclosure.

Figure 22A:
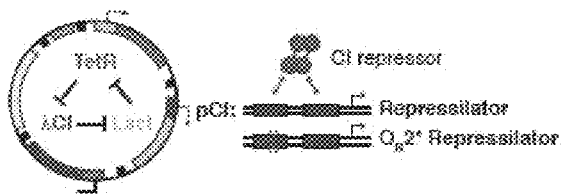
FIGS. 22A-D demonstrate cell-free repressilator characterization.

A motif can identify a class of genetic circuits in which the pattern of interaction between molecular components is maintained, but the specific genetic and molecular elements may be varied. For example, a three element oscillator in which the three elements mutually repress expression of another protein, as shown in FIG. 22A and described in more detail in Example 37, defines a motif in which different specific proteins might be used to implement any of the three genetically encoded components, as long as the pattern of mutual repression is maintained. Likewise, the motif of an incoherent feed-forward loop, as described in FIG. 4 and FIG. 5A and exemplified in Examples 6-8 and Examples 10-11, can be implemented with different repressor and activator pieces, as long as the pattern of a fast-activating axis and slower repressing axis is maintained.

In genetic circuits herein described molecular components can be connected in one or more motifs within a genetic circuit. For example, in a 3-element or 5-element repression circuit, the motif of transcriptional repression from pairs of recombinant genetic components (eg. pLac-tetR, pTet-lambdaCI) can be linked together to form the final genetic circuit, as exemplified in Example 38 and FIGS. 26A-C. In some embodiments, molecular components can be connected in one or more motifs to achieve desired functionality at a higher-order of complexity.

Figure 3A:
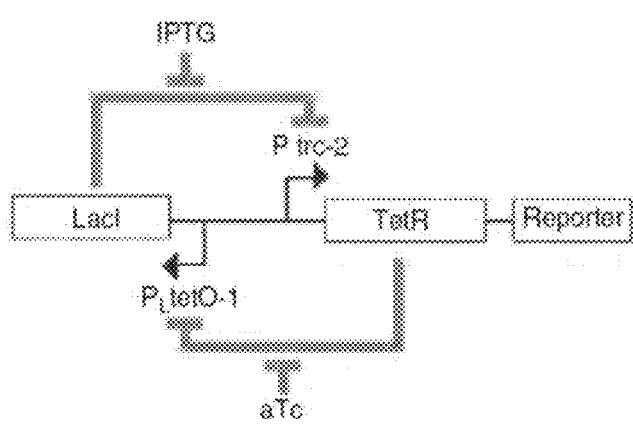
FIG. 3A shows a genetic toggle switch gene circuit layout. TetR represses PLtetO-1 but TetR's action is inhibited by inducer aTc; LacI represses Ptrc-2 but LacI's action is inhibited by inducer IPTG.

In some embodiments, a genetic circuit can be a genetic toggle switch that comprises two repressors mutually repressing each other. For example, FIG. 3A shows a genetic toggle switch having two repressors TetR and LacI which mutually repress each other. The circuit can be flipped between "high" and "low" states using chemical inducers isopropyl-b-D-thiogalactopyranoside (IPTG) and anhydrotetracycline (aTc). For example, when aTc is added to the system to inhibit tetR, lacI will be highly expressed and the reporter will be OFF. Conversely, when IPTG is added to inhibit lacI, tetR and the reporter will be highly expressed. This is further exemplified in Example 47.

Figure 3B:
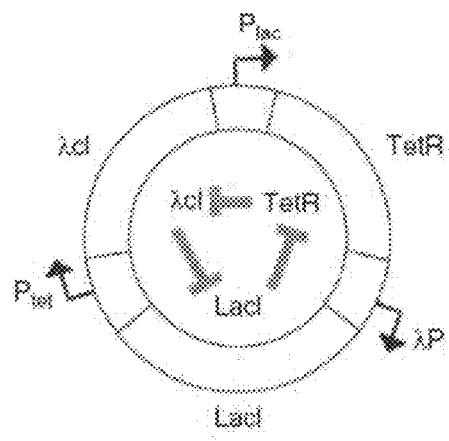
FIG. 3B shows a repressilator gene circuit layout. TetR represses expression of λcI which in turn represses expression of LacI. Finally, LacI represses TetR expression, completing the repressilator cycle.

In some embodiments, a genetic circuit can be a repressilator that comprises an odd plurality of repressors that perform a function (namely, an oscillatory output). For example, FIG. 3B shows a repressilator having three repressors, sequentially repressing each other. The first repressor protein (TetR) inhibits the second repressor gene whose protein product (lcI) in turn inhibits the third repressor gene (lacI). Additionally, the third repressor protein (LacI) inhibits the first repressor gene, completing a negative feedback loop with a long cascade. In other embodiments, the repressilator can contain 5 repressors, 7 repressors, or 2n+1 repressors where n is an integer greater than 0. This is further exemplified in Examples 33-40.

In some embodiments, a genetic circuit can be or comprise a feed-forward loop. A feed-forward loop ("FFL") is a type of genetic circuit consisting in a three-gene motif composed of two input recombinant genetic components (i.e. two input transcription regulatory factors) and one output reporting element. Each of the three interactions in the three nodes can be either activating or repressing. There are a total of eight types of FFLs: four are coherent and the other four are incoherent [12]. FIG. 4 shows these eight types of feedforward loops (FFLs). Transcription regulatory factor X regulates transcription regulatory factor Y, and both jointly regulate Z. Regular arrowhead indicates that the interactions between two nodes is activating. T shaped arrowheads indicate that the interactions between two recombinant genetic components is repressing. In coherent FFLs, the sign of the direct path from transcription factor X to output Z is the same as the overall sign of the indirect path through transcription factor Y. Incoherent FFLs have opposite signs for the two paths. In a feed forward loop circuit, the X and Y inputs can be combined either using a logical AND or OR gate thus giving different dynamics properties in each case. The coherent feed forward loop allow the creation of a delay either on activation or on deactivation depending on the logical function between the two input X and Y. When the output logical gate is an AND function, the delay appears on activation, while when the output gate is an OR function, the delay appears on deactivation.

In an incoherent feed forward loop (IFFL), the two inputs have two different logical levels: one molecule (molecule X for example) is an activator while the other molecule is a repressor of the promoter controlling the expression of the output. This way, when the input signal is on, the expression of molecule X starts activating both the promoters controlling the expression of Y and Z; transcription starts and the amount of Y and Z molecules increases. Nevertheless, when the concentration of Y has reached its repression threshold, repression starts and the concentration of Z molecule decrease to its steady state.

Figure 5A:
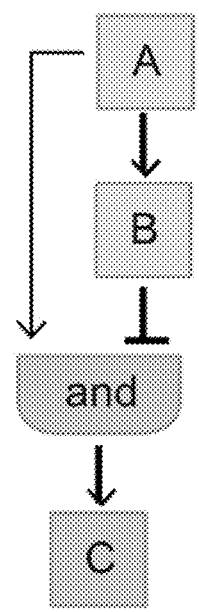
FIG. 5A depicts an exemplary incoherent feed forward loop. The boxes labeled A, B and C are genetic molecular components, each representing a translation or transcription unit.
Figure 5B:
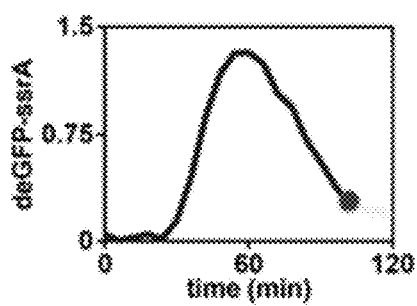
FIG. 5B shows a pulse shaped waveform produced from the incoherent feedforward loop of FIG. 5A.

An exemplary incoherent feed forward loop is depicted in FIG. 5A. The boxes labeled A, B and C are molecular components, each representing a translation or transcription unit. For example, A creates protein A via transcription and translation. In the IFFL shown in FIG. 5A. A activates both B and C, while B represses C. The Boolean AND logic indicates that C is only expressed when both A is present and B is absent. Under appropriate conditions, the IFFL of FIG. 5A is expected to produce a pulse shaped waveform as shown in FIG. 5B which outputs the concentration of protein C as a function of time in the presence of dilution and/or degradation of the proteins. Protein C is usually a reporter such as Green Fluorescent Protein (GFP) whose concentration can be quantified by measuring the fluorescence excitation and emission. The logic for this loop depends on the fact that both transcription and translation events require time to occur, thus encoding delays into the system. In particular, as protein A is produced, it activates the production of both protein B and C. Thus, initially, the concentration of protein C increases. However, when the concentration of protein B reaches a threshold value, it exerts a significant enough repression on gene C such that the production rate of protein C drops below its overall dilution/degradation rate, causing its concentration to fall and generating a pulse shaped waveform shown in FIG. 5B.

In the illustration of FIGS. 5A and 5B the output of the IFFL, which is meant to generate a pulse, is from the production of reporting element C, which in this case is a fluorescent protein. However, during the process of debugging the circuit the intermediates of the circuit (eg. A and B) can also be detected by alternate methods, such as Western Blot (as exemplified in Example 56), protein gels (as exemplified in Example 56), liquid/gas chromatography-mass spectrometry (as exemplified in Example 55), and other techniques identifiable by a skilled person; or can be detected by the addition of a reporting element using the same promoter as A and B (as exemplified in FIGS. 23B-E, where reporter elements are using shared promoters as those in the genetic circuit); or can be detected by chancing the coding sequence for A and B to be a fusion protein with a reportable element (as seen in [15]), or can be detected among other methods.

Figure 11A:
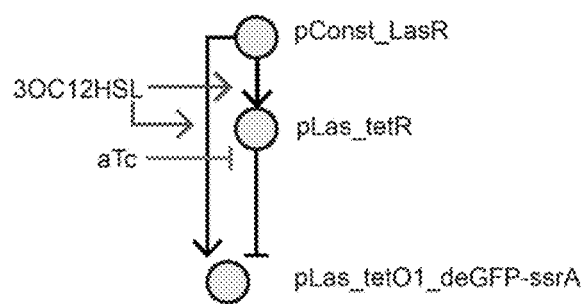
FIG. 11A shows an exemplary incoherent feed-forward loop motif (IFFL) having three genetic molecular components.

In one particular genetic circuit shown in FIG. 11A and the Example sections, node A is provided by pLac-UTR1-lasR plasmid, node B is provided by pLas-UTR1-tetR plasmid and node C is provided by plastetO-UTR1-deGFP plasmid.

In some genetic circuits one or more motifs comprised in the genetic circuit can form a metabolic pathway which is a sequence of chemical reactions catalyzed by enzymes in which a product of one enzyme acts as the substrate for the next. In some cases, a genetic circuit can comprise or be a metabolic pathway, according to the circuit design. Examples of metabolic pathways include a violacein production pathway (which converts tyrosine to violacein) [16] and described in more detail in Examples 49 to 59, a 1,4 BDO production pathway (which converts succinate to 1,4 BDO) [17], or a artemicinic acid pathway (which converts acetyl CoA to amorphadiene) [18], among others. Metabolic pathways can be comprised in a genetic circuit of the present disclosure alone or together with other motifs as will be understood by a skilled person upon reading of the present disclosure.

In some embodiments where the circuit design of the genetic circuit comprises a metabolic pathway, the input of the circuit can be a substrate to be converted by the sequence of chemical reactions of the pathway, the output of the circuit can be a product of the sequence of chemical reaction of the pathways. In some embodiments where genetic circuit comprises a metabolic pathaway, compounds involved in the metabolic pathway can be molecular components of the circuit e.g. in embodiments where the molecular components comprise substrates or metabolites of the metabolic pathways and/or minerals, vitamins, and other cofactors required by enzymes of a metabolic pathways to function. In some embodiments where the genetic circuit comprises a metabolic pathway, molecular components of the pathway can be composed of polynucleotides, polypeptides and/or other simple or complex molecules, typically consisting of chemical species that can exist in an in vitro or in vivo system. Examples of metabolic pathways involving polypeptides include the valinomycin pathway, which creates the polypeptide valinomycin from amino acids using the genes vml1 and vlm2 [19].

In some embodiments, one or more molecular components of genetic circuits herein described can be a "transcription regulatory factor" or "transcription factor".

The term "transcription regulatory factor" or "transcription factor" as used herein refers to any type of factors that can function by acting on a regulatory DNA element such as a promoter or enhancer sequence. The transcription regulatory factors can be broadly classified into a transcription repression factor (also referred to as "repressor") and a transcription activation factor (also referred to as "activator"). The transcription repression factor acts on a regulatory DNA element to repress the transcription of a gene, thereby reducing the expression level of the gene. The transcription activation factor acts on a regulatory DNA element to promote the transcription of a gene, thereby increasing the expression level of the gene. Both the transcription repression factors and the transcription activation factors can be used as one or more components in the gene circuits herein described.

In particular, a transcription regulatory factor has typically at least one DNA-binding domain that can bind to a specific sequence of enhancer or promoter sequences. Some transcription factors bind to a DNA promoter sequence near the transcription start site and help form the transcription initiation complex. Other transcription factors bind to other regulatory sequences, such as enhancer sequences, and can either stimulate or repress transcription of the related gene. An example of the engineering of the binding site can be seen in Example 16.

Other regulatory mechanisms exist within cells and can be part of a genetic circuit that is being designed, built, implemented, tested or debugged. Examples of regulatory additional regulatory mechanisms include covalent modifications to proteins in which molecular modifications are made to a protein that change its conformation and affects the activity of the protein as it pertains to inhibition, activation, sequestration, acting on a substrate or other biomolecular functions; allosteric modifications to proteins in which a molecular component binds to a protein and changes its conformation (shape) resulting in a change of activity; confirmation and/or chemical modifications to mRNA that affects the ability of the mRNA to be translated to a protein; or other similar cellular regulatory mechanisms and described in standard textbooks [20] and/or understood by a person skilled in the art.

Examples of specific transcription repression factors include TetR, LacI. LambdaCI, PhlF, SrpR, QacI, BetR, LmrA, AmeR, LitR, met, and other identifiable by a skilled person, as well as homologues of known repression factors, that function in both prokarayotic and eukarayotic systems. Examples of transcription activation factors include AraC, LasR, LuxR, IpgC, MxiE, Gal4, GCN4, GR, SP1, CREB, etc as well as homologues of known activation factors, that function in both prokarayotic and eukarayotic systems.

Examples of other factors that affect expression of a gene and can be used to regulate gene of a genetic component include those based on ribonucleic acid such as: CRISPR-CAS systems, siRNA, riboregulators, transcriptional RNA based activators and repressors [8], and other systems that can be naturally derived, purely synthetically derived, or synthetically derived from natural systems. These factors can be transcriptional or translational activators or repressors.

Examples of regulatory mechanisms that are listed include the use of transcriptional repressors such as tetR and activators such as lasR in Examples 1-18, and the use of homologues of tetR, such as srpR and phlF, as well as different transcriptional repressors such as lambdaCI and lacI in Examples 33-40.

In the genetic circuits of the cell-free biomolecular breadboard herein described at least one molecular component of the circuit is a reportable molecular component detectable in a cell-free system and/or in a target environment when the genetic circuit operates according to the circuit design.

The term "reportable molecular component" as used herein indicates a molecular component capable of detection in one or more systems and/or environments. The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

In some embodiments of the genetic circuit according to the disclosure, the reportable molecular component can be a molecular component linked or comprising a label wherein the term label refers to a compound capable of emitting a labeling signal, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image (as seen for fluorescent reporter Citrine, Cerulean, sfGFP, and mCherry in Examples 33-39, or for deGFP in Examples 40-48). As a consequence, the wording "labeling signal" as used herein indicates the signal emitted from the label that allows detection of the label, including but not limited to radioactivity, fluorescence, chemiluminescence, production of a compound in outcome of an enzymatic reaction (as seen specifically in FIG. 59 with the production of colored compounds, and more generally in Examples 49-59) and the like.

Typically, the at least one molecular component detectable when the genetic circuit operates according to the circuit design comprises the component providing the output of the circuit according to the circuit design. This is the case, for example, for fluorescent reporters reporting on an oscillator in Examples 33-39, or for violacein in Examples 49-59. Accordingly, in genetic circuit of the disclosure operativeness of the genetic circuit can be detected by detecting the reportable molecular component of the circuit molecular component detectable in a cell-free system and/or in a target environment when the genetic circuit operates according to the circuit design.

In the cell-free biomolecular breadboard herein described, methods and arrangements are provided that allow testing of molecular components of a genetic circuits and/or of related combination in a cell-free system under conditions of a target environment to provide selected molecular components and/or related combination before testing or detecting operativeness of the circuit in the cell-free system and/or the target environment. Accordingly, methods and arrangements herein described allow in several embodiments to reduce the testing of the genetic circuit in the cell-free systems and/or target environment by selecting in the cell-free system molecular components and related combination that are compatible and can be provided under the conditions of the target environment.

The term "cell-free system" as used herein refers a combination of reactants capable of performing reactions occurring in a cellular environment, in a mixture where the reactants are comprised outside the cellular environment. Exemplary reactions occurring in a cellular environment comprise protein synthesis, transcription, translation, DNA replication and/or additional biological reactions occurring in a cellular environment identifiable by a person skilled in the art. The combination forming a cell free system, can comprise a template for the production of a macromolecule (eg. DNA, RNA) and supporting monomers (eg. amino acids, nucleotides), co-factors, enzymes, and additional compounds that are part of the cellular environment. Cell-free systems, by definition, do not include whole cells capable of replicating but its components are typically derived from a cell.

In some embodiments herein described, a cell free system can be an in vitro system formed by a cell-free mixture of the reactants forming the cell-free system and can comprise a combination of cytoplasmic and/or nuclear components from cells comprising reactants for protein synthesis, transcription, translation, DNA replication and/or additional biological reactions occurring in a cellular environment identifiable by a person skilled in the art.

In some embodiments, the cell-free system can be an in silico combination of reactants provided together with rules concerning the related reactions in the cellular environment. In the in silico system, combinations of cellular components are typically simulated in a program to virtually execute biochemical reactions that would occur in a corresponding physical mixture. Examples of this include the SimBiology toolbox from MATLAB, the Systems Biology Markup Language [21] along with one of its implementations, among others. An in silico system utilizing MATLAB SimBiology is exemplified as well in Examples 19-30.

In some embodiments, the cell-free system of methods and arrangements of the disclosure can be formed by a combination of in vitro cell-free mixture and in silico combination of reactants as will be understood by a skilled person upon reading of the present disclosure.

In some embodiments herein described, a cell-free system can be as a transcription-translation system (herein also "TX-TL") and in particular a TX-TL system from *E. coli* [22]. The TX-TL system contains a reagent required for the transcription of deoxyribosenucleic acid (DNA) and the translation of messenger ribonucleic acid (mRNA) into proteins. Operations such as DNA replication may be but are not required to be implemented in a TX-TL system.

In other embodiments, a cell-free system can be formed by reactants from a crude cell extract such as crude *E. coli* S30 extract [23], reactants from well-defined components such as the PURE system [24], reactants from commercial systems (eg. Promega S30), or reactants cell extracts such as wheat-germ [25] or rabbit reticulocyte [26].

In several embodiments herein described, molecular components of a genetic circuit and/or related combinations are tested in the cell-free system under conditions of a target environment where the genetic circuit is to be operated to identify the genetic circuit operative in the target environment. In particular, in embodiments of a methods and arrangements herein described, the molecular components forming the circuit are tested under the condition of the target environment first separately and then in combinations in a cell-free system to eliminate molecular components that will result in recombinant genetic components and/or corresponding circuit that are inoperative in the target environment.

The term "target environment" as used herein indicates the aggregate of surrounding components and related conditions where a genetic circuit can be operated and comprises in vivo environments and in vitro environments.

In vivo environments can include single or multi-celled organisms or combinations of such organisms in which the genetically encoded circuit can be introduced by transformation or equivalent means that would be known to individuals skilled in the field. An example in vivo target environment is a cell, such as that of the organism where the genetic circuit was prototyped (e.g. if based on a cell-free system of E. coli, then the target environment is a E. coli cell; if based on a cell-free system of wheat germ, then the target environment is a wheat germ cell or cell line). However, in certain embodiments the target environment may be agnostic to the organism in which it was prototyped (e.g. if based on a cell-free system of E. coli, than the target environment is wheat germ). The in vivo target environment can be a single cell, a collection of cells, a cell-line, or a organism. The in vivo target environment is capable of reproducing itself.

In vitro environments comprise non-living environments comprising components capable of performing transcription and translation. In vitro environments can be provided by cell-free systems such as TX-TL, as well as variants of such systems that may be obtained by lyophilization or other processing that maintains the ability of the in vitro environment to perform transcription and translation on the addition of chemicals (including water) that create conditions under which transcription and translation can occur. An example in vitro target environment is an in vitro mixture such as TX-TL, in a batch-mode format of a range of volumes such as, but not limited to, 1 pL to 10 uL, 10 uL to 1 mL, 1 mL to 2 L, or 2 L to 2000 L, with no regeneration of molecular components that are utilized in the operation of the circuit. The in vitro mixture can also be of a lyophilized format, of a partially replenished format (eg. dialysis cassette within an energy reservoir composing of ATP, amino acids, cofactors and other molecular components), or of a steady-state format (eg. a bio-reactor that pumps in a energy reservoir and pumps out used reagent at given times to emulate the division of a cell, such as described in [27]). This in vitro target environment can be used to produce materials, such as chemicals that are toxic or otherwise not economical to be produced in cells, or to perform a task as dictated from the genetic circuit. The in vitro target environment is incapable of reproducing itself.

The target environment typically comprises compounds that can be found in a cellular environment and in some embodiments, can also comprise cellular and/or genetic molecular components required for operation of the circuit.

In some embodiments the testing of the components can be performed in cell free mixtures such as a mixture of cytoplasmic and/or nuclear components from cells comprising reactants for in vitro protein synthesis, transcription DNA replication and/or additional biological reactions occurring in a cellular environment identifiable by a skilled person. In some embodiments the testing can be performed in an in silico cell-free system.

Figure 2:
FIG. 2 shows a transcription and translation process using a TX-TL cell-free system.

In some embodiments of methods herein described, the cell-free system can be formed by constituent reactants from the TX-TL system. In some of those embodiments, the TX-TL reaction mixture can be prepared according to the following steps. Firstly, a crude cell extract, an amino acid solution, and an energy solution are prepared. Next, three components for making the TX-TL system are prepared, including a crude cell extract, amino acid solution and an energy solution. The amino acid solution and the energy solution are then combined to make a TX-TL buffer. The next step is to calibrate the crude cell extract to determine the maximal concentration of $Mg^{2+}$, $K^+$ and Dithiothreitol (DTT) concentrations to produce TX-TL reactions with maximal levels of expression. Thirdly, the calibration results are used to make a three-tube system including a tube of TX-TL buffer, a tube of crude cell extract and a tube of DNA. The final step is to execute TX-TL reactions using the TX-TL reagents prepared as shown in FIG. 2. The TX-TL systems herein described can be used to demonstrate synthetic biology circuits as well as traditional cell-free applications. Detailed methods of how to prepare a TX-TL system can be found in the a previous publication by Sun and co-workers [15], which is incorporated herein by reference herein in its entirety.

In some embodiments, the testing of the molecular components or combinations thereof can be performed by providing, sets of polynucleotides, polypeptides and/or metabolites, each set capable of reacting in the provided cell-free mixture to provide a molecular component of the genetic circuit. In those embodiments, the provided sets can be reacted in the cell-free system separately to select one or more set capable of providing each molecular component of the circuit under the conditions of the target environment. Selected sets of polynucleotides, polypeptides and/or metabolites can be tested in combinations in the cell-free system to select the set capable of providing the molecular component under the conditions of the target environment.

In some embodiments the set of polynucleotides, polypeptides and/or metabolites provided comprises polynucleotides, polypeptides and/or metabolites forming a transcriptional and translational unit for a genetic molecular component of the circuit. In those embodiments the set of polynucleotides, polypeptides and/or metabolites comprises the gene of the genetic molecular component as well as molecular components required for the related transcription and possibly translation of the gene to provide the genetic molecular component in the cell-free mixture.

In some embodiments, the set of polynucleotides, polypeptides and/or metabolites provided comprises a cellular molecular component of the circuit alone or in combination with compounds possibly required for the activating, inhibiting, binding and/or converting reactions connecting the cellular molecular component with other molecular components of the genetic circuits.

The term "polynucleotide" as used herein indicates an organic polymer composed of two or more monomers including nucleotides or nucleosides. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids.

The term "polypeptide" or "protein" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. As used herein the term "amino acid", "amino acidic monomer", or "amino acid residue" refers to any of the twenty naturally occurring amino acids, non-natural amino acids, and artificial amino acids and includes both D an L optical isomers. In particular, non-natural amino acids include D-stereoisomers of naturally occurring amino acids (these including useful ligand building blocks because they are not susceptible to enzymatic degradation). The term "artificial amino acids" indicate molecules that can be readily coupled together using standard amino acid coupling chemistry, but with molecular structures that do not resemble the naturally occurring amino acids. The term "amino acid analog" refers to an amino acid in which one or more individual atoms have been replaced, either with a different atom, isotope, or with a different functional group but is otherwise identical to original amino acid from which the analog is derived. Proteins can have a secondary, tertiary, and possibly quaternary structure as will be understood by a skilled person.

The term "metabolites" used herein refer to the products of enzyme-catalyzed reactions that occur either in vitro or in vivo. In general, metabolites have a finite half-life and they do not accumulate in cells. Many metabolites are regulators that control the pace of metabolism. Metabolites provided in the set of polynucleotides, polypeptides and/or metabolites herein described comprise small molecules that are present in the cellular environment (e.g. NAD, FAD, ATP, GTP, CTP, TTP, AMP, GMP, ADP, GDP, Vitamin B1, B12, citric acid, glucose, pyruvate, 3-phosphoglyceric acid, phosphoenolpyruvate), amino acids, as well as any small molecules that are not present in the cellular environment but support the function of the cell-free system, such as a crowding agent (e.g. PEG-8000, FiColl 400, and spermidine), reducing agent (e.g. DTT, and b-mercaptoethanol), external non-native sugar source (maltose, maltodextrin, fructose, etc), buffering agents (e.g. HEPES, Tris-Cl, and acetic acid). These can also include small molecules that are not present in the cellular environment and important for the genetic circuit to function, such as inducers (e.g. aTc, IPTG, 3OC12HSL, 3OC6HSL, and vanillin), substrates (e.g. malachite green, and Spinach) or items that form the input or intermediate of a pathway (e.g. succinate for conversion to 1,4 BDO or metabolic intermediates by the genetic circuit or metabolic pathway, tryptophan for conversion to violacein or metabolic intermediates as exemplified in Examples 49-59).

In embodiments, wherein the cell-free system is an in vitro mixture, polynucleotides, polypeptides and/or metabolites are physically provided according to methods identifiable by a skilled person. For example polynucleotides can be provided by de novo synthesis of DNA, traditional cloning of DNA from natural organisms, or a variety of DNA assembly techniques such as Gibson, Golden Gate, and additional methods identifiable by a person skilled in the art. Specific methods can be found in Example 46 and FIGS. 33A-B.

If the cell-free system is an in silico mixture, the activity of the polynucleotides, polypeptides and/or metabolites can be encoded in the in silico model, taking into account resource limitations; it can then be run with an execution line as in Example 21.

In some embodiments polynucleotides of the set comprise regulatory regions such as promoters, transcription factor binding sites, operators, activator binding sites, repressor binding sites, enhancers, protein-protein binding domains, RNA binding domains, DNA binding domains, and other control elements known to a person skilled in the art.

In some embodiments polypeptides provided in the set of polynucleotides, polypeptides and/or metabolites comprise polypeptides involved in the production a certain genetic molecular component and can comprise regulating factors involved in the translation of the polynucleotide encoding for the molecular component such as chaperone proteins, sigma factors, cofactors, translational elements, scaffolds, co-activating proteins, split proteins, and other associated elements known to a person skilled in the art.

Figure 33A:
FIGS. 33A-B show in one embodiment the specific pieces for the rapid assembly procedure.
Figure 33B:
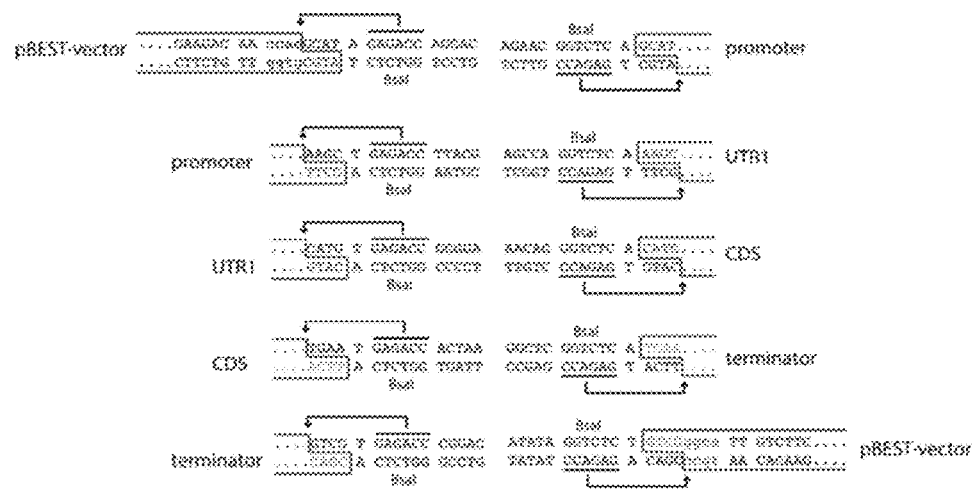

In some embodiments, the polynucleotides can be provided by breaking down the gene or RNA into separate pieces (e.g. coding regions and one or more regulatory regions) and then re-combine the pieces in a set manner, as illustrated in Example 46 and FIGS. 33A-B. For example, to provide the physical DNA of a gene forming a genetic molecular component to be tested, the physical DNA can be broken down into sub-units (promoter, UTR, coding sequence, terminator) that can then be rapidly assembled into testable, expressable genetic components (on linear DNA). For rapid (8 hour) assembly and test cycles, one can implement the process described in Examples 40-48.

In some embodiments were the cell-free system is an in vitro cell-free mixture, the polynucleotides can be provided by many accepted processes for providing polynucleotides forming the gene of a genetic molecular component to be tested or other polynucleotides, including cloning methods such as Golden Gate Assembly, Isothermal Assembly, and others known to those skilled in the art; PCR off of already assembled plasmids or the direct use of already assembled plasmids; or providing the physical pieces, in part or whole, by DNA synthesis, among other methods.

In particular, in some of those embodiments DNA can be physically added into the final mixture at a concentration typically in the "sub-saturating" range, where this range is defined as the amount from 0 nM to the nM amount where a doubling of DNA does not lead to a subsequent increase of the expressed mRNA or protein. This amount varies from plasmid to plasmid depending on the transcriptional and translational strength of the sub-components making up the physical DNA, but is typically less than 64 nM and usually around 0 nM-16 nM, as demonstrated in Examples 2-59 where there are DNA concentrations given for circuit testing. In other embodiments, the DNA provided may be in a saturated phase state, or a set weight state (in ng or ug).

Additional, techniques and protocols to provide DNA, other polynucleotides as well as polypeptides and/or metabolites in a cell-free system are identifiable by a skilled person upon reading of the present disclosure.

In embodiments herein described the sets of polynucleotide polypeptide and/or metabolite are first tested in the cell-free system and/or cell-free reaction mixture under the conditions of the target environment.

The term "condition" of the target environment refers to an environment that is most similar to the final target environment. For example, in a cell-free mixture corresponding to a in vivo target environment of E. coli strain JM109, the cell-free mixture itself can be produced from prokaryotes or eukaryotes, preferably from bacteria, more preferably from a gram negative bacteria, even more preferably from any E. coli strain and more preferably from E. coli JM109. Likewise, for a genetic circuit that is meant to operate in a final in vitro target environment of a mobile paper device for sensing [28], a cell-free mixture that does not have regeneration of metabolites is more preferred, and a cell-free mixture that does have regeneration of metabolites is less preferred.

In some embodiments, the condition of the target environment can be provided by regulatory sequences or regulatory factors affecting the transcription and/or translation of the molecular component to match the regulatory sequence of the target environment. For example protein synthesis in eukaryotes differs from prokaryotes. The 5' end of the mRNA has a modified chemical structure recognized by the ribosome, which then binds the mRNA and moves along it until it finds the first AUG codon. A characteristic pattern of bases (called a "Kozak sequence") is sometimes found around that codon and assists in positioning the mRNA correctly in a manner reminiscent of the Shine-Dalgarno sequence, but not involving base pairing with the ribosomal RNA. Accordingly, in molecular components formed by a protein expressed in prokaryotes forming part of a circuit operative in a eukaryotic system, a modification of the regulatory sequences in the set of polynucleotide, polypeptide and/or metabolite can be provided to test the prokaryotic protein component in the eukaryotic environment where the circuit is to be run.

In some embodiments, the conditions of the target environment can be provided by different RBSs bind ribosomes with different efficiencies. For example in E. coli, having the sequence of TTTAGAGAAAGAGGAGAAATACTAG (SEQ ID NO: 44) is a high ribosomal binding site (RBS) sequence which means that any gene directly following this sequence (directly 3'- to this sequence) will be translated at a higher rate. This in turn provides for more or greater expression levels of the protein encoded by the gene which follows a high RBS sequence. Accordingly, in molecular components formed by a protein expressed in an original environment with original expression level, and forming part of a circuit to be operated in an another environment in a different expression level, a modification of the RBS in the set of polynucleotide, polypeptide and/or metabolite can be provided to test the protein component in the another environment where the circuit is to be run. For example, in Examples 6-11, 16 different RBS units are tested in the context of the expression of tetR and deGFP-ssrA in a feed-forward loop circuit; each of these RBS units results in a different expression level of the tetR or deGFP-ssrA protein, and therefore a different behavior of the circuit in vitro or in vivo as seen in Example 11 and FIG. 12A. Therefore, to tune for the final functional behavior of the genetic circuit desired (in the feed-forward loop, a pulse of specified duration), a strong RBS, medium RBS, weak RBS, or variation thereof can be chosen to affect translational efficiency. Example of RBSs with varying binding efficiencies include BCDs and MCDs as used in the Example sections. One family of RBS sequences commonly used include synthetic monocistronic designs (MCD), such as B0030 ATTAAAGAGGAGAAA (SEQ ID NO: 45) or B0034 AAAGAGGAGAAA (SEQ ID NO: 46) from _http://partsregistry.org. Other MCDs include B0031, B0032, and B0033. While these RBS sequences can be grouped into strong, medium, and weak RBS sequences, the final translational strength of each element can be estimated broadly but cannot be pre-determined without conducting extensive experiments An additional family of RBS sequences include synthetic bicistronic designs (BCD), such as BCD2 GGGCCCAAGTTCACTTAAAAAGGAGATCAACAATGAAAGCAATTTTCGTACT GAAACATCTTAATCATGCTAAGGAGGTTTTCT (SEQ ID NO: 22), or BCD22 GGGCCCAAGTTCACTTAAAAAGGAGATCAACAATGAAAGCAATTTTCGTACT GAAACATCTTAATCATGCGGTGGAGGGTTTCT (SEQ ID NO: 19), among others. These BCD units developed [1] are able to provide greater predictability of the final translational strength of each element by removing secondary structure constraints from mRNA, albeit not a 1 to 1 correlation.

In embodiments of methods and arrangements where sets of polynucleotides polypeptides and/or metabolites are tested alone and/or in combination, the testing can be performed in the cell-free system to build a circuit and/or debug a circuit to be operated in a target environment.

The term "build" as used herein indicates the process of assembling molecular components to provide a genetic circuit. The term "debug" as used herein indicates the identifying and/or removing errors in a genetic circuit which results in a genetic circuit that does not operate according to the circuit design. Debugging can include testing motifs or sub-sections of a complete circuit for functionality, identifying those that are functional and then combining the functional motifs or sub-sections of a complete circuit while ruling out those that are non-functional, as shown in FIG. 6 (Step 4) and exemplified in Examples 33-40. Debugging can also include breaking down a genetic component into its sub-components (promoter, RBS, coding sequence, terminator) and varying one or more of these components to generate a large library, which can then be tested and reduced down to functional units, as exemplified with promoter variation libraries in Examples 2-5 and Example 12, or ribosome binding site variation libraries in Examples 6-11. Debugging can also include testing different assembly mechanisms for expected output, as in Example 45. Debugging can also include exploring the possible design space of a metabolic pathway, by optimizing for the production of an end product or intermediates by adding, removing, or modifying the concentrations of a genetic molecular component or cellular molecular component, as exemplified in general through metabolic engineering applications and specifically in Examples 49-59. Debugging can also include determining concentration of genetic components to be produced, such that the concentration in the cell-free mixture and in the in vivo target environment is matched through plasmid copy number (Example 9) or general sensitivity analysis to indicate important variables in the circuit (Examples 17, 18, 31, 32). Debugging can also include the use of an in silico breadboard to aid in the removal of non-functional designs or the identification of important characteristics of a circuit, as determined in Examples 19-30.

In some embodiments the genetic circuit to be built and/or debugged can be performed. In some embodiments the genetic circuit to be built and/or debugged can be designed ex novo by providing molecular components connected by activating/inhibiting, binding and/or converting reactions to provide a function. In those embodiments, designing the genetic circuit can be performed by providing a circuit design in which molecular components are connected to produce the function. The designing can thus involve isolating the function and identifying the motifs connecting molecular components to provide the function. For example, in the example of engineering tetO1-responsive promoters in Example 16 and FIGS. 39A-D, the function desired is repression of a pLas activated promoter in response to tetR. Based on this function, the promoter unit is engineered to include different tetO1 operator sites and tested to determine which operator site stops production from the promoter in the presence of tetR while maintaining the ability of the promoter to be activated by lasR. As another example, in a pathway from glucose to butanol, an artificial pathway can be constructed which is built to provide a function (eg. produce butanol in E. coli) that is not naturally present in a cell, as described in [29].

In some embodiments providing a genetic circuit can be performed by modifying a pre-existing genetic circuit. In some of those embodiments a pre-existing circuit, either in structure (such as the ring oscillator structure, which is known to give an oscillatory output as exemplified in Examples 33-40), or in actual components (such as the violacein pathway as exemplified in Examples 49-59) can be provided. Parts of the pre-existing circuit can be replaced by different parts, either natural, such as occurring in a microbial setting or synthetic, such as being developed originally from a computational assay. For example, for a protein such as tetR, one can produce different natural homologs of tetR from different microboial organisms (by mining a bioinformatics database, for example National Center for Biotechnology Information Entrez Gene) or from a directed evolution assay and selection or screen, or one can produce different synthetic versions of tetR, from artificially changing the sequence of the gene. By using different homologues of tetR (eg. SrpR, PhlF), the existing structure of a ring oscillator is utilized but different pieces are implemented to build variants on the pre-existing circuit.

In some embodiments of a method to build and/or debug a genetic circuit herein described, the molecular components forming the recombinant genetic components of the circuit are tested under the condition of the target environment first separately and then in combinations in a cell-free system and/or in a cell-free reaction mixture under to eliminate molecular components that will result in recombinant genetic components and/or corresponding circuit that are inoperative in the target environment.

In some embodiments, the conditions of the target environment can be provided by polynucleotides with a variety of methylation, phosphorylation, or modification patterns that can be absent in other environments; for example, *E. coli* methylation patterns on "GATC" can cause DNA restriction, or Type I and Type II restriction endonucleases can restrict DNA templates from being used in certain in vivo environments. These conditions can be emulated by supplementing the cell-free system with the restriction endonuclease; or can be overcome by utilizing different DNA pieces and/or saturating the system with DNA and/or otherwise disabling the methylation or modification restriction pattern.

In some embodiments, one or more set of polynucleotide polypeptide and/or metabolites, each capable of providing one molecular component of the genetic circuit, is first tested in the cell-free system and/or cell-free reaction mixture under the condition of the target environment to select for each of the one or more set, the polynucleotides, polypeptides and/or metabolites capable of reacting in the cell-free mixture to provide the molecular component of the circuit. Example 12 and FIGS. 9A-F are examples of testing a set of different polynucleotide-varied promoters to select the molecular component of the circuit operative in the target environment (in this case a promoter for use in a reporter element). Another example of testing of set of polynucleotide, polypeptides and/or metabolites providing one molecular component of the circuit is in Example 16, where different polynucleotide-varied operator sites are tested to select molecular component for a genetic molecular component repressor unit.

In some embodiments combinations of two or more sets of polynucleotide polypeptide and/or metabolites, each capable of providing one molecular component of the genetic circuit, can be tested under conditions of the target environment in a same or separate cell-free mixtures, each comprising constituent chemicals of the cell-free system. In some of those embodiments the testing of combinations results in selecting combinations of the two or more sets of selected polynucleotides, polypeptides and/or metabolites, each capable of reacting in the cell-free mixture, to provide at least two molecular components of the genetic circuit under conditions of the target environment. Reference is made in this connection to the exemplary motif-by-motif construction of FIG. 11A performed by testing separately an activating component (see e.g. Example 12) and the repressing component (see e.g. Example 16), detecting two selected genetic molecular components, and combining the two selected molecular components to make a functional FFL as seen in vivo (see e.g. FIG. 11E and Example 8).

In some embodiments of methods and related arrangements of the present disclosure, the two or more sets of polynucleotide polypeptide and/or metabolites, each capable of providing one molecular component of the genetic circuit forming the combination, comprise one or more set of selected polynucleotide polypeptide and/or metabolites each capable of providing in the cell-free system and/or cell-free reaction mixture, one molecular component of the genetic circuit under the condition of the target environment.

In embodiments of methods and related arrangement to build and/or debug a genetic circuit herein described, the one or more set of selected polynucleotides, polypeptides and/or metabolites and/or the selected combinations of the two or more sets of polynucleotides, polypeptides and/or metabolites can be contacted with a cell-free mixture comprising constituent chemicals of the cell-free system, and retested resulting in selecting a combination of the each set of selected polynucleotides, polypeptides and/or metabolites capable of providing in the cell-free mixture the reportable molecular component of the genetic circuit to be operated in the target environment, Examples can be found in the violacein pathway from Examples 49-59. In particular the determination that from a complete reconstitution of the pathway in Example 54 to detect reportable molecular component violacein, the intermediate reportable molecular component is important to note, resulted in a retesting with varied enzyme concentrations to detect intermediates (see e.g. Example 58).

In some embodiments, the testing of the molecular components of the circuit and/or combinations thereof, can be performed to select the molecular component and/or combinations thereof, and related sets of polynucleotides, polypeptides and/or metabolites, rather than specific sets of polynucleotides, polypeptides and/or metabolites as will be understood by a skilled person upon reading of the present disclosure. For example, in testing the molecular components of the FFL motif repressible element in Example 16, it can be understood that other repressible elements that function similarly, such as lacI, can be tested similarly in cell-free systems. As another example, by testing the promoter strengths of five promoters in Example 12 and FIGS. 18A-18E, it can be understood by someone skilled in the art that the same promoters but with tetO1 operators engineered as used in Examples 8 and 10 and FIGS. 17B-17F will behave similarly, without the need for re-testing the related promoters.

In embodiments of methods and related arrangement to debug a genetic circuit a variation of the genetic circuit can be provided by replacing one or more molecular components of the genetic circuit with a molecular component or a combination thereof selected by the testing of one or more molecular components or a combination thereof.

In some of those embodiments, the variation of the genetic circuit can be performed to select one or more molecular components that provide a functional circuit (herein also functional component). In some of those embodiments, the providing can be performed by detecting one or more reportable elements of the circuit and in particular the reportable element detectable when the circuit operates according to circuit design, to determine of the outcome of the experiment is the desired outcome. For example if it is known in Example 16 that the genetic circuit output is a pulse, and the functional component test is to determine if a promoter can be made that responds to tetR and aTc, then any promoter unit that is non-responsive to tetR (eg. does not decrease signal in response to tetR) or to aTc (eg. does not increase signal when aTc is provided in the presence of tetR) would be non-functional for the purposes of the disclosure. Another variant of this test can be that of having a promoter known to be responsive to a protein (such as tetR or aTc), but rather the output of the circuit is an increased repression, in which case the functional component being tested for would be the tetR protein, and variants of the tetR protein would be provided and tested to produce transfer functions. This is demonstrated in FIG. 23A, FIG. 26A, FIG. 26B and Example 38 in the case of tetR variants to build an oscillator. In some embodiments the functional component can be a molecular component, genetic component, or sub-component thereof. Typically, the functional component will be varied among different variants, concentrations and other parameters to determine its identity.

In some embodiment of methods to debug a circuit, the circuit can be separated into sub-circuits or motifs for testing, and the results of the testing of the sub-circuits or motifs to can be combined together to debug the circuit. An example of these embodiments is outlined in FIG. 23A where each individual reporter-repressor pair is tested to determine a transfer function characteristic for each pair (and in this case, the reporter is not the final reporter of the oscillator circuit, but merely a reporter to determine the repressor function); using this information, the complete circuit is then constructed from the sub-circuit or motif.

In embodiments, of methods to debug a genetic circuit, the method can also comprise iterating the testing of the one or more molecular components and/or combinations thereof and/or the providing a variation of the circuit, to debug in the cell-free system the genetic circuit to be operated in the target environment. An example of can be found in the metabolic engineering Example 49-59; specifically, to debug the production of violacein, an iteration of testing different coding sequence concentrations of pathway members and measuring multiple reportable elements is undertaken in Example 58. Another example of this embodiment is in the FFL Example 11, where multiple variants of RBSs is provided for a reportable and repressible element of the circuit to determine a pulsatile output; iteration and comparison is done in the in vivo target environment through Example 8, and further circuit iteration in the top element is done in vitro compared to in vivo through Example 32.

In some embodiments of methods to build and/or debug a genetic circuit, two or more sets of polynucleotides, polypeptides and/or metabolites can be combined in a single cell-free system and tested and characterized together. For example, if a circuit is broken into sub-circuits, sub-sets, or motifs, and each is tested separately and known to work, the separate sub-circuits can then be combined together to assemble a final circuit product. An example of this is in Examples 33-37 where in a 3-node oscillator three sub-sets of repressor-promoter pairs are tested independently, and then combined in a single cell-free system for testing together. If the final target environment of the circuit is in vivo, parameters such as stoichiometric amounts of the sets are balanced in vitro the same balance as in vivo; for example, if using 1 nM of set 1 of DNA with 10 units of a molecular component and 4 nM of set 2 of DNA with 10 units of another molecular component, than one would expect in vivo to put set 1 on a low-copy plasmid and set 2 on a medium copy plasmid that is stoichiometrically 4× the copy number; and match the molecular component concentration 1 to 1, as demonstrated in Example 9.

In some embodiments of the methods to build and/or debug a circuit herein described the testing of the molecular components and/or related set of polynucleotides, polypeptides and/or metabolites can be performed, in parallel in the cell-free system. In some of those embodiments, the in-parallel testing allows testing in parallel of multiple variants of the circuit, and of sub-circuits or motifs, thus resulting in an increased efficiency of testing and debugging genetic circuits compared to other approaches. In particular in some of those embodiments, experiments can be performed in very high-throughput format (eg. 384-well plates, droplets), and/or do not have restrictions on DNA input type (eg. multiple linear or plasmid DNAs can be tested in one cell-free mixture at once, while in a cellular target environment one is limited only to those compatible with the cell's growth and function) or reporter usage (eg. each cell-free mixture can have the same reportable molecular components providing the output of a circuit, but test a different sub-circuit, circuit variant or motif). In some embodiments, the reportable molecular component is one molecular component providing the output of the genetic circuit in accordance with the circuit design (eg. a fluorescent protein that is produced as a final output element). In other embodiments, multiple reportable molecular components are comprised in the genetic circuit and associated with operation of the circuit according to the circuit design (eg. multiple fluorescent proteins that are produced during the course of the genetic circuit, or fluorescent proteins linked to a functional protein in the circuit). In some embodiments, the reportable molecular component can be a chemical, small molecule, or metabolite produced directly or indirectly by a recombinant genetic component (eg. absorbance from a NADPH assay, the chemical conversation of one chemical to another, a pH change resulting from the activity of a recombinant genetic element).

In some embodiments, at least one of the testing, at least one detecting and/or at least one of the providing of methods to design, build, implement, debug and/or test of the present disclosure is performed can be performed "in parallel" which indicates performance of the testing, detecting and/or providing by a plurality of reactions occurring at a same time. Accordingly, for example, parallel testing and/or detecting indicates a testing and/or detecting that is performed by multiple reactions performed concurrently to reduce the test time. For example, parallel testing can be performed by two or more reactions either in silico or in cell-free mixtures, each testing a different molecular component and/or a combination of molecular components to detect, provide and/or select a same or different molecular component, a combination thereof, a signal and/or a functional characteristic of a molecular component, of a combination thereof and/or of a circuit.

The detection of the reportable molecular component can be performed by various methods identifiable by those skilled in the art, such as in vitro methods: fluorescence, absorbance, mass spectrometry, flow cytometry colorimetric, visual, UV, gas chromatography, liquid chromatography, protein gels, Western blot, thin layer chromatography, radioactivity. In particular a labeling signal can be quantitative or qualitatively detected with these techniques as will be understood by a skilled person. For example, a fluorescent protein such as GFP can be detected with an excitation range of 485 and an emission range of 515, and mRFP can be detected with an excitation range of 580 and an emission range of 610. Other fluorescent proteins include sfGFP, deGFP, eGFP, Venus, YFP, Cerulean, Citrine, CFP, eYFP, eCFP, mRFP, mCherry, mmCherry. Other detectable reports do not require excitation to detect; for example, In FIG. 59 and Example 54 each metabolic intermediate has a detectable color without necessary exication, which can be read in a basic spetrofluoromoter. Other detectable signals include dyes such as dsRed. Alexafluor, fluorescin, etc. . . . that may be bound to genetic components and then released upon an activity (eg. sequestration, FRET, digestion).

For example, in Examples 33-39 the reportable molecular component is the fluorescent protein deGFP and in Examples 40-48 it is Citrine, Cerulean, sfGFP, and mCherry. Note however that each non-fluorescent protein, such as tetR, lacI, etc. can also act as a reportable element if said protein is run under conditions that can detect its presence (eg. Western Blot, or antibody stain). The reportable element can also be a small molecule, such as in the case of Examples 55-57 where the production of deoxyviolacein, violacein, and proviolacein, that are processed versions of violacein, are detected using GC/LC-MS or thin layer chromatography. In some embodiments, e genetic molecular components comprising a protein such as VioA, VioB, and other identifiable by a skilled person can also be reportable elements if run on a system that can read proteins.

For in silico measurement, it is possible to directly measure that value of variables in the model that correspond to the concentrations of the genetic and molecular components of the circuit and to store, plot or analyze the resulting values for the purpose of measuring the operation of the genetic circuit.

In some embodiments at least one reportable molecular component is detectable in a cell-free system and in a target environment when the genetic circuit operates according to the circuit design.

In some embodiments, the detection of a reporting component in the context of the overall methods of the disclosure consists of allowing the operation of the genetic circuit in the cell-free environment for some period of time, at which point the method of detection is applied to an in vitro or in silico sample of the reaction. The genetic circuit can either continue to be operated in the cell-free system and further data points can be collected, or the operation of the circuit can be terminated by disposing of the reagents for an in vitro system or terminating the simulation program for an in silico system.

In some embodiments, methods and arrangements are provided to build and debug a genetic circuit of the disclosure which combines the steps of methods to build a circuit and methods to debug a circuit herein described.

In an exemplary embodiment the method can comprise the following steps (1) Designing the circuit, by providing a circuit design with an emphasis on the final functionality of the circuit. This designing step can be done on a complete circuit basis, (eg. outlining all of the pieces to achieve the desired functionality), or can be done on a sub-circuit basis, (e.g. designing sub-modules individually to test and then building submodules out). In an example illustrated in FIG. 24 if an oscillatory output is desired, such functionality can be accomplished by a structure of odd-numbered repressing genetic and/or cellular molecular components. The submodules can then be designed as repressor pairs to be tested (TetR, PhlF, LacI, CI, SrpR, etc. . . . ). In some embodiments, performance of this step can involve modeling of the motifs and/or subcircuit to assist in selecting and assembling the submodules.

(2) Building the circuit or sub-circuit, by physically creating genetic molecular components or cellular components to test and providing sub-sets of those molecular components according to approaches identifiable by a skilled person. For example in providing one or more genetic components of the circuit, if the genetic components are already present on an existing plasmid or other vector, such plasmid or vector can be used directly (eg. FIGS. 22A-D, where the repressilator is directly tested). Otherwise, sub-components of a genetic component (promoters, coding sequences, UTRs, terminators, etc) can be created by and assembled together, preferably using the method described in Examples 45-46, rapid linear DNA assembly.

(3) Testing the circuit or sub-circuit. The built pieces of DNA or other nucleic acids and/or proteins of genetic components, and cellular molecular components of the circuit comprising at least one reportable molecular components are then run in the cell-free systems. For example, molecular components of the circuit can be run in TX-TL system by providing the genetic and/or cellular molecular components and related sets of polynucleotides, polypeptides and/or metabolites in the setting of a tube, 384-well plate, continual steady state system, or other system to run the reaction, in line with the methodology outlined in [15]. In an exemplary embodiment outlined in FIG. 23B, a plasmid DNA encoding pPhlF-SrpR, pSrpR-BetI, pBetI-PhlF and a pPhlF-Citrine reporter plasmid is the actual DNA tested; while in an exemplary embodiment illustrated in FIG. 23C, three individual linear DNAs, each encoding pTetR-PhlF, pPhlF-SrpR, and pSrpR-tetR as well as a pTetR-Cerulean plasmid is the actual DNA tested. In the exemplary embodiment illustrated in FIGS. 9A-F, physical DNAs are used in association with molecular components 3OC12HSL (in varying amounts) and IPTG to generate time-trace curves a plasmid pLac-lasR and a reporter plasmid pLas-deGFP.

(4) Debugging the circuit or sub-circuit. This step can be carried out when the circuit or sub-circuit tested does not perform as expected, and can involves switching out non-functional parts for functional parts, or otherwise changing the structure of the circuit until a functional variant of the circuit is detected. For example, in the exemplary embodiment illustrated in FIG. 23D if it is not known a priori that odd numbers of repressors are needed to create an oscillating output, one would test an even (4) number of repressors, but the result would indicate switch-like behavior as opposed to oscillatory output. Based on this identified restriction it is possible to re-design the circuit accordingly to have an odd number for testing.

Figure 7:
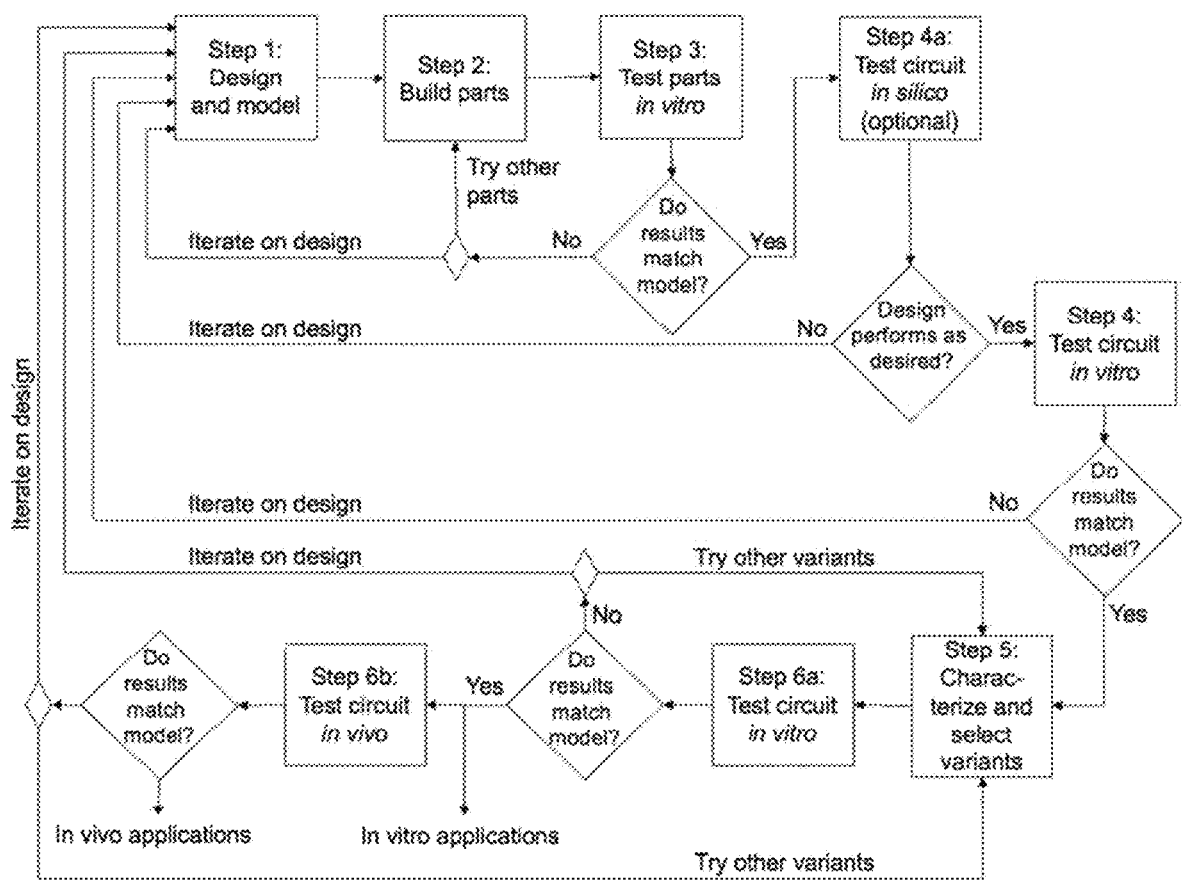
FIG. 7 shows a schematic illustrating the basic "workflow" of an exemplary prototyping and debugging of a biomolecular circuit, represented as a flow chart. The results of in vitro and in vivo experiments are compared to the results predicted by models. The steps are iterated if elements do not match.

Additional combinations of the testing of molecular components of the circuit and/or of combinations thereof and/or of related sets of polynucleotides, polypeptides and/or metabolites, and of the providing variants of the genetic circuit according to methods to build and/or debug a genetic circuit herein described, would be identifiable by a skilled person upon reading of the present disclosure For example, a further exemplary approach is illustrated in FIG. 7 which shows a flow chart representing a basic workflow of prototyping and debugging a biomolecular circuit according to the method above. The workflow is also referred to as "design, build, test" (DBT) cycles, with each cycle involving a combination of models, cell-free expression systems and in vivo circuits and steps of designing, building, testing and redesigning. The flow chart shown in FIG. 7 represents an exemplary integration of the testing and providing variants of the genetic circuit and demonstrates providing an exemplary illustration of how methods of the disclosure can be implemented.

In the illustration of FIG. 7, in Step 1 a model is provided which is a representation of the circuit in one of several possible forms: (a) a graphical representation consisting of nodes and edges, in which the nodes represent molecular and/or genetic components and the edges represent inhibition, activation, binding or converting interactions between the parts; (b) a set of mathematical equations that described the operation of the circuit; or (c) a computational model (computer algorithm) that can be used to obtain simulation data or other representations of the expected output of the circuit. All uses of the model provide a skilled designer with a description of the desired operation of the circuit, including how the circuit interacts with exogenous inputs and other components (molecules, DNA, RNA, proteins) that are present in a cell. Using the model, a skilled engineer can design a circuit that implements a desired function. The output of Step 1 can be a conceptual design consisting of a set of nodes that interact with each other and with molecules available in the cell to carry out a function. In addition to these parts, the circuit can further contain additional molecular species that are present in a cell or in the cell's environment that the components interact with.

In Step 2 of the method illustrated in the exemplary schematic of FIG. 7, individual nodes are built. There are many ways to build the individual nodes using either de novo synthesis of DNA, traditional cloning of DNA from natural organisms, or a variety of DNA assembly techniques (Gibson, Golden Gate, etc). The specific method used to construct a library of components (promoters, RBS's, coding sequences, terminators) along with a sequence of "connectors" that can be used to rapidly assembly a circuit.

In Step 3 of the method illustrated in the exemplary schematic of FIG. 7, once the individual parts are built, they are characterized to understand how they will function when assembled together into a circuit or pathway. The characterization of the parts is done by running cell-free assays in which either a single node or a larger subset of the nodes that will be used in a circuit are introduced into a cell-free expression system The following sequence of steps is performed to characterize a part according to the exemplary method of FIG. 7.

In Step 3.1, one or more pieces of linear or plasmid DNA representing the part is combined with the cell-free extract and an energy buffer in a container (test tube, well on a microtiter plate, or similar). The use of linear DNA allows for rapid prototyping.

In Step 3.2, additional chemicals can be added to the container to establish different conditions under which the part is to be characterized. For example, inducers may be added in different concentrations to characterize the function of a repressor protein.

In Step 3.3, the container is heated to a temperature an incubated for a period of time.

In Step 3.4, a measurement is taken, using an optical assay (absorbance or fluorescence), a chemical assay (mass spec) or other analytical technique.

In Step 3.5, the previous two steps are iterated at a specific rate and for a duration of time.

If the results of measurements on individual nodes do not match the mathematical models of Step 1 of the exemplary illustration of FIG. 7, the data from Step 3 can be used to improve the mathematical models and Step 1 can be repeated using these improved models.

In Step 4 of the method illustrated in the exemplary schematic of FIG. 7, once the individual nodes are characterized, they can be combined to form the design circuit or subcircuits (i.e. motifs). The combining of Step 4 can be carried out by the following substeps:

In step 4.1, a specific concentration of each part is mixed in a container containing extract and buffer. Different concentrations of different parts can be used to create a collection of variants that will be tested.

Steps 4.2 to 4.5 are similar to Steps 3.2-3.5 as previously described.

In an optional Step 4a, circuits can be tested in silico. An in silico approach can be used that uses as an input characterized parts from Step 3 and simulates, in silico, different formulations of the parts to form the design circuit or sub-circuits. This is done most accurately to reflect the findings one would obtain in vitro. The in silico toolbox can also provide data on the predicted function of the circuit in vivo.

In Step 5 of the method illustrated in the exemplary schematic of FIG. 7, using the data from Step 4, the performance of the circuit is characterized by analyzing the data and determining which combinations of parts, and in what relative concentrations, when combined together implement the function that is designed in Step 1.

At the end of Step 5 of the exemplary method of FIG. 7, a single DBT cycle is complete. At this stage, if the circuit does not perform as designed, the data from Step 5 and previous steps can be used to redesign the circuit, returning to any prior step in the workflow.

In Step 6 of exemplary method of FIG. 7, once a specific combination of nodes has been determined to provide the designed function in the breadboard, the nodes are combined so that multiple nodes are combined on pieces of DNA compatible with the cell. Typically, the circuit is consolidated onto 1, 2 or 3 plasmids that have compatible origins of replications (eg. can survive in the cell together). In this form, the circuit can be tested both in vitro using the cell-free system (in Step 6a) and in vivo using a cell (in Step 6b). For example the following steps can be used to create a plasmid form of the circuit that can be then tested for operativeness under the conditions of the target environment. Firstly, the specific nodes are designed to be in the stoichiometric ratios determined to be the most effective in vitro to match in vivo. Items that require low expression are put on low copy number plasmids while those that require high expression are put on high copy number plasmids. Promoter or ribosome binding site (RBS) can be varied in strengths. Next, the nodes are then engineered such that the final plasmids can be transformed into a cell for verification.

The in vitro verification of operativeness under the conditions of the target environment (Step 6a) can be performed in the exemplary method schematically illustrated in FIG. 7, by carrying out the following steps. Firstly, a specific concentration of the plasmid or other DNA sequence that contains multiple nodes is mixed in a container containing extract and buffer. If more than one piece of DNA is used, different concentrations of different plasmids can be used to create a collection of variants that will be tested. The following steps are similar to Steps 3.2-3.5 as previously described.

The output from Step 6a of the exemplary method schematically illustrated in FIG. 7 is a set of data that measure the performance of the circuit under desired conditions in a cell-free environment. These data are compared to the desired operation of the circuit (as represented by the design and model from Step 1 of FIG. 7,). If the results are the same, the circuit is operational in an in vitro environment. If the output from this step does not match the model, the data from Step 6a and previous steps can be used to redesign the circuit, returning to any prior step in the workflow. In some embodiments of the DBT cycles, the workflow can return to either Step 1 or Step 5 of the exemplary method schematically illustrated in FIG. 7, at this point.

The in vivo verification of operativeness under the conditions of the target environment in the exemplary method illustrated in FIG. 7 can be performed by carrying out the following steps. Firstly, cells are chemically, electrically or thermally treated to allow them to transport DNA from their external environment into the cytoplasm of the cell. Secondly, plasmids containing the DNA implementing a circuit, instantiated on one or more plasmids, are introduced into the environment of the treated cells. Thirdly, the plasmids are transformed into the cells by the introduction of an environmental stimulus (eg, temperature) that causes some fraction of the cells to incorporate one or more plasmids into the cytoplasm. Fourthly, the cells are transferred to container that contains growth media and an antibiotic, such that only those cells containing the desired circuit elements can divide and grow. The following steps are similar to Steps 3.3-3.5 as previously described.

The output from Step 6b of the exemplary method illustrated in FIG. 7, is a set of data that measure the performance of the circuit under desired conditions in a cell. These data are compared to the desired operation of the circuit (as represented by the design and model from Step 1) of the method of FIG. 7. If the results are the same, the circuit is operational in an in vivo environment. If the output from this step does not match the model, the data from Step 6b and previous steps can be used to redesign the circuit, returning to any prior step in the workflow. In some embodiments of the DBT cycles, the workflow can return to either Step 1 or Step 5 at this point.

At the end of this multi-step process schematically illustrated in FIG. 7, a single implementation iteration is complete. If the circuit does not perform as desired in the in vivo setting, the data from Step 6 and previous steps can be used to redesign the circuit, returning to any prior step in the workflow.

In some embodiments, one or more of the testing and providing genetic variants and related steps can be performed in an in silico cell-free system. In particular, steps can be performed in silico as part of the method for designing and debugging a genetic circuit. In some of those embodiment the testing and/or providing variant of the genetic circuit can be performed with an optional integration of in silico cell-free method that can comprise decomposing the desired circuit design into components, generating computational models containing biochemical reactions corresponding to the reactions present in the in vitro cell-free biomolecular breadboard for each component of the circuit design, characterizing the in silico models of each component or combinations of components by fitting the dynamic behavior of computer simulations of the models to the corresponding dynamic behavior measured in vitro, estimation of parameters from experimental data using appropriate computer algorithms, addition of the thus characterized parts into an in silico library of parts, and simulation of the full circuit by composition of components drawn from the library corresponding various experimental conditions, resulting in in silico predictions of the dynamic behavior of the circuit. The method then involves comparing this behavior to equivalent in vitro experimental data and using these comparisons to debug the operation of the in vitro implementation and modify the components of the genetic circuit based on the data and comparisons An example of an overall process for use of an in silico cell-free system in methods of the present disclosure is shown in FIG. 45 and involves the following six steps.

Figure 45:
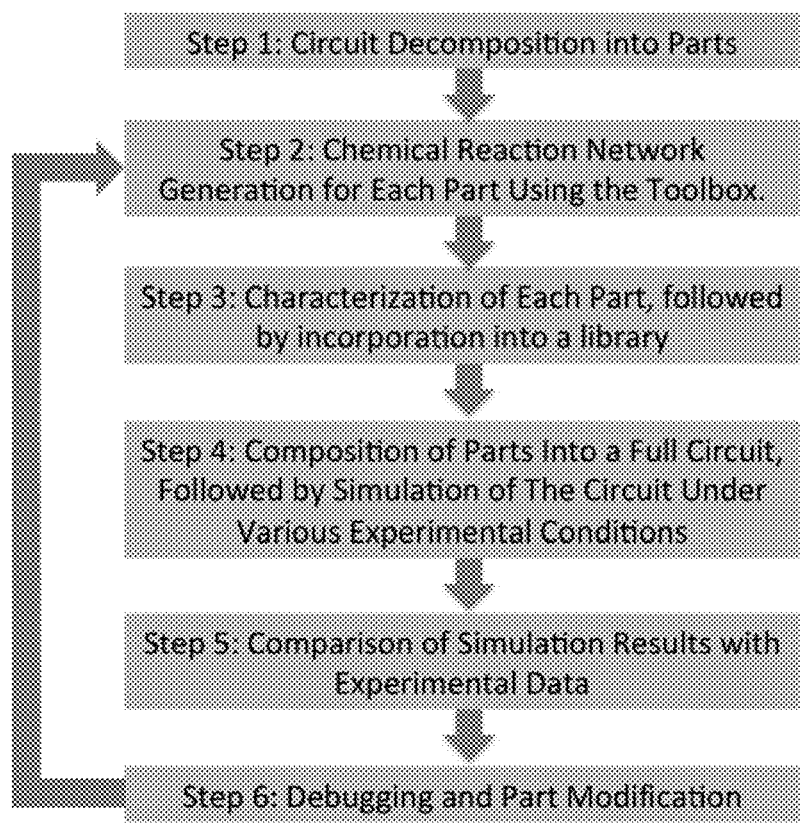
FIG. 45 provides a flow diagram that illustrates an implementation of the in silico modeling to predict circuit behavior by first characterizing parts.

Step 1 of the method shown in the exemplary illustration of FIG. 45 involves decomposing the circuit into parts. This step can be carried out in multiple ways, with flexible definitions of the parts. The definitions chosen for the parts can be performed so that it is possible to compose the parts into different circuits, and then characterize the behavior of each part by making the part carry out a function in the in vitro system. Thus, for example, in this context, the tetR repressor protein taken in isolation does not provide a useful definition of part, since it does not have a function independent of the pTet promoter and a reporter protein. The 5 parts into which the IFFL circuit (FIG. 11A for example) is decomposed are given in FIG. 50, where the parts are defined in the context of characterization experiments we carried out.

Step 2 of the method shown in the exemplary illustration of FIG. 45 is generating simulatable differential equation models for each part to be characterized. The only requirement from these models is that they be separate for each genetic or cellular molecular component, and in such a way that they be composable into larger circuits, such that the larger circuit model is also simulatable. ODE models can be chosen derived from mass action chemical kinetics applied to the biochemical equations present in the cell-free system. Generation of these models can be implemented using an in silico toolbox written for this purpose (Examples 21-26). The toolbox allows for individual models to be created for each part, each part's model to be characterizable (see Step 3 below, and (Examples 27-28), and composable into a larger circuit which can be simulated under various variations in experimental conditions (Examples 29-30).

Figure 52:
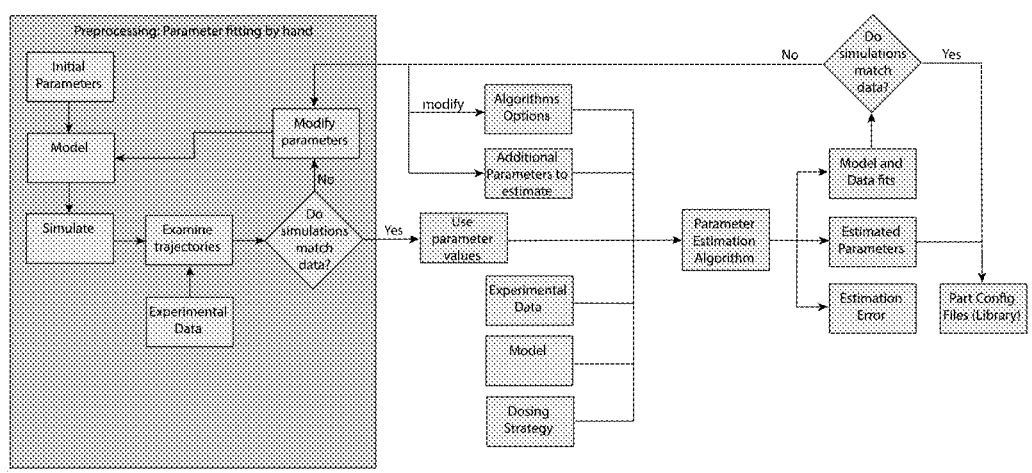
FIG. 52 provides a flowchart that illustrates the overall parameter estimation procedure in one embodiment.

Step 3 of the method shown in the exemplary illustration of FIG. 45 is a characterization of each part, followed by incorporation into a library. The characterization involves subjecting the parts to variations in experimental conditions both in silico and in vitro, then fitting the in silico (models') behavior to the in vitro behavior of the parts. The fitting itself is carried out by using parameter estimation algorithms, and the overall procedure is outlined in FIG. 52. In the context of FIG. 7, FIG. 52 implements Steps 1 to 4 of FIG. 7. In particular, the model already contains initial parameters, and this can be used to get initial simulations of the parts and circuit (Step 1), which can be used to create preliminary comparisions to experimental data (diamond under Step 3) and the iterative procedure shown in FIG. 52 is implemented by the iteration loop between Steps 3 and 1 in FIG. 7. One specific implementation of parameter estimation of the method schematically illustrated in FIG. 45 can be performed using MATLAB SimBiology's in built parameter estimation capabilities in conjunction with the models created in Step 2 of the method schematically illustrated in FIG. 45. In some embodiments there might be dependencies in the parameter estimation procedure arising from the fact that estimating parameters for some parts my require information on other parts. For example, when the tetR repression strength parameters are characterized using the circuit pLac-tetR repressing ptet-deGFP, knowledge of the constitutive expression strength of pLac and pTet is required. These dependencies can result in carrying out the characterization in a certain order. An example of such an order is given in the FIG. 53. After part characterization, the characterized parts can be stored in a digital library, as described in Example 28, and drawn upon when needed for composition into circuits. In the example, this corresponds to a folder in the toolbox where the code and parameter files for components (such as promoters, ribosome binding sites and proteins) which comprise parts can be stored.

Step 4 of the method schematically shown in the exemplary illustration of FIG. 45 is the assembling of components and parts from Step 3 into the full circuit and their simulation under various experimental perturbations, such as the variation of DNA or inducer molecule concentrations. This corresponds to Step 4a in FIG. 7. This step, in our example, can be implemented by the toolbox, and is given by the FIG. 55 and Example 29.

Step 5 of the method schematically shown in the exemplary illustration of FIG. 45 involves comparing simulations of the full circuit behavior under the various experimental perturbations (for example DNA and inducer concentration variations) to corresponding experiments in vitro. FIGS. 43A-F and 44 give this step in the context of our example.

Step 6 of the method schematically shown in the exemplary illustration of FIG. 45 involves debugging of the system if the predicted in silico behavior does not match the in vitro behavior. This is elaborated upon in Example 30. It might turn out that the parts and experiments we define need to be at a finer resolution. For example, tagging the RNA with aptamers may be used to allow measuring the RNA, and thus characterization of the parameters for transcription and translation separately, and perhaps more reliably. Another example would be to decouple repressor protein production from repression by adding purified repressor protein to a mixture containing the repressible promoter controlling a reporter. All of these steps involve greater effort on the part of the designer, but potentially help to identify sources of error and lead to more reliable circuit characterization.

Additional, implementation of the methods of the present disclosure where some of the testing, providing and/or detecting can be performed with steps or sub-steps performed in silico are provided in the Examples and further implementations can be identified by a skilled person upon reading of the present disclosure.

In some embodiments, methods and arrangements herein described can be used to testing a cell-free system variation of a genetic circuit to be operated in a target environment. In some embodiments the testing can be performed for the purpose of characterization or understanding the function of the circuit. In some embodiments, the testing can be performed to identify effect of a text compound and/or modification of environment conditions of the circuit.

In some of those embodiments, a method can comprise providing a variation of the genetic circuit by replacing one or more molecular components of the genetic circuit with the one or more molecular components selected by the testing and/or by adding to the genetic circuit the one or more molecular components selected by the testing. For example, providing a variation of the circuit can be performed by varying one polynucleotide forming or comprised in a molecular component of the circuit to account for different protein mutants, protein mutants. In some of those embodiments, variants of the one polynucleotide can be identified from a bioinformatics or computational library as applied in Examples 49-59 and then individually tested in the context of the genetic circuit in separate cell-free mixtures. A desired variant based on the desired function of the circuit can then be chosen.

In some embodiments of methods of testing a variation of a genetic circuit, wherein variants can be provided by breaking down the parts of a genetic molecular component (e.g. gene or RNA) into separate pieces (e.g. coding regions and one or more regulatory regions) and then re-combine the pieces in a set manner, as illustrated in Examples 45-48 to provide multiple variants each formed by a different combination of the pieces. For example, to be able to generate multiple variants of the physical DNA to be tested, the physical DNA can be broken down into sub-units (promoter, UTR, coding sequence, terminator)

Figure 22C:
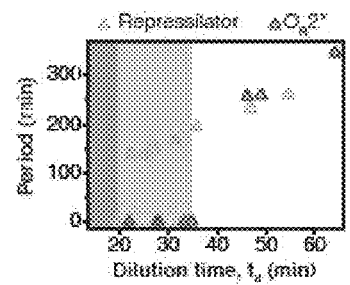
Figure 22B:
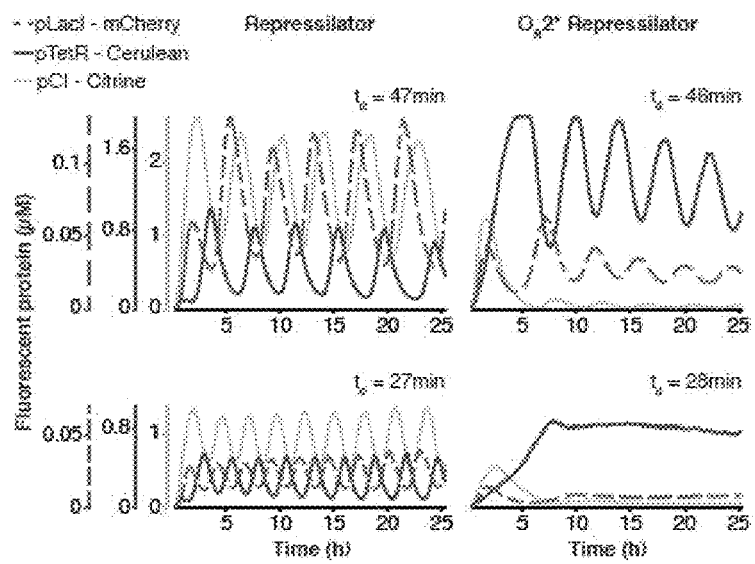

In some embodiments of methods of testing a variation of a genetic circuit, variants of the genetic circuit can be provided by adjusting protein production levels performed e.g. by changing transcriptional units (eg. promoters) or translational units (eg. RBS), the method also comprises varying protein production by physically varying the concentration of the genetic component provided in the reaction. This serves to emulate a change in transcriptional or translational units, but allows for rapid adjustment of protein concentration that would otherwise not be possible in an in vivo target environment but is possible in the in vivo setting. For example, in FIGS. 43A-F and 44 and Examples 17 and 18 demonstrating a sensitivity analysis, instead of modifying the RBS or promoter of the tetR producing, deGFP producing, or lasR producing plasmid DNA, the plasmid DNA itself is varied and the resulting response in the reporting element is measured. Doing so saves significant time as new genetic components do not need to be built to test the effect of tetR, deGFP, or lasR. When converting results to an in vivo target environment, a corresponding weak, medium, or strong RBS can be put in replacement of the low, medium, or high DNA concentration, respectively; this is demonstrated in FIG. 16 and Example 32, where the in vitro experiment was conducted by varying lasR plasmid DNA, but the in vivo equivalent is by varying BCD from weak BCD22 to medium BCD20 to strong BCD2. The conversion can also occur by varying the plasmid copy number that components are put on; this is demonstrated in FIGS. 43A-F and 44 and Examples 17 and 18 were from the tetR, deGFP, or lasR DNA concentration variation experiments it is seen that the circuit is extremely sensitive to tetR but linear to deGFP; therefore when translating to in vivo the tetR producing plasmid is put on a low copy pSC101, while the deGFP is put on a high copy colE1 in Example 10 and 11. Those skilled in the art will realize there is the possibility of an operator site mismatch, as seen in FIG. 22A-C that is introduced by increasing the concentration of a DNA element (or modifying the element), and can compensate for this mismatch through adding additional operator sites or adjusting the circuit prediction accordingly in vitro or in silico.

In some embodiments of methods of testing a variation of a genetic circuit, variants of the genetic circuit can be provided by modifying one or more parameter or property of the set of polynucleotides, polypeptides and/or metabolites and monitor the resulting change of the transcriptional and/or translational activity of a reporter protein. In particular, the one or more parameter or property of the set of polynucleotides, polypeptides and/or metabolites that can be modified include the concentration of the polynucleotides, polypeptides and/or metabolites, the sequence of polynucleotides and/or polypeptides that constitute the regulating and reporting molecular components, the temperature of the system, the buffer conditions, and other factors that can affect the expression level of a reporter protein. In some of those embodiments, one or more parameters or properties of the combined two or more sets of polynucleotides, polypeptides and/or metabolites can be varied and the resulting change in the transcriptional or translations level of expression of the reporter can be monitored and detected.

In embodiments of methods of testing a variation of a genetic circuit, one or more parameter or property of the set of polynucleotides, polypeptides and/or metabolites can be modified that comprise the concentration of the polynucleotides, polypeptides and/or metabolites, the sequence of polynucleotides and/or polypeptides that constitute the regulating and reporting molecular components and other factors that can affect the expression level of a reporter protein.

In some embodiments of methods of testing a variation of a genetic circuit, providing a variant of the genetic circuit can be performed by testing and characterization of a single set of polynucleotides, polypeptides and/or metabolites involve adding into the cell-free system linkage molecules such as inducers and enzymes and monitor the resulting change in the transcriptional and/or translational activity of a reporter protein. Small molecules are frequently used to vary the function of a circuit in the context of keeping genetic components constant; for example, in Example 31 varying aTc concentration adjusts the activity of tetR repression, therefore shifting the reporting element strength and pulse duration, while varying 3OC12 concentration in Example 14 adjusts the activity of lasR activation, also varying reporting element strength. The small molecules can also act on endogenous proteins that are not provided by the user, but innate to the system; for example, in FIGS. 9A-F (in vitro) and FIGS. 11A-G (in vivo), cell-free mixtures that are made from strains that retain functional copies of the lacI gene. In this example, the endogenous lacI can affect the performance of a genetic circuit; therefore, IPTG can be provided to sequester endogenous lacI such that user-provided genetic components with pLacO1 are not repressed. Addition of IPTG can also be provided, for example, if the target environment is a lacI knockout strain, but the cell-free mixture used has lacI present; so that the IPTG can then allow for a better emulation of the final target environment.

Figure 22D:
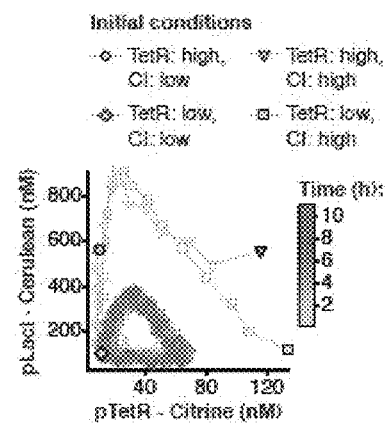

In some embodiments of methods of testing a variation of a genetic circuit, providing a variant of the genetic circuit can be performed by modifying molecular components or parameters to affect the expression in vitro include purified proteins, such as gamS, which is shown in Example 42-43 to protect linear DNA cassettes from degradation by endogenous exonucleases in *E. coli* S30 cell-free mixtures. By blocking endogenous exonucleases, the addition of gamS allows for genetic circuits to be encoded on linear DNA genetic components as opposed to plasmid DNA genetic components, which saves time in prototyping in vitro. In FIG. 22D, one can also add purified proteins which directly affect the genetic circuit; in this case, to test the ability of an oscillator to maintain oscillation in vitro, purified protein amounts of a genetic component lambdaCI, tetR, and lacI are added to the reaction to artificially start the reaction at one axis, and the resulting response of the circuit is observed. These components can be either purified separately and stored in a buffer compatible with TX-TL in Example 42, or can be pre-made in a separate TX-TL reaction and then added to the new reaction. Additional proteins, such as ClpX, can be added to the reaction to speed up the degradation of -ssrA tagged proteins such as in FIGS. 56A-B: this has the effect of decreasing available protein amounts in the system, and is the only substantial way to decrease protein concentration in a system that does not have dilution of the cell-free mixture.

In some embodiments of methods of testing a variation of a genetic circuit, providing a variant of the genetic circuit can be performed by adding polynucleotides, such as DNA and RNA to the mixture that can affect in vitro expression. For example, in the middle of the reaction DNA can be added that codes for additional proteins if proteins are to be timed in a certain order to emulate the in vivo production timing. In addition, purified RNA can be added that is able to activate or repress genetic components.

Various embodiments of providing variants of a genetic circuit indicated for the methods of testing a variation of a genetic circuit, can also be used in method of building and/or debugging a genetic circuit as will be understood by a skilled person.

In embodiments, of methods of testing a variation of a genetic circuit, operativeness of a variated circuit can be tested by detection of a reportable molecular component detectable when the circuit operates according to the circuit design, in a manner similar to the testing performed in methods to build and/or debug a genetic circuit herein described.

In some embodiments detection of a reportable molecular component can be performed by testing expression of a reportable molecular component controlled by other molecular components of the circuit and monitored at a transcription level. In particular, the transcription level of gene expression can be controlled by regulatory sequence with different strength (such as promoters with different strength) and in methods where variants of the genetic circuit or portions thereof are provided the providing can be performed by modifying these regulatory sequences and/or expression level of the transcription regulatory factors as well as the interactions between the transcription regulatory factors and the regulatory sequence of the gene encoding the reporter protein. Reference is made for example, to the procedure of Example 5, where transcriptional production of a protein is controlled by five variants of the pLas promoter, and these variants result in different amounts of protein being produced, with the amounts of protein per promoter in TX-TL roughly corresponding to the amounts of protein per promoter in vivo. Therefore, one can vary the promoter unit and expect a corresponding difference in protein production in vitro, in vivo, and in silico. It is noted in the disclosure that a priori, it is difficult to those skilled in the art to design promoters with specific transcriptional strength, but promoters can be tested in the in vitro mixture or the in vivo target environment and strengths assigned experimentally.

In some embodiments detection of a reportable molecular component can be performed by detection of expression of the reportable component controlled by other molecular components of the circuit at a translational level. In particular, the translational level of the protein expression can be controlled by using RBS sequences with varying RBS binding efficiency. Thus, in methods where variants of the genetic circuit or portions thereof are provided the providing can be performed by modifying the protein expression at a translational level by modifying the RBS. Additional exemplary molecular components capable of controlling a protein at the translational level include small RNA methods, such as riboregulators [7], or natural methods, such as antisense RNA [30], or small-molecule interference [31], and additional components identifiable by a skilled person.

In embodiments of methods to test a variation of a genetic circuits the methods can also also comprise iterating the testing of one or more molecular components and providing a variation of the genetic circuit to provide in the cell-free system a variated genetic circuit to be operated in the target environment.

In some embodiments of the methods to design, build, implement debug and/or test a genetic circuit herein described the target environment comprises two or more target environments and the testing, providing variants of the circuit and/or the detecting can be performed in different target environment of the two or more target environments as will be understood by a skilled person.

In some embodiments, methods to design, build, implement and/or test a genetic circuit herein described can be used to perform cell-free prototyping of a genetic circuit. The term "cell-free prototyping" indicates the combination of techniques required to implement the design, build, test and debug operations using a cell-free biomolecular breadboard required to create a genetic circuit that can be operated in said target environment. In particular, an exemplary cell-free biomolecular breadboard in the sense of the disclosure comprises components required for implementing a "design, build, test" (DBT) cycle, including a combination of models, cell-free expression systems and in vivo biological environments In embodiments herein described, molecular components, combinations thereof and/or related sets of polynucleotide polypeptides and/or metabolites, can be provided possibly together with cell-free mixtures or other devices, tools, protocols, and compositions, in one or more arrangements to build and/or debug in a cell-free system, a genetic circuit to be operated in a target environment, and/or in one or more arrangements to test a variation of a genetic circuit to be operated in a target environment.

In some embodiments, the arrangement can comprise a combination of the each set of selected polynucleotides, polypeptides and/or metabolites, the combination of the each set of selected polynucleotides, polypeptides and/or metabolites, capable of providing when comprised in a single cell-free mixtures the reporting molecular component forming one node of the genetic circuit according to methods for building and/or debugging a genetic circuit of the present disclosure.

In some embodiments, the arrangement can comprise a combination of the each set of selected polynucleotides, polypeptides and/or metabolites, the combination of the each set capable of providing when comprised in a single cell-free mixtures the reportable molecular component the genetic circuit built and/or debugged according to methods, of the present disclosure; and at least one reagent capable of performing a variation of the genetic circuit and in particular a variation in at least one of the molecular components of the genetic circuit.

In some embodiments, the arrangement can comprise a combination of the each set of selected polynucleotides, polypeptides and/or metabolites, the combination of the each set of selected polynucleotides, polypeptides and/or metabolites capable of providing when comprised in a single cell-free mixtures the reportable molecular component forming of the genetic circuit built according to methods for building and/or debugging a genetic circuit of the present disclosure. The arrangement can further comprise at least one set polynucleotides, polypeptides and/or metabolites providing additional molecular components for simultaneous, combined or sequential use in method to test a variation of the genetic circuit according to the present disclosure.

In some embodiments, arrangements herein described can comprise one or more in silico toolboxes to generate computational models containing biochemical reactions corresponding to the reactions present in the in vitro cell-free biomolecular breadboard, a set of instructions and algorithms to estimate parameters by fitting the models to experimental data collected in vitro, a set of instructions and algorithms for composing characterized parts in silico into the full circuit, followed by simulation of the circuit under various experimental perturbations to get predictions under these experimental perturbations, and set of instructions for plotting the in silico predictions against in vitro experimental data.

In some embodiments, an arrangement can be a customized kit of genetic and molecular components, where the customized kit is to prototype a circuit (e.g provided from a third party), and the kit composes the genetic components or sub-components necessary to conduct prototyping the genetic circuit while utilizing the biomolecular breadboard and its associated methods. The arrangement has a well defined subset of genetic components that are based on the circuit to be prototyped using the biomolecular breadboard, which includes (1) all genetic components necessary for the circuit to run, as well as (2) homologs to the components, (3) individual subparts and homologs, and (4) a set of "standard parts" that those skilled in the art would require, such as promoters (e.g. constitutive promoters, inducible promoters, and repressible promoters), ribosome binding sites (e.g. BCD RBSs, MCD RBSs), coding sequences and/or RNA regulatory sequences (e.g. transcriptional activating factors, transcriptional repressing factors, translational activating factors, translational inhibiting factors, fluorescent reporters, and absorbance reporters) and terminators (e.g. T500, B1002, synthetic terminators, and natural terminators). The arrangement can also have a defined subset of molecular components that are based on the circuit to be prototyped using the biomolecular breadboard, which includes all the small molecule inducers already present in the circuit, plus a standard set well-known to those skilled in the art (eg. aTc, IPTG, 3OC6HSL, 3OC12HSL, arabinose, C4HSL). The kit can be supplemented by a user with other genetic and molecular components as necessary to performing the testing, providing and contacting and/or building of the methods herein described.

In some embodiments, this arrangement can include, in addition to the in vitro mixture, an in silico mixture where reactions can be modeled and virtually run. This in silico mixture can be preloaded with components that are requested by the third party, including individual parts and their reactions as well as generic parts for which the reactions are known, such that the third party is able to utilize the in silico mixture to design their genetic circuit as well as verify the findings of the in vitro mixture.

In some embodiments, the arrangement can include multiple in vitro mixtures that target the target environment. In some of those embodiments the multiple in vitro mixtures comprise multiple in vitro mixtures from different organisms (eg. *E. coli*, other prokaryotic organisms and eukaryotic organisms), multiple in vitro mixtures from the same organisms but of different strains (eg. *E. coli* MG1655, *E. coli* BL21, *E. coli* BL21DE3, *E. coli* MG1655Z1, and *E. coli* KL740), multiple in vitro mixtures from the same organisms and the same strain but optimized for different target environments (e.g. high pH, low pH, presence of radiolabeled amino acids or metabolites, and presence of non-natural amino acids), or other in vitro mixtures identifiable by a skilled person.

In some embodiments, the in vitro mixture can be provided in different end-use environments, such as a batch mode reaction, continual steady-state reaction, lyophilized reaction, droplet microfluidics reaction, dialysis cassette reaction, and other end-use environments identifiable by those skilled in the art.

An example of this arrangement is one that can be used to build, implement, debug or test the feed-forward loop Examples 6-11 according to methods herein described. According to this example a kit can include:

- each specific piece of DNA that generates the circuit, such as pConst-lasR, pLas-tetR, pLas-tetO-deGFP-ssrA, pConst-araC, pAraC-lacI, pAraC-lacO-deGFP-ssrA, pLas-lacI, pLas-lacO-deGFP-ssrA, pAraC-tetR, pAraC-tetO1-deGFP-ssrA, and others identifiable by a skilled person;
- control elements provided as separate pieces that can be assembled by the method of Example 45-48 such as pConst, pLas, pAraC, pLas-tetO, pLas-lacO, pAraC-tetO, pAraC-lacO, pTet, pLac; UTR1, BCD2, BCD7, BCD11, BCD13, BCD12, BCD14, BCD20, BCD16, BCD24, BCD22, B0030, B0031, B0032, B0034; lasR, araC, tetR, lacI, deGFP, deGFP-ssrA, mRFP, mRFP-ssrA, lasR-ssrA, araC-ssrA, tetR-ssrA, lacI-ssrA; T500, B1002; and others identifiable by a skilled person; and standard parts typically together with instructions for the building pulse generators as control mechanisms in *E. coli*, that are either based on lasR or araC activators and tetR or lacI repressors according to one or more methods herein described, In the exemplary of kit that can be used to build, implement, debug or test the feed-forward loop Examples 6-11 according to methods herein described, the kit can also comprise molecular components such as aTc, IPTG, arabinose, as well as standard molecular components. The in silico mixture can be pre-loaded with the dynamics of each genetic component's activity. The in vitro mixtures included typically depend on the target environment, For example if the genetic circuit is to be operated in *E. coli*, then a standard TX-TL made from *E. coli* can be included, alone or together with variants of the strain (eg. a lacI knockout, and/or a T7-expressing strain). If the target environment is in vivo, the components of the kit can be provided for use in a batch mode reaction, or a continual steady-state system.

Another example of this arrangements wherein the in vitro mixture can be provided in different end-use environments, is the kit that can be used to build, implement, debug or test the the violacein metabolic pathway example in Examples 49-59. According to this example, a kit can include:

- each specific piece of DNA that generates the circuit, such as pConst-vioA, pConst-vioB, pConst-vioE, pConst-vioC, pConst-vioD, and others identifiable by a skilled person;
- control elements provided as separate pieces that can be easily assembled by the method of Example 45-48 such as pConst (e.g. pJ3151, pT7, pT4, pOR21Pr); UTR1, BCD2, BCD7, BCD11, BCD13, BCD12, BCD14, BCD20, BCD16, BCD24, BCD22, B0030, B0031, B0032, B0034; vioA, vioB, vioE, vioC, vioD; T500, B1002; and
- standard parts typically together with instructions for building a metabolic pathway, (e.g. with the goal of optimizing the production of end-violacein product) according to one or more methods herein described In the exemplary kit that can be used to build, implement, debug or test the violacein metabolic pathway example in Examples 49-59, the kit can also comprise molecular components of the circuit, in this case pathway intermediates, such as such as Tryptophan, IPA, CPA, Prodeoxyviolacein, Deoxyviolacein, Proviolacein, Violacein, as well as standard molecular components. The in silico mixture can be pre-loaded with the dynamics of each genetic component's activity. The in vitro mixtures included typically depend on the target environment. For example if the genetic circuit is meant to be operated in *E. coli*, then a standard TX-TL made from *E. coli* can be included, alone or together with variants on the strain (eg. a lacI knockout, a T7-expressing strain, a strain optimized for small molecule production), or on the condition of the TX-TL (e.g. more basic or acidic, or optimized for production at high OD). If the target environment is an in vivo target environment for scale up, the components of the kit can be provided for use a batch mode reaction, or a continual steady-state system. If the target environment is an in vitro target environment, the components of the kit can be provided for use in a cell-free system utilizing a large bioreactor, with oxygen pumped in to achieve maximum production.

Further effects and characteristics of the present disclosure will become more apparent hereinafter from the following detailed disclosure of by way of illustration only with reference to an experimental section.

EXAMPLES

The biomolecular breadboards and related methods and systems for testing and debugging herein described are further illustrated in the following examples, which are provided by way of illustration and are not intended to be limiting.

In particular, the following examples illustrate exemplary methods and protocols for preparing sets of polynucleotides and polypeptides, testing and characterizing these sets of polynucleotides and polypeptides, building genetic circuits, and testing and debugging genetic circuits. A person skilled in the art will appreciate the applicability and the necessary modifications to adapt the features described in detail in the present section, to additional genetic circuits and biomolecular breadboards and related methods and systems according to embodiments of the present disclosure.

In vivo strain preparation and testing: For in vivo assays, plasmids are cloned onto compatible vectors, such as (colE1/carbR, pSC101/kanR, p15A/specR) [32-34]¶ and chemically transformed into a competent cell strain. This cell strain can be a BL-21 derived expression strain carrying lacIQ on a miniF/cmR (ExpressIQ, New England Biolabs), for example, or another strain suitable for a in vitro target environment. For a typical single strain assay, cells are selected for on antibiotic resistant agar plates before use. For a typical multi-panel assays, cells are recovered for 2 hours at 29 C in SOC medium (Sigma) before outgrowth at a 1.25% dilution in MOPS-EZ Rich (Teknova) 0.4% glycerol selective media containing antibiotics against the strain (eg. if resistant to cmR, kanR, carbR, and specR, 10 µg/mL chloramphenicol, 50 µg/mL kanamycin, 100 µg/mL carbenicillin, and 100 µg/mL spectinomycin) and storage at −80 C. To conduct a typical in vivo assays, cells are grown in the same selective MOPS media to stationery phase at 29 C. Cells are then diluted 1% into 500 uL per well in 96-well MatriPlates (Brooks Life Sciences) with half-antibiotic concentration previously used. If multiple plate readers are used, such as three of (Biotek H1/MF), these are calibrated for fluorescent intensity and absorbance. Plates were measured every 6 minutes for the reporting component (eg. if, deGFP, 485 nm/515 nm gain 61 and 100), and OD, 600 nm under a linear continuous shaking mode. At OD 0.1-0.2, cells are induced with the appropriate inducer (eg. aTc, IPTG, and/or 3OC12HSL) and then measured for an additional 16 hours until stationery phase.

Cell-Extract Preparation:

Preparation and execution of TX-TL is according to previously described protocols [15], with a modification of the strain used (e.g. to ExpressIQ (New England Biolabs)) if that is the strain to match the in vivo target environment. However, if the target environment is different, then to get results as close as possible the same target environment should be made into the TX-TL using the protocols in [15]. If this is not possible or not convenient, the results from another target environment can also be utilized in lieu; however, the correlation between the biomolecular breadboard and the target environment may be lower. This resulted in an extract, (eg. "eZS8") with certain conditions, in this case: 9.9 mg/mL protein, 9.5 mM Mg-glutamate, 95 mM K-glutamate, 0.33 mM DTT, 1.5 mM each amino acid except leucine, 1.25 mM leucine, 50 mM HEPES, 1.5 mM ATP and GTP, 0.9 mM CTP and UTP, 0.2 mg/mL tRNA, 0.26 mM CoA, 0.33 mM NAD, 0.75 mM cAMP, 0.068 mM folinic acid, 1 mM spermidine, 30 mM 3-PGA, 2% PEG-8000. For different TX-TL preparations, different conditions are used to obtain optimal expression conditions. To optimize for signal, Mg-glutamate and K-glutamate is typically optimized. Only one extract should be used to prevent extract-to-extract variation.

Cell-Free Execution:

Reactions are typically conducted in 10-20 µL in a 384-well plate (Nunc) at 29° C., and read for the reporting component (eg. if deGFP, then in a Synergy H1/MF plate reader (Biotek) at 485 nm/515 nm gain 61; if Venus, 505 nm/535 nm, gain 61; if mRFP, 580 nm/610 nm, gain 100). The complete instructions for preparing and running cell-free reactions is described in [15]. However, cell-free reactions can also be run in different modes, such as a continual steady-state system [27], or a long-term dilution system [35], or in a large vessel [36], among others.

Plasmid Preparation:

DNA is cloned using standard molecular biology procedures [28-30] and propagated in a compatible strain, such as JM109 recA-lacIQ (Zymo Research) strain for purification. Note that the strain for propogation should be chosen dependent on the property of the plasmid; for example, a pLacO1 promoter [4] plasmid should be propogated in as lacI repressor strain, while a pLambdaCI [37] promoter should be propogated in a lambdaCI repressor strain (eg. KL740), while a non- or low-expressing plasmid can be propogated in a traditional JM109, BL21, DH5alpha, or other cloning strain. DNA can also be made purely synthetically, or from isolation from natural sources. It is important that the plasmids produced are compatible for the in vitro mixture and for the target environment (eg. in methylation patterns, endonuclease cut sites, etc. . . . ) Small scale purifications are done by miniprep (PureYield, Promega) followed by a PCR purification for desalting (QiaQuick, Qiagen). The presence of minimal salt is important for efficient expression of plasmids in cell-free mixtures. Large scale purifications are done by midiprep or maxiprep (NucleoBond Xtra Midi or NucleoBond Xtra Maxi, Macherey-Nagel). All plasmids were isolated from strains in stationery phase and sequenced before use.

Quantitative PCR for Determining Plasmid Copy Number:

To match the concentrations of the plasmids in the same relative ratios as they are in vivo, it is good practice to preform a quantitative PCR (qPCR) against the same plasmids in the in vivo target environment. Two samples corresponding to a high and a low expressing strain from active in vivo assays are isolated at OD 0.9 at 29 C in selective growth media (eg. MOPS with half antibiotic concentration). Glycerol was added to a 25% final working concentration, and samples were stored at −80 C until use. Samples are used directly at a 1:500 dilution in a 50 µL qPCR reaction with 200 nM primers. Samples are run with Power Sybr Green PCR (Life Technologies), and measured in a MX3005 (Stratagene) at 95 C for 10 min followed by 40 cycles of 95 C for 15 seconds and 6 C for 1 min. Primers used are chosen by OligoAnalyzer Software (Integrated DNA Technologies) and amplify a constant region in the plasmid (eg., in the kanR, specR, and carbR region of the pSC101, p15A, and colE1 plasmid respectively, if using a three-plasmid system with those resistance markers). Each sample is repeated three times in a sample and over three samples. Data is analyzed using the comparative Ct method against the a constant region, such as a kanR gene. Standard curves to verify equivalent efficiency are made using 1:10 dilutions of the template against each primer set.

Protein Purification:

Proteins may need to be purified to be added into TX-TL; or to be used as a standard. For fluorescent proteins eGFP, mRFP, and Venus and variants eGFP-ssrA, mRFP-ssrA, and Venus-ssrA, coding sequences were cloned into a T7-lacO inducible vector containing a N-terminus His6 tag using standard techniques and propagated in a BL21-DE3 strain (New England Biolabs). Proteins are purified following a similar protocol as in [38], but were grown in TB broth in lieu of LB broth, induced with 1 mM IPTG (final concentration), and selected for a band between 25 kDa-35 kDa corresponding to the fluorescent protein in question. Fluorescent proteins were further processed in a Supradex 20 10/300 column to select for pure, active proportions, and flash-frozen at −80° C. in a storage buffer consisting of: 50 mM Tris-Cl pH 7.5, 100 mM NaCl, 1 mM DTT, 1 mM EDTA, 2% DMSO. Note that this storage buffer is critical for proteins to be functional in TX-TL, as typical glycerol-based storage buffers significantly decrease protein expression.[38] Final concentrations in this example are: deGFP-ssrA, 164.8 uM; deGFP, 184.8 uM; mRFP-ssrA, 185.6 uM; mRFP, 170.6 uM; Venus-ssrA, 87.9 uM; Venus, 147.5 uM.

Some proteins may need more specialized methods of purification, if traditional purification methods are not effective at maintaining active protein. For example, for ClpX, a monomeric N-terminal deletion variant Flag-clpXdeltaN-LinkedHexamer-His6 was used [39](Addgene #22143), as purifying the wildtype with a N-terminal Histag using general Ni-NTA purification techniques resulted in a loss of activity. The Ni-NTA purification procedure listed in [40] was used, followed by Supradex 20 10/300 and functional testing for pure, active proportions above 250 kDa. Active proportions were flash frozen in the same buffer used for fluorescent proteins. Final concentration of ClpX was 1.95 uM.

Linear DNA Preparation from PCR:

To generate PCR products, the process is described below. PCR products are amplified using Pfu Phusion Polymerase (New England Biolabs), and were DpnI digested. Plasmids are either miniprepped using a PureYield column (Promega) or midiprepped using a NucleoBond Xtra Midi column (Macherey-Nagel). All plasmids are processed at stationery phase. Before use in the cell-free reaction, both plasmids and PCR products undergo an additional PCR purification step using a QiaQuick column (Qiagen) which removed excess salt detrimental to TX-TL, and are eluted and stored in 10 mM Tris-Cl solution, pH 8.5 at 4° C. for short term storage and −20° C. for long term storage.

Rapid In Vitro Assembly of Linear DNA for Linear DNA Testing:

Linear DNA fragments are amplified using Pfu Phusion Polymerase (New England Biolabs), DpnI digested for 5 minutes at 37° C. (New England Biolabs) while verified with agarose gel electrophoresis, and PCR purified using previously described procedures. Fragments are then assembled in vitro using either Isothermal assembly or Golden Gate assembly. For Isothermal assembly, Gibson Assembly Master Mix (New England Biolabs) was used according to manufacturer instructions with 1:3 molar ratio vector:insert, and reacted at 1 hour at 50° C. [41] For Golden Gate assembly, a 15 µL reaction was set up consisting of equimolar amounts of vector and insert, 1.5 µL 10×NEB T4 Buffer (New England Biolabs), 1.5 µL 10×BSA (New England Biolabs), 1 µL BsaI (New England Biolabs), and 1 µL T4 Ligase at 2 million units/mL (New England Biolabs) [42]. Reactions were run in a thermocycler at: 10 cycles of 2 min/37° C., 3 min/20° C., 1 cycle 5 min/50° C., 5 min/80° C. For Golden Gate assembly, constructs with internal BsaI cut sites were silently mutated beforehand using a QuikChange Lightning Multi Site-Directed Mutagenesis Kit (Agilent).

Amplification of Linear DNA Cassette for Testing in Cell-Free System:

The in vitro linear DNA assembly protocol is followed. Overlap primers are then designed to bind over the vector:promoter and vector:terminator junctions such that while the Tm of the final primer was above 60° C., the Tm of binding on each junction side was below 40° C. Then, 1 µL of the resulting assembly product is PCR amplified for 35 cycles in a 50 µL PCR reaction, and verified by agarose gel electrophoresis. If the resulting band was 80% or more pure, the DNA is PCR purified using previously described procedures and used directly in TX-TL. Simultaneously, 2 µL of the assembly product was transformed into cells using standard chemically competent or electrically competent procedures. The cells are grown, miniprepped, and sequenced. PCR products off of the resulting plasmids are used as a positive control.

LC-MS Analysis of TX-TL Produced Metabolites:

TX-TL reaction are pelleted, washed, and depending on where the metabolite is, can be isolated from the supernatant or the pellet. Percipitated products can be redissolved in 70% ethanol, or in methanol. The sample is injected onto a 1.7 µm reverse phase column, run with buffers such as 10 nM Ammonium Formate in 1% ACN or in Acetonitrile, with typical flow-rates of 0.5 ml/min and gradients from 0 to 90%.

Example 1: Feed-Forward Loop Functionality

The structure of a three-node circuit is used as an example, which when run together is the structure of a feed-forward motif. An incoherent feed-forward loop motif is chosen as the synthetic circuit to examine with lasR-responsive activating components and tetR-responsive repressive components. This circuit should generate a pulse.

The feed-forward loop motif is a previously defined motif [12], that when combined together generates a pulsatile response at its last node. It is the combination of a 1-step activating branch, combined with a two-step repressing branch. The response of this motif is expected to generate a pulse.

Figure 36A:
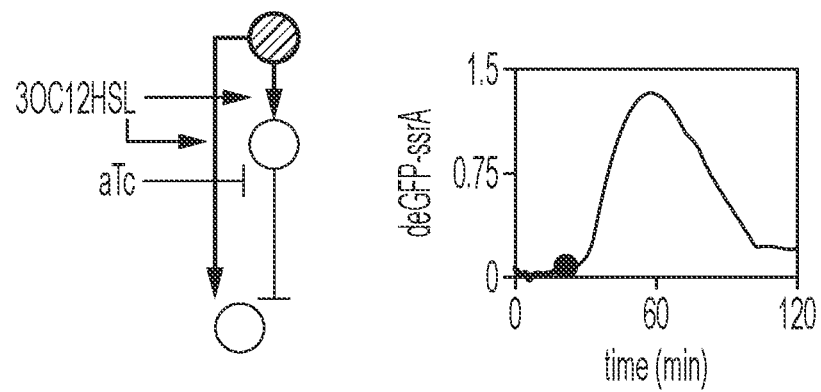
FIGS. 36A-D show the process of generating a pulse in an incoherent feed-forward loop in one embodiment.

FIG. 36A shows an activation from the top node of signal towards the middle node and the bottom node. It can be thought of as turning on the top node, and letting "signal" flow towards the middle node and the bottom node. Not abstracting away, the top node is the production of a lasR protein, which in tandem with 3OC12HSL activates the middle node and the bottom node to begin producing protein. This can occur in the context of a cell or a cell-free system.

Figure 36B:
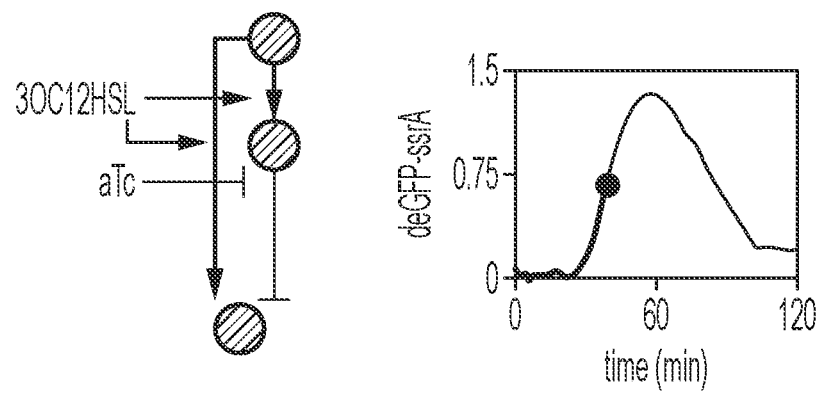

In FIG. 36B, middle node at this point is activated and producing signal. In particular, the middle node is making a tetR protein and the bottom node is making a deGFP-ssrA. The deGFP-ssrA, when produced, undergoes a fluorescent protein folding procedure and then can be visualized as a fluorescent signal over time. Shown here is the signal going up as the result of production from the bottom node.

Figure 36C:
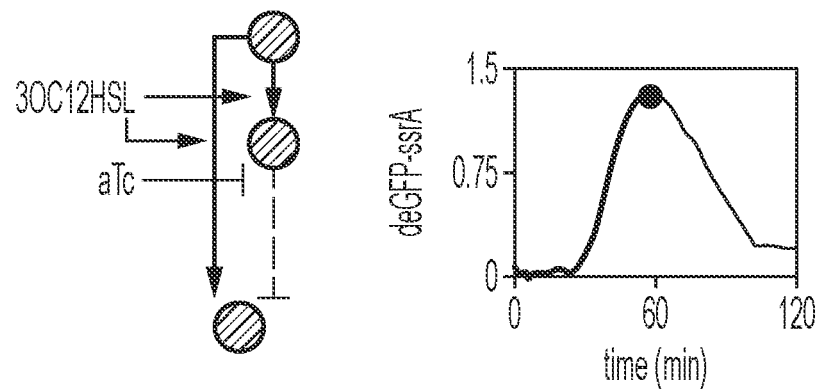

In FIG. 36C, the tetR produced from the middle node is able to bind to the bottom node's tetO1 box. If the tetR binds to the bottom node's tetO1 box, transcription is interrupted and the bottom node will stop expressing. However, tetR is also able to bind to aTc, which can be thought of sequestering away the protein. If this occurs, the tetR is inactivated. However, because the middle node is on and aTc is not replenished, tetR is constantly being produced; therefore, at some point aTc will be exhausted. When this occurs, free tetR will bind to the bottom node and deGFP-ssrA production will end. Shown in the right is signal pausing its upward trend as free tetR binds and stops expression from the bottom node.

Figure 36D:
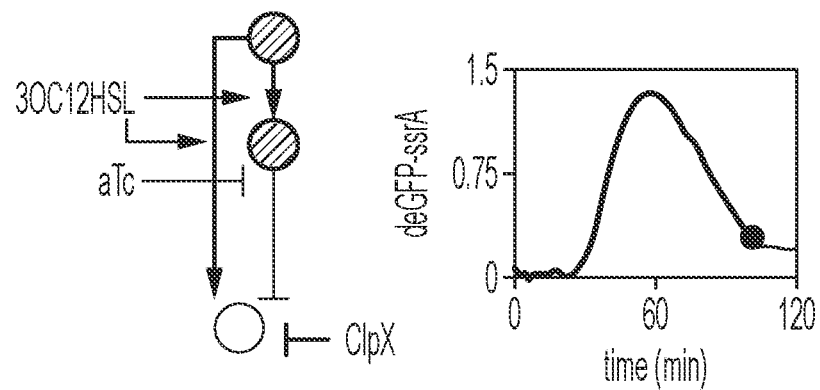

In FIG. 36D, there is enough free tetR from the second node to shut down production of deGFP-ssrA from the third node. At this point, production has ended but there is present deGFP-ssrA that has been previously made. This protein in a batch mode cell-free system (eg. occurring in 1 tube with no replenishment of solution) can be degraded by present ClpXP [43]. In a cellular system, the protein would be degraded by present ClpXP as well as diluted by cellular division. As a result, the amount of deGFP-ssrA signal decreases over time.

Example 2: In Vivo Experiment Setup for an Open-Loop to Explore Transcriptional Strength: Strain Preparation and Testing Plasmids were constructed to express an open-loop version of the feed-forward loop shown in FIG. 9A. Plasmid 360 (PlacO1_BCD22_lasR_T500) (SEQ ID NO: 1) is the plasmid carrying the top node of the open-loop shown in FIG. 9A. Plasmid 360 is on a p15A spectinomycin resistant plasmid. Five additional plasmids (i.e. plasR variants: POrig_tetO1, P1_tetO1, P2_tetO1, P3_tetO1 and P4_tetO1) (SEQ ID NO: 2-SEQ ID NO: 6) were constructed, each with varying lasR promoter unit and with an engineered tetO1 box (denoted with "_tetO1"). These five plasmids carry the bottom node of the open-loop shown in FIG. 9A.

The plasmids were prepared by conventional cloning techniques known to a person skilled in the art. In this example, the plasmids were prepared using golden gate cloning followed by transformation, colony picking, miniprep, and then sequencing to verify clonality. The plasmids can be alternatively made by any other accepted methods, including other assembly techniques and DNA synthesis methods.

Because each node is encoded on a plasmid, the nodes are carried by different backbones to be compatible with each other in the in vitro mixture and in the target environment. If the target environment is in vivo, then one must be aware of plasmid origin of replication compatibility as will be understood by a person skilled in the art. In this example, plasmid 360 is carried on a p15A plasmid and the plasR transcriptional variants are carried on a colE1 plasmid. Plasmids other than p15A plasmid and colE1 plasmid can also be selected depending on the desired copy number of the sequence, such as pSC101, pBBR1, a bacterial artificial chromosome etc. The determination of the plasmid origin of replication is based on the copy number desired for the coding sequence to be expressed, higher copy numbers, such as colE1, should be chosen for coding sequences that are higher expressed, while lower copy numbers such as pSC101 for coding sequences that are lower expressed. Another factor is temperature sensitivity. For example, colE1 plasmids have lower copy numbers at 29° C. than 37° C., while pSC101 and p15A plasmids have stable expression to temperature. Depending on if this is valuable trait, a temperature sensitive plasmid may be chosen.

In addition, each plasmid needs to have a different antibiotic cassette, which allows the final strain to be selected for. In this case, plasmid 360 contains a specR gene and the plasR transcriptional variants contains ampR. Other compatible antibiotic cassettes can also be used such as ampicillin, spectinomycin, zeocin, kanamycin, chloramphenicol, streptinomycin, and others as will be identified by a person skilled in the art.

The detailed protocol is as follows. For in vivo assays, plasmids were cloned into two to three compatible vectors (colE1/carbR, pSC101/kanR, p15A/specR) and transformed into a BL-21 Rosetta2 strain grown at 29 C. The B1-21 Rosetta2 strain has chloramphenicol resistance. Cells were recovered for 2 hours at 29 C in SOC medium (Sigma) before outgrowth at a 1.25% dilution in MOPS-EZ Rich (Teknova) 0.4% glycerol selective media containing 10 µg/mL chloramphenicol, 100 µg/mL carbenicillin, and 100 µg/mL spectinomycin and storage at −80 C. To conduct the in vivo assays, cells were grown in the same selective MOPS media to stationery phase at 29 C. Cells were then diluted 1% into 500 uL per well in 96-well MatriPlates (Brooks Life Sciences) with half-antibiotic concentration previously used. A plate reader was used and calibrated for fluorescent intensity and absorbance. Plates were measured every 6 minutes at deGFP, 485 nm/515 nm gain 61 and 100, and OD (optimal density), 600 nm under a linear continuous shaking mode. At OD 0.1-0.2, cells were induced with IPTG, and 3OC12HSL and then measured for an additional 16 hours until stationery phase.

It is noted that the media is selected to be a clear media with glycerol. The glycerol serves to ensure the pLacO1 promoter is fully repressed before induction. The media is clear to aid in visualization. In this example, the IPTG serves to remove any lac repression on the plasmid of the top node, i.e. the 360 plasmid. The 3OC12HSL serves to activate the lasR from the expression of 360 plasmid.

FIG. 17A shows the sequence listing for plasmid 360 (PlacO1_BCD22_lasR_T500) (SEQ ID NO: 1). FIG. 17B shows the sequence listing for plasmid 428 (PRsaL-tetO1_BCD2_deGFP-ssrA_B1002) (SEQ ID NO: 2) utilizing promoter "POrig_tetO1". FIG. 17C shows the sequence listing for plasmid 347 (PLasI_1SNP_-10-tetO1_BCD2_deGFP-ssrA_B1002) (SEQ ID NO: 3) utilizing promoter "P1_tetO1". FIG. 17D shows the sequence listing for plasmid 429 (PLasI-tetO1_BCD2_deGFP-ssrA_B1002) (SEQ ID NO: 4) utilizing promoter "P2_tetO1". FIG. 17E shows the sequence listing for plasmid 430 (PLasB-tetO1_BCD2_deGFP-ssrA_B1002) (SEQ ID NO: 5) utilizing promoter "P3_tetO1". FIG. 17F shows the sequence listing for plasmid 431 (PRasL long (las)-tetO1_BCD2_deGFP-ssrA_B1002) (SEQ ID NO: 6) utilizing promoter "P4_tetO1".

Figure 8:
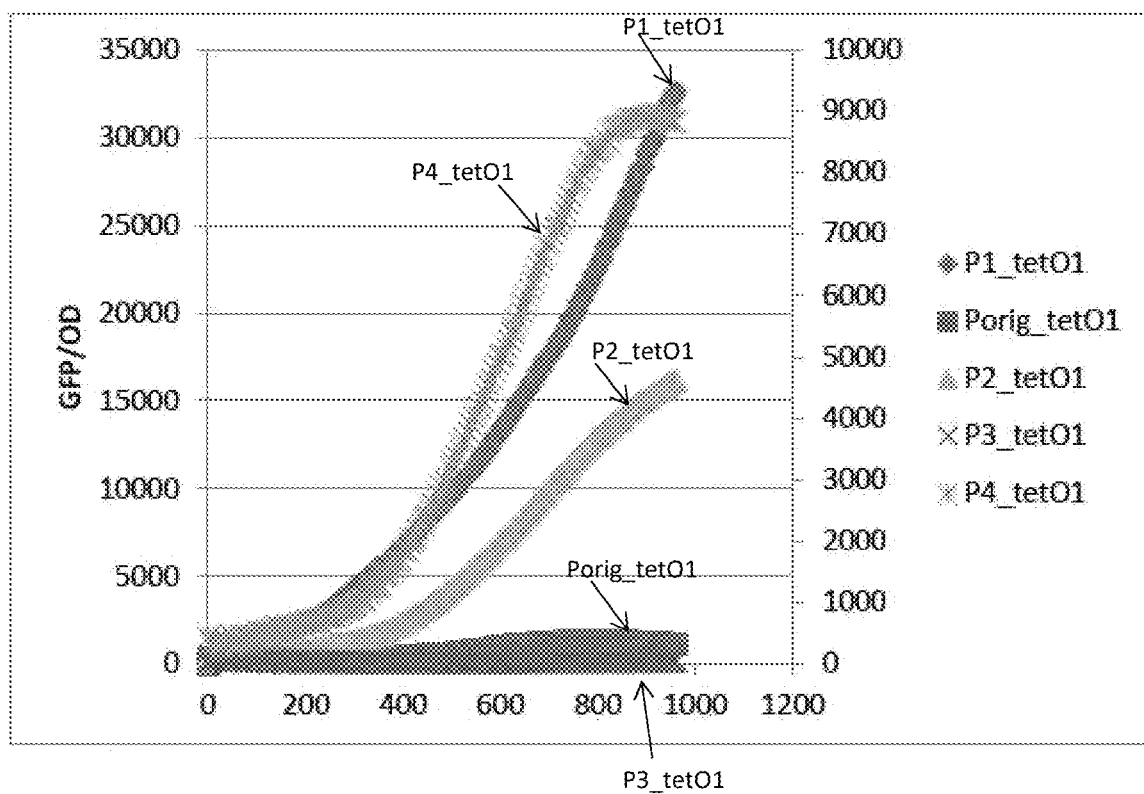
FIG. 8 plots a time evolution of the GFP signal exhibited by the reporter protein deGFP-ssrA, normalized by the OD in one embodiment, collected in vivo. Each strain plotted is a combination of the plasmid 360 and a pLas variant reporter plasmid.

FIG. 8 shows the GFP signal exhibited by the reporter protein deGFP-ssrA, normalized by the OD. In FIG. 8, the Y axis is GFP signal over OD signal at any given time and the X axis is time in minutes. Note that each strain plotted is a combination of the plasmid 360 and a pLas variant reporter plasmid.

Figure 10:
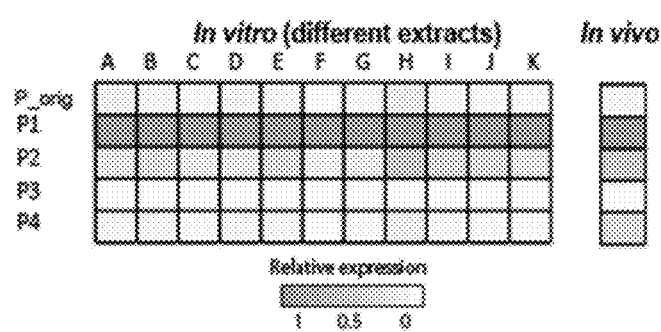
FIG. 10 shows a heatmap for in vitro (left) and in vivo (right). For the in vitro section, each row corresponds to a pLas variant (i.e. promoter) while each column corresponds to a different extract (A-K). Promotor Vmax values at t=180 minutes are compared across different extracts. Extract A is the primary extract used for FIGS. 9, 12, 14, 15, 16, 38, 39, 41, 43, 44, 54. Extracts A and D are an ExpressIQ strain, B-C and E-I are a BL21 Rosetta2 strain, J is a MGZ1 strain, and K a JS006 strain. For the in vivo section, the first derivative of the data, e.g. dGFP/dOD, is taken from FIG. 8 and the maximum value of each is plotted on a heatmap. Dark gray is a relative expression of 1 and white is a relative expression of 0.

The raw value of the first derivative of the data in FIG. 8, i.e. dGFP/dOD, is taken and the maximum value for each is plotted on a heatmap scaled in a way such that the largest expressing unit is given a value of 1, or dark gray; and the lowest expressing unit having a value of 0, or white (see the in vivo section of FIG. 10). The scaled heatmap can be later compared to data produced in vitro on the left side of FIG. 10.

Example 3: In Vitro Cell-Free Preparation to Explore Transcriptional Strength: Plasmids Preparation In this example, the same two-node circuit shown in FIG. 9A is tested in the prepared cell-free system. Each reaction mixture contains a plasmid "163" at a concentration of 1 nM. This plasmid is denoted as pLacO1-UTR1-lasR carrying the top node as shown in FIG. 9A. Each reaction mixture also contains a "pLas variant" plasmid (i.e. P_orig, P1, P2, P3 and P4) as described in Example 2. The concentration of the pLas variant plasmid is 2 nM. This plasmid is denoted as pLas-variants-UTR1-deGFP carrying the bottom node as shown in FIG. 9A. Each reaction mixture also contains IPTG at a concentration of 1 mM, which removes residual lacI from the circuit that is native to the extract. Each one of these reactions is then run with 1:10 dilutions of 3OC12, from 10 uM, to 0.1 nM and a negative control. In other words, there are 5×7+1 reactions, where the "5" indicates 5 different pLas variants, the "7" indicates 7 different 3OC12 dilutions, and the "+1" is a negative control with no DNA present at all to subtract background.

FIG. 18A shows the sequence listing for plasmid 165 (PRsaL_UTR1_deGFP_T500) (SEQ ID NO: 7) denoted as "Porig". FIG. 18B shows the sequence listing for plasmid 196 (PLasI_1SNP_-10_UTR1_deGFP_T500) (SEQ ID NO: 8) utilizing promoter "P1". FIG. 18C shows the sequence listing for plasmid 197 (PLasI-_UTR1_deGFP_T500) (SEQ ID NO: 9) utilizing promoter "P2". FIG. 18D shows the sequence listing for plasmid 198 (PLasB_UTR1_deGFP_T500) (SEQ ID NO: 10) utilizing promoter "P3". FIG. 18E shows the sequence listing for plasmid 199 (PRasL long (las)-_UTR1_deGFP_T500) (SEQ ID NO: 11) utilizing promoter "P4". FIG. 18F shows the sequence listing for plasmid 163 (pLacO1-UTR1-lasR) (SEQ ID NO: 12).

Example 4: In Vitro Cell-Free Preparation to Explore Transcriptional Strength: Data Characterization The results from the above execution are shown in FIGS. 9B-F where the signal is plotted as a function of time for each 3OC12HSL trace. FIG. 9G shows a table with the data derived from endpoint values in TX-TL per promoter at t=300 min for varying 3OC12HSL, where each experiment is conducted three times with newly prepared DNA sources.

Figure 9H:
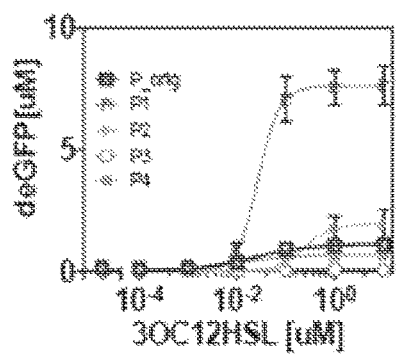
FIG. 9H plots the deGFP amount as a function of 3OC12HSL concentration for each pLas variant in one embodiment. Circuit tested in this embodiment is composed of 1 nM pLac-lasR plasmid and 1 nM plasmid with varying lasR-activated promoter producing deGFP. The endpoints from t=300 min from 3 independent experiments are shown in FIG. 9H.

The end values at t=300 from each of the plots in FIGS. 9B-F can then be collected for plotting FIG. 9H. FIG. 9H plots the deGFP amount as a function of 3OC12HSL concentration for each pLas variant. The experiments were repeated three times to obtain error bars.

To build the color chart shown in "in vitro (different extracts)" section of FIG. 10. Promoter Vmax values at t=180 minutes or highest expressing value of each pLas variant are determined and then the mean of the three runs is plotted on a color scale, where the weakest is assigned a color of white and the strongest is assigned a color of gray.

Example 5: Data Comparison Between In Vivo and In Vitro, Using Transcriptional Strength as a Metric In FIG. 10, each column in the in vitro section represents a different extract preparation which has been prepared and optimized according to the methods described in [15]. Extract A is used in this experiment. Extracts A and D are an ExpressIQ strain, B-C and E-I are a BL21 Rosetta2 strain, J is a MGZ1 strain, and K a JS006 strain. The data from in vitro is then compared to the data obtained from in vivo described in Example 2 and shown in "in vivo" section of FIG. 10.

Based on the heatmap, one can see that there is a clear pattern in expression from strong items and weak items. In other words, promoter, P1, is the strongest throughout the 11 in vitro extracts, while promoter. P3, is the weakest throughout the 11 in vitro extracts, in consistent with the results in the tested in vivo case. P2 is a medium strength promoter in both the cell-free and cell system, and P_orig and P4 are weak promoters in both systems.

The results in this example indicate that the transcriptional elements such as promoters in the context of a circuit can be modified in vitro and provide a prediction of the transcriptional strength in vivo. While the prediction is not on a quantitative level, it indicates that there is a qualitative significance of the two environments, e.g. promoters that are weak in vitro in the context of a circuit are also weak in vivo, and vice versa.

Promoters can also be compared relative to each other. The order of promoter strength in vitro is P1/P2/P_Orig/P4/P3, while the order of promoter strength in vivo is P1/P2/P4/P_orig/P3. Given that the comparisons are qualitative and not quantitative, this provides enough support to justify using promoter sets in vitro and reliably predict the corresponding in vivo result without having to do the full in vivo set. Alternately, by collecting both the in vitro and in vivo environment and seeing correlation on a limited subset, one can expand by using different transcriptional promoters without having to test in vivo.

Example 6: In Vivo Experiment Setup for an Incoherent Feedforward Loop to Explore Translational Strength: Plasmids Preparation In this example, the incoherent feed-forward loop motif (IFFL) shown in FIG. 11A was chosen as the synthetic circuit to examine with lasR-responsive activating components and tetR-responsive repressive components. The IFFL shown in FIG. 11A contains three nodes: 1 top node, a middle node and a bottom node.

Each of the nodes represents a piece of DNA, either in linear of plasmid form, composed of (1) pConst: a constitutive promoter that can initiate transcription (2) a Ribosome binding site, (3) a coding sequence, and (4) a terminator.

The promoter ideally binds a sigma70 factor, which is a sigma factor that targets RNA polymerase to initiate transcription. This can be a broad family of promoters, including: pTet, pLac [4], pOR2-OR1-Pr [33], pTac, etc. In other variants, the constitutive promoter can also bind a T7 RNA polymerase, eg. pT7.

In the top node shown in FIG. 11A, the pConst is pLacO1. The RBS is UTR1. The coding sequence is LasR. The terminator is T500. The DNA is configured on a plasmid.

In the middle node, the promoter is a lasR responsive promoter. This specific promoter is responsive to a transcriptional regulator, lasR, originally from *Psuedomonas aeruginosa* PAO1. The lasR protein, assisted by N-3-oxodo-decanoyl homoserine lactone (3OC12-HSL), is able to bind to the lasR responsive promoter to recruit a sigma70 factor and initiate RNA transcription. The RBS in the middle node is UTR1 and the coding sequence encodes a tetR repressor protein.

In the bottom node, the promoter is a las-responsive promoter with a tetO1 programmed operator element. To program a tetO1 element into a las-responsive promoter, a tetO1 DNA operator piece having a sequence "TCCC-TATCAGTGATAGAGA" (SEQ ID NO: 47) needs to be included [4] The RBS in the bottom node is UTR1 and the coding sequence encodes a deGFP. deGFP can be visualized with absorbance 485 emittance 515 in a common plate reader.

Plasmid 360 (Plac_BCD20_lasR_T500) (SEQ ID NO: 1) corresponds to the circuit top node and is shared among all circuits as previously described. The sequence of plasmid 360 is previously shown in FIG. 17A.

Plasmid carrying deGFP-ssrA coding gene corresponds to the circuit bottom node and has 16 variants with varying RBS (ribosome binding sites) sequence and a same shared backbone sequence. The deGFP-ssrA concentrations can be adjusted by RBS tuning as will be understood by a person skilled in the art. In other words, RBS sequences with different binding efficiencies were used. Strong RBSs result in high expression of deGFP-ssrA while weak RBSs result in low expression.

FIG. 19A shows the sequence listing of the shared backbone sequence of the plasmids carrying the deGFP-ssrA coding gene (PLasI_1SNP_-10_tetO1 (P1_tetO1)-(blank)-deGFP-ssrA-B1002) (SEQ ID NO: 13).

FIG. 19B lists 16 variant RBS sequences to be inserted to the plasmid backbone sequence shown in FIG. 19A. UTR1 (SEQ ID NO: 14) (a strong UTR derived from lambda phage), 10 bi-cistronic devices (BCDs) (SEQ ID NO: 14-19, 23-26), and 5 commonly used monocistronic RBSs (MCDs) were tested (B0030-B0034) (SEQ ID NO: 20-21, 27-29). BCDs were previously known to provide predictive results irrespective of secondary structure, in contrast to MCD's. It was hypothesized that while MCD expression can be hard to predict, it can also be used to verify data matching between TX-TL and in vivo.

TetR Plasmid corresponds to the middle node that produces tetR. Similar to the deGFP plasmids described above, this middle plasmid also has 16 variants with varying RBS sequences. Each plasmid contains a same, shared backbone sequence and a variant RBS sequence inserted after the backbone sequence. FIG. 19C shows the sequence listing of the shared backbone sequence of the plasmids carrying tetR (PLasI_1 SNP_-10(P)-(blank)-tetR-T500) (SEQ ID NO: 30). The same 16 variant RBS sequences to be inserted to the plasmid backbone sequence as shown in FIG. 19B.

Thus, a total of 33 plasmids were constructed using the standard molecular biology techniques previously described.

Example 7: In Vivo Experiment Setup for the Incoherent Feedforward Loop to Explore Translational Strength: Strain Construction A total of 256 strains were made. Each strain contains a plasmid 360. In addition, a strain also has (1) a middle node tetR producing plasmid and (2) a lower node deGFP-ssrA producing plasmid. Therefore, the total combinations are: 1×16×16=256 strains. To produce all of the strains, an ExpressIQ strain that overexpresses lacI was transformed with plasmid 360 and selected for against spectinomycin antibiotic. This strain was then made chemically competent using standard techniques, and double-transformed with 1 of the middle node and 1 of the lower node plasmid simultaneously. Cells were recovered for 2 hours at 29° C. in SOC medium (Sigma) before outgrowth at a 1.25% dilution in MOPS-EZ Rich (Teknova) 0.4% glycerol selective media containing 10 µg/mL chloramphenicol, 50 µg/mL kanamycin, 100 µg/mL carbenicillin, and 100 µg/mL spectinomycin and storage at −80 C.

Example 8: In Vivo Experiment Setup for an Incoherent Feedforward Loop to Explore Translational Strength: In Vivo Assays To conduct the in vivo assays, cells were grown in the same selective MOPS media to stationery phase at 29° C. Cells were then diluted 1% into 500 uL per well in 96-well MatriPlates (Brooks Life Sciences) with half-antibiotic concentration previously used. Three plate readers were used (Biotek H1/MF), which were calibrated for fluorescent intensity and absorbance. Plates were measured every 6 minutes at deGFP, 485 nm/515 nm gain 61 and 100, and OD, 600 nm under a linear continuous shaking mode. At OD 0.1-0.2, cells were induced with variable aTc, 1 uM IPTG, and 1 uM 3OC12HSL and then measured for an additional 16 hours until stationery phase. The amount of 3OC12HSL and IPTG were determined for induction of the open loop case in Example 1 without introducing toxicity related to overexpression.

Figure 11B:
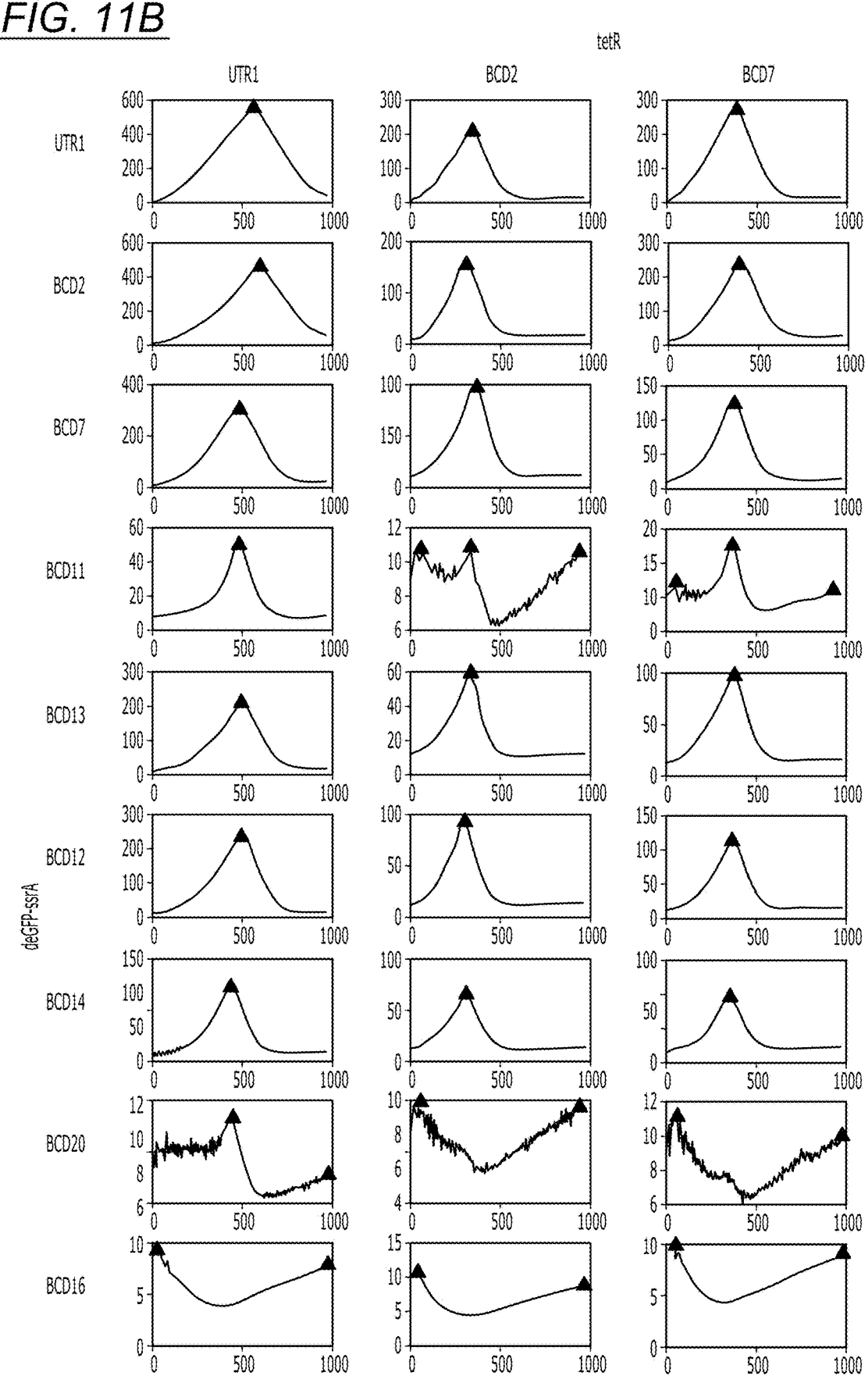
FIG. 11B show in one in vivo embodiment normalized GFP signals over time post-induction for all 256 strains, collected at the aTc 1000 ng/mL level.

The aTc amounts used were: 1000 ng/mL, 100 ng/mL, 10 ng/mL, and 0 ng/mL. For each aTc amount, a full 16×16 grid was conducted in vivo. A sample set of raw data is shown in FIG. 11B.

This sample set represents the GFP signal over the OD signal (i.e. GFP/OD), over time post-induction for all 256 strains, collected at the aTc 1000 ng/mL level. Each sub-panel represents a different strain, with the Y axis as a relative fluorescence unit (rfu) of GFP over OD and the X axis as time in minutes.

Notations such as "UTR1" "BCD2" "BCD7" shown for each row (left side of FIG. SB) are ribosome binding sites of the deGFP-ssrA plasmid. The same notations shown for each column (top of FIG. 11B) are ribosome binding sites of the tetR plasmids.

Figure 11C:
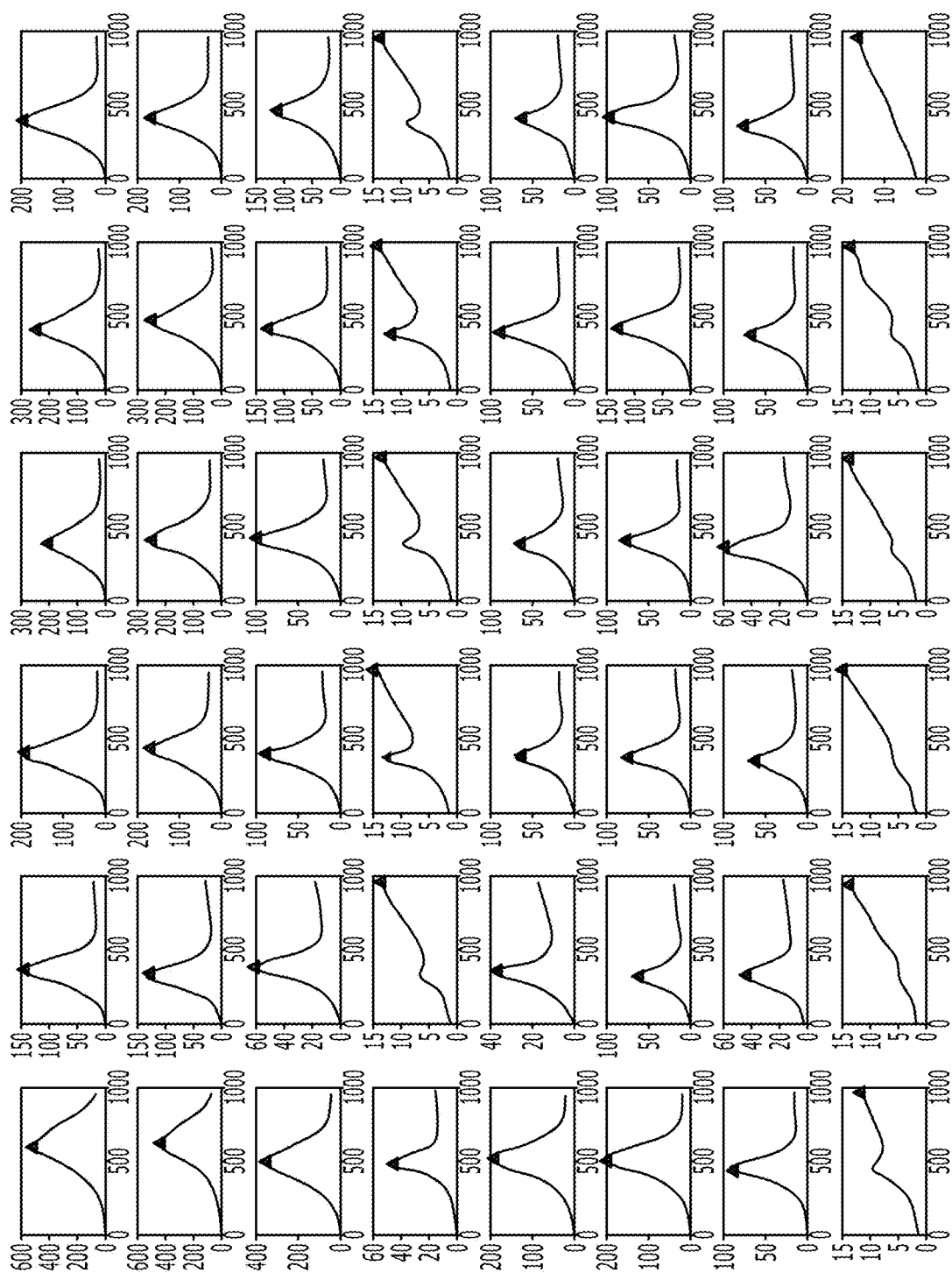
FIG. 11C shows GFP signals over time post-induction for all 256 strains, collected at the aTc 1000 ng/mL level.
Figure 11C:
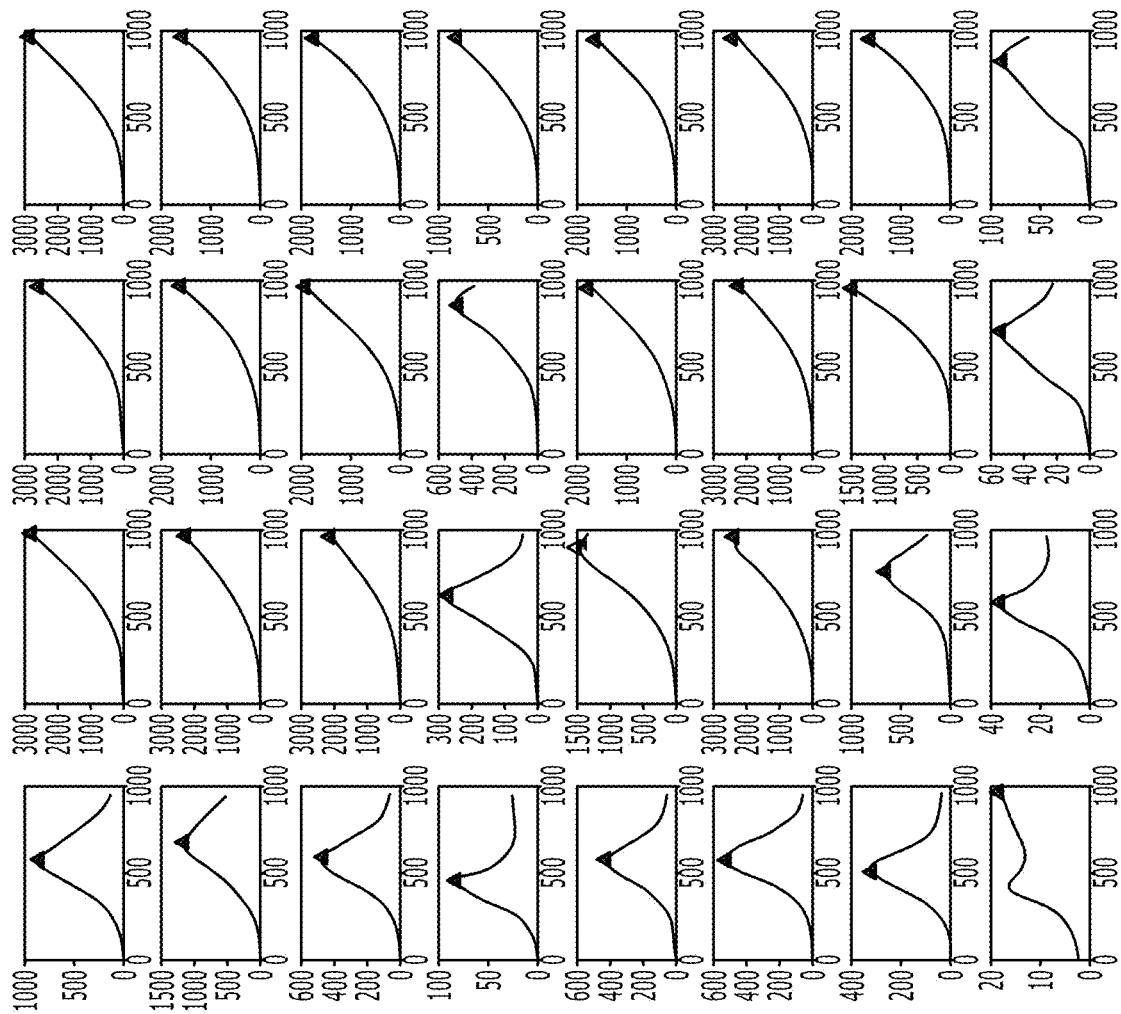
Figure 11D:
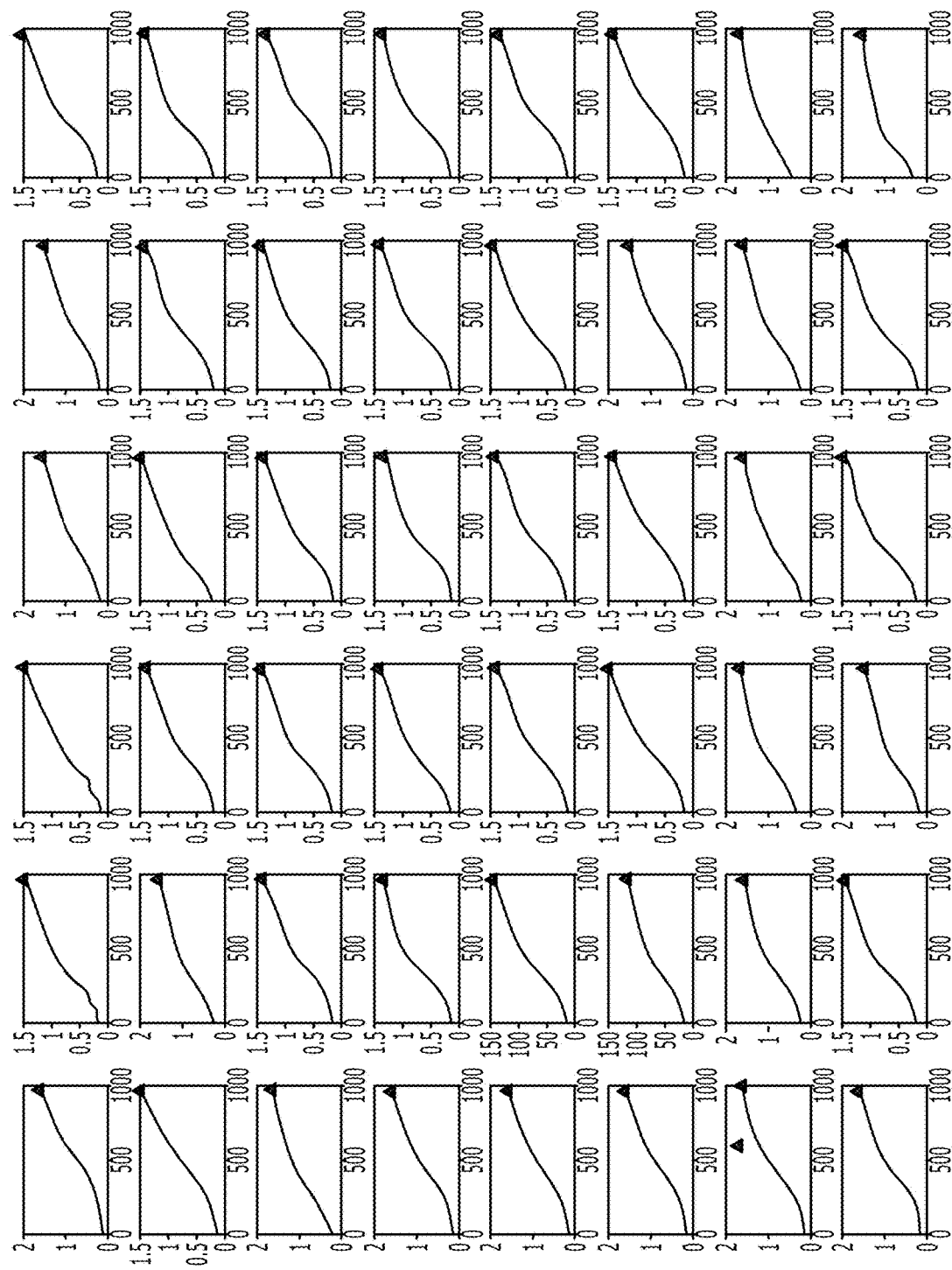
FIG. 11D shows OD signals over time post-induction for all 256 strains, collected at the aTc 1000 ng/mL level.

FIG. 11C shows the GFP signal only with OD. FIG. 11D shows the OD signal only without GFP signal. Note that for FIG. 11D all of the curves are in similar shapes, indicating that all of the strains have similar fitness and are growing at the same speed. This can be used as a control of the data.

Figure 11E:
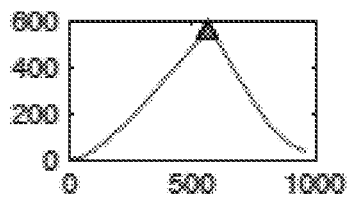
FIG. 11E shows a sample data trace for GFP/OD for UTR1 deGFP-ssrA (row) and UTR1 tetR (column) case with aTc 1000 ng/mL.
Figure 11F:
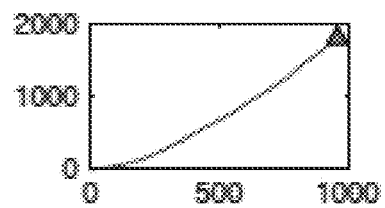
FIG. 11F shows a sample data trace for GFP/OD for UTR1 deGFP-ssrA (row) and B0034 tetR (column) case with aTc 1000 ng/mL.
Figure 11G:
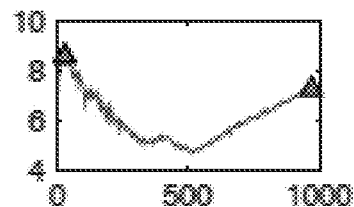
FIG. 11G shows a sample data trace for GFP/OD for BCD24 deGFP-ssrA (row) and UTR1 tetR (column) case with aTc 1000 ng/mL.

FIGS. 11E-G demonstrate how the detected GFP/OD signal is converted to a heatmap value. FIG. 11E shows a sample data trace for GFP/OD for UTR1 deGFP-ssrA (row) and UTR1 tetR (column) case with aTc 1000 ng/mL. The Y axis is a relative fluorescence unit (rfu) and the X axis is time in minutes. Note here that the trace shows an increase in signal, followed by a peak (marked by a triangle) and then a decrease of signal. The numerical value of the peak of signal is taken for the purposes of converting the data to a form that can be represented by a heatmap.

FIG. 11F shows a sample data trace for GFP/OD for UTR1 deGFP-ssrA (row) and B0034 tetR (column) case with aTc 1000 ng/mL. The Y axis is a relative fluorescence unit (rfu) and the X axis is time in minutes. Note that in this case the trace does not go down. Therefore, the numerical value of the maximal signal (marked as a triangle) is taken for the purposes of converting the data to a form that can be represented by a heatmap.

FIG. 11G shows a sample data trace for GFP/OD for BCD24 deGFP-ssrA (row) and UTR1 tetR (column) case with aTc 1000 ng/mL. Note that in this case the trace is at the negative control level of signal and there is no real data. Therefore, for the purposes of converting the data to a form that can be represented by a heatmap, the numerical value of the maximal signal is taken (the triangle at zero point). However, this numerical value is below the edge of detection.

With each panel of the 256 panels converted to a heatmap value, the colors are plotted on a re-scaled 0 to 1000. The resulting values are plotted in a 16×16 arrays shown in FIG. 12B. On the rows are the RBS variants for the deGFP-ssrA and on the columns are the RBS variants of the tetR. Note that multiple aTc amounts are plotted: the left side panel corresponds to aTc at 1000 ng/mL, the middle one corresponds to aTc at 100 ng/mL and the bottom one corresponds to aTc at 10 ng/mL.

Example 9: In Vitro Cell-Free Preparation for the Incoherent Feedforward Loop to Explore Translational Strength: Quantitative PCR for Determining Plasmid Copy Number Similar to the in vivo experiment setup described in Example 7, the same plasmids for the in vivo study were used in vitro, namely a total of 33 plasmids (1 for the top node lasR, 16 for the middle node tetR, 16 for the bottom node deGFP-ssrA, see FIG. 11A).

In order to match the concentrations of the plasmids in the same relative ratios as in vivo, a quantitative PCR (qPCR) was performed against two of the in vivo strains generated previously.

The qPCR was preformed using primers that bind to the antibiotic cassette regions of the plasmids. In particular, the following primers were used.

| Seq. ID | Primer Sequence |
|---------|-----------------|
| ZS41016f | ATCATTCCGTGGCGTTATCC (SEQ ID NO: 48) |
| ZS41016r | GTCAGCAAGATAGCCAGATCAA (SEQ ID NO: 49) |
| ZS41017f | GGCGTCAACACGGGATAATA (SEQ ID NO: 50) |
| ZS41017r | GGGTTACATCGAACTGGATCTC (SEQ ID NO: 51) |
| ZS41018f | CGTTGGCTACCCGTGATATT (SEQ ID NO: 52) |
| ZS41018r | CTCGTCAAGAAGGCGATAGAAG (SEQ ID NO: 53) |

The qPCR was performed on two strains; one with the full circuit including plasmid 360, BCD2 tetR and BCD2 deGFP-ssrA (corresponding to sequence IDs: 360/344/347) and the other with the full circuit including plasmid 360, BCD22 tetR and BCD22 deGFP-ssrA (corresponding to sequence IDs: 360/346/349). These two strains are on the opposite corners of the 256-panel map in terms of expression, thus it was hypothesized that they would be representative of copy number across the panel if they were aligned.

Template dilutions of 1:10, 1:100, and 1:1000 were used and three replicates of each experiment were performed, thus producing nine data points shown in FIGS. 13A-D. FIGS. 13A and 13B show the Ct graphs for two different strains respectively, and FIGS. 13C and 13D show relative plasmid amounts for two different strains respectively.

The ratios of each result were normalized to 1 unit of pSC101 to obtain a relative ratio of 1 copy pSC101 (kanR plasmid, expressing tetR): 2 copies p15A (cmR plasmid, expressing lasR): 8 copies of colE1 (ampR plasmid, expressing deGFP-ssrA). This relative ratio, 1:2:8, is then used for in vitro experiments. In specific, based on the Ct values the relative amounts of each plasmid can be calculated, and then divided by the relative amount of the pSC101 plasmid to obtain a ratio-metric number (as opposed to an absolute amount using a control standard).

Example 10: In Vitro Cell-Free Preparation for the Incoherent Feedforward Loop to Explore Translational Strength: In Vitro Execution To run the in vitro experiments, the concentrations in all experiments of plasmid 360 (Plac_BCD20_lasR_T500) (SEQ ID NO: 1) were set to 1 nM; the concentrations of the tetR producing RBS-variant plasmids were set to 0.5 nM; and the concentrations of the deGFP-ssrA producing RBS-variant plasmids were set to 4 nM. These concentrations were chosen to be in the 1:2:8 molar ratio determined by qPCR, and also below saturating phase DNA amounts for the reporter. Here, the definition of saturation phase is the level at which a doubling of DNA concentration does not lead to a doubling of signal.

Each experiment was also run with 1 mM of IPTG present, which removes residual lacI, 1 uM of 3OC12HSL for maximum induction of the lasR plasmid, and 1:5000 dilution of QSH620, a quantum dot that allows for determination of pipetting accuracy.

The extract chosen was eZS8, which has been previously described. This extract was made out of the ExpressIQ strain that was used for the in vivo prototyping.

Similar to the in vivo case, 4 dilutions of aTc were conducted: 10 uM, 1 uM, 0.1 uM, and 0 uM. For each dilution, the 256-panel set of experiments were conducted; data was collected over 12 hours, with measurements every 6 minutes at GFP 485/515 gain 61 and gain 100 in Biotek 3 plate readers calibrated against each other.

Figure 14A:
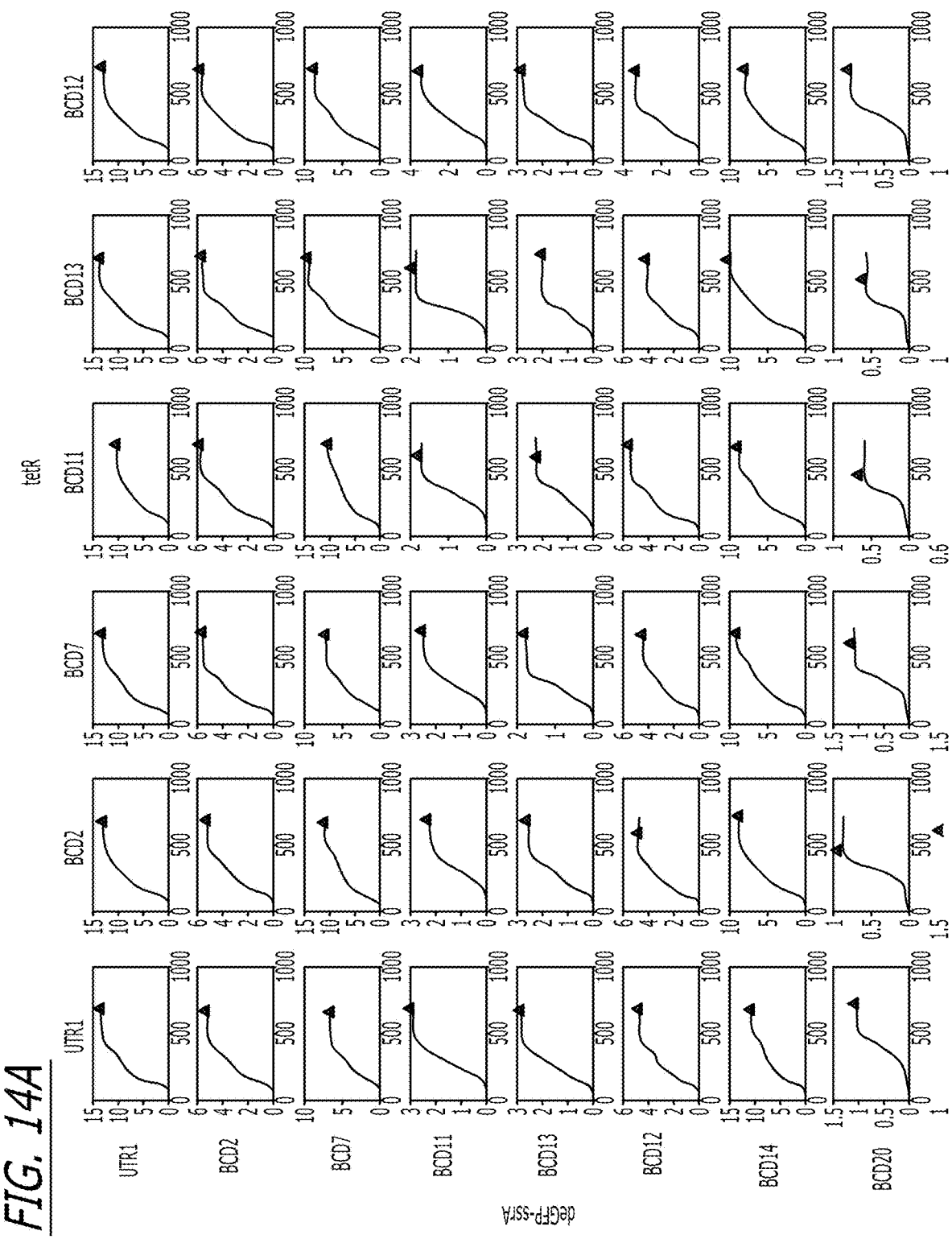
FIG. 14A shows in one in vitro embodiment normalized GFP signals over time post-induction for all 256 strains, collected at the aTc 10 uM level. Each subpanel represents a different strain, with the Y axis as a relative fluorescence unit (rfu) and the X axis as time in minutes. The RBS corresponding to the deGFP-ssrA plasmid is shown on the left side for each row and the RBS corresponding to the tetR plasmid is shown on the top for each column.

A sample set of raw data is shown in FIG. 14A. This 16×16 sample set represents the GFP signal over time post-induction for all 256 strains, collected at the aTc 10 uM level. Similar to the in vivo data shown in FIG. 11C, each subpanel represents a different strain, with the Y axis as a relative fluorescence unit (rfu) and the X axis as time in minutes. The ribosome binding site corresponding to the deGFP-ssrA plasmid is shown on the left side for each row and the ribosome binding site corresponding to the tetR plasmid is shown on the top for each column. The signal has been calibrated against a fluorescent deGFP control, such that the absolute values represent uM of protein of deGFP-ssrA detected.

Figure 14B:
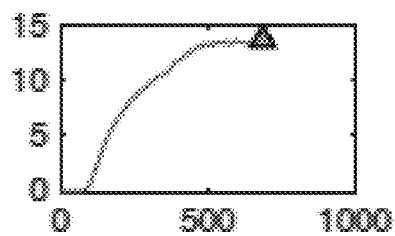
FIG. 14B shows a sample data trace for GFP/OD for UTR1 deGFP-ssrA and UTR1 tetR case with aTc at 10 uM.

FIG. 14B shows a sample data trace for GFP/OD for UTR1 deGFP-ssrA and UTR1 tetR case with aTc at 10 uM. Note that in this case the trace shows an increase in signal. There is no degradation of signal because all ClpX degradation as been exhausted. The Y axis is a relative fluorescence unit (rfu) and the X axis is time in minutes. In this case, the numerical value of the maximum expression after 6 hours or 300 minutes was taken to convert the data to a form that can be represented by a heatmap.

Figure 12A:
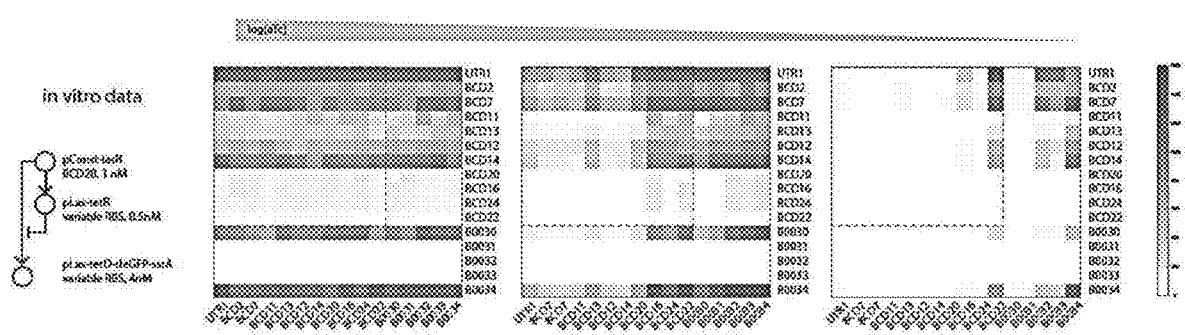
FIGS. 12A and 12B show an exemplary translational variation of an exemplary feed-forward loop in vitro and in vivo, where the repressor and the reporter components are varied by RBS. In vitro, lasR, tetR, and deGFP-ssrA are expressed in a 2:1:8 ratio. In vitro, they are put on p15A, pSC101*, and colE1 plasmids and found to be in a 2:1:8 ratio. The dotted line outlines RBSs using predictive bicistronic devices developed in [1]. Data for in vivo is taken as the peak pulse (or endpoint expression after 16 hr for open loop), data for in vitro is taken as endpoint expression after 6 hr.

With each panel of the 256 panels converted to a heatmap value, the colors are plotted on a re-scaled 0 (white) to 1000 (gray), similar to in vivo described in Example 8. The resulting values are shown in FIG. 12A. On the rows are the RBS variants for the deGFP-ssrA and on the column are the RBS variants of the tetR. Note that multiple aTc amounts are plotted: the left panel corresponds to 10 uM, the middle panel to 1 uM, and the bottom panel to 0.1 uM.

Figure 12B:
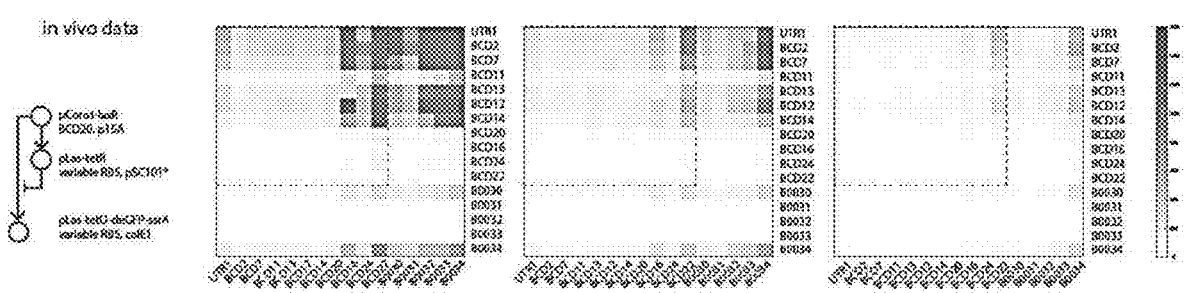

Example 11: Comparison Between In Vivo and In Vitro Cell-Free System for the Incoherent Feedforward Loop to Explore Translational Strength It is noted that the aTc exact amounts cannot be scaled between in vitro and in vivo conditions because how much aTc enters the cell in the cellular condition vs. outside of the cell is difficult to measure. However, one can assign relative sliding scales based on behavior to compare these two environments. In other words, either of the panels from in vitro (FIG. 12A) can be aligned with either of the panels from in vivo in (FIG. 12B).

When the plots are viewed horizontally (i.e. looking at deGFP-ssrA concentration), it can be generally noted that those RBS units that have signal (UTR1, BCD2, BCD7, BCD11, BCD13, BCD12, BCD14, B0030, B0034) in vitro also have signal in vivo. Likewise, all of the RBS units that have minimal signal (BCD20, BCD16, BCD24, BCD22, B0031, B0032, B0033) in vitro also correspond to minimal signal in vivo.

Figure 12C:
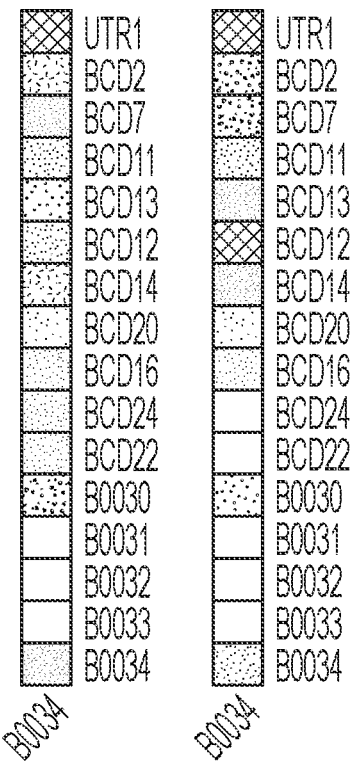
FIG. 12C shows one column of tetR expression (B0034) from in vitro (left) and in vivo (right). Each column contains 16 deGFP variants with varying RBS sequences.

FIG. 12C shows one column of weak tetR expression (B0034) from in vitro (left) and in vivo (right). Each column contains 16 deGFP variants, i.e. different levels of deGFP expression. The in vitro data has aTc at 10 uM and the in vivo data has aTc at 1000 ng/mL.

Figure 12D:
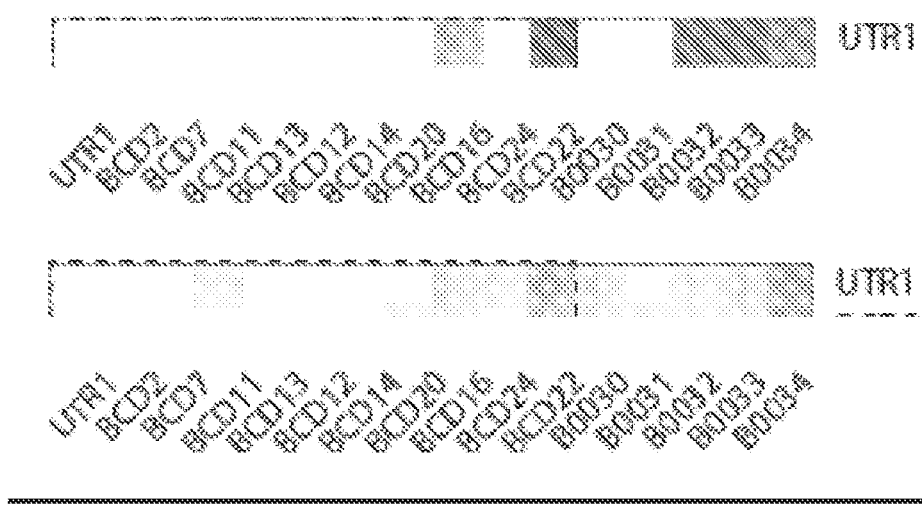
FIG. 12D shows one row of deGFP-ssrA (UTR1) from in vitro (top) and in vivo (bottom). Each row contains 16 tetR variants with varying RBS sequences.

Similarly, when the plots are viewed vertically, the same correlation is also observed between in vitro and in vivo. FIG. 12D shows one row of deGFP-ssrA (UTR1) from in vitro (top) and in vivo (bottom). Each row contains 16 tetR variants, i.e. different levels of tetR expression. The data shows that RBS units that are weak (such as BCD20, BCD22, B0034) in vitro are also weak in vivo, while RBS units that are strong in vitro (such as UTR1, BCD2, BCD7, BCD11, BCD13, BCD14, BCD20, BCD24, B0030, B0031) are also strong in vivo. Some RBS units here, such as B0032 and B0033, are not as certain.

It is noted that the signal is recorded for the deGFP-ssrA output, not for the tetR protein amount. Therefore, the more deGFP-ssrA produced, the weaker tetR repression is and the weaker the tetR RBS unit is.

It is also noted that although the correlation at the tetR level is observed as shown in FIG. 12D, such correlation is not as strong as on the deGFP-ssrA level (FIG. 12C). This is expected for two reasons: 1) the end-point assay is visualized on the bottom node (i.e. deGFP-ssrA level), while the item being varied is the RBS of a middle node, tetR and 2) tetR concentration is strongly dependent on aTc concentration, and aTc concentration is difficult to tune when comparing in vitro to in vivo.

The results of FIGS. 12A-D show that in vitro data corresponded well to the in vivo data. Among the 256 panels shown in FIGS. 12A-B, an approximate 70% correlation can be estimated between in vitro and in vivo. Particularly for the MCDs, from B0030 to B0034, both in vitro and in vivo reflected weakly-expressed tetR with strongly-expressed deGFP, indicating that the correspondence was not due to BCD activity alone. Other metrics of analysis were also tested, such as time to repression, and similar results were obtained. The correlation between the in vitro and in vivo indicates that the in vitro TX-TL cell-free environment can be used to represent and prototype the in vivo environment qualitatively.

Example 12: Using Biomolecular Breadboard to do Part Mining and Characterization in Vitro: Running Individual Promoters In order to build a feed-forward loop motif and to generate a pulse), one needs a promoter with certain functions. (1) strong Vmax (2) good dynamic range (3) responds to 3OC12HSL and lasR.

It is established in the previous examples that transcription and translation, which is a fundamental part of biological circuits, are correlated between the in vitro and in vivo environment. With this knowledge, one can build a functional feed-forward motif using previously used as well as new parts.

One can start by mining a lasR responsive promoter. One can then choose an incoherent feed-forward loop motif as the synthetic circuit to examine with lasR-responsive activating components and tetR-responsive repressive components. This circuit should generate a pulse. However, it is unclear which activator parts are the best to use. It is hypothesized that TX-TL would be an ideal platform for screening parts for relevant parameters such as $K_m$, $V_{max}$, dynamic range, and expression leak shown to be relevant in vivo. [44] These are also relevant modeling parameters. A lasR-responsive promoter, pRsaL (P_orig), was first characterized from previously published work by testing its ability to express non-tagged deGFP in the presence of lasR and 3OC12HSL. [45]. While the promoter was responsive to lasR, the $V_{max}$ of the promoter was lower than anticipated and the dynamic range was under 6-fold. To find a more robust part, TX-TL was used to screen four more promoters taken from the Registry of Standard Biological Parts or from RNAseq data of known responsive elements. [46] Parametrization data comparable to published values of cooperativity was also collected. [47] Out of the screen, P1 showed a 7-fold improved $V_{max}$ over P_orig and a 29-fold dynamic range. The basal leakiness of the promoters was also characterized without lasR present. P1 was then used for the downstream lasR-responsive promoter due to its high $V_{max}$. The sequences for each promoter are listed in FIG. 37.

To run the circuit described above, each reaction has plasmid "163", which is pLacO1-UTR1-lasR-T500 (FIG. 18F). The circuit is run with 1 nM concentration. Each reaction is run with 1 mM IPTG present, which removes residual lacI from the circuit that is native to the extract Then, for each "pLas variant" plasmid, the plasmid is run with 1 nM using the promoter sequence in FIG. 37. Each one of these reactions is then run with 1:10 dilutions of 3OC12, from 10 uM, to 0.1 nM and a negative control.

FIG. 9B-F shows that by varying the pLas-variant promoter, one can get different max signal strengths. Here, each DNA is supplied in plasmid form on a different piece of DNA; however the DNA can either be linear or plasmid, can be on the same strand, or on different strands. The DNA can also either be natural source (from a bacteria) or from an artificial source (synthesis, PCR, oligonucleotide, etc. . . . ) (A) Each lasR promoter variant is tested in TX-TL by varying 3OC12HSL. Shown in each plot is the mean of 3 independent experiments. B) A previous reporter from the literature, pRsaL (P1), is tested. C) pLasI with a mutation in the −10 region (P2) is tested. D) pLasI wildtype (P3) is tested. E) pLasB wildtype (P4) is tested. F) pRsaL with a extended region is tested.)

It is noted in FIG. 9B-F that the original part for the circuit, P_orig, does not yield as much expression as P1. Therefore, the in vitro environment notes to the user that P1 is preferable over P_orig. The other outputs all show weaker Vmax.

The educated user would run different promoters in the circuit context and determine the ideal promoter unit to move forward in their design-build-test cycle. The data separately collected demonstrates that in the context of a circuit, the in vitro environment matches the in vivo environment, which would provide the user confidence that the data collected in the biomolecular breadboard is comparable to the in vivo environment and the biomolecular breadboard can be used to prototype genetic circuits in a target in vivo environment.

Example 13: Using Biomolecular Breadboard to do Part Mining and Characterization In Vitro: Collecting Statistics Statistics collected from running the breadboard with the promoters specified are in FIG. 9G. These are collected by matching the data to a Hill function fit for this instance (i.e. a promoter transfer function). The statistics will be used in downstream design.

Example 14: Using Biomolecular Breadboard to do Part Mining and Characterization In Vitro: Understanding Response to Small Molecule To understand how the promoters respond to 3° C. 12HSL, FIGS. 9B-F plot the deGFP signal as a function of time for each 3OC12 trace. FIG. 9H plots the deGFP amount as a function of 3OC12HSL concentration for each pLas variant. FIG. 9H together with the statistics in FIG. 9G shows the properties of each promoter and note to the user that for full activation of P1 one would need to have 3OC12HSL concentration in the 1-10 uM range (in cell-free) in order to obtain the corresponding transfer function shape expected in vivo.

Figure 9I:
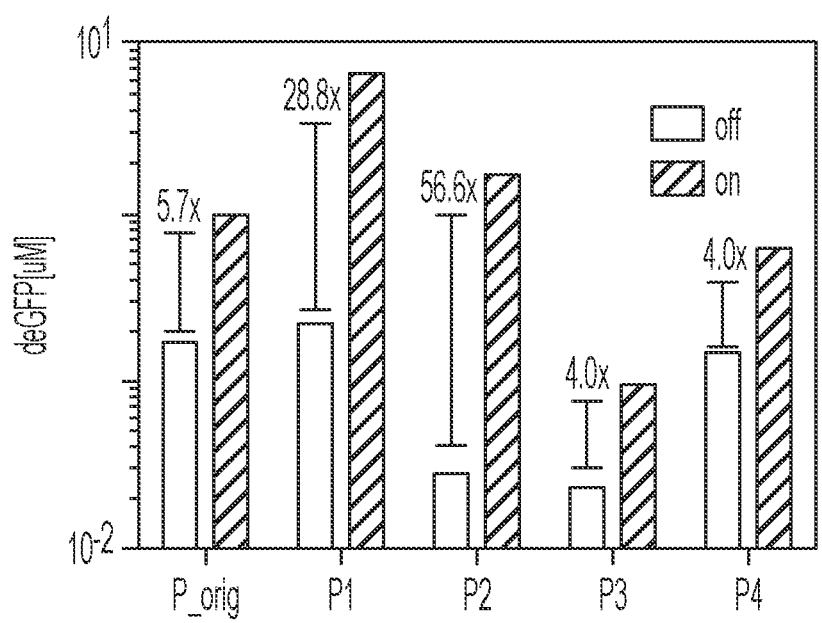
FIG. 9I compares the maximum signal to the minimum signal for each promoter and determine a fold-change dynamic range for each promoter.

Using the same data, one can also compare the maximum signal to the minimum signal for each promoter and determine a fold-change dynamic range for each promoter (see FIG. 9I), which can help in the engineering choice. In this case, using P3, for example, would be a poor choice due to low response to 3OC12 and low dynamic range (4×).

Figure 38A:
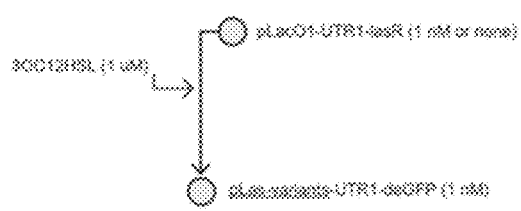
FIG. 38A shows an open loop of an incoherent feedforward loop in which the lasR protein is removed.
Figure 38B:
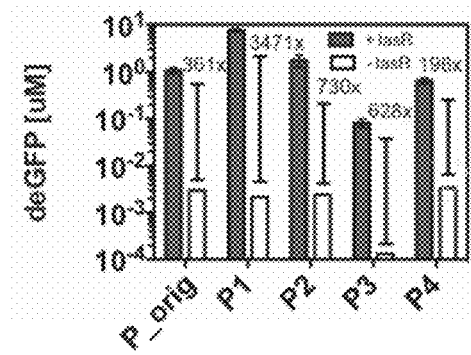
FIG. 38B shows the deGFP signal detected for each promoter variant (P_orig and P1 to P4) when lasR is present (dark gray) or absent (white).

Example 15: Using Biomolecular Breadboard to do Part Mining and Characterization In Vitro: Understanding Promoter Leakiness with or without Inducer Assume a user in the process of the experiment aims to determine in the absence of the protein inducer if there is leaky expression. This can be tested in a specific experiment by removing the lasR protein, as shown in FIG. 38A. This would test for "leakiness" and promiscuity in binding. In this experiment, the same reporter sequences listed in FIG. 37 are used at 1 nM concentration. Plasmid "163", which is pLacO1-UTR1-lasR-T500, is either present (gray bars) or not present (white bars). 3OC12 is set at 1 uM, and IPTG at 1 mM. The endpoint expression after 5 hours is subtracted from the negative and used to plot FIG. 38B.

Example 16: Using Biomolecular Breadboard to do Part Mining and Characterization In Vitro: De Novo Part Design The tetO1 operator element TCCCTATCAGTGA-TAGAGA (SEQ ID NO: 47) is put in the vicinity of the known promoter region around the −35 to the −10 region to make a hybrid promoter, a pLas-tetO variant. The best region to put the operator element can only be determined experimentally. However, since the mechanism of repression is steric, it is assumed to be best blocking a −35 or -10, or close to the +1 to block RNA transcription. An example of the variants tested can be found in FIG. 39A, where the wildtype promoter sequence is compared to a variant after the −10 and a variant after the +1.

It should be noted in this example that the promoter's effectiveness can be tested in vitro instead of in vivo. To test if the built promoter is functional, lasR was expressed from plasmid 163 at 1 nM. A tetR source, pLacO1-UTR1-tetR-T500, was also expressed at 1 nM. 1 mM of IPTG was also added to stop lac repression. Next, the wildtype reporter without tetO1, variant 1 designed, aka 212 (see FIG. 40A), or variant 2 designed, aka 213 (see FIG. 40B) were expressed at 1 nM. All experiments contain 10 uM 3OC12HSL to maximize lasR activation. Finally, aTc was varied in 1:10 dilutions from 10 uM to 0.001 uM and 0 uM. This is run in the eZS8 extract using previously conditions for running cell-free in [15].

Figure 39A:
FIG. 39A shows rational design of two placements of tetO operator sites, variant 1 and variant 2, compared to wildtype (SEQ ID NO: 38-40).
Figure 39B:
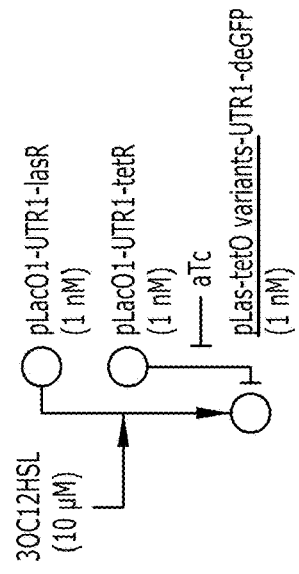
FIG. 39B shows circuit diagram used for testing repression, where aTc is varied in the presence of a tetR-producing construct.
Figure 39C:
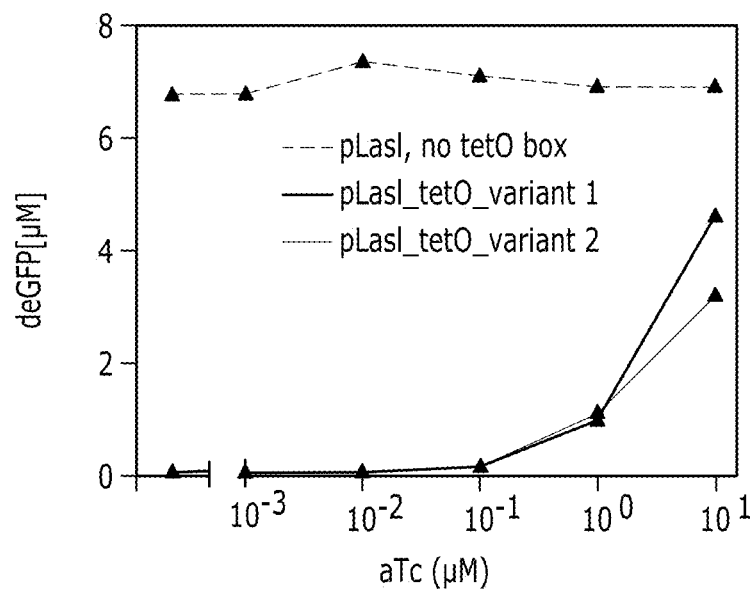
FIG. 39C shows endpoint fluorescence detected at t=300 min for the wildtype and two variants with varying aTc.
Figure 39D:
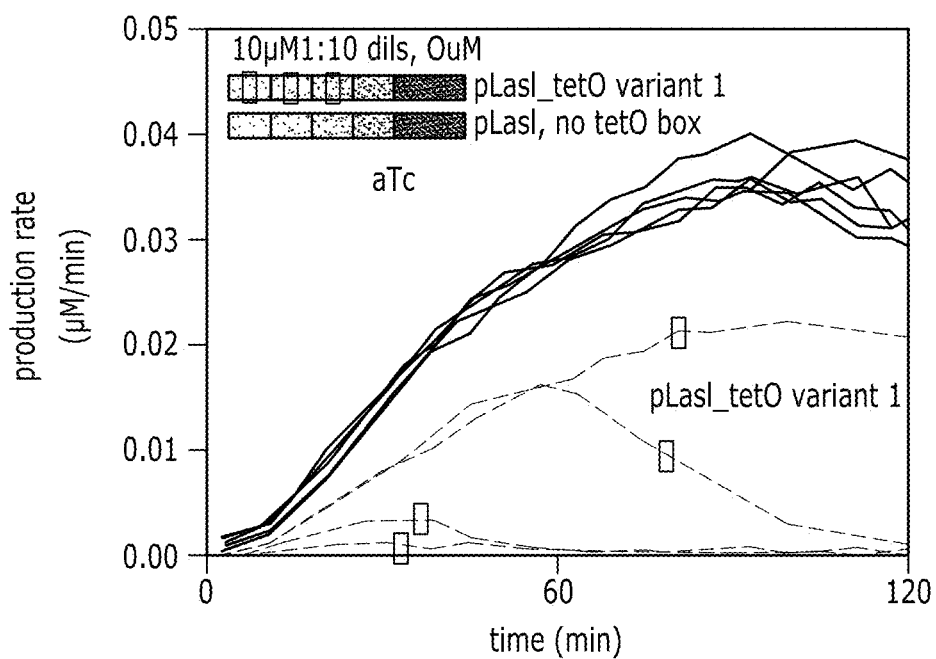
FIG. 39D shows first derivative indicating production rate (y-axis) of the wildtype promoter versus the two engineered promoters, with time on the x-axis.

FIGS. 39A-D show rationally designed las promoter with tetO operator sites. FIG. 39A shows design of two placements of tetO operator sites, variant 1 and variant 2, compared to wildtype. The difference is in the location of the tetO box. FIG. 39B shows circuit diagram used for testing repression, where aTc is varied in the presence of a tetR-producing construct. In FIG. 39C, each promoter variant along with wildtype is tested for repression ability with varying aTc. Shown are endpoint fluorescence at t=300 min. FIG. 39D shows first derivative indicating production rate of promoters.

FIG. 39C plots the endpoint after 5 hours for each sample to obtain the transfer function. Note here that the wildtype promoter does not respond to tetR or aTc, while the variants respond to tetR and aTc. Therefore, it is concluded that the engineering is successful, and furthermore both variants are fairly successful. In another representation in FIG. 39D, the first derivative of the time traces was taken to demonstrate that the tetR is effecting the engineered promoter with a tetO1 variant, and not the wildtype.

Example 17: Using Biomolecular Breadboard to do Part Mining and Characterization In Vitro: Sensitivity Analysis and Assemble of Entire Circuit In Vitro The user would like to understand the effect of each parameter in the context of the circuit and has collected data on individual pieces through part characterization and part building, as described above. At this point, the biological breadboard has been used for multiple cycles of (Design, Build, Test, Learn). This cycle would consolidate all of the pieces to determine how all pieces interact.

First, working completely in vitro each parameter in the circuit can be changed and a sensitivity analysis can be conducted. This example demonstrates a change of each parameter on the end performance of the circuit. Note that in this example, for each panel the variable being tested is being changed in either physical DNA or inducer concentration while all other aspects of the circuit are kept the same. In this way, the perturbation in the output is takes into account not only the perturbation, but its effect on the overall circuit.

Figure 41:
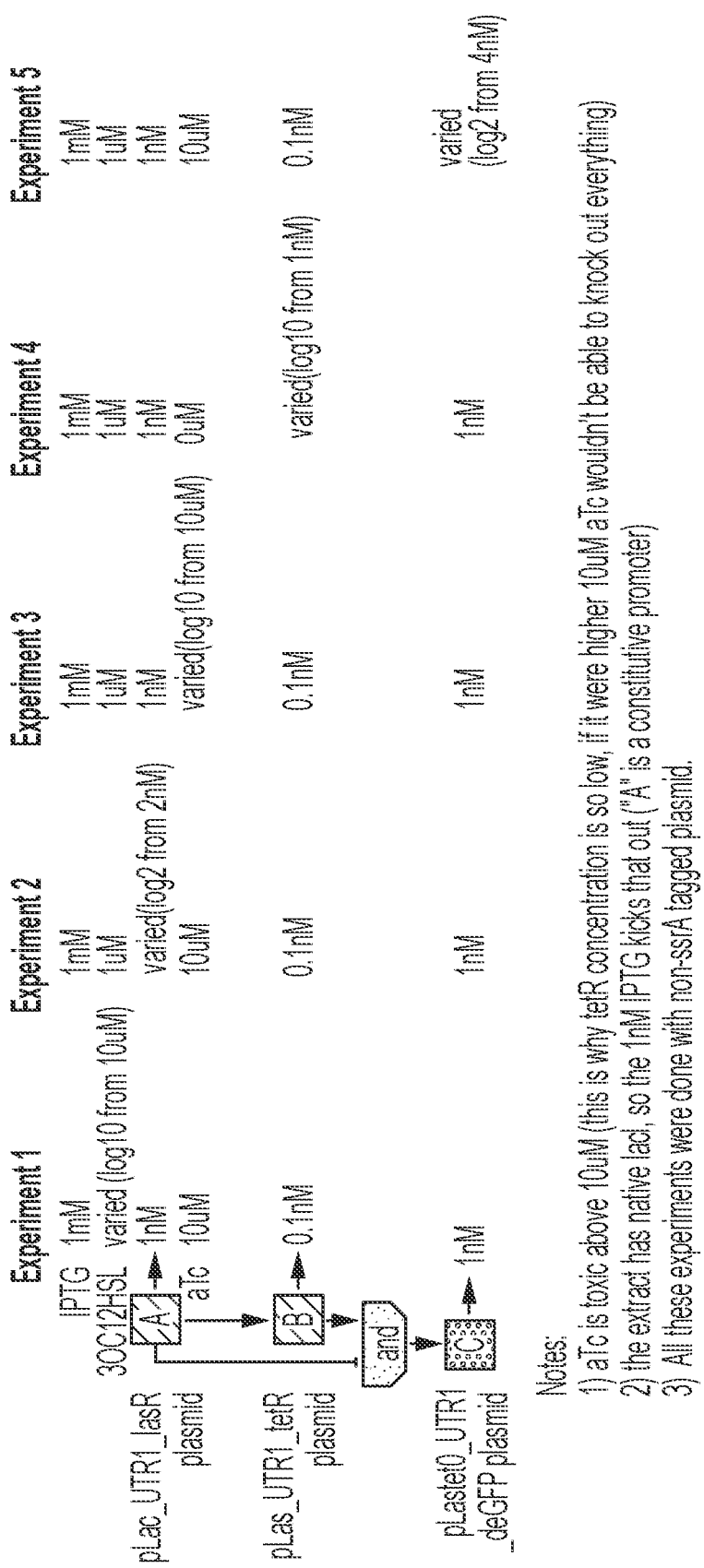
FIG. 41 shows components and their concentrations used for each sensitivity analysis experiment in vitro, with the results shown in FIGS. 43A-F and FIG. 44.

In this example, FIG. 41 demonstrates what components were used for each experiment. In particular, the top node (A) refers to plasmid 163 (sequence previously provided), the middle node (B) refers to plasmid 220 (pLas(P1)_UTR1_tetR_B1002) (SEQ ID NO: 43) (see FIG. 42), and (C) refers to plasmid 212 (P1_tetO(variant1)-UTR-deGFP-T500) (SEQ ID NO: 42). The inducers and concentrations are given per experiment.

Figure 43A:
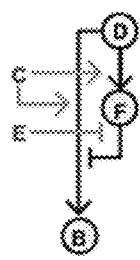
FIGS. 43A-F show the results from the in vitro and in silico sensitivity analysis of the incoherent feedforward loop, with each plot corresponding to an experiment setup in FIG. 41.
Figure 43B:
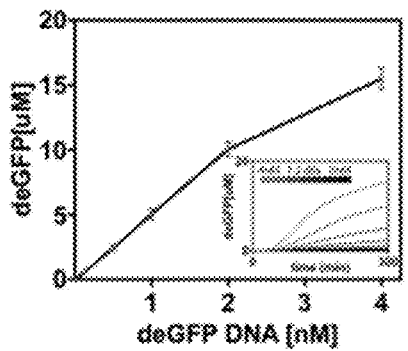
Figure 43C:
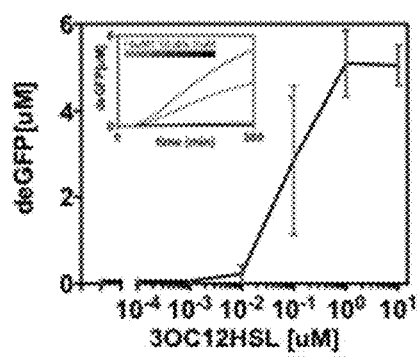
Figure 43D:
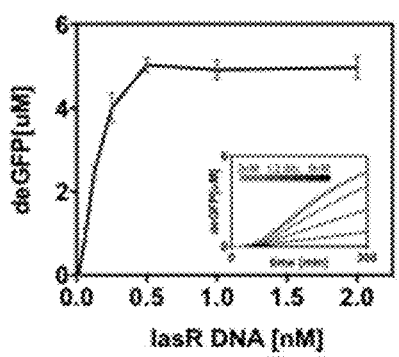
Figure 43E:
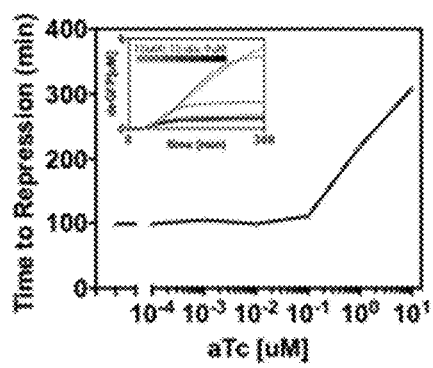
Figure 43F:
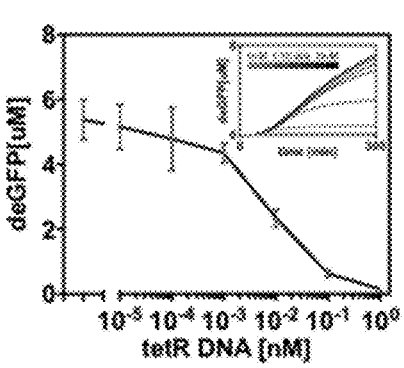

Note that Experiment 1 corresponds in the FIG. 43C, Experiment 2 to FIG. 43D, Experiment 3 to FIG. 43E Experiment 4 to FIG. 43F. Experiment 5 to FIG. 43B. All experiments were performed in cell-free system eZS8, and three repeats were conducted of each to obtain error bars of 1 standard deviation.

FIGS. 43A-F shows in vitro and in silico sensitivity analysis of the IFFL. A) For the I-FFL, each of five parameters is individually modified, while other parameters are kept constant at 1 uM 3OC12HSL, 10 uM aTc, 1 nM pLac-lasR, 0.1 nM pLas-tetR, and 1 nM pLas-tetO-deGFP. All reactions contain 1 mM IPTG to remove residual lacI, and are run in triplicate using new DNA sources. B) pLas-tetO-deGFP plasmid is varied and output deGFP is measured at t=300 minutes. Experiment data is shown in black. Inlet shows time-series data. C) 3OC12 is varied and output deGFP is measured at t=300 minutes. D) pLac-lasR plasmid is varied and output deGFP is measured at t=300 minutes. E) aTc is varied and time to repression is shown. Time to repression is determined as the time where production rate reaches half-maximum. F) pLas-tetR plasmid is varied. No aTc was added to this experiment to probe the direct effect of tetR.

Based on these results, one can gain a general understanding of the circuit functionality. For example, this analysis states that deGFP is a linear response to signal (FIG. 43B), while inducers 3OC12 (FIG. 43C) and aTc (FIG. 43E) and protein tetR (FIG. 43F) are sigmoidal responses. These are not trivial analyses, especially the tetR DNA concentration and relationship to circuit response, as it is extremely hard to vary tetR DNA and production concentration precisely in vivo. In addition, a non-trivial analysis is the lasR DNA variation mode (FIG. 43D), which demonstrates a linear output response above 1 nM of DNA. Described here is a method to systemically vary all parameters in a given circuit. This approach can be generally applied for any multi-node circuit.

Figure 44:
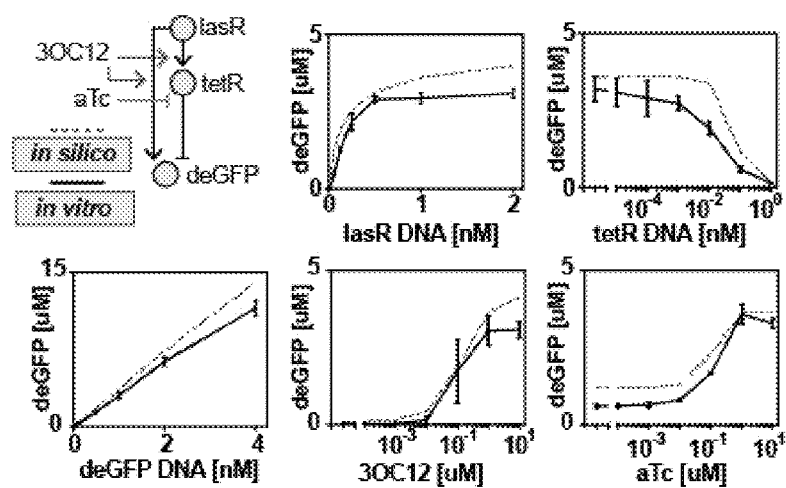
FIG. 44 shows the in vitro results from FIGS. 43A-F overlaid with the modeling data obtained from the in silico portion of the biomolecular breadboard (dotted lines).

Example 18: Using Biomolecular Breadboard to do Part Mining and Characterization in Vitro: Sensitivity Analysis, Collecting in Silico Data to Support In Vitro Result In silico modeling can also be conducted to verify the in vitro findings. FIG. 44 shows the in vitro results from FIGS.

43A-F overlaid with the modeling data (dotted lines). Modeling data represents the in silico prediction of the circuit performance based on training data from the individual pieces in vitro.

Example 19: In Silico Portion of Biomolecular Breadboard: Background and Method

In silico modeling can be conducted in the biomolecular breadboard in parallel to the in vitro experiments previously described. To do so, each individual piece can be characterized in the in vitro model and the data collected from the in vitro model can be collected for the in silico model. When individual pieces are collected, the complete circuit can then be simulated in silico and the resulting data can be used to validate the in vitro collected.

Extracts can be calibrated from extract-to-extract. Alternatively, a user can run training data in each extract set to obtain quantitatively consistent data when a quantitative validation is desired.

The in silico modeling section pertains to predicting the behavior of a genetic circuit, such as the IFFL circuit previously described, using the TXTL Modeling Toolbox, based on characterizations of the behavior of parts of the IFFL.

The Incoherent Feed-Forward Loop is used as an example for the part characterization and circuit behavior prediction methodology. A MATLAB SimBiology based in silico package, called the TXTL Modeling Toolbox ("the toolbox") is shown, and is used as a tool to generate models of parts, which can then be characterized by fitting them to experimental data (by estimating parameters for the models). The in silico parts, embodied in MATLAB function files and parameter files, can then be stored in an in silico library of parts. Parts can then be drawn from this library and composed into a circuit, which can be simulated, and in particular, this is done specifically for the IFFL. The simulated behavior of the circuit is a prediction of the circuit behavior, which can be compared to the behavior of the overall system in vitro.

The in silico modeling methods are described as shown in the flow chart of FIG. 45. The flow chart in FIG. 45 shows that the first step is to decompose a system (like the IFFL) into parts (Step 1), followed by the creation of chemical reaction network and mathematical models of these parts using the TXTL Modeling Toolbox (Step 2). This is followed by characterization of the parts by fitting the part behavior to experimental data using parameter estimation algorithms (Step 3). These characterized parts can then be used to build a library of characterized parts, from which one can draw upon parts to create a full circuit such as the IFFL (Step 4). As a next step, the IFFL is simulated to obtain its in silico behavior, which can be compared to its in vitro behavior for various experimental conditions (Step 5). Finally, if the behavior of the systems do not match, the workflow returns to Step 2 in which the previously built mathematical models are re-evaluated. Steps 2-6 are then repeated.

Each of the steps in FIG. 45 is described in great details in the following examples.

Example 20: In Silico Portion of Biomolecular Breadboard: (Step 1) Circuit Decomposition into Parts Step 1 of FIG. 45 is described in this example, in which the circuit is decomposed into parts or nodes.

The following three guidelines were followed when defining the parts. (1) the parts need to be defined independently of the circuit. (2) the parts can be composed with other parts to form larger systems. (3) the parts have sufficient components to carry out a function such as repression, activation, termination.

An illustrative example of a part is the tetR-pTet-aTc repression system. The system is defined independent of the circuits to be formed, such as IFFL, the Negative Auto Regulation circuit or the Gardner-Collins Genetic Toggle Switch (Guideline 1). It can be composed with other similar systems (such as the Lac or Lambda repressor systems) to form circuits such as the Genetic Toggle or the Repressilator (Guideline 2). It has a clearly defined function, i.e. repression (Guideline 3). The tetR protein by itself, on the other hand, cannot carry out repression, and thus is not considered to be an entire part. The tetR protein with the pTet promoter is a part, though here tetR-pTet-aTc is selected to be the part definition, with the function defined as inducible repression.

The parts decomposed from the IFFL circuit of FIG. 5A are: the ptet-tetR-aTc repression induction system, the plaslasR-3OC12HSL inducible activation system and the pLac promoter (for constitutive protein expression).

The characterization experiments (FIG. 50) will further modify these part definitions to: the ptet promoter, the plac promoter, the tetR repressor, the aTc inducer, the plas-lasR-3OC12HSL inducible activation system.

Example 21: In Silico Portion of Biomolecular Breadboard: (Step 2) Chemical Reaction Network Generation for Each Part Using the Toolbox Before the parts can be characterized by estimating parameters belonging to mathematical models of the parts, the mathematical model for each part needs to be created. Instead of creating a model from scratch for each part, where many of the features of models corresponding to different parts are similar (processes such as transcription and translation occur during the functioning of almost all parts), a toolbox has been developed, which automatically generates the mathematical model and chemical reaction network (CRN) associated with each part.

High-Level Description of the Toolbox

The toolbox is essentially a software package that simulates the in vitro breadboard in silico. It is an analogue of the SPICE software package in electrical engineering, or more generally other computer aided design (CAD) software that exists in other fields. The toolbox accomplishes its goals by first generating the equations for the chemical reactions that occur in the TXTL cell-free lysate in vitro system when a piece of DNA is added to that system. A version of the toolbox that can be used for the purposes of part characterization and circuit behavior prediction is described herein.

The toolbox is created using the MATLAB SimBiology package. However, the implementation of the in silico modeling methods is not limited to any specific programming language or framework. Other languages or frameworks, such as the Systems Biology Markup Language (SBML) can also be used for implementation. The general concepts related to computer science, the theory of bio/chemical reactions and dynamics systems will be understood to a person skilled in the art.

Figure 46:
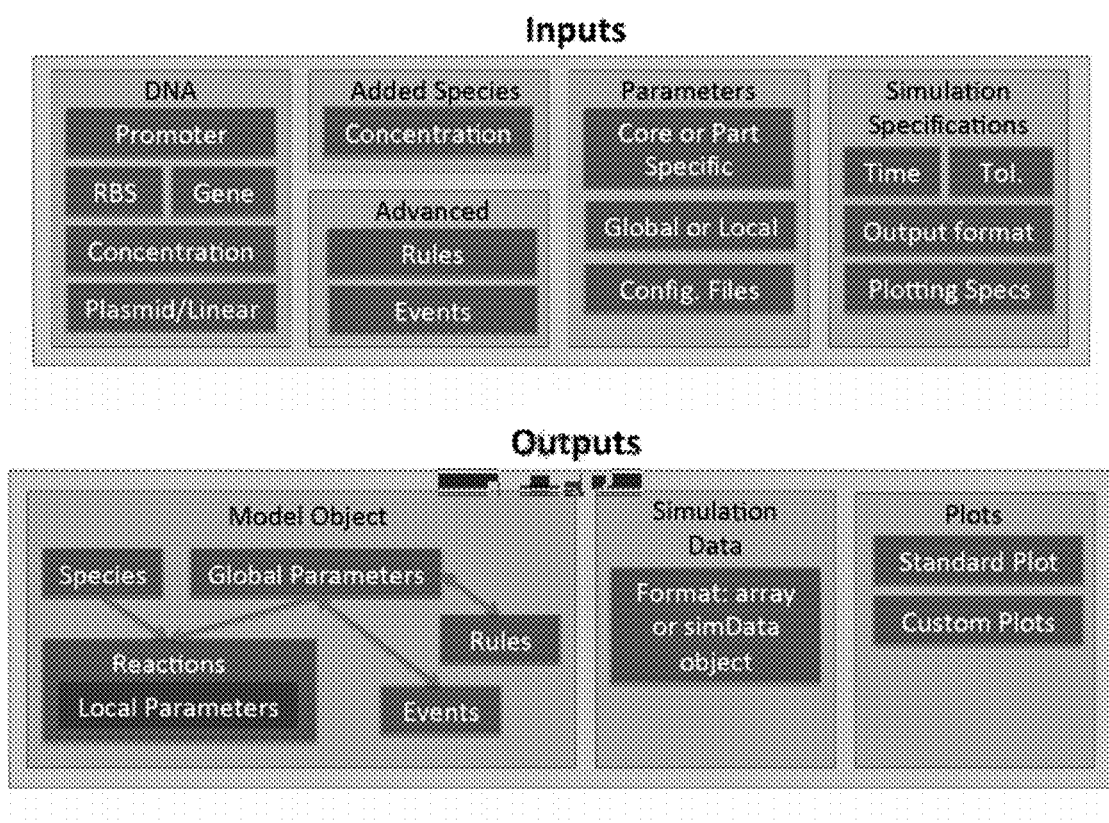
FIG. 46 provides a set of inputs and outputs of the toobox used for the in silico modeling in one embodiment.

At a high level, the toolbox can be described as a set of inputs and outputs shown in FIG. 46. FIG. 47 shows an example of how a circuit built out of the tetR-pTet-aTc part and the GFP reporter part can be entered into the toolbox. This is a set of commands that closely mimic the experimental protocol of the in vitro TXTL cell-free extract prototyping system for the negative auto-regulation circuit, whereby a transcription factor represses its own production.

The first two commands in FIG. 47, txtl_extract and txtl_buffer, access a list of parameters pertaining to the extract and buffer batch E1 corresponding to a list of parameters stored in a .csv configuration file in the trunk/config directory. Each command returns a model object with handles tube1 and tube2. These model objects contain species (at initial concentrations) and reactions pertaining to the extract and buffer. The detailed contents of these model objects will be elucidated below.

The next three lines create a new empty model object with a handle called tube3, and then populate this model object with various species associated with the DNA specified by the txtl_add_dna commands. The txtl_add_dna command takes as an input the following arguments: (tube3, 'ptet(50)', 'rbs(20)', 'tetR(1200)', 1, 'plasmid'), which is described in details, as follows:

(a) tube3: a handle to the model object (tube3) to add the DNA and associated species to;

(b) ptet (50): a unique promoter ID string followed by an optional promoter length (in base pairs) specification. The promoter ID string (lets call it <PROMOTER>) must correspond to two files found in the trunk/components directory: the txtl_prom_<PROMOTER>.m file, which is the code associated with the promoter and sets up the species, reactions, and parameters associated with the promoter, and the txtl_param_<PROMOTER>.csv file, which contains the values of all the parameters associated with the promoter given by <PROMOTER>. The length of the promoter is optional, because if it is not specified in parenthesis, a default length is applied from the parameter configuration file (txtl_param_<PROMOTER>.csv);

(c) rbs(20) and tetR(1200) specify the RBS and the gene used. The RBS currently does not have separate code and parameter configuration files, but we expect that as the toolbox is used for different RBSs, the RBS will use separate files just like different promoters and genes do;

(d) 1: a numeric argument that specifies the concentration of the DNA to be added, taken to be in nM (nanomolar);

(e) plasmid': a string specifying whether the DNA specified by this command is plasmid or linear. The only difference between plasmid and linear DNA is that linear DNA degrades (at a rate inversely proportional to its length) under the action of the RecBCD exonuclease, a process that can be attenuated by the gamS protein in both the in vitro and this in silico systems.

The next command, txtl_combine, simply combines the contents of the three model objects, i.e., the reactions objects and species objects, into a single model object, and creates a model object, which has a volume equal to the sum of the volumes of the three constituent model objects. The amount of species is conserved.

The txtl_addspecies command is optional. This command is being used to add a species object representing 500 nM of the small molecule anhydrotetracycline (aTc) to the model object. This molecule binds to the tetR repressor to sequester and remove its ability to repress the pTet promoter.

The next command, txtl_runsim, sets up the reactions in the model object, including some of the species that cannot be set up earlier and certain event objects in the model object, simulates the resulting complete model object, and generates output data from the simulations. The output data in this particular case is arranges as a SimBiology simData object, which has both the simulation data and various metadata associated with the simulation data.

The final command shown in FIG. 47 is the txtl_plot command, which takes the model object and the simData objects as imputs, and generates a standard plots of the time evolution of the various proteins, DNA, RNA and resource species (amino acids, nucleotides, RNA polymerase, ribosomes) in the system.

The output of the txtl_plot command is shown in FIGS. 48A-C. This is the standardized plot produced by the txtl_plot command. This plot shows the various proteins in the system (top subplot), the DNA and RNA in the system (bottom left), and the resource usage (bottom right). In the bottom left subplot, the RNA concentrations are given by the solid lines, and is the axis on the left, while the DNA concentrations follow the same color scheme, correspond to free (unbound) DNA, and are given by the dashed lines, with the axis on the right. In the bottom right subplot, the resource concentrations are normalized to 1. Details of the various dynamics that generate these curves are provided in the detailed description of the toolbox.

At this level of description, a user can specify SimBiology events and rules and add them to the model object. The user can also create custom plots with the data, and create parameters which are global in scope (i.e, are not scoped at the reaction level).

Example 22: In Silico Portion of Biomolecular Breadboard: Detailed Lower-Level Description of the Toolbox and Species Syntax At this level, the syntax and semantics of the elements that comprise the toolbox will be described.

Along with mathematical processing, the toolbox also processes information using strings, in the form of regular expressions. In particular, it uses strings to denote species and complexes formed by species, and reactions are either directly specified in terms of exact species strings, or they are specified in terms of regular expressions which match patterns in the species which are to participate in that reaction.

The syntax used to specify species and bound complexes is described below, followed by listing all the reactions the toolbox can generate.

The Syntax Used to Specify Species:

The main classes of species in the toolbox are DNA, RNA, proteins, small molecules (such as inducers), protein multimers, special enzymes like RNAse or RecBCD. Many of these species can have modifiers on them.

The syntax for naming DNA, RNA and protein follows the overall pattern DNA <PROMOTER>--<UTR>--<GENE>, RNA <UTR>--<GENE>, protein <GENE>, respectively. Here, the strings DNA, RNA and protein are followed by a space, and then followed by the strings specifying the polynucleotide sequences associated with the promoter, untranslated region and gene/coding sequence. These strings are used to access files containing information on the reactions and parameters which are needed to simulate the polynucleotide sequences in silico. The strings are specified from information contained in three sets of specifications: promoter specifications (<promspec>), ribosome binding site specifications (<rbsspec>) and/or coding sequence specifications (<genespec>). Here <promspec>, <rbsspec> and <genespec> are placeholders for the actual strings specifying the names of the polynucleotide sequences in the promoter, UTR and coding sequence regions on the DNA, along with the lengths of the respective polynucleotide sequences in base pairs. These specifications are used as an input to the txtl_add_dna function shown in FIG. 47, and are elaborated on in Table 1.

TABLE 1

The promoter, UTR and coding sequence specifications for the txtl_add_dna command.

| Specification | Overall structure | Examples |
|---|---|---|
| <promspec> | promoter(length)<br>junk(length)-promote(length) | junk(100)-ptet(50)<br>ptet(50) |
| <rbsspec> | rbs(length)<br>attenuator(length)-<br>attenuator(length)-rbs(length)<br>antisense(length) | rbs(50)<br>att1(300)-<br>att2(300)-rbs(55)<br>anti1(81) |
| <genespec> | geneName(length)<br>geneName(length)-lva(length) | tetR(1000)<br>deGFP(1200)-lva(20) |

Table 2 illustrates some examples of the use of polynucleotide name information from the three types of specifications to define DNA RNA and protein species names. A double dash (--) is used to separate <PROMOTER>, <UTR> and <GENE> from one another and a single dash (-) to separate strings representing polynucleotides within each of these regions. For example, the lva degradation tag is separated from the main gene name (tetR) by a single hyphen. Similarly, junk DNA, which is used to protect linear DNA from degradation by exonucleases, is separated from the promoter name ptet by a single dash.

TABLE 2

DNA, RNA and protein naming convention

| Species Type | Convention | Illustrative Example |
|---|---|---|
| DNA | DNA <PROMOTER>--<UTR>--<GENE> | DNA ptet--rbs--tetR<br>DNA junk-ptet--rbs-att1--tetR-lva |
| RNA | RNA <UTR>--<GENE> | RNA rbs--tetR<br>RNA rbs-att1--tetR-lva |
| protein | protein <GENE> | protein tetR<br>protein tetR-lva |

For proteins that can dimerize or tetramerize, a string dimer or tetramer is appended to the end of the protein string. For example, the tetR protein dimerizes, while the lacI protein tetramerizes. The strings associated with these proteins are shown in Table 3.

TABLE 3

Strings used to represent protein multimers and some of their variants

| tetR monomer | protein tetR |
| | protein tetR-lva |
| tetR dimer | protein tetRdimer |
| | protein tetR-lvadimer |
| lacI monomer | protein lacI |
| | protein lacI-lva |
| lacI dimer | protein lacIdimer |
| | protein lacI-lvadimer |
| lacI tetramer | protein lacItetramer |
| | protein lacI-lvatetramer |

The small molecules simply use unique strings with no structure. Examples of small molecules are provided in Table 4, which also shows special proteins such as gamS and sigma70 having strings with the protein naming convention structure.

TABLE 4

Strings used to represent species suh as small molecules and special proteins, and descriptions of these species.

| Small molecule or special proteins/enzymes | Details |
|---|---|
| aTc | anhydrotetracycline. Inducer which binds to tetR protein to sequester it. |
| IPTG | Isopropyl beta-D-1-thiogalactopyranoside. Binds to lacI repressor to sequester it. |
| 3OC12HSL | Inducer for the lasR activator |
| RNase | Enzyme that degrades RNA |
| RecBCD | Enzyme that degrades linear DNA |
| AA | Amino Acids |
| AGTP | A species representing the sum of the concentration of ATP and GTP. |
| CUTP | A species representing the sum of the concentration of CTP and UTP |
| Ribo | Ribosome |
| RNAP | RNA polymerase |
| RNAP 70 | RNA polymerse bound to sigma 70 sigma factor protein |
| protein gamS | gamS protein, binds to RecBCD to sequester it. |
| protein sigma70 | sigma 70 sigma factor |

Finally, the naming syntax for complexes formed of species names is described herein. The convention X:Y will be adopted for species X and Y bound to each other to form a complex. Larger complexes will be defined inductively. For example, the complex AA:AGTP:Ribo:RNA rbs--deGFP represents AA, AGTP, Ribo and RNA rbs--deGFP bound to one another in a large complex. When there is a space in the name of a species or a complex, SimBiology requires square brackets placed around the species or complex. Thus, [AA:AGTP:Ribo:RNA rbs--deGFP] will refer to the same complex as the one above, especially when used in reactions (see the list of biochemical reactions below).

Example 23: In Silico Portion of Biomolecular Breadboard: Detailed Lower-Level Description of the Toolbox and Biochemical Reactions List Biochemical Reactions List:
Described herein are the biochemical reactions that are set up when a piece of DNA is added to the system. The main reactions can be divided into the following subsets: transcription, translation, post translational modification (maturation, multimerization), RNA degradation, linear DNA degradation and protection, protein degradation, inducer binding, transcription factor binding and energy resource degradation. Other special reactions may exist for exotic parts. Each of the main reactions are illustrated as follows:
Transcription:
R1) RNA polymerase Binding to Sigma Factor to form the RNAP70 complex
RNAP+[protein sigma70]<->RNAP70
R2) DNA binding to the resulting RNAP70 complex
[DNA ptet--rbs--tetR]+RNAP70<->[RNAP70:DNA ptet--rbs--tetR]
R3) RNAP70:DNA complex binding to AGTP and CUTP nucleotide species in all four permutations
[RNAP70:DNA ptet--rbs--tetR]+AGTP<->[AGTP:RNAP70:DNA ptet--rbs--tetR]
[RNAP70:DNA ptet--rbs--tetR]+CUTP<->[CUTP:RNAP70:DNA ptet--rbs--tetR]
[AGTP:RNAP70:DNA ptet--rbs--tetR]+CUTP<->[CUTP:AGTP:RNAP70:DNA ptet--rbs--tetR]

[CUTP:RNAP70:DNA ptet--rbs--tetR]+AGTP<->[CUTP: AGTP:RNAP70:DNA ptet--rbs--tetR]

R4) RNA production step, which also produces DNA with the RNAP70 at termination site

[CUTP:AGTP:RNAP70:DNA ptet--rbs--tetR]->[term_RNAP70:DNA ptet--rbs--tetR]+[RNA rbs--tetR]

R5) Consumption reaction, which returns RNAP70 and DNA, consuming nucleotides, but does not produce RNA.

[CUTP:AGTP:RNAP70:DNA ptet--rbs--tetR]->RNAP70+ [DNA ptet--rbs--tetR]

R6) The RNAP70 bound to terminator site of DNA complex dissociates into its constituents

[term_RNAP70:DNA ptet--rbs--tetR]->RNAP70+[DNA ptet--rbs--tetR]

Translation:

R7) RNA binding to Ribosome

[RNA rbs--tetR]+Ribo<->[Ribo:RNA rbs--tetR]

R8) Ribosome RNA complex binding to amino acid and ATP GTP resources

[Ribo:RNA rbs--tetR]+AA+AGTP<->[AA:AGTP:Ribo: RNA rbs--tetR]

R9) Consumption Reaction for translation

[AA:AGTP:Ribo:RNA rbs--tetR]->[RNA rbs--tetR]+Ribo

R10) Protein production reaction for translation

[AA:AGTP:Ribo:RNA rbs--tetR]->[RNA rbs--tetR]+[protein tetR]+Ribo

Post translational modification:

R11a) Protein maturation/folding

[protein deGFP]->[protein deGFP*]

[protein ClpX]->[protein ClpX*]

RNA Degradation:

R12) RNA, in its various bound forms, binding to RNase

[RNA rbs--tetR]+RNase<->[RNA rbs--tetR:RNase]

[AA:AGTP:Ribo:RNA rbs--tetR]+RNase<->[AA:AGTP: Ribo:RNA rbs--tetR:RNase]

[Ribo:RNA rbs--tetR]+RNase<->[Ribo:RNA rbs--tetR: RNase]

R13) Degradation step

[RNA rbs--tetR:RNase]->RNase

[AA:AGTP:Ribo:RNA rbs--tetR:RNase]->AGTP+AA+ Ribo+RNase

[Ribo:RNA rbs--tetR:RNase]->Ribo+RNase

Linear DNA degrdation and protection:

R14) DNA degradation by RecBCD, enzymatic reaction

[DNA ptet--rbs--tetR]+RecBCD<->[DNA ptet--rbs--tetR: RecBCD]

[DNA ptet--rbs--tetR:RecBCD]->RecBCD

R15) RecBCD sequestration by gamS

RecBCD+[protein gamS]<->[RecBCD:gamS]

Transcription Factor and Inducer Binding and Regulation

R16) tetR dimerization

2 [protein tetR]<->[protein tetRdimer]

R17) DNA binding with tetR. This either cannot bind to RNAP70 for trasncription, or binds weakly (large dissociation constant), and is hence sequestered

[DNA ptet--rbs--tetR]+[protein tetRdimer]<->[DNA ptet--rbs--tetR:protein tetRdimer]

R18) tetR getting sequestered by aTc

[protein tetRdimer]+2 aTc<->[2 aTc:protein tetRdimer]

Energy Resource Degradation

R19) AGTP degrades after 3 hours, i.e., the rate of the following reaction changes from 0 to nonzero at 3 hours. This is implemented using a SimBiology event

AGTP->AGTP UNUSABLE

R20: Protein degration reactions (mediated by ClpX)

[protein tetR-lva]+[protein ClpX]<->[protein ClpX:protein tetR-lva]

[protein ClpX:protein tetR-lva]+AGTP->[protein tetR-lva**]+[protein ClpX]

[protein ClpX]->null

Example 24: In Silica Portion of Biomolecular Breadboard: Detailed Lower-Level Description of the Toolbox and Overall Function Structure Described herein is the overall function structure of the toolbox.

Figure 49:
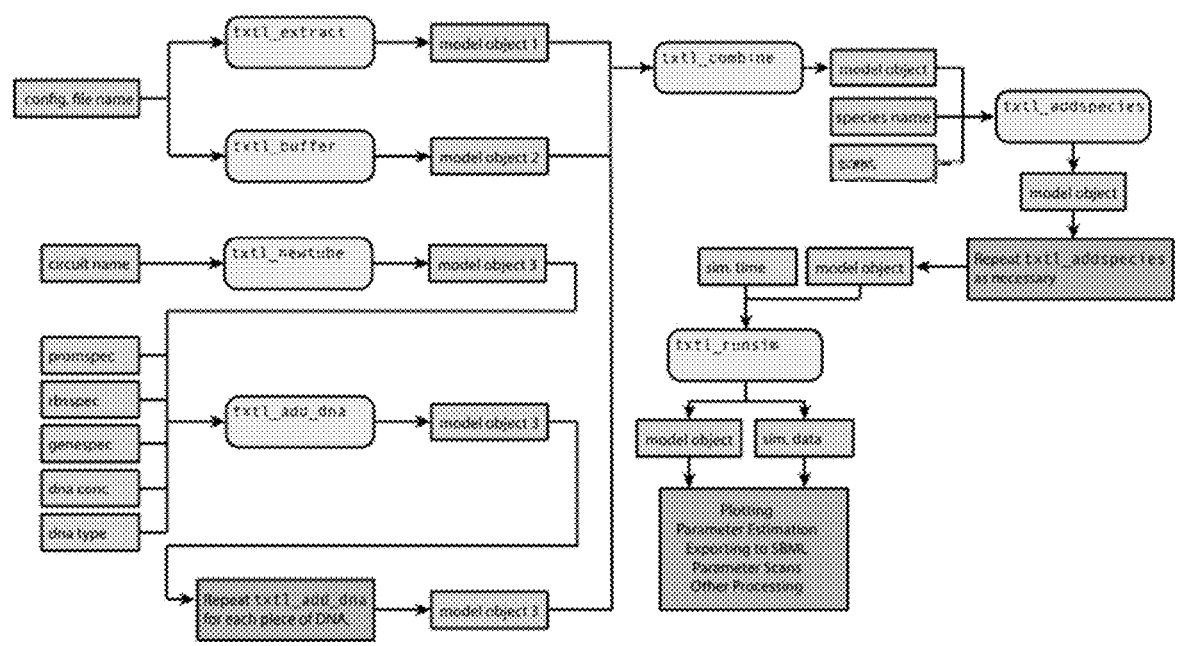
FIG. 49 provides a flow diagram illustrating the information flow between user level functions in the in silico modeling toolbox, showing the dependencies between the functions a user can see.

FIG. 49 provides the flow of information in the toolbox, which shows an overall flow of information between user level functions. The information flow within each of the functions (depicted by boxes with rounded corners in FIG. 49) is described in details below.

Each of the functions (depicted by round-edged boxes in FIG. 49) is described in Table 5.

TABLE 5

The processing carried out by the main user level functions of the toolbox

| Function Name | Description of processing | Additional details (note the R# refers to reaction number in the List of Biochemical Reactions section above |
|---|---|---|
| txtl_newtube | Set up a new model object with a single compartment, and the UserData field populated by the data structure: struct('ReactionConfig', {[ ]}, 'DNAinfo', {[ ]}, 'First Run', {[ ]}, 'Vesicule', 0) | ReactionConfig will hold the parameters from the configuration file in the form of the values of the properties of a class called txtl_reaction_config. DNAinfo will contain the information provided as arguments to the fucntion txtl_add_dna, and includes <promspec>, <rbsspec>, <genespec>, the concentration of the DNA, and the type of the DNA. This information is needed at various points in the code to make certain decisions (see description of the other functions for examples of where this information is used -- for example, in txtl_runsim) |

TABLE 5-continued

The processing carried out by the main user level functions of the toolbox

| Function Name | Description of processing | Additional details (note the R# refers to reaction number in the List of Biochemical Reactions section above |
|---|---|---|
| txtl_extract | 1) Setup new model object<br>2) Setup reaction config object and add it to the model object's UserData<br>3) Setup core extract specific proteins (various enzymes and other proteins)<br>4) Setup sigma factor binding reaction and RecBCD sequestration reaction. | Species added: RNAP, Protein sigma70, protein sigma28, Ribo, RNase<br><br>Reactions (R1) and (R15). |
| txtl_buffer | 1) Setup new model object<br>2) Setup reaction config object and add it to the model object's UserData<br>3) Setup resource species | Species added: AGTP, CUTP and AA |
| txtl_add_dna (preamble) | 1) Extract relevant information from <promspec>, <rbsspec> and <genespec>.<br><br>2) Setup various booloean variables (flags) depending on the promspec, rbsspec and genespec from previous step | Relevant information can be, for example, junk DNA and length on promoter end, or lva tag and length on gene, attenuator sequences and length on rbs. This information gets used to set DNA, RNA and protein degradation and transcription and translation rates, and to make decisions about whether specific parts of the code should be run. See point 2 in this preamble.<br>eg: if the genespec has an lva string, set the protein degradation flag to true. The full list of flags that can be set are:<br>geneSpec: lva, terminator and no_protein<br>rbsspec: attenuator, antisense, rbs<br>promspec: junk and thio |
| txtl_add_dna (setup species mode)<br>Note that more information on this mode and the other mode (Setup Reactions) can be found in the section below labeled Setup Species and Setup Reactions Driver Mode Structure) | 3) Append the DNA information to the DNAinfo field of the UserData of the current tube.<br><br><br><br><br><br><br><br><br>4) Call txtl_protein_<geneName> and setup all the species specified by that file. | The information is the <promspec>, <rbsspec>, <genespec>, the concentration of DNA, the type of DNA (plasmid or linear), mode, and a string specifying that the reactions have not been set up yet (this information is used by txtl_runsim later to decide to rerun txtl_add_dna in setup reactions mode, and to populate the input of the txtl_add_dna. command if it is indeed to be run in setup reactions mode)<br>Uses the geneName from the genespec. If the length was not specified in genespec, then the defauls length from the protein's config file (which is called by the file txtl_protein_<geneName> is used).<br>Examples of species set up:<br>When the <geneName> is tetR, the species aTc is set up. Furthermore, the function txtl_dimerize is called, which sets up <protein name>dimer. Here, <protein name> can be protein tetR or protein tetR-lva.<br>Another example: for the deGFP protein, the species signifyng mature folded protein, <protein name>*, is set up, where <protein |

TABLE 5-continued

The processing carried out by the main user level functions of the toolbox

| Function Name | Description of processing | Additional details (note the R# refers to reaction number in the List of Biochemical Reactions section above |
|---|---|---|
| | 5) Call txtl_utr_<rbsName> and setup the species specified by that file. | name> is protein deGFP or protein deGFP-lva. Uses the rbsName from the rbsspec. If the rbs file does not exist, then it uses a default rbs. There is also support for the attentuator/antisense RNA based transcriptional regulation system. In the setup species mode, the species added to the tube are Ribo and [Ribo:<rnaName>], where <rnaName> is RNA<rbsName>--<geneName>. where <rbsName> is, for example, rbs, and <geneName> is, for for example, deGFP or tetR. Ie, the full <rnaName> can be, for example, RNA rbs-tetR. |
| | 6) Call txtl_prom_<promoterName> and setup the relevant species. | The species set up in the tube are: For the ptet promoter (file txtl_prom_ptet. m): RNAP70, RNAP70:<dnaName> Heren <dnaName> is, for example, DNA ptet--rbs--tetR-lva. |
| | 7) Set up the species associated with translation | The species set up are: AA; [AA: AGTP: <riboboundName>] where <riboboundName> is, for example, Ribo:RNA rbs--tetR; Ribo (note that if any species are already present, SimBiology does not add them again. For example, Ribo may already have been set up in txtl_utr_rbs) |
| | 8) Setup the species associated with protein degradation, with rate determind by the length of the protein obtained from the geneSpec (or default values from the config file) | |
| | 9) If the DNA being added is linear, then setup the species associated with linear DNA degradation. | |
| txtl_add_dna (Setup Reactions) | 10) get the list of all the species in the tube so far. | |
| | 11) Setup the reactions associated with the protein coded for by the gene of this DNA | Inducer Binding reactions (R18) Maturation reactions (R11) Dimerization reactions (R16) For tetR, the reactions are: <tetR dimer> + 2 aTc <-> 2 aTc:<tetR dimer>, where <tetR dimer> is the version of dimerized tetR protein which is present in the system (protein tetRdimer or protein tetR-lvadimer) This function also calls txtl_dimerize, which sets up the dimerization reaction: 2 <proteinName> <-> <proteinName>dimer, where <proteinName> is protein tetR or protein tetR-lva. For deGFP, the reactions are <proteinName> -> <proteinName>* |
| | 12) Setup the reactions associated with the utr | Ribosome bindiing to RNA (R7) In the case of the RBS, the reactions are <rnaName> + Ribo <-> |

TABLE 5-continued

The processing carried out by the main user level functions of the toolbox

| Function Name | Description of processing | Additional details (note the R# refers to reaction number in the List of Biochemical Reactions section above |
|---|---|---|
| | 13) Setup the reactions associated with the promoter (ie, transcription, and TF mediated regulation) | [Ribo:<rnaName>], where <RNAName> is a string like RNA rbs--tetR-lva<br>1) DNA binding to RNAP70 (R2)<br>2) Transcription reactions (via the function txtl_transcription) (R3-R6)<br>3) Promoter regulation reactions (R17) |
| | 14) setup the reactions associated with translation | RNA-Ribosome complex binding to AA and AGTP (R8)<br>Translation consumption reaction (R9)<br>Protein production reaction (R10) |
| | 15) Setup reactions associated with DNA degradation, if linear DNA is present.<br>16) Setup reactions associated with mrna degradation (The RNase degrades RNA (in its many bound forms) via the simple enzymatic reaction).<br>17) If a degradation tag on the gene and ClpX protein in the model object are both present, setup protein degradation reactions | DNA degradation by RecBCD using the simple enzymatic reaction mechanism (R14)<br>RNA and its bound forms binding to RNase (R12)<br>The RNase bound complexes degrading the RNA (R13)<br><br>Reactions R20:<br>Tagged protein binding to ClpX<br>Degradation reaction<br>ClpX degradation reaction |
| txtl_runsim | 1) Check if any proteins exist in the species list which are not encoded by DNA, and add the relevant reactions and species associated with those proteins. | Since the txtl_addspecies or addspecies functions can be used to add proteins, and these fucntions do not call the proteins file txtl_protein_<proteinName>, (as txtl_add_dna would), we need to compare the list of species to the list of DNA's, and if any proteins exist which do not have corresponding DNA< we need to call that protein's file in setup reaction mode to set up all associated reactions. |
| | 2) run txtl_add_dna for each DNA in Setup Reactions mode. The information on the DNA needed to populate the input arguments of txtl_add_dna can be found in the DNAinfo field in the UserData of the model object.<br>3) If this is the first call of txtl_runsim (this information can be found in the FirstRun field of the UserData of the Model Object), then set up AGTP degradation reactions, along with an event which sets the AGTP degradation rate from 0 to nonzero at 150-180 minutes.<br>4) If this is a second or later run of runsim, append data from previous simulations to data arrays which will have the current simulation data appended to them.<br>5) Run the simulation and return the data as outputs. If this is a second or later run, append the data to the previous data, and return the total data. | |

Example 25: In Silico Portion of Biomolecular Breadboard: Detailed Lower-Level Description of the Toolbox and Setup of Species and Reactions Driver Mode Structure Most of the functions in the toolbox (such as txtl_add_dna, and most of the functions it calls) have a Setup Species and a Setup Reactions mode. First, all of these files are called in the Setup Species mode, then called in the Setup Reactions mode. The reason is that in some cases, certain reactions that are conditioned upon the exact version of the species present in the model need to be set up.

For example, setting up reactions for the pTet promoter requires knowledge of the exact version of the tetR dimer present in the system, since the tetR dimer must bind with the pTet promoter, but this dimer may exist in the lva tagged or non lva tagged form. Thus, at the time of the setting up of the reaction of the pTet promoter binding to the tetR dimer, the tetR dimer species must have been specified in the model. The only failsafe way of doing this turns out to be to use the above mentioned separate setup species and setup reactions modes, with setup species mode preceding the setup reactions mode.

Example 26: In Silico Portion of Biomolecular Breadboard: Detailed Lower-Level Description of the Toolbox and Directory Structure of the Toolbox The directory structure of the toolbox is provided in Table 6. The top level directory is called trunk, and all the directories shown in Table 6 are subdirectories of trunk.

TABLE 6

List of subdirectories of trunk, their respective purpose, and examples of files present in them.

| Directory in trunk | Purpose | Example of functions or files in the directory |
|---|---|---|
| core | Contains the core functions of the toolbox. | txtl_extract.m<br>txtl_buffer.m<br>txtl_add_dna.m<br>txtl_combine.m<br>txtl_runsim.m<br>txtl_plot.m<br>txtl_addspecies.m<br>txtl_addreaction.m<br>txtl_dna_degradation.m<br>txtl_dimerize.m<br>txtl_component_config.m<br>txtl_newtube.m<br>txtl protein degradation.m<br>txtl_mrna_degradation.m<br>txtl_reaction_config.m<br>txtl_transcription.m<br>txtl_translation.m<br>txtl_utr_rbs.m<br>etc . . . |
| components | The code (.m) files and the configuration (.csv) files associated with promoters and proteins. The promoter code files are named txtl_prom_<PROMOTER>.m. the untranslated region code files are named txtl_utr_<RBS>.m while the protein code files are named txtl_protein_<GENE>.m. The parameter config files are named | txtl_prom_p70.m<br>txtl_prom_ptet.m<br>txtl_prom_pBAD.m<br>txtl_protein_deGFP.m<br>txtl_protein_tetR.m<br>txtl_protein_ClpX.m<br>txtl_protein_lacI.m<br>txtl_param_lacI.csv<br>txtl_param_ptet.csv<br>txtl_param_plac.csv<br>txtl_param_deGFP.csv<br>txtl_utr_rbs.m<br>txtl_utr_rbs1.m<br>txtl_utr_rbs2.m |

TABLE 6-continued

List of subdirectories of trunk, their respective purpose, and examples of files present in them.

| Directory in trunk | Purpose | Example of functions or files in the directory |
|---|---|---|
| | txtl_param_<NAME>.csv, where <NAME> is either the promoter name (represented by <PROMOTER> above) or the protein name (represented by <GENE> above.) So far we have not incorporated separate config files for rbs's, but forsee this as a feature to include as RBS parameter data becoms available. | etc . . . |
| examples | Example scripts in the toolbox which show how it can be used. | geneexpr.m<br>Constitutive production of GFP negautoreg.m<br>The negative autoregulation circuit<br>etc . . . |
| auxiliary | Various support functions that get called by other functions | findStringInAList.m<br>parseGetEqOutput.m<br>plotCustomSpecies2.m<br>etc . . . |
| config | The config files to set up the core parameters and concentrations in txtl_extract, txtl_buffer, when setting up transcription, translation, various degradation reactions and various resource binding reactions. | E6_config.cav<br>E30_config.csv<br>E30VNPRL_config.csv<br>etc . . . |
| doc | documentation | usermanual.pdf |

Example 27: In Silico Portion of Biomolecular Breadboard: Detailed Lower-Level Description of the Toolbox, Parts Generated in Silico FIG. 50 shows five characterization experiments carried out to generate training data. FIGS. 51A-D provide the top level codes and the corresponding species and reactions in the model objects created by the toolbox for these five experiments. A list of estimated parameters is also provided, together with parameters from previous characterization that were used as inputs to the experiments 2-5. The parameter estimation methodology will be described in detail in the next section, with reference to FIGS. 52 and 53.

To train the model, the TX-TL data collected from these 5 Experiments was used, as described in FIG. 50. These TX-TL experiments were conducted in the same extract as the final circuits are built in, and are used to test basic properties to allow for the building of circuits using these properties in different compositions in silico.

Figure 51A:
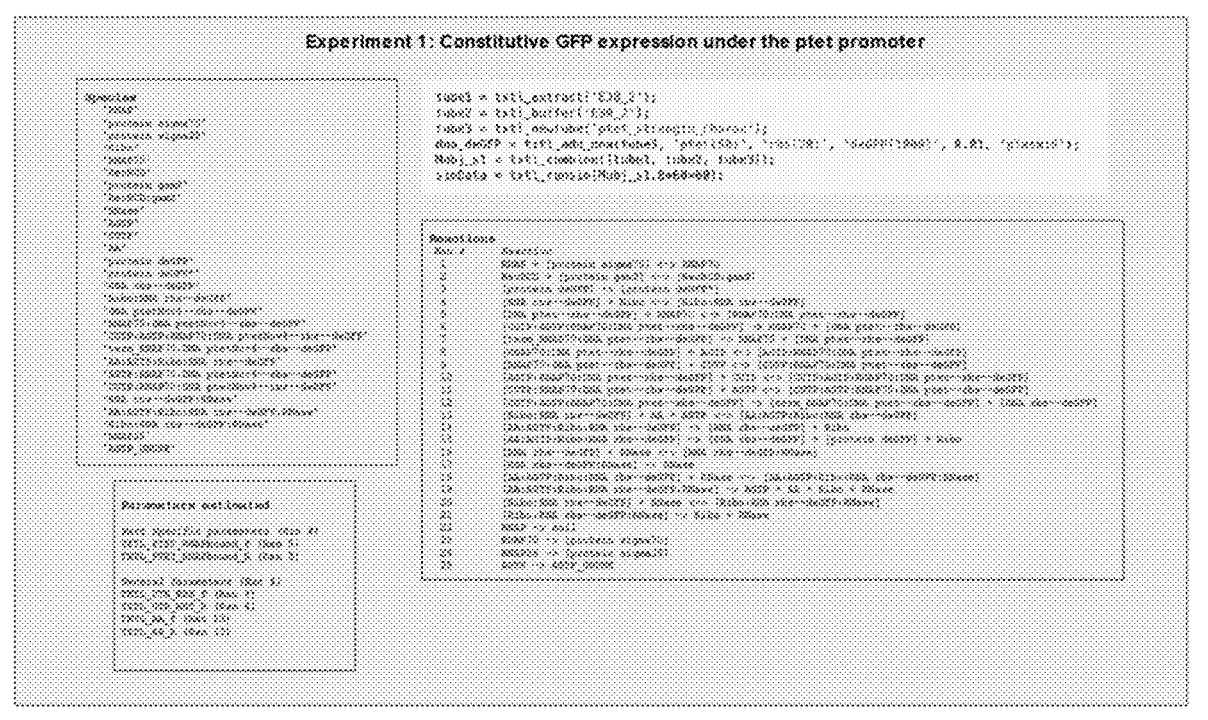
Figure 51B:
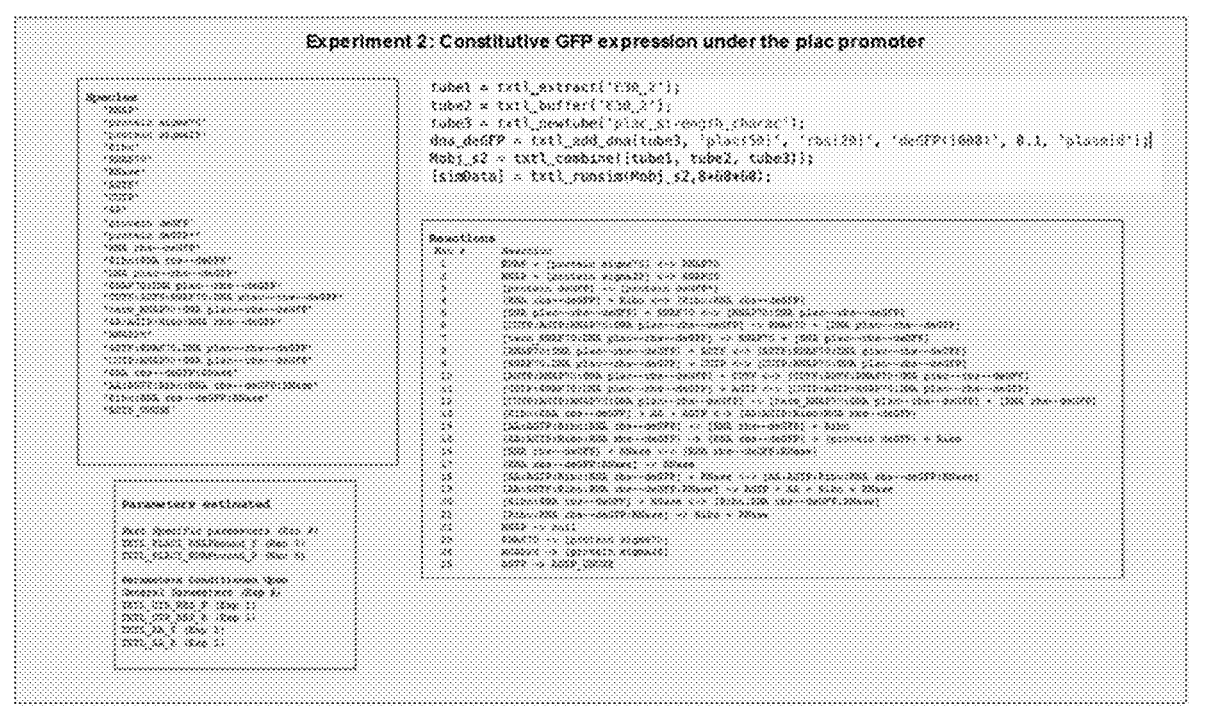

FIG. 51A shows model setup and parameters estimated for Experiment 1 of FIG. 50. FIG. 51B shows model setup and parameters estimation for Experiment 2 of FIG. 50. The parameter estimation carried out for this part used parameters estimated in the parameter estimation for Experiment 1. In particular, the Ribosome binding and amino acid binding parameters were also estimated in that experiment, and thus used here as fixed, i.e., the estimation of the parameters in this experiment was conditioned upon those values.

Figure 51C:
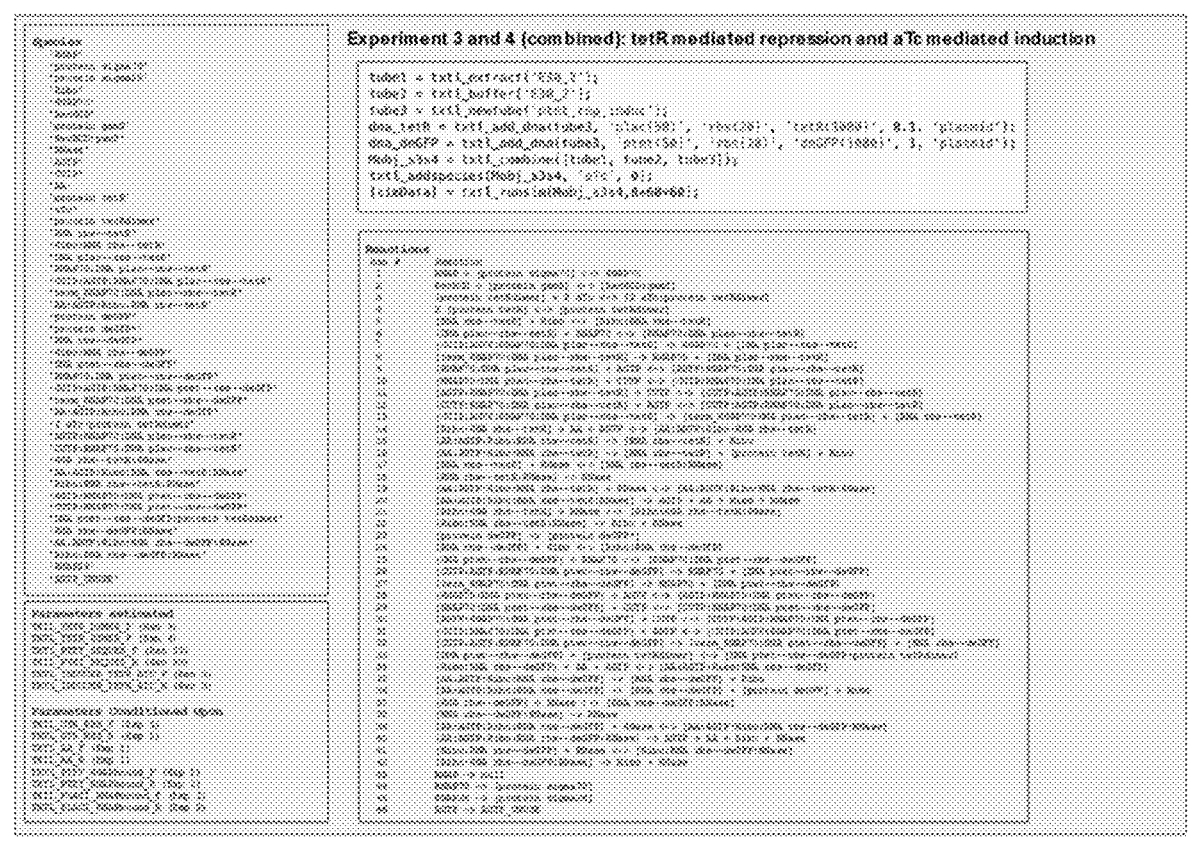

FIG. 51C shows details of the model used for simulating tetR repression and aTc induction. The parameter estimation for Experiment 3 and 4 of FIG. 50 was carried out simultaneously because these experiments are closely related.

Figure 51D:
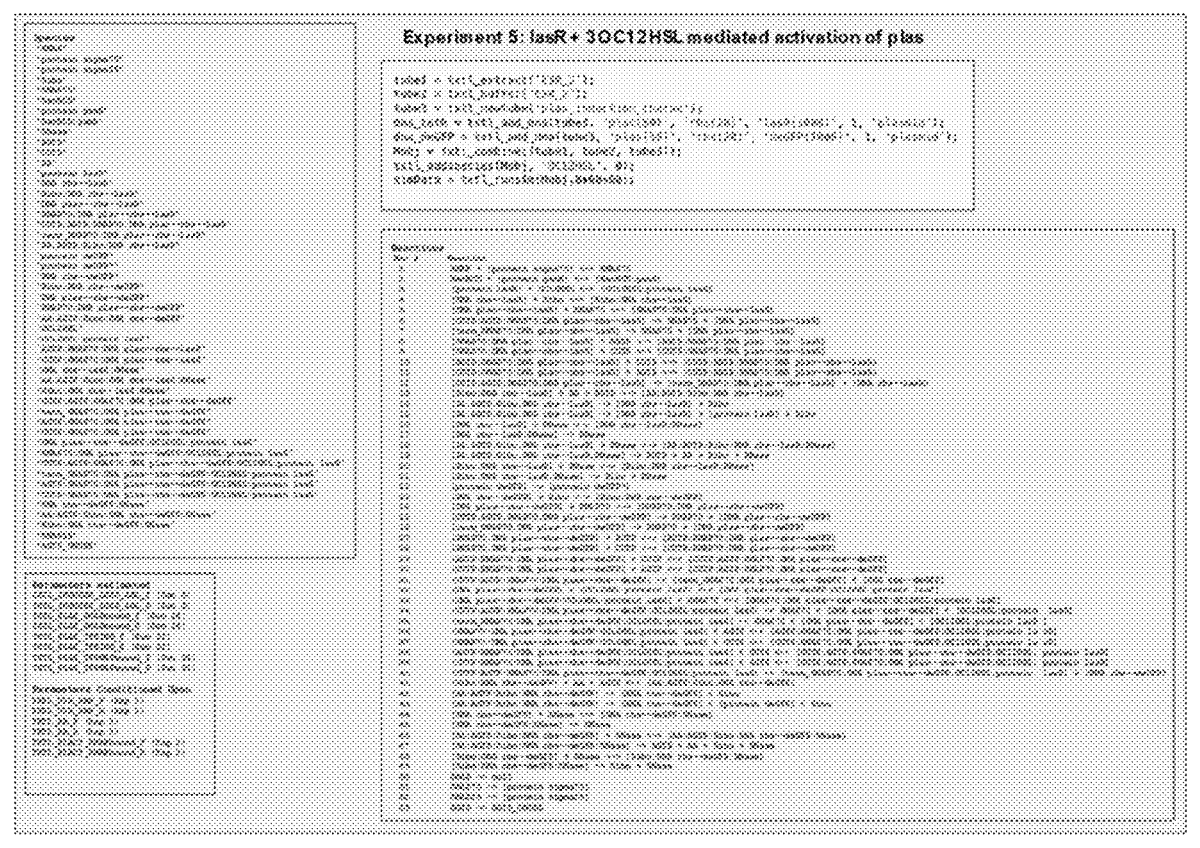

FIG. 51D shows the lasR activation system model and parameters estimation, corresponding to Experiment 5 of FIG. 50.

Example 28: In Silico Portion of Biomolecular Breadboard: (Step 3) Characterization of Each Part Followed by Incorporation into a Library Parameter estimation algorithms were used to fit the part models to experimental data. Many deterministic or stochastic algorithms can be used as will be understood by a person skilled in the art.

In this example, the parameter estimation method takes as inputs: (1) Experimental data to fit models to; (2) Models capable of generating simulation data to fit to the experimental data; (3) A list of parameters in the models that are to be estimated in the process of fitting; (4) Initial values of the parameters. While these can be randomly generated, often parameter estimation algorithms perform better with judicious choice of these initial values. Thus, a preprocessing step is carried out where initial guesses of parameters are made by fitting data to models by hand. This involves changing parameter values, and looking at how the species concentration versus time curves change, and iterating until the behavior of the model resembles the data to some degree. This way, the chances of converging to local minima is increased (of the cost function, in parameter space) are increased, which has a greater chance of leading to good fits between model and data; (5) Since each model is fit to an experiment where some reagent or species initial concentration was varied, a dosing strategy needs to be specified, so the parameter estimation method can carry out the equivalent variation in silico while carrying out the parameter estimation. This is called the Dosing strategy, and can be specified in, for example, SimBiology's parameter estimation methodology; (6) Simulation Options can be specified, like error tolerances, which solver or estimation method to use, etc. These are quite dependent on the estimation method being used, and often need to be iterated upon.

The output from this step provides a list of estimated parameters and various statistical measures of the associated errors/confidence in the parameter estimates.

These outputs can be used to populate the parameter configuration files for the corresponding parts, and these parts can then be added to a library of characterized parts. This library is the components directory in the trunk directory, as shows in Table 6. It consists of the part code files (.m files for MATLAB), and the parameter configuration files (.csv files containing parameters for each part). This general methodology is described in FIG. 52.

FIG. 52 shows the overall parameter estimation procedure. The parameters were firstly fit by inspection and manual adjustment to get close to local optima. Then, parameter estimation algorithms were used. This parameter estimation strategy was applied to the models shown in FIGS. 51A-D, which also shows the parameters that were estimated for each model, and when parameters for a given estimation were used as inputs and held fixed for the next estimation (i.e, the next estimation was conditioned upon the previous ones).

Figure 53:
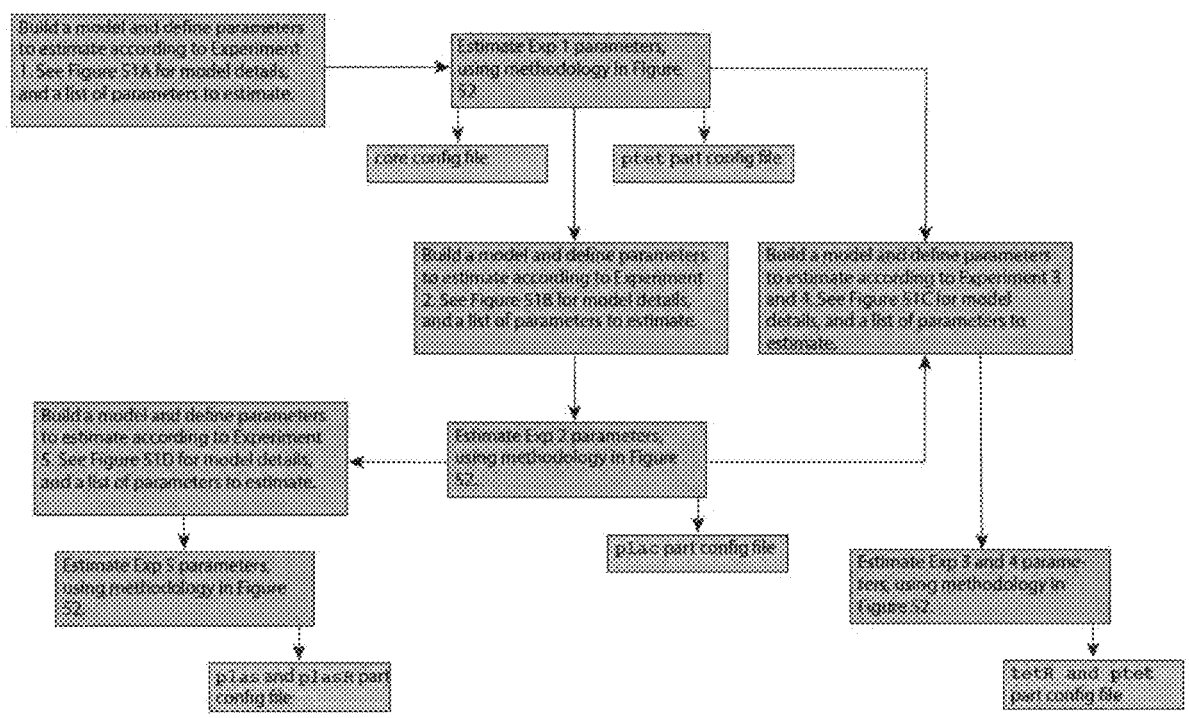
FIG. 53 provides a flowchart that illustrates the part characterization procedure in one embodiment.
Figure 54B:
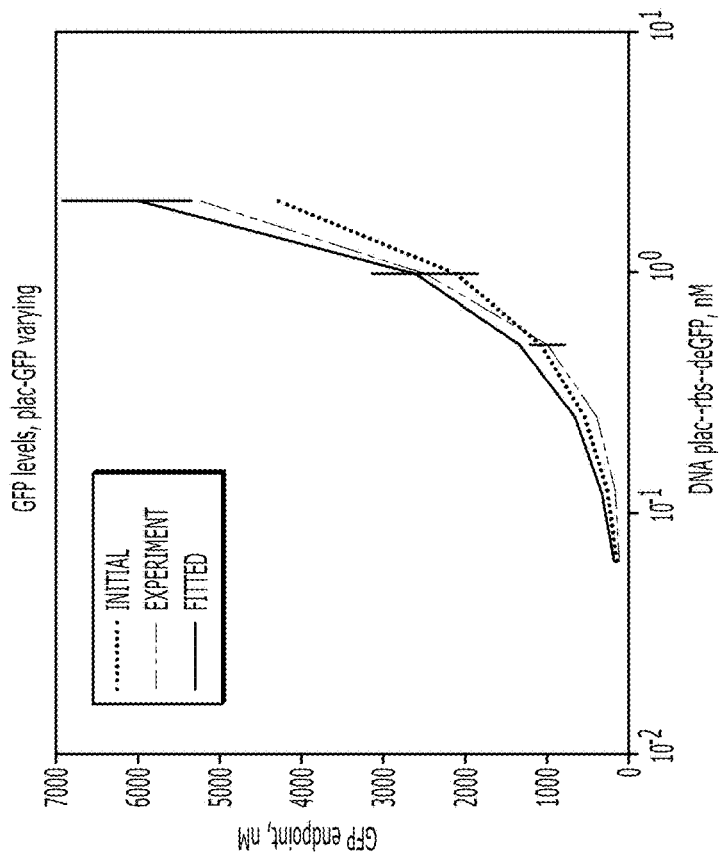
FIGS. 54A-E show the results of the part characterization procedure by estimating parameters to fit the experimental data from Experiments 1 to 5 in FIG. 50 to the models in FIGS. 51A-D. The Y axis in each figure is the end point concentration of GFP for that experiment, while the X axis is the concentration of the species being varied. There are three lines in the plots: The mean and standard deviation from the experimental data is given by the lighter solid line with error bars. The dotted line is the simulation result after the preprocessing stage of the parameter estimation, as described in FIG. 52. The dark solid line is the result of the full parameter estimation, as described in FIG. 52.
Figure 54A:
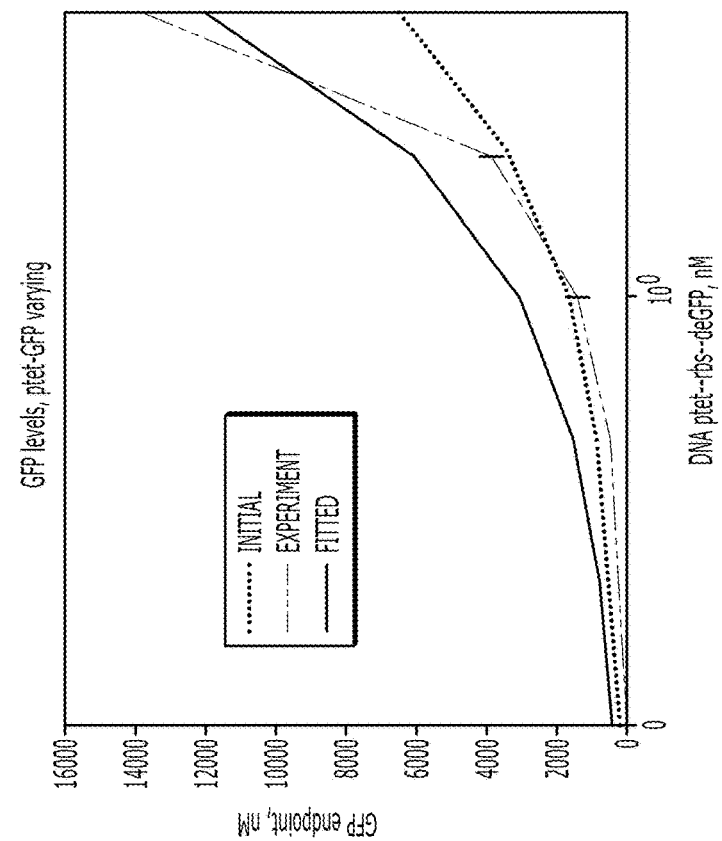
Figures 54C, 54D:
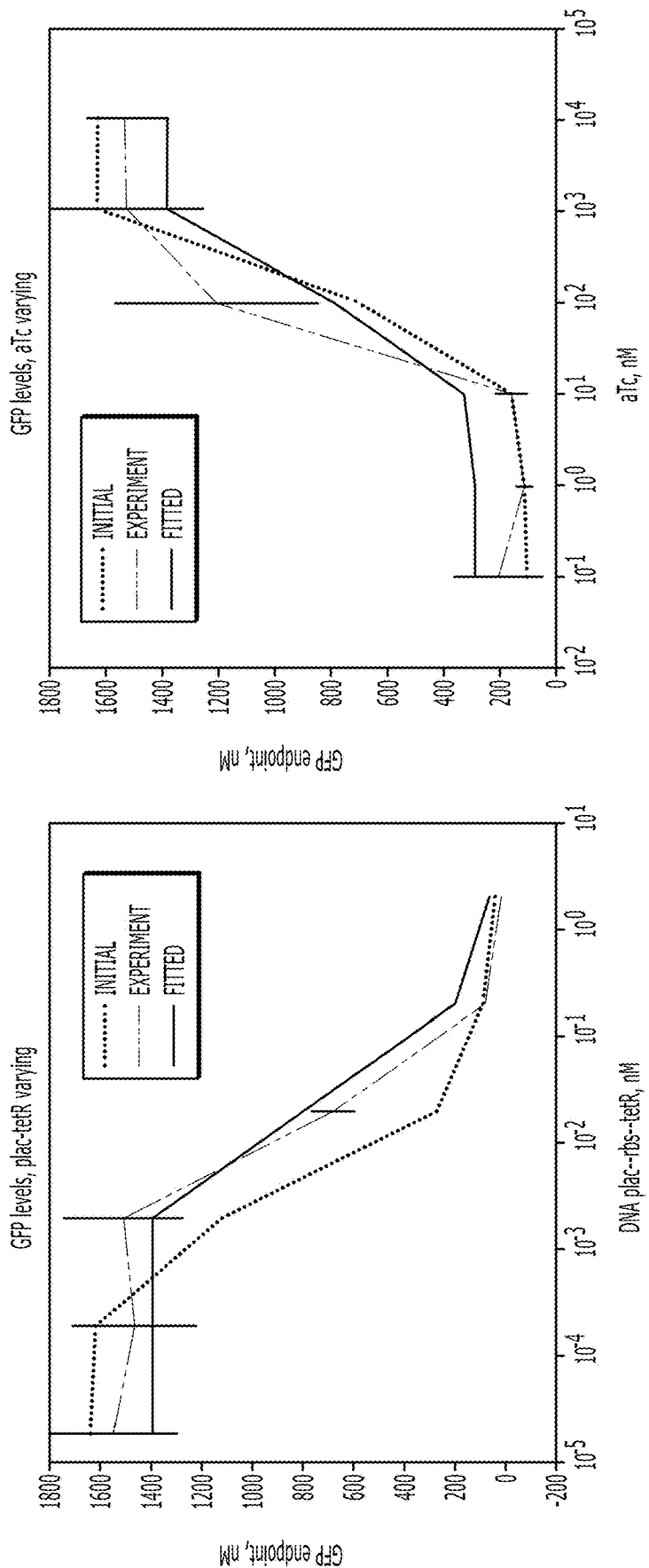
Figure 54E:
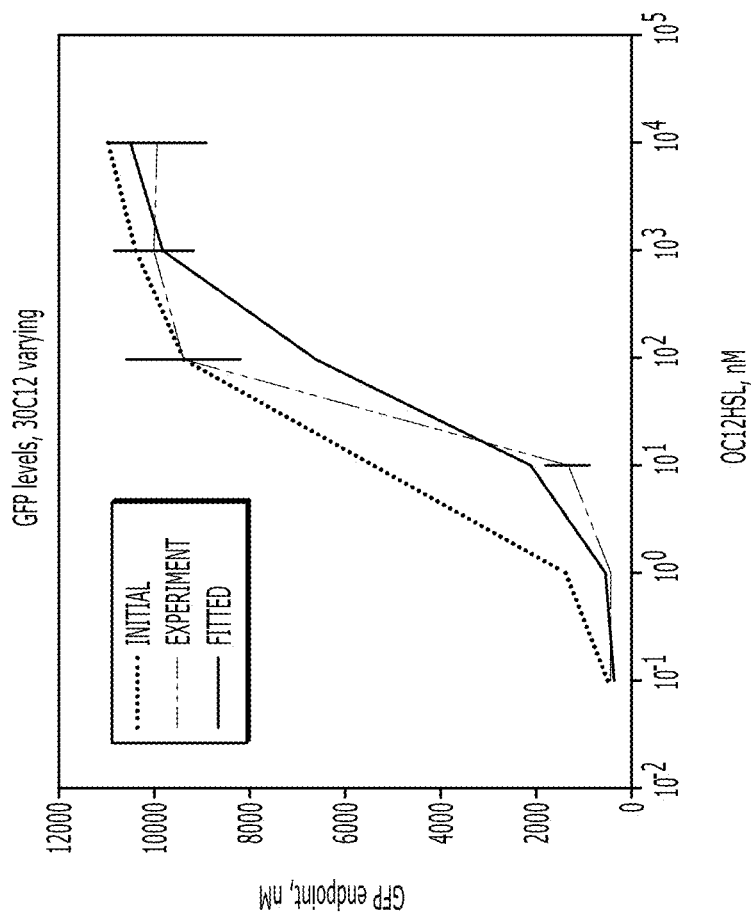

FIG. 53 shows the part characterization procedure, and how the parameters estimated for Experiment 1 are used fixed for the estimation of other parameters for the remaining parts. In this way, whenever parameters are common between parts, they have the same values.

The results of fitting the models to the in vitro data are shown in FIGS. 54A-E. This information is generated by running the code shown in FIG. 51, according to the methodology specified in FIGS. 52 and 53 to populate the part and core configuration files with the values of the parameters specified in FIGS. 51A-D. Simulation data is generated at two points in FIG. 52: Once after the preprocessing stage (when the answer to the first diamond stating "Do simulations Match Data" is Yes) and then again if the answer to the second diamond is 'Yes'. This data corresponds to the 'initial' and 'fitted' lines in FIGS. 54A-E (dotted and dark solid lines respectively). Once the data is generated using the code, the corresponding data from the in vitro experiments is imported into MATLAB, and arranged in appropriate numeric arrays. The end points of the simulation data and experimental in vitro data are then extracted, and the mean and standard deviation from the experimental data is computed in MATLAB, and plotted as the light solid line in each sub plot in FIGS. 54A-E.

In FIGS. 54A-E, the Y axis in each sub figure is the end point concentration of GFP for one of the experiments described in FIG. 50, while the X axis is the concentration of the species being varied. The subfigures correspond to the experiments as follows. Top left: varying pTet-GFP DNA, as per Experiment 1. Top right: varying the pLac-GFP DNA, as per Experiment 2. Middle left: Varying the tetR DNA, as per experiment 3. Middle right: Varying the aTc, as per experiment 4. Bottom: Varying the 3OC12HSL, as per experiment 5.

Example 29: In Silico Portion of Biomolecular Breadboard: (Step 4) Composition of the Parts into a Full Circuit Followed by Simulation of the Circuit Under Various Experimental Conditions The composition of parts into the full IFFL circuit requires building the IFFL from the characterized parts from the components directory. It is noted that in this implementation, along with informing the config files for ptet (txtl_param_ptet.csv), plac (txtl_param_plac.csv), tetR (txtl_param_tetR), lasR (txtl_param_lasR) and plas (txtl_param_lasR), the ptet and plas parameters were also used to inform parameters for the combinatorial promoter used in component C of the IFFL (Component C in FIG. 41). The IFFL toolbox code is given below in FIG. 55.

FIG. 44 compares the in vitro results from FIGS. 43A-F with the in silico modeling data (dotted lines) generated from the methods described above.

Example 30: In Silico Portion of Biomolecular Breadboard: (Step 6) Debugging and Part Modification When the simulation results do not match the experimental data, the model can be modified, the parts can be refitted, or more data can be collected under different experimental conditions.

One example of data collection under different experimental conditions is the direct measurement of tetR repression strength by purifying tetR protein and adding it to a tube containing a reporter under the control of the ptet promoter.

Other examples of better characterization data include: (1) To tag all the RNAs with aptamer sequences to be able to measure RNA directly, and to thus obtain more accurate parameter estimates. (2) To collect plas-lasR-3OC12HSL system data in more parts, like with and without 3OC12HSL or varying lasR amounts. (3) To test the plastetO combinatorial promoter, instead of using the plas and ptet parameters for the combinatorial promoter.

Different model adjustment can be made depending on the desired model accuracy and intended use. Other parameter estimation algorithms such as simulated annealing, genetic algorithms, and MCMC methods can also be used in case a large number of local minima is expected.

Step 6 of the workflow in FIG. 45 can return to any previous stage of the procedure and the steps can then be repeated.

Example 31: Biomolecular Breadboard Sensitivity Analysis: Sensitivity to aTc

The biomolecular breadboard was also used to conduct a sensitivity analysis of adjustable parameters in the circuit. In this example, in silico testing can be conducted in parallel and overlayed with in vitro results.

The results of the sensitivity analysis were complied with ClpXP degradation to predict the amount of tetR, aTc, lasR, and deGFP-ssrA DNA necessary to induce pulsatile behavior, assuming maximal lasR activation with saturating 3OC12HSL.

ClpXP degradation in TX-TL can be understood by adding in fluorescently tagged -ssrA versions and non -ssrA versions of deGFP into a cell-free system and observing degradation over time from different starting concentrations of deGFP. From FIGS. 56A-B one can see that degradation is a steady state initially, but decreases as ClpXP degradation potential is exhausted.

Figure 15:
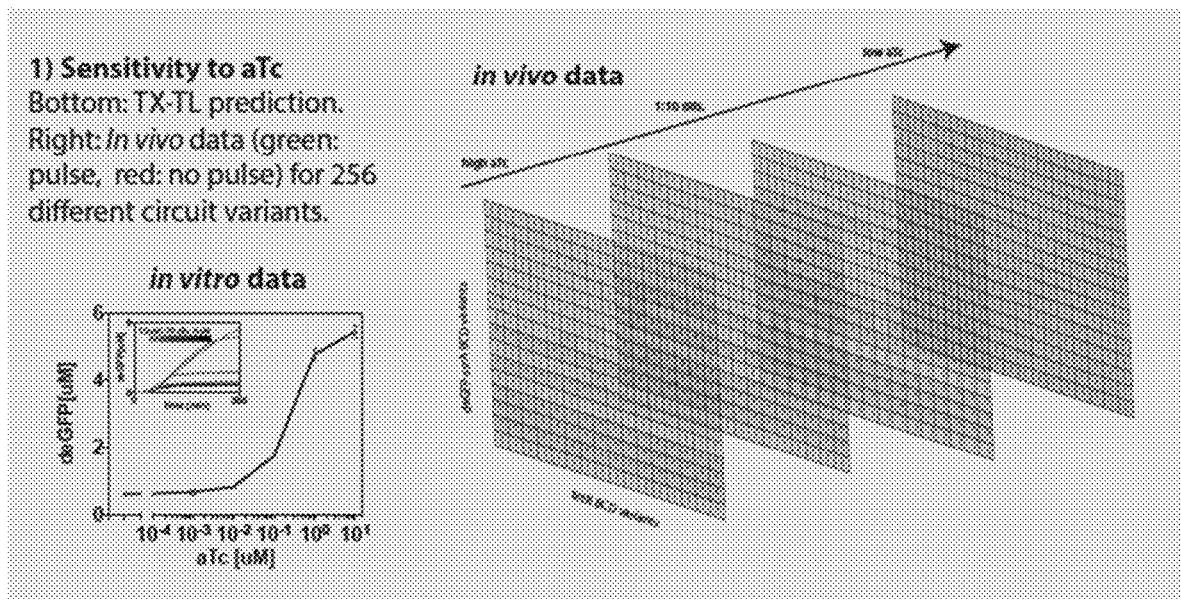
FIG. 15 shows, in one embodiment, aTc variation in vitro (left) and in vivo (right). The in vitro plot shows the deGFP expression (y-axis) as a function of aTc amount (x-axis). The in vivo plots show 16×16 GFP grid data with varying aTc amounts (from left to right: 1000 ng/mL, 100 ng/mL, 10 ng/mL, and 0 ng/mL). Dark gray shows no pulse and light gray shows a pulse.

As shown in FIG. 15, too much aTc or too little tetR expression results in an open loop system, while the opposite results in circuit shutdown before deGFP-ssrA production rate is able to overcome ClpXP degradation rate. It was then proceeded to verify the findings of the biomolecular breadboard in vivo. FIG. 15 shows aTc variation in vitro (left) and in vivo (right). The in vitro plot on the left shows the deGFP expression (y-axis) as a function of aTC amount (x-axis). The in vivo plots on the right show GFP signal data corresponding to the previously described 16×16 grids with varying aTc amounts (from left to right: 1000 ng/mL, 100 ng/mL, 10 ng/mL, and 0 ng/mL). Dark gray shows a pulse and light gray shows no pulse.

In particular, the in vivo data was based on the quantitative data values shown in FIG. 12B, but converted to a quantitative representation: 0 or 1. Value 0 means that no pulse is generated (dark gray) while value 1 means that a pulse is generated (light gray).

It is noted that as the amount of aTc decreases, the amount of signal also decreases in vivo. The same trend can also be observed in FIGS. 12A-B.

Example 32: Biomolecular Breadboard Sensitivity Analysis: Sensitivity to lasR

In the process of running the biomolecular breadboard, the user may see an unexpected result such as that the top level gain does not change the end performance of the circuit. While the change in lasR is focused in this example, this can be generalized to any unexpected result. This unexpected result is collected in the in vitro environment and can be verified with in silico modeling.

In this example, the in vivo data was collected by running the same procedure in those previous examples with the following exceptions.

For the high gain and the low gain versions, two plasmids were made to substitute for 360 (Plac_BCD22_lasR_T500) (SEQ ID NO: 1). These plasmids for the high gain were 373: Plac_BCD2_lasR_T500 (SEQ ID NO: 31), and 374: Plac_BCD22_lasR_T500 (SEQ ID NO: 32). Sequences of plasmid 373 and 374 are listed in FIG. 20A and FIG. 20B, respectively.

By varying the RBS on these plasmids, the strains using plasmid 373 should produce significantly more lasR than strains using plasmid 360 that produces the normal amount of lasR and strains using plasmid 374 that produces significantly less lasR. Here, the term "gain" refers to the amount of lasR that is driving the top node of the circuit. The unexpected finding from in vitro is that above a certain amount of lasR, the output response of the circuit remains the same, i.e. at high lasR the circuit's output is invariant to lasR concentration.

A set of 64 strains were then made, with the combinations of 8 RBS variants for a deGFP-ssrA plasmid and the same 8 RBS variants for a tetR plasmid (UTR1/BCD7/BCD13/BCD14/BCD16/BCD22/B0031/B0033). Thus, in addition to the 256 strains combining 360, 16 RBS variants deGFP-ssrA and 16 RBS variants tetR previously described, there are 64 strains of 373×8 RBS deGFP-ssrA×8 RBS tetR and 64 strains of 374×8 RBS deGFP-ssrA×8 RBS tetR.

The experiments were conducted in the same way as previously described for the in vivo translational experiment. BCD2 is presumed to have a strength of 15-50 units, BCD20 having 2.5-20 units, and BDC22 having 1 unit based on a previous publication by Mutalik et al. [48]

Figure 16:
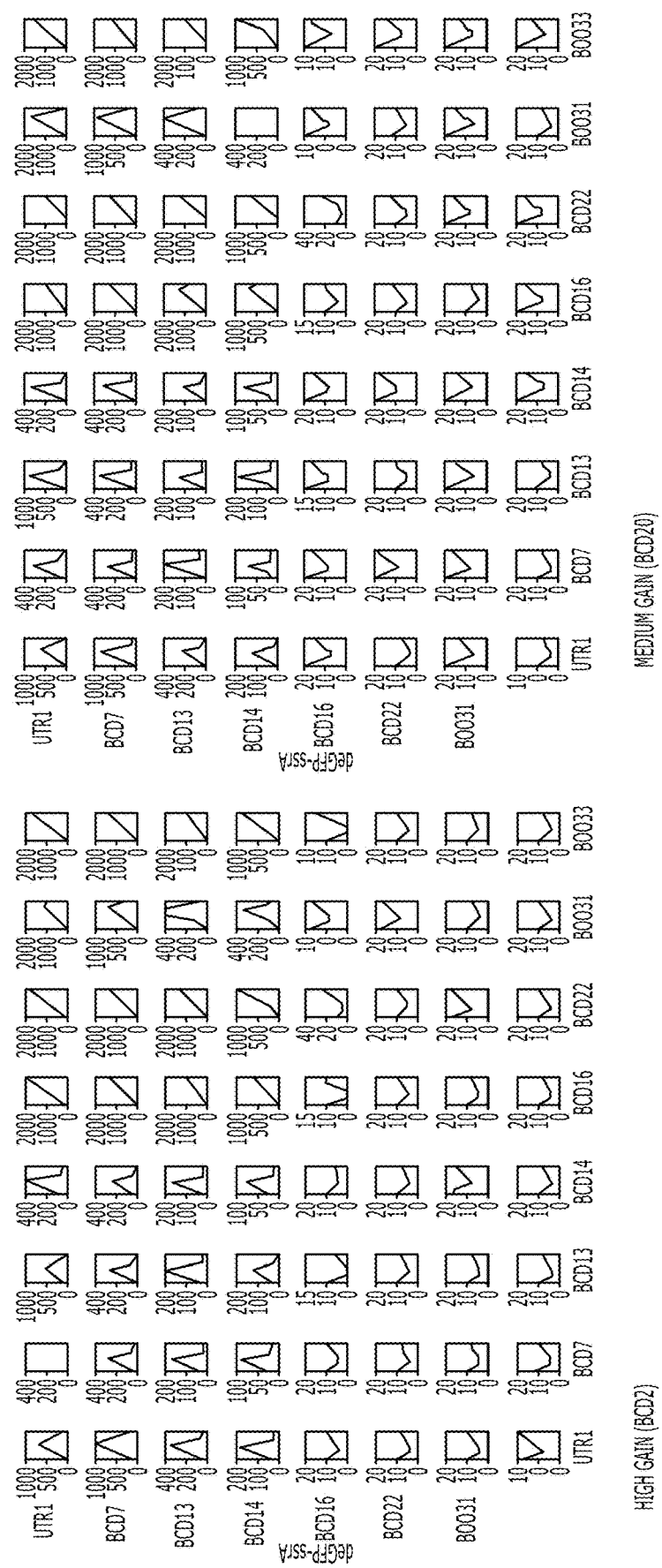
FIG. 16 shows, in one embodiment, the effect of lasR variation in vitro (bottom left) and in vivo (right). Left, shows endpoint deGFP expression (y-axis) in the context of a FFL with changing lasR DNA concentration (x-axis); the insert in the figure shows deGFP signal (x-axis) with time (y-axis) for different amounts of lasR DNA concentration. The right side shows in vivo results from three sets of strains—one with a high-expressing RBS expressing lasR (BCD2, left), one with a medium-expressing RBS expressing lasR (BCD20, right), and one with a low-expressing RBS expressing lasR (BCD22, bottom). In each subfigure of the strain, the RBS for deGFP-ssrA expressing plasmid is given by row, the RBS for tetR expressing plasmid by column, and each subfigure shows time (x-axis) and signal in GFP/OD (rfu) (y-axis).

FIG. 16 shows unexpected result in biomolecular breadboard—that the circuit is relatively invariant to lasR concentration—and verification through in vivo data. Shown in the left is cell-free data collected by varying lasR concentration in the context of the 3-node feed-forward loop. Shown in the right is the in vivo data collected, where the top plasmid—pLac-BCDX-lasR—is varied in BCD strength from panel to panel. In each panel, each row corresponds to a BCD for deGFP plasmid, and each column corresponds to a BCD for tetR plasmid.

FIG. 16 demonstrates that the unexpected results observed in vitro are verifiable when compared to in vivo. When the corresponding gain is changed in vivo using a high strength, medium strength, or low strength RBS for lasR production, the same trend in expression can be seen—namely, high and medium gain produce the same pulse output, while low gain does not produce signal. This indicates that the in vitro results correlate to the in vivo result, indicating that an increase in the top-node strength affects the output pulse. Such correlation can be predicted by in silico modeling and the in vitro experiments.

Example 33: Cell-Free Characterization of Genetic Ring Oscillators: DNA and Strain Construction Examples 33-40 are related to rapid cell-free forward engineering of genetic ring oscillators. These examples demonstrate that cell-free systems can be used to characterize and engineer complex dynamics behaviors of genetic networks by implementing and characterizing 3-node, 4-node and 5-node negative feedback architectures in vitro.

DNA was constructed using either Golden Gate Assembly or Isothermal Assembly. For linear DNA, all DNA was constructed using previously published Rapid Assembly protocols on a "v1-1" vector [49]. Linear DNA constructs are summarized in FIG. 21A. The original repressilator plasmid, pZS1 [3] was used as a template for initial characterization and for construction of the $O_R2^*$ mutant. Transfer function plasmids were constructed by Transcriptic, Inc.

For other plasmids, partial sequences were either obtained from Addgene or synthesized on gBlocks or ssDNA annealed oligonucleotides (Integrated DNA Technologies). Specific plasmids required secondary-structure free segments, which were designed by R2oDNA [50]. JS006 [51] was co-transformed with origin-of-replication compatible plasmids to create engineered strains. Specifically, negative-feedback oscillator units were cloned onto pSC101* low copy plasmids (ampR or kanR), while reporters were cloned onto colE1 medium copy plasmids (kanR or cmR) (FIGS. 21B-D). To modulate the reporter copy number, all experiments were conducted below 37° C. [52]. Strain passage was minimized to avoid plasmid deletions due to the recA+ nature of JS006 and the high complexity of oscillator plasmids or triple-reporter plasmid. Based on the in vitro and in silico results, strong transcriptional and translational [1] units were used to maximize gain.

Example 34: Cell-Free Characterization of Genetic Ring Oscillators: In Vitro Experiments and Analysis

TX-TL Reactions

Preparation of TX-TL was conducted as described previously [15], but using strain "JS006" co-transformed with Rosetta2 plasmid and performing a 1:2:1 extract:DNA:buffer ratio. This resulted in extract "eZS4" with: 8.7 mg/mL protein, 10.5 mM Mg-glutamate, 100 mM K-glutamate, 0.25 mM DTT, 0.75 mM each amino acid except leucine, 0.63 mM leucine, 50 mM HEPES, 1.5 mM ATP and GTP, 0.9 mM CTP and UTP, 0.2 mg/mL tRNA, 0.26 mM CoA, 0.33 mM NAD, 0.75 mM cAMP, 0.068 mM folinic acid, 1 mM spermidine, 30 mM 3-PGA, 2% PEG-8000. For experiments utilizing linear DNA GamS was added to a final concentration of 3.5 µM [49].

Steady-State Reactions

Experiments were performed in a microfluidic nano-reactor device as described previously [15, 27] with some modifications to optimize the conditions for the lysate-based TX-TL mix. Reaction temperature was 33° C. Lysate was diluted to 2× of the final concentration in 5 mM HEPES 5 mM NaCl buffer (pH 7.2). The reaction buffer mix was combined with template DNA and brought to a final concentration of 2×. For a 24 h experiment 30 µl of these stocks were prepared. During the experiment, lysate and buffer/DNA solutions were kept in separate tubing feeding onto the chip, cooled to approximately 6° C., and combined on-chip. The experiments were run with dilution rates (µ) between approximately 2.8 and 0.5 h$^{-1}$, which corresponds to dilution times, $t_d=\ln(2)\,\mu^{-1}$, between 15 and 85 min. These were achieved with dilution steps exchanging between 7 and 25% of the reactor volume with time intervals of 7 to 10 min, which alternately added fresh lysate stock or fresh buffer/DNA solution into the reactors. Dilution rates were calibrated before each experiment. Initial conditions for the limit cycle analysis of the repressilator network were set by adding pre-synthesized repressor protein at the beginning of each experiment. For this, CI repressor (together with Citrine reporter) and TetR repressor (together with Cerulean reporter) were expressed for 2.5 h in batch. On chip the initial reaction was mixed to be composed of 25% pre-synthesis reaction and 75% fresh TX-TL mix and repressilator template DNA. Then, the experiment was performed at a $t_d$ of 19.2±0.3 min. Initial conditions for the 4-node experiment were 2.5 µM aTc or 250 µM IPTG, and the experiment was performed at a $t_d$ of 44.5±0.9 min. DNA template concentrations used in steady-state reactions are listed in FIGS. 21E-F. Arbitrary fluorescence values were converted to absolute concentrations from a calibration using purified Citrine, Cerulean, and mCherry, which were prepared using previously published protocols utilizing a His6 purification method followed by size-exclusion chromatography and a Bradford assay to determine protein concentration[49].

Transfer Function Measurement

Figure 26A:
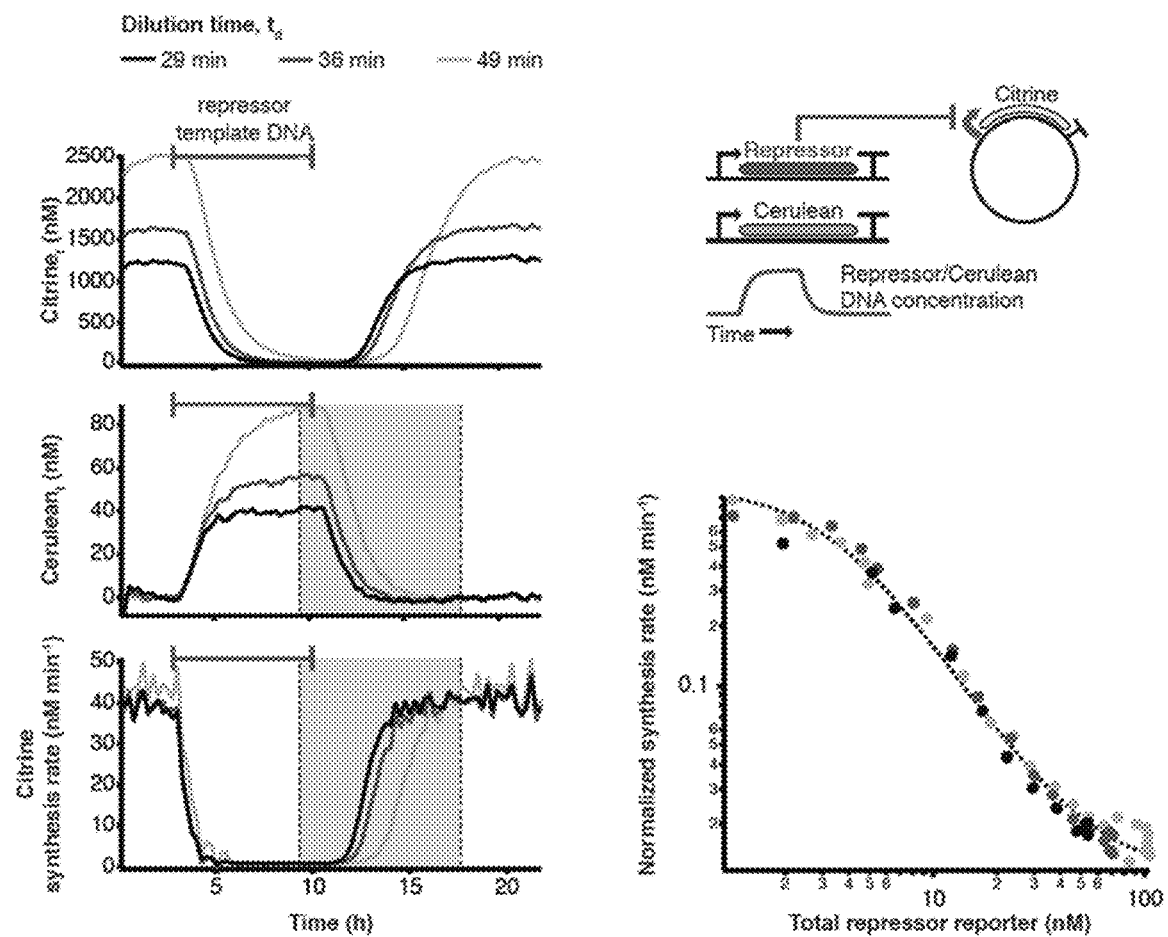
FIG. 26A shows in one embodiment the measurement of transfer functions of the repressor. Promoter pairs were determined using the cell-free framework. Shown are experimental results and analysis using LacI-pLacI(r) as an example. Transfer functions were obtained by plotting Citrine synthesis rates from highest to lowest repressor concentration (grey shaded area) against total Cerulean concentration and were identical for different dilution times set in the nano-reactor device.

Transfer functions of the repressor—promoter pairs were determined in the nano-reactor device at a minimum of two different dilution times (FIG. 26A). All tested promoters were cloned into a plasmid in front of a BCD7 ribosomal binding site and the Citrine open reading frame. A non-saturating concentration of 1 nM plasmid was used in the experiment. The repressors were expressed from linear templates carrying the J23151 promoter and the BCD7 ribosomal binding site with time-varying concentrations, which were increased from 0 to 2.5 nM and decreased back to 0 during the course of the experiment [27]. Simultaneously, Cerulean was expressed as a reporter for the repressor concentration from a linear template at an identical concentration as the repressor template. From the concentration of the Citrine reporter, the synthesis rate of the fluorescent protein over time were calculated using a model of steady state protein synthesis in the nano-reactor device[27], $$P_d(t+\Delta t)=P_d(t)+syn(t)\cdot\Delta t-mat\cdot P_d(t)\cdot\Delta t-dil\cdot P_d(t) \quad\text{(eq. 1)}$$

$$P_f(t+\Delta t)=P_f(t)+mat\cdot P_d(t)\cdot\Delta t-dil\cdot P_d(t) \quad\text{(eq. 2)}$$

where $P_d$ and $P_f$ are dark and fluorescent reporter concentration respectively, t is time, $\Delta t$ is the time interval between dilution steps, dil is the volume fraction replaced per dilution step, which was determined during the calibration of the device, and mat is maturation rate of the fluorescent protein. Maturation times of Citrine and Cerulean were determined as described previously [27] and were 15±4 min for Cerulean and 29±3 min for Citrine. Dark fluorescent protein was calculated from (eq. 2):

$$P_d(t) = \frac{P_f(t+\Delta t) - P_f(t) + dil\cdot P_f(t)}{mat\cdot \Delta t} \quad\text{(eq. 3)}$$

and the synthesis rate was calculated from equation (1):

$$syn(t)=P_d(t+\Delta t)-P_d(t)+mat\cdot P_d(t)\cdot\Delta t+dil\cdot P_d(t). \quad\text{(eq. 4)}$$

The sum of measured fluorescent Cerulean concentration and (eq. 3) for dark Cerulean was used as a measure of the total repressor protein present at any time during the experiment. The synthesis rates were normalized to their respective maximal values ($v_{max}$) and plotted against the concentration of the repressor reporter using only repressor concentrations higher than 1 nM. The transfer curves were then fit to a Hill function $$y = f(x) = y_{min} + (1 - y_{min})\frac{K_M^n}{K_M^n + x^n} \quad\text{(eq. 5)}$$

where y is the synthesis rate, $y_{min}$ in is the minimum synthesis rate, n is the Hill coefficient and $K_M$ is the Michaelis Menten constant for half maximal promoter activity. The fitting was performed in Igor Pro using orthogonal distance regression with ODRPACK95 assuming a 90/error in the measurements of Citrine and Cerulean fluorescence.

$V_{max}$ Measurements

Relative promoter strengths ($v_{max}$ values) were determined using the transfer function promoter plasmids. In vitro strengths were determined in 5 µl TX-TL reactions at a DNA template concentration of 1 nM. Reactions were assembled in 384-well plates, overlaid with 35 µl Chill-Out Liquid wax (BioRad) and analyzed using a Biotek SynergyMx plate reader set to 33° C. reaction temperature, and reading Citrine fluorescence with Exc: 510±9 nm and Em: 540±9 nm. For comparison, Citrine fluorescence at 6 h was normalized to the value of pLacI. In vivo strengths were determined using E. coli JS006 transformed with the same plasmids. Cells were grown at 29° C. in MOPS medium supplemented with 0.4% glycerol and 0.2% casaminoacids. For each strain, three independent overnight cultures were diluted 1:50 and grown to mid-log phase. They were then diluted to a starting $OD_{600}$ of 0.15 into 100 µl growth medium in a 96-well plate and grown in the plate reader at 29° C. with periodic shaking measuring Citrine fluorescence. Fluorescence values were normalized to OD resulting in steady state values after 2 h. Average steady state values were normalized to pLacI for comparison with the in vitro measurement.

Example 35: Cell-Free Characterization of Genetic Ring Oscillators: In Vivo Experiments and Analysis Mother machine [53] experiments were conducted with custom-made microfluidic chips (mold courtesy of M. Delincé and J. McKinney, EPFL). E. coli cells were trapped in channels of 30 µm length, 2 µm width and 1.2 µm height. Before loading onto the device, cells were grown from a frozen stock to stationery phase. Cells were then concentrated 10-fold and loaded onto the chip. Experiments were performed using LB medium supplemented with 0.075% Tween-20 at a flow rate of 400 µl/h. Oscillation traces were collected from single mother machine traps using the background subtracted average fluorescence intensity of the entire trap.

CellASIC experiments were conducted using B04A plates (Merck Millipore, Darmstadt Germany). Flow rates were varied between 0.25 psi-2 psi. Cells were grown from frozen stock in media at running temperature to stationery phase. Cells were then diluted 1:100 for 2 hours, and loaded on a equilibrated plate at 1:1000 or less to achieve single-cell loading efficiencies per chamber. To vary cellular doubling times, different growth media were used: LB (BD Biosciences), M9CA (Sigma Aldrich) with 0.2% glucose, 2xYT (MP Bio), MOPS EZ Rich (Teknova).

Cells were imaged in time series every 10-20 min using a 100x phase objective minimizing both lamp intensity (12% Xcite 120, Excelitas Inc. Waltam MA or 1-2% CoolLED pE-2, Custom interconnected Ltd., UK) and exposure times (<500 ms) to limit photo-toxicity.

Images were processed and stitched [54], if necessary, using Fiji/ImageJ [55]. Fluorescence traces of cell populations with synchronized oscillations were extracted from CellASIC movies using background corrected mean fluorescence intensity from the entire field of view. For cells that were not synchronized over the complete field of view, regions of oscillating sister cells at the edge of the microcolony were tracked. ImageJ was used to define polygonal regions around those cells and manually shifted the polygonal region to track the front of growing cells. Periods were determined from fluorescence traces derived from mother machine and CellASIC movies by measuring the time from one oscillation peak to the next peak. Doubling times were estimated by averaging over the doubling times of at least ten individual cells.

Example 36: Cell-Free Characterization of Genetic Ring Oscillators: The Model

An n-node negative cyclic feedback biocircuit is considered and the genes, mRNAs and proteins are denoted by $G_1$, $G_2, \ldots, G_n$, and $M_1, M_2, \ldots, M_n$ and $P_1, P_2, \ldots, P_n$, respectively. Let $r_i(t)$ and $p_i(t)$ denote the concentrations of mRNA $M_i$ and protein $P_i$, respectively. For example, the novel 3-node ring oscillator in FIG. 23B is defined by n=3, $r_1(t)$=[BetI mRNA], $r_2(t)$=[PhlF mRNA], $r_3(t)$=[SrpR mRNA], $p_1(t)$=[BetI protein], $p_2(t)$=[PhlF protein], $p_3(t)$=[SrpR protein].

Our mathematical model considers transcription, translation and degradation of mRNA and protein molecules as summarized in Table 7, where $a_i$ and $b_i$ represent the degradation rates of $M_i$ and $P_i$, respectively, and $c_i$ and $\beta_i$ are the translation and transcription rates. The constants $K_{i-1}$ and $v_i$ are the Michaelis-Menten constant and the Hill coefficient associated with the protein $P_{i-1}$ and the corresponding promoter on gene $G_i$. Hereafter subscripts 0 and n+1 were used as the substitutes of n and 1, respectively, to avoid notational clutter.

TABLE 7

Stoichiometry and reaction rates

| Description | Reaction | Reaction rate |
|---|---|---|
| Transcription of $M_i$ | $G_i + P_{i-1} \rightarrow G_i + P_{i-1} + M_i$ | $\beta_i \frac{K_{i-1}^{v_i}}{K_{i-1}^{v_i} + p_{i-1}^{v_i}}$ |
| Translation of $M_i$ | $M_i \rightarrow M_i + P_i$ | $c_i r_i$ |
| Degradation of $M_i$ | $M_i \rightarrow \varnothing$ | $a_i r_i$ |
| Degradation of $P_i$ | $P_i \rightarrow \varnothing$ | $b_i p_i$ |

Using the law of mass action and the quasi-steady state approximation, the dynamics of the mRNA and protein concentrations can be modeled by the following ordinary differential equations (ODE)

$$\dot{r}_i(t) = -(a_i + \mu)r_i(t) + \beta_i g \frac{K_{i-1}^{v_i}}{K_{i-1}^{v_i} + p_{i-1}^{v_i}(t)}, \quad (eq. 6)$$

$$\dot{p}_i(t) = -(b_i + \mu)p_i(t) + c_i r_i(t),$$

where i=1, 2, ..., n, and g is the concentration of the circuit plasmid. The constant µ is the dilution rate of mRNA and proteins by the microfluidic device. The dilution time of the microfluidic device is defined by $$T_d := \frac{\ln(2)}{\mu}. \quad (eq. 7)$$

Figure 25A:
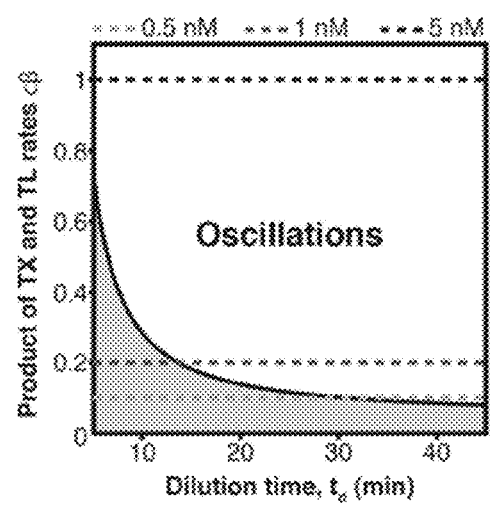
FIG. 25A shows in one embodiment oscillation parameter regime for a 3-node repressilator network in terms of dilution time and synthesis rates. Transcription (TX) and translation (TL) rates supporting oscillations at different dilution times for a 3-node repressilator network.
Figure 25B:
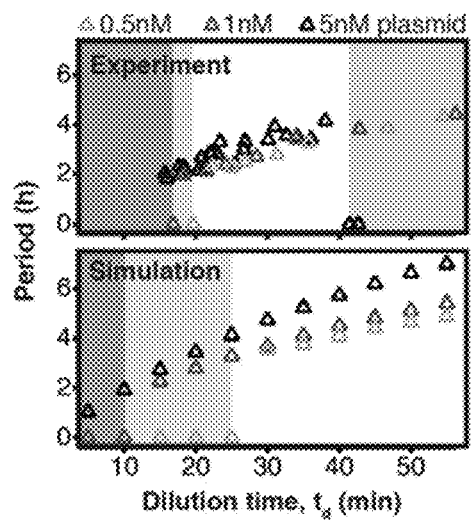
FIG. 25B shows the existence of oscillations and periods for a 3-node repressilator network in terms of dilution time.
Figure 25C:
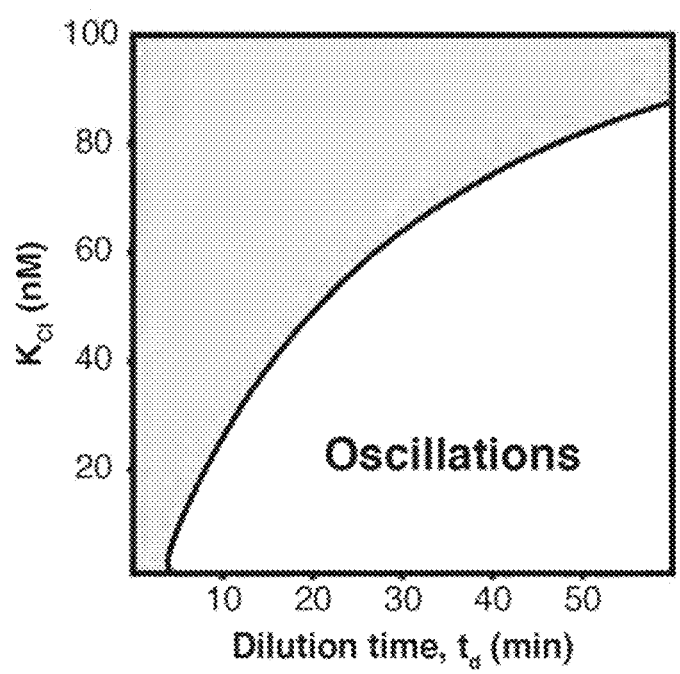
FIG. 25C shows the oscillation parameter regime for a 3-node repressilator network in terms of dilution time and repressor binding affinity.

The ODE model (eq. 6) was numerically simulated using ode45 solver of MATLAB R2013b to obtain qualitative insight into the period as well as the oscillatory parameter regime (FIGS. 25A-C). The parameters summarized in Table 8 were used for the simulations.

TABLE 8

Parameters used for simulations

| | Description | Parameter value |
|---|---|---|
| $a_i$ | Degradation rate of mRNAs (min$^{-1}$) | ln(2)/8 (half-life time: 8 minutes) |
| $b_i$ | Degradation rate of proteins (min$^{-1}$) | ln(2)/90 (half-life time: 90 minutes) |
| $\beta_i$ | Transctiption rate (nM · min$^{-1}$ · plasmid concentration$^{-1}$) | 0.4 |
| $c_i$ | Translation rate (nM · min$^{-1}$ · mRNA concentration$^{-1}$) | 0.5 |
| $K_i$ | Michaelis-Menten constant (nM) | 5.0 |
| $v_i$ | Hill-coefficient | 2.0 |

Figure 23E:
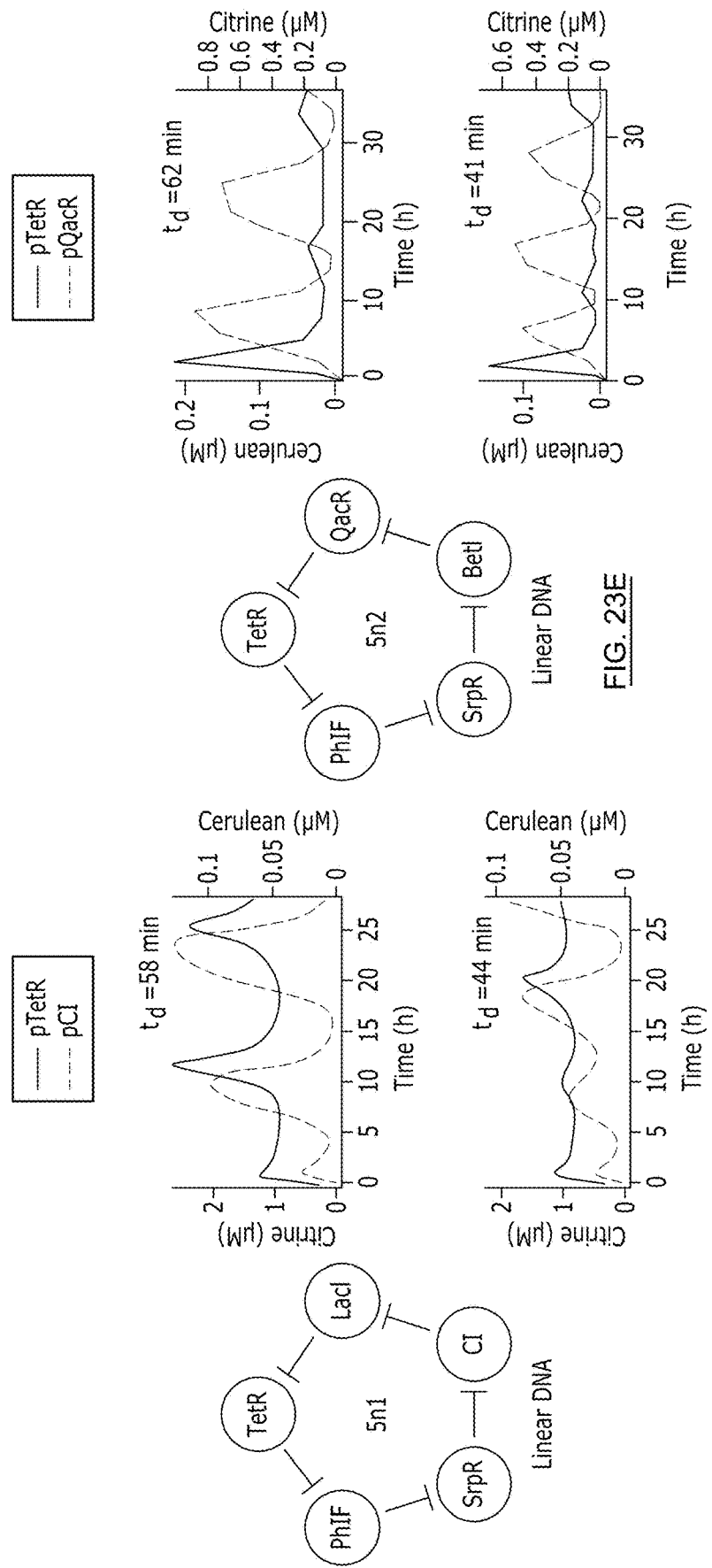
Figure 23F:
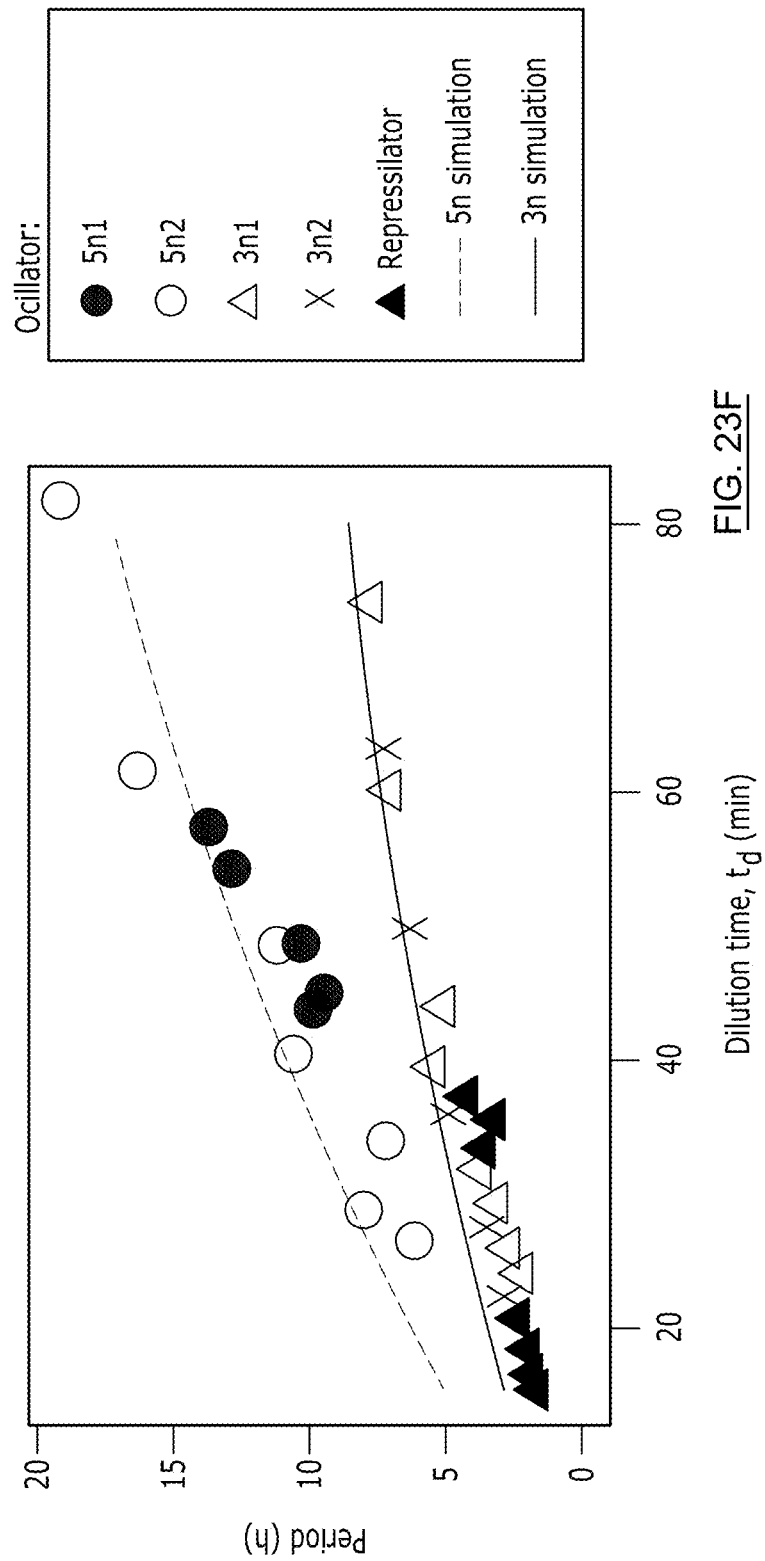

The plasmid concentration g was set as g=5.0 nM for FIG. 23F. The initial concentrations for the simulations were $r_1(0)=30$, $p_1(0)=0$ and $r_i(0)=p_i(0)=0$ for i=2, 3, . . . , n.

The period of oscillations was calculated based on the autocorrelation of the simulated protein concentration $p_1(t)$. More specifically, let $$R(\tau) := \int_{T_1}^{T_2} p_1(t+\tau)p_1(t)dt, \quad (eq.\ 8)$$

where $T_1$ is a positive constant such that $p_1(t)$ is steady state at $t=T_1$, and $T_2$ is a sufficiently large constant compared to the period of oscillations. The period of oscillations $T_{period}$ was determined by $T_{period}=\min_{\tau>0} \mathrm{argmax}_\tau R(\tau)$. The simulation result is also consistent with the analytic estimation of the oscillation period in Hori et al. [56] in that the period increases monotonically with the dilution time $T_d$.

The parameter region for oscillations (FIG. 25A) was obtained based on the analysis result (Theorem 3) by Hori et al.[57]. Since parameter values do not depend on the subscript i as shown in the parameters table above, the subscript i was removed and define $a:=a_1$ ($=a_2=\ldots a_n$). In the same way, b, c, $\beta$, K and v were defined.

It was shown that the protein concentrations $p_i$ (i=1, 2, . . . , n) oscillate if both of the following inequalities are satisfied [57, 58].

$$v > W(n, Q), \quad (eq.\ 9)$$

$$c\beta > \left(\frac{W(n,Q)}{v - W(n,Q)}\right)^{\frac{1}{v}} \left(\frac{v}{v - W(n,Q)}\right) K(a+d)(b+d), \quad (eq.\ 10)$$

where $$W(n, Q) := \frac{2\left(-\cos\left(\frac{\pi}{n}\right) + \sqrt{\cos^2\left(\frac{\pi}{n}\right) + Q^2\sin^2\left(\frac{\pi}{n}\right)}\right)}{Q^2 \sin^2\left(\frac{\pi}{n}\right)},$$

and $$Q := \frac{\sqrt{(a+d)(b+d)}}{(a+b+2d)/2}.$$

To obtain the parameter region in FIG. 25A, we substituted n=3 and the parameters shown in the table above into the right-hand side of the inequality condition (eq. 10), then $T_d(=\ln(2)/\mu)$ was varied between 5 to 80. The inequality (eq. 9) was always satisfied for these parameters.

The parameter region of FIG. 25C was obtained by the local stability analysis of the model (eq. 6). The previous theoretical result [57] showed that the model (eq. 6) has a unique equilibrium point and the protein concentrations $p_i$ (i=1, 2, . . . , n) show stable oscillations if the Jacobian matrix evaluated at the equilibrium point has an eigenvalue in the open right-half complex plane. Based on this result, the Jacobian eigenvalues was computed with varying $K_3$, which was denoted by $K_{cI}$, and $T_d$. The values in the parameters table above were used for the other parameters. The plasmid concentration was set as g=5.0 nM in the computation.

Example 37: Cell-Free Characterization of an Original Repressilator and its Mutant An existing repressilator [3] was chosen as a model circuit to test whether the cell-free system can be used to run and characterize the synthetic in vivo circuit. The original repressilator network was implemented in the cell-free system and long-term sustained oscillations with periods matching the in vivo study was observed (FIGS. 22A-D). The original repressilator was compared to a modified version containing a point mutation in one of the CI repressor binding sites in the promoter regulating Lac (FIG. 22A). This mutation increases the repressor concentration necessary for half-maximal repression (K), and reduces cooperativity [59]. At long dilution times ($t_d$) both circuits oscillated, but with shifted absolute reporter protein concentrations (FIG. 22B). At decreasing dilution times amplitudes decreased and periods became faster with a linear dependence on $t_d$. Faster dilution times, however, did not support oscillations for the modified network (FIG. 22B-C). Experimentally, the range of dilution times supporting oscillations can serve as a measure for robust oscillator function, which generally diminishes with decreasing synthesis rates or when binding of one repressor to its promoter is weakened as in the $O_R2^*$ mutant (FIGS. 25A-C). Initial conditions can influence the dynamic behavior of nonlinear systems but are difficult to control in cells. In order to explore the dynamics of the repressilator in response to different initial conditions, the starting concentrations of TetR and CI repressor were varied. For all conditions tested the system quickly approached limit cycle oscillations and was invariant to initial conditions (FIG. 22D). This analysis of the repressilator network in phase space provides an example for an experimental characterization that would be challenging or impossible to perform in a cellular environment.

Example 38: Engineering Novel Negative Feedback Circuits

Figure 26B:
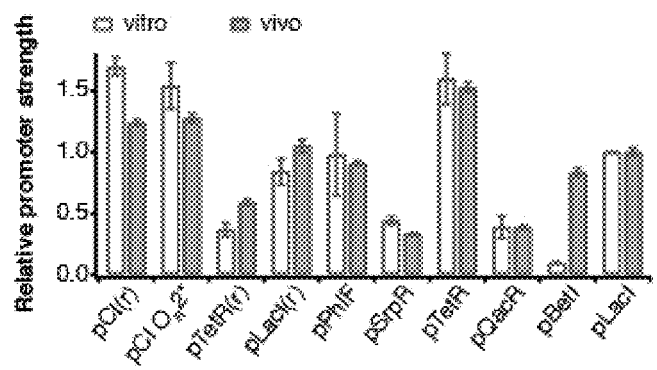
FIG. 26B shows in one embodiment comparison of relative promoter strengths in vitro and in vivo. Comparison of relative promoter strengths ($v_{max}$), determined in vitro and in vivo. pCI(r), pTetR(r), and pLacI(r) are from [3], pTetR is from [2] and pLacI from [4]. Error bars indicate standard deviations of three replicates.
Figure 26C:
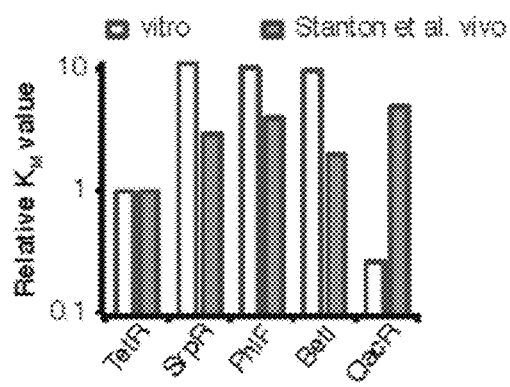
FIG. 26C shows in one embodiment comparison of half-maximal repressor concentrations needed for repression in vitro and in vivo. Comparison of $K_M$ values measured in vitro in this study with $K_M$ values determined in vivo by Stanton et al. [2]. $K_M$ values were normalized to the $K_M$ of TetR.

The cell-free system also allows rapid characterization of individual network components. The transfer functions of repressor-promoter pairs in the repressilator network were measured (FIG. 23A and FIGS. 26A-C) and it is found that the network is symmetric in terms of transfer functions. In the CI promoter $O_R2^*$ mutant, the expected shift in K value and decreased steepness of the transfer function were observed. TetR repressor homologs were also characterized as building blocks for novel negative feedback circuits (FIG. 23A) and with the exception of QacR observed similar transfer functions as observed in vivo [2] (FIG. 23 and FIGS. 26B-C).

Using three new repressors, BetI, PhlF and SrpR, a novel 3-node (3n) circuit, 3n1, was constructed and high-amplitude oscillations were observed over a broad range of dilution times with the same dependence of amplitude and period on $t_d$ as for the repressilator (FIG. 23B). In the characterization of the repressilator network and the 3n1 oscillator, dilution rates were found to be critical for the existence, period and amplitude of oscillations. Protein degradation is similar to dilution in that it results in removal of repressor proteins. In order to study the effect of degradation, a second 3n network (3n2) was constructed using TetR, PhlF and SrpR repressors on linear DNA. One version of the circuit used strong ssrA ClpXP degradation tags, while the second used untagged repressors. Oscillations were observed for both circuits (FIG. 23C). However, the circuit without ssrA-tag mediated protein degradation exhibited slower oscillations, which extended to lower dilution times, showing that protein degradation, just like dilution, affects oscillator function and period. Effects of ClpXP-mediated protein degradation, which have been shown to be important for existence and frequency of oscillations in vivo [60, 61], can thus be emulated in a cell-free environment. The repressilator (FIGS. 22A-D) and the novel 3n1 network (FIG. 23B) were characterized on plasmid DNA, reasoning that this is the closest approximation to the situation in a cell and because promoter strengths compare better when measured on a plasmid [44, 49]. However, for a more rapid analysis of novel networks and network variants it is advantageous if laborious cloning steps are not required to obtain initial results on circuit performance. Construction and comparison of two 3n2 network variants, which only required a few PCR reactions to synthesize the linear DNA templates, showed that it is possible to go from theoretical design of a circuit to first experimental results in a very short timeframe (FIG. 23C). Next, this concept was tested for novel and more complex network architectures.

Theory predicts that ring architectures built from an odd number of repressors oscillate, while even-numbered architectures have stable steady states [56, 62]. A 4-node circuit from LacI, TetR, PhlF and SrpR was experimentally built and tested on linear DNA. Initial pulses of LacI inducer IPTG or TetR inducer aTc allowed us to switch expression into either one of the two stable steady states (FIG. 23D). Stable steady states were reached after an initial adjustment phase of 5 to 10 h and remained stable until the experiment was terminated after 22 h. These results show that non-oscillating networks also function in the cell-free environment and that the oscillations observed for the 3-node networks are determined by network architecture and not established by particular reaction conditions in the microfluidic reactor.

Figure 24:
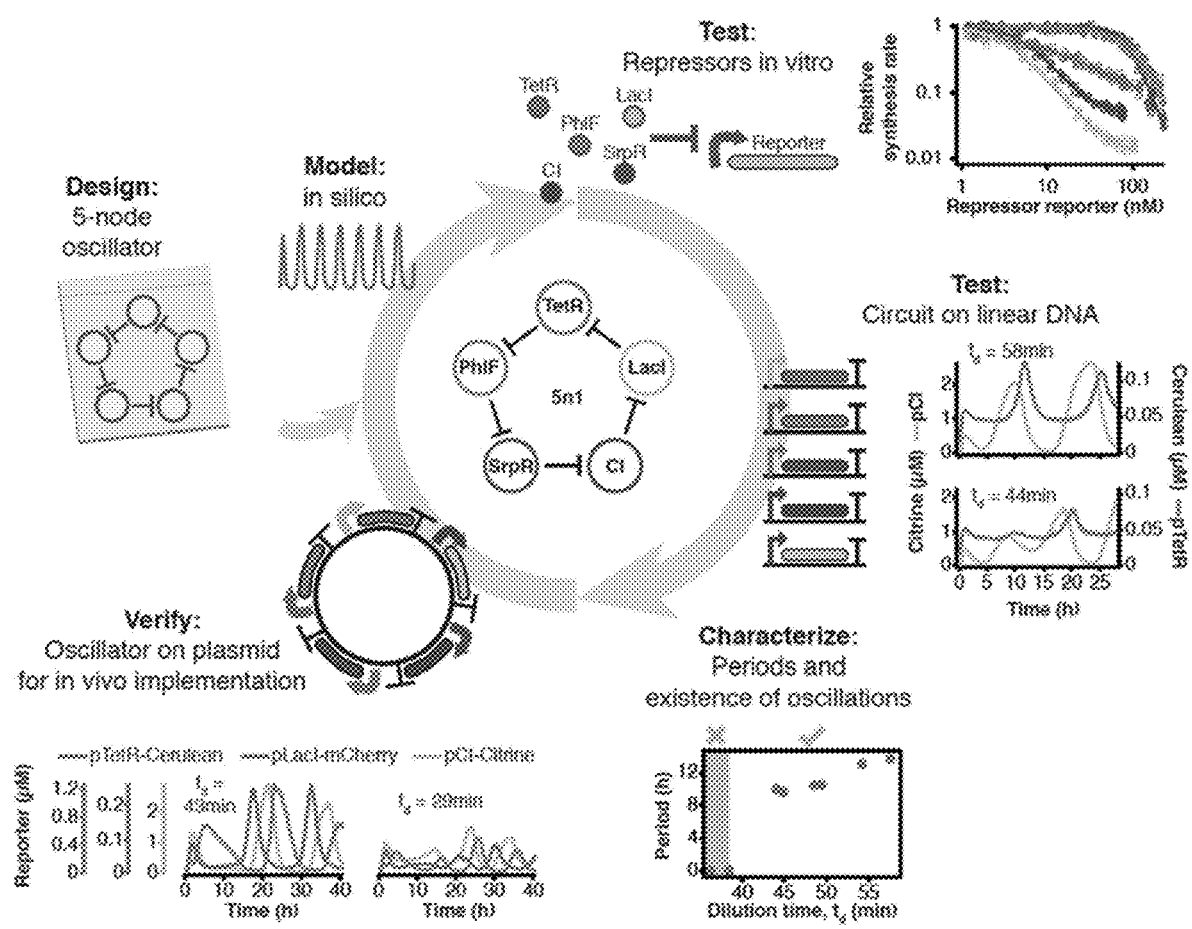
FIG. 24 shows an exemplary embodiment of engineering an exemplary 5-node negative feedback oscillator using the cell-free framework. A novel network architecture, which shows the intended behavior in silico is first assembled on linear DNA using in vitro characterized parts. Initial circuit testing on linear DNA is advantageous because: i) linear DNA can be synthesized in a few hours, ii) it allows rapid testing of multiple circuit variants, iii) and allows expression strengths of network components to be easily tuned by varying their relative concentrations. A functional circuit can then be further characterized to identify parameter ranges that support the desired behavior and to experimentally test hypotheses. If an in vivo implementation is intended, the cloned plasmids are verified for correct function in vitro before in vivo implementation.

Encouraged by the robust oscillations observed in the 3n networks and the expected behavior of the 4-node bistable switch, two 5-node ring networks (5n) was built to test our prototyping environment on another novel synthetic network architecture (FIG. 23E). These circuits are expected to oscillate, as they were built from an odd number of repressors. Despite their considerable complexity both circuits indeed oscillated over a broad range of dilution times. The period of the 5n networks (up to 19 h) was significantly longer than that of the 3n networks (up to 8 h). Comparing all ssrA-tagged 3n and 5n ring architectures, it is shown that the observed periods could be accurately predicted for all four networks by computational simulations (FIG. 23F). The cell-free system allows characterization of complex networks from rapid testing on linear DNA to verifying networks cloned onto a single plasmid, which is the closest approximation to cellular implementation (FIG. 6 and FIG. 24).

Figure 27A:
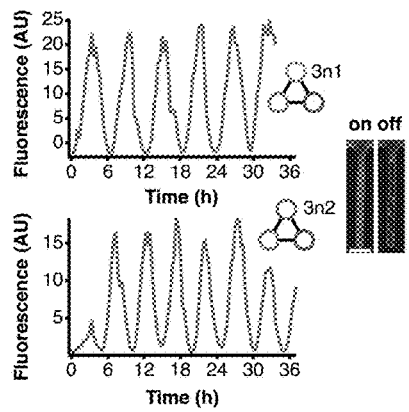
FIGS. 27A-E show in one embodiment novel 3-node and 5-node ring oscillators in cells.
Figure 28A:
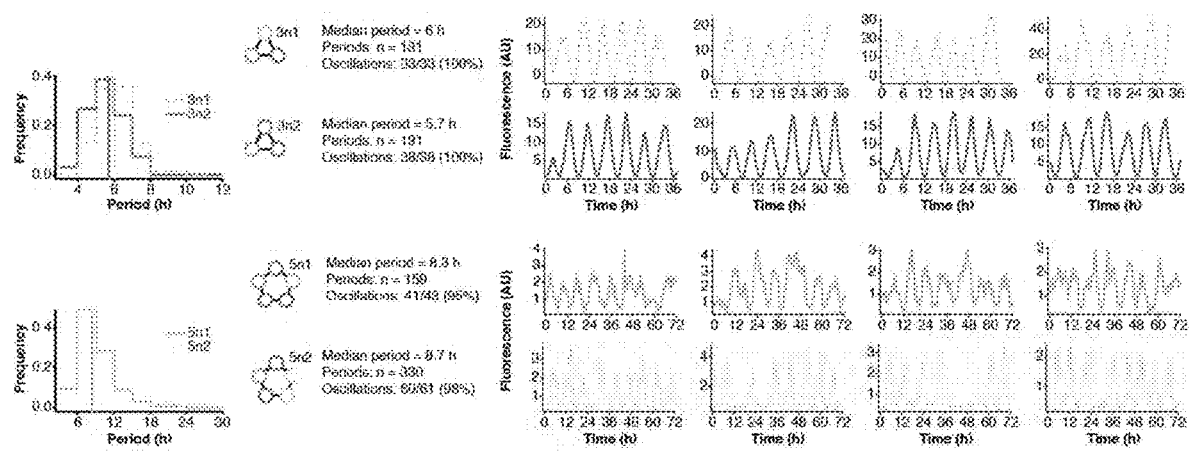
FIG. 28A shows in one embodiment robust oscillations of 3-node and 5-node oscillators in vivo. 3-node (top) and 5-node networks (bottom) oscillate with periods that depend on the network size in vivo. Shown are the distributions of observed period lengths with medians indicated by dashed lines. Both 3-node and 5-node networks exhibited robust oscillation with all growing cells oscillating for the 3-node networks and more than 95% of growing cells oscillating for the 5-node networks (defined as at least two distinct oscillation peaks per trace). Both 3-node networks were analyzed using a strong pPhlF sfGFP-ssrA reporter and the two 5-node networks were analyzed using a weak pPhlF sfGFP-ssrA reporter.

Example 39: Transfer of Cell-Free Prototyped 3- and 5-Node Oscillators to E. coli To validate our cell-free approach, the 3n1 and 3n2 networks were cloned onto low-copy plasmids and co-transformed each with a medium-copy reporter plasmid into lacI-JS006 E. coli [51]. When tested on a microfluidic device (mother machine[53]), both 3n oscillators showed regular oscillations with periods of 6±1 h for at least 30 h (FIG. 27A). Both oscillators were surprisingly robust as all cells undergoing healthy cellular division oscillated (n=71) (FIG. 28A).

Figure 27B:
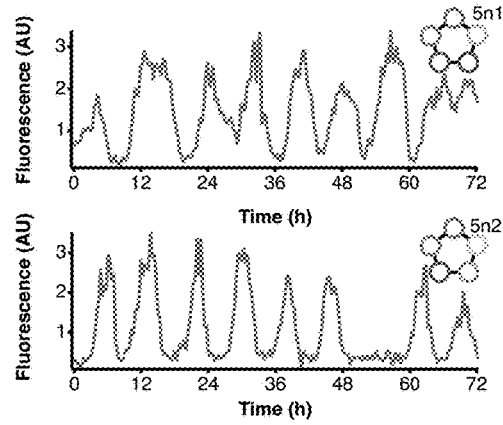

The 5n oscillators were also tested in vivo. Like the 3n networks, both 5n oscillators were cloned onto low-copy number plasmids to transfer the two networks initially prototyped on linear DNA (FIG. 23E) into E. coli. FIG. 24 shows the complete cell-free prototyping cycle for the 5n1 oscillator from design by testing on linear DNA to validation of the final cloned oscillator plasmid. In E. coli, 5n1 was not viable when co-transformed with a high expression-strength reporter, but was viable with a low expression-strength reporter. Specifically, 5n1 with a high expression-strength reporter caused slow growth rates and high cell death rates when run on the mother machine—it is hypothesized that this is due to loading effects from high protein production, as decreasing the reporter expression strength resolved cell viability issues [63]. When tested with a low expression-strength reporter both 5n oscillators showed robust oscillations in E. coli that were maintained for at least 70 h, and over 95% of all analyzed traps containing healthy cells oscillated (n=104). In addition, both 5n networks oscillated with similar periods: 8 h for 5n1, and 9 h for 5n2 (FIG. 27B and FIG. 28A).

Figure 27C:
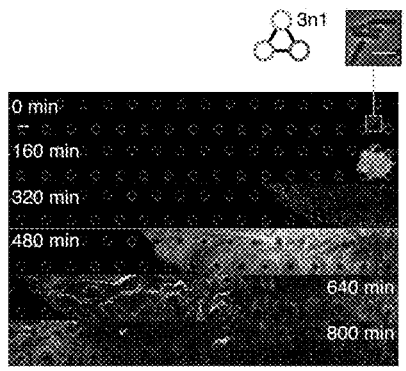
Figure 28B:
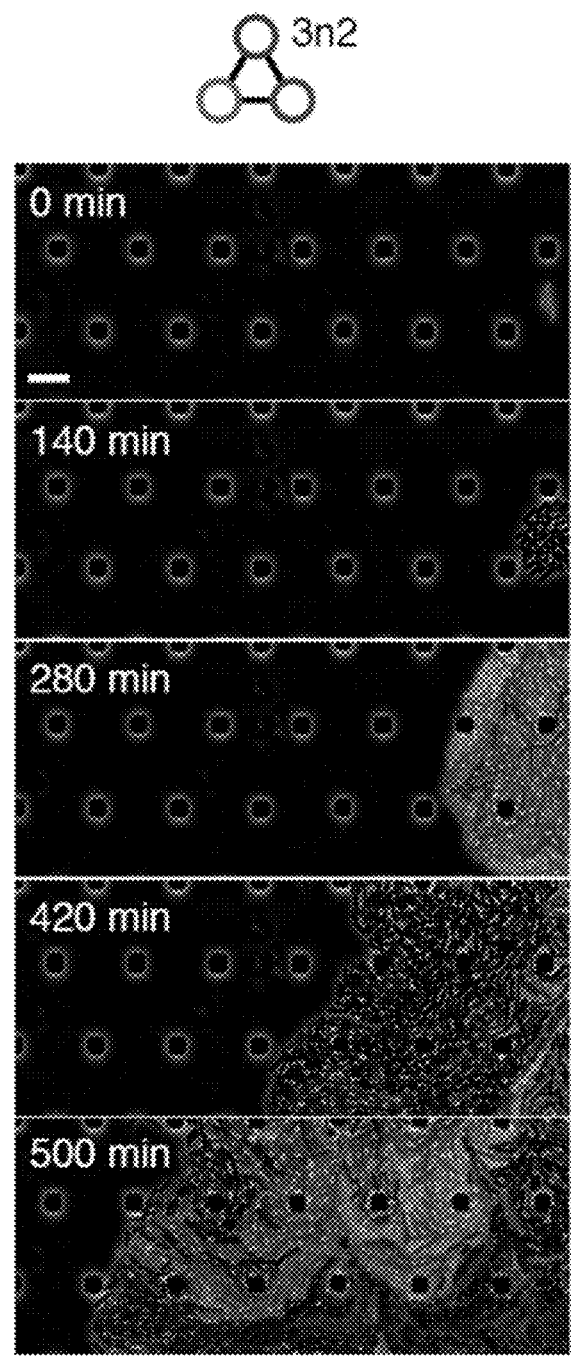
FIG. 28B shows in one embodiment population-level oscillations of 3n2 oscillator in vivo. 3n2 oscillator displays phase synchrony in vivo. 3n2 is run under a strong pPhlF sfGFP-ssrA reporter in the CellASIC microfluidic device. Scale bar: 10 μm.
Figure 28C:
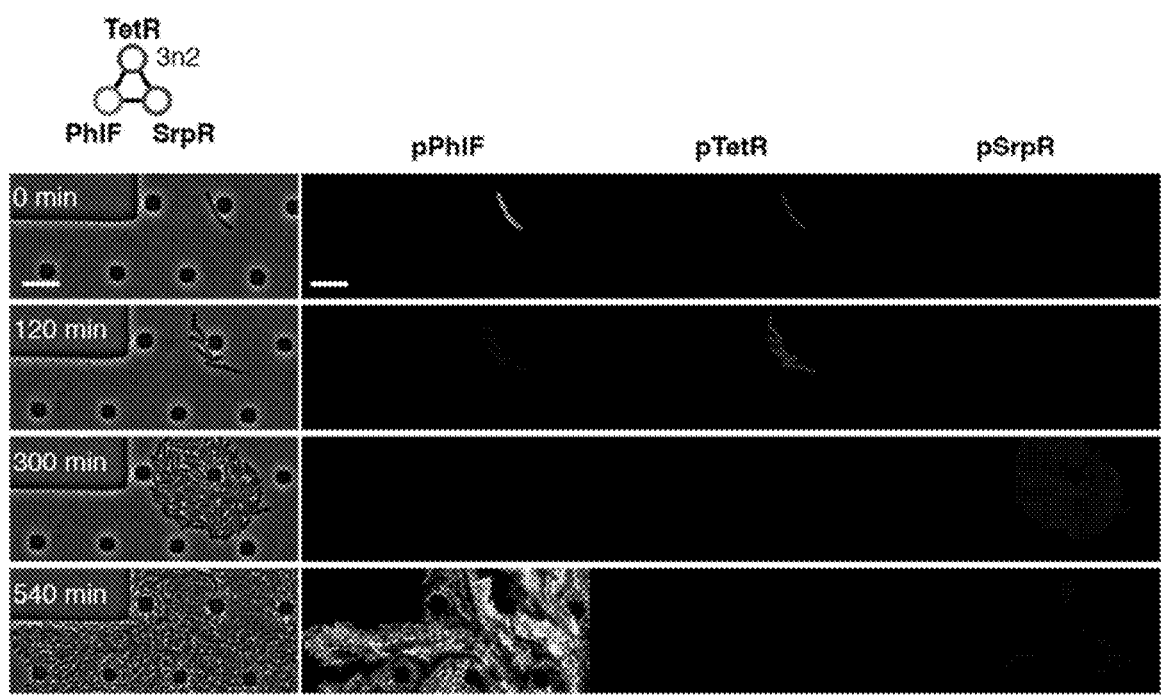
FIG. 28C shows in one embodiment three-color oscillations and population-level oscillations of 3n2 oscillator in vivo. 3n2 displays phase synchrony observing 3 reporters simultaneously. Reporters are a strong pPhlF Citrine-ssrA, pTetR mCherry-ssrA, and pSrpR Cerulean-ssrA. Shown is one oscillation cycle. Scale bars: 10 μm.
Figure 28D:
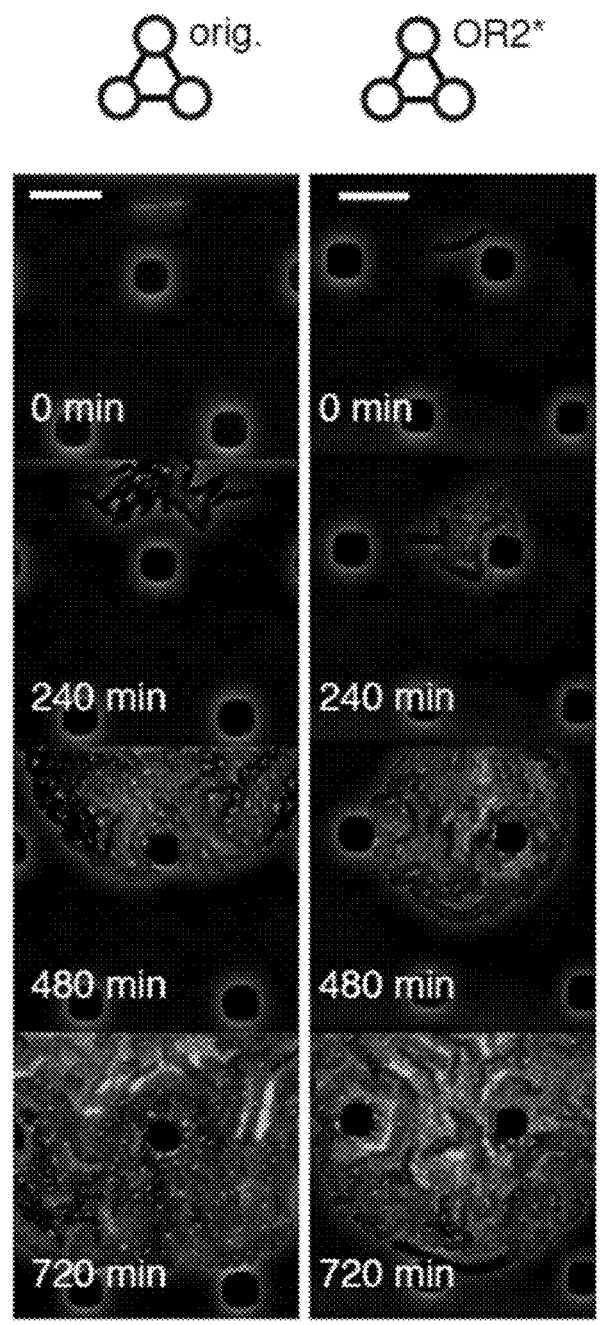
FIG. 28D shows original repressilator and $O_R2^*$ mutant repressilator do not show population-level oscillations. Original repressilator and $O_R2^*$ repressilator do not show phase synchrony. These are run under pTetR(r)-eGFP(ASV) in M9 minimal media; oscillations were not supported in LB. Scale bars: 10 μm.

Both 3n oscillators were also tested on a CellASIC system, which allows planar single-layer colony formation. Starting from a single cell, striking oscillation pulses of the entire growing microcolony (FIG. 27C and FIG. 28B) were observed. These population level pulses were also apparent when using three different fluorescent reporters simultaneously (FIG. 28C). Population level oscillations was not observed in either the original repressilator, the $O_R2^*$ mutant (FIG. 28D) or the 5n networks. Synchronized oscillations were not reported with the original repressilator [3], and have only been observed in oscillators using intercellular communication [64, 65]. In contrast to these quorum-sensing mechanisms that can actively couple and synchronize oscillator states [64, 65] the population-wide in-phase oscillations observed are not believed to be due to an active coupling mechanism. It is hypothesized that the population-level oscillations of the 3n1 and 3n2 networks are due to increased repressor concentrations as compared to the original repressilator network, which increases the inheritance of the period phenotype and minimizes the rapid de-phasing expected from stochastic cellular protein fluctuations [66]. However, a quantitative characterization of this slow de-phasing phenotype requires more in depth understanding of stochastic effects in vivo.

Figure 27D:
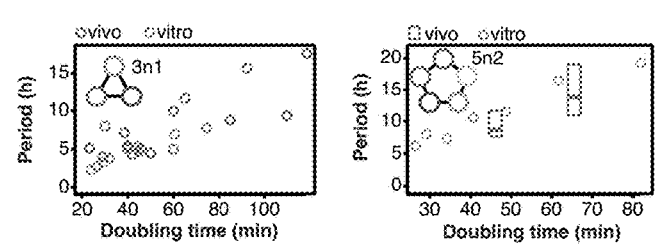

Because cells stayed synchronized, it is able to analyze the population as a whole to make general conclusions of oscillator behavior. Dilution time was varied by using different media conditions and media flow rates, and found a direct relationship between division times and period, consistent with the cell-free data collected. Oscillation periods of the 5n oscillators were also consistent with our cell-free results and showed a similar dependence on doubling time (FIG. 27D).

Figure 27E:
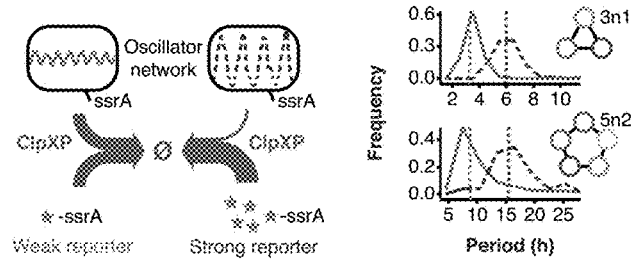

Finally, 3n1 and 5n2 were compared with weak and strong reporters in vivo to analyze the effect of protein degradation on the oscillator period. It is theorized that given a constant concentration of ClpXP, stronger reporters would result in more ClpXP loading, thereby slowing the period of oscillation. ClpXP is thought to influence oscillation dynamics in vivo in this manner [60]. It is found that in the mother machine, both the period distributions of 3n1 and 5n2 showed this characteristic (FIG. 27E), which reflects our cell-free findings of differential -ssrA tag dependent period length (FIG. 23C).

Example 40: Rapid Cell-Free Forward Engineering of Novel Genetic Ring Oscillators: Further Discussion It is shown in the previous examples that synthetic dynamic networks can be readily implemented, characterized, and engineered in a cell-free system and subsequently transferred to cellular hosts (FIG. 6 and FIG. 24). The results demonstrate the utility of this approach for biological systems engineering and component characterization. The cell-free system resulted in the experimental validation of previous theoretical predictions on even- and odd-numbered cyclic negative feedback circuits [56, 62] and enabled the in vivo implementation of robust 5-node genetic oscillators. The cell-free environment can thus fill the gap between theoretical network design and in vivo implementation of biological systems and provide a simplified and controlled environment that drastically reduces the design-build-test cycle [49]. In order to match the cell-free and cellular environments as closely as possible, a extract-based TX-TL expression system from the same E. coli strain used for in vivo experiments was prepared by a method that preserves the endogenous biosynthetic and protein degradation machinery [11, 15, 33, 67]. Similar expression systems had previously been applied to the prototyping of promoters and ribosomal binding sites [44, 49]. It is shown here that they can also be used for the prototyping of entire genetic networks when they are analyzed in a microfluidic system that emulates cellular growth. Oscillation periods in negative feedback ring oscillators are mainly determined by degradation and dilution rates [56], which explains the good correspondence between oscillation periods in our cell-free environment and in E. coli. By constructing and testing novel network architectures it is shown that almost all prototyping can be done on linear DNA, which requires less than 8 hours to assemble and test. This allows rapid screening of different network topologies and rapid screening of parameters important for the desired function of a network.

Some differences between the cell-free and cellular environment were observed, particularly in the difficulty of predicting cellular toxicity and loading effects of the 5n oscillators in vivo, and some differences between promoter and repressor strengths. With a better understanding of loading effects cell-free prototyping environments may predict when cells will be overloaded. The complete cell-free prototyping cycle that worked for 5n1 (FIG. 24) was not entirely successful for the 5n2 network. 5n2 showed similar oscillations as compared to 5n1 when analyzed on linear DNA in the cell-free environment (FIG. 23E) and on plasmid DNA in E. coli (FIGS. 27A-E), but oscillations for 5n2 was not observed when run from the same plasmid DNA in the cell-free environment. It is hypothesized that this is due to differences in expression efficiencies from linear and plasmid DNA in cell-free prototyping environments [44, 49], and/or differences between repressor strengths in the cell-free and the cellular environment (particularly for QacR, FIGS. 25B-C).

While more work is necessary describing and explaining differences between in vitro and in vivo environments, the observed behavior of complex networks in the cell-free environment reflected network behavior in vivo well. Cell-free systems are thus a powerful emulator of the cellular environment allowing precise control over experimental conditions and enabling studies that are difficult or time consuming to perform in cells. it will not only be useful for prototyping and characterizing novel synthetic systems but also facilitate in-depth analyses of native biological networks in a simplified setting. With further developments in cell-free lysate systems and supporting technologies, the cell-free approach is posed to play an increasing role in biological systems engineering and provides a unique opportunity to design, build, and analyze biological systems.

Example 41: Linear DNA for Rapid Prototyping of Synthetic Biological Circuits in a Cell-Free System: Rapid Assembly of Linear DNA Overview Examples 41-48 are related to protocols and methods of using linear DNA for rapid prototyping of synthetic circuits.

While most circuits implemented in S30 based extracts utilize plasmid DNA to avoid exonuclease degradation from endogenous RecBCD, linear DNA can be protected from degradation with the RecBCD inhibitor bacteriophage gamS protein both in vivo and in other S30 extracts[68, 69]. The ability to run circuits off of linear DNA opens up possibilities for rapid prototyping, as linear DNA can be created in high yields either synthetically or entirely in vitro in just a few hours. Linear DNA could also enable applications not possible with plasmid DNA, such as the expression and analysis of toxic proteins by bypassing in vivo transformation and selection.

Figure 29A:
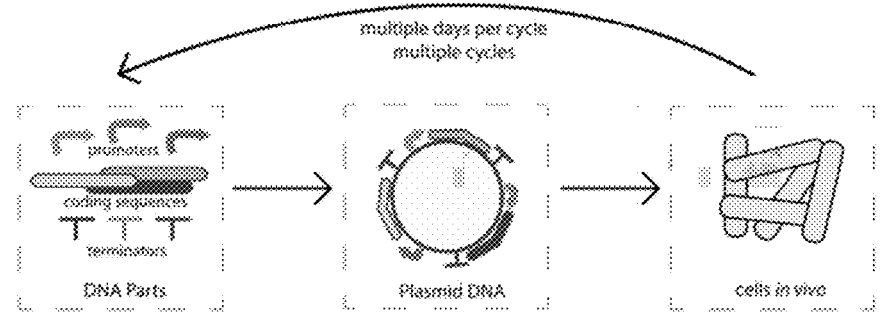
FIGS. 29A-B demonstrate in one embodiment an overview of rapid prototyping procedure of gene circuits.
Figure 29B:
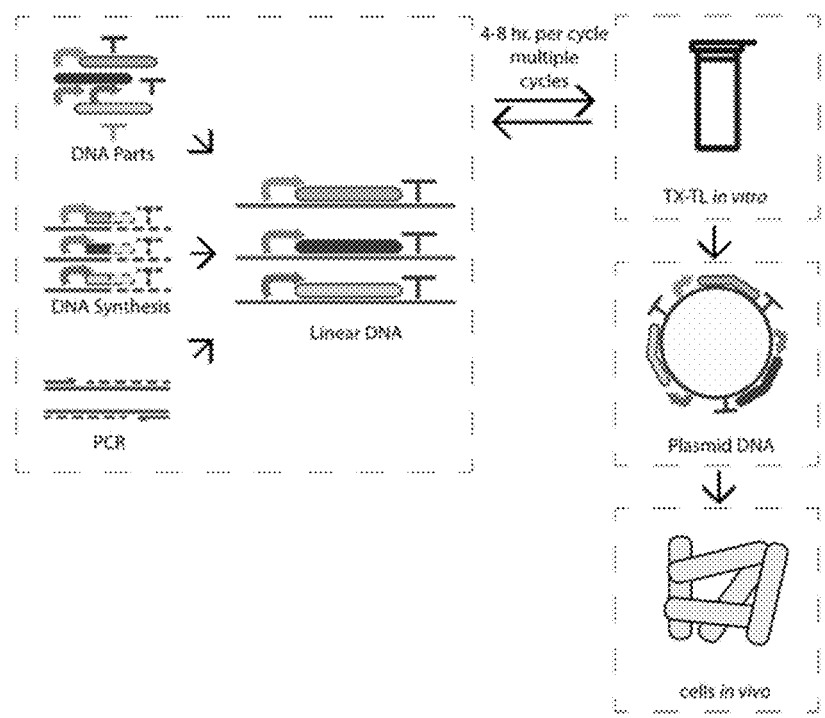

A rapid, entirely in vitro assembly technique is developed to assemble regulatory elements and basic circuits from standard or custom pieces in under 4 hours, with complete testing in under 8 hours. This in vitro assembly technique generates linear DNA, which can be tested in the in vitro system. FIGS. 29A-B demonstrates the use of linear DNA, where construction on linear DNA and testing in TX-TL means minimal cycles are needed of plasmid DNA construction and circuit implementation in vivo.

Example 42: Linear DNA for Rapid Prototyping of Synthetic Biological Circuits in a Cell-Free System: GamS Protein Purification To generate gamS, the protein purification process is followed as described below. The composition of buffers used was: buffer L: 50 mM Tris-Cl pH 8, 500 mM NaCl, 5 mM imidazole, 0.10% Triton X; buffer W: 50 mM Tris-Cl pH 8, 500 mM NaCl, 25 mM imidazole; buffer E: 50 mM Tris-Cl pH 8, 500 mM NaCl, 250 mM imidazole; buffer S: 50 mM Tris-Cl pH 7.5, 100 mM NaCl, 1 mM DTT, 1 mM EDTA, 2% DMSO. A frozen stock of P_araBAD-gamS in a BL21-DE3 E. coli strain was grown overnight in LB-carbenicillin media. 100 mL was used to inoculate 1 L LB-carbenicillin to an OD 600 nm of 0.4-0.6 at 37° C., 220 rpm. Cells were then incubated to 0.25% arabinose (final concentration) and grown for four additional hours at 25 C, 220 rpm, before being pelleted and frozen at −80° C. Cells were resuspended in buffer L, mechanically lysed, and incubated with Ni-NTA agarose (Qiagen). Ni-NTA agarose was washed twice with 15 column volumes of buffer W and eluted in buffer E. Fractions with a ~13 kD band were concentrated and dialyzed into buffer S overnight, and further purified on a 26/60 Sephadex 75 column. Protein concentration was verified by Bradford, concentrated to 3 mg/ml using an Ultra-0.5 3K MWCO Centrifugal Filter (Ambion), and stored in buffer S at −80° C. Protein purity was verified by gel. Purification steps were verified by SDS-PAGE gel electrophoresis.

Figure 30A:
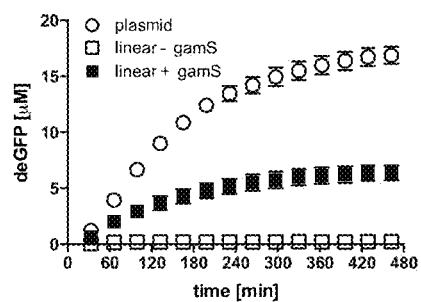
FIGS. 30A-D show in one embodiment the activity of gamS in protecting linear DNA.
Figure 30B:
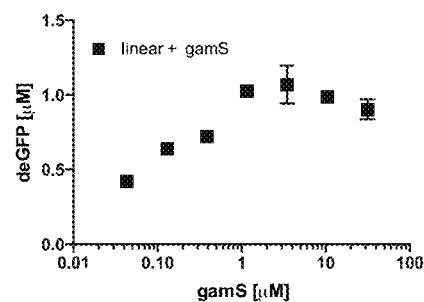
Figure 30C:
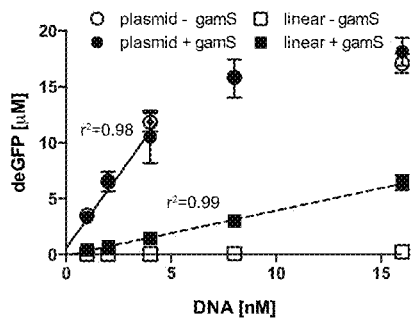
Figure 30D:
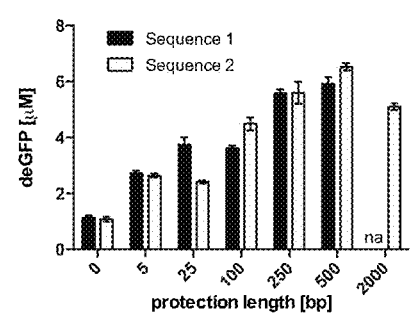

Example 43: Linear DNA for Rapid Prototyping of Synthetic Biological Circuits in a Cell-Free System: GamS Protection Assays GamS, a truncated form of lambda gam, was used by adding it to the cell-free system to protect linear DNA from RecBCD degradation. A gamS working concentration of 3.5 µM was determined by comparing the protective ability of dilutions of purified protein on 2 nM of linear DNA without steric protection. FIGS. 30A-D show the activity of gamS in protecting linear DNA. FIG. 30A compares of deGFP time-series fluorescence for plasmid DNA, linear DNA without gamS protection, and linear DNA with gamS protection. Plasmid DNA used is pBEST-OR2-OR1-Pr-UTR1-deGFP-T500, linear DNA is an 810 bp PCR product with no steric protection ends, and each is supplied at 16 nM. FIG. 30B shows endpoint deGFP expression after 8 hours of 2 nM of linear DNA plotted against signal for different working concentrations of gamS, without prior incubation of the protein with crude extract. FIG. 30C shows endpoint deGFP expression from plasmid and linear DNA with or without gamS protection, at increasing DNA concentrations. Correlation of 0.98 on plasmid DNA is for 0 nM-4 nM values only; correlation of 0.99 on linear DNA is for 0 nM-16 nM. FIG. 30D shows protection of 2 nM of linear DNA using different amounts of non-coding DNA at template ends. Each length corresponds to an amount of non-coding base pairs at each end of the linear DNA, and Sequence 1 is independent of Sequence 2. Readout is endpoint deGFP fluorescence after 8 hours, and experiment is in the presence of gamS protein. Error bars represent one standard deviation from three independent experiments.

Steric protection sequences are preferable to prevent linear DNA degradation even in the presence of gamS. Three sets of sequences were used for steric protection assays. One set was based on the vector backbone of previously published pBEST-OR2-OR1-Pr-UTR1-deGFP-T500 (Addgene #40019). Another set, referred to as "Sequence 2" (see FIG. 30D), was derived from the coding sequence of gltB and lhr. These sequences were found by parsing the NCBI GenBank MG1655 record in BioPython for all known coding sequences and sorting by sizeSequences were analyzed using Geneious 6.0 (Biomatters Ltd).

Example 44: Linear DNA for Rapid Prototyping of Synthetic Biological Circuits in a Cell-Free System: Plasmid DNA and PCR Product Preparation Plasmids used in this study were constructed using standard cloning procedures and maintained in a KL740 strain if using an OR2-OR1 promoter (29° C.), a MG1655Z1 strain if using a Pl-tetO1 or Pl-lacO1 promoter, a BL21-DE3 strain for protein purification, a BL21 strain for promoter characterization, or a JM109 strain for all other constructs. KL740 upregulates a temperature sensitive lambda cI repressor, and MG1655Z1 upregulates tetR and lacI. PCR products were amplified using Pfu Phusion Polymerase (New England Biolabs) for all constructs except for those labeled with AlexaFluor-588-5-dUTP, which used Taq Polymerase (New England Biolabs), and were DpnI digested. Plasmids were either miniprepped using a PureYield column (Promega) or midiprepped using a NucleoBond Xtra Midi column (Macherey-Nagel). All plasmids were processed at stationery phase. Before use in the cell-free reaction, both plasmids and PCR products underwent an additional PCR purification step using a QiaQuick column (Qiagen), which removed excess salt detrimental to TX-TL, and were eluted and stored in 10 mM Tris-Cl solution, pH 8.5 at 4° C. for short-term storage and −20° C. for long-term storage.

Example 45: Linear DNA for Rapid Prototyping of Synthetic Biological Circuits in a Cell-Free System: Rapid Assembly of Linear DNA Produces Same Result as Regular PCR After having established linear DNA circuit prototyping, we seek to create a method for rapid assembly of linear pieces that would enable us to go from assembly to testing in 4-8 hours, and simultaneously allow us to generate plasmid DNA post-transformation. Unlike other in vivo assembly methods, which ultimately require efficiency as well as selectivity, we were primarily concerned with selectivity as our templates would be end amplified by PCR.

Figure 31A:
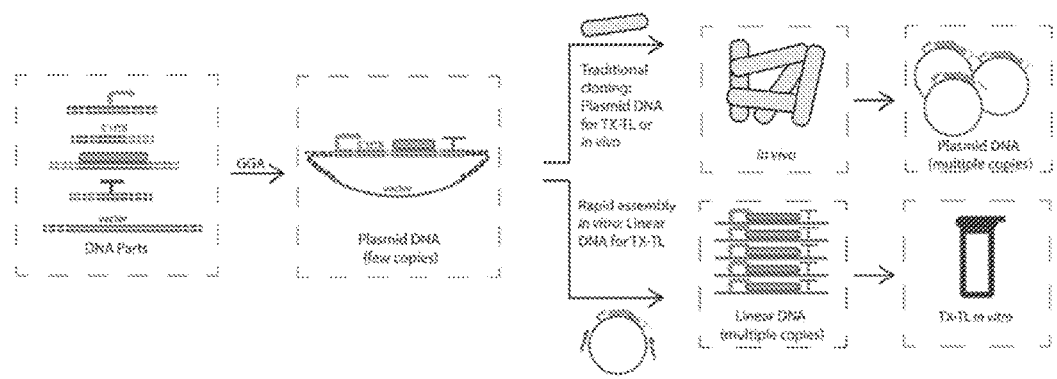
FIGS. 31A-C demonstrate in one embodiment the rapid assembly conceptual method and result comparing linear DNA made by rapid assembly vs. those made by PCR.
Figure 31B:
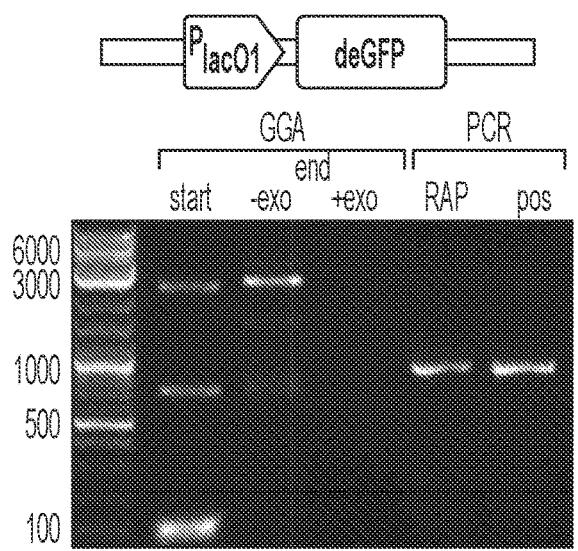
Figure 31C:
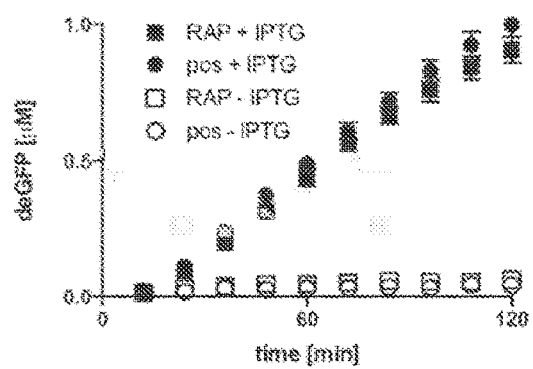

Described herein is the rapid assembly conceptual method and result comparing linear DNA made by rapid assembly vs. those made by PCR. FIG. 31A shows an overview of the rapid assembly and prototyping procedure, where DNA parts are assembled using Golden Gate assembly ("GGA") to create a plasmid, which is then directly used as a PCR template to create linear DNA at high concentrations suitable for TX-TL. In parallel, the assembly product can also be propagated in vivo to yield more copies of clonal plasmid. Time comparisons for both methods can be found in Table 9. FIG. 31B shows agarose gel of a gene assembled from 5 standard pieces of 66 bp, 103 bp, 110 bp, 707 bp, and 2376 bp. Shown are 50 ng each of starting fragments (except 66 bp), fragments post-assembly before and after exonuclease digestion ("exo"), and rapid assembly PCR product ("RAP") compared to post-cloned PCR product ("pos"). Arrow indicates expected size of 892 bp. FIG. 31C Functional testing of 4 nM of rapid assembly or post-cloned products, with or without 0.5 mM IPTG inducer. Experiment conducted in the presence of 2 nM Pl-tetO1-lacI linear DNA. Linear DNA is protected with 31 bp of steric protection and with gamS. Error bars represent one standard deviation from three independent experiments.

It is demonstrated in Table 9 that using rapid assembly techniques to generate linear DNA for immediate testing in TX-TL can save significant amount of time compared to conventional plasmid generation techniques.

TABLE 9

Time consumption in rapid assembly vs. conventional techniques

| | Rapid Assembly[1] | Conventional Techniques (plasmid generation) |
|---|---|---|
| PCR of segments | na | 1 h 15 min |
| DpnI digest | na | 5 min |
| Assembly reaction | 1 h | 1 h |
| Transformation and Recovery | na | 1 h 30 min |
| Overnight growth on plates | na | 16 h |
| Colony isolation and liquid media growth | na | 8 h |
| Miniprep | na | 30 min |
| PCR of rapid assembly product | 1 h 15 min | |
| PCR Cleanup | 15 min | 15 min |
| Setup TX-TL | 15 min | 15 min |
| TOTAL pre-TX-TL | 2 h 45 min | 1 d+ |
| TOTAL post-TX-TL | 4 h-8 h | 1 d+ |

Figure 32A:
FIG. 32A shows in one embodiment a four-piece negative feedback gene assembled from standard pieces.
Figure 32B:
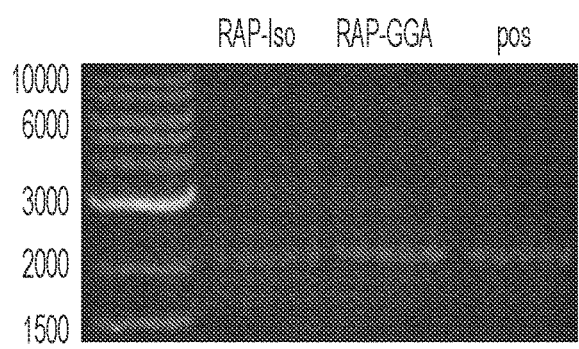
FIG. 32B shows comparison by agarose gel electrophoresis of rapid assembly product made by Isothermal assembly ("RAP-iso"), rapid assembly product made by Golden Gate assembly ("RAP-GGA"), and post-cloned PCR product ("pos"). Arrow indicates expected band. Linear DNA is protected with 250 bp of steric protection and with gamS.
Figure 32C:
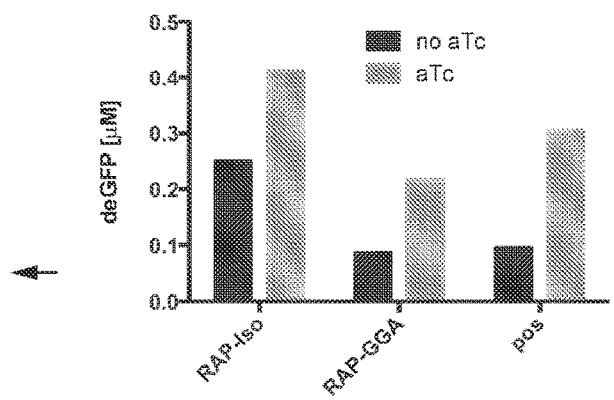
FIG. 32C shows functional testing of 6 nM of rapid assembly products compared to post-cloned PCR product with or without 10 μM aTc.

Example 46: Linear DNA for Rapid Prototyping of Synthetic Biological Circuits in a Cell-Free System: Specific Linear DNA Technique It is desired to have modularity of pre-made pieces to be assembled into linear DNA. Three methods of in vivo assembly for adoption purely in vitro were initially tested: Isothermal assembly, Chain Reaction Cloning, and Golden Gate assembly.[41, 42, 70] Each method is based on a different mechanism of action—recombination-based cloning, blunt-end cloning, or sticky-end cloning. Of these three, only Isothermal assembly and Golden Gate assembly produced enough yield to obtain constructs. In FIG. 32A, a four-piece negative feedback gene is assembled from standard pieces. FIG. 32B compares by agarose gel electrophoresis of rapid assembly product made by Isothermal assembly ("RAP-iso"), rapid assembly product made by Golden Gate assembly ("RAP-GGA"), and post-cloned PCR product ("pos"). Arrow indicates expected band. Linear DNA is protected with 250 bp of steric protection and with gamS. FIG. 32C shows results from functional testing of 6 nM of rapid assembly products compared to post-cloned PCR product with or without 10 μM aTc.

A standard assembly procedure based on Golden Gate assembly was developed. By using a standard assembly, any mis-ligation would be less likely to lead to mis-assembled products capable of expression. Our standard Golden Gate assembly procedure also allowed us to recycle commonly used parts and to ensure functional activity of the desired product. Our standard consisted of five pieces—a promoter, 5' untranslated region (UTR), coding sequence, terminator, and vector. It was designed to be compatible with previously used non-coding sequences and primers on the pBEST vector backbone. The specific pieces for the rapid assembly procedure are shown below. FIG. 33A shows a five-piece standard adopted with specific ligation ends for a promoter, 5' UTR, coding sequence, terminator, and vector based on the previously used pBEST backbone. FIG. 33B shows a diagram of sequences for ligation at each site.

Figure 34A:
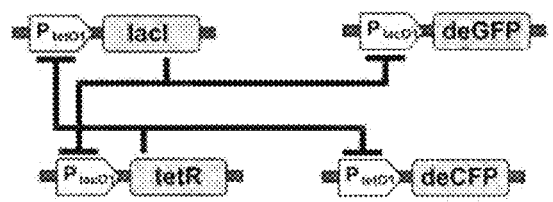
FIG. 34A shows in one embodiment a four-piece genetic switch.
Figure 34B:
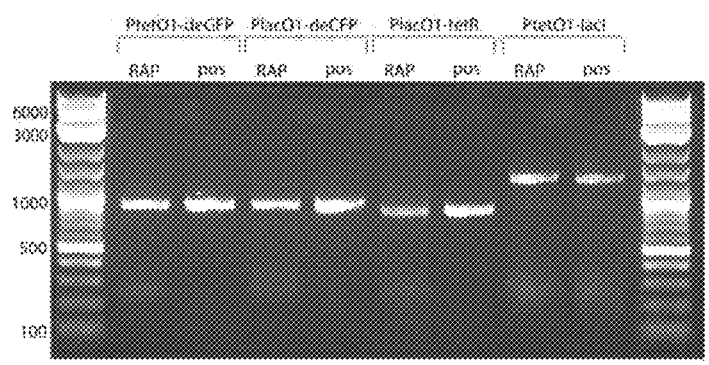
FIG. 34B shows comparison of rapid assembly product ("RAP") to post-cloned PCR product ("pos") for four linear pieces formed, using overlap primers.
Figure 34C:
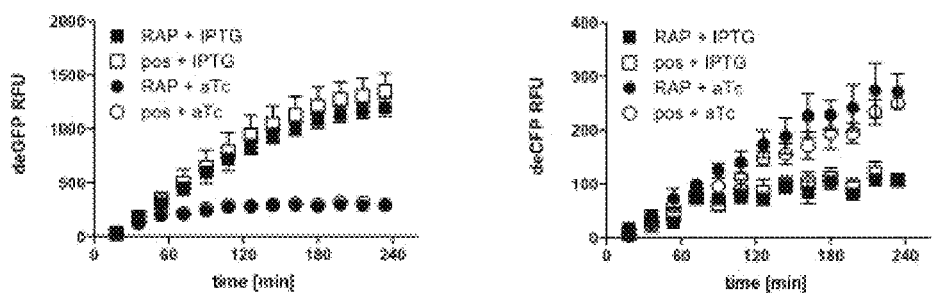
FIG. 34C shows functional assay of RAP products versus post-cloned PCR products for "on" or "off" states of genetic switch. 2 nM of reporter and 1 nM of repressor is tested, and "+ IPTG" indicates the 0.5 mM IPTG, 0 μM aTc state while "−IPTG" indicates the 0 mM IPTG, 10 μM aTc state. Linear DNA is protected with 31 bp of steric protection and with gamS. Error bars represent one standard deviation from three independent experiments.

Example 47: Linear DNA for Rapid Prototyping of Synthetic Biological Circuits in a Cell-Free System: Verification of Rapid Linear DNA Tested in TX-TL Versus Regular PCR Product For more complex circuits, we verified our rapid assembly procedure by repeating the construction of a genetic switch, but from rapid assembly products. Specific bands were formed from PCR off of the rapid assembly product, and TX-TL runs demonstrated similar results for the product and the positive control when responding to IPTG and aTc. This prototyping took under 7 hours of time. FIG. 34A four-piece genetic switch. FIG. 34B Comparison of rapid assembly product ("RAP") to post-cloned PCR product ("pos") for four linear pieces formed, using overlap primers. FIG. 34C Functional assay of RAP products versus post-cloned PCR products for "on" or "off" states of genetic switch. 2 nM of reporter and 1 nM of repressor is tested, and "+IPTG" indicates the 0.5 mM IPTG, 0 μM aTc state while "−IPTG" indicates the 0 mM IPTG, 10 μM aTc state. Linear DNA is protected with 31 bp of steric protection and with gamS. Error bars represent one standard deviation from three independent experiments

Figure 35:
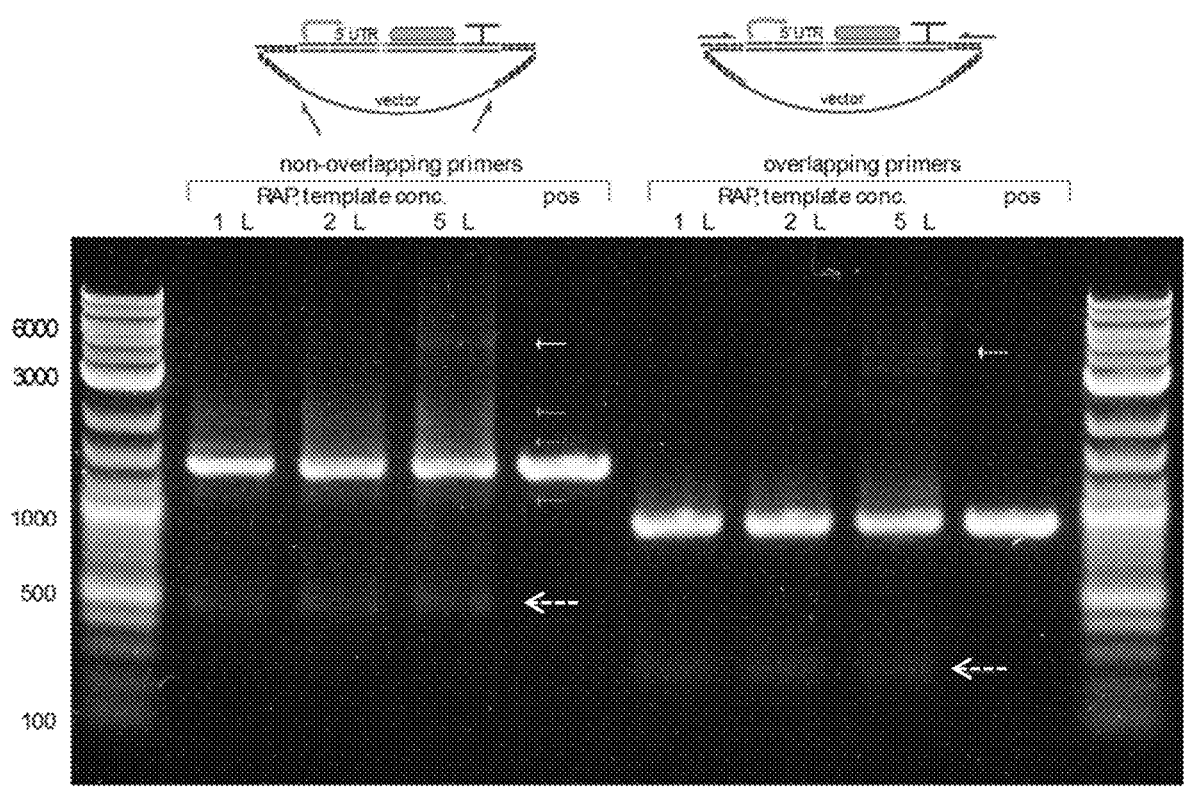
FIG. 35 shows in one embodiment purity of rapid assembly product as a function of template concentration and of overlapping primers. For a standard 5-piece assembly, the rapid assembly product ("RAP") is amplified off either 1 μL, 2 μL, or 5 μL of template in a 50 μL PCR reaction. A post-cloned PCR product ("pos") is also produced. Non-overlapping primers refer to binding sites which do not cross the assembly junction between the vector and promoter and the vector and terminator; overlapping primers cross this junction. Solid white arrow: template DNA; Gray arrows: Non-specific products removed by overlapping primers; Dashed white arrow: non-specific products retained by overlapping primers. Red arrow is presumed to be self-ligated vector based on size.

Example 48: Linear DNA for Rapid Prototyping of Synthetic Biological Circuits in a Cell-Free System: Utilization of Overlap Primers Utilization of overlapping primers is critical to the specificity of the resulting rapid assembly product. 4 bp binding overhangs with increased specificity were created. [71] Using different overhangs with little overlap was necessary, as decreased specificity with multiple base pair overlaps. The PCR primers were also designed to overlap at the junction sites of vector and promoter and vector and terminator, respectively, which further minimized non-specific products. This decreased steric protection ends to 31 bp. To verify this, in FIG. 35 for a standard 5-piece assembly, the rapid assembly product ("RAP") is amplified off 1 μL, 2 μL, or 5 μL of template in a 50 μL PCR reaction. A post-cloned PCR product ("pos") is also produced. Non-overlapping primers refer to binding sites that do not cross the assembly junction between the vector and promoter and the vector and terminator; overlapping primers cross this junction. White arrow: template DNA; Blue arrows: Non-specific products removed by overlapping primers; Red arrow: non-specific products retained by overlapping primers. Red arrow is presumed to be self-ligated vector based on size.

Example 49: Metabolic Pathway Engineering in Cell-Free Systems, Using Violacein: Overview Examples 49-59 are related to protocols and methods of engineering metabolic pathways in cell-free systems, using violacein as an example of a metabolic pathway to be engineered. This work was published as [5].

TX-TL is used to determine optimal enzyme expression levels to optimize the expression of violacein, a valuable chemical with antibacterial and anticancer properties that is a potent natural product. The pathway is in TX-TL by providing the DNAs encoding for the pathway into the cell-free mixture, and providing the starting component of the metabolic pathway, tryptophan. It is determined that intermediates are produced based on the colors of the resulting reactions when certain pathway enzymes are excluded. Analysis of the final violacein product using absorption and LC-MS indicated approximate 70 ng per 10 uL reaction produced. By conducting design space exploration, it is hypothesized that VioC and VioD DNA concentrations can be increased to increase violacein product formation.

Metabolic engineering allows for the production of biological based materials using mainly biological mechanisms as opposed to chemical ones. This is valuable when the end-goal is to remove dependence on petroleum, eg. by using alternate sugar feedstock to produce biofuels (farnescene, Amyris) or plastics (1,4 BDO, Genomatica), or to produce complex products that cannot be produced using existing chemical processes and instead require isolation from natural products (artemisinin, previously from the wormwood plant, now from yeast by Amyris; shikimic acid, from star anise, now from *E. coli* by Roche). However, the process of metabolic engineering is laborious and requires significant manipulation of genetic constructs in vivo; the engineering of artemisinin is estimated to have taken 150 years of research and development, and the engineering of a 1,3 BDO biosynthetic pathway 450 person-years of research and development. A cycle of Cloning can require weeks or more [72]. A faster engineering process to optimize metabolic pathways is therefore desired.

By using a TX-TL system based on *E. coli*, one can utilize linear DNA and plasmid DNA to rapidly explore a metabolic pathway and its associated products, as well as determine bottlenecks in expression and optimal enzyme concentrations. By testing linear DNA expressible constructs with steric protection (100 bp) at each end with the presence of gamS, the resulting products in a cell-free mixture can be analyzed using high-throughput methods such as UV visualization and highly specific methods such as LC-MS. The throughput of the process allows for quick and efficient diagnosis of metabolic circuits and the understanding of metabolic design space.

Example 50: Metabolic Pathway Engineering in Cell-Free Systems, Using Violacein: Using TX-TL to Increase Final Product Yield In this demonstration, the violacein pathway is prototyped in TX-TL with the goal of improving product yield. Rate-limiting steps and flux through the pathway can be determined by these testing steps. Each enzyme can be successfully reconstituted. Findings include: a dependence on the coding sequence length to the expression level in the in vitro system, and a potential bottleneck of VioC and VioD protein as determined by relieving of a violacein concentration bottleneck with increased concentrations of VioC and VioD DNA. These findings are expected to be repeatable when the pathway is implemented in an in vivo target environment.

Example 51: Metabolic Pathway Engineering in Cell-Free Systems, Using Violacein: Using TX-TL to Debug Circuits to Determine Yield Loss Area Note that while the example looks at improving the yield of violacein, one can also use cell-free systems to debug a pathway, and detect fluxes of the conversion of substrates that are accepted on by recombinant genetic components. For example, in the violacein example, if there are 5 variants of vioA, named vioA1, vioA2, vioA3, vioA4, and vioA5, and it is found that vioA3 produces the most IPA to tryptophan ratio, then it can be assumed that the flux in the pathway can be maximized by the use of vioA3. In addition, if the whole pathway is implemented and there are bottlenecks in the activity of an enzyme, the substrate before the enzyme should be relatively high in amount.

Figure 57:
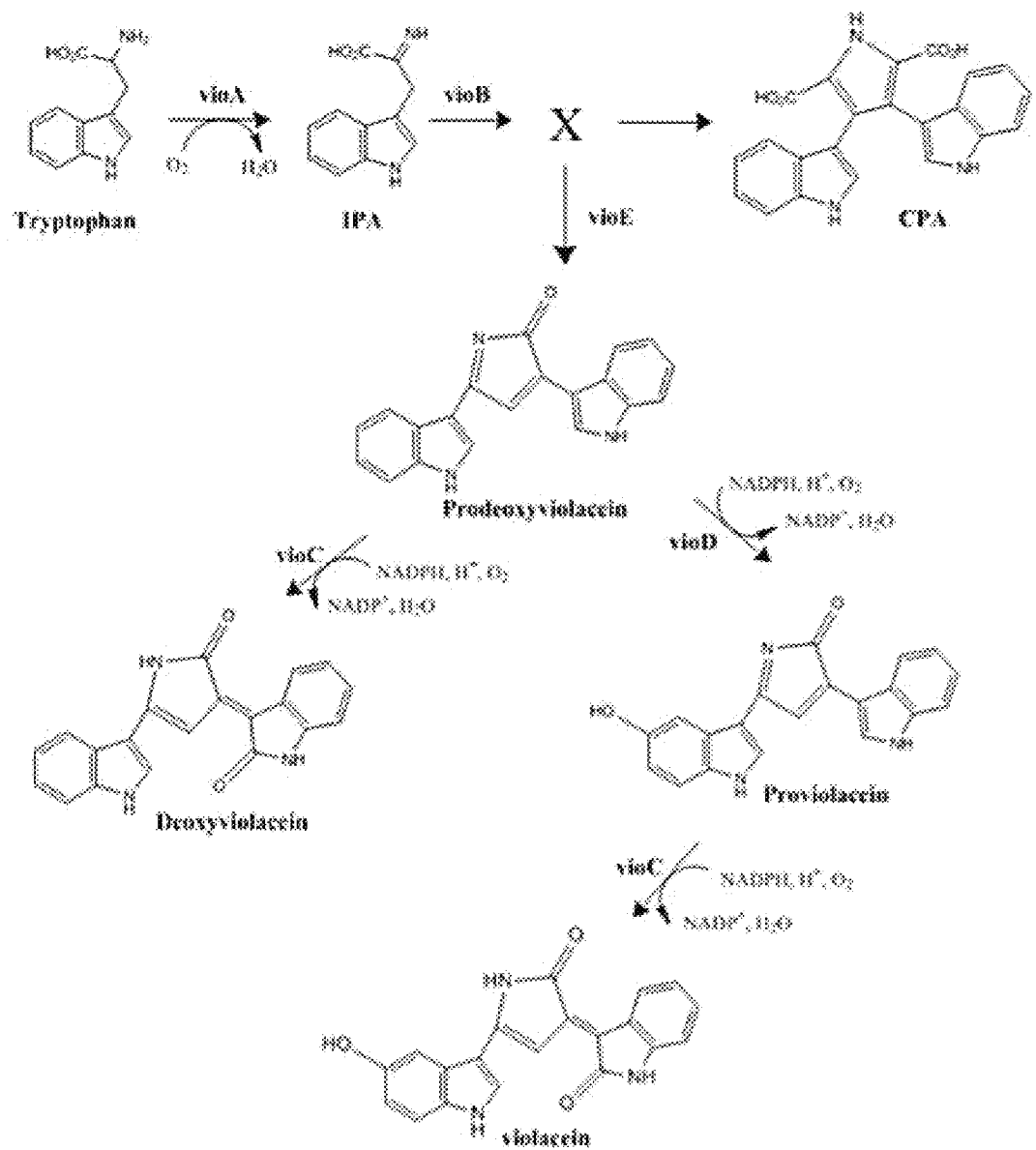
FIG. 57, originally from [5], shows the metabolic pathway for metabolizing tryptophan to violacein, using enzymes vioA, vioB, vioC, vioD, and vioE. The letter "X" represents an unknown intermediate.

Example 52: Metabolic Pathway Engineering in Cell-Free Systems, Using Violacein: Violacein Pathway and Reconstitution in Cell-Free Violacein is a valuable bacterial pigment chemical first isolated from *Choromobacterium violaceum*. However, the chemical is expensive to isolate from this original source due to the strain's low productivity and difficulty to commercialize a production process using a non-common utilized host [16]. The pathway for the production of violacein is well-defined, as shown in FIG. 57, starting from tryptophan and converting through intermediates indole-3-pyruvate (IPA), prodeoxyviolacein, deoxyviolacein, proviolacein, before producing violacein. Interestingly, the pathway has many branch points, such as a side-production of chromopyrrolic acid (CPA). The pathway also contains an IPA imine diamer whose exact structure is unknown and can be represented by "X.". Note that in this representation, the recombinant genetic components are vioA, vioB, vioE, vioC, and vioD.

Each coding sequence, vioA, vioB, vioC, vioD, and vioE was cloned under a strong promoter in front of the coding sequences of each enzyme (J23151). The promoter sequence is from [16], UTR from [1], CDS from [73], and terminator sequence ECK120033736 (T14) from [6], as outlined in FIG. 58. Linear DNAs from each piece were made with 100 bp of steric protection, and the DNA was assembled using a Golden Gate procedure [71].

To run the reaction, one can start by using equimolar concentrations of each linear DNA; the resulting products were insoluable, but could be extracted with 70% ethanol percipitation. To explore intermediate production products from the pathway, specific linear DNA's can be left out, which should force the pathway to stop flux before the input processed by the excluded linear DNA.

The extract produced is from a BL21-Rosetta2 strain, and extracts were prepared based on the protocol listed in [15] from 1 L of culture. Extracts went homogenization in lieu of lysis, and later processing steps were conducted in line with [74], but with a 80 minute heat-incubation step.

Example 53: Metabolic Pathway Engineering in Cell-Free Systems, Using Violacein: Reading and Running Cell-Free Reactions In a typical run, DNA is added to a mix of buffer and extract as described in [15] and a reaction is conducted at least 4 hours. Reaction products are then pelleted to isolate the non-soluable component, and pellets are washed with water and then dissolved in 70% ethanol to soluabilize percipipated samples. This sample was then measured for absorbance at 572 nm to read the reproable element.

LC-MS was used for a more specific determination of violacein production. Post-production in TX-TL, reaction products were pelleted, washed once with water, and then dissolved in methanol before injection on a Acquity UPLCr BEH C18 1.7 um reverse phase column at a flow rate of 0.5 ml/min. The reactions were run in 10 mM ammonium formate with 1% CAN. A gradient was applied from 0 to 90% in acetonitrile and held for 0.2 minutes. A mass window range of 0.344 kDa, 0.328 kDa, and 0.312 Da and elution times of 1.93, 1.65, and 1.83 min detected violacein, deoxyviolacein, and prodeoxyviolacein respectively.

Figure 59:
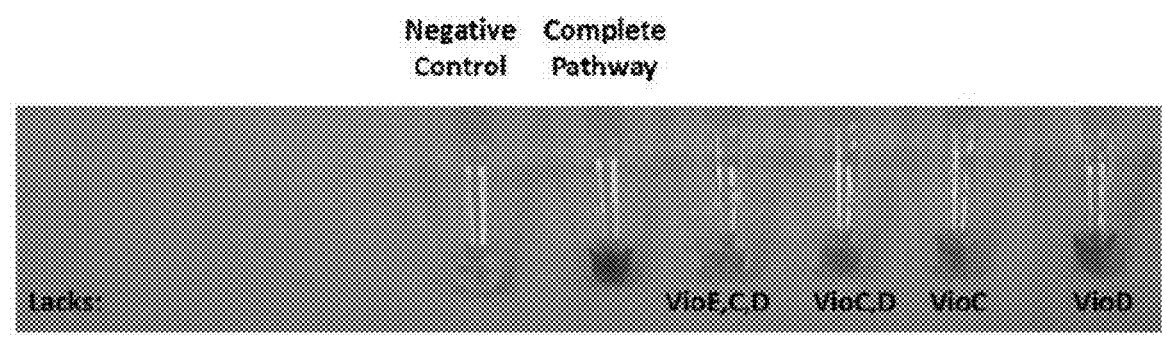
FIG. 59, originally from [5], demonstrates different colored metabolites that result from excluding certain genes in the pathway. Specifically, the complete pathway creates a dark violet reaction, while the exclusion of VioE, VioC, and VioD creates a non-colored reaction; the exclusion of VioC and VioD creates a pink reaction; the exclusion of VioC creates a orange reaction; and the exclusion of VioD creates a light violet reaction.

Example 54: Metabolic Pathway Engineering in Cell-Free Systems, Using Violacein: Confirming Production Using Absorbance or Visual Assays Upon running of the pathway in TX-TL at equimolar concentrations of linear DNA for each enzyme, one can see the production of various colored products depending on which vioacein enzyme is excluded from the mix. Post-extraction of the pellet in 70% ethanol, one can visually see a difference in color from the reactions (FIG. 59). While volacein has a chacteristic violect color, the extracts produced from reactions lacking vioE/C/D, vioC/D, vioC, and vioD produce a charastically different color, with vioE/C/D in particular producing a colorless product similar to the negative control. The light violet product produced from the VioD lacking reaction is assumed to be deoxyviolacein based on the enzyme expression pathway.

Figure 60:
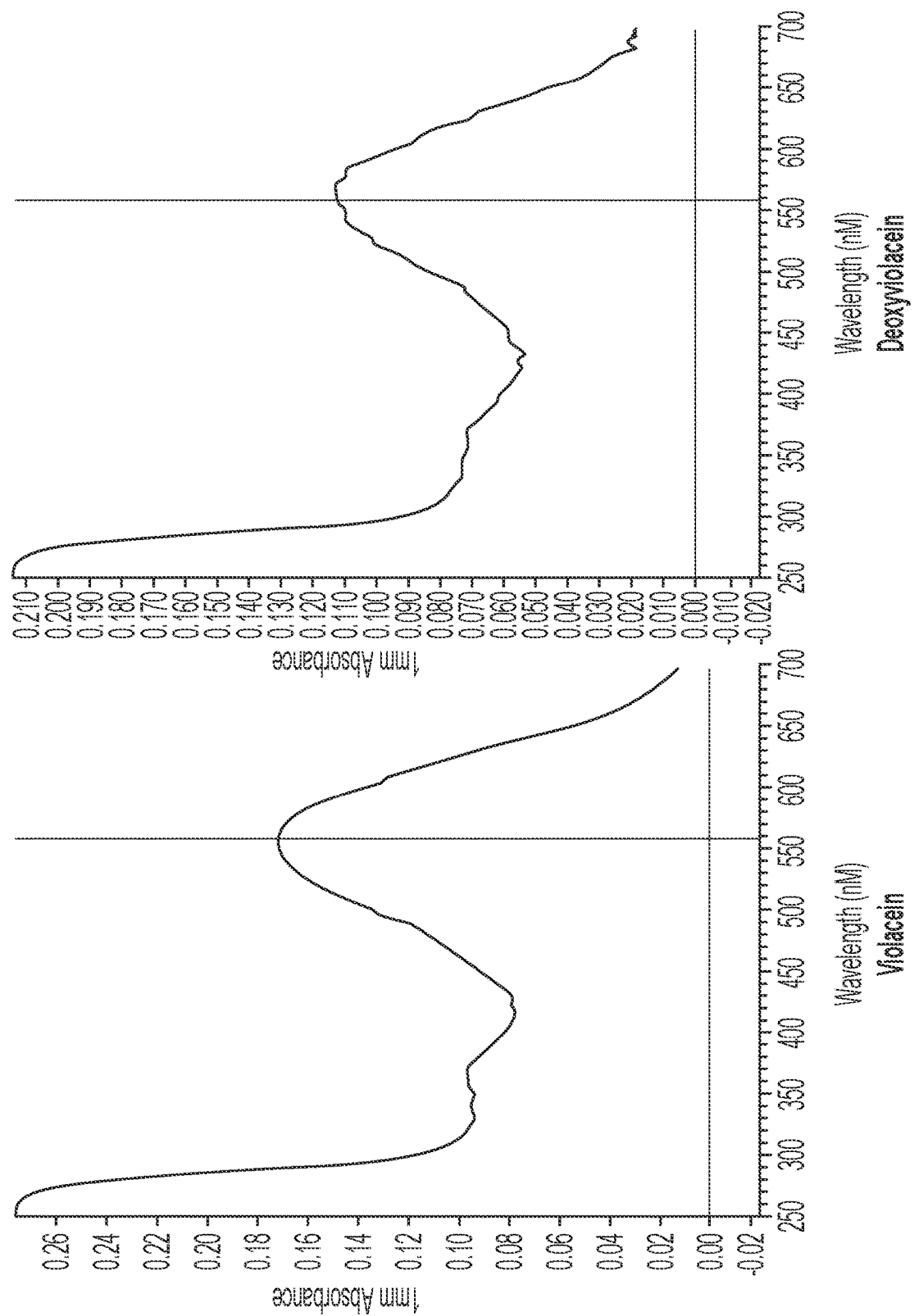
FIG. 60, originally from [5], demonstrates a read on a Nanodrop 2000 of the result of a TX-TL using a complete pathway (left) versus a TX-TL lacking VioC (right). This is measuring absorbance at different wavelengths; the vertical line indicates the published peaks for violacein (left) and deoxyviolacein (right).

Exploring further the full pathway the samples were read on a Nanodrop 2000 for absorbance. The sample with the complete pathway (violacein, left) and lacking VioC (deoxyviolacein, right) have peaks that line up with published peaks in blue [16, 75] (FIG. 60).

Figure 61A:
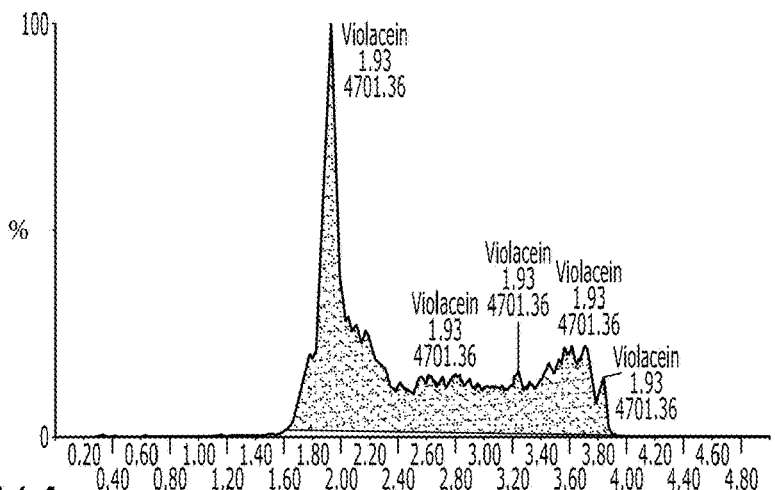
FIGS. 61A-C, originally from [5], demonstrates the detection of violacein (FIG. 61A), deoxyviolacein (FIG. 61B), and prodeoxyviolacein (FIG. 61C) by LC-MS in a TX-TL containing the complete pathway.
Figure 61B:
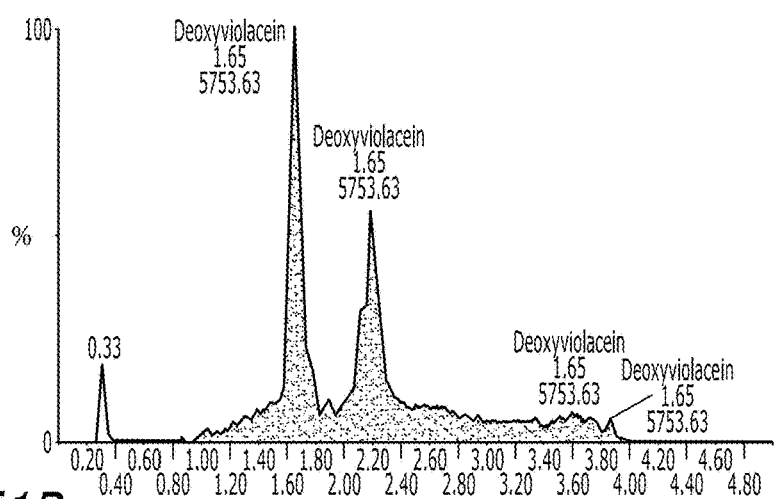
Figure 61C:
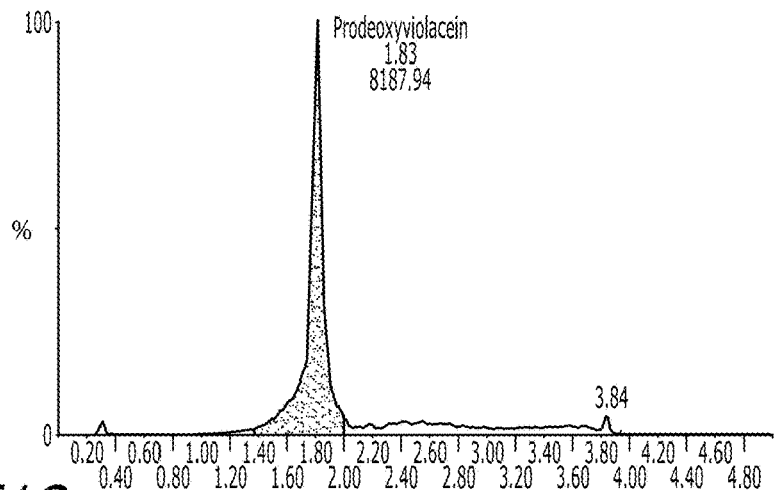

Example 55: Metabolic Pathway Engineering in Cell-Free Systems, Using Violacein: Confirming Production Using LC-MS One can further analyze the reactions using LC-MS for specificity. Against pure violacein standard, equimolar 4 nM of linear DNA for each enzyme was run in TX-TL, and in the protocol listed previously resulting metabolics were read on a LC-MS. While the LC-MS detected volacein present in (a), there is also deoxyviolacein contaminant in (b) and prodeoxyviolacein in (c), which is not un-expected given the branch point in the production of vioacein. (FIGS. 61A-C).

Figure 62:
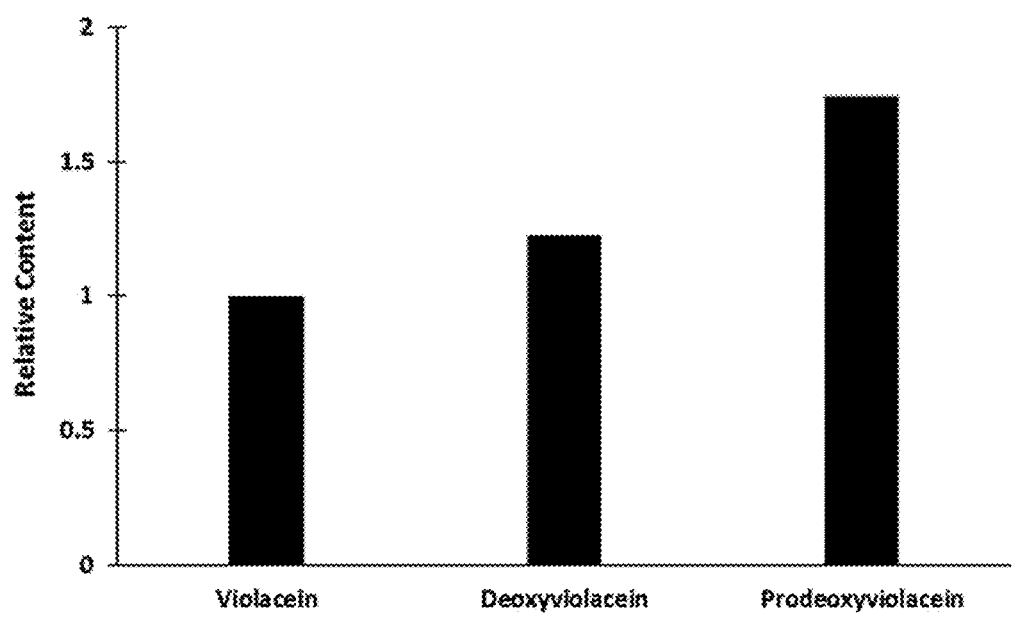
FIG. 62, originally from [5], demonstrates the peak detection of violacein, deoxyviolacein, and prodeoxyvilacein in FIGS. 61A-C, normalized to the violacein detection amount.

Prodeoxyviolacein, an upstream intermediate, is also present at 1.7 times a higher concentration in violacein. This indicates that the reaction was not driven to completion, and suggests that vioC and vioD could be rate limiting, eg. increasing the concentrations of vioC and/o vioD DNA could relieve the rate-limiting step (FIG. 62). Against the commercial standard, we estimate violacein production a 19.8 uM.

Figure 63B:
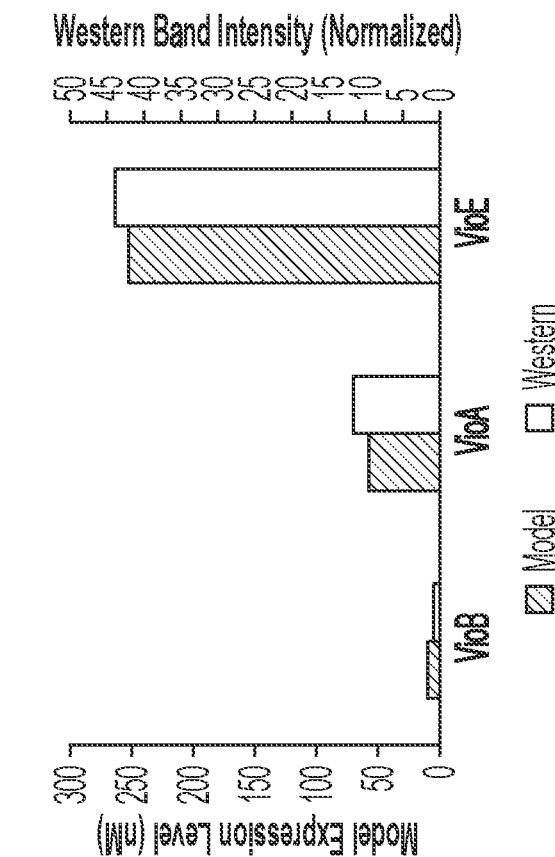
FIGS. 63A-B, originally from [5], demonstrate a Western blot in FIG. 63A of vioA, vioE, and vioB from either the complete pathway (columns 2 and 3) or from a vioB only reaction (column 4), with a latter given as a standard (column 1). The quantitative amounts of each protein in a Western blot is given in par in FIG. 63B, where the left hand bar (dark gray) in each column is a model prediction amount and the right hand bar (light gray) in each column is the Western blot quantitative amounts.
Figure 63A:
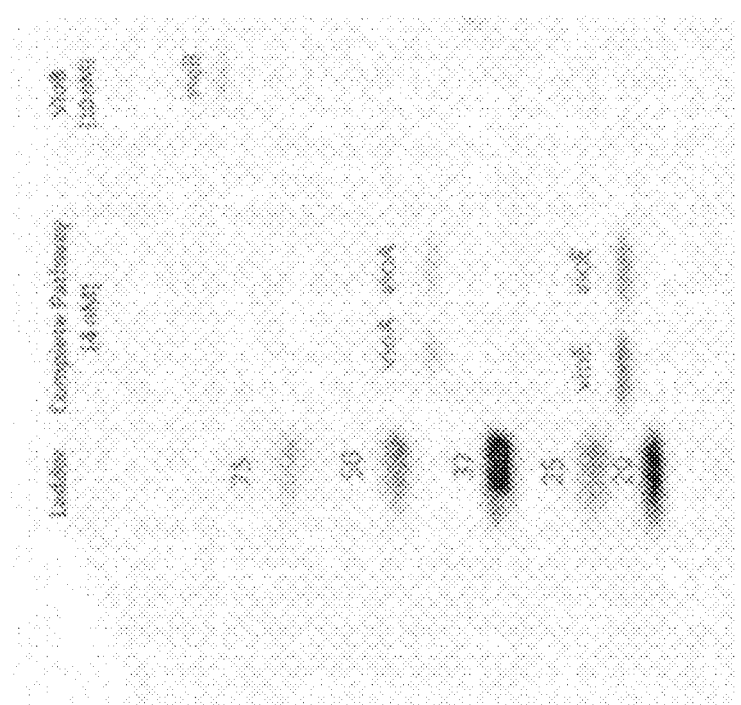

Example 56: Metabolic Pathway Engineering in Cell-Free Systems, Using Violacein: Confirming Production Using Western Blotting One can also verify the production of the enzymes in the system using a Western blot assay. To do so, VioA, VioB, and VioE coding sequences were modified with a C-terminus Strep tag. The enzymes were again expressed at equimolar concentration at 4 nM on linear DNA, and then visualized on a SDS-PAGE gel using Biorad's Precision Protein™ StrepTactin-HRP Conjugate antibodies. VioE concentrations were higher than VioA concentrations when the complete pathway was expressed, and vioB was detectable in a separate TX-TL reaction. Enzyme levels based on band intensity are also shown, against a model result (FIGS. 63A-B).

Figure 64:
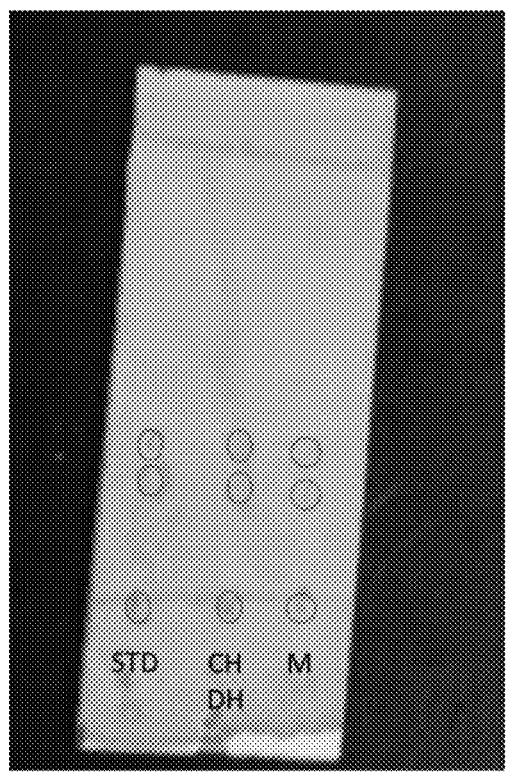
FIG. 64, originally from [5], demonstrates Thin Layer Chromatography of a standard control of violacein, a TX-TL reaction with all components at 4 nM with the exception of vioC and vioD at 6.5 nM, and a TX-TL reaction with all components at 4 nM.

Example 57: Metabolic Pathway Engineering in Cell-Free Systems, Using Violacein: Confirming Production Using Thin Layer Chromatography To analyze the metabolites, one can also use thin layer chromatography. Three samples were compared: a violacein standard, a experiment where vioC and vioD were provided in increased concentration of 6.5 nM (CHDH) relative to other constructs at 4 nM, and an experiment where each construct is at 4 nM (M). Samples are eluted in 20% dichloromethane in methanol. The resulting run provided three separate spots, which are visualized under UV and had Rf values of 0.21 and 0.38. (FIG. 64).

Figure 65:
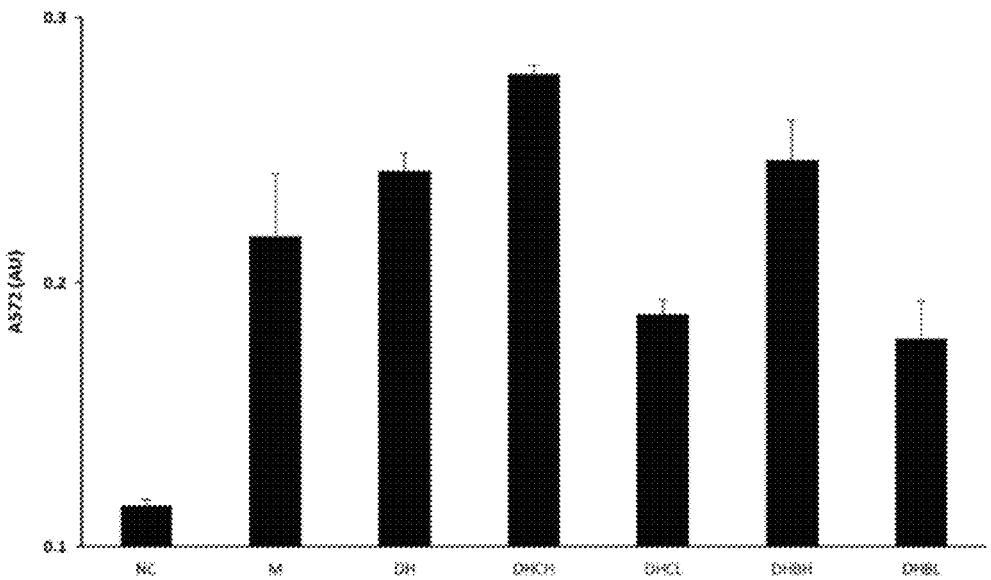
FIG. 65, originally from [5], demonstrates the production of crude violacein as determined by absorbance at 572 nm of different reactions with different amounts of linear DNA encoding for vioA, vioB, vioC, vioD, and vioE.

Example 58: Metabolic Pathway Engineering in Cell-Free Systems, Using Violacein: Design Space Exploration of Metabolic Pathway One can vary the concentration for the linear DNAs in order to conduct design space exploration. To do so, one can set the default pathway as 4 nM of each linear DNA, and then set low concentrations as 2.5 nM of linear DNA and high concentrations as 6.5 nM of linear DNA. Different combinations of low, medium, and high levels of linear DNA for each violacein coding sequence can then be added and analyzed using absorbance at 572 nm to quantitatively determine amount of crude violacein produced (as violacein intermediates can also be captured by this assay and is not distinguishable) (FIG. 65). By conducting this experiment, one finds that increasing VioD concentration can increase crude yield, as well as increasing independently VioC. VioB however does not affect crude yield. This suggests that in the pathway, the limiting reagent is VioC and VioD enzyme concentrations.

Figure 66:
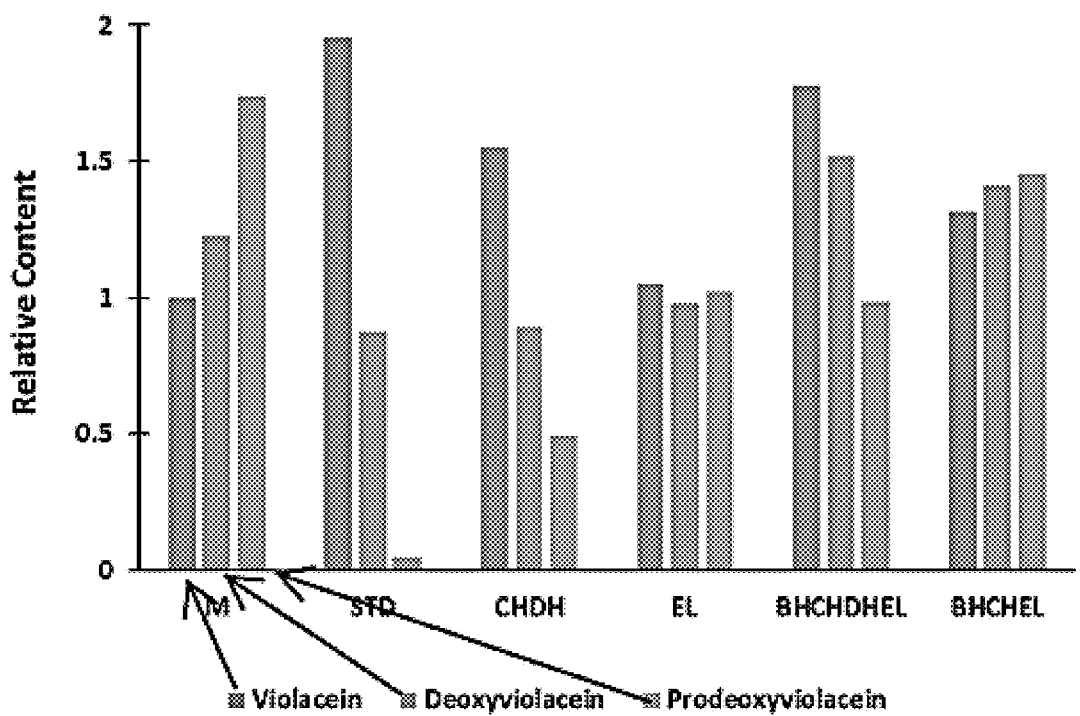
FIG. 66, originally from [5], demonstrates the production of violacein, deoxyviolacein, and prodeoxyviolacein as measured by LC-MS of different reactions with different amounts of linear DNA encoding for vioA, vioB, vioC, vioD, and vioE. In the bar chart (top), for each of "M", "STD", "CHDH", "EL", "BHCHDHEL", and "BHCHEL" the left bar is measuring violacein, the middle bar is measuring deoxyviolacein, and the right bar is measuring prodeoxyviolacein.

To distinguish between vioalcein and intermediates, as well as attempt to increase concentration of violacein production, one can use LC-MS to analyze specific production of violacein. Different concentrations of vioB, vioC, vioD, and vioE are increased and decreased and the final violacein concentration, deoxyviolacein concentration, and prodeoxyviolacein concentration is measured (FIG. 66). As supported by the previous figure, high VioC and VioD can produce more violacein and less prodeoxyviolacein compared to all enzymes at regular (4 nM linear DNA concentration). While other modifications changed violacein yield, it is hard to determine without future experiments their exact effect.

Example 59: Metabolic Pathway Engineering in Cell-Free Systems, Using Violacein: Discussion of Results and In Vivo Target Environment Prediction By using TX-TL to vary concentrations of linear DNA cassettes encoding for enzymes of the violacein pathway, one can explore bottlenecks in the pathway and productin of intermediates. One finds that removal of intermediate enzymes results in different colored components (eg. non-violacein products), while vioC and vioD are the production bottlenecks in the pathway, that if increased can remove a buildup of prodeoxyviolacein.

The omitting of each of the enzymes and their characteristic resulting color indicates that each enzyme is necessary for the production of violacein. Therefore, if the circuit is run in vivo, we expect that the result obtained in vivo would be the same as in vitro; eg. removal of the any of the enzymes in the pathway would cause the buildup of the intermediate and significantly less violacein than if all enzymes were present. We expect that, if the samples done in vivo with knockout versions of each enzyme were collected, the metabolites would show the characteric color as in FIG. 59. We also expect that all else equal, if there is a buildup of prodeoxyviolacein, that buildup can be resolved by increasing the concentration of vioC and vioD, and that vioC and vioD may be the rate-limiting step in vivo if all enzymes are provided at a same DNA encoding concentration.

VioC and VioD as the rate-limited step in TX-TL is further supported by the experiments conducted where vioC and vioD increases in linear DNA improved yields, as measured by crue violacein concentration and by LC-MS of violacein and intermediates. This is in contract to the modification of vioB, which had no significant effect, as expected due to the position of vioB upstream of the pathway.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified methods and arrangements to additional genetic circuit, related nodes, molecular components, sets of polynucleotides, polypeptides and/or metabolites, in according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P1818-US-Sequence-Listing-ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Mutalik, V. K., et al., *Precise and reliable gene expression via standard transcription and translation initiation elements*. Nat Methods, 2013. 10(4): p. 354-60.
2. Stanton, B. C., et al., Genomic mining of prokaryotic repressors for orthogonal logic gates. Nat Chem Biol, 2014. 10(2): p. 99-105.
3. Elowitz, M. B. and S. Leibler, *A synthetic oscillatory network of transcriptional regulators*. Nature, 2000. 403 (6767): p. 335-8.
4. Lutz, R. and H. Bujard, *Independent and tight regulation of transcriptional units in Escherichia coli via the LacR/O, the TetR/O and AraC/I1-I2 regulatory elements*. Nucleic Acids Res, 1997. 25(6): p. 1203-10.
5. Nguyen, H. B., et al., *Design Space Exploration of the Violacein Pathway in Escherichia coli Based Transcription Translation Cell-Free System* (TX-77). bioRxiv, 2016.
6. Chen, Y.-J., et al., *Characterization of 582 natural and synthetic terminators and quantification of their design constraints*. Nat Methods, 2013. 10(7): p. 659-664.
7. Isaacs, F. J., et al., *Engineered riboregulators enable post-transcriptional control of gene expression*. Nature Biotechnology, 2004. 22(7): p. 841-847.
8. Chappell, J., et al., *The centrality of RNA for engineering gene expression*. Biotechnology Journal, 2013. 8(12): p. 1379-1395.
9. Brewster, R. C., et al., *The transcription factor titration effect dictates level of gene expression*. Cell, 2014. 156(6): p. 1312-23.
10. Moon, T. S., et al., *Genetic programs constructed from layered logic gates in single cells. Nature*, 2012. 491 (7423): p. 249-53.
11. Shin, J. and V. Noireaux, *An E. coli cell-free expression toolbox: application to synthetic gene circuits and artificial cells*. ACS Synth Biol. 2012. 1(1): p. 29-41.
12. Mangan, S. and U. Alon, *Structure and function of the feed-forward loop network motif*. Proc Natl Acad Sci USA, 2003. 100(21): p. 11980-5.
13. Hooshangi, S., S. Thiberge, and R. Weiss, *Ultrasensitivity and noise propagation in a synthetic transcriptional cascade*. Proc Natl Acad Sci USA, 2005. 102(10): p. 3581-6.
14. Gardner, T. S., C. R. Cantor, and J. J. Collins, *Construction of a genetic toggle switch in Escherichia coli*. Nature, 2000. 403(6767): p. 339-42.
15. Sun, Z. Z., *Protocols for Implementing an Escherichia coli Based TX-77. Cell-Free Erpression System for Synthetic Biology*. Journal of Visualized Experiments, 2013. 79.
16. Jiang, P. X., et al., *Reconstruction of the violacein biosynthetic pathway from Duganella sp. B2 in different heterologous hosts*. Appl Microbiol Biotechnol, 2010. 86(4): p. 1077-88.
17. Yim, H., et al., *Metabolic engineering of Escherichia coli for direct production of 1,4-butanediol*. Nat Chem Biol, 2011. 7(7): p. 445-52.
18. Paddon, C. J., et al., *High-level semi-synthetic production of the potent antimalarial artemisinin*. Nature, 2013. 496(7446): p. 528-32.
19. Jaitzig, J., et al., *Reconstituted biosynthesis of the nonribosomal macrolactone antibiotic valinomycin in Escherichia coli*. ACS Synth Biol, 2014. 3(7): p. 432-8.

20. Del Vecchio, D. and R. M. Murray, *Biomolecular feedback systems*. 2015, Princeton: Princeton University Press. vi, 275 pages.
21. Hucka, M., et al., *The systems biology markup language (SBML): a medium for representation and exchange of biochemical network models*. Bioinformatics, 2003. 19(4): p. 524-31.
22. Sun, Z. Z., et al., *Protocols for Implementing an Escherichia Coli Based TX-TL Cell-Free Expression System for Synthetic Biology*. Journal of Visualized Experiments, 2013. e50762.
23. Zubay, G., *In-Vitro Synthesis of Protein in Microbial Systems*. Annual Review of Genetics, 1973. 7: p. 267-287.
24. Shimizu, Y., et al., *Cell-free translation reconstituted with purified components*. Nature Biotechnology, 2001. 19(8): p. 751-755.
25. Vinarov, D. A., C. L. L. Newman, and J. L. Markley, *Wheat germ cell-free platform for eukaryotic protein production*. FEBS Journal, 2006. 273(18): p. 4160-4169.
26. Lodish, H. F., R. Weinberg, and H. L. Ozer, *Translation of mRNA from simian virus 40-infected cells into simian virus 40 capsid protein by cell-free extracts*. Journal of Virology, 1974. 13(3): p. 590-595.
27. Niederholtmeyer, H., V. Stepanova, and S. J. Maerkl, *Implementation of cell-free biological networks at steady state*. Proc Natl Acad Sci USA, 2013.
28. Pardee, K., et al., *Paper-based synthetic gene networks*. Cell, 2014. 159(4): p. 940-54.
29. Atsumi, S., et al., *Metabolic engineering of Escherichia coli for 1-butanol production*. Metab Eng, 2008. 10(6): p. 305-311.
30. Wagner, E. G., S. Altuvia, and P. Romby, *Antisense RNAs in bacteria and their genetic elements*. Adv Genet, 2002. 46: p. 361-98.
31. Winkler, W., A. Nahvi, and R. R. Breaker, *Thiamine derivatives bind messenger RNAs directly to regulate bacterial gene expression*. Nature, 2002. 419(6910): p. 952-6.
32. Lee, T. S., et al., *BglBrick vectors and datasheets: A synthetic biology platform for gene expression*. J Biol Eng, 2011. 5: p. 12.
33. Shin, J. and V. Noireaux, *Efficient cell-free expression with the endogenous E. Coli RNA polymerase and sigma factor 70*. J Biol Eng, 2010. 4: p. 8.
34. Whitaker, W. R., et al., *Engineering robust control of two-component system phosphotransfer using modular scaffolds*. Proc Natl Acad Sci USA, 2012. 109(44): p. 18090-5.
35. Karzbrun, E., et al., *Synthetic biology. Programmable on-chip DNA compartments as artificial cells*. Science, 2014. 345(6198): p. 829-32.
36. Zawada, J. F., et al., *Microscale to manufacturing scale-up of cell-free cytokine production—a new approach for shortening protein production development timelines*. Biotechnol Bioeng, 2011. 108(7): p. 1570-8.
37. Meyer, B. J., R. Maurer, and M. Ptashne, *Gene regulation at the right operator (OR) of bacteriophage lambda. II. OR1, OR2, and OR3: their roles in mediating the effects of repressor and cro*. J Mol Biol, 1980. 139(2): p. 163-94.
38. Sun, Z. Z., et al., *Linear DNA for Rapid Prototyping of Synthetic Biological Circuits in an Escherichia coli Based TX-TL Cell-Free System*. ACS Synth Biol, 2014. 3(6): p. 387-397.
39. Martin, A., T. A. Baker, and R. T. Sauer, *Rebuilt AAA+motors reveal operating principles for ATP-fuelled machines*. Nature, 2005. 437(7062): p. 1115-20.
40. Davis, J. H., T. A. Baker, and R. T. Sauer, *Engineering synthetic adaptors and substrates for controlled ClpXP degradation*. J Biol Chem, 2009. 284(33): p. 21848-55.
41. Gibson, D. G., et al., *Enzymatic assembly of DNA molecules up to several hundred kilobases*. Nat Methods, 2009. 6(5): p. 343-5.
42. Engler, C., R. Kandzia, and S. Marillonnet, *A one pot, one step, precision cloning method with high throughput capability*. PLoS One, 2008. 3(11): p. e3647.
43. Baker, T. A. and R. T. Sauer, *ClpXP, an ATP-powered unfolding and protein-degradation machine*. Biochim Biophys Acta, 2012. 1823(1): p. 15-28.
44. Chappell, J., K. Jensen, and P. S. Freemont, *Validation of an entirely in vitro approach for rapid prototyping of DNA regulatory elements for synthetic biology*. Nucleic Acids Res, 2013. 41(5): p. 3471-81.
45. Tamsir, A., J. J. Tabor, and C. A. Voigt, *Robust multicellular computing using genetically encoded NOR gates and chemical 'wires'* Nature, 2011. 469(7329): p. 212-5.
46. Wurtzel, O., et al., *The single-nucleotide resolution transcriptome of Pseudomonas aeruginosa grown in body temperature*. PLoS Pathog, 2012. 8(9): p. e1002945.
47. Schuster, M., M. L. Urbanowski, and E. P. Greenberg, *Promoter specificity in Pseudomonas aeruginosa quorum sensing revealed by DNA binding of purified LasR*. Proc Natl Acad Sci USA, 2004. 101(45): p. 15833-9.
48. Mutalik, V. K., et al., *Precise and reliable gene expression via standard transcription and translation initiation elements*. Nat Meth, 2013. 10(4): p. 354-360.
49. Sun, Z. Z., et al., *Linear DNA for rapid prototyping of synthetic biological circuits in ar Escherichia coli based TX-TL cell-free system*. ACS Synth Biol, 2013.
50. Casini, A., et al., *R2oDNA Designer: Computational Design of Biologically Neutral Synthetic DNA Sequences*. ACS Synth Biol, 2014. 3(8): p. 525-528.
51. Stricker, J., et al., *A fast, robust and tunable synthetic gene oscillator*. Nature, 2008. 456(7221): p. 516-9.
52. Fitzwater, T., et al., *Conditional high copy number ColE1 mutants: resistance to RNAJ inhibition in vivo and in vitro*. The EMBO journal, 1988. 7(10): p. 3289-3297.
53. Wang, P., et al., *Robust growth of Escherichia coli*. Curr Biol, 2010. 20(12): p. 1099-103.
54. Preibisch, S., S. Saalfeld, and P. Tomancak, *Globally optimal stitching of tiled 3D microscopic image acquisitions*. Bioinformatics, 2009. 25(11): p. 1463-1465.
55. Schindelin, J., et al., *Fiji: an open-source platform for biological-image analysis*. Nat Methods, 2012. 9(7): p. 676-682.
56. Hori, Y., M. Takada, and S. Hara, *Biochemical oscillations in delayed negative cyclic feedback: Existence and profiles*. Automatica, 2013. 49(9): p. 2581-2590.
57. Hori, Y., T.-H. Kim, and S. Hara, *Existence criteria of periodic oscillations in cyclic gene regulatory networks*. Automatica, 2011. 47(6): p. 1203-1209.
58. Niederholtmeyer, H., et al., *Rapid cell-free forward engineering of novel genetic ring oscillators*. eLife, 2015.
59. Rosenfeld, N., et al., *Gene regulation at the single-cell level*. Science, 2005. 307(5717): p. 1962-1965.
60. Cookson, N. A., et al., *Queueing up for enzymatic processing: correlated signaling through coupled degradation*. Mol Syst Biol, 2011. 7: p. 561.
61. Prindle, A., et al., *Rapid and tunable post-translational coupling of genetic circuits*. Nature, 2014. 508(7496): p. 387-91.
62. Smith, H., *Oscillations and multiple steady states in a cyclic gene model with repression*. Journal of mathematical biology, 1987. 25(2): p. 169-190.

63. Ceroni, F., et al., *Quantifying cellular capacity identifies gene expression designs with reduced burden.* Nat Methods, 2015. 12(5): p. 415-418.
64. Danino, T., et al., *A synchronized quorum of genetic clocks.* Nature, 2010. 463(7279): p. 326-30.
65. Prindle, A., et al., *A sensing array of radically coupled genetic/'biopixels ' Nature,* 2012. 481(7379): p. 39-44.
66. Kiviet, D. J., et al., *Stochasticity of metabolism and growth at the single-cell level.* Nature, 2014. 514(7522): p. 376-379.
67. Shin, J. and V. Noireaux, *Study of messenger RNA inactivation and protein degradation in an Escherichia coli cell-free expression system.* J Biol Eng, 2010. 4: p. 9.
68. Murphy, K. C., *The lambda Gain protein inhibits RecBCD binding to dsDNA ends.* J Mol Biol, 2007. 371(1): p. 19-24.
69. Sitaraman, K., et al., *A novel cell-free protein synthesis system.* J Biotechnol, 2004. 110(3): p. 257-63.
70. Pachuk, C. J., et al., *Chain reaction cloning: a one-step method for directional ligation of multiple DNA fragments.* Gene, 2000. 243(1-2): p. 19-25.
71. Sarrion-Perdigones. A., et al., *GoldenBraid: an iterative cloning system for standardized assembly of reusable genetic modules.* PLoS One, 2011. 6(7): p. e21622.
72. Ro, D. K., et al., *Production of the antimalarial drug precursor artemisinic acid in engineered yeast.* Nature, 2006. 440(7086): p. 940-3.
73. Lee, M. E., et al., *Expression-level optimization of a multi-enzyme pathway in the absence of a high-throughput assay.* Nucleic Acids Res, 2013. 41(22): p. 10668-78.
74. Kwon, Y.-C. and M. C. Jewett, *High-throughput preparation methods of crude extract for robust cell-free protein synthesis.* Scientific reports, 2015. 5: p. 8663.
75. Balibar, C. J. and C. T. Walsh, *In vitro biosynthesis of violacein from L-tryptophan by the enzymes VioA-E from Chromobacterium violaceum.* Biochemistry, 2006. 45(51): p. 15444-57.

The invention claimed is:

1. A method of building in a cell-free system a genetic circuit operative in a target environment, the method comprising:
   (a) providing a plurality of linear DNAs, each linear DNA capable of reacting in a cell-free system to express a molecular component of a genetic circuit, wherein the molecular component is connected to another molecular component in accordance to a circuit design having at least two biochemical reactions, in which at least one molecular component is a reportable molecular component detectable in the cell-free system and in a target environment when the genetic circuit operates according to the circuit design;
   (b) providing a model to represent the genetic circuit;
   (c) testing combinations of the plurality of linear DNAs under conditions of the target environment in separate cell-free mixtures, so as to select combinations of linear DNAs capable of reacting in the cell-free system to provide the molecular components of the genetic circuit under conditions of the target environment;

(d) iterating steps (a)-(c) until the selected combinations of linear DNAs are able to produce molecular components that match the model; wherein between successive iterations, one or more of the following are being varied: cell-free extracts, energy buffers, additional chemicals at different concentrations, temperature, incubation time, concentration of the linear DNAs, sequence of the linear DNAs, and buffer conditions; and (e) contacting the selected combinations with a cell-free mixture, and retesting the selected combinations so as to select a final combination of linear DNAs capable of providing in the cell-free system the reportable molecular component of the genetic circuit operative in the target environment.

2. The method of claim 1, wherein the circuit design comprise one or more motifs selected from a feed forward loop, a cascade, an oscillator, and a metabolic pathway.

3. The method of claim 1, wherein the reportable molecular component provides the output of the genetic circuit according to the circuit design.

4. The method of claim 1, wherein the cell-free system is a transcription-translation (TX-TL) system.

5. The method of claim 1, wherein the testing step comprises:
generating differential equation models for each molecular component of the genetic circuit;
characterizing each molecular component in silico;
assembling in silico two or more molecular components into the genetic circuit; and
simulating the genetic circuit under a plurality of conditions.

6. The method of claim 5, wherein the characterizing step comprises:
subjecting each molecular component to the plurality of conditions in a mathematical model and in the cell-free mixture; and
fitting the mathematical model based on the cell-free mixture.

7. The method of claim 1, wherein the testing is performed by in parallel testing of two or more combinations.

8. The method of claim 1, wherein each linear DNA is capable of reacting in the cell-free system to provide a predetermined molecular component of the genetic circuit under the conditions of the target environment.

9. The method of claim 8, further comprising:
testing each linear DNA in separate cell-free mixtures, under the conditions of the target environment.

10. The method of claim 9, wherein the testing of each linear DNA in said separate cell-free mixtures, is performed by in parallel testing.

11. The method of claim 9, further comprising:
providing a variation of the genetic circuit by replacing one or more molecular components of the genetic circuit with a replacement molecular component, thus providing a variated circuit.

12. The method of claim 11, further comprising:
iterating the testing each linear DNA step and/or the testing step on the variated genetic circuit and the providing a variation step, to debug in the cell-free system the genetic circuit to be operated in the target environment.

13. The method of claim 12, wherein the providing a variation step and/or the iterating step are performed in silico.

14. The method of claim 1, wherein the molecular components of the genetic circuit comprise at least one genetic molecular component and optionally one or more cellular molecular components, each genetic molecular component formed by a gene and an RNA transcribed from the gene or a portion thereof, and optionally a polypeptide translated from the transcribed RNA.

15. The method of claim 14, wherein the RNA is selected from a messenger RNA (mRNA), a short interfering RNA (siRNA), and an RNA capable of acting as a regulating factor in a cellular environment.

16. The method of claim 14, wherein genes of the at least one genetic molecular component are comprised within a same polynucleotide.

17. The method of claim 16, wherein the same polynucleotide is a linear DNA.

18. The method of claim 1, wherein the cell-free mixture comprises constituent components from the target environment.

19. The method of claim 1, further comprising designing the genetic circuit before the testing step.

20. The method of claim 1, further comprising:
providing a variation of the genetic circuit by replacing one or more molecular components of the genetic circuit with a replacement molecular component from the selected combinations, thus resulting in a variated genetic circuit.

21. The method of claim 20, further comprising:
iterating the testing step on the variated genetic circuit and the providing a variation step, to debug in the cell-free system the genetic circuit to be operated in the target environment.

22. The method of claim 21, wherein the providing a variation step and/or the iterating step are performed in silico.

23. An arrangement to build in a cell-free system a genetic circuit to be operated in a target environment in accordance with the method of claim 1, the arrangement comprising the final combination of linear DNAs.

24. The method of claim 1, wherein the circuit design produces a natural product.

25. The method of claim 24, wherein the natural product is violacein.

26. A method of building in a cell-free system a genetic circuit operative in a target environment, the method comprising:
(a) providing a plurality of linear DNAs, each linear DNA capable of reacting in a cell-free system to express a molecular component of a genetic circuit, wherein the molecular component is connected to another molecular component in accordance to a circuit design having at least two biochemical reactions, in which at least one molecular component is a reportable molecular component detectable in the cell-free system and in a target environment when the genetic circuit operates according to the circuit design;
(b) providing a model to represent the genetic circuit;
(c) testing combinations of the plurality of linear DNAs under conditions of the target environment in separate cell-free mixtures, so as to select combinations of linear DNAs capable of reacting in the cell-free system to provide the molecular components of the genetic circuit under conditions of the target environment;
(d) iterating steps (a)-(c) until the selected combinations of linear DNAs are able to produce molecular components that match the model; wherein between successive iterations, one or more of the following are being varied: cell-free extracts, energy buffers, additional chemicals at different concentrations, temperature, incubation time, concentration of the linear DNAs, sequence of the linear DNAs, and buffer conditions;

(e) simulating the genetic circuit in silico to predict its dynamic behavior under various experimental conditions, and comparing simulation results to experimental data from step (c), so as to debug and modify one or more molecular components as needed; and (f) contacting the selected combinations with a cell-free mixture, and retesting the selected combinations so as to select a final combination of linear DNAs capable of providing in the cell-free system the reportable molecular component of the genetic circuit operative in the target environment.

27. The method of claim 26, wherein the circuit design produces a natural product.

28. The method of claim 27, wherein the natural product is violacein.

* * * * *

```
                         SEQUENCE LISTING

<160> NUMBER OF SEQ ID NOS: 53

<210> SEQ ID NO 1
<211> LENGTH: 3466
<212> TYPE: DNA
<213> ORGANISM: Artificial Sequence
<220> FEATURE:
<223> OTHER INFORMATION: synthetic polynucleotide

<400> SEQUENCE: 1
atgcatgttt gtcttcttga tcgggcacgt aagaggttcc aactttcacc ataatgaaat      60
aagatcacta ccgggcgtat tttttgagtt atcgagattt tcaggagcta aggaagctaa     120
aatgcgctca cgcaactggt ccagaacctt gaccgaacgc agcggtggta acggcgcagt     180
ggcggttttc atggcttgtt atgactgttt ttttggggta cagtctatgc ctcgggcatc     240
caagcagcaa gcgcgttacg ccgtgggtcg atgtttgatg ttatggagca gcaacgatgt     300
tacgcagcag ggcagtcgcc ctaaaacaaa gttaaacatc atgagggaag cggtgatcgc     360
cgaagtatcg actcaactat cagaggtagt tggcgtcatc gagcgccatc tcgaaccgac     420
gttgctggcc gtacatttgt acggctccgc agtggatggc ggcctgaagc cacacagtga     480
tattgatttg ctggttacgg tgaccgtaag gcttgatgaa acaacgcggc gagctttgat     540
caacgacctt ttggaaactt cggcttcccc tggagagagc gagattctcc gcgctgtaga     600
agtcaccatt gttgtgcacg acgacatcat tccgtggcgt tatccagcta agcgcgaact     660
gcaatttgga gaatggcagc gcaatgacat tcttgcaggt atcttcgagc cagccacgat     720
cgacattgat ctggctatct tgctgacaaa agcaagagaa catagcgttg ccttggtagg     780
tccagcggcg gaggaactct ttgatccggt tcctgaacag gatctatttg aggcgctaaa     840
tgaaaccttg acgctatgga actcgccgcc cgactgggct ggcgatgagc gaaatgtagt     900
gcttacgttg tcccgcattt ggtacagcgc agtaaccggc aaaatcgcgc cgaaggatgt     960
cgctgccgac tgggcaatgg agcgcctgcc ggcccagtat cagcccgtca tacttgaagc    1020
tagacaggct tatcttggac aagaagaaga tcgcttggcc tcgcgcgcag atcagttgga    1080
agaatttgtc cactacgtga aaggcgagat caccaaggta gtcggcaaat aatttgatat    1140
cgagctcgct tggactcctg ttgatagatc cagtaatgac ctcagaactc catctggatt    1200
tgttcagaac gctcggttgc cgccgggcgt tttttattgg tgagaatcca agcctcggtg    1260
```

```
agaatccaag cctcgatcaa cgtctcattt tcgccaaaag ttggcccagg gcttcccggt   1320
atcaacaggg acaccaggat ttatttattc tgcgaagtga tcttccgtca caggtattta   1380
ttcggcgcaa agtgcgtcgg gtgatgctgc caacttactg atttagtgta tgatggtgtt   1440
tttgaggtgc tccagtggct tctgtttcta tcagctgtcc ctcctgttca gctactgacg   1500
gggtggtgcg taacggcaaa agcaccgccg acatcagcg gtagcggagt gtatactggc   1560
ttactatgtt ggcactgatg agggtgtcag tgaagtgctt catgtggcag agaaaaaag   1620 gctgcaccgg tgcgtcagca gaatatgtga tacaggatat attccgcttc ctcgctcact   1680
gactcgctac gctcggtcgt tcgactgcgg cgagcggaaa tggcttacga acggggcgga   1740
gatttcctgg aagatgccag gaagatactt aacagggaag tgagagggcc gcggcaaagc   1800
cgttttccca taggctccgc cccctgaca agcatcacga atctgacgc tcaaatcagt   1860 ggtggcgaaa cccgacagga ctataaagat accaggcgtt tcccctggc ggctccctcg   1920 tgcgctctcc tgttcctgcc tttcggttta ccggtgtcat tccgctgtta tggccgcgtt   1980
tgtctcattc cacgcctgac actcagttcc gggtaggcag ttcgctccaa gctgactgt   2040 atgcacgaac cccccgttca gtccgaccgc tgcgccttat ccggtaacta tcgtcttgag   2100
tccaacccgg aaagacatgc aaaagcacca ctggcagcag ccactggtaa ttgatttaga   2160
ggagttagtc ttgaagtcat gcgccggtta aggctaaact gaaaggacaa gttttggtga   2220
ctgcgctcct ccaagccagt tacctcggtt caaagagttg gtagctcaga gaaccttcga   2280
aaaaccgccc tgcaaggcgg ttttttcgtt ttcagagcaa gagattacgc gcagaccaaa   2340
acgatctcaa gaagatcatc ttattaatca gataaaatat ttctagattt cagtgcaatt   2400
tatctcttca aatgtagcac ctgaagtcag ccccatacga tataagttgt aattctcatg   2460
tttgacagct tatcatcgat aagcttccga tggcgcgccg agaggcttta cactttatgc   2520
ttccggctga agacaaggca cgactctcaa ggacagaaaa gcccgccttt cggcgggctt   2580
tgagttcatt attagagagt aataagaccc aaattaacgg ccataatggc cgctacgcgg   2640
cgggaggtca caccgaactt ccgccgaata tttcccatat ggaagttcac attggcttcc   2700
gagcagttgc agataaccga tatctcccaa ctggtcttgc cgatggcgca ccactgcaac   2760
acttccttct cccggctggt cagaaccacc ggtttgctga ccggatgttc gaaggccagt   2820
ccggcaccgc tttgcagtgc gtagtccttg agcatccaca gggtcggcag gaccgactct   2880
atgaaacggt tggcctcggc ccggttttcc gcttccacgc tgaggctcag cgcgccgagt   2940
tcgccgcgag caccatgcag cggcatggtc agcccataca ccaggccggc ggccgaggct   3000
tcctcgaaga actcgtgctg ctttcgcgtc tggtagatgg acggttccca gaaaatcggc   3060
agtacgctct gggtacagtg actgaccgtc ggtcgaccc gcgcgtagcc agcccggtcg   3120
taatgctcgc gccaggcggc cgggtagttg ccgacgatga aggcgttctc gtagtcctgg   3180
ctgtccttag gcaacaggcc gaacaggatc ttcgagaatc caaggtcgct cgccatcttc   3240
tggaggatgg cgctccactc caattttcca cttgagcgtt ccagctcaag aaaaccgtca   3300
accaaggcca ttagaaactt tcctcagcat gattaagatg tttcagtacg aaaattgctt   3360
tcattgttga tctcctttt aagtgaactt gggcccgctt gctgtgctca gtatcttgtt   3420
atccgctcac aatgtcaatg ttatccgctc acatttatga acagca              3466
```

<210> SEQ ID NO 2
<211> LENGTH: 3277
<212> TYPE: DNA
<213> ORGANISM: Artificial Sequence
<220> FEATURE:
<223> OTHER INFORMATION: synthetic polynucleotide

<400> SEQUENCE: 2

| | | | | |
|---|---|---|---|---|
| gcattgctgt | tcaactagca | aatgagatag | atttcggtga | acccggaccc ttgctaggct | 60 |
| cgatccctat | cagtgataga | gaagcgggcc | caagttcact | taaaaaggag atcaacaatg | 120 |
| aaagcaattt | tcgtactgaa | acatcttaat | catgctaagg | aggttttcta atggagcttt | 180 |
| tcactggcgt | tgttcccatc | ctggtcgagc | tggacggcga | cgtaaacggc cacaagttca | 240 |
| gcgtgtccgg | cgagggcgag | ggcgatgcca | cctacggcaa | gctgaccctg aagttcatct | 300 |
| gcaccaccgg | caagctgccc | gtgccctggc | ccaccctcgt | gaccaccctg acctacggcg | 360 |
| tgcagtgctt | cagccgctac | cccgaccaca | tgaagcagca | cgacttcttc aagtccgcca | 420 |
| tgcccgaagg | ctacgtccag | gagcgcacca | tcttcttcaa | ggacgacggc aactacaaga | 480 |
| cccgcgccga | ggtgaagttc | gagggcgaca | ccctggtgaa | ccgcatcgag ctgaagggca | 540 |
| tcgacttcaa | ggaggacggc | aacatcctgg | ggcacaagct | ggagtacaac tacaacagcc | 600 |
| acaacgtcta | tatcatggcc | gacaagcaga | agaacggcat | caaggtgaac ttcaagatcc | 660 |
| gccacaacat | cgaggacggc | agcgtgcagc | tcgccgacca | ctaccagcag aacacccccca | 720 |
| tcggcgacgg | ccccgtgctg | ctgcccgaca | accactacct | gagcacccag tccgccctga | 780 |
| gcaaagaccc | caacgagaag | cgcgatcaca | tggtcctgct | ggagttcgtg accgccgccg | 840 |
| ggatcgcagc | aaacgacgaa | aactacgctt | tagctgctta | atgaactcgc aaaaaacccc | 900 |
| gcttcggcgg | ggttttttcg | cccttgagag | tcgggcattg | tcttcgctcc ttccggtggg | 960 |
| cgcggggcat | gactatcgtc | gccgcactta | tgactgtgtt | ctttatcatg caactcgtag | 1020 |
| gacaggtgcc | ggcagcgctc | ttccgcttcc | tcgctcactg | actcgctgcg ctcggtcgtt | 1080 |
| cggctgcggc | gagcggtatc | agctcactca | aaggcggtaa | tacggttatc cacagaatca | 1140 |
| ggggataacg | caggaaagaa | catgtgagca | aaaggccagc | aaaaggccag gaaccgtaaa | 1200 |
| aaggccgcgt | tgctggcgtt | tttccatagg | ctccgccccc | ctgacgagca tcacaaaaat | 1260 |
| cgacgctcaa | gtcagaggtg | gcgaaacccg | acaggactat | aaagatacca ggcgtttccc | 1320 |
| cctggaagct | ccctcgtgcg | ctctcctgtt | ccgaccctgc | cgcttaccgg atacctgtcc | 1380 |
| gcctttctcc | cttcgggaag | cgtggcgctt | tctcatagct | cacgctgtag gtatctcagt | 1440 |
| tcggtgtagg | tcgttcgctc | caagctgggc | tgtgtgcacg | aaccccccgt tcagcccgac | 1500 |
| cgctgcgcct | tatccggtaa | ctatcgtctt | gagtccaacc | cggtaagaca cgacttatcg | 1560 |
| ccactggcag | cagccactgg | taacaggatt | agcagagcga | ggtatgtagg cggtgctaca | 1620 |
| gagttcttga | agtggtggcc | taactacggc | tacactagaa | gaacagtatt tggtatctgc | 1680 |
| gctctgctga | agccagttac | cttcggaaaa | agagttggta | gctcttgatc cggcaaacaa | 1740 |
| accaccgctg | gtagcggtgg | tttttttgtt | tgcaagcagc | agattacgcg cagaaaaaaa | 1800 |
| ggatctcaag | aagatccttt | gatcttttct | acggggtctg | acgctcagtg gaacgaaaac | 1860 |
| tcacgttaag | ggattttggt | catgagatta | tcaaaaagga | tcttcaccta gatccttta | 1920 |
| aattaaaaat | gaagttttaa | atcaatctaa | agtatatatg | agtaaacttg gtctgacagt | 1980 |
| taccaatgct | taatcagtga | ggcacctatc | tcagcgatct | gtctatttcg ttcatccata | 2040 |
| gttgcctgac | tccccgtcgt | gtagataact | acgatacggg | agggcttacc atctggcccc | 2100 |
| agtgctgcaa | tgataccgcg | tgacccacgc | tcaccggctc | cagatttatc agcaataaac | 2160 |
| cagccagccg | gaagggccga | gcgcagaagt | ggtcctgcaa | ctttatccgc ctccatccag | 2220 |

| | |
|---|---|
| tctattaatt gttgccggga agctagagta agtagttcgc cagttaatag tttgcgcaac | 2280 |
| gttgttgcca ttgctacagg catcgtggtg tcacgctcgt cgtttggtat ggcttcattc | 2340 |
| agctccggtt cccaacgatc aaggcgagtt gcatgatccc ccatgttgtg caaaaaagcg | 2400 |
| gttagctcct tcggtcctcc gatcgttgtc agaagtaagt tggccgcagt gttatcactc | 2460 |
| atggttatgg cagcactgca taattctctt actgtcatgc catccgtaag atgcttttct | 2520 |
| gtgactggtg agtactcaac caagtcattc tgagaatagt gtatgcggcg accgagttgc | 2580 |
| tcttgcccgg cgtcaacacg ggataatacc gcgccacata gcagaacttt aaaagtgctc | 2640 |
| atcattggaa aacgttcttc ggggcgaaaa ctctcaagga tcttaccgct gttgagatcc | 2700 |
| agttcgatgt aacccactcg tgcacccaac tgatcttcag catcttttac tttcaccagc | 2760 |
| gtttctgggt gagcaaaaac aggaaggcaa aatgccgcaa aaaagggaat aagggcgaca | 2820 |
| cggaaatgtt gaatactcat actcttcctt tttcaatatt attgaagcat ttatcagggt | 2880 |
| tattgtctca tgagcggata catatttgaa tgtatttaga aaaataaaca ataggggtt | 2940 |
| ccgcgcacat ttccccgaaa agtgccacct gacgtctaag aaaccattat tatcatgaca | 3000 |
| ttaacctata aaaataggcg tatcacgagg ccctttcgtg ttcaagaatt ctggcgaatc | 3060 |
| ctctgaccag ccagaaaacg acctttctgt ggtgaaaccg gatgctgcaa ttcagagcgc | 3120 |
| cagcaagtgg gggacagcag atgacctgac cgccgcagag tggatgtttg acatggtgat | 3180 |
| gactatcgca ccatcagcca gaaaaccgaa ttttgctggg tgggctaacg atatccgcct | 3240 |
| gatgcgtgaa cgtgacggac gtaacgaaga caaccac | 3277 |

<210> SEQ ID NO 3
<211> LENGTH: 3309
<212> TYPE: DNA
<213> ORGANISM: Artificial Sequence
<220> FEATURE:
<223> OTHER INFORMATION: synthetic polynucleotide

<400> SEQUENCE: 3

| | |
|---|---|
| gcattgctgt tcttcgagcc tagcaagggt ccgggttcac cgaaatctat ctcatttgct | 60 |
| agttataaaa ttatgaaatt tgcgtaaatt ccctatcagt gatagagatt cagaagcggg | 120 |
| cccaagttca cttaaaaagg agatcaacaa tgaaagcaat tttcgtactg aaacatctta | 180 |
| atcatgctaa ggaggttttc taatggagct tttcactggc gttgttccca tcctggtcga | 240 |
| gctggacggc gacgtaaacg gccacaagtt cagcgtgtcc ggcgagggcg agggcgatgc | 300 |
| cacctacggc aagctgaccc tgaagttcat ctgcaccacc ggcaagctgc ccgtgccctg | 360 |
| gcccaccctc gtgaccaccc tgacctacgg cgtgcagtgc ttcagccgct accccgacca | 420 |
| catgaagcag cacgacttct tcaagtccgc catgcccgaa ggctacgtcc aggagcgcac | 480 |
| catcttcttc aaggacgacg gcaactacaa gacccgcgcc gaggtgaagt tcgagggcga | 540 |
| caccctggtg aaccgcatcg agctgaaggg catcgacttc aaggaggacg gcaacatcct | 600 |
| ggggcacaag ctggagtaca actacaacag ccacaacgtc tatatcatgg ccgacaagca | 660 |
| gaagaacggc atcaaggtga acttcaagat ccgccacaac atcgaggacg gcagcgtgca | 720 |
| gctcgccgac cactaccagc agaacacccc catcggcgac ggccccgtgc tgctgcccga | 780 |
| caaccactac ctgagcaccc agtccgccct gagcaaagac cccaacgaga gcgcgatca | 840 |
| catggtcctg ctggagttcg tgaccgccgc cgggatcgca gcaaacgacg aaaactacgc | 900 |
| tttagctgct taatgaactc gcaaaaaacc ccgcttcggc ggggtttttt cgcccttgag | 960 |
| agtcgggcat tgtcttcgct ccttccggtg ggcgcggggc atgactatcg tcgccgcact | 1020 |

```
tatgactgtg ttctttatca tgcaactcgt aggacaggtg ccggcagcgc tcttccgctt   1080
cctcgctcac tgactcgctg cgctcggtcg ttcggctgcg gcgagcggta tcagctcact   1140
caaaggcggt aatacggtta tccacagaat caggggataa cgcaggaaag aacatgtgag   1200
caaaaggcca gcaaaaggcc aggaaccgta aaaaggccgc gttgctggcg tttttccata   1260
ggctccgccc ccctgacgag catcacaaaa atcgacgctc aagtcagagg tggcgaaacc   1320
cgacaggact ataaagatac caggcgtttc ccctggaag ctcccgtg cgctctcctg   1380 ttccgaccct gccgcttacc ggatacctgt ccgcctttct cccttcggga agcgtggcgc   1440
tttctcatag ctcacgctgt aggtatctca gttcggtgta ggtcgttcgc tccaagctgg   1500
gctgtgtgca cgaacccccc gttcagcccg accgctgcgc cttatccggt aactatcgtc   1560
ttgagtccaa cccggtaaga cacgacttat cgccactggc agcagccact ggtaacagga   1620
ttagcagagc gaggtatgta ggcggtgcta cagagttctt gaagtggtgg cctaactacg   1680
gctacactag aagaacagta tttggtatct gcgctctgct gaagccagtt accttcggaa   1740
aaagagttgg tagctcttga tccggcaaac aaaccaccgc tggtagcggt ggtttttttg   1800
tttgcaagca gcagattacg cgcagaaaaa aaggatctca agaagatcct ttgatctttt   1860
ctacggggtc tgacgctcag tggaacgaaa actcacgtta agggattttg gtcatgagat   1920
tatcaaaaag gatcttcacc tagatccttt taaattaaaa atgaagtttt aaatcaatct   1980
aaagtatata tgagtaaact tggtctgaca gttaccaatg cttaatcagt gaggcaccta   2040
tctcagcgat ctgtctattt cgttcatcca tagttgcctg actccccgtc gtgtagataa   2100
ctacgatacg ggagggctta ccatctggcc ccagtgctgc aatgataccg cgtgacccac   2160
gctcaccggc tccagattta tcagcaataa accagccagc cggaagggcc gagcgcagaa   2220
gtggtcctgc aactttatcc gcctccatcc agtctattaa ttgttgccgg gaagctagag   2280
taagtagttc gccagttaat agtttgcgca acgttgttgc cattgctaca ggcatcgtgg   2340
tgtcacgctc gtcgtttggt atggcttcat tcagctccgg ttcccaacga tcaaggcgag   2400
ttgcatgatc ccccatgttg tgcaaaaaag cggttagctc cttcggtcct ccgatcgttg   2460
tcagaagtaa gttggccgca gtgttatcac tcatggttat ggcagcactg cataattctc   2520
ttactgtcat gccatccgta agatgctttt ctgtgactgg tgagtactca accaagtcat   2580
tctgagaata gtgtatgcgg cgaccgagtt gctcttgccc ggcgtcaaca cgggataata   2640
ccgcgccaca tagcagaact ttaaaagtgc tcatcattgg aaaacgttct cggggcgaa   2700 aactctcaag gatcttaccg ctgttgagat ccagttcgat gtaacccact cgtgcaccca   2760
actgatcttc agcatctttt actttcacca gcgtttctgg gtgagcaaaa acaggaaggc   2820
aaaatgccgc aaaaaaggga ataagggcga cacggaaatg ttgaatactc atactcttcc   2880
tttttcaata ttattgaagc atttatcagg gttattgtct catgagcgga tacatatttg   2940
aatgtattta gaaaaataaa caataggggt tccgcgcac atttccccga aaagtgccac   3000
ctgacgtcta agaaaccatt attatcatga cattaaccta taaaaatagg cgtatcacga   3060
ggccctttcg tgttcaagaa ttctggcgaa tcctctgacc agccagaaaa cgacctttct   3120
gtggtgaaac cggatgctgc aattcagagc gccagcaagt gggggacagc agatgacctg   3180
accgccgcag agtggatgtt tgacatggtg atgactatcg caccatcagc cagaaaaccg   3240
aattttgctg ggtgggctaa cgatatccgc ctgatgcgtg aacgtgacgg acgtaacgaa   3300
gacaaccac                                                          3309
```

<210> SEQ ID NO 4
<211> LENGTH: 3309
<212> TYPE: DNA
<213> ORGANISM: Artificial Sequence
<220> FEATURE:
<223> OTHER INFORMATION: synthetic polynucleotide

<400> SEQUENCE: 4

```
gcattgctgt tcttcgagcc tagcaagggt ccgggttcac cgaaatctat ctcatttgct      60
agttataaaa ttatgaaatt tgcataaatt ccctatcagt gatagagatt cagaagcggg     120
cccaagttca cttaaaaagg agatcaacaa tgaaagcaat tttcgtactg aaacatctta     180
atcatgctaa ggaggttttc taatggagct tttcactggc gttgttccca tcctggtcga     240
gctggacggc gacgtaaacg gccacaagtt cagcgtgtcc ggcgagggcg agggcgatgc     300
cacctacggc aagctgaccc tgaagttcat ctgcaccacc ggcaagctgc ccgtgccctg     360
gcccaccctc gtgaccaccc tgacctacgg cgtgcagtgc ttcagccgct accccgacca     420
catgaagcag cacgacttct tcaagtccgc catgcccgaa ggctacgtcc aggagcgcac     480
catcttcttc aaggacgacg gcaactacaa gacccgcgcc gaggtgaagt tcgagggcga     540
caccctggtg aaccgcatcg agctgaaggg catcgacttc aaggaggacg gcaacatcct     600
ggggcacaag ctggagtaca actacaacag ccacaacgtc tatatcatgg ccgacaagca     660
gaagaacggc atcaaggtga acttcaagat ccgccacaac atcgaggacg gcagcgtgca     720
gctcgccgac cactaccagc agaacacccc catcggcgac ggccccgtgc tgctgcccga     780
caaccactac ctgagcaccc agtccgccct gagcaaagac cccaacgaga gcgcgatca     840 catggtcctg ctggagttcg tgaccgccgc cgggatcgca gcaaacgacg aaaactacgc     900
tttagctgct taatgaactc gcaaaaaacc ccgcttcggc ggggtttttt cgcccttgag     960
agtcgggcat tgtcttcgct ccttccggtg ggcgcgggc atgactatcg tcgccgcact    1020
tatgactgtg ttctttatca tgcaactcgt aggacaggtg ccggcagcgc tcttccgctt    1080
cctcgctcac tgactcgctg cgctcggtcg ttcggctgcg gcgagcggta tcagctcact    1140
caaaggcggt aatacggtta tccacagaat caggggataa cgcaggaaag aacatgtgag    1200
caaaaggcca gcaaaaggcc aggaaccgta aaaaggccgc gttgctggcg ttttttccata    1260 ggctccgccc ccctgacgag catcacaaaa atcgacgctc aagtcagagg tggcgaaacc    1320
cgacaggact ataaagatac caggcgtttc ccctggaag ctccctcgtg cgctctcctg    1380
ttccgaccct gccgcttacc ggatacctgt ccgcctttct cccttcggga agcgtggcgc    1440
tttctcatag ctcacgctgt aggtatctca gttcggtgta ggtcgttcgc tccaagctgg    1500
gctgtgtgca cgaaccccc gttcagcccg accgctgcgc cttatccggt aactatcgtc    1560
ttgagtccaa cccggtaaga cacgacttat cgccactggc agcagccact ggtaacagga    1620
ttagcagagc gaggtatgta ggcggtgcta cagagttctt gaagtggtgg cctaactacg    1680
gctacactag aagaacagta tttggtatct gcgctctgct gaagccagtt accttcggaa    1740
aaagagttgg tagctcttga tccggcaaac aaaccaccgc tggtagcggt ggtttttttg    1800
tttgcaagca gcagattacg cgcagaaaaa aaggatctca agaagatcct ttgatctttt    1860
ctacggggtc tgacgctcag tggaacgaaa actcacgtta agggattttg gtcatgagat    1920
tatcaaaaag gatcttcacc tagatccttt taaattaaaa atgaagtttt aaatcaatct    1980
aaagtatata tgagtaaact tggtctgaca gttaccaatg cttaatcagt gaggcaccta    2040
tctcagcgat ctgtctattt cgttcatcca tagttgcctg actccccgtc gtgtagataa    2100
```

```
ctacgatacg ggagggctta ccatctggcc ccagtgctgc aatgataccg cgtgacccac    2160
gctcaccggc tccagattta tcagcaataa accagccagc cggaagggcc gagcgcagaa    2220
gtggtcctgc aactttatcc gcctccatcc agtctattaa ttgttgccgg gaagctagag    2280
taagtagttc gccagttaat agtttgcgca acgttgttgc cattgctaca ggcatcgtgg    2340
tgtcacgctc gtcgtttggt atggcttcat tcagctccgg ttcccaacga tcaaggcgag    2400
ttgcatgatc ccccatgttg tgcaaaaaag cggttagctc cttcggtcct ccgatcgttg    2460
tcagaagtaa gttggccgca gtgttatcac tcatggttat ggcagcactg cataattctc    2520
ttactgtcat gccatccgta agatgctttt ctgtgactgg tgagtactca accaagtcat    2580
tctgagaata gtgtatgcgg cgaccgagtt gctcttgccc ggcgtcaaca cgggataata    2640
ccgcgccaca tagcagaact ttaaaagtgc tcatcattgg aaaacgttct cggggcgaa     2700 aactctcaag gatcttaccg ctgttgagat ccagttcgat gtaacccact cgtgcaccca    2760
actgatcttc agcatctttt actttcacca gcgtttctgg gtgagcaaaa acaggaaggc    2820
aaaatgccgc aaaaaaggga taagggcga cacggaaatg ttgaatactc atactcttcc    2880
tttttcaata ttattgaagc atttatcagg gttattgtct catgagcgga tacatatttg    2940
aatgtattta gaaaaataaa caaataggggg ttccgcgcac atttccccga aaagtgccac    3000
ctgacgtcta agaaaccatt attatcatga cattaaccta taaaaatagg cgtatcacga    3060
ggccctttcg tgttcaagaa ttctggcgaa tcctctgacc agccagaaaa cgacctttct    3120
gtggtgaaac cggatgctgc aattcagagc gccagcaagt gggggacagc agatgacctg    3180
accgccgcag agtggatgtt tgacatggtg atgactatcg caccatcagc cagaaaaccg    3240
aattttgctg ggtgggctaa cgatatccgc ctgatgcgtg aacgtgacgg acgtaacgaa    3300
gacaaccac                                                            3309

<210> SEQ ID NO 5
<211> LENGTH: 3593
<212> TYPE: DNA
<213> ORGANISM: Artificial Sequence
<220> FEATURE:
<223> OTHER INFORMATION: synthetic polynucleotide

<400> SEQUENCE: 5
gcattgctgt tctgcagcag cggatcgtcg gcgagcgtca cctgaagctg gtgctgaaaa      60
gcgaatgcgg ctcgctgcaa ctggatggca ttgccttcaa catcgaccgc gagcagtggc     120
ccaaccctac cgtgcgctgg gccgagctgg cctacaagct cgacgtcaac gaattccgcg     180
gccaggaaag cgtgcaactg atgatcgtcc acatggcccc tcgctgagcg cgtcccggag     240
ctgggggcaa cctagctgcc acctgctttt ctgctagcta ttccagcgaa acatacagaa     300
tttccggcga aatcaaggct acctgccagt tctggcaggt ttggccgcgg gttctttttg     360
gtccctatca gtgatagaga tacacgaaag caccgtcaag cgggcccaag ttcacttaaa     420
aaggagatca acaatgaaag caattttcgt actgaaacat cttaatcatg ctaaggaggt     480
tttctaatgg agcttttcac tggcgttgtt cccatcctgg tcgagctgga cggcgacgta     540
aacggccaca agttcagcgt gtccggcgag ggcgagggcg atgccaccta cggcaagctg     600
accctgaagt tcatctgcac caccggcaag ctgcccgtgc cctggcccac cctcgtgacc     660
accctgacct acggcgtgca gtgcttcagc cgctaccccg accacatgaa gcagcacgac     720
ttcttcaagt ccgccatgcc cgaaggctac gtccaggagc gcaccatctt cttcaaggac     780
```

```
gacggcaact acaagacccg cgccgaggtg aagttcgagg gcgacaccct ggtgaaccgc      840
atcgagctga agggcatcga cttcaaggag gacggcaaca tcctgggggca caagctggag     900 tacaactaca acagccacaa cgtctatatc atggccgaca gcagaagaa cggcatcaag       960 gtgaacttca agatccgcca caacatcgag gacggcagcg tgcagctcgc cgaccactac      1020
cagcagaaca cccccatcgg cgacggcccc gtgctgctgc ccgacaacca ctacctgagc      1080
acccagtccg ccctgagcaa agaccccaac gagaagcgcg atcacatggt cctgctggag      1140
ttcgtgaccg ccgccgggat cgcagcaaac gacgaaaact acgctttagc tgcttaatga      1200
actcgcaaaa aaccccgctt cggcgggggtt ttttcgccct tgagagtcgg gcattgtctt     1260
cgctccttcc ggtgggcgcg gggcatgact atcgtcgccg cacttatgac tgtgttcttt      1320
atcatgcaac tcgtaggaca ggtgccggca gcgctcttcc gcttcctcgc tcactgactc      1380
gctgcgctcg gtcgttcggc tgcggcgagc ggtatcagct cactcaaagg cggtaatacg      1440
gttatccaca gaatcagggg ataacgcagg aaagaacatg tgagcaaaag gccagcaaaa      1500
ggccaggaac cgtaaaaagg ccgcgttgct ggcgtttttc cataggctcc gccccccctga     1560 cgagcatcac aaaaatcgac gctcaagtca gaggtggcga acccgacag gactataaag       1620 ataccaggcg tttccccctg gaagctccct cgtgcgctct cctgttccga ccctgccgct      1680
taccggatac ctgtccgcct ttctcccttc gggaagcgtg gcgctttctc atagctcacg      1740
ctgtaggtat ctcagttcgg tgtaggtcgt tcgctccaag ctgggctgtg tgcacgaacc      1800
ccccgttcag cccgaccgct gcgccttatc cggtaactat cgtcttgagt ccaacccggt      1860
aagacacgac ttatcgccac tggcagcagc cactggtaac aggattagca gagcgaggta     1920
tgtaggcggt gctacagagt tcttgaagtg gtggcctaac tacggctaca ctagaagaac      1980
agtatttggt atctgcgctc tgctgaagcc agttaccttc ggaaaaagag ttggtagctc      2040
ttgatccggc aaacaaacca ccgctggtag cggtggtttt tttgtttgca agcagcagat      2100
tacgcgcaga aaaaaaggat ctcaagaaga tcctttgatc ttttctacgg ggtctgacgc      2160
tcagtggaac gaaaactcac gttaagggat tttggtcatg agattatcaa aaaggatctt      2220
cacctagatc cttttaaatt aaaaatgaag ttttaaatca atctaaagta tatatgagta      2280
aacttggtct gacagttacc aatgcttaat cagtgaggca cctatctcag cgatctgtct      2340
atttcgttca tccatagttg cctgactccc cgtcgtgtag ataactacga tacgggaggg      2400
cttaccatct ggccccagtg ctgcaatgat accgcgtgac ccacgctcac cggctccaga      2460
tttatcagca ataaaccagc cagccggaag ggccgagcgc agaagtggtc ctgcaacttt      2520
atccgcctcc atccagtcta ttaattgttg ccgggaagct agagtaagta gttcgccagt      2580
taatagtttg cgcaacgttg ttgccattgc tacaggcatc gtggtgtcac gctcgtcgtt      2640
tggtatggct tcattcagct ccggttccca acgatcaagg cgagttgcat gatcccccat      2700
gttgtgcaaa aaagcggtta gctccttcgg tcctccgatc gttgtcagaa gtaagttggc      2760
cgcagtgtta tcactcatgg ttatggcagc actgcataat tctcttactg tcatgccatc      2820
cgtaagatgc ttttctgtga ctggtgagta ctcaaccaag tcattctgag aatagtgtat      2880
gcggcgaccg agttgctctt gcccggcgtc aacacgggat aataccgcgc acatagcag      2940 aactttaaaa gtgctcatca ttggaaaacg ttcttcgggg cgaaaactct caaggatctt      3000
accgctgttg agatccagtt cgatgtaacc cactcgtgca cccaactgat cttcagcatc      3060
ttttactttc accagcgttt ctgggtgagc aaaaacagga aggcaaaatg ccgcaaaaaa      3120
gggaataagg gcgacacgga aatgttgaat actcatactc ttcctttttc aatattattg      3180
```

| | |
|---|---|
| aagcatttat cagggttatt gtctcatgag cggatacata tttgaatgta tttagaaaaa | 3240 |
| taaacaaata ggggttccgc gcacatttcc ccgaaaagtg ccacctgacg tctaagaaac | 3300 |
| cattattatc atgacattaa cctataaaaa taggcgtatc acgaggccct tcgtgttca | 3360 |
| agaattctgg cgaatcctct gaccagccag aaaacgacct ttctgtggtg aaaccggatg | 3420 |
| ctgcaattca gagcgccagc aagtggggga cagcagatga cctgaccgcc gcagagtgga | 3480 |
| tgtttgacat ggtgatgact atcgcaccat cagccagaaa accgaatttt gctgggtggg | 3540 |
| ctaacgatat ccgcctgatg cgtgaacgtg acggacgtaa cgaagacaac cac | 3593 |

<210> SEQ ID NO 6
<211> LENGTH: 3287
<212> TYPE: DNA
<213> ORGANISM: Artificial Sequence
<220> FEATURE:
<223> OTHER INFORMATION: synthetic polynucleotide

<400> SEQUENCE: 6

| | |
|---|---|
| gcattgctgt tcaactagca aatgagatag atttcggtga acccggaccc ttgctaggct | 60 |
| ctccctatca gtgatagaga gaagaaacgt caagcgggcc caagttcact taaaaaggag | 120 |
| atcaacaatg aaagcaattt tcgtactgaa acatcttaat catgctaagg aggttttcta | 180 |
| atggagcttt tcactggcgt tgttcccatc ctggtcgagc tggacggcga cgtaaacggc | 240 |
| cacaagttca gcgtgtccgg cgagggcgag ggcgatgcca cctacggcaa gctgaccctg | 300 |
| aagttcatct gcaccaccgg caagctgccc gtgccctggc ccaccctcgt gaccaccctg | 360 |
| acctacggcg tgcagtgctt cagccgctac cccgaccaca tgaagcagca cgacttcttc | 420 |
| aagtccgcca tgcccgaagg ctacgtccag gagcgcacca tcttcttcaa ggacgacggc | 480 |
| aactacaaga cccgcgccga ggtgaagttc gagggcgaca ccctggtgaa ccgcatcgag | 540 |
| ctgaagggca tcgacttcaa ggaggacggc aacatcctgg ggcacaagct ggagtacaac | 600 |
| tacaacagcc acaacgtcta tatcatggcc gacaagcaga agaacggcat caaggtgaac | 660 |
| ttcaagatcc gccacaacat cgaggacggc agcgtgcagc tcgccgacca ctaccagcag | 720 |
| aacacccca tcggcgacgg ccccgtgctg ctgcccgaca ccactacct gagcacccag | 780 |
| tccgccctga gcaaagaccc caacgagaag cgcgatcaca tggtcctgct ggagttcgtg | 840 |
| accgccgccg ggatcgcagc aaacgacgaa aactacgctt agctgcctta atgaactcgc | 900 |
| aaaaaacccc gcttcggcgg ggttttttcg cccttgagag tcgggcattg tcttcgctcc | 960 |
| ttccggtggg cgcggggcat gactatcgtc gccgcactta tgactgtgtt ctttatcatg | 1020 |
| caactcgtag gacaggtgcc ggcagcgctc ttccgcttcc tcgctcactg actcgctgcg | 1080 |
| ctcggtcgtt cggctgcggc gagcggtatc agctcactca aaggcggtaa tacggttatc | 1140 |
| cacagaatca ggggataacg caggaaagaa catgtgagca aaaggccagc aaaaggccag | 1200 |
| gaaccgtaaa aaggccgcgt tgctggcgtt tttccatagg ctccgccccc ctgacgagca | 1260 |
| tcacaaaaat cgacgctcaa gtcagaggtg gcgaaacccg acaggactat aaagatacca | 1320 |
| ggcgtttccc cctggaagct ccctcgtgcg ctctcctgtt ccgaccctgc cgcttaccgg | 1380 |
| atacctgtcc gcctttctcc cttcgggaag cgtggcgctt tctcatagct cacgctgtag | 1440 |
| gtatctcagt tcggtgtagg tcgttcgctc caagctgggc tgtgtgcacg aaccccccgt | 1500 |
| tcagcccgac cgctgcgcct tatccggtaa ctatcgtctt gagtccaacc cggtaagaca | 1560 |
| cgacttatcg ccactggcag cagccactgg taacaggatt agcagagcga ggtatgtagg | 1620 |

| | |
|---|---|
| cggtgctaca gagttcttga agtggtggcc taactacggc tacactagaa gaacagtatt | 1680 |
| tggtatctgc gctctgctga agccagttac cttcggaaaa agagttggta gctcttgatc | 1740 |
| cggcaaacaa accaccgctg gtagcggtgg ttttttttgtt tgcaagcagc agattacgcg | 1800 |
| cagaaaaaaa ggatctcaag aagatccttt gatcttttct acggggtctg acgctcagtg | 1860 |
| gaacgaaaac tcacgttaag ggattttggt catgagatta tcaaaaagga tcttcaccta | 1920 |
| gatcctttta aattaaaaat gaagttttaa atcaatctaa agtatatatg agtaaacttg | 1980 |
| gtctgacagt taccaatgct taatcagtga ggcacctatc tcagcgatct gtctatttcg | 2040 |
| ttcatccata gttgcctgac tccccgtcgt gtagataact acgatacggg agggcttacc | 2100 |
| atctggcccc agtgctgcaa tgataccgcg tgacccacgc tcaccggctc cagatttatc | 2160 |
| agcaataaac cagccagccg gaagggccga gcgcagaagt ggtcctgcaa ctttatccgc | 2220 |
| ctccatccag tctattaatt gttgccggga agctagagta agtagttcgc cagttaatag | 2280 |
| tttgcgcaac gttgttgcca ttgctacagg catcgtggtg tcacgctcgt cgtttggtat | 2340 |
| ggcttcattc agctccggtt cccaacgatc aaggcgagtt gcatgatccc ccatgttgtg | 2400 |
| caaaaaagcg gttagctcct tcggtcctcc gatcgttgtc agaagtaagt tggccgcagt | 2460 |
| gttatcactc atggttatgg cagcactgca taattctctt actgtcatgc catccgtaag | 2520 |
| atgcttttct gtgactggtg agtactcaac caagtcattc tgagaatagt gtatgcggcg | 2580 |
| accgagttgc tcttgcccgg cgtcaacacg ggataatacc gcgccacata gcagaacttt | 2640 |
| aaaagtgctc atcattggaa aacgttcttc ggggcgaaaa ctctcaagga tcttaccgct | 2700 |
| gttgagatcc agttcgatgt aacccactcg tgcacccaac tgatcttcag catcttttac | 2760 |
| tttcaccagc gtttctgggt gagcaaaaac aggaaggcaa aatgccgcaa aaaagggaat | 2820 |
| aagggcgaca cggaaatgtt gaatactcat actcttcctt tttcaatatt attgaagcat | 2880 |
| ttatcagggt tattgtctca tgagcggata catatttgaa tgtatttaga aaaataaaca | 2940 |
| aataggggtt ccgcgcacat ttccccgaaa agtgccacct gacgtctaag aaaccattat | 3000 |
| tatcatgaca ttaacctata aaaataggcg tatcacgagg cccttcgtg ttcaagaatt | 3060 |
| ctggcgaatc ctctgaccag ccagaaaacg accttttctgt ggtgaaaccg gatgctgcaa | 3120 |
| ttcagagcgc cagcaagtgg gggacagcag atgacctgac cgccgcagag tggatgtttg | 3180 |
| acatggtgat gactatcgca ccatcagcca gaaaaccgaa ttttgctggg tgggctaacg | 3240 |
| atatccgcct gatgcgtgaa cgtgacggac gtaacgaaga caaccac | 3287 |

<210> SEQ ID NO 7
<211> LENGTH: 3215
<212> TYPE: DNA
<213> ORGANISM: Artificial Sequence
<220> FEATURE:
<223> OTHER INFORMATION: synthetic polynucleotide

<400> SEQUENCE: 7

| | |
|---|---|
| gcattgctgt tccgctgggc atgcaactag caaatgagat agatttcggt gaacccggac | 60 |
| ccttgctagg ctcgaaagca ataattttgt ttaactttaa gaaggagata taccatggag | 120 |
| cttttcactg gcgttgttcc catcctggtc gagctggacg gcgacgtaaa cggccacaag | 180 |
| ttcagcgtgt ccggcgaggg cgagggcgat gccacctacg gcaagctgac cctgaagttc | 240 |
| atctgcacca ccggcaagct gcccgtgccc tggcccaccc tcgtgaccac cctgacctac | 300 |
| ggcgtgcagt gcttcagccg ctaccccgac cacatgaagc agcacgactt cttcaagtcc | 360 |
| gccatgcccg aaggctacgt ccaggagcgc accatcttct tcaaggacga cggcaactac | 420 |

-continued

```
aagacccgcg ccgaggtgaa gttcgagggc gacaccctgg tgaaccgcat cgagctgaag     480
ggcatcgact tcaaggagga cggcaacatc ctggggcaca agctggagta caactacaac     540
agccacaacg tctatatcat ggccgacaag cagaagaacg gcatcaaggt gaacttcaag     600
atccgccaca acatcgagga cggcagcgtg cagctcgccg accactacca gcagaacacc     660
cccatcggcg acggccccgt gctgctgccc gacaaccact acctgagcac ccagtccgcc     720
ctgagcaaag accccaacga gaagcgcgat cacatggtcc tgctggagtt cgtgaccgcc     780
gccgggatct aatgaagcat ctggtgaata actcgagcaa agcccgccga aggcgggct      840 tttctgtgtc gaccgatgcc cttgagagtc gggcattgtc ttcgctcctt ccggtgggcg     900
cggggcatga ctatcgtcgc cgcacttatg actgtgttct ttatcatgca actcgtagga     960
caggtgccgg cagcgctctt ccgcttcctc gctcactgac tcgctgcgct cggtcgttcg    1020
gctgcggcga gcggtatcag ctcactcaaa ggcggtaata cggttatcca cagaatcagg    1080
ggataacgca ggaaagaaca tgtgagcaaa aggccagcaa aaggccagga accgtaaaaa    1140
ggccgcgttg ctggcgtttt tccataggct ccgcccccct gacgagcatc acaaaaatcg    1200
acgctcaagt cagaggtggc gaaacccgac aggactataa agataccagg cgtttccccc    1260
tggaagctcc ctcgtgcgct ctcctgttcc gaccctgccg cttaccggat acctgtccgc    1320
ctttctccct tcgggaagcg tggcgctttc tcatagctca cgctgtaggt atctcagttc    1380
ggtgtaggtc gttcgctcca agctgggctg tgtgcacgaa ccccccgttc agcccgaccg    1440
ctgcgcctta tccggtaact atcgtcttga gtccaacccg gtaagacacg acttatcgcc    1500
actggcagca gccactggta acaggattag cagagcgagg tatgtaggcg gtgctacaga    1560
gttcttgaag tggtggccta actacggcta cactagaaga acagtatttg gtatctgcgc    1620
tctgctgaag ccagttacct tcggaaaaag agttggtagc tcttgatccg gcaaacaaac    1680
caccgctggt agcggtggtt tttttgtttg caagcagcag attacgcgca gaaaaaaagg    1740
atctcaagaa gatcctttga tcttttctac ggggtctgac gctcagtgga acgaaaactc    1800
acgttaaggg attttggtca tgagattatc aaaaaggatc ttcacctaga tccttttaaa    1860
ttaaaaatga agttttaaat caatctaaag tatatatgag taaacttggt ctgacagtta    1920
ccaatgctta atcagtgagg cacctatctc agcgatctgt ctatttcgtt catccatagt    1980
tgcctgactc cccgtcgtgt agataactac gatacgggag ggcttaccat ctggccccag    2040
tgctgcaatg ataccgcgtg acccacgctc accggctcca gatttatcag caataaacca    2100
gccagccgga agggccgagc gcagaagtgg tcctgcaact ttatccgcct ccatccagtc    2160
tattaattgt tgccgggaag ctagagtaag tagttcgcca gttaatagtt tgcgcaacgt    2220
tgttgccatt gctacaggca tcgtggtgtc acgctcgtcg tttggtatgg cttcattcag    2280
ctccggttcc caacgatcaa ggcgagttgc atgatccccc atgttgtgca aaaaagcggt    2340
tagctccttc ggtcctccga tcgttgtcag aagtaagttg gccgcagtgt tatcactcat    2400
ggttatggca gcactgcata attctcttac tgtcatgcca tccgtaagat gcttttctgt    2460
gactggtgag tactcaacca agtcattctg agaatagtgt atgcggcgac cgagttgctc    2520
ttgcccggcg tcaacacggg ataataccgc gccacatagc agaactttaa aagtgctcat    2580
cattggaaaa cgttcttcgg ggcgaaaact ctcaaggatc ttaccgctgt tgagatccag    2640
ttcgatgtaa cccactcgtg cacccaactg atcttcagca tcttttactt tcaccagcgt    2700
ttctgggtga gcaaaaacag gaaggcaaaa tgccgcaaaa aagggaataa gggcgacacg    2760
```

| | |
|---|---:|
| gaaatgttga atactcatac tcttcctttt tcaatattat tgaagcattt atcagggtta | 2820 |
| ttgtctcatg agcggataca tatttgaatg tatttagaaa aataaacaaa taggggttcc | 2880 |
| gcgcacattt ccccgaaaag tgccacctga cgtctaagaa accattatta tcatgacatt | 2940 |
| aacctataaa aataggcgta tcacgaggcc ctttcgtgtt caagaattct ggcgaatcct | 3000 |
| ctgaccagcc agaaaacgac cttctgtgg tgaaaccgga tgctgcaatt cagagcgcca | 3060 |
| gcaagtgggg gacagcagat gacctgaccg ccgcagagtg gatgtttgac atggtgatga | 3120 |
| ctatcgcacc atcagccaga aaaccgaatt ttgctgggtg ggctaacgat atccgcctga | 3180 |
| tgcgtgaacg tgacggacgt aacgaagaca accac | 3215 |

<210> SEQ ID NO 8
<211> LENGTH: 3248
<212> TYPE: DNA
<213> ORGANISM: Artificial Sequence
<220> FEATURE:
<223> OTHER INFORMATION: synthetic polynucleotide
<400> SEQUENCE: 8

| | |
|---|---:|
| gcattgctgt tccgctgggc atgcttcgag cctagcaagg gtccgggttc accgaaatct | 60 |
| atctcatttg ctagttataa aattatgaaa tttgcgtaaa ttcttcagaa gcaataattt | 120 |
| tgtttaactt taagaaggag atataccatg gagcttttca ctggcgttgt tcccatcctg | 180 |
| gtcgagctgg acggcgacgt aaacggccac aagttcagcg tgtccggcga gggcgagggc | 240 |
| gatgccacct acggcaagct gaccctgaag ttcatctgca ccaccggcaa gctgcccgtg | 300 |
| ccctggccca ccctcgtgac caccctgacc tacggcgtgc agtgcttcag ccgctacccc | 360 |
| gaccacatga agcagcacga cttcttcaag tccgccatgc ccgaaggcta cgtccaggag | 420 |
| cgcaccatct tcttcaagga cgacggcaac tacaagaccc gcgccgaggt gaagttcgag | 480 |
| ggcgacaccc tggtgaaccg catcgagctg aagggcatcg acttcaagga ggacggcaac | 540 |
| atcctggggc acaagctgga gtacaactac aacagccaca cgtctatat catgccgac | 600 |
| aagcagaaga acggcatcaa ggtgaacttc aagatccgcc acaacatcga ggacggcagc | 660 |
| gtgcagctcg ccgaccacta ccagcagaac ccccccatcg gcgacggccc cgtgctgctg | 720 |
| cccgacaacc actacctgag cacccagtcc gccctgagca agacccccaa cgagaagcgc | 780 |
| gatcacatgg tcctgctgga gttcgtgacc gccgccggga tctaatgaag catctggtga | 840 |
| ataactcgag caaagcccgc cgaaaggcgg gcttttctgt gtcgaccgat gcccttgaga | 900 |
| gtcgggcatt gtcttcgctc cttccggtgg gcgcggggca tgactatcgt cgccgcactt | 960 |
| atgactgtgt tctttatcat gcaactcgta ggacaggtgc cggcagcgct cttccgcttc | 1020 |
| ctcgctcact gactcgctgc gctcggtcgt tcggctgcgg cgagcggtat cagctcactc | 1080 |
| aaaggcggta atacggttat ccacagaatc agggaataac gcaggaaaga acatgtgagc | 1140 |
| aaaaggccag caaaaggcca ggaaccgtaa aaaggccgcg ttgctggcgt ttttccatag | 1200 |
| gctccgcccc cctgacgagc atcacaaaaa tcgacgctca agtcagaggt ggcgaaaccc | 1260 |
| gacaggacta taaagatacc aggcgtttcc ccctggaagc tccctcgtgc gctctcctgt | 1320 |
| tccgaccctg ccgcttaccg gatacctgtc cgcctttctc ccttcgggaa gcgtggcgct | 1380 |
| ttctcatagc tcacgctgta ggtatctcag ttcggtgtag tcgttcgct ccaagctggg | 1440 |
| ctgtgtgcac gaaccccccg ttcagcccga ccgctgcgcc ttatccggta actatcgtct | 1500 |
| tgagtccaac ccggtaagac acgacttatc gccactggca gcagccactg gtaacaggat | 1560 |
| tagcagagcg aggtatgtag gcggtgctac agagttcttg aagtggtggc ctaactacgg | 1620 |

```
ctacactaga agaacagtat ttggtatctg cgctctgctg aagccagtta ccttcggaaa      1680
aagagttggt agctcttgat ccggcaaaca aaccaccgct ggtagcggtg gttttttttgt    1740 ttgcaagcag cagattacgc gcagaaaaaa aggatctcaa gaagatcctt tgatcttttc     1800 tacgggtct gacgctcagt ggaacgaaaa ctcacgttaa gggattttgg tcatgagatt      1860
atcaaaaagg atcttcacct agatcctttt aaattaaaaa tgaagtttta atcaatcta      1920 aagtatatat gagtaaactt ggtctgacag ttaccaatgc ttaatcagtg aggcacctat     1980
ctcagcgatc tgtctatttc gttcatccat agttgcctga ctccccgtcg tgtagataac     2040
tacgatacgg gagggcttac catctggccc cagtgctgca atgataccgc gtgacccacg     2100
ctcaccggct ccagatttat cagcaataaa ccagccagcc ggaagggccg agcgcagaag     2160
tggtcctgca actttatccg cctccatcca gtctattaat tgttgccggg aagctagagt     2220
aagtagttcg ccagttaata gtttgcgcaa cgttgttgcc attgctacag gcatcgtggt     2280
gtcacgctcg tcgtttggta tggcttcatt cagctccggt tcccaacgat caaggcgagt     2340
tgcatgatcc cccatgttgt gcaaaaaagc ggttagctcc ttcggtcctc cgatcgttgt     2400
cagaagtaag ttggccgcag tgttatcact catggttatg gcagcactgc ataattctct     2460
tactgtcatg ccatccgtaa gatgcttttc tgtgactggt gagtactcaa ccaagtcatt     2520
ctgagaatag tgtatgcggc gaccgagttg ctcttgcccg gcgtcaacac gggataatac     2580
cgcgccacat agcagaactt taaaagtgct catcattgga aaacgttctt cggggcgaaa     2640
actctcaagg atcttaccgc tgttgagatc cagttcgatg taacccactc gtgcacccaa     2700
ctgatcttca gcatctttta ctttcaccag cgtttctggg tgagcaaaaa caggaaggca     2760
aaatgccgca aaaagggaa taagggcgac acggaaatgt tgaatactca tactcttcct     2820
ttttcaatat tattgaagca tttatcaggg ttattgtctc atgagcggat acatatttga     2880
atgtatttag aaaaataaac aaataggggt tccgcgcaca tttccccgaa aagtgccacc     2940
tgacgtctaa gaaaccatta ttatcatgac attaacctat aaaaataggc gtatcacgag     3000
gccctttcgt gttcaagaat tctggcgaat cctctgacca gccagaaaac gacctttctg     3060
tggtgaaacc ggatgctgca attcagagcg ccagcaagtg ggggacagca gatgacctga    3120
ccgccgcaga gtggatgttt gacatggtga tgactatcgc accatcagcc agaaaaccga    3180
attttgctgg gtgggctaac gatatccgcc tgatgcgtga acgtgacgga cgtaacgaag    3240
acaaccac                                                              3248
```

<210> SEQ ID NO 9
<211> LENGTH: 3248
<212> TYPE: DNA
<213> ORGANISM: Artificial Sequence
<220> FEATURE:
<223> OTHER INFORMATION: synthetic polynucleotide

<400> SEQUENCE: 9

```
gcattgctgt tccgctgggc atgcttcgag cctagcaagg gtccgggttc accgaaatct       60
atctcatttg ctagttataa aattatgaaa tttgcataaa ttcttcagaa gcaataattt     120
tgtttaactt taagaaggag atataccatg gagctttca ctggcgttgt tcccatcctg      180
gtcgagctgg acggcgacgt aaacggccac aagttcagcg tgtccggcga gggcgagggc     240
gatgccacct acggcaagct gaccctgaag ttcatctgca ccaccggcaa gctgcccgtg     300
ccctggccca cccctcgtgac cacctgacc tacggcgtgc agtgcttcag ccgctacccc    360
```

```
gaccacatga agcagcacga cttcttcaag tccgccatgc ccgaaggcta cgtccaggag    420
cgcaccatct tcttcaagga cgacggcaac tacaagaccc gcgccgaggt gaagttcgag    480
ggcgacaccc tggtgaaccg catcgagctg aagggcatcg acttcaagga ggacggcaac    540
atcctgggc acaagctgga gtacaactac aacagccaca acgtctatat catggccgac     600
aagcagaaga acggcatcaa ggtgaacttc aagatccgcc acaacatcga ggacggcagc    660
gtgcagctcg ccgaccacta ccagcagaac ccccccatcg gcgacggccc cgtgctgctg    720
cccgacaacc actacctgag cacccagtcc gccctgagca agacccccaa cgagaagcgc    780
gatcacatgg tcctgctgga gttcgtgacc gccgccggga tctaatgaag catctggtga    840
ataactcgag caaagcccgc cgaaaggcgg gcttttctgt gtcgaccgat gcccttgaga    900
gtcgggcatt gtcttcgctc cttccggtgg gcgcggggca tgactatcgt cgccgcactt    960
atgactgtgt tctttatcat gcaactcgta ggacaggtgc cggcagcgct cttccgcttc   1020
ctcgctcact gactcgctgc gctcggtcgt tcggctgcgg cgagcggtat cagctcactc   1080
aaaggcggta atacggttat ccacagaatc aggggataac gcaggaaaga acatgtgagc   1140
aaaaggccag caaaaggcca ggaaccgtaa aaaggccgcg ttgctggcgt ttttccatag   1200
gctccgcccc cctgacgagc atcacaaaaa tcgacgctca agtcagaggt ggcgaaaccc   1260
gacaggacta taaagatacc aggcgtttcc ccctggaagc tccctcgtgc gctctcctgt   1320
tccgaccctg ccgcttaccg gatacctgtc cgcctttctc ccttcgggaa gcgtggcgct   1380
ttctcatagc tcacgctgta ggtatctcag ttcggtgtag gtcgttcgct ccaagctggg   1440
ctgtgtgcac gaaccccccg ttcagcccga ccgctgcgcc ttatccggta actatcgtct   1500
tgagtccaac ccggtaagac acgacttatc gccactggca gcagccactg gtaacaggat   1560
tagcagagcg aggtatgtag gcggtgctac agagttcttg aagtggtggc ctaactacgg   1620
ctacactaga agaacagtat ttggtatctg cgctctgctg aagccagtta ccttcggaaa   1680
aagagttggt agctcttgat ccggcaaaca aaccaccgct ggtagcggtg ttttttttgt   1740
ttgcaagcag cagattacgc gcagaaaaaa aggatctcaa gaagatcctt tgatcttttc   1800
tacggggtct gacgctcagt ggaacgaaaa ctcacgttaa gggattttgg tcatgagatt   1860
atcaaaaagg atcttcacct agatcctttt aaattaaaaa tgaagtttta aatcaatcta   1920
aagtatatat gagtaaactt ggtctgacag ttaccaatgc ttaatcagtg aggcaccctat  1980
ctcagcgatc tgtctatttc gttcatccat agttgcctga ctccccgtcg tgtagataac   2040
tacgatacgg gagggcttac catctggccc cagtgctgca atgataccgc gtgacccacg   2100
ctcaccggct ccagatttat cagcaataaa ccagccagcc ggaagggccg agcgcagaag   2160
tggtcctgca actttatccg cctccatcca gtctattaat tgttgccggg aagctagagt   2220
aagtagttcg ccagttaata gtttgcgcaa cgttgttgcc attgctacag gcatcgtggt   2280
gtcacgctcg tcgtttggta tggcttcatt cagctccggt tcccaacgat caaggcgagt   2340
tgcatgatcc cccatgttgt gcaaaaaagc ggttagctcc ttcggtcctc cgatcgttgt   2400
cagaagtaag ttggccgcag tgttatcact catggttatg gcagcactgc ataattctct   2460
tactgtcatg ccatccgtaa gatgcttttc tgtgactggt gagtactcaa ccaagtcatt   2520
ctgagaatag tgtatgcggc gaccgagttg ctcttgcccg gcgtcaacac gggataatac   2580
cgcgccacat agcagaactt taaaagtgct catcattgga aaacgttctt cggggcgaaa   2640
actctcaagg atcttaccgc tgttgagatc cagttcgatg taacccactc gtgcacccaa   2700
ctgatcttca gcatctttta ctttcaccag cgtttctggg tgagcaaaaa caggaaggca   2760
```

```
aaatgccgca aaaaagggaa taagggcgac acggaaatgt tgaatactca tactcttcct    2820
ttttcaatat tattgaagca tttatcaggg ttattgtctc atgagcggat acatatttga    2880
atgtatttag aaaaataaac aatagggggt tccgcgcaca tttccccgaa aagtgccacc    2940
tgacgtctaa gaaaccatta ttatcatgac attaacctat aaaaataggc gtatcacgag    3000
gccctttcgt gttcaagaat tctggcgaat cctctgacca gccagaaaac gacctttctg    3060
tggtgaaacc ggatgctgca attcagagcg ccagcaagtg ggggacagca gatgacctga    3120
ccgccgcaga gtggatgttt gacatggtga tgactatcgc accatcagcc agaaaaccga    3180
attttgctgg gtgggctaac gatatccgcc tgatgcgtga acgtgacgga cgtaacgaag    3240
acaaccac                                                            3248

<210> SEQ ID NO 10
<211> LENGTH: 3530
<212> TYPE: DNA
<213> ORGANISM: Artificial Sequence
<220> FEATURE:
<223> OTHER INFORMATION: synthetic polynucleotide

<400> SEQUENCE: 10
gcattgctgt tccgctgggc atgctgcagc agcggatcgt cggcgagcgt cacctgaagc      60
tggtgctgaa aagcgaatgc ggctcgctgc aactggatgg cattgccttc aacatcgacc     120
gcgagcagtg gcccaaccct accgtgcgct gggccgagct ggcctacaag ctcgacgtca     180
acgaattccg cggccaggaa agcgtgcaac tgatgatcgt ccacatggcc cctcgctgag     240
cgcgtcccgg agctgggggc aacctagctg ccacctgctt ttctgctagc tattccagcg     300
aaaacataca gatttccggc gaaatcaagg ctacctgcca gttctggcag gtttggccgc     360
gggttctttt tggtacacga aagcaccgtc aagcaataat tttgtttaac tttaagaagg     420
agatatacca tggagctttt cactggcgtt gttcccatcc tggtcgagct ggacggcgac     480
gtaaacggcc acaagttcag cgtgtccggc gagggcgagg gcgatgccac ctacggcaag     540
ctgacccctg agttcatctg caccaccggc aagctgcccg tgccctggcc caccctcgtg     600
accaccctga cctacggcgt gcagtgcttc agccgctacc ccgaccacat gaagcagcac     660
gacttcttca agtccgccat gcccgaaggc tacgtccagg agcgcaccat cttcttcaag     720
gacgacggca actacaagac ccgcgccgag gtgaagttcg agggcgacac cctggtgaac     780
cgcatcgagc tgaagggcat cgacttcaag gaggacggca acatcctggg gcacaagctg     840
gagtacaact acaacagcca caacgtctat atcatggccg acaagcagaa gaacggcatc     900
aaggtgaact tcaagatccg ccacaacatc gaggacggca gcgtgcagct cgccgaccac     960
taccagcaga acacccccat cggcgacggc cccgtgctgc tgcccgacaa ccactacctg    1020
agcacccagt ccgccctgag caaagacccc aacgagaagc gcgatcacat ggtcctgctg    1080
gagttcgtga ccgccgccgg gatctaatga agcatctggt gaataactcg agcaaagccc    1140
gccgaaaggc gggcttttct gtgtcgaccg atgcccttga gagtcgggca ttgtcttcgc    1200
tccttccggt gggcgcgggg catgactatc gtcgccgcac ttatgactgt gttctttatc    1260
atgcaactcg taggacaggt gccggcagcg ctcttccgct tcctcgctca ctgactcgct    1320
gcgctcggtc gttcggctgc ggcgagcggt atcagctcac tcaaaggcgg taatacggtt    1380
atccacagaa tcagggggata acgcaggaaa gaacatgtga gcaaaaggcc agcaaaaggc    1440
caggaaccgt aaaaaggccg cgttgctggc gtttttccat aggctccgcc cccctgacga    1500
```

| | | | | | |
|---|---|---|---|---|---|
| gcatcacaaa | aatcgacgct | caagtcagag | gtggcgaaac | ccgacaggac | tataaagata | 1560 |
| ccaggcgttt | cccctggaa | gctccctcgt | gcgctctcct | gttccgaccc | tgccgcttac | 1620 |
| cggatacctg | tccgcctttc | tcccttcggg | aagcgtggcg | ctttctcata | gctcacgctg | 1680 |
| taggtatctc | agttcggtgt | aggtcgttcg | ctccaagctg | ggctgtgtgc | acgaaccccc | 1740 |
| cgttcagccc | gaccgctgcg | ccttatccgg | taactatcgt | cttgagtcca | acccggtaag | 1800 |
| acacgactta | tcgccactgg | cagcagccac | tggtaacagg | attagcagag | cgaggtatgt | 1860 |
| aggcggtgct | acagagttct | tgaagtggtg | gcctaactac | ggctacacta | gaagaacagt | 1920 |
| atttggtatc | tgcgctctgc | tgaagccagt | taccttcgga | aaagagttg | gtagctcttg | 1980 |
| atccggcaaa | caaccaccg | ctggtagcgg | tggttttttt | gtttgcaagc | agcagattac | 2040 |
| gcgcagaaaa | aaggatctc | aagaagatcc | tttgatcttt | tctacggggt | ctgacgctca | 2100 |
| gtggaacgaa | aactcacgtt | aagggatttt | ggtcatgaga | ttatcaaaaa | ggatcttcac | 2160 |
| ctagatcctt | ttaaattaaa | aatgaagttt | taaatcaatc | taaagtatat | atgagtaaac | 2220 |
| ttggtctgac | agttaccaat | gcttaatcag | tgaggcacct | atctcagcga | tctgtctatt | 2280 |
| tcgttcatcc | atagttgcct | gactccccgt | cgtgtagata | actacgatac | gggagggctt | 2340 |
| accatctggc | cccagtgctg | caatgatacc | gcgtgaccca | cgctcaccgg | ctccagattt | 2400 |
| atcagcaata | aaccagccag | ccggaagggc | cgagcgcaga | agtggtcctg | caactttatc | 2460 |
| cgcctccatc | cagtctatta | attgttgccg | ggaagctaga | gtaagtagtt | cgccagttaa | 2520 |
| tagtttgcgc | aacgttgttg | ccattgctac | aggcatcgtg | gtgtcacgct | cgtcgtttgg | 2580 |
| tatggcttca | ttcagctccg | gttcccaacg | atcaaggcga | gttgcatgat | cccccatgtt | 2640 |
| gtgcaaaaaa | gcggttagct | ccttcggtcc | tccgatcgtt | gtcagaagta | agttggccgc | 2700 |
| agtgttatca | ctcatggtta | tggcagcact | gcataattct | cttactgtca | tgccatccgt | 2760 |
| aagatgcttt | tctgtgactg | gtgagtactc | aaccaagtca | ttctgagaat | agtgtatgcg | 2820 |
| gcgaccgagt | tgctcttgcc | cggcgtcaac | acgggataat | accgcgccac | atagcagaac | 2880 |
| tttaaaagtg | ctcatcattg | gaaaacgttc | ttcggggcga | aaactctcaa | ggatcttacc | 2940 |
| gctgttgaga | tccagttcga | tgtaacccac | tcgtgcaccc | aactgatctt | cagcatcttt | 3000 |
| tactttcacc | agcgtttctg | ggtgagcaaa | aacaggaagg | caaaatgccg | caaaaaaggg | 3060 |
| aataagggcg | acacggaaat | gttgaatact | catactcttc | cttttcaat | attattgaag | 3120 |
| catttatcag | ggttattgtc | tcatgagcgg | atacatattt | gaatgtattt | agaaaaataa | 3180 |
| acaaataggg | gttccgcgca | catttccccg | aaaagtgcca | cctgacgtct | aagaaaccat | 3240 |
| tattatcatg | acattaacct | ataaaaatag | gcgtatcacg | aggcccttc | gtgttcaaga | 3300 |
| attctggcga | atcctctgac | cagccagaaa | acgacctttc | tgtggtgaaa | ccggatgctg | 3360 |
| caattcagag | cgccagcaag | tggggacag | cagatgacct | gaccgccgca | gagtggatgt | 3420 |
| ttgacatggt | gatgactatc | gcaccatcag | ccagaaaacc | gaattttgct | gggtgggcta | 3480 |
| acgatatccg | cctgatgcgt | gaacgtgacg | gacgtaacga | agacaaccac | | 3530 |

<210> SEQ ID NO 11
<211> LENGTH: 3217
<212> TYPE: DNA
<213> ORGANISM: Artificial Sequence
<220> FEATURE:
<223> OTHER INFORMATION: synthetic polynucleotide

<400> SEQUENCE: 11
gcattgctgt tccgctgggc atgcaactag caaatgagat agatttcggt gaacccggac      60

```
ccttgctagg ctcgaagaaa cgtcaagcaa taattttgtt taactttaag aaggagatat    120
accatggagc ttttcactgg cgttgttccc atcctggtcg agctggacgg cgacgtaaac    180
ggccacaagt tcagcgtgtc cggcgagggc gagggcgatg ccacctacgg caagctgacc    240
ctgaagttca tctgcaccac cggcaagctg cccgtgccct ggcccaccct cgtgaccacc    300
ctgacctacg gcgtgcagtg cttcagccgc taccccgacc acatgaagca gcacgacttc    360
ttcaagtccg ccatgcccga aggctacgtc caggagcgca ccatcttctt caaggacgac    420
ggcaactaca agacccgcgc cgaggtgaag ttcgagggcg acaccctggt gaaccgcatc    480
gagctgaagg gcatcgactt caaggaggac ggcaacatcc tggggcacaa gctggagtac    540
aactacaaca gccacaacgt ctatatcatg gccgacaagc agaagaacgg catcaaggtg    600
aacttcaaga tccgccacaa catcgaggac ggcagcgtgc agctcgccga ccactaccag    660
cagaacaccc ccatcggcga cggccccgtg ctgctgcccg acaaccacta cctgagcacc    720
cagtccgccc tgagcaaaga ccccaacgag aagcgcgatc acatggtcct gctggagttc    780
gtgaccgccg ccgggatcta tgaagcatct tggtgaataa ctcgagcaaa gcccgccgaa    840
aggcgggctt ttctgtgtcg accgatgccc ttgagagtcg ggcattgtct tcgctccttc    900
cggtgggcgc ggggcatgac tatcgtcgcc gcacttatga ctgtgttctt tatcatgcaa    960
ctcgtaggac aggtgccggc agcgctcttc cgcttcctcg ctcactgact cgctgcgctc    1020
ggtcgttcgg ctgcggcgag cggtatcagc tcactcaaag gcggtaatac ggttatccac    1080
agaatcaggg gataacgcag gaaagaacat gtgagcaaaa ggccagcaaa aggccaggaa    1140
ccgtaaaaag gccgcgttgc tggcgttttt ccataggctc cgcccccctg acgagcatca    1200
caaaaatcga cgctcaagtc agaggtggcg aaacccgaca ggactataaa gataccaggc    1260
gtttccccct ggaagctccc tcgtgcgctc tcctgttccg accctgccgc ttaccggata    1320
cctgtccgcc tttctccctt cgggaagcgt ggcgctttct catagctcac gctgtaggta    1380
tctcagttcg gtgtaggtcg ttcgctccaa gctgggctgt gtgcacgaac cccccgttca    1440
gcccgaccgc tgcgccttat ccggtaacta tcgtcttgag tccaacccgg taagacacga    1500
cttatcgcca ctggcagcag ccactggtaa caggattagc agagcgaggt atgtaggcgg    1560
tgctacagag ttcttgaagt ggtggcctaa ctacggctac actagaagaa cagtatttgg    1620
tatctgcgct ctgctgaagc cagttacctt cggaaaaaga gttggtagct cttgatccgg    1680
caaacaaacc accgctggta gcggtggttt ttttgtttgc aagcagcaga ttacgcgcag    1740
aaaaaaagga tctcaagaag atcctttgat cttttctacg gggtctgacg ctcagtggaa    1800
cgaaaactca cgttaaggga ttttggtcat gagattatca aaaaggatct tcacctagat    1860
ccttttaaat taaaaatgaa gttttaaatc aatctaaagt atatatgagt aaacttggtc    1920
tgacagttac caatgcttaa tcagtgaggc acctatctca gcgatctgtc tatttcgttc    1980
atccatagtt gcctgactcc ccgtcgtgta gataactacg atacgggagg gcttaccatc    2040
tggccccagt gctgcaatga taccgcgtga cccacgctca ccggctccag atttatcagc    2100
aataaaccag ccagccggaa gggccgagcg cagaagtggt cctgcaactt tatccgcctc    2160
catccagtct attaattgtt gccgggaagc tagagtaagt agttcgccag ttaatagttt    2220
gcgcaacgtt gttgccattg ctacaggcat cgtggtgtca cgctcgtcgt ttggtatggc    2280
ttcattcagc tccggttccc aacgatcaag gcgagttgca tgatccccca tgttgtgcaa    2340
aaaagcggtt agctccttcg gtcctccgat cgttgtcaga agtaagttgg ccgcagtgtt    2400
```

| | |
|---|---|
| atcactcatg gttatggcag cactgcataa ttctcttact gtcatgccat ccgtaagatg | 2460 |
| cttttctgtg actggtgagt actcaaccaa gtcattctga aatagtgta tgcggcgacc | 2520 |
| gagttgctct tgcccggcgt caacacggga taataccgcg ccacatagca gaactttaaa | 2580 |
| agtgctcatc attggaaaac gttcttcggg gcgaaaactc tcaaggatct taccgctgtt | 2640 |
| gagatccagt tcgatgtaac ccactcgtgc acccaactga tcttcagcat cttttacttt | 2700 |
| caccagcgtt tctgggtgag caaaaacagg aaggcaaaat gccgcaaaaa agggaataag | 2760 |
| ggcgacacgg aaatgttgaa tactcatact cttcctttt caatattatt gaagcattta | 2820 |
| tcagggttat tgtctcatga gcggatacat atttgaatgt atttagaaaa ataaacaaat | 2880 |
| aggggttccg cgcacatttc cccgaaaagt gccacctgac gtctaagaaa ccattattat | 2940 |
| catgacatta acctataaaa ataggcgtat cacgaggccc tttcgtgttc aagaattctg | 3000 |
| gcgaatcctc tgaccagcca gaaaacgacc tttctgtggt gaaaccggat gctgcaattc | 3060 |
| agagcgccag caagtggggg acagcagatg acctgaccgc cgcagagtgg atgtttgaca | 3120 |
| tggtgatgac tatcgcacca tcagccagaa aaccgaattt tgctgggtgg gctaacgata | 3180 |
| tccgcctgat gcgtgaacgt gacggacgta acgaaga | 3217 |

<210> SEQ ID NO 12
<211> LENGTH: 3267
<212> TYPE: DNA
<213> ORGANISM: Artificial Sequence
<220> FEATURE:
<223> OTHER INFORMATION: synthetic polynucleotide

<400> SEQUENCE: 12

| | |
|---|---|
| atgctatgtt gtcttcgctc cttccggtgg gcgcggggca tgactatcgt cgccgcactt | 60 |
| atgactgtgt tctttatcat gcaactcgta ggacaggtgc cggcagcgct cttccgcttc | 120 |
| ctcgctcact gactcgctgc gctcggtcgt tcggctgcgg cgagcggtat cagctcactc | 180 |
| aaaggcggta atacggttat ccacagaatc agggataac gcaggaaaga acatgtgagc | 240 |
| aaaaggccag caaaaggcca ggaaccgtaa aaaggccgcg ttgctggcgt ttttccatag | 300 |
| gctccgcccc cctgacgagc atcacaaaaa tcgacgctca gtcagaggt ggcgaaaccc | 360 |
| gacaggacta taaagatacc aggcgtttcc ccctggaagc tccctcgtgc gctctcctgt | 420 |
| tccgaccctg ccgcttaccg gatacctgtc cgcctttctc ccttcgggaa gcgtggcgct | 480 |
| ttctcatagc tcacgctgta ggtatctcag ttcggtgtag gtcgttcgct ccaagctggg | 540 |
| ctgtgtgcac gaaccccccg ttcagcccga ccgctgcgcc ttatccggta actatcgtct | 600 |
| tgagtccaac ccggtaagac acgacttatc gccactggca gcagccactg gtaacaggat | 660 |
| tagcagagcg aggtatgtag gcggtgctac agagttcttg aagtggtggc ctaactacgg | 720 |
| ctacactaga agaacagtat ttggtatctg cgctctgctg aagccagtta ccttcggaaa | 780 |
| aagagttggt agctcttgat ccggcaaaca aaccaccgct ggtagcggtg ttttttgt | 840 |
| ttgcaagcag cagattacgc gcagaaaaaa aggatctcaa gaagatcctt tgatcttttc | 900 |
| tacggggtct gacgctcagt ggaacgaaaa ctcacgttaa gggattttgg tcatgagatt | 960 |
| atcaaaaagg atcttcacct agatcctttt aaattaaaaa tgaagtttta atcaatcta | 1020 |
| aagtatatat gagtaaactt ggtctgacag ttaccaatgc ttaatcagtg aggcacctat | 1080 |
| ctcagcgatc tgtctatttc gttcatccat agttgcctga ctccccgtcg tgtagataac | 1140 |
| tacgatacgg gagggcttac catctggccc cagtgctgca atgataccgc gtgacccacg | 1200 |
| ctcaccggct ccagatttat cagcaataaa ccagccagcc ggaagggccg agcgcagaag | 1260 |

-continued

```
tggtcctgca actttatccg cctccatcca gtctattaat tgttgccggg aagctagagt    1320
aagtagttcg ccagttaata gtttgcgcaa cgttgttgcc attgctacag gcatcgtggt    1380
gtcacgctcg tcgtttggta tggcttcatt cagctccggt tcccaacgat caaggcgagt    1440
tgcatgatcc cccatgttgt gcaaaaaagc ggttagctcc ttcggtcctc cgatcgttgt    1500
cagaagtaag ttggccgcag tgttatcact catggttatg gcagcactgc ataattctct    1560
tactgtcatg ccatccgtaa gatgcttttc tgtgactggt gagtactcaa ccaagtcatt    1620
ctgagaatag tgtatgcggc gaccgagttg ctcttgcccg gcgtcaacac gggataatac    1680
cgcgccacat agcagaactt taaaagtgct catcattgga aaacgttctt cggggcgaaa    1740
actctcaagg atcttaccgc tgttgagatc cagttcgatg taacccactc gtgcacccaa    1800
ctgatcttca gcatctttta ctttcaccag cgtttctggg tgagcaaaaa caggaaggca    1860
aaatgccgca aaaaagggaa taagggcgac acggaaatgt tgaatactca tactcttcct    1920
ttttcaatat tattgaagca tttatcaggg ttattgtctc atgagcggat acatatttga    1980
atgtatttag aaaaataaac aaatagggt tccgcgcaca tttccccgaa aagtgccacc    2040
tgacgtctaa gaaaccatta ttatcatgac attaacctat aaaaataggc gtatcacgag    2100
gccctttcgt gttcaagaat ctggcgaat cctctgacca gccagaaaac gacctttctg    2160
tggtgaaacc ggatgctgca attcagagcg ccagcaagtg ggggacagca gatgacctga    2220
ccgccgcaga gtggatgttt gacatggtga tgactatcgc accatcagcc agaaaaccga    2280
attttgctgg gtgggctaac gatatccgcc tgatgcgtga acgtgacgga cgtaacgaag    2340
acaaggcacg actctcaagg gcatcggtcg acacagaaaa gcccgccttt cggcgggctt    2400
tgctcgagtt attcaccaga tgcttcatta ttagagagta ataagaccca aattaacggc    2460
cataatggcc gctacgcggc gggaggtcac accgaacttc cgccgaatat ttcccatatg    2520
gaagttcaca ttggcttccg agcagttgca gataaccgat atctcccaac tggtcttgcc    2580
gatggcgcac cactgcaaca cttccttctc ccggctggtc agaaccaccg gtttgctgac    2640
cggatgttcg aaggccagtc cggcaccgct ttgcagtgcg tagtccttga gcatccacag    2700
ggtcggcagg accgactcta tgaaacggtt ggcctcggcc cggttttccg cttccacgct    2760
gaggctcagc gcgccgagtt cgccgcgagc accatgcagc ggcatggtca gcccatacac    2820
caggccggcg gccgaggctt cctcgaagaa ctcgtgctgc tttcgcgtct ggtagatgga    2880
cggttcccag aaaatcggca gtacgctctg ggtacagtga ctgaccgtcg ggtcgacccg    2940
cgcgtagcca gcccggtcgt aatgctcgcg ccaggcggcc gggtagttgc cgacgatgaa    3000
ggcgttctcg tagtcctggc tgtccttagg caacaggccg aacaggatct tcgagaatcc    3060
aaggtcgctc gccatcttct ggaggatggc gctccactcc aattttccac ttgagcgttc    3120
cagctcaaga aaaccgtcaa ccaaggccat ggtatatctc cttcttaaag ttaaacaaaa    3180
ttattgcttg ctgtgctcag tatcttgtta tccgctcaca atgtcaatgt tatccgctca    3240
catttatgca tgcccagcgg aacagca                                        3267
```

<210> SEQ ID NO 13
<211> LENGTH: 3225
<212> TYPE: DNA
<213> ORGANISM: Artificial Sequence
<220> FEATURE:
<223> OTHER INFORMATION: synthetic polynucleotide

<400> SEQUENCE: 13

```
aatggagctt ttcactggcg ttgttcccat cctggtcgag ctggacggcg acgtaaacgg    60
ccacaagttc agcgtgtccg gcgagggcga gggcgatgcc acctacggca agctgaccct   120
gaagttcatc tgcaccaccg gcaagctgcc cgtgccctgg cccaccctcg tgaccaccct   180
gacctacggc gtgcagtgct tcagccgcta ccccgaccac atgaagcagc acgacttctt   240
caagtccgcc atgcccgaag gctacgtcca ggagcgcacc atcttcttca aggacgacgg   300
caactacaag acccgcgccg aggtgaagtt cgagggcgac accctggtga accgcatcga   360
gctgaagggc atcgacttca aggaggacgg caacatcctg gggcacaagc tggagtacaa   420
ctacaacagc cacaacgtct atatcatggc cgacaagcag aagaacggca tcaaggtgaa   480
cttcaagatc cgccacaaca tcgaggacgg cagcgtgcag ctcgccgacc actaccagca   540
gaacaccccc atcggcgacg gccccgtgct gctgcccgac aaccactacc tgagcaccca   600
gtccgccctg agcaaagacc ccaacgagaa gcgcgatcac atggtcctgc tggagttcgt   660
gaccgccgcc gggatcgcag caaacgacga aaactacgct ttagctgctt aatgaactcg   720
caaaaaaccc cgcttcggcg gggttttttc gcccttgaga gtcgggcatt gtcttcgctc   780
cttccggtgg gcgcggggca tgactatcgt cgccgcactt atgactgtgt tctttatcat   840
gcaactcgta ggacaggtgc cggcagcgct cttccgcttc ctcgctcact gactcgctgc   900
gctcggtcgt tcggctgcgg cgagcggtat cagctcactc aaaggcggta atacggttat   960
ccacagaatc aggggataac gcaggaaaga acatgtgagc aaaaggccag caaaaggcca  1020
ggaaccgtaa aaaggccgcg ttgctggcgt ttttccatag gctccgcccc cctgacgagc  1080
atcacaaaaa tcgacgctca agtcagaggt ggcgaaaccc gacaggacta taaagatacc  1140
aggcgtttcc ccctggaagc tccctcgtgc gctctcctgt tccgaccctg ccgcttaccg  1200
gatacctgtc cgcctttctc ccttcgggaa gcgtggcgct ttctcatagc tcacgctgta  1260
ggtatctcag ttcggtgtag gtcgttcgct ccaagctggg ctgtgtgcac gaaccccccg  1320
ttcagcccga ccgctgcgcc ttatccggta actatcgtct gagtccaacc cggtaagac   1380 acgacttatc gccactggca gcagccactg gtaacaggat tagcagagcg aggtatgtag  1440
gcggtgctac agagttcttg aagtggtggc ctaactacgg ctacactaga agaacagtat  1500
ttggtatctg cgctctgctg aagccagtta ccttcggaaa aagagttggt agctcttgat  1560
ccggcaaaca aaccaccgct ggtagcggtg gttttttgt ttgcaagcag cagattacgc   1620
gcagaaaaaa aggatctcaa gaagatcctt tgatctttc tacggggtct gacgctcagt   1680
ggaacgaaaa ctcacgttaa gggattttgg tcatgagatt atcaaaaagg atcttcacct  1740
agatcctttt aaattaaaaa tgaagtttta atcaatcta aagtatatat gagtaaactt    1800
ggtctgacag ttaccaatgc ttaatcagtg aggcacctat ctcagcgatc tgtctatttc   1860
gttcatccat agttgcctga ctccccgtcg tgtagataac tacgatacgg gagggcttac   1920
catctggccc cagtgctgca atgataccgc gtgacccacg ctcaccggct ccagatttat   1980
cagcaataaa ccagccagcc ggaagggccg agcgcagaag tggtcctgca actttatccg   2040
cctccatcca gtctattaat tgttgccggg aagctagagt aagtagttcg ccagttaata   2100
gtttgcgcaa cgttgttgcc attgctacag gcatcgtggt gtcacgctcg tcgtttggta   2160
tggcttcatt cagctccggt tcccaacgat caaggcgagt tgcatgatcc cccatgttgt   2220
gcaaaaaagc ggttagctcc ttcggtcctc cgatcgttgt cagaagtaag ttggccgcag   2280
tgttatcact catggttatg gcagcactgc ataattctct tactgtcatg ccatccgtaa   2340
gatgcttttc tgtgactggt gagtactcaa ccaagtcatt ctgagaatag tgtatgcggc   2400
```

-continued

```
gaccgagttg ctcttgcccg gcgtcaacac gggataatac cgcgccacat agcagaactt    2460
taaaagtgct catcattgga aaacgttctt cggggcgaaa actctcaagg atcttaccgc    2520
tgttgagatc cagttcgatg taacccactc gtgcacccaa ctgatcttca gcatctttta    2580 cttcaccag cgtttctggg tgagcaaaaa caggaaggca aaatgccgca aaaaggggaa     2640
taagggcgac acggaaatgt tgaatactca tactcttcct ttttcaatat tattgaagca    2700
tttatcaggg ttattgtctc atgagcggat acatatttga atgtatttag aaaaataaac    2760 aaatagggt tccgcgcaca tttccccgaa aagtgccacc tgacgtctaa gaaaccatta    2820
ttatcatgac attaacctat aaaaataggc gtatcacgag gccctttcgt gttcaagaat    2880
tctggcgaat cctctgacca gccagaaaac gacctttctg tggtgaaacc ggatgctgca    2940
attcagagcg ccagcaagtg ggggacagca gatgacctga ccgccgcaga gtggatgttt    3000
gacatggtga tgactatcgc accatcagcc agaaaaccga ttttgctgg gtgggctaac     3060 gatatccgcc tgatgcgtga acgtgacgga cgtaacgaag acaaccacgc attgctgttc    3120
ttcgagccta gcaagggtcc gggttcaccg aaatctatct catttgctag ttataaaatt    3180
atgaaatttg cgtaaattcc ctatcagtga tagagattca gaagc                   3225
```

```
<210> SEQ ID NO 14
<211> LENGTH: 34
<212> TYPE: DNA
<213> ORGANISM: Artificial Sequence
<220> FEATURE:
<223> OTHER INFORMATION: synthetic polynucleotide

<400> SEQUENCE: 14
ataaattttg tttaacttta agaaggagat atac                                34

<210> SEQ ID NO 15
<211> LENGTH: 84
<212> TYPE: DNA
<213> ORGANISM: Artificial Sequence
<220> FEATURE:
<223> OTHER INFORMATION: synthetic polynucleotide

<400> SEQUENCE: 15
gggcccaagt tcacttaaaa aggagatcaa caatgaaagc aatttcgta ctgaaacatc     60 ttaatcatgc tggggagggt ttct                                           84

<210> SEQ ID NO 16
<211> LENGTH: 84
<212> TYPE: DNA
<213> ORGANISM: Artificial Sequence
<220> FEATURE:
<223> OTHER INFORMATION: synthetic polynucleotide

<400> SEQUENCE: 16
gggcccaagt tcacttaaaa aggagatcaa caatgaaagc aatttcgta ctgaaacatc     60 ttaatcatgc aatggaggct ttct                                           84

<210> SEQ ID NO 17
<211> LENGTH: 84
<212> TYPE: DNA
<213> ORGANISM: Artificial Sequence
<220> FEATURE:
<223> OTHER INFORMATION: synthetic polynucleotide

<400> SEQUENCE: 17
```

```
gggcccaagt tcacttaaaa aggagatcaa caatgaaagc aatttcgta ctgaaacatc    60 ttaatcatgc ggtggagggt ttct                                          84

<210> SEQ ID NO 18
<211> LENGTH: 84
<212> TYPE: DNA
<213> ORGANISM: Artificial Sequence
<220> FEATURE:
<223> OTHER INFORMATION: synthetic polynucleotide

<400> SEQUENCE: 18
gggcccaagt tcacttaaaa aggagatcaa caatgaaagc aatttcgta ctgaaacatc    60 ttaatcatgc ttaggagtct ttct                                          84

<210> SEQ ID NO 19
<211> LENGTH: 84
<212> TYPE: DNA
<213> ORGANISM: Artificial Sequence
<220> FEATURE:
<223> OTHER INFORMATION: synthetic polynucleotide

<400> SEQUENCE: 19
gggcccaagt tcacttaaaa aggagatcaa caatgaaagc aatttcgta ctgaaacatc    60 ttaatcatgc ctaggaagtt ttct                                          84

<210> SEQ ID NO 20
<211> LENGTH: 27
<212> TYPE: DNA
<213> ORGANISM: Artificial Sequence
<220> FEATURE:
<223> OTHER INFORMATION: synthetic polynucleotide

<400> SEQUENCE: 20
tactagagtc acacaggaaa cctactc                                       27

<210> SEQ ID NO 21
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 21
tactagagtc acacaggact actc                                          24

<210> SEQ ID NO 22
<211> LENGTH: 84
<212> TYPE: DNA
<213> ORGANISM: Artificial Sequence
<220> FEATURE:
<223> OTHER INFORMATION: synthetic polynucleotide

<400> SEQUENCE: 22
gggcccaagt tcacttaaaa aggagatcaa caatgaaagc aatttcgta ctgaaacatc    60 ttaatcatgc taaggaggtt ttct                                          84

<210> SEQ ID NO 23
<211> LENGTH: 84
<212> TYPE: DNA
<213> ORGANISM: Artificial Sequence
<220> FEATURE:
<223> OTHER INFORMATION: synthetic polynucleotide

<400> SEQUENCE: 23
```

```
gggcccaagt tcacttaaaa aggagatcaa caatgaaagc aattttcgta ctgaaacatc    60
ttaatcatgc gggggagtgt ttct                                          84

<210> SEQ ID NO 24
<211> LENGTH: 84
<212> TYPE: DNA
<213> ORGANISM: Artificial Sequence
<220> FEATURE:
<223> OTHER INFORMATION: synthetic polynucleotide

<400> SEQUENCE: 24
gggcccaagt tcacttaaaa aggagatcaa caatgaaagc aattttcgta ctgaaacatc    60
ttaatcatgc tgcggagggt ttct                                          84

<210> SEQ ID NO 25
<211> LENGTH: 84
<212> TYPE: DNA
<213> ORGANISM: Artificial Sequence
<220> FEATURE:
<223> OTHER INFORMATION: synthetic polynucleotide

<400> SEQUENCE: 25
gggcccaagt tcacttaaaa aggagatcaa caatgaaagc aattttcgta ctgaaacatc    60
ttaatcatgc tgaggaaagt ttct                                          84

<210> SEQ ID NO 26
<211> LENGTH: 84
<212> TYPE: DNA
<213> ORGANISM: Artificial Sequence
<220> FEATURE:
<223> OTHER INFORMATION: synthetic polynucleotide

<400> SEQUENCE: 26
gggcccaagt tcacttaaaa aggagatcaa caatgaaagc aattttcgta ctgaaacatc    60
ttaatcatgc gatggacggt ttct                                          84

<210> SEQ ID NO 27
<211> LENGTH: 28
<212> TYPE: DNA
<213> ORGANISM: Artificial Sequence
<220> FEATURE:
<223> OTHER INFORMATION: synthetic polynucleotide

<400> SEQUENCE: 27
tactagagat taaagaggag aaatactc                                      28

<210> SEQ ID NO 28
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 28
tactagagtc acacaggaaa gtactc                                        26

<210> SEQ ID NO 29
<211> LENGTH: 25
<212> TYPE: DNA
<213> ORGANISM: Artificial Sequence
<220> FEATURE:
<223> OTHER INFORMATION: synthetic polynucleotide
```

<400> SEQUENCE: 29
tactagagaa agaggagaaa tactc                                           25

<210> SEQ ID NO 30
<211> LENGTH: 4322
<212> TYPE: DNA
<213> ORGANISM: Artificial Sequence
<220> FEATURE:
<223> OTHER INFORMATION: synthetic polynucleotide

<400> SEQUENCE: 30

| | | | | | |
|---|---|---|---|---|---|
| aatgtctaga | ttagataaaa | gtaaagtgat | taacagcgca | ttagagctgc | ttaatgaggt | 60 |
| cggaatcgaa | ggtttaacaa | cccgtaaact | cgcccagaag | ctaggtgtag | agcagcctac | 120 |
| attgtattgg | catgtaaaaa | ataagcgggc | tttgctcgac | gccttagcca | ttgagatgtt | 180 |
| agataggcac | catactcact | tttgcccttt | agaaggggaa | agctggcaag | attttttacg | 240 |
| taataacgct | aaaagtttta | gatgtgcttt | actaagtcat | cgcgatggag | caaaagtaca | 300 |
| tttaggtaca | cggcctacag | aaaaacagta | tgaaactctc | gaaatcaat | tagcctttt | 360 |
| atgccaacaa | ggttttcac | tagagaatgc | attatatgca | ctcagcgctg | tggggcattt | 420 |
| tactttaggt | tgcgtattgg | aagatcaaga | gcatcaagtc | gctaaagaag | aaagggaaac | 480 |
| acctactact | gatagtatgc | cgccattatt | acgacaagct | atcgaattat | ttgatcacca | 540 |
| aggtgcagag | ccagccttct | tattcggcct | tgaattgatc | atatgcggat | tagaaaaaca | 600 |
| acttaaatgt | gaaagtgggt | cttaatgaac | tcaaagcccg | ccgaaaggcg | ggcttttctg | 660 |
| tccttgagag | tcgtatgttg | tcttctaagg | atccaaactc | gagtaaggat | ctccaggcat | 720 |
| caaataaaac | gaaaggctca | gtcgaaagac | tgggcctttc | gttttatctg | ttgtttgtcg | 780 |
| gtgaacgctc | tctactagag | tcacactggc | tcaccttcgg | gtgggccttt | ctgcgtttat | 840 |
| acctagggta | cgggttttgc | tgcccgcaaa | cgggctgttc | tggtgttgct | agtttgttat | 900 |
| cagaatcgca | gatccggctt | cagccggttt | gccggctgaa | agcgctattt | cttccagaat | 960 |
| tgccatgatt | ttttccccac | gggaggcgtc | actggctccc | gtgttgtcgg | cagctttgat | 1020 |
| tcgataagca | gcatcgcctg | tttcaggctg | tctatgtgtg | actgttgagc | tgtaacaagt | 1080 |
| tgtctcaggt | gttcaatttc | atgttctagt | tgctttgttt | tactggtttc | acctgttcta | 1140 |
| ttaggtgtta | catgctgttc | atctgttaca | ttgtcgatct | gttcatggtg | aacagctttg | 1200 |
| aatgcaccaa | aaactcgtaa | aagctctgat | gtatctatct | tttttacacc | gttttcatct | 1260 |
| gtgcatatgg | acagttttcc | ctttgatatg | taacggtgaa | cagttgttct | acttttgttt | 1320 |
| gttagtcttg | atgcttcact | gatagataca | agagccataa | gaacctcaga | tccttccgta | 1380 |
| tttagccagt | atgttctcta | gtgtggttcg | ttgttttttgc | gtgagccatg | agaacgaacc | 1440 |
| attgagatca | tacttacttt | gcatgtcact | caaaaatttt | gcctcaaaac | tggtgagctg | 1500 |
| aatttttgca | gttaaagcat | cgtgtagtgt | ttttcttagt | ccgttatgta | ggtaggaatc | 1560 |
| tgatgtaatg | gttgttggta | ttttgtcacc | attcattttt | atctggttgt | tctcaagttc | 1620 |
| ggttacgaga | tccatttgtc | tatctagttc | aacttggaaa | atcaacgtat | cagtcgggcg | 1680 |
| gcctcgctta | tcaaccacca | atttcatatt | gctgtaagtg | tttaaatctt | tacttattgg | 1740 |
| tttcaaaacc | cattggttaa | gccttttaaa | ctcatggtag | ttattttcaa | gcattaacat | 1800 |
| gaacttaaat | tcatcaaggc | taatctctat | atttgccttg | tgagttttct | tttgtgttag | 1860 |
| ttcttttaat | aaccactcat | aaatcctcat | agagtatttg | ttttcaaaag | acttaacatg | 1920 |
| ttccagatta | tattttatga | attttttaa | ctggaaaaga | taaggcaata | tctcttcact | 1980 |

```
aaaaactaat tctaattttt cgcttgagaa cttggcatag tttgtccact ggaaaatctc    2040
aaagccttta accaaaggat tcctgatttc cacagttctc gtcatcagct ctctggttgc    2100
tttagctaat acaccataag cattttccct actgatgttc atcatctgag cgtattggtt    2160
ataagtgaac gataccgtcc gttctttcct tgtagggttt tcaatcgtgg ggttgagtag    2220
tgccacacag cataaaatta gcttggtttc atgctccgtt aagtcatagc gactaatcgc    2280
tagttcattt gctttgaaaa caactaattc agacatacat ctcaattggt ctaggtgatt    2340
ttaatcacta taccaattga gatgggctag tcaatgataa ttactagtcc ttttcccggg    2400
tgatctgggt atctgtaaat tctgctagac ctttgctgga aaacttgtaa attctgctag    2460
accctctgta aattccgcta gacctttgtg tgttttttt gtttatattc aagtggttat     2520
aatttataga ataagaaag aataaaaaaa gataaaaaga atagatccca gccctgtgta     2580
taactcacta ctttagtcag ttccgcagta ttacaaaagg atgtcgcaaa cgctgtttgc    2640
tcctctacaa aacagacctt aaaccctaa aggcttaagt agcaccctcg caagctcggg     2700
caaatcgctg aatattcctt ttgtctccga ccatcaggca cctgagtcgc tgtcttttc     2760 gtgacattca gttcgctgcg ctcacggctc tggcagtgaa tggggtaaa tggcactaca     2820 ggcgcctttt atggattcat gcaaggaaac tacccataat acaagaaaag cccgtcacgg    2880
gcttctcagg gcgttttatg gcgggtctgc tatgtggtgc tatctgactt tttgctgttc    2940
agcagttcct gccctctgat tttccagtct gaccacttcg gattatcccg tgacaggtca    3000
ttcagactgg ctaatgcacc cagtaaggca gcggtatcat caacaggctt acccgtctta    3060
ctgtccctag tgcttggatt ctcaccaata aaaaacgccc ggcggcaacc gagcgttctg    3120
aacaaatcca gatggagttc tgaggtcatt actggatcta tcaacaggag tccaagcgag    3180
ctctcgaacc ccagagtccc gctcagaaga actcgtcaag aaggcgatag aaggcgatgc    3240
gctgcgaatc gggagcggcg ataccgtaaa gcacgaggaa gcggtcagcc cattcgccgc    3300
caagctcttc agcaatatca cgggtagcca acgctatgtc ctgatagcgg tccgccacac    3360
ccagccggcc acagtcgatg aatccagaaa agcggccatt ttccaccatg atattcggca    3420
agcaggcatc gccatgggtc acgacgagat cctcgccgtc gggcatgcgc gccttgagcc    3480
tggcgaacag ttcggctggc gcgagcccct gatgctcttc gtccagatca tcctgatcga    3540
caagaccggc ttccatccga gtacgtgctc gctcgatgcg atgtttcgct tggtggtcga    3600
atgggcaggt agccggatca agcgtatgca gccgccgcat tgcatcagcc atgatggata    3660
cttttctcgg aggagcaagg tgagatgaca ggagatcctg ccccggcact cgcccaata    3720 gcagccagtc ccttcccgct tcagtgacaa cgtcgagcac agctgcgcaa ggaacgcccg    3780
tcgtggccag ccacgatagc cgcgctgcct cgtcctgcag ttcattcagg gcaccggaca    3840
ggtcggtctt gacaaaaaga accgggcgcc cctgcgctga cagccggaac acggcggcat    3900
cagagcagcc gattgtctgt tgtgcccagt catagccgaa tagcctctcc acccaagcgg    3960
ccggagaacc tgcgtgcaat ccatcttgtt caatcatgcg aaacgatcct catcctgtct    4020
cttgatcaga tcatgatccc ctgcgccatc agatccttgg cggcaagaaa gccatccagt    4080
ttactttgca gggcttccca accttaccag agggcgcccc agctggcaat tccgacgtcg    4140
gtgcctaatg agtgagctaa cttacattaa ttgcgttgcg ctcactgccc gctttccagt    4200
cgggaaacct gaagacaaat gtgcattgct gttcttcgag cctagcaagg gtccgggttc    4260
accgaaatct atctcatttg ctagttataa aattatgaaa tttgcgtaaa ttcttcagaa    4320
``` gc 4322

<210> SEQ ID NO 31
<211> LENGTH: 3466
<212> TYPE: DNA
<213> ORGANISM: Artificial Sequence
<220> FEATURE:
<223> OTHER INFORMATION: synthetic polynucleotide

<400> SEQUENCE: 31

```
atgcatgttt gtcttcttga tcgggcacgt aagaggttcc aactttcacc ataatgaaat     60
aagatcacta ccgggcgtat tttttgagtt atcgagattt tcaggagcta aggaagctaa    120
aatgcgctca cgcaactggt ccagaacctt gaccgaacgc agcggtggta acggcgcagt    180
ggcggttttc atggcttgtt atgactgttt ttttggggta cagtctatgc ctcgggcatc    240
caagcagcaa gcgcgttacg ccgtgggtcg atgtttgatg ttatggagca gcaacgatgt    300
tacgcagcag ggcagtcgcc ctaaaacaaa gttaaacatc atgagggaag cggtgatcgc    360
cgaagtatcg actcaactat cagaggtagt tggcgtcatc gagcgccatc tcgaaccgac    420
gttgctggcc gtacatttgt acggctccgc agtggatggc ggcctgaagc cacacagtga    480
tattgatttg ctggttacgg tgaccgtaag gcttgatgaa acaacgcggc gagctttgat    540
caacgacctt ttggaaactt cggcttcccc tggagagagc gagattctcc gcgctgtaga    600
agtcaccatt gttgtgcacg acgacatcat tccgtggcgt tatccagcta agcgcgaact    660
gcaatttgga gaatggcagc gcaatgacat tcttgcaggt atcttcgagc cagccacgat    720
cgacattgat ctggctatct tgctgacaaa agcaagagaa catagcgttg ccttggtagg    780
tccagcggcg gaggaactct ttgatccggt tcctgaacag gatctatttg aggcgctaaa    840
tgaaacctta acgctatgga actcgccgcc cgactgggct ggcgatgagc gaaatgtagt    900
gcttacgttg tcccgcattt ggtacagcgc agtaaccggc aaaatcgcgc cgaaggatgt    960
cgctgccgac tgggcaatgg agcgcctgcc ggcccagtat cagcccgtca tacttgaagc   1020
tagacaggct tatcttggac aagaagaaga tcgcttggcc tcgcgcgcag atcagttgga   1080
agaatttgtc cactacgtga aaggcgagat caccaaggta gtcggcaaat aatttgatat   1140
cgagctcgct tggactcctg ttgatagatc cagtaatgac ctcagaactc catctggatt   1200
tgttcagaac gctcggttgc cgccgggcgt tttttattgg tgagaatcca gcctcggtg    1260
agaatccaag cctcgatcaa cgtctcattt tcgccaaaag ttggcccagg cttcccggt    1320
atcaacaggg acaccaggat ttatttattc tgcgaagtga tcttccgtca caggtattta   1380
ttcggcgcaa agtgcgtcgg gtgatgctgc caacttactg atttagtgta tgatggtgtt   1440
tttgaggtgc tccagtggct tctgtttcta tcagctgtcc ctcctgttca gctactgacg   1500
gggtggtgcg taacggcaaa agcaccgccg gacatcagcg tagcggagt gtatactggc    1560
ttactatgtt ggcactgatg agggtgtcag tgaagtgctt catgtggcag agaaaaaag    1620
gctgcaccgg tgcgtcagca gaatatgtga tacaggatat attccgcttc ctcgctcact   1680
gactcgctac gctcggtcgt tcgactgcgg cgagcggaaa tggcttacga acggggcgga   1740
gatttcctgg aagatgccag gaagatactt aacaggaag tgagggcc gcggcaaagc     1800
cgttttccca taggctccgc cccctgaca agcatcacga atctgacgc tcaaatcagt     1860
ggtggcgaaa cccgacagga ctataaagat accaggcgtt tccccctggc ggctccctcg   1920
tgcgctctcc tgttcctgcc tttcggttta ccggtgtcat tccgctgtta ggccgcgtt    1980
tgtctcattc cacgcctgac actcagttcc gggtaggcag ttcgctccaa gctggactgt   2040
```

```
atgcacgaac cccccgttca gtccgaccgc tgcgccttat ccggtaacta tcgtcttgag   2100
tccaacccgg aaagacatgc aaaagcacca ctggcagcag ccactggtaa ttgatttaga   2160
ggagttagtc ttgaagtcat gcgccggtta aggctaaact gaaaggacaa gttttggtga   2220
ctgcgctcct ccaagccagt tacctcggtt caaagagttg gtagctcaga gaaccttcga   2280
aaaaccgccc tgcaaggcgg ttttttcgtt ttcagagcaa gagattacgc gcagaccaaa   2340
acgatctcaa gaagatcatc ttattaatca gataaaatat ttctagattt cagtgcaatt   2400
tatctcttca aatgtagcac ctgaagtcag ccccatacga tataagttgt aattctcatg   2460
tttgacagct tatcatcgat aagcttccga tggcgcgccg agaggcttta cactttatgc   2520
ttccggctga agacaaggca cgactctcaa ggacagaaaa gcccgccttt cggcgggctt   2580
tgagttcatt attagagagt aataagaccc aaattaacgg ccataatggc cgctacgcgg   2640
cgggaggtca caccgaactt ccgccgaata tttcccatat ggaagttcac attggcttcc   2700
gagcagttgc agataaccga tatctcccaa ctggtcttgc cgatggcgca ccactgcaac   2760
acttccttct cccggctggt cagaaccacc ggtttgctga ccggatgttc gaaggccagt   2820
ccggcaccgc tttgcagtgc gtagtccttg agcatccaca gggtcggcag gaccgactct   2880
atgaaacggt tggcctcggc ccggttttcc gcttccacgc tgaggctcag cgcgccgagt   2940
tcgccgcgag caccatgcag cggcatggtc agcccataca ccaggccggc ggccgaggct   3000
tcctcgaaga actcgtgctg ctttcgcgtc tggtagatgg acggttccca gaaaatcggc   3060
agtacgctct gggtacagtg actgaccgtc ggtcgaccc gcgcgtagcc agcccggtcg   3120
taatgctcgc gccaggcggc cgggtagttg ccgacgatga aggcgttctc gtagtcctgg   3180
ctgtccttag gcaacaggcc gaacaggatc ttcgagaatc caaggtcgct cgccatcttc   3240
tggaggatgg cgctccactc caattttcca cttgagcgtt ccagctcaag aaaaccgtca   3300
accaaggcca ttagaaaacc tccttagcat gattaagatg tttcagtacg aaaattgctt   3360
tcattgttga tctccttttt aagtgaactt gggcccgctt gctgtgctca gtatcttgtt   3420
atccgctcac aatgtcaatg ttatccgctc acatttatga acagca               3466
```

<210> SEQ ID NO 32
<211> LENGTH: 3466
<212> TYPE: DNA
<213> ORGANISM: Artificial Sequence
<220> FEATURE:
<223> OTHER INFORMATION: synthetic polynucleotide

<400> SEQUENCE: 32

```
atgcatgttt gtcttcttga tcgggcacgt aagaggttcc aactttcacc ataatgaaat     60
aagatcacta ccgggcgtat tttttgagtt atcgagattt tcaggagcta aggaagctaa    120
aatgcgctca cgcaactggt ccagaacctt gaccgaacgc agcggtggta acggcgcagt    180
ggcggttttc atggcttgtt atgactgttt ttttggggta cagtctatgc ctcgggcatc    240
caagcagcaa gcgcgttacg ccgtgggtcg atgtttgatg ttatggagca gcaacgatgt    300
tacgcagcag ggcagtcgcc ctaaaacaaa gttaaacatc atgagggaag cggtgatcgc    360
cgaagtatcg actcaactat cagaggtagt tggcgtcatc gagcgccatc tcgaaccgac    420
gttgctggcc gtacatttgt acggctccgc agtggatggc ggcctgaagc cacacagtga    480
tattgatttg ctggttacgg tgaccgtaag gcttgatgaa acaacgcggc gagctttgat    540
caacgacctt ttggaaactt cggcttcccc tggagagagc gagattctcc gcgctgtaga    600
```

```
agtcaccatt gttgtgcacg acgacatcat tccgtggcgt tatccagcta agcgcgaact   660
gcaatttgga gaatggcagc gcaatgacat tcttgcaggt atcttcgagc cagccacgat   720
cgacattgat ctggctatct tgctgacaaa agcaagagaa catagcgttg ccttggtagg   780
tccagcggcg gaggaactct ttgatccggt tcctgaacag gatctatttg aggcgctaaa   840 tgaaaccta acgctatgga actcgccgcc cgactgggct ggcgatgagc gaaatgtagt   900
gcttacgttg tcccgcattt ggtacagcgc agtaaccggc aaaatcgcgc gaaggatgt   960 cgctgccgac tgggcaatgg agcgcctgcc ggcccagtat cagcccgtca tacttgaagc  1020
tagacaggct tatcttggac aagaagaaga tcgcttggcc tcgcgcgcag atcagttgga  1080
agaatttgtc cactacgtga aaggcgagat caccaaggta gtcggcaaat aatttgatat  1140
cgagctcgct tggactcctg ttgatagatc cagtaatgac ctcagaactc catctggatt  1200
tgttcagaac gctcggttgc cgccgggcgt tttttattgg tgagaatcca agcctcggtg  1260
agaatccaag cctcgatcaa cgtctcattt tcgccaaaag ttgggcccagg gcttcccggt  1320 atcaacaggg acaccaggat ttatttattc tgcgaagtga tcttccgtca caggtattta  1380
ttcggcgcaa agtgcgtcgg gtgatgctgc caacttactg atttagtgta tgatggtgtt  1440
tttgaggtgc tccagtggct tctgtttcta tcagctgtcc ctcctgttca gctactgacg  1500
gggtggtgcg taacggcaaa agcaccgccg gacatcagcg gtagcggagt gtatactggc  1560
ttactatgtt ggcactgatg agggtgtcag tgaagtgctt catgtggcag agaaaaaaag  1620
gctgcaccgg tgcgtcagca gaatatgtga tacaggatat attccgcttc ctcgctcact  1680
gactcgctac gctcggtcgt tcgactgcgg cgagcggaaa tggcttacga acggggcgga  1740
gatttcctgg aagatgccag gaagatactt aacagggaag tgagagggcc gcggcaaagc  1800
cgttttccca taggctccgc cccctgaca agcatcacga atctgacgc tcaaatcagt  1860 ggtggcgaaa cccgacagga ctataaagat accaggcgtt tcccctggc ggctccctcg  1920 tgcgctctcc tgttcctgcc tttcggttta ccggtgtcat tccgctgtta tggccgcgtt  1980
tgtctcattc cacgcctgac actcagttcc gggtaggcag ttcgctccaa gctggactgt  2040
atgcacgaac ccccgttca gtccgaccgc tgcgccttat ccggtaacta tcgtcttgag  2100
tccaacccgg aaagacatgc aaaagcacca ctggcagcag ccactggtaa ttgatttaga  2160
ggagttagtc ttgaagtcat gcgccggtta aggctaaact gaaaggacaa gttttggtga  2220
ctgcgctcct ccaagccagt tacctcggtt caaagagttg gtagctcaga gaaccttcga  2280
aaaaccgccc tgcaaggcgg ttttttcgtt ttcagagcaa gagattacgc gcagaccaaa  2340
acgatctcaa gaagatcatc ttattaatca gataaaatat ttctagattt cagtgcaatt  2400
tatctcttca aatgtagcac ctgaagtcag ccccatacga tataagttgt aattctcatg  2460
tttgacagct tatcatcgat aagcttccga tggcgcgccg agaggcttta cactttatgc  2520
ttccggctga agacaaggca cgactctcaa ggacagaaaa gccgcctttt cggcgggctt  2580
tgagttcatt attagagagt aataagaccc aaattaacgg ccataatggc cgctacgcgg  2640
cgggaggtca caccgaactt ccgccgaata tttcccatat ggaagttcac attggcttcc  2700
gagcagttgc agataaccga tatctcccaa ctggtcttgc cgatggcgca ccactgcaac  2760
acttccttct cccggctggt cagaaccacc ggtttgctga ccggatgttc gaaggccagt  2820
ccggcaccgc tttgcagtgc gtagtccttg agcatccaca gggtcggcag gaccgactct  2880
atgaaacggt tggcctcggc ccggtttttcc gcttccacgc tgaggctcag cgcgccgagt  2940
tcgccgcgag caccatgcag cggcatggtc agcccataca ccaggccggc ggccgaggct  3000
```

```
tcctcgaaga actcgtgctg ctttcgcgtc tggtagatgg acggttccca gaaaatcggc    3060
agtacgctct gggtacagtg actgaccgtc gggtcgaccc gcgcgtagcc agcccggtcg    3120
taatgctcgc gccaggcggc cgggtagttg ccgacgatga aggcgttctc gtagtcctgg    3180
ctgtccttag gcaacaggcc gaacaggatc ttcgagaatc caaggtcgct cgccatcttc    3240
tggaggatgg cgctccactc caattttcca cttgagcgtt ccagctcaag aaaaccgtca    3300
accaaggcca ttagaaaact tcctaggcat gattaagatg tttcagtacg aaaattgctt    3360
tcattgttga tctcctttt aagtgaactt gggcccgctt gctgtgctca gtatcttgtt    3420
atccgctcac aatgtcaatg ttatccgctc acatttatga acagca                  3466

<210> SEQ ID NO 33
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 33
agaacggtct cagcattgct gttcaactag caaatgagat agatttcggt gaacccggac    60
ccttgctagg ctcgaaagct gagaccttac                                    90

<210> SEQ ID NO 34
<211> LENGTH: 136
<212> TYPE: DNA
<213> ORGANISM: Artificial Sequence
<220> FEATURE:
<223> OTHER INFORMATION: synthetic polynucleotide

<400> SEQUENCE: 34
agaacggtct cagcattgct gttccgctgg gcatgcttcg agcctagcaa gggtccgggt    60
tcaccgaaat ctatctcatt tgctagttat aaaattatga aatttgcgta aattcttcag    120
aagctgagac cttacg                                                  136

<210> SEQ ID NO 35
<211> LENGTH: 136
<212> TYPE: DNA
<213> ORGANISM: Artificial Sequence
<220> FEATURE:
<223> OTHER INFORMATION: synthetic polynucleotide

<400> SEQUENCE: 35
agaacggtct cagcattgct gttccgctgg gcatgcttcg agcctagcaa gggtccgggt    60
tcaccgaaat ctatctcatt tgctagttat aaaattatga aatttgcata aattcttcag    120
aagctgagac cttacg                                                  136

<210> SEQ ID NO 36
<211> LENGTH: 418
<212> TYPE: DNA
<213> ORGANISM: Artificial Sequence
<220> FEATURE:
<223> OTHER INFORMATION: synthetic polynucleotide

<400> SEQUENCE: 36
agaacggtct cagcattgct gttccgctgg gcatgctgca gcagcggatc gtcggcgagc    60
gtcacctgaa gctggtgctg aaaagcgaat gcggctcgct gcaactggat ggcattgcct    120
tcaacatcga ccgcgagcag tggcccaacc ctaccgtgcg ctgggccgag ctggcctaca    180
```

```
agctcgacgt caacgaattc cgcggccagg aaagcgtgca actgatgatc gtccacatgg      240
cccctcgctg agcgcgtccc ggagctgggg gcaacctagc tgccacctgc ttttctgcta      300
gctattccag cgaaaacata cagatttccg gcgaaatcaa ggctacctgc cagttctggc      360
aggtttggcc gcgggttctt tttggtacac gaaagcaccg tcaagctgag accttacg       418

<210> SEQ ID NO 37
<211> LENGTH: 112
<212> TYPE: DNA
<213> ORGANISM: Artificial Sequence
<220> FEATURE:
<223> OTHER INFORMATION: synthetic polynucleotide

<400> SEQUENCE: 37
agaacggtct cagcattgct gttccgctgg gcatgcaact agcaaatgag atagatttcg      60
gtgaacccgg acccttgcta ggctcgaaga acgtcaagc tgagacctta cg              112

<210> SEQ ID NO 38
<211> LENGTH: 102
<212> TYPE: DNA
<213> ORGANISM: Artificial Sequence
<220> FEATURE:
<223> OTHER INFORMATION: synthetic polynucleotide

<400> SEQUENCE: 38
ttcgagccta gcaagggtcc gggttcaccg aaatctatct catttgctag ttataaaatt      60
atgaaatttg cgtaaattcc ctatcagtga tagagatttc ag                        102

<210> SEQ ID NO 39
<211> LENGTH: 104
<212> TYPE: DNA
<213> ORGANISM: Artificial Sequence
<220> FEATURE:
<223> OTHER INFORMATION: synthetic polynucleotide

<400> SEQUENCE: 39
ttcgagccta gcaagggtcc gggttcaccg aaatctatct catttgctag ttataaaatt      60
atgaaatttg cgtaaatttc ttcagtccct atcagtgata gaga                      104

<210> SEQ ID NO 40
<211> LENGTH: 85
<212> TYPE: DNA
<213> ORGANISM: Artificial Sequence
<220> FEATURE:
<223> OTHER INFORMATION: synthetic polynucleotide

<400> SEQUENCE: 40
ttcgagccta gcaagggtcc gggttcaccg aaatctatct catttgctag ttataaaatt      60
atgaaatttg cgtaaatttc ttcag                                            85

<210> SEQ ID NO 41
<211> LENGTH: 3265
<212> TYPE: DNA
<213> ORGANISM: Artificial Sequence
<220> FEATURE:
<223> OTHER INFORMATION: synthetic polynucleotide

<400> SEQUENCE: 41
gcattgctgt tccgctgggc atgcttcgag cctagcaagg gtccgggttc accgaaatct      60
atctcatttg ctagttataa aattatgaaa tttgcgtaaa ttccctatca gtgatagaga     120
ttcagaagca ataattttgt ttaactttaa gaaggagata taccatggag ctttcactg      180
```

```
gcgttgttcc catcctggtc gagctggacg gcgacgtaaa cggccacaag ttcagcgtgt    240
ccggcgaggg cgagggcgat gccacctacg gcaagctgac cctgaagttc atctgcacca    300
ccggcaagct gcccgtgccc tggcccaccc tcgtgaccac cctgacctac ggcgtgcagt    360
gcttcagccg ctaccccgac cacatgaagc agcacgactt cttcaagtcc gccatgcccg    420
aaggctacgt ccaggagcgc accatcttct tcaaggacga cggcaactac aagacccgcg    480
ccgaggtgaa gttcgagggc gacaccctgg tgaaccgcat cgagctgaag ggcatcgact    540
tcaaggagga cggcaacatc ctggggcaca agctggagta caactacaac agccacaacg    600
tctatatcat ggccgacaag cagaagaacg gcatcaaggt gaacttcaag atccgccaca    660
acatcgagga cggcagcgtg cagctcgccg accactacca gcagaacacc cccatcggcg    720
acggccccgt gctgctgccc gacaaccact acctgagcac ccagtccgcc ctgagcaaag    780
accccaacga gaagcgcgat cacatggtcc tgctggagtt cgtgaccgcc gccgggatct    840
aatgaagcat ctggtgaata actcgagcaa agcccgccga aaggcgggct tttctgtgtc    900
gaccgatgcc cttgagagtc gggcattgtc ttcgctcctt ccggtgggcg cggggcatga    960
ctatcgtcgc cgcacttatg actgtgttct ttatcatgca actcgtagga caggtgccgg   1020
cagcgctctt ccgcttcctc gctcactgac tcgctgcgct cggtcgttcg gctgcggcga   1080
gcggtatcag ctcactcaaa ggcggtaata cggttatcca cagaatcagg gataacgca   1140 ggaaagaaca tgtgagcaaa aggccagcaa aaggccagga accgtaaaaa ggccgcgttg   1200
ctggcgtttt tccataggct ccgcccccct gacgagcatc acaaaaatcg acgctcaagt   1260
cagaggtggc gaaacccgac aggactataa agataccagg cgtttccccc tggaagctcc   1320
ctcgtgcgct ctcctgttcc gaccctgccg cttaccggat acctgtccgc ctttctccct   1380
tcgggaagcg tggcgctttc tcatagctca cgctgtaggt atctcagttc ggtgtaggtc   1440
gttcgctcca agctgggctg tgtgcacgaa ccccccgttc agcccgaccg ctgcgcctta   1500
tccggtaact atcgtcttga gtccaacccg gtaagacacg acttatcgcc actggcagca   1560
gccactggta acaggattag cagagcgagg tatgtaggcg gtgctacaga gttcttgaag   1620
tggtggccta actacggcta cactagaaga acagtatttg gtatctgcgc tctgctgaag   1680
ccagttacct tcggaaaaag agttggtagc tcttgatccg gcaaacaaac caccgctggt   1740
agcggtggtt ttttttgttg caagcagcag attacgcgca gaaaaaaagg atctcaagaa   1800
gatcctttga tcttttctac ggggtctgac gctcagtgga acgaaaactc acgttaaggg   1860
attttggtca tgagattatc aaaaaggatc ttcacctaga tccttttaaa ttaaaaatga   1920
agttttaaat caatctaaag tatatatgag taaacttggt ctgacagtta ccaatgctta   1980
atcagtgagg cacctatctc agcgatctgt ctatttcgtt catccatagt tgcctgactc   2040
cccgtcgtgt agataactac gatacgggag ggcttaccat ctggccccag tgctgcaatg   2100
ataccgcgtg acccacgctc accggctcca gatttatcag caataaacca gccagccgga   2160
agggccgagc gcagaagtgg tcctgcaact ttatccgcct ccatccagtc tattaattgt   2220
tgccgggaag ctagagtaag tagttcgcca gttaatagtt tgcgcaacgt tgttgccatt   2280
gctacaggca tcgtggtgtc acgctcgtcg tttggtatgg cttcattcag ctccggttcc   2340
caacgatcaa ggcgagttgc atgatccccc atgttgtgca aaaaagcggt tagctccttc   2400
ggtcctccga tcgttgtcag aagtaagttg gccgcagtgt tatcactcat ggttatggca   2460
gcactgcata attctcttac tgtcatgcca tccgtaagat gcttttctgt gactggtgag   2520
```

| | |
|---|---|
| tactcaacca agtcattctg agaatagtgt atgcggcgac cgagttgctc ttgcccggcg | 2580 |
| tcaacacggg ataataccgc gccacatagc agaactttaa aagtgctcat cattggaaaa | 2640 |
| cgttcttcgg ggcgaaaact ctcaaggatc ttaccgctgt tgagatccag ttcgatgtaa | 2700 |
| cccactcgtg cacccaactg atcttcagca tcttttactt tcaccagcgt ttctgggtga | 2760 |
| gcaaaaacag gaaggcaaaa tgccgcaaaa aagggaataa gggcgacacg gaaatgttga | 2820 |
| atactcatac tcttcctttt tcaatattat tgaagcattt atcagggtta ttgtctcatg | 2880 |
| agcggataca tatttgaatg tatttagaaa aataaacaaa taggggttcc gcgcacattt | 2940 |
| ccccgaaaag tgccacctga cgtctaagaa accattatta tcatgacatt aacctataaa | 3000 |
| aataggcgta tcacgaggcc ctttcgtgtt caagaattct ggcgaatcct ctgaccagcc | 3060 |
| agaaaacgac ctttctgtgg tgaaaccgga tgctgcaatt cagagcgcca gcaagtgggg | 3120 |
| gacagcagat gacctgaccg ccgcagagtg gatgtttgac atggtgatga ctatcgcacc | 3180 |
| atcagccaga aaaccgaatt ttgctgggtg ggctaacgat atccgcctga tgcgtgaacg | 3240 |
| tgacggacgt aacgaagaca accac | 3265 |

<210> SEQ ID NO 42
<211> LENGTH: 3267
<212> TYPE: DNA
<213> ORGANISM: Artificial Sequence
<220> FEATURE:
<223> OTHER INFORMATION: synthetic polynucleotide

<400> SEQUENCE: 42

| | |
|---|---|
| gcattgctgt tccgctgggc atgcttcgag cctagcaagg gtccgggttc accgaaatct | 60 |
| atctcatttg ctagttataa aattatgaaa tttgcgtaaa ttcttcagtc cctatcagtg | 120 |
| atagagaaag caataatttt gtttaacttt aagaaggaga tataccatgg agcttttcac | 180 |
| tggcgttgtt cccatcctgg tcgagctgga cggcgacgta aacggccaca gttcagcgt | 240 |
| gtccggcgag ggcgagggcg atgccaccta cggcaagctg accctgaagt tcatctgcac | 300 |
| caccggcaag ctgcccgtgc cctggcccac cctcgtgacc accctgacct acggcgtgca | 360 |
| gtgcttcagc cgctacccg accacatgaa gcagcacgac ttcttcaagt ccgccatgcc | 420 |
| cgaaggctac gtccaggagc gcaccatctt cttcaaggac gacggcaact acaagacccg | 480 |
| cgccgaggtg aagttcgagg gcgacaccct ggtgaaccgc atcgagctga agggcatcga | 540 |
| cttcaaggag gacggcaaca tcctggggca caagctggag tacaactaca acagccacaa | 600 |
| cgtctatatc atggccgaca gcagaagaa cggcatcaag gtgaacttca gatccgcca | 660 |
| caacatcgag gacggcagcg tgcagctcgc cgaccactac cagcagaaca cccccatcgg | 720 |
| cgacggcccc gtgctgctgc ccgacaacca ctacctgagc acccagtccg ccctgagcaa | 780 |
| agaccccaac gagaagcgcg atcacatggt cctgctggag ttcgtgaccg ccgccgggat | 840 |
| ctaatgaagc atctggtgaa taactcgagc aaagcccgcc gaaaggcggg cttttctgtg | 900 |
| tcgaccgatg cccttgagag tcgggcattg tcttcgctcc ttccggtggg cgcggggcat | 960 |
| gactatcgtc gccgcactta tgactgtgtt ctttatcatg caactcgtag acaggtgcc | 1020 |
| ggcagcgctc ttccgcttcc tcgctcactg actcgctgcg ctcggtcgtt cggctgcggc | 1080 |
| gagcggtatc agctcactca aaggcggtaa tacggttatc cacagaatca ggggataacg | 1140 |
| caggaaagaa catgtgagca aaaggccagc aaaaggccag gaaccgtaaa aaggccgcgt | 1200 |
| tgctggcgtt tttccatagg ctccgccccc ctgacgagca tcacaaaaat cgacgctcaa | 1260 |
| gtcagaggtg gcgaaacccg acaggactat aaagatacca ggcgtttccc cctggaagct | 1320 |

```
ccctcgtgcg ctctcctgtt ccgaccctgc cgcttaccgg ataccgtgtcc gcctttctcc    1380
cttcgggaag cgtggcgctt tctcatagct cacgctgtag gtatctcagt tcggtgtagg    1440
tcgttcgctc caagctgggc tgtgtgcacg aaccccccgt tcagcccgac cgctgcgcct    1500
tatccggtaa ctatcgtctt gagtccaacc cggtaagaca cgacttatcg ccactggcag    1560
cagccactgg taacaggatt agcagagcga ggtatgtagg cggtgctaca gagttcttga    1620
agtggtggcc taactacggc tacactagaa gaacagtatt tggtatctgc gctctgctga    1680
agccagttac cttcggaaaa agagttggta gctcttgatc cggcaaacaa accaccgctg    1740
gtagcggtgg ttttttttgtt tgcaagcagc agattacgcg cagaaaaaaa ggatctcaag    1800
aagatccttt gatcttttct acggggtctg acgctcagtg gaacgaaaac tcacgttaag    1860
ggatttttggt catgagatta tcaaaaagga tcttcaccta gatccttttta aattaaaaat    1920
gaagttttaa atcaatctaa agtatatatg agtaaacttg gtctgacagt taccaatgct    1980
taatcagtga ggcacctatc tcagcgatct gtctatttcg ttcatccata gttgcctgac    2040
tccccgtcgt gtagataact acgatacggg agggcttacc atctggcccc agtgctgcaa    2100
tgataccgcg tgacccacgc tcaccggctc cagatttatc agcaataaac cagccagccg    2160
gaagggccga gcgcagaagt ggtcctgcaa ctttatccgc ctccatccag tctattaatt    2220
gttgccggga agctagagta agtagttcgc cagttaatag tttgcgcaac gttgttgcca    2280
ttgctacagg catcgtggtg tcacgctcgt cgtttggtat ggcttcattc agctccggtt    2340
cccaacgatc aaggcgagtt gcatgatccc ccatgttgtg caaaaaagcg gttagctcct    2400
tcggtcctcc gatcgttgtc agaagtaagt tggccgcagt gttatcactc atggttatgg    2460
cagcactgca taattctctt actgtcatgc catccgtaag atgcttttct gtgactggtg    2520
agtactcaac caagtcattc tgagaatagt gtatgcggcg accgagttgc tcttgcccgg    2580
cgtcaacacg ggataatacc gcgccacata gcagaacttt aaaagtgctc atcattggaa    2640
aacgttcttc ggggcgaaaa ctctcaagga tcttaccgct gttgagatcc agttcgatgt    2700
aacccactcg tgcacccaac tgatcttcag catctttac tttcaccagc gtttctgggt    2760
gagcaaaaac aggaaggcaa aatgccgcaa aaagggaat aagggcgaca cggaaatgtt    2820
gaatactcat actcttcctt tttcaatatt attgaagcat ttatcagggt tattgtctca    2880
tgagcggata catatttgaa tgtatttaga aaaataaaca aataggggtt ccgcgcacat    2940
ttccccgaaa agtgccacct gacgtctaag aaaccattat tatcatgaca ttaacctata    3000
aaaataggcg tatcacgagg ccctttcgtg ttcaagaatt ctggcgaatc ctctgaccag    3060
ccagaaaacg acctttctgt ggtgaaaccg gatgctgcaa ttcagagcgc cagcaagtgg    3120
gggacagcag atgacctgac cgccgcagag tggatgtttg acatggtgat gactatcgca    3180
ccatcagcca gaaaaccgaa ttttgctggg tgggctaacg atatccgcct gatgcgtgaa    3240
cgtgacggac gtaacgaaga caaccac                                         3267
```

<210> SEQ ID NO 43
<211> LENGTH: 3179
<212> TYPE: DNA
<213> ORGANISM: Artificial Sequence
<220> FEATURE:
<223> OTHER INFORMATION: synthetic polynucleotide

<400> SEQUENCE: 43

```
gcattgctgt tccgctgggc atgcttcgag cctagcaagg gtccgggttc accgaaatct    60
```

-continued

| | |
|---|---|
| atctcatttg ctagttataa aattatgaaa tttgcgtaaa ttcttcagaa gcaataattt | 120 |
| tgtttaactt taagaaggag ataccatg tctagattag ataaaagtaa agtgattaac | 180 |
| agcgcattag agctgcttaa tgaggtcgga atcgaaggtt aacaacccg taaactcgcc | 240 |
| cagaagctag gtgtagagca gcctacattg tattggcatg taaaaaataa gcgggctttg | 300 |
| ctcgacgcct tagccattga gatgttagat aggcaccata ctcacttttg ccctttagaa | 360 |
| ggggaaagct ggcaagattt tttacgtaat aacgctaaaa gttttagatg tgctttacta | 420 |
| agtcatcgcg atggagcaaa agtacattta ggtacacggc ctacagaaaa acagtatgaa | 480 |
| actctcgaaa atcaattagc ctttttatgc caacaaggtt tttcactaga gaatgcatta | 540 |
| tatgcactca gcgctgtggg gcattttact ttaggttgcg tattggaaga tcaagagcat | 600 |
| caagtcgcta aagaagaaag ggaaacacct actactgata gtatgccgcc attattacga | 660 |
| caagctatcg aattatttga tcaccaaggt gcagagccag ccttcttatt cggccttgaa | 720 |
| ttgatcatat gcggattaga aaacaactt aaatgtgaaa gtgggtctta atgaactcgc | 780 |
| aaaaaacccc gcttcggcgg ggttttttcg cgtcgaccga tgcccttgag agtcgggcat | 840 |
| tgtcttcgct ccttccggtg ggcgcggggc atgactatcg tcgccgcact tatgactgtg | 900 |
| ttctttatca tgcaactcgt aggacaggtg ccggcagcgc tcttccgctt cctcgctcac | 960 |
| tgactcgctg cgctcggtcg ttcggctgcg gcgagcggta tcagctcact caaaggcggt | 1020 |
| aatacggtta tccacagaat caggggataa cgcaggaaag aacatgtgag caaaaggcca | 1080 |
| gcaaaaggcc aggaaccgta aaaaggccgc gttgctggcg ttttttccata ggctccgccc | 1140 |
| ccctgacgag catcacaaaa atcgacgctc aagtcagagg tggcgaaacc cgacaggact | 1200 |
| ataaagatac caggcgtttc ccctggaag ctccctcgtg cgctctcctg ttccgaccct | 1260 |
| gccgcttacc ggatacctgt ccgcctttct cccttcggga agcgtggcgc tttctcatag | 1320 |
| ctcacgctgt aggtatctca gttcggtgta ggtcgttcgc tccaagctgg gctgtgtgca | 1380 |
| cgaaccccc gttcagcccg accgctgcgc cttatccggt aactatcgtc ttgagtccaa | 1440 |
| cccggtaaga cacgacttat cgccactggc agcagccact ggtaacagga ttagcagagc | 1500 |
| gaggtatgta ggcggtgcta cagagttctt gaagtggtgg cctaactacg gctacactag | 1560 |
| aagaacagta tttggtatct gcgctctgct gaagccagtt accttcggaa aaagagttgg | 1620 |
| tagctcttga tccggcaaac aaaccaccgc tggtagcggt ggttttttg tttgcaagca | 1680 |
| gcagattacg cgcagaaaaa aaggatctca agaagatcct ttgatctttt ctacggggtc | 1740 |
| tgacgctcag tggaacgaaa actcacgtta agggattttg gtcatgagat tatcaaaaag | 1800 |
| gatcttcacc tagatccttt taaattaaaa atgaagtttt aaatcaatct aaagtatata | 1860 |
| tgagtaaact tggtctgaca gttaccaatg cttaatcagt gaggcaccta tctcagcgat | 1920 |
| ctgtctattt cgttcatcca tagttgcctg actccccgtc gtgtagataa ctacgatacg | 1980 |
| ggagggctta ccatctggcc ccagtgctgc aatgataccg cgtgacccac gctcaccggc | 2040 |
| tccagattta tcagcaataa accagccagc cggaagggcc gagcgcagaa gtggtcctgc | 2100 |
| aactttatcc gcctccatcc agtctattaa ttgttgccgg gaagctagag taagtagttc | 2160 |
| gccagttaat agtttgcgca acgttgttgc cattgctaca ggcatcgtgg tgtcacgctc | 2220 |
| gtcgtttggt atggcttcat tcagctccgg ttcccaacga tcaaggcgag ttgcatgatc | 2280 |
| ccccatgttg tgcaaaaaag cggttagctc cttcggtcct ccgatcgttg tcagaagtaa | 2340 |
| gttggccgca gtgttatcac tcatggttat ggcagcactg cataattctc ttactgtcat | 2400 |
| gccatccgta agatgctttt ctgtgactgg tgagtactca accaagtcat tctgagaata | 2460 |

-continued

```
gtgtatgcgg cgaccgagtt gctcttgccc ggcgtcaaca cgggataata ccgcgccaca   2520
tagcagaact ttaaaagtgc tcatcattgg aaaacgttct tcggggcgaa aactctcaag   2580
gatcttaccg ctgttgagat ccagttcgat gtaacccact cgtgcaccca actgatcttc   2640
agcatctttt actttcacca gcgtttctgg gtgagcaaaa acaggaaggc aaaatgccgc   2700
aaaaaaggga ataagggcga cacggaaatg ttgaatactc atactcttcc ttttcaata   2760 ttattgaagc atttatcagg gttattgtct catgagcgga tacatatttg aatgtattta   2820
gaaaaataaa caaataggggg ttccgcgcac atttccccga aaagtgccac ctgacgtcta   2880
agaaaccatt attatcatga cattaaccta taaaaatagg cgtatcacga ggccctttcg   2940
tgttcaagaa ttctggcgaa tcctctgacc agccagaaaa cgaccttctc gtggtgaaac   3000
cggatgctgc aattcagagc gccagcaagt ggggacagc agatgacctg accgccgcag   3060
agtggatgtt tgacatggtg atgactatcg caccatcagc cagaaaaccg aattttgctg   3120
ggtgggctaa cgatatccgc ctgatgcgtg aacgtgacgg acgtaacgaa gacaaccac   3179
```

```
<210> SEQ ID NO 44
<211> LENGTH: 25
<212> TYPE: DNA
<213> ORGANISM: Artificial Sequence
<220> FEATURE:
<223> OTHER INFORMATION: synthetic polynucleotide

<400> SEQUENCE: 44
tttagagaaa gaggagaaat actag                                         25

<210> SEQ ID NO 45
<211> LENGTH: 15
<212> TYPE: DNA
<213> ORGANISM: Artificial Sequence
<220> FEATURE:
<223> OTHER INFORMATION: synthetic polynucleotide

<400> SEQUENCE: 45
attaaagagg agaaa                                                    15

<210> SEQ ID NO 46
<211> LENGTH: 12
<212> TYPE: DNA
<213> ORGANISM: Artificial Sequence
<220> FEATURE:
<223> OTHER INFORMATION: synthetic polynucleotide

<400> SEQUENCE: 46
aaagaggaga aa                                                       12

<210> SEQ ID NO 47
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 47
tccctatcag tgatagaga                                                19

<210> SEQ ID NO 48
<211> LENGTH: 20
<212> TYPE: DNA
<213> ORGANISM: Artificial Sequence
<220> FEATURE:
```

```
<223> OTHER INFORMATION: synthetic polynucleotide

<400> SEQUENCE: 48
atcattccgt ggcgttatcc                                                    20

<210> SEQ ID NO 49
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 49
gtcagcaaga tagccagatc aa                                                 22

<210> SEQ ID NO 50
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 50
ggcgtcaaca cgggataata                                                    20

<210> SEQ ID NO 51
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 51
gggttacatc gaactggatc tc                                                 22

<210> SEQ ID NO 52
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 52
cgttggctac ccgtgatatt                                                    20

<210> SEQ ID NO 53
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 53
ctcgtcaaga aggcgataga ag                                                 22
```